US012766110B2

(12) United States Patent
Jang et al.

(10) Patent No.: US 12,766,110 B2
(45) **Date of Patent: *Oct. 20, 2026**

(54) EXTRACELLULAR VESICLES COMPRISING STING-AGONIST

(71) Applicant: LONZA SALES AG, Basel (CH)

(72) Inventors: Su Chul Jang, Cambridge, MA (US); Chang Ling Sia, Cambridge (UA); Nuruddeen D. Lewis, Andover, MA (US); Rane A. Harrison, Andover, MA (US); Raymond J. Moniz, Arlington, MA (US); Sriram Sathyanarayanan, Lexington, MA (US); Douglas E. Williams, Boston, MA (US); Kyriakos Economides, Grafton, MA (US)

(73) Assignee: LONZA SALES AG, Basel (CH)

( * ) Notice: Subject to any disclaimer, the term of this patent is extended or adjusted under 35 U.S.C. 154(b) by 1345 days.

This patent is subject to a terminal disclaimer.

(21) Appl. No.: 17/040,805

(22) PCT Filed: Mar. 22, 2019

(86) PCT No.: PCT/US2019/023727

§ 371 (c)(1),
(2) Date: Sep. 23, 2020

(87) PCT Pub. No.: WO2019/183578

PCT Pub. Date: Sep. 26, 2019

(65) Prior Publication Data

US 2021/0322327 A1 Oct. 21, 2021

Related U.S. Application Data

(60) Provisional application No. 62/647,491, filed on Mar. 23, 2018, provisional application No. 62/680,501, filed on Jun. 4, 2018, provisional application No. 62/688,600, filed on Jun. 22, 2018, provisional application No. 62/756,247, filed on Nov. 6, 2018, provisional application No. 62/822,019, filed on Mar. 21, 2019.

(51) Int. Cl.

| | |
|---|---|
| ***A61K 9/50*** | (2006.01) |
| ***A61K 9/00*** | (2006.01) |
| ***A61K 31/7084*** | (2006.01) |
| ***A61K 39/395*** | (2006.01) |
| ***A61P 35/00*** | (2006.01) |
| ***A61P 35/04*** | (2006.01) |
| ***A61P 37/04*** | (2006.01) |

(52) U.S. Cl.

CPC .......... *A61K 9/5068* (2013.01); *A61K 9/0019* (2013.01); *A61K 9/5089* (2013.01); *A61K 31/7084* (2013.01); *A61K 39/3955* (2013.01); *A61P 35/00* (2018.01); *A61P 35/04* (2018.01); *A61P 37/04* (2018.01)

(58) Field of Classification Search

CPC .............. A61K 31/7084; A61K 9/5068; A61K 9/5089; A61K 9/5184; A61K 9/0019

See application file for complete search history.

(56) References Cited

U.S. PATENT DOCUMENTS

| | | | | |
|---|---|---|---|---|
| 10,195,290 | B1 | 2/2019 | Dooley et al. | |
| 10,562,929 | B2 | 2/2020 | Vernejoul et al. | |
| 11,992,527 | B2 * | 5/2024 | Moniz | A61K 9/5176 |
| 2016/0362441 | A1 | 12/2016 | Vernejoul et al. | |
| 2017/0239283 | A1 | 8/2017 | Gough et al. | |
| 2020/0123219 | A1 * | 4/2020 | Stephan | A61K 39/39 |

FOREIGN PATENT DOCUMENTS

| | | | |
|---|---|---|---|
| CN | 102349998 | A | 2/2012 |
| CN | 103025890 | A | 4/2013 |
| WO | WO-2013185052 | A1 | 12/2013 |
| WO | WO-2014093936 | A1 | 6/2014 |
| WO | WO-2014179335 | A1 | 11/2014 |
| WO | WO-2014179760 | A1 | 11/2014 |
| WO | WO-2014189805 | A1 | 11/2014 |
| WO | WO-2014189806 | A1 | 11/2014 |
| WO | WO-2015017652 | A1 | 2/2015 |
| WO | WO-2015077354 | A1 | 5/2015 |
| WO | WO-2015108595 | A1 | 7/2015 |
| WO | WO-2015185565 | A1 | 12/2015 |
| WO | WO-2016096174 | A1 | 6/2016 |

(Continued)

OTHER PUBLICATIONS

Bridgeman, Published Sep. 11, 2015, Science, vol. 349, Issue 6253, pp. 1228-1232 (Year: 2015).*

(Continued)

*Primary Examiner* — Renee Claytor
*Assistant Examiner* — Jaret J Crews
(74) *Attorney, Agent, or Firm* — MEDLER FERRO WOODHOUSE & MILLS PLLC

(57) ABSTRACT

Provided herein are compositions comprising EV, e.g., exosome, encapsulated STING agonists and methods of producing the compositions described. Also provided herein are methods of modulating an immune response via administration of a therapeutic amount of EV, e.g., exosomes encapsulating STING agonists. The immune response may be an IENβ response or activation of myeloid dendritic cells (mDCs). Also provided herein are methods of modulating an immune response that does not induce systemic inflammation via administration of exosomes encapsulating STING agonists.

13 Claims, 119 Drawing Sheets

Specification includes a Sequence Listing.

(56) References Cited

FOREIGN PATENT DOCUMENTS

| | | | |
|---|---|---|---|
| WO | WO-2016096577 | A1 | 6/2016 |
| WO | WO-2016120305 | A1 | 8/2016 |
| WO | WO-2016145102 | A1 | 9/2016 |
| WO | 2016/201323 | A1 | 12/2016 |
| WO | WO-2017027645 | A1 | 2/2017 |
| WO | WO-2017027646 | A1 | 2/2017 |
| WO | WO-2017075477 | A1 | 5/2017 |
| WO | 2017/117585 | A1 | 7/2017 |
| WO | WO-2017175147 | A1 | 10/2017 |
| WO | WO-2017175156 | A1 | 10/2017 |
| WO | WO-2018100558 | A2 | 6/2018 |
| WO | WO-2019040920 | A1 | 2/2019 |
| WO | WO-2019099942 | A1 | 5/2019 |
| WO | WO-2019183578 | A1 | 9/2019 |

OTHER PUBLICATIONS

Bridgeman et al., Published Sep. 11, 2015, Science, vol. 349, Issue 6253, pp. 1228-1232 (Year: 2015).*

Jang et al., "Abstract 944: exoSTING: An engineered exosome therapeutic that selectively delivers STING agonist to the tumor resident antigen-presenting cells resulting in improved tumor antigen-specific adaptive immune response." *Cancer Research*, 79 (Supplement 13): 944 (2019).

Jang et al., "Abstract 618: Selective delivery of exosome-mediated STING agonist to antigen presenting cells results in significantly improved potency and reduced toxicity." *Journal for ImmunoTherapy of Cancer*, 6(Supplement 13): 333-334 (2018).

Ha, D., et al., "Exosomes as therapeutic drug carriers and delivery vehicles across biological membranes: current perspectives and future challenges," *Acta Pharmaceutica Sinica B*, 6(4): 287-296, Elsevier, Netherlands (2016).

Luga, V., et al., "Exosomes Mediate Stromal Mobilization of Autocrine Wnt-PCP Signaling in Breast Cancer Cell Migration," *Cell*, 151(7): 1542-1556, Cell Press, United States (2012).

Nishikawa, Y., et al., "Modulation of Stimulator of Interferon Genes (STING) Expression by Interferon-γ in Human Keratinocytes," *Biochem. Genet.*, 56(1): 93-102, Springer Science+Business Media, Germany (2017).

Phanthaphol, N., et al., "Chimeric Antigen Receptor T Cells Targeting Integrin αvβ6 Expressed on Cholangiocarcinoma Cells," *Frontiers in Oncology*, 11: 657868, 13 pages, Frontiers Media S.A., Switzerland (2021).

Tang, X.J., et al., "Therapeutic potential of CAR-T cell-derived exosomes: a cell-free modality for targeted cancer therapy," *Oncotarget*, 6(42): 44179-44190, Impact Journals, United States (2015).

Yang, M.Q., et al., "Interferon regulatory factor 1 priming of tumour-derived exosomes enhances the antitumour immune response," *Br. J. Cancer*, 118: 62-71, Nature Portfolio, Germany (2017).

Cocucci, E., and Meldolesi, J., "Ectosomes and Exosomes: Shedding the Confusion Between Extracellular Vesicles," Trends in Cell Biology 25(6):364-372, Elsevier Science, United Kingdom (2015).

Corrales, L., et al., "Direct Activation of STING in the Tumor Microenvironment Leads to Potent and Systemic Tumor Regression and Immunity," Cell Reports 11(7):1018-1030, Elsevier Inc (May 2015).

Demaria, O., et al., "STING Activation of Tumor Endothelial Cells Initiates Spontaneous and Therapeutic Antitumor Immunity," Proceedings of the National Academy of Sciences of the United States of America 112(50):15408-15413, National Academy of Sciences, United States (Dec. 2015).

Dobeli, H., et al., "Role of the Carboxy-terminal Sequence on the Biological Activity of Human Interferon (IFN-y)," Journal of Biotechnology 7:199-216, Elsevier Science Publishers B.V., Netherlands (Mar. 1988).

Fu, J., et al., "STING agonist formulated cancer vaccines can cure established tumors resistant to PD-1 blockade," Science Translational Medicine 7(283):283ra52, American Association for the Advancement of Science, United States (2015).

Gayle, R.B., III, et al., "Identification of Regions in Interleukin-1α Important for Activity," The Journal of Biological Chemistry 268(29):22105-22111, The American Society for Biochemistry and Molecular Biology, Inc., United States (Oct. 1993).

Gentili, M., et al., "Transmission of Innate Immune signaling by Packaging of cGAMP in Viral Particles," Science 349(6253):1232-1236, American Association for the Advancement of Science, United States (Sep. 2015).

Hanson, M.C., et al., "Nanoparticulate STING Agonists Are Potent Lymph Node-Targeted Vaccine Adjuvants," Journal of Clinical Investigation 125(6): 2532-2546, American Society for Clinical Investigation, United States (Jun. 2015).

International Search Report and Written Opinion for Application No. PCT/US2019/023727, European Patent Office, Netherlands, mailed on Sep. 12, 2019, 24 pages.

Kitai, Y., et al., "DNA-Containing Exosomes Derived from Cancer Cells Treated with Topotecan Activate a STING-Dependent Pathway and Reinforce Antitumor Immunity," Journal of Immunology 198(4):1649-1659 American Association of Immunologists, United States (Feb. 2017).

Klinghoffer, R.A., et al., "A technology platform to assess multiple cancer agents simultaneously within a patient's tumor," Sci Transl Med 7(284): 284ra58, American Association for the Advancement of Science, United States (2015).

Koshy, S.T., et al., "Liposomal Delivery Enhances Immune Activation by STING Agonists for Cancer Immunotherapy," Advanced Biosystems 1(1-2):1600013, Wiley-VCH Verlag GmbH & Co, Germany (Feb. 2017).

Lioux, T., et al., "Design, Synthesis, and Biological Evaluation of Novel Cyclic Adenosine-Inosine Monophosphate (cAIMP) Analogs That Activate Stimulator of Interferon Genes (STING)," Journal of Medicinal Chemistry 59(22):10253-10267 (2016).

Liu, Y., et al., "Activated STING in a Vascular and Pulmonary Syndrome," New England Journal of Medicine 371:507-518, Massachusetts Medical Society, United States (2014).

Mei, B., et al., "Rational Design of a Fully active, Long-acting PEGylated Factor VIII for Hemophilia A Treatment," Blood 116(2):270-279, The American Society of Hematology, United States (Jul. 2010).

Miyabe, H., et al., "A New Adjuvant Delivery System 'Cyclic Di-Gmp/Ysk05 Liposome' For Cancer Immunotherapy," Journal of Controlled Release 184:20-27, Elsevier Science Publishers, Netherlands (Jun. 2014).

Papapetrou, E.P., et al., "Genetic Modification of Hematopoietic Stem Cells with Nonviral Systems: Past Progress and Future Prospects," Gene Therapy 12:S118-S130, Nature Publishing Group, United Kingdom (2005).

Ron, D., et al., "Expression of Biologically Active Recombinant Keratinocyte Growth Factor. Structure/Function Analysis of Amino-Terminal Truncation Mutants," Journal of Biological Chemistry 268:2984-2988, American Society for Biochemistry and Molecular Biology Inc., United States (1993).

Sisquella, X., et al., "Malaria Parasite DNA-Harbouring Vesicles Activate Cytosolic Immune Sensors," Nature Communications 8:1985, Nature Publishing Group, United Kingdom (Dec. 2017).

Sivick, K.E., et al., "Magnitude of Therapeutic STING Activation Determines CD8 + T Cell-Mediated Anti-Tumor Immunity," Cell Rep 25(11):3074-3085, Cell Press, United States (Dec. 2018).

Wiklander, O.P., et al., "Extracellular Vesicle in Vivo Biodistribution is Determined by Cell Source, Route of Administration and Targeting," Journal of Extracellular Vesicles 4:26316, Taylor and Francis Ltd., Sweden (2015).

* cited by examiner

IFNß Production

| EC50 | Free STING | STING Exo | STING Exo Degly | STING Exo Desial | STING Exo PTGFRN | STING Exo PTGFRN Degly | STING Exo PTGFRN Desialy |
|---|---|---|---|---|---|---|---|
| Donor 1 | 9.9 | 0.15 | 0.035 | 0.059 | 0.018 | 0.0083 | 0.0078 |
| Donor 2 | 6.4 | 0.15 | 0.074 | 0.03 | 0.006 | 0.0026 | 0.0019 |
| Average Fold-Change | N/A | 65 | 257 | 186 | 445 | 1117 | 1021 |

FIG. 9

Monocyte Activation

| EC50 | Free STING | STING Exo | STING Exo Degly | STING Exo Desial | STING Exo PTGFRN | STING Exo PTGFRN Degly | STING Exo PTGFRN Desialy |
|---|---|---|---|---|---|---|---|
| Donor 1 | 1.0 | 0.007 | 0.00072 | 0.00086 | 0.00016 | 0.00009 | 0.00001 |
| Donor 2 | 0.6 | 0.006 | 0.001 | 0.00055 | 0.00037 | 0.00013 | 0.00007 |
| Average Fold-Change | N/A | **121** | **1004** | **1141** | **3990** | **8001** | **54509** |

FIG. 11 mDC Activation

| EC50 | Free STING | STING Exo | STING Exo Degly | STING Exo Desial | STING Exo PTGFRN | STING Exo PTGFRN Degly | STING Exo PTGFRN Desialy |
|---|---|---|---|---|---|---|---|
| Donor 1 | 1.2 | 0.0085 | 0.0015 | 0.0011 | 0.00016 | 0.00015 | 0.00004 |
| Donor 2 | 0.05 | 0.0050 | 0.0012 | 0.0004 | 0.0007 | 0.00009 | 0.00003 |
| Average Fold-Change | N/A | 78 | 443 | 630 | 3945 | 4318 | 16756 |

FIG. 13

| Samples | STING concen. (uM) |
|---|---|
| STING Exo | 7.75 |
| STING Exo Degly | 6.72 |
| STING Exo Desialy | 4.89 |
| STING Exo-PTGFRN | 3.06 |
| STING Exo-PTGFRN Degly | 3.32 |
| STING Exo-PTGFRN Desialy | 2.96 |

EXPRESSION IN TUMOR

EXPRESSION IN TUMOR

EXPRESSION IN DRAINING LYMPH NODE

EXPRESSION IN SPLEEN

EXPRESSION IN SERUM

EXPRESSION IN TUMOR

EXPRESSION IN TUMOR

EXPRESSION IN DRAINING LYMPH NODE

EXPRESSION IN DRAINING LYMPH NODE

EXPRESSION IN SPLEEN

EXPRESSION IN SERUM

EXPRESSION IN SERUM

EXPRESSION IN LUNG

EXPRESSION IN SPLEEN

EXPRESSION IN SERUM

PBS

Exo STING Agonist (8ng)

Exo STING Agonist (40ng)

Exo STING Agonist (200ng)

*image composite showing one of duplicate wells*

INTERFERON BETA EXPRESSION

CXCL9 EXPRESSION

CXCL10 EXPRESSION

INTERFERON GAMMA EXPRESSION

EXPRESSION IN SERUM

EXPRESSION IN SERUM

| STING agonist (30 µg) | STING agonist (0.3 µg) | exoSTING |
|---|---|---|
| 8.9 min | 11.5 min | 119.7 min |

| STING agonist (20 µg) |
|---|
| 1.2 min |

| exoSTING (0.1 µg) | exoSTING (0.3 µg) | exoSTING (0.6 µg) |
|---|---|---|
| 1.2 min | 1.8 min | 8.5 min |

EXPRESSION IN LIVER

EXPRESSION IN LIVER

EXPRESSION IN SPLEEN

EXPRESSION IN SPLEEN

EXPRESSION IN SERUM

EXPRESSION IN SERUM

CXCL9 EXPRESSION

INTERFERON GAMMA EXPRESSION

EXPRESSION IN SERUM

EXPRESSION IN SERUM

SEQUENCE LISTING

```
<160> NUMBER OF SEQ ID NOS: 202

<210> SEQ ID NO 1
<211> LENGTH: 879
<212> TYPE: PRT
<213> ORGANISM: Homo sapiens

<400> SEQUENCE: 1

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
```

```
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540
```

-continued

```
Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875
```

<210> SEQ ID NO 2
<211> LENGTH: 731
<212> TYPE: PRT
<213> ORGANISM: Homo sapiens

<400> SEQUENCE: 2

```
Pro Ser Ala Arg Pro Pro Pro Ser Leu Ser Leu Arg Glu Gly Glu Pro
1               5                   10                  15

Phe Glu Leu Arg Cys Thr Ala Ala Ser Ala Ser Pro Leu His Thr His
            20                  25                  30

Leu Ala Leu Leu Trp Glu Val His Arg Gly Pro Ala Arg Arg Ser Val
```

-continued

```
        35                  40                  45

Leu Ala Leu Thr His Glu Gly Arg Phe His Pro Gly Leu Gly Tyr Glu
    50                  55                  60

Gln Arg Tyr His Ser Gly Asp Val Arg Leu Asp Thr Val Gly Ser Asp
65                  70                  75                  80

Ala Tyr Arg Leu Ser Val Ser Arg Ala Leu Ser Ala Asp Gln Gly Ser
                85                  90                  95

Tyr Arg Cys Ile Val Ser Glu Trp Ile Ala Glu Gln Gly Asn Trp Gln
            100                 105                 110

Glu Ile Gln Glu Lys Ala Val Glu Val Ala Thr Val Val Ile Gln Pro
        115                 120                 125

Ser Val Leu Arg Ala Ala Val Pro Lys Asn Val Ser Val Ala Glu Gly
    130                 135                 140

Lys Glu Leu Asp Leu Thr Cys Asn Ile Thr Thr Asp Arg Ala Asp Asp
145                 150                 155                 160

Val Arg Pro Glu Val Thr Trp Ser Phe Ser Arg Met Pro Asp Ser Thr
                165                 170                 175

Leu Pro Gly Ser Arg Val Leu Ala Arg Leu Asp Arg Asp Ser Leu Val
            180                 185                 190

His Ser Ser Pro His Val Ala Leu Ser His Val Asp Ala Arg Ser Tyr
        195                 200                 205

His Leu Leu Val Arg Asp Val Ser Lys Glu Asn Ser Gly Tyr Tyr Tyr
    210                 215                 220

Cys His Val Ser Leu Trp Ala Pro Gly His Asn Arg Ser Trp His Lys
225                 230                 235                 240

Val Ala Glu Ala Val Ser Ser Pro Ala Gly Val Gly Val Thr Trp Leu
                245                 250                 255

Glu Pro Asp Tyr Gln Val Tyr Leu Asn Ala Ser Lys Val Pro Gly Phe
            260                 265                 270

Ala Asp Asp Pro Thr Glu Leu Ala Cys Arg Val Val Asp Thr Lys Ser
        275                 280                 285

Gly Glu Ala Asn Val Arg Phe Thr Val Ser Trp Tyr Tyr Arg Met Asn
    290                 295                 300

Arg Arg Ser Asp Asn Val Val Thr Ser Glu Leu Leu Ala Val Met Asp
305                 310                 315                 320

Gly Asp Trp Thr Leu Lys Tyr Gly Glu Arg Ser Lys Gln Arg Ala Gln
                325                 330                 335

Asp Gly Asp Phe Ile Phe Ser Lys Glu His Thr Asp Thr Phe Asn Phe
            340                 345                 350

Arg Ile Gln Arg Thr Thr Glu Glu Asp Arg Gly Asn Tyr Tyr Cys Val
        355                 360                 365

Val Ser Ala Trp Thr Lys Gln Arg Asn Asn Ser Trp Val Lys Ser Lys
    370                 375                 380

Asp Val Phe Ser Lys Pro Val Asn Ile Phe Trp Ala Leu Glu Asp Ser
385                 390                 395                 400

Val Leu Val Val Lys Ala Arg Gln Pro Lys Pro Phe Phe Ala Ala Gly
                405                 410                 415

Asn Thr Phe Glu Met Thr Cys Lys Val Ser Ser Lys Asn Ile Lys Ser
            420                 425                 430

Pro Arg Tyr Ser Val Leu Ile Met Ala Glu Lys Pro Val Gly Asp Leu
        435                 440                 445

Ser Ser Pro Asn Glu Thr Lys Tyr Ile Ile Ser Leu Asp Gln Asp Ser
    450                 455                 460
```

Val Val Lys Leu Glu Asn Trp Thr Asp Ala Ser Arg Val Asp Gly Val
465 470 475 480

Val Leu Glu Lys Val Gln Glu Asp Glu Phe Arg Tyr Arg Met Tyr Gln
485 490 495

Thr Gln Val Ser Asp Ala Gly Leu Tyr Arg Cys Met Val Thr Ala Trp
500 505 510

Ser Pro Val Arg Gly Ser Leu Trp Arg Glu Ala Ala Thr Ser Leu Ser
515 520 525

Asn Pro Ile Glu Ile Asp Phe Gln Thr Ser Gly Pro Ile Phe Asn Ala
530 535 540

Ser Val His Ser Asp Thr Pro Ser Val Ile Arg Gly Asp Leu Ile Lys
545 550 555 560

Leu Phe Cys Ile Ile Thr Val Glu Gly Ala Ala Leu Asp Pro Asp Asp
565 570 575

Met Ala Phe Asp Val Ser Trp Phe Ala Val His Ser Phe Gly Leu Asp
580 585 590

Lys Ala Pro Val Leu Leu Ser Ser Leu Asp Arg Lys Gly Ile Val Thr
595 600 605

Thr Ser Arg Arg Asp Trp Lys Ser Asp Leu Ser Leu Glu Arg Val Ser
610 615 620

Val Leu Glu Phe Leu Leu Gln Val His Gly Ser Glu Asp Gln Asp Phe
625 630 635 640

Gly Asn Tyr Tyr Cys Ser Val Thr Pro Trp Val Lys Ser Pro Thr Gly
645 650 655

Ser Trp Gln Lys Glu Ala Glu Ile His Ser Lys Pro Val Phe Ile Thr
660 665 670

Val Lys Met Asp Val Leu Asn Ala Phe Lys Tyr Pro Leu Leu Ile Gly
675 680 685

Val Gly Leu Ser Thr Val Ile Gly Leu Leu Ser Cys Leu Ile Gly Tyr
690 695 700

Cys Ser Ser His Trp Cys Cys Lys Lys Glu Val Gln Glu Thr Arg Arg
705 710 715 720

Glu Arg Arg Arg Leu Met Ser Met Glu Met Asp
725 730

<210> SEQ ID NO 3
<211> LENGTH: 611
<212> TYPE: PRT
<213> ORGANISM: Homo sapiens

<400> SEQUENCE: 3

Val Ala Thr Val Val Ile Gln Pro Ser Val Leu Arg Ala Ala Val Pro
1 5 10 15

Lys Asn Val Ser Val Ala Glu Gly Lys Glu Leu Asp Leu Thr Cys Asn
20 25 30

Ile Thr Thr Asp Arg Ala Asp Asp Val Arg Pro Glu Val Thr Trp Ser
35 40 45

Phe Ser Arg Met Pro Asp Ser Thr Leu Pro Gly Ser Arg Val Leu Ala
50 55 60

Arg Leu Asp Arg Asp Ser Leu Val His Ser Ser Pro His Val Ala Leu
65 70 75 80

Ser His Val Asp Ala Arg Ser Tyr His Leu Leu Val Arg Asp Val Ser
85 90 95

Lys Glu Asn Ser Gly Tyr Tyr Tyr Cys His Val Ser Leu Trp Ala Pro

-continued

```
            100                 105                 110

Gly His Asn Arg Ser Trp His Lys Val Ala Glu Ala Val Ser Ser Pro
        115                 120                 125

Ala Gly Val Gly Val Thr Trp Leu Glu Pro Asp Tyr Gln Val Tyr Leu
    130                 135                 140

Asn Ala Ser Lys Val Pro Gly Phe Ala Asp Asp Pro Thr Glu Leu Ala
145                 150                 155                 160

Cys Arg Val Val Asp Thr Lys Ser Gly Glu Ala Asn Val Arg Phe Thr
                165                 170                 175

Val Ser Trp Tyr Tyr Arg Met Asn Arg Arg Ser Asp Asn Val Val Thr
            180                 185                 190

Ser Glu Leu Leu Ala Val Met Asp Gly Asp Trp Thr Leu Lys Tyr Gly
        195                 200                 205

Glu Arg Ser Lys Gln Arg Ala Gln Asp Gly Asp Phe Ile Phe Ser Lys
    210                 215                 220

Glu His Thr Asp Thr Phe Asn Phe Arg Ile Gln Arg Thr Thr Glu Glu
225                 230                 235                 240

Asp Arg Gly Asn Tyr Tyr Cys Val Val Ser Ala Trp Thr Lys Gln Arg
                245                 250                 255

Asn Asn Ser Trp Val Lys Ser Lys Asp Val Phe Ser Lys Pro Val Asn
            260                 265                 270

Ile Phe Trp Ala Leu Glu Asp Ser Val Leu Val Val Lys Ala Arg Gln
        275                 280                 285

Pro Lys Pro Phe Phe Ala Ala Gly Asn Thr Phe Glu Met Thr Cys Lys
    290                 295                 300

Val Ser Ser Lys Asn Ile Lys Ser Pro Arg Tyr Ser Val Leu Ile Met
305                 310                 315                 320

Ala Glu Lys Pro Val Gly Asp Leu Ser Ser Pro Asn Glu Thr Lys Tyr
                325                 330                 335

Ile Ile Ser Leu Asp Gln Asp Ser Val Val Lys Leu Glu Asn Trp Thr
            340                 345                 350

Asp Ala Ser Arg Val Asp Gly Val Val Leu Glu Lys Val Gln Glu Asp
        355                 360                 365

Glu Phe Arg Tyr Arg Met Tyr Gln Thr Gln Val Ser Asp Ala Gly Leu
    370                 375                 380

Tyr Arg Cys Met Val Thr Ala Trp Ser Pro Val Arg Gly Ser Leu Trp
385                 390                 395                 400

Arg Glu Ala Ala Thr Ser Leu Ser Asn Pro Ile Glu Ile Asp Phe Gln
                405                 410                 415

Thr Ser Gly Pro Ile Phe Asn Ala Ser Val His Ser Asp Thr Pro Ser
            420                 425                 430

Val Ile Arg Gly Asp Leu Ile Lys Leu Phe Cys Ile Ile Thr Val Glu
        435                 440                 445

Gly Ala Ala Leu Asp Pro Asp Asp Met Ala Phe Asp Val Ser Trp Phe
    450                 455                 460

Ala Val His Ser Phe Gly Leu Asp Lys Ala Pro Val Leu Leu Ser Ser
465                 470                 475                 480

Leu Asp Arg Lys Gly Ile Val Thr Thr Ser Arg Arg Asp Trp Lys Ser
                485                 490                 495

Asp Leu Ser Leu Glu Arg Val Ser Val Leu Glu Phe Leu Leu Gln Val
            500                 505                 510

His Gly Ser Glu Asp Gln Asp Phe Gly Asn Tyr Tyr Cys Ser Val Thr
        515                 520                 525
```

Pro Trp Val Lys Ser Pro Thr Gly Ser Trp Gln Lys Glu Ala Glu Ile
    530                 535                 540

His Ser Lys Pro Val Phe Ile Thr Val Lys Met Asp Val Leu Asn Ala
545                 550                 555                 560

Phe Lys Tyr Pro Leu Leu Ile Gly Val Gly Leu Ser Thr Val Ile Gly
                565                 570                 575

Leu Leu Ser Cys Leu Ile Gly Tyr Cys Ser Ser His Trp Cys Cys Lys
            580                 585                 590

Lys Glu Val Gln Glu Thr Arg Arg Glu Arg Arg Arg Leu Met Ser Met
        595                 600                 605

Glu Met Asp
    610

<210> SEQ ID NO 4
<211> LENGTH: 485
<212> TYPE: PRT
<213> ORGANISM: homo sapien

<400> SEQUENCE: 4

Ser Pro Ala Gly Val Gly Val Thr Trp Leu Glu Pro Asp Tyr Gln Val
1               5                   10                  15

Tyr Leu Asn Ala Ser Lys Val Pro Gly Phe Ala Asp Asp Pro Thr Glu
            20                  25                  30

Leu Ala Cys Arg Val Val Asp Thr Lys Ser Gly Glu Ala Asn Val Arg
        35                  40                  45

Phe Thr Val Ser Trp Tyr Tyr Arg Met Asn Arg Arg Ser Asp Asn Val
    50                  55                  60

Val Thr Ser Glu Leu Leu Ala Val Met Asp Gly Asp Trp Thr Leu Lys
65                  70                  75                  80

Tyr Gly Glu Arg Ser Lys Gln Arg Ala Gln Asp Gly Asp Phe Ile Phe
                85                  90                  95

Ser Lys Glu His Thr Asp Thr Phe Asn Phe Arg Ile Gln Arg Thr Thr
            100                 105                 110

Glu Glu Asp Arg Gly Asn Tyr Tyr Cys Val Val Ser Ala Trp Thr Lys
        115                 120                 125

Gln Arg Asn Asn Ser Trp Val Lys Ser Lys Asp Val Phe Ser Lys Pro
    130                 135                 140

Val Asn Ile Phe Trp Ala Leu Glu Asp Ser Val Leu Val Val Lys Ala
145                 150                 155                 160

Arg Gln Pro Lys Pro Phe Phe Ala Ala Gly Asn Thr Phe Glu Met Thr
                165                 170                 175

Cys Lys Val Ser Ser Lys Asn Ile Lys Ser Pro Arg Tyr Ser Val Leu
            180                 185                 190

Ile Met Ala Glu Lys Pro Val Gly Asp Leu Ser Ser Pro Asn Glu Thr
        195                 200                 205

Lys Tyr Ile Ile Ser Leu Asp Gln Asp Ser Val Val Lys Leu Glu Asn
    210                 215                 220

Trp Thr Asp Ala Ser Arg Val Asp Gly Val Val Leu Glu Lys Val Gln
225                 230                 235                 240

Glu Asp Glu Phe Arg Tyr Arg Met Tyr Gln Thr Gln Val Ser Asp Ala
                245                 250                 255

Gly Leu Tyr Arg Cys Met Val Thr Ala Trp Ser Pro Val Arg Gly Ser
            260                 265                 270

Leu Trp Arg Glu Ala Ala Thr Ser Leu Ser Asn Pro Ile Glu Ile Asp 275 280 285

Phe Gln Thr Ser Gly Pro Ile Phe Asn Ala Ser Val His Ser Asp Thr
290 295 300

Pro Ser Val Ile Arg Gly Asp Leu Ile Lys Leu Phe Cys Ile Ile Thr
305 310 315 320

Val Glu Gly Ala Ala Leu Asp Pro Asp Asp Met Ala Phe Asp Val Ser
325 330 335

Trp Phe Ala Val His Ser Phe Gly Leu Asp Lys Ala Pro Val Leu Leu
340 345 350

Ser Ser Leu Asp Arg Lys Gly Ile Val Thr Thr Ser Arg Arg Asp Trp
355 360 365

Lys Ser Asp Leu Ser Leu Glu Arg Val Ser Val Leu Glu Phe Leu Leu
370 375 380

Gln Val His Gly Ser Glu Asp Gln Asp Phe Gly Asn Tyr Tyr Cys Ser
385 390 395 400

Val Thr Pro Trp Val Lys Ser Pro Thr Gly Ser Trp Gln Lys Glu Ala
405 410 415

Glu Ile His Ser Lys Pro Val Phe Ile Thr Val Lys Met Asp Val Leu
420 425 430

Asn Ala Phe Lys Tyr Pro Leu Leu Ile Gly Val Gly Leu Ser Thr Val
435 440 445

Ile Gly Leu Leu Ser Cys Leu Ile Gly Tyr Cys Ser Ser His Trp Cys
450 455 460

Cys Lys Lys Glu Val Gln Glu Thr Arg Arg Glu Arg Arg Arg Leu Met
465 470 475 480

Ser Met Glu Met Asp
485

<210> SEQ ID NO 5
<211> LENGTH: 343
<212> TYPE: PRT
<213> ORGANISM: Homo sapiens

<400> SEQUENCE: 5

Lys Pro Val Asn Ile Phe Trp Ala Leu Glu Asp Ser Val Leu Val Val
1 5 10 15

Lys Ala Arg Gln Pro Lys Pro Phe Phe Ala Ala Gly Asn Thr Phe Glu
20 25 30

Met Thr Cys Lys Val Ser Ser Lys Asn Ile Lys Ser Pro Arg Tyr Ser
35 40 45

Val Leu Ile Met Ala Glu Lys Pro Val Gly Asp Leu Ser Ser Pro Asn
50 55 60

Glu Thr Lys Tyr Ile Ile Ser Leu Asp Gln Asp Ser Val Val Lys Leu
65 70 75 80

Glu Asn Trp Thr Asp Ala Ser Arg Val Asp Gly Val Val Leu Glu Lys
85 90 95

Val Gln Glu Asp Glu Phe Arg Tyr Arg Met Tyr Gln Thr Gln Val Ser
100 105 110

Asp Ala Gly Leu Tyr Arg Cys Met Val Thr Ala Trp Ser Pro Val Arg
115 120 125

Gly Ser Leu Trp Arg Glu Ala Ala Thr Ser Leu Ser Asn Pro Ile Glu
130 135 140

Ile Asp Phe Gln Thr Ser Gly Pro Ile Phe Asn Ala Ser Val His Ser
145 150 155 160

-continued

Asp Thr Pro Ser Val Ile Arg Gly Asp Leu Ile Lys Leu Phe Cys Ile
165 170 175

Ile Thr Val Glu Gly Ala Ala Leu Asp Pro Asp Asp Met Ala Phe Asp
180 185 190

Val Ser Trp Phe Ala Val His Ser Phe Gly Leu Asp Lys Ala Pro Val
195 200 205

Leu Leu Ser Ser Leu Asp Arg Lys Gly Ile Val Thr Thr Ser Arg Arg
210 215 220

Asp Trp Lys Ser Asp Leu Ser Leu Glu Arg Val Ser Val Leu Glu Phe
225 230 235 240

Leu Leu Gln Val His Gly Ser Glu Asp Gln Asp Phe Gly Asn Tyr Tyr
245 250 255

Cys Ser Val Thr Pro Trp Val Lys Ser Pro Thr Gly Ser Trp Gln Lys
260 265 270

Glu Ala Glu Ile His Ser Lys Pro Val Phe Ile Thr Val Lys Met Asp
275 280 285

Val Leu Asn Ala Phe Lys Tyr Pro Leu Leu Ile Gly Val Gly Leu Ser
290 295 300

Thr Val Ile Gly Leu Leu Ser Cys Leu Ile Gly Tyr Cys Ser Ser His
305 310 315 320

Trp Cys Cys Lys Lys Glu Val Gln Glu Thr Arg Arg Glu Arg Arg Arg
325 330 335

Leu Met Ser Met Glu Met Asp
340

<210> SEQ ID NO 6
<211> LENGTH: 217
<212> TYPE: PRT
<213> ORGANISM: Homo sapiens

<400> SEQUENCE: 6

Val Arg Gly Ser Leu Trp Arg Glu Ala Ala Thr Ser Leu Ser Asn Pro
1 5 10 15

Ile Glu Ile Asp Phe Gln Thr Ser Gly Pro Ile Phe Asn Ala Ser Val
20 25 30

His Ser Asp Thr Pro Ser Val Ile Arg Gly Asp Leu Ile Lys Leu Phe
35 40 45

Cys Ile Ile Thr Val Glu Gly Ala Ala Leu Asp Pro Asp Asp Met Ala
50 55 60

Phe Asp Val Ser Trp Phe Ala Val His Ser Phe Gly Leu Asp Lys Ala
65 70 75 80

Pro Val Leu Leu Ser Ser Leu Asp Arg Lys Gly Ile Val Thr Thr Ser
85 90 95

Arg Arg Asp Trp Lys Ser Asp Leu Ser Leu Glu Arg Val Ser Val Leu
100 105 110

Glu Phe Leu Leu Gln Val His Gly Ser Glu Asp Gln Asp Phe Gly Asn
115 120 125

Tyr Tyr Cys Ser Val Thr Pro Trp Val Lys Ser Pro Thr Gly Ser Trp
130 135 140

Gln Lys Glu Ala Glu Ile His Ser Lys Pro Val Phe Ile Thr Val Lys
145 150 155 160

Met Asp Val Leu Asn Ala Phe Lys Tyr Pro Leu Leu Ile Gly Val Gly
165 170 175

Leu Ser Thr Val Ile Gly Leu Leu Ser Cys Leu Ile Gly Tyr Cys Ser
180 185 190

-continued

```
Ser His Trp Cys Cys Lys Lys Glu Val Gln Glu Thr Arg Arg Glu Arg
        195                 200                 205

Arg Arg Leu Met Ser Met Glu Met Asp
    210                 215


<210> SEQ ID NO 7
<211> LENGTH: 66
<212> TYPE: PRT
<213> ORGANISM: homo sapiens

<400> SEQUENCE: 7

Ser Lys Pro Val Phe Ile Thr Val Lys Met Asp Val Leu Asn Ala Phe
1               5                   10                  15

Lys Tyr Pro Leu Leu Ile Gly Val Gly Leu Ser Thr Val Ile Gly Leu
            20                  25                  30

Leu Ser Cys Leu Ile Gly Tyr Cys Ser Ser His Trp Cys Cys Lys Lys
        35                  40                  45

Glu Val Gln Glu Thr Arg Arg Glu Arg Arg Arg Leu Met Ser Met Glu
    50                  55                  60

Met Asp
65


<210> SEQ ID NO 8
<211> LENGTH: 21
<212> TYPE: PRT
<213> ORGANISM: Homo sapiens

<400> SEQUENCE: 8

Met Gly Arg Leu Ala Ser Arg Pro Leu Leu Leu Ala Leu Leu Ser Leu
1               5                   10                  15

Ala Leu Cys Arg Gly
            20


<210> SEQ ID NO 9
<211> LENGTH: 385
<212> TYPE: PRT
<213> ORGANISM: Homo sapiens

<400> SEQUENCE: 9

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140
```

Thr Val Glu Asp Leu Gly Ser Lys Ile Leu Leu Thr Cys Ser Leu Asn
145 150 155 160

Asp Ser Ala Thr Glu Val Thr Gly His Arg Trp Leu Lys Gly Gly Val
165 170 175

Val Leu Lys Glu Asp Ala Leu Pro Gly Gln Lys Thr Glu Phe Lys Val
180 185 190

Asp Ser Asp Asp Gln Trp Gly Glu Tyr Ser Cys Val Phe Leu Pro Glu
195 200 205

Pro Met Gly Thr Ala Asn Ile Gln Leu His Gly Pro Pro Arg Val Lys
210 215 220

Ala Val Lys Ser Ser Glu His Ile Asn Glu Gly Glu Thr Ala Met Leu
225 230 235 240

Val Cys Lys Ser Glu Ser Val Pro Pro Val Thr Asp Trp Ala Trp Tyr
245 250 255

Lys Ile Thr Asp Ser Glu Asp Lys Ala Leu Met Asn Gly Ser Glu Ser
260 265 270

Arg Phe Phe Val Ser Ser Ser Gln Gly Arg Ser Glu Leu His Ile Glu
275 280 285

Asn Leu Asn Met Glu Ala Asp Pro Gly Gln Tyr Arg Cys Asn Gly Thr
290 295 300

Ser Ser Lys Gly Ser Asp Gln Ala Ile Ile Thr Leu Arg Val Arg Ser
305 310 315 320

His Leu Ala Ala Leu Trp Pro Phe Leu Gly Ile Val Ala Glu Val Leu
325 330 335

Val Leu Val Thr Ile Ile Phe Ile Tyr Glu Lys Arg Arg Lys Pro Glu
340 345 350

Asp Val Leu Asp Asp Asp Asp Ala Gly Ser Ala Pro Leu Lys Ser Ser
355 360 365

Gly Gln His Gln Asn Asp Lys Gly Lys Asn Val Arg Gln Arg Asn Ser
370 375 380

Ser
385

<210> SEQ ID NO 10
<211> LENGTH: 247
<212> TYPE: PRT
<213> ORGANISM: Homo sapiens

<400> SEQUENCE: 10

Pro Gly Thr Val Phe Thr Thr Val Glu Asp Leu Gly Ser Lys Ile Leu
1 5 10 15

Leu Thr Cys Ser Leu Asn Asp Ser Ala Thr Glu Val Thr Gly His Arg
20 25 30

Trp Leu Lys Gly Gly Val Val Leu Lys Glu Asp Ala Leu Pro Gly Gln
35 40 45

Lys Thr Glu Phe Lys Val Asp Ser Asp Asp Gln Trp Gly Glu Tyr Ser
50 55 60

Cys Val Phe Leu Pro Glu Pro Met Gly Thr Ala Asn Ile Gln Leu His
65 70 75 80

Gly Pro Pro Arg Val Lys Ala Val Lys Ser Ser Glu His Ile Asn Glu
85 90 95

Gly Glu Thr Ala Met Leu Val Cys Lys Ser Glu Ser Val Pro Pro Val
100 105 110

Thr Asp Trp Ala Trp Tyr Lys Ile Thr Asp Ser Glu Asp Lys Ala Leu
115 120 125

-continued

```
Met Asn Gly Ser Glu Ser Arg Phe Phe Val Ser Ser Ser Gln Gly Arg
    130                 135                 140

Ser Glu Leu His Ile Glu Asn Leu Asn Met Glu Ala Asp Pro Gly Gln
145                 150                 155                 160

Tyr Arg Cys Asn Gly Thr Ser Ser Lys Gly Ser Asp Gln Ala Ile Ile
                165                 170                 175

Thr Leu Arg Val Arg Ser His Leu Ala Ala Leu Trp Pro Phe Leu Gly
            180                 185                 190

Ile Val Ala Glu Val Leu Val Leu Val Thr Ile Ile Phe Ile Tyr Glu
        195                 200                 205

Lys Arg Arg Lys Pro Glu Asp Val Leu Asp Asp Asp Asp Ala Gly Ser
    210                 215                 220

Ala Pro Leu Lys Ser Ser Gly Gln His Gln Asn Asp Lys Gly Lys Asn
225                 230                 235                 240

Val Arg Gln Arg Asn Ser Ser
                245


<210> SEQ ID NO 11
<211> LENGTH: 168
<212> TYPE: PRT
<213> ORGANISM: Homo sapiens

<400> SEQUENCE: 11

His Gly Pro Pro Arg Val Lys Ala Val Lys Ser Ser Glu His Ile Asn
1               5                   10                  15

Glu Gly Glu Thr Ala Met Leu Val Cys Lys Ser Glu Ser Val Pro Pro
            20                  25                  30

Val Thr Asp Trp Ala Trp Tyr Lys Ile Thr Asp Ser Glu Asp Lys Ala
        35                  40                  45

Leu Met Asn Gly Ser Glu Ser Arg Phe Phe Val Ser Ser Ser Gln Gly
    50                  55                  60

Arg Ser Glu Leu His Ile Glu Asn Leu Asn Met Glu Ala Asp Pro Gly
65                  70                  75                  80

Gln Tyr Arg Cys Asn Gly Thr Ser Ser Lys Gly Ser Asp Gln Ala Ile
                85                  90                  95

Ile Thr Leu Arg Val Arg Ser His Leu Ala Ala Leu Trp Pro Phe Leu
            100                 105                 110

Gly Ile Val Ala Glu Val Leu Val Leu Val Thr Ile Ile Phe Ile Tyr
        115                 120                 125

Glu Lys Arg Arg Lys Pro Glu Asp Val Leu Asp Asp Asp Asp Ala Gly
    130                 135                 140

Ser Ala Pro Leu Lys Ser Ser Gly Gln His Gln Asn Asp Lys Gly Lys
145                 150                 155                 160

Asn Val Arg Gln Arg Asn Ser Ser
                165


<210> SEQ ID NO 12
<211> LENGTH: 66
<212> TYPE: PRT
<213> ORGANISM: homo sapiens

<400> SEQUENCE: 12

Ser His Leu Ala Ala Leu Trp Pro Phe Leu Gly Ile Val Ala Glu Val
1               5                   10                  15

Leu Val Leu Val Thr Ile Ile Phe Ile Tyr Glu Lys Arg Arg Lys Pro
            20                  25                  30
```

-continued

```
Glu Asp Val Leu Asp Asp Asp Asp Ala Gly Ser Ala Pro Leu Lys Ser
        35                  40                  45

Ser Gly Gln His Gln Asn Asp Lys Gly Lys Asn Val Arg Gln Arg Asn
    50                  55                  60

Ser Ser
65


<210> SEQ ID NO 13
<211> LENGTH: 18
<212> TYPE: PRT
<213> ORGANISM: homo sapiens

<400> SEQUENCE: 13

Met Ala Ala Ala Leu Phe Val Leu Leu Gly Phe Ala Leu Leu Gly Thr
1               5                   10                  15

His Gly


<210> SEQ ID NO 14
<211> LENGTH: 613
<212> TYPE: PRT
<213> ORGANISM: homo sapiens

<400> SEQUENCE: 14

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala Arg Glu Val Leu Val
            20                  25                  30

Pro Glu Gly Pro Leu Tyr Arg Val Ala Gly Thr Ala Val Ser Ile Ser
        35                  40                  45

Cys Asn Val Thr Gly Tyr Glu Gly Pro Ala Gln Gln Asn Phe Glu Trp
    50                  55                  60

Phe Leu Tyr Arg Pro Glu Ala Pro Asp Thr Ala Leu Gly Ile Val Ser
65                  70                  75                  80

Thr Lys Asp Thr Gln Phe Ser Tyr Ala Val Phe Lys Ser Arg Val Val
                85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205

Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255
```

-continued

```
Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala Glu
        275                 280                 285

Lys Arg Ala Val Leu Ala His Val Asp Val Gln Thr Leu Ser Ser Gln
    290                 295                 300

Leu Ala Val Thr Val Gly Pro Gly Glu Arg Arg Ile Gly Pro Gly Glu
305                 310                 315                 320

Pro Leu Glu Leu Leu Cys Asn Val Ser Gly Ala Leu Pro Pro Ala Gly
                325                 330                 335

Arg His Ala Ala Tyr Ser Val Gly Trp Glu Met Ala Pro Ala Gly Ala
            340                 345                 350

Pro Gly Pro Gly Arg Leu Val Ala Gln Leu Asp Thr Glu Gly Val Gly
        355                 360                 365

Ser Leu Gly Pro Gly Tyr Glu Gly Arg His Ile Ala Met Glu Lys Val
    370                 375                 380

Ala Ser Arg Thr Tyr Arg Leu Arg Leu Glu Ala Ala Arg Pro Gly Asp
385                 390                 395                 400

Ala Gly Thr Tyr Arg Cys Leu Ala Lys Ala Tyr Val Arg Gly Ser Gly
                405                 410                 415

Thr Arg Leu Arg Glu Ala Ala Ser Ala Arg Ser Arg Pro Leu Pro Val
            420                 425                 430

His Val Arg Glu Glu Gly Val Val Leu Glu Ala Val Ala Trp Leu Ala
        435                 440                 445

Gly Gly Thr Val Tyr Arg Gly Glu Thr Ala Ser Leu Leu Cys Asn Ile
    450                 455                 460

Ser Val Arg Gly Gly Pro Pro Gly Leu Arg Leu Ala Ala Ser Trp Trp
465                 470                 475                 480

Val Glu Arg Pro Glu Asp Gly Glu Leu Ser Ser Val Pro Ala Gln Leu
                485                 490                 495

Val Gly Gly Val Gly Gln Asp Gly Val Ala Glu Leu Gly Val Arg Pro
            500                 505                 510

Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
    530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
            580                 585                 590

Val Thr Gly Ala Thr Val Leu Gly Thr Ile Thr Cys Cys Phe Met Lys
        595                 600                 605

Arg Leu Arg Lys Arg
    610


<210> SEQ ID NO 15
<211> LENGTH: 456
<212> TYPE: PRT
<213> ORGANISM: homo sapiens

<400> SEQUENCE: 15

Ala Pro Pro Gly Pro Arg Gly Arg Gln Ala Pro Thr Ser Pro Pro Arg
1               5                   10                  15
```

```
Met Thr Val His Glu Gly Gln Glu Leu Ala Leu Gly Cys Leu Ala Arg
            20                  25                  30

Thr Ser Thr Gln Lys His Thr His Leu Ala Val Ser Phe Gly Arg Ser
        35                  40                  45

Val Pro Glu Ala Pro Val Gly Arg Ser Thr Leu Gln Glu Val Val Gly
    50                  55                  60

Ile Arg Ser Asp Leu Ala Val Glu Ala Gly Ala Pro Tyr Ala Glu Arg
65                  70                  75                  80

Leu Ala Ala Gly Glu Leu Arg Leu Gly Lys Glu Gly Thr Asp Arg Tyr
                85                  90                  95

Arg Met Val Val Gly Gly Ala Gln Ala Gly Asp Ala Gly Thr Tyr His
            100                 105                 110

Cys Thr Ala Ala Glu Trp Ile Gln Asp Pro Asp Gly Ser Trp Ala Gln
        115                 120                 125

Ile Ala Glu Lys Arg Ala Val Leu Ala His Val Asp Val Gln Thr Leu
    130                 135                 140

Ser Ser Gln Leu Ala Val Thr Val Gly Pro Gly Glu Arg Arg Ile Gly
145                 150                 155                 160

Pro Gly Glu Pro Leu Glu Leu Leu Cys Asn Val Ser Gly Ala Leu Pro
                165                 170                 175

Pro Ala Gly Arg His Ala Ala Tyr Ser Val Gly Trp Glu Met Ala Pro
            180                 185                 190

Ala Gly Ala Pro Gly Pro Gly Arg Leu Val Ala Gln Leu Asp Thr Glu
        195                 200                 205

Gly Val Gly Ser Leu Gly Pro Gly Tyr Glu Gly Arg His Ile Ala Met
    210                 215                 220

Glu Lys Val Ala Ser Arg Thr Tyr Arg Leu Arg Leu Glu Ala Ala Arg
225                 230                 235                 240

Pro Gly Asp Ala Gly Thr Tyr Arg Cys Leu Ala Lys Ala Tyr Val Arg
                245                 250                 255

Gly Ser Gly Thr Arg Leu Arg Glu Ala Ala Ser Ala Arg Ser Arg Pro
            260                 265                 270

Leu Pro Val His Val Arg Glu Glu Gly Val Val Leu Glu Ala Val Ala
        275                 280                 285

Trp Leu Ala Gly Gly Thr Val Tyr Arg Gly Glu Thr Ala Ser Leu Leu
    290                 295                 300

Cys Asn Ile Ser Val Arg Gly Gly Pro Pro Gly Leu Arg Leu Ala Ala
305                 310                 315                 320

Ser Trp Trp Val Glu Arg Pro Glu Asp Gly Glu Leu Ser Ser Val Pro
                325                 330                 335

Ala Gln Leu Val Gly Gly Val Gly Gln Asp Gly Val Ala Glu Leu Gly
            340                 345                 350

Val Arg Pro Gly Gly Gly Pro Val Ser Val Glu Leu Val Gly Pro Arg
        355                 360                 365

Ser His Arg Leu Arg Leu His Ser Leu Gly Pro Glu Asp Glu Gly Val
    370                 375                 380

Tyr His Cys Ala Pro Ser Ala Trp Val Gln His Ala Asp Tyr Ser Trp
385                 390                 395                 400

Tyr Gln Ala Gly Ser Ala Arg Ser Gly Pro Val Thr Val Tyr Pro Tyr
                405                 410                 415

Met His Ala Leu Asp Thr Leu Phe Val Pro Leu Leu Val Gly Thr Gly
            420                 425                 430
```

Val Ala Leu Val Thr Gly Ala Thr Val Leu Gly Thr Ile Thr Cys Cys
435 440 445

Phe Met Lys Arg Leu Arg Lys Arg
450 455

<210> SEQ ID NO 16
<211> LENGTH: 320
<212> TYPE: PRT
<213> ORGANISM: Homo sapiens

<400> SEQUENCE: 16

Ala His Val Asp Val Gln Thr Leu Ser Ser Gln Leu Ala Val Thr Val
1 5 10 15

Gly Pro Gly Glu Arg Arg Ile Gly Pro Gly Glu Pro Leu Glu Leu Leu
20 25 30

Cys Asn Val Ser Gly Ala Leu Pro Pro Ala Gly Arg His Ala Ala Tyr
35 40 45

Ser Val Gly Trp Glu Met Ala Pro Ala Gly Ala Pro Gly Pro Gly Arg
50 55 60

Leu Val Ala Gln Leu Asp Thr Glu Gly Val Gly Ser Leu Gly Pro Gly
65 70 75 80

Tyr Glu Gly Arg His Ile Ala Met Glu Lys Val Ala Ser Arg Thr Tyr
85 90 95

Arg Leu Arg Leu Glu Ala Ala Arg Pro Gly Asp Ala Gly Thr Tyr Arg
100 105 110

Cys Leu Ala Lys Ala Tyr Val Arg Gly Ser Gly Thr Arg Leu Arg Glu
115 120 125

Ala Ala Ser Ala Arg Ser Arg Pro Leu Pro Val His Val Arg Glu Glu
130 135 140

Gly Val Val Leu Glu Ala Val Ala Trp Leu Ala Gly Gly Thr Val Tyr
145 150 155 160

Arg Gly Glu Thr Ala Ser Leu Leu Cys Asn Ile Ser Val Arg Gly Gly
165 170 175

Pro Pro Gly Leu Arg Leu Ala Ala Ser Trp Trp Val Glu Arg Pro Glu
180 185 190

Asp Gly Glu Leu Ser Ser Val Pro Ala Gln Leu Val Gly Gly Val Gly
195 200 205

Gln Asp Gly Val Ala Glu Leu Gly Val Arg Pro Gly Gly Gly Pro Val
210 215 220

Ser Val Glu Leu Val Gly Pro Arg Ser His Arg Leu Arg Leu His Ser
225 230 235 240

Leu Gly Pro Glu Asp Glu Gly Val Tyr His Cys Ala Pro Ser Ala Trp
245 250 255

Val Gln His Ala Asp Tyr Ser Trp Tyr Gln Ala Gly Ser Ala Arg Ser
260 265 270

Gly Pro Val Thr Val Tyr Pro Tyr Met His Ala Leu Asp Thr Leu Phe
275 280 285

Val Pro Leu Leu Val Gly Thr Gly Val Ala Leu Val Thr Gly Ala Thr
290 295 300

Val Leu Gly Thr Ile Thr Cys Cys Phe Met Lys Arg Leu Arg Lys Arg
305 310 315 320

<210> SEQ ID NO 17
<211> LENGTH: 179
<212> TYPE: PRT
<213> ORGANISM: homo sapiens

<400> SEQUENCE: 17

Arg Glu Glu Gly Val Val Leu Glu Ala Val Ala Trp Leu Ala Gly Gly
1 5 10 15

Thr Val Tyr Arg Gly Glu Thr Ala Ser Leu Leu Cys Asn Ile Ser Val
20 25 30

Arg Gly Gly Pro Pro Gly Leu Arg Leu Ala Ala Ser Trp Trp Val Glu
35 40 45

Arg Pro Glu Asp Gly Glu Leu Ser Ser Val Pro Ala Gln Leu Val Gly
50 55 60

Gly Val Gly Gln Asp Gly Val Ala Glu Leu Gly Val Arg Pro Gly Gly
65 70 75 80

Gly Pro Val Ser Val Glu Leu Val Gly Pro Arg Ser His Arg Leu Arg
85 90 95

Leu His Ser Leu Gly Pro Glu Asp Glu Gly Val Tyr His Cys Ala Pro
100 105 110

Ser Ala Trp Val Gln His Ala Asp Tyr Ser Trp Tyr Gln Ala Gly Ser
115 120 125

Ala Arg Ser Gly Pro Val Thr Val Tyr Pro Tyr Met His Ala Leu Asp
130 135 140

Thr Leu Phe Val Pro Leu Leu Val Gly Thr Gly Val Ala Leu Val Thr
145 150 155 160

Gly Ala Thr Val Leu Gly Thr Ile Thr Cys Cys Phe Met Lys Arg Leu
165 170 175

Arg Lys Arg

<210> SEQ ID NO 18
<211> LENGTH: 24
<212> TYPE: PRT
<213> ORGANISM: Homo sapiens

<400> SEQUENCE: 18

Val Ala Leu Val Thr Gly Ala Thr Val Leu Gly Thr Ile Thr Cys Cys
1 5 10 15

Phe Met Lys Arg Leu Arg Lys Arg
20

<210> SEQ ID NO 19
<211> LENGTH: 27
<212> TYPE: PRT
<213> ORGANISM: Homo sapiens

<400> SEQUENCE: 19

Met Gly Ala Leu Arg Pro Thr Leu Leu Pro Pro Ser Leu Pro Leu Leu
1 5 10 15

Leu Leu Leu Met Leu Gly Met Gly Cys Trp Ala
20 25

<210> SEQ ID NO 20
<211> LENGTH: 1195
<212> TYPE: PRT
<213> ORGANISM: homo sapiens

<400> SEQUENCE: 20

Met Lys Cys Phe Phe Pro Val Leu Ser Cys Leu Ala Val Leu Gly Val
1 5 10 15

Val Ser Ala Gln Arg Gln Val Thr Val Gln Glu Gly Pro Leu Tyr Arg
20 25 30

-continued

```
Thr Glu Gly Ser His Ile Thr Ile Trp Cys Asn Val Ser Gly Tyr Gln
        35                  40                  45

Gly Pro Ser Glu Gln Asn Phe Gln Trp Ser Ile Tyr Leu Pro Ser Ser
    50                  55                  60

Pro Glu Arg Glu Val Gln Ile Val Ser Thr Met Asp Ser Ser Phe Pro
65                  70                  75                  80

Tyr Ala Ile Tyr Thr Gln Arg Val Arg Gly Gly Lys Ile Phe Ile Glu
                85                  90                  95

Arg Val Gln Gly Asn Ser Thr Leu Leu His Ile Thr Asp Leu Gln Ala
            100                 105                 110

Arg Asp Ala Gly Glu Tyr Glu Cys His Thr Pro Ser Thr Asp Lys Gln
        115                 120                 125

Tyr Phe Gly Ser Tyr Ser Ala Lys Met Asn Leu Val Val Ile Pro Asp
    130                 135                 140

Ser Leu Gln Thr Thr Ala Met Pro Gln Thr Leu His Arg Val Glu Gln
145                 150                 155                 160

Asp Pro Leu Glu Leu Thr Cys Glu Val Ala Ser Glu Thr Ile Gln His
                165                 170                 175

Ser His Leu Ser Val Ala Trp Leu Arg Gln Lys Val Gly Glu Lys Pro
            180                 185                 190

Val Glu Val Ile Ser Leu Ser Arg Asp Phe Met Leu His Ser Ser Ser
        195                 200                 205

Glu Tyr Ala Gln Arg Gln Ser Leu Gly Glu Val Arg Leu Asp Lys Leu
    210                 215                 220

Gly Arg Thr Thr Phe Arg Leu Thr Ile Phe His Leu Gln Pro Ser Asp
225                 230                 235                 240

Gln Gly Glu Phe Tyr Cys Glu Ala Ala Glu Trp Ile Gln Asp Pro Asp
                245                 250                 255

Gly Ser Trp Tyr Ala Met Thr Arg Lys Arg Ser Glu Gly Ala Val Val
            260                 265                 270

Asn Val Gln Pro Thr Asp Lys Glu Phe Thr Val Arg Leu Glu Thr Glu
        275                 280                 285

Lys Arg Leu His Thr Val Gly Glu Pro Val Glu Phe Arg Cys Ile Leu
    290                 295                 300

Glu Ala Gln Asn Val Pro Asp Arg Tyr Phe Ala Val Ser Trp Ala Phe
305                 310                 315                 320

Asn Ser Ser Leu Ile Ala Thr Met Gly Pro Asn Ala Val Pro Val Leu
                325                 330                 335

Asn Ser Glu Phe Ala His Arg Glu Ala Arg Gly Gln Leu Lys Val Ala
            340                 345                 350

Lys Glu Ser Asp Ser Val Phe Val Leu Lys Ile Tyr His Leu Arg Gln
        355                 360                 365

Glu Asp Ser Gly Lys Tyr Asn Cys Arg Val Thr Glu Arg Glu Lys Thr
    370                 375                 380

Val Thr Gly Glu Phe Ile Asp Lys Glu Ser Lys Arg Pro Lys Asn Ile
385                 390                 395                 400

Pro Ile Ile Val Leu Pro Leu Lys Ser Ser Ile Ser Val Glu Val Ala
                405                 410                 415

Ser Asn Ala Ser Val Ile Leu Glu Gly Glu Asp Leu Arg Phe Ser Cys
            420                 425                 430

Ser Val Arg Thr Ala Gly Arg Pro Gln Gly Arg Phe Ser Val Ile Trp
        435                 440                 445
```

-continued

```
Gln Leu Val Asp Arg Gln Asn Arg Arg Ser Asn Ile Met Trp Leu Asp
    450                 455                 460

Arg Asp Gly Thr Val Gln Pro Gly Ser Ser Tyr Trp Glu Arg Ser Ser
465                 470                 475                 480

Phe Gly Gly Val Gln Met Glu Gln Val Gln Pro Asn Ser Phe Ser Leu
                485                 490                 495

Gly Ile Phe Asn Ser Arg Lys Glu Asp Glu Gly Gln Tyr Glu Cys His
            500                 505                 510

Val Thr Glu Trp Val Arg Ala Val Asp Gly Glu Trp Gln Ile Val Gly
        515                 520                 525

Glu Arg Arg Ala Ser Thr Pro Ile Ser Ile Thr Ala Leu Glu Met Gly
    530                 535                 540

Phe Ala Val Thr Ala Ile Ser Arg Thr Pro Gly Val Thr Tyr Ser Asp
545                 550                 555                 560

Ser Phe Asp Leu Gln Cys Ile Ile Lys Pro His Tyr Pro Ala Trp Val
                565                 570                 575

Pro Val Ser Val Thr Trp Arg Phe Gln Pro Val Gly Thr Val Glu Phe
            580                 585                 590

His Asp Leu Val Thr Phe Thr Arg Asp Gly Gly Val Gln Trp Gly Asp
        595                 600                 605

Arg Ser Ser Ser Phe Arg Thr Arg Thr Ala Ile Glu Lys Ala Glu Ser
    610                 615                 620

Ser Asn Asn Val Arg Leu Ser Ile Ser Arg Ala Ser Asp Thr Glu Ala
625                 630                 635                 640

Gly Lys Tyr Gln Cys Val Ala Glu Leu Trp Arg Lys Asn Tyr Asn Asn
                645                 650                 655

Thr Trp Thr Arg Leu Ala Glu Arg Thr Ser Asn Leu Leu Glu Ile Arg
            660                 665                 670

Val Leu Gln Pro Val Thr Lys Leu Gln Val Ser Lys Ser Lys Arg Thr
        675                 680                 685

Leu Thr Leu Val Glu Asn Lys Pro Ile Gln Leu Asn Cys Ser Val Lys
    690                 695                 700

Ser Gln Thr Ser Gln Asn Ser His Phe Ala Val Leu Trp Tyr Val His
705                 710                 715                 720

Lys Pro Ser Asp Ala Asp Gly Lys Leu Ile Leu Lys Thr Thr His Asn
                725                 730                 735

Ser Ala Phe Glu Tyr Gly Thr Tyr Ala Glu Glu Glu Gly Leu Arg Ala
            740                 745                 750

Arg Leu Gln Phe Glu Arg His Val Ser Gly Gly Leu Phe Ser Leu Thr
        755                 760                 765

Val Gln Arg Ala Glu Val Ser Asp Ser Gly Ser Tyr Tyr Cys His Val
    770                 775                 780

Glu Glu Trp Leu Leu Ser Pro Asn Tyr Ala Trp Tyr Lys Leu Ala Glu
785                 790                 795                 800

Glu Val Ser Gly Arg Thr Glu Val Thr Val Lys Gln Pro Asp Ser Arg
                805                 810                 815

Leu Arg Leu Ser Gln Ala Gln Gly Asn Leu Ser Val Leu Glu Thr Arg
            820                 825                 830

Gln Val Gln Leu Glu Cys Val Val Leu Asn Arg Thr Ser Ile Thr Ser
        835                 840                 845

Gln Leu Met Val Glu Trp Phe Val Trp Lys Pro Asn His Pro Glu Arg
    850                 855                 860

Glu Thr Val Ala Arg Leu Ser Arg Asp Ala Thr Phe His Tyr Gly Glu
```

865 870 875 880

Gln Ala Ala Lys Asn Asn Leu Lys Gly Arg Leu His Leu Glu Ser Pro
885 890 895

Ser Pro Gly Val Tyr Arg Leu Phe Ile Gln Asn Val Ala Val Gln Asp
900 905 910

Ser Gly Thr Tyr Ser Cys His Val Glu Glu Trp Leu Pro Ser Pro Ser
915 920 925

Gly Met Trp Tyr Lys Arg Ala Glu Asp Thr Ala Gly Gln Thr Ala Leu
930 935 940

Thr Val Met Arg Pro Asp Ala Ser Leu Gln Val Asp Thr Val Val Pro
945 950 955 960

Asn Ala Thr Val Ser Glu Lys Ala Ala Phe Gln Leu Asp Cys Ser Ile
965 970 975

Val Ser Arg Ser Ser Gln Asp Ser Arg Phe Ala Val Ala Trp Tyr Ser
980 985 990

Leu Arg Thr Lys Ala Gly Gly Lys Arg Ser Ser Pro Gly Leu Glu Glu
995 1000 1005

Gln Glu Glu Glu Arg Glu Glu Glu Glu Glu Glu Glu Glu Asp Asp
1010 1015 1020

Asp Asp Asp Asp Pro Thr Glu Arg Thr Ala Leu Leu Ser Val Gly
1025 1030 1035

Pro Asp Ala Val Phe Gly Pro Glu Gly Ser Pro Trp Glu Gly Arg
1040 1045 1050

Leu Arg Phe Gln Arg Leu Ser Pro Val Leu Tyr Arg Leu Thr Val
1055 1060 1065

Leu Gln Ala Ser Pro Gln Asp Thr Gly Asn Tyr Ser Cys His Val
1070 1075 1080

Glu Glu Trp Leu Pro Ser Pro Gln Lys Glu Trp Tyr Arg Leu Thr
1085 1090 1095

Glu Glu Glu Ser Ala Pro Ile Gly Ile Arg Val Leu Asp Thr Ser
1100 1105 1110

Pro Thr Leu Gln Ser Ile Ile Cys Ser Asn Asp Ala Leu Phe Tyr
1115 1120 1125

Phe Val Phe Phe Tyr Pro Phe Pro Ile Phe Gly Ile Leu Ile Ile
1130 1135 1140

Thr Ile Leu Leu Val Arg Phe Lys Ser Arg Asn Ser Ser Lys Asn
1145 1150 1155

Ser Asp Gly Lys Asn Gly Val Pro Leu Leu Trp Ile Lys Glu Pro
1160 1165 1170

His Leu Asn Tyr Ser Pro Thr Cys Leu Glu Pro Pro Val Leu Ser
1175 1180 1185

Ile His Pro Gly Ala Ile Asp
1190 1195

<210> SEQ ID NO 21
<211> LENGTH: 798
<212> TYPE: PRT
<213> ORGANISM: homo sapiens

<400> SEQUENCE: 21

Met Asn Leu Gln Pro Ile Phe Trp Ile Gly Leu Ile Ser Ser Val Cys
1 5 10 15

Cys Val Phe Ala Gln Thr Asp Glu Asn Arg Cys Leu Lys Ala Asn Ala
20 25 30

-continued

```
Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
```

-continued

```
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795


<210> SEQ ID NO 22
<211> LENGTH: 1032
<212> TYPE: PRT
<213> ORGANISM: homo sapiens

<400> SEQUENCE: 22

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30
```

-continued

```
Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
```

```
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

Ser Pro Gln Thr Asp Lys Leu Phe Asn Ile Leu Asp Val Gln Thr Thr
        835                 840                 845

Thr Gly Glu Cys His Phe Glu Asn Tyr Gln Arg Val Cys Ala Leu Glu
    850                 855                 860

Gln Gln Lys Ser Ala Met Gln Thr Leu Lys Gly Ile Val Arg Phe Leu
865                 870                 875                 880
```

Ser Lys Thr Asp Lys Arg Leu Leu Tyr Cys Ile Lys Ala Asp Pro His
885 890 895

Cys Leu Asn Phe Leu Cys Asn Phe Gly Lys Met Glu Ser Gly Lys Glu
900 905 910

Ala Ser Val His Ile Gln Leu Glu Gly Arg Pro Ser Ile Leu Glu Met
915 920 925

Asp Glu Thr Ser Ala Leu Lys Phe Glu Ile Arg Ala Thr Gly Phe Pro
930 935 940

Glu Pro Asn Pro Arg Val Ile Glu Leu Asn Lys Asp Glu Asn Val Ala
945 950 955 960

His Val Leu Leu Glu Gly Leu His His Gln Arg Pro Lys Arg Tyr Phe
965 970 975

Thr Ile Val Ile Ile Ser Ser Ser Leu Leu Leu Gly Leu Ile Val Leu
980 985 990

Leu Leu Ile Ser Tyr Val Met Trp Lys Ala Gly Phe Phe Lys Arg Gln
995 1000 1005

Tyr Lys Ser Ile Leu Gln Glu Glu Asn Arg Arg Asp Ser Trp Ser
1010 1015 1020

Tyr Ile Asn Ser Lys Ser Asn Asp Asp
1025 1030

<210> SEQ ID NO 23
<211> LENGTH: 660
<212> TYPE: PRT
<213> ORGANISM: homo sapiens

<400> SEQUENCE: 23

Met Glu Leu Gln Pro Pro Glu Ala Ser Ile Ala Val Val Ser Ile Pro
1 5 10 15

Arg Gln Leu Pro Gly Ser His Ser Glu Ala Gly Val Gln Gly Leu Ser
20 25 30

Ala Gly Asp Asp Ser Glu Leu Gly Ser His Cys Val Ala Gln Thr Gly
35 40 45

Leu Glu Leu Leu Ala Ser Gly Asp Pro Leu Pro Ser Ala Ser Gln Asn
50 55 60

Ala Glu Met Ile Glu Thr Gly Ser Asp Cys Val Thr Gln Ala Gly Leu
65 70 75 80

Gln Leu Leu Ala Ser Ser Asp Pro Pro Ala Leu Ala Ser Lys Asn Ala
85 90 95

Glu Val Thr Glu Thr Gly Phe His His Val Ser Gln Ala Asp Ile Glu
100 105 110

Phe Leu Thr Ser Ile Asp Pro Thr Ala Ser Ala Ser Gly Ser Ala Gly
115 120 125

Ile Thr Gly Thr Met Ser Gln Asp Thr Glu Val Asp Met Lys Glu Val
130 135 140

Glu Leu Asn Glu Leu Glu Pro Glu Lys Gln Pro Met Asn Ala Ala Ser
145 150 155 160

Gly Ala Ala Met Ser Leu Ala Gly Ala Glu Lys Asn Gly Leu Val Lys
165 170 175

Ile Lys Val Ala Glu Asp Glu Ala Glu Ala Ala Ala Ala Ala Lys Phe
180 185 190

Thr Gly Leu Ser Lys Glu Glu Leu Leu Lys Val Ala Gly Ser Pro Gly
195 200 205

Trp Val Arg Thr Arg Trp Ala Leu Leu Leu Leu Phe Trp Leu Gly Trp

-continued

```
    210                 215                 220

Leu Gly Met Leu Ala Gly Ala Val Val Ile Ile Val Arg Ala Pro Arg
225                 230                 235                 240

Cys Arg Glu Leu Pro Ala Gln Lys Trp Trp His Thr Gly Ala Leu Tyr
                245                 250                 255

Arg Ile Gly Asp Leu Gln Ala Phe Gln Gly His Gly Ala Gly Asn Leu
            260                 265                 270

Ala Gly Leu Lys Gly Arg Leu Asp Tyr Leu Ser Ser Leu Lys Val Lys
        275                 280                 285

Gly Leu Val Leu Gly Pro Ile His Lys Asn Gln Lys Asp Asp Val Ala
    290                 295                 300

Gln Thr Asp Leu Leu Gln Ile Asp Pro Asn Phe Gly Ser Lys Glu Asp
305                 310                 315                 320

Phe Asp Ser Leu Leu Gln Ser Ala Lys Lys Lys Ser Ile Arg Val Ile
                325                 330                 335

Leu Asp Leu Thr Pro Asn Tyr Arg Gly Glu Asn Ser Trp Phe Ser Thr
            340                 345                 350

Gln Val Asp Thr Val Ala Thr Lys Val Lys Asp Ala Leu Glu Phe Trp
        355                 360                 365

Leu Gln Ala Gly Val Asp Gly Phe Gln Val Arg Asp Ile Glu Asn Leu
    370                 375                 380

Lys Asp Ala Ser Ser Phe Leu Ala Glu Trp Gln Asn Ile Thr Lys Gly
385                 390                 395                 400

Phe Ser Glu Asp Arg Leu Leu Ile Ala Gly Thr Asn Ser Ser Asp Leu
                405                 410                 415

Gln Gln Ile Leu Ser Leu Leu Glu Ser Asn Lys Asp Leu Leu Leu Thr
            420                 425                 430

Ser Ser Tyr Leu Ser Asp Ser Gly Ser Thr Gly Glu His Thr Lys Ser
        435                 440                 445

Leu Val Thr Gln Tyr Leu Asn Ala Thr Gly Asn Arg Trp Cys Ser Trp
    450                 455                 460

Ser Leu Ser Gln Ala Arg Leu Leu Thr Ser Phe Leu Pro Ala Gln Leu
465                 470                 475                 480

Leu Arg Leu Tyr Gln Leu Met Leu Phe Thr Leu Pro Gly Thr Pro Val
                485                 490                 495

Phe Ser Tyr Gly Asp Glu Ile Gly Leu Asp Ala Ala Ala Leu Pro Gly
            500                 505                 510

Gln Pro Met Glu Ala Pro Val Met Leu Trp Asp Glu Ser Ser Phe Pro
        515                 520                 525

Asp Ile Pro Gly Ala Val Ser Ala Asn Met Thr Val Lys Gly Gln Ser
    530                 535                 540

Glu Asp Pro Gly Ser Leu Leu Ser Leu Phe Arg Arg Leu Ser Asp Gln
545                 550                 555                 560

Arg Ser Lys Glu Arg Ser Leu Leu His Gly Asp Phe His Ala Phe Ser
                565                 570                 575

Ala Gly Pro Gly Leu Phe Ser Tyr Ile Arg His Trp Asp Gln Asn Glu
            580                 585                 590

Arg Phe Leu Val Val Leu Asn Phe Gly Asp Val Gly Leu Ser Ala Gly
        595                 600                 605

Leu Gln Ala Ser Asp Leu Pro Ala Ser Ala Ser Leu Pro Ala Lys Ala
    610                 615                 620

Asp Leu Leu Leu Ser Thr Gln Pro Gly Arg Glu Glu Gly Ser Pro Leu
625                 630                 635                 640
```

Glu Leu Glu Arg Leu Lys Leu Glu Pro His Glu Gly Leu Leu Leu Arg
645 650 655

Phe Pro Tyr Ala
660

<210> SEQ ID NO 24
<211> LENGTH: 1023
<212> TYPE: PRT
<213> ORGANISM: homo sapiens

<400> SEQUENCE: 24

Met Gly Lys Gly Val Gly Arg Asp Lys Tyr Glu Pro Ala Ala Val Ser
1 5 10 15

Glu Gln Gly Asp Lys Lys Gly Lys Lys Gly Lys Lys Asp Arg Asp Met
20 25 30

Asp Glu Leu Lys Lys Glu Val Ser Met Asp Asp His Lys Leu Ser Leu
35 40 45

Asp Glu Leu His Arg Lys Tyr Gly Thr Asp Leu Ser Arg Gly Leu Thr
50 55 60

Ser Ala Arg Ala Ala Glu Ile Leu Ala Arg Asp Gly Pro Asn Ala Leu
65 70 75 80

Thr Pro Pro Pro Thr Thr Pro Glu Trp Ile Lys Phe Cys Arg Gln Leu
85 90 95

Phe Gly Gly Phe Ser Met Leu Leu Trp Ile Gly Ala Ile Leu Cys Phe
100 105 110

Leu Ala Tyr Ser Ile Gln Ala Ala Thr Glu Glu Glu Pro Gln Asn Asp
115 120 125

Asn Leu Tyr Leu Gly Val Val Leu Ser Ala Val Val Ile Ile Thr Gly
130 135 140

Cys Phe Ser Tyr Tyr Gln Glu Ala Lys Ser Ser Lys Ile Met Glu Ser
145 150 155 160

Phe Lys Asn Met Val Pro Gln Gln Ala Leu Val Ile Arg Asn Gly Glu
165 170 175

Lys Met Ser Ile Asn Ala Glu Glu Val Val Val Gly Asp Leu Val Glu
180 185 190

Val Lys Gly Gly Asp Arg Ile Pro Ala Asp Leu Arg Ile Ile Ser Ala
195 200 205

Asn Gly Cys Lys Val Asp Asn Ser Ser Leu Thr Gly Glu Ser Glu Pro
210 215 220

Gln Thr Arg Ser Pro Asp Phe Thr Asn Glu Asn Pro Leu Glu Thr Arg
225 230 235 240

Asn Ile Ala Phe Phe Ser Thr Asn Cys Val Glu Gly Thr Ala Arg Gly
245 250 255

Ile Val Val Tyr Thr Gly Asp Arg Thr Val Met Gly Arg Ile Ala Thr
260 265 270

Leu Ala Ser Gly Leu Glu Gly Gly Gln Thr Pro Ile Ala Ala Glu Ile
275 280 285

Glu His Phe Ile His Ile Ile Thr Gly Val Ala Val Phe Leu Gly Val
290 295 300

Ser Phe Phe Ile Leu Ser Leu Ile Leu Glu Tyr Thr Trp Leu Glu Ala
305 310 315 320

Val Ile Phe Leu Ile Gly Ile Ile Val Ala Asn Val Pro Glu Gly Leu
325 330 335

Leu Ala Thr Val Thr Val Cys Leu Thr Leu Thr Ala Lys Arg Met Ala

-continued 340 345 350

Arg Lys Asn Cys Leu Val Lys Asn Leu Glu Ala Val Glu Thr Leu Gly
355 360 365

Ser Thr Ser Thr Ile Cys Ser Asp Lys Thr Gly Thr Leu Thr Gln Asn
370 375 380

Arg Met Thr Val Ala His Met Trp Phe Asp Asn Gln Ile His Glu Ala
385 390 395 400

Asp Thr Thr Glu Asn Gln Ser Gly Val Ser Phe Asp Lys Thr Ser Ala
405 410 415

Thr Trp Leu Ala Leu Ser Arg Ile Ala Gly Leu Cys Asn Arg Ala Val
420 425 430

Phe Gln Ala Asn Gln Glu Asn Leu Pro Ile Leu Lys Arg Ala Val Ala
435 440 445

Gly Asp Ala Ser Glu Ser Ala Leu Leu Lys Cys Ile Glu Leu Cys Cys
450 455 460

Gly Ser Val Lys Glu Met Arg Glu Arg Tyr Ala Lys Ile Val Glu Ile
465 470 475 480

Pro Phe Asn Ser Thr Asn Lys Tyr Gln Leu Ser Ile His Lys Asn Pro
485 490 495

Asn Thr Ser Glu Pro Gln His Leu Leu Val Met Lys Gly Ala Pro Glu
500 505 510

Arg Ile Leu Asp Arg Cys Ser Ser Ile Leu Leu His Gly Lys Glu Gln
515 520 525

Pro Leu Asp Glu Glu Leu Lys Asp Ala Phe Gln Asn Ala Tyr Leu Glu
530 535 540

Leu Gly Gly Leu Gly Glu Arg Val Leu Gly Phe Cys His Leu Phe Leu
545 550 555 560

Pro Asp Glu Gln Phe Pro Glu Gly Phe Gln Phe Asp Thr Asp Asp Val
565 570 575

Asn Phe Pro Ile Asp Asn Leu Cys Phe Val Gly Leu Ile Ser Met Ile
580 585 590

Asp Pro Pro Arg Ala Ala Val Pro Asp Ala Val Gly Lys Cys Arg Ser
595 600 605

Ala Gly Ile Lys Val Ile Met Val Thr Gly Asp His Pro Ile Thr Ala
610 615 620

Lys Ala Ile Ala Lys Gly Val Gly Ile Ile Ser Glu Gly Asn Glu Thr
625 630 635 640

Val Glu Asp Ile Ala Ala Arg Leu Asn Ile Pro Val Ser Gln Val Asn
645 650 655

Pro Arg Asp Ala Lys Ala Cys Val Val His Gly Ser Asp Leu Lys Asp
660 665 670

Met Thr Ser Glu Gln Leu Asp Asp Ile Leu Lys Tyr His Thr Glu Ile
675 680 685

Val Phe Ala Arg Thr Ser Pro Gln Gln Lys Leu Ile Ile Val Glu Gly
690 695 700

Cys Gln Arg Gln Gly Ala Ile Val Ala Val Thr Gly Asp Gly Val Asn
705 710 715 720

Asp Ser Pro Ala Leu Lys Lys Ala Asp Ile Gly Val Ala Met Gly Ile
725 730 735

Ala Gly Ser Asp Val Ser Lys Gln Ala Ala Asp Met Ile Leu Leu Asp
740 745 750

Asp Asn Phe Ala Ser Ile Val Thr Gly Val Glu Glu Gly Arg Leu Ile
755 760 765

```
Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val  Tyr Asp Glu Val Arg  Lys Leu Ile
        995                 1000                1005

Ile Arg  Arg Arg Pro Gly Gly  Trp Val Glu Lys Glu  Thr Tyr Tyr
    1010                1015                1020


<210> SEQ ID NO 25
<211> LENGTH: 1020
<212> TYPE: PRT
<213> ORGANISM: homo sapiens

<400> SEQUENCE: 25

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
            20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
            100                 105                 110

Tyr Gly Ile Gln Ala Ala Met Glu Asp Glu Pro Ser Asn Asp Asn Leu
```

-continued

```
        115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160

Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
            180                 185                 190

Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
    210                 215                 220

Arg Ser Pro Glu Phe Thr His Glu Asn Pro Leu Glu Thr Arg Asn Ile
225                 230                 235                 240

Cys Phe Phe Ser Thr Asn Cys Val Glu Gly Thr Ala Arg Gly Ile Val
                245                 250                 255

Ile Ala Thr Gly Asp Arg Thr Val Met Gly Arg Ile Ala Thr Leu Ala
            260                 265                 270

Ser Gly Leu Glu Val Gly Arg Thr Pro Ile Ala Met Glu Ile Glu His
        275                 280                 285

Phe Ile Gln Leu Ile Thr Gly Val Ala Val Phe Leu Gly Val Ser Phe
    290                 295                 300

Phe Val Leu Ser Leu Ile Leu Gly Tyr Ser Trp Leu Glu Ala Val Ile
305                 310                 315                 320

Phe Leu Ile Gly Ile Ile Val Ala Asn Val Pro Glu Gly Leu Leu Ala
                325                 330                 335

Thr Val Thr Val Cys Leu Thr Leu Thr Ala Lys Arg Met Ala Arg Lys
            340                 345                 350

Asn Cys Leu Val Lys Asn Leu Glu Ala Val Glu Thr Leu Gly Ser Thr
        355                 360                 365

Ser Thr Ile Cys Ser Asp Lys Thr Gly Thr Leu Thr Gln Asn Arg Met
    370                 375                 380

Thr Val Ala His Met Trp Phe Asp Asn Gln Ile His Glu Ala Asp Thr
385                 390                 395                 400

Thr Glu Asp Gln Ser Gly Ala Thr Phe Asp Lys Arg Ser Pro Thr Trp
                405                 410                 415

Thr Ala Leu Ser Arg Ile Ala Gly Leu Cys Asn Arg Ala Val Phe Lys
            420                 425                 430

Ala Gly Gln Glu Asn Ile Ser Val Ser Lys Arg Asp Thr Ala Gly Asp
        435                 440                 445

Ala Ser Glu Ser Ala Leu Leu Lys Cys Ile Glu Leu Ser Cys Gly Ser
    450                 455                 460

Val Arg Lys Met Arg Asp Arg Asn Pro Lys Val Ala Glu Ile Pro Phe
465                 470                 475                 480

Asn Ser Thr Asn Lys Tyr Gln Leu Ser Ile His Glu Arg Glu Asp Ser
                485                 490                 495

Pro Gln Ser His Val Leu Val Met Lys Gly Ala Pro Glu Arg Ile Leu
            500                 505                 510

Asp Arg Cys Ser Thr Ile Leu Val Gln Gly Lys Glu Ile Pro Leu Asp
        515                 520                 525

Lys Glu Met Gln Asp Ala Phe Gln Asn Ala Tyr Met Glu Leu Gly Gly
    530                 535                 540
```

-continued

```
Leu Gly Glu Arg Val Leu Gly Phe Cys Gln Leu Asn Leu Pro Ser Gly
545                 550                 555                 560

Lys Phe Pro Arg Gly Phe Lys Phe Asp Thr Asp Glu Leu Asn Phe Pro
                565                 570                 575

Thr Glu Lys Leu Cys Phe Val Gly Leu Met Ser Met Ile Asp Pro Pro
            580                 585                 590

Arg Ala Ala Val Pro Asp Ala Val Gly Lys Cys Arg Ser Ala Gly Ile
        595                 600                 605

Lys Val Ile Met Val Thr Gly Asp His Pro Ile Thr Ala Lys Ala Ile
    610                 615                 620

Ala Lys Gly Val Gly Ile Ile Ser Glu Gly Asn Glu Thr Val Glu Asp
625                 630                 635                 640

Ile Ala Ala Arg Leu Asn Ile Pro Met Ser Gln Val Asn Pro Arg Glu
                645                 650                 655

Ala Lys Ala Cys Val Val His Gly Ser Asp Leu Lys Asp Met Thr Ser
            660                 665                 670

Glu Gln Leu Asp Glu Ile Leu Lys Asn His Thr Glu Ile Val Phe Ala
        675                 680                 685

Arg Thr Ser Pro Gln Gln Lys Leu Ile Ile Val Glu Gly Cys Gln Arg
    690                 695                 700

Gln Gly Ala Ile Val Ala Val Thr Gly Asp Gly Val Asn Asp Ser Pro
705                 710                 715                 720

Ala Leu Lys Lys Ala Asp Ile Gly Ile Ala Met Gly Ile Ser Gly Ser
                725                 730                 735

Asp Val Ser Lys Gln Ala Ala Asp Met Ile Leu Leu Asp Asp Asn Phe
            740                 745                 750

Ala Ser Ile Val Thr Gly Val Glu Glu Gly Arg Leu Ile Phe Asp Asn
        755                 760                 765

Leu Lys Lys Ser Ile Ala Tyr Thr Leu Thr Ser Asn Ile Pro Glu Ile
    770                 775                 780

Thr Pro Phe Leu Leu Phe Ile Ile Ala Asn Ile Pro Leu Pro Leu Gly
785                 790                 795                 800

Thr Val Thr Ile Leu Cys Ile Asp Leu Gly Thr Asp Met Val Pro Ala
                805                 810                 815

Ile Ser Leu Ala Tyr Glu Ala Ala Glu Ser Asp Ile Met Lys Arg Gln
            820                 825                 830

Pro Arg Asn Ser Gln Thr Asp Lys Leu Val Asn Glu Arg Leu Ile Ser
        835                 840                 845

Met Ala Tyr Gly Gln Ile Gly Met Ile Gln Ala Leu Gly Gly Phe Phe
    850                 855                 860

Thr Tyr Phe Val Ile Leu Ala Glu Asn Gly Phe Leu Pro Ser Arg Leu
865                 870                 875                 880

Leu Gly Ile Arg Leu Asp Trp Asp Asp Arg Thr Met Asn Asp Leu Glu
                885                 890                 895

Asp Ser Tyr Gly Gln Glu Trp Thr Tyr Glu Gln Arg Lys Val Val Glu
            900                 905                 910

Phe Thr Cys His Thr Ala Phe Phe Ala Ser Ile Val Val Val Gln Trp
        915                 920                 925

Ala Asp Leu Ile Ile Cys Lys Thr Arg Arg Asn Ser Val Phe Gln Gln
    930                 935                 940

Gly Met Lys Asn Lys Ile Leu Ile Phe Gly Leu Leu Glu Glu Thr Ala
945                 950                 955                 960
```

-continued

```
Leu Ala Ala Phe Leu Ser Tyr Cys Pro Gly Met Gly Val Ala Leu Arg
            965                 970                 975

Met Tyr Pro Leu Lys Val Thr Trp Trp Phe Cys Ala Phe Pro Tyr Ser
            980                 985                 990

Leu Leu Ile Phe Ile Tyr Asp Glu  Val Arg Lys Leu Ile  Leu Arg Arg
        995                 1000                 1005

Tyr Pro  Gly Gly Trp Val Glu  Lys Glu Thr Tyr Tyr
    1010                 1015                 1020


<210> SEQ ID NO 26
<211> LENGTH: 1026
<212> TYPE: PRT
<213> ORGANISM: homo sapiens

<400> SEQUENCE: 26

Met Gly Ser Gly Gly Ser Asp Ser Tyr Arg Ile Ala Thr Ser Gln Asp
1               5                   10                  15

Lys Lys Asp Asp Lys Asp Ser Pro Lys Lys Asn Lys Gly Lys Glu Arg
            20                  25                  30

Arg Asp Leu Asp Asp Leu Lys Lys Glu Val Ala Met Thr Glu His Lys
        35                  40                  45

Met Ser Val Glu Glu Val Cys Arg Lys Tyr Asn Thr Asp Cys Val Gln
    50                  55                  60

Gly Leu Thr His Ser Lys Ala Gln Glu Ile Leu Ala Arg Asp Gly Pro
65                  70                  75                  80

Asn Ala Leu Thr Pro Pro Pro Thr Thr Pro Glu Trp Val Lys Phe Cys
                85                  90                  95

Arg Gln Leu Phe Gly Gly Phe Ser Ile Leu Leu Trp Ile Gly Ala Ile
            100                 105                 110

Leu Cys Phe Leu Ala Tyr Gly Ile Gln Ala Gly Thr Glu Asp Asp Pro
        115                 120                 125

Ser Gly Asp Asn Leu Tyr Leu Gly Ile Val Leu Ala Ala Val Val Ile
    130                 135                 140

Ile Thr Gly Cys Phe Ser Tyr Tyr Gln Glu Ala Lys Ser Ser Lys Ile
145                 150                 155                 160

Met Glu Ser Phe Lys Asn Met Val Pro Gln Gln Ala Leu Val Ile Arg
                165                 170                 175

Glu Gly Glu Lys Met Gln Val Asn Ala Glu Glu Val Val Val Gly Asp
            180                 185                 190

Leu Val Glu Ile Lys Gly Gly Asp Arg Val Pro Ala Asp Leu Arg Ile
        195                 200                 205

Ile Ser Ala His Gly Cys Lys Val Asp Asn Ser Ser Leu Thr Gly Glu
    210                 215                 220

Ser Glu Pro Gln Thr Arg Ser Pro Asp Cys Thr His Asp Asn Pro Leu
225                 230                 235                 240

Glu Thr Arg Asn Ile Thr Phe Phe Ser Thr Asn Cys Val Glu Gly Thr
                245                 250                 255

Ala Arg Gly Val Val Val Ala Thr Gly Asp Arg Thr Val Met Gly Arg
            260                 265                 270

Ile Ala Thr Leu Ala Ser Gly Leu Glu Val Gly Lys Thr Pro Ile Ala
        275                 280                 285

Ile Glu Ile Glu His Phe Ile Gln Leu Ile Thr Gly Val Ala Val Phe
    290                 295                 300

Leu Gly Val Ser Phe Phe Ile Leu Ser Leu Ile Leu Gly Tyr Thr Trp
305                 310                 315                 320
```

-continued

```
Leu Glu Ala Val Ile Phe Leu Ile Gly Ile Ile Val Ala Asn Val Pro
                325                 330                 335

Glu Gly Leu Leu Ala Thr Val Thr Val Cys Leu Thr Leu Thr Ala Lys
            340                 345                 350

Arg Met Ala Arg Lys Asn Cys Leu Val Lys Asn Leu Glu Ala Val Glu
        355                 360                 365

Thr Leu Gly Ser Thr Ser Thr Ile Cys Ser Asp Lys Thr Gly Thr Leu
    370                 375                 380

Thr Gln Asn Arg Met Thr Val Ala His Met Trp Phe Asp Asn Gln Ile
385                 390                 395                 400

His Glu Ala Asp Thr Thr Glu Asp Gln Ser Gly Thr Ser Phe Asp Lys
                405                 410                 415

Ser Ser His Thr Trp Val Ala Leu Ser His Ile Ala Gly Leu Cys Asn
            420                 425                 430

Arg Ala Val Phe Lys Gly Gly Gln Asp Asn Ile Pro Val Leu Lys Arg
        435                 440                 445

Asp Val Ala Gly Asp Ala Ser Glu Ser Ala Leu Leu Lys Cys Ile Glu
    450                 455                 460

Leu Ser Ser Gly Ser Val Lys Leu Met Arg Glu Arg Asn Lys Lys Val
465                 470                 475                 480

Ala Glu Ile Pro Phe Asn Ser Thr Asn Lys Tyr Gln Leu Ser Ile His
                485                 490                 495

Glu Thr Glu Asp Pro Asn Asp Asn Arg Tyr Leu Leu Val Met Lys Gly
            500                 505                 510

Ala Pro Glu Arg Ile Leu Asp Arg Cys Ser Thr Ile Leu Leu Gln Gly
        515                 520                 525

Lys Glu Gln Pro Leu Asp Glu Glu Met Lys Glu Ala Phe Gln Asn Ala
    530                 535                 540

Tyr Leu Glu Leu Gly Gly Leu Gly Glu Arg Val Leu Gly Phe Cys His
545                 550                 555                 560

Tyr Tyr Leu Pro Glu Glu Gln Phe Pro Lys Gly Phe Ala Phe Asp Cys
                565                 570                 575

Asp Asp Val Asn Phe Thr Thr Asp Asn Leu Cys Phe Val Gly Leu Met
            580                 585                 590

Ser Met Ile Asp Pro Pro Arg Ala Ala Val Pro Asp Ala Val Gly Lys
        595                 600                 605

Cys Arg Ser Ala Gly Ile Lys Val Ile Met Val Thr Gly Asp His Pro
    610                 615                 620

Ile Thr Ala Lys Ala Ile Ala Lys Gly Val Gly Ile Ile Ser Glu Gly
625                 630                 635                 640

Asn Glu Thr Val Glu Asp Ile Ala Ala Arg Leu Asn Ile Pro Val Ser
                645                 650                 655

Gln Val Asn Pro Arg Asp Ala Lys Ala Cys Val Ile His Gly Thr Asp
            660                 665                 670

Leu Lys Asp Phe Thr Ser Glu Gln Ile Asp Glu Ile Leu Gln Asn His
        675                 680                 685

Thr Glu Ile Val Phe Ala Arg Thr Ser Pro Gln Gln Lys Leu Ile Ile
    690                 695                 700

Val Glu Gly Cys Gln Arg Gln Gly Ala Ile Val Ala Val Thr Gly Asp
705                 710                 715                 720

Gly Val Asn Asp Ser Pro Ala Leu Lys Lys Ala Asp Ile Gly Val Ala
                725                 730                 735
```

-continued

```
Met Gly Ile Ala Gly Ser Asp Val Ser Lys Gln Ala Ala Asp Met Ile
            740                 745                 750

Leu Leu Asp Asp Asn Phe Ala Ser Ile Val Thr Gly Val Glu Glu Gly
        755                 760                 765

Arg Leu Ile Phe Asp Asn Leu Lys Lys Ser Ile Ala Tyr Thr Leu Thr
    770                 775                 780

Ser Asn Ile Pro Glu Ile Thr Pro Phe Leu Leu Phe Ile Met Ala Asn
785                 790                 795                 800

Ile Pro Leu Pro Leu Gly Thr Ile Thr Ile Leu Cys Ile Asp Leu Gly
                805                 810                 815

Thr Asp Met Val Pro Ala Ile Ser Leu Ala Tyr Glu Ala Ala Glu Ser
            820                 825                 830

Asp Ile Met Lys Arg Gln Pro Arg Asn Pro Arg Thr Asp Lys Leu Val
        835                 840                 845

Asn Glu Arg Leu Ile Ser Met Ala Tyr Gly Gln Ile Gly Met Ile Gln
    850                 855                 860

Ala Leu Gly Gly Phe Phe Ser Tyr Phe Val Ile Leu Ala Glu Asn Gly
865                 870                 875                 880

Phe Leu Pro Gly Asn Leu Val Gly Ile Arg Leu Asn Trp Asp Asp Arg
                885                 890                 895

Thr Val Asn Asp Leu Glu Asp Ser Tyr Gly Gln Gln Trp Thr Tyr Glu
            900                 905                 910

Gln Arg Lys Val Val Glu Phe Thr Cys His Thr Ala Phe Phe Val Ser
        915                 920                 925

Ile Val Val Val Gln Trp Ala Asp Leu Ile Ile Cys Lys Thr Arg Arg
    930                 935                 940

Asn Ser Val Phe Gln Gln Gly Met Lys Asn Lys Ile Leu Ile Phe Gly
945                 950                 955                 960

Leu Phe Glu Glu Thr Ala Leu Ala Ala Phe Leu Ser Tyr Cys Pro Gly
                965                 970                 975

Met Asp Val Ala Leu Arg Met Tyr Pro Leu Lys Pro Ser Trp Trp Phe
            980                 985                 990

Cys Ala Phe Pro Tyr Ser Phe Leu  Ile Phe Val Tyr Asp  Glu Ile Arg
        995                 1000                 1005

Lys Leu  Ile Leu Arg Arg Asn  Pro Gly Gly Trp Val  Glu Lys Glu
    1010                 1015                 1020

Thr Tyr  Tyr
    1025


<210> SEQ ID NO 27
<211> LENGTH: 1029
<212> TYPE: PRT
<213> ORGANISM: Homo sapiens

<400> SEQUENCE: 27

Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Lys Met Val Lys
            20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80
```

-continued

Thr Arg Gly Gly Pro Asn Thr Val Thr Pro Pro Pro Thr Thr Pro Glu
85 90 95

Trp Val Lys Phe Cys Lys Gln Leu Phe Gly Gly Phe Ser Leu Leu Leu
100 105 110

Trp Thr Gly Ala Ile Leu Cys Phe Val Ala Tyr Ser Ile Gln Ile Tyr
115 120 125

Phe Asn Glu Glu Pro Thr Lys Asp Asn Leu Tyr Leu Ser Ile Val Leu
130 135 140

Ser Val Val Val Ile Val Thr Gly Cys Phe Ser Tyr Tyr Gln Glu Ala
145 150 155 160

Lys Ser Ser Lys Ile Met Glu Ser Phe Lys Asn Met Val Pro Gln Gln
165 170 175

Ala Leu Val Ile Arg Gly Gly Glu Lys Met Gln Ile Asn Val Gln Glu
180 185 190

Val Val Leu Gly Asp Leu Val Glu Ile Lys Gly Gly Asp Arg Val Pro
195 200 205

Ala Asp Leu Arg Leu Ile Ser Ala Gln Gly Cys Lys Val Asp Asn Ser
210 215 220

Ser Leu Thr Gly Glu Ser Glu Pro Gln Ser Arg Ser Pro Asp Phe Thr
225 230 235 240

His Glu Asn Pro Leu Glu Thr Arg Asn Ile Cys Phe Phe Ser Thr Asn
245 250 255

Cys Val Glu Gly Thr Ala Arg Gly Ile Val Ile Ala Thr Gly Asp Ser
260 265 270

Thr Val Met Gly Arg Ile Ala Ser Leu Thr Ser Gly Leu Ala Val Gly
275 280 285

Gln Thr Pro Ile Ala Ala Glu Ile Glu His Phe Ile His Leu Ile Thr
290 295 300

Val Val Ala Val Phe Leu Gly Val Thr Phe Phe Ala Leu Ser Leu Leu
305 310 315 320

Leu Gly Tyr Gly Trp Leu Glu Ala Ile Ile Phe Leu Ile Gly Ile Ile
325 330 335

Val Ala Asn Val Pro Glu Gly Leu Leu Ala Thr Val Thr Val Cys Leu
340 345 350

Thr Leu Thr Ala Lys Arg Met Ala Arg Lys Asn Cys Leu Val Lys Asn
355 360 365

Leu Glu Ala Val Glu Thr Leu Gly Ser Thr Ser Thr Ile Cys Ser Asp
370 375 380

Lys Thr Gly Thr Leu Thr Gln Asn Arg Met Thr Val Ala His Met Trp
385 390 395 400

Phe Asp Met Thr Val Tyr Glu Ala Asp Thr Thr Glu Glu Gln Thr Gly
405 410 415

Lys Thr Phe Thr Lys Ser Ser Asp Thr Trp Phe Met Leu Ala Arg Ile
420 425 430

Ala Gly Leu Cys Asn Arg Ala Asp Phe Lys Ala Asn Gln Glu Ile Leu
435 440 445

Pro Ile Ala Lys Arg Ala Thr Thr Gly Asp Ala Ser Glu Ser Ala Leu
450 455 460

Leu Lys Phe Ile Glu Gln Ser Tyr Ser Ser Val Ala Glu Met Arg Glu
465 470 475 480

Lys Asn Pro Lys Val Ala Glu Ile Pro Phe Asn Ser Thr Asn Lys Tyr
485 490 495

-continued

```
Gln Met Ser Ile His Leu Arg Glu Asp Ser Ser Gln Thr His Val Leu
            500                 505                 510

Met Met Lys Gly Ala Pro Glu Arg Ile Leu Glu Phe Cys Ser Thr Phe
        515                 520                 525

Leu Leu Asn Gly Gln Glu Tyr Ser Met Asn Asp Glu Met Lys Glu Ala
    530                 535                 540

Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
                565                 570                 575

Phe Asn Thr Asp Glu Ile Asn Phe Pro Met Asp Asn Leu Cys Phe Val
            580                 585                 590

Gly Leu Ile Ser Met Ile Asp Pro Pro Arg Ala Ala Val Pro Asp Ala
        595                 600                 605

Val Ser Lys Cys Arg Ser Ala Gly Ile Lys Val Ile Met Val Thr Gly
    610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Glu Val Ala Ala Arg Leu Lys Ile
                645                 650                 655

Pro Ile Ser Lys Val Asp Ala Ser Ala Ala Lys Ala Ile Val Val His
            660                 665                 670

Gly Ala Glu Leu Lys Asp Ile Gln Ser Lys Gln Leu Asp Gln Ile Leu
        675                 680                 685

Gln Asn His Pro Glu Ile Val Phe Ala Arg Thr Ser Pro Gln Gln Lys
    690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
            740                 745                 750

Asp Met Ile Leu Leu Asp Asp Asn Phe Ala Ser Ile Val Thr Gly Val
        755                 760                 765

Glu Glu Gly Arg Leu Ile Phe Asp Asn Leu Lys Lys Ser Ile Met Tyr
    770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
            820                 825                 830

Ala Glu Ser Asp Ile Met Lys Arg Leu Pro Arg Asn Pro Lys Thr Asp
        835                 840                 845

Asn Leu Val Asn His Arg Leu Ile Gly Met Ala Tyr Gly Gln Ile Gly
    850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
            900                 905                 910

Thr Tyr Glu Gln Arg Lys Val Val Glu Phe Thr Cys Gln Thr Ala Phe
```

915 920 925

Phe Val Thr Ile Val Val Val Gln Trp Ala Asp Leu Ile Ile Ser Lys
930 935 940

Thr Arg Arg Asn Ser Leu Phe Gln Gln Gly Met Arg Asn Lys Val Leu
945 950 955 960

Ile Phe Gly Ile Leu Glu Glu Thr Leu Leu Ala Ala Phe Leu Ser Tyr
965 970 975

Thr Pro Gly Met Asp Val Ala Leu Arg Met Tyr Pro Leu Lys Ile Thr
980 985 990

Trp Trp Leu Cys Ala Ile Pro Tyr Ser Ile Leu Ile Phe Val Tyr Asp
995 1000 1005

Glu Ile Arg Lys Leu Leu Ile Arg Gln His Pro Asp Gly Trp Val
1010 1015 1020

Glu Arg Glu Thr Tyr Tyr
1025

<210> SEQ ID NO 28
<211> LENGTH: 279
<212> TYPE: PRT
<213> ORGANISM: homo sapiens

<400> SEQUENCE: 28

Met Thr Lys Asn Glu Lys Lys Ser Leu Asn Gln Ser Leu Ala Glu Trp
1 5 10 15

Lys Leu Phe Ile Tyr Asn Pro Thr Thr Gly Glu Phe Leu Gly Arg Thr
20 25 30

Ala Lys Ser Trp Gly Leu Ile Leu Leu Phe Tyr Leu Val Phe Tyr Gly
35 40 45

Phe Leu Ala Ala Leu Phe Ser Phe Thr Met Trp Val Met Leu Gln Thr
50 55 60

Leu Asn Asp Glu Val Pro Lys Tyr Arg Asp Gln Ile Pro Ser Pro Gly
65 70 75 80

Leu Met Val Phe Pro Lys Pro Val Thr Ala Leu Glu Tyr Thr Phe Ser
85 90 95

Arg Ser Asp Pro Thr Ser Tyr Ala Gly Tyr Ile Glu Asp Leu Lys Lys
100 105 110

Phe Leu Lys Pro Tyr Thr Leu Glu Glu Gln Lys Asn Leu Thr Val Cys
115 120 125

Pro Asp Gly Ala Leu Phe Glu Gln Lys Gly Pro Val Tyr Val Ala Cys
130 135 140

Gln Phe Pro Ile Ser Leu Leu Gln Ala Cys Ser Gly Met Asn Asp Pro
145 150 155 160

Asp Phe Gly Tyr Ser Gln Gly Asn Pro Cys Ile Leu Val Lys Met Asn
165 170 175

Arg Ile Ile Gly Leu Lys Pro Glu Gly Val Pro Arg Ile Asp Cys Val
180 185 190

Ser Lys Asn Glu Asp Ile Pro Asn Val Ala Val Tyr Pro His Asn Gly
195 200 205

Met Ile Asp Leu Lys Tyr Phe Pro Tyr Tyr Gly Lys Lys Leu His Val
210 215 220

Gly Tyr Leu Gln Pro Leu Val Ala Val Gln Val Ser Phe Ala Pro Asn
225 230 235 240

Asn Thr Gly Lys Glu Val Thr Val Glu Cys Lys Ile Asp Gly Ser Ala
245 250 255

```
Asn Leu Lys Ser Gln Asp Asp Arg Asp Lys Phe Leu Gly Arg Val Met
            260                 265                 270

Phe Lys Ile Thr Ala Arg Ala
        275


<210> SEQ ID NO 29
<211> LENGTH: 1258
<212> TYPE: PRT
<213> ORGANISM: Homo sapiens

<400> SEQUENCE: 29

Met Gly Asp Met Ala Asn Asn Ser Val Ala Tyr Ser Gly Val Lys Asn
1               5                   10                  15

Ser Leu Lys Glu Ala Asn His Asp Gly Asp Phe Gly Ile Thr Leu Ala
            20                  25                  30

Glu Leu Arg Ala Leu Met Glu Leu Arg Ser Thr Asp Ala Leu Arg Lys
        35                  40                  45

Ile Gln Glu Ser Tyr Gly Asp Val Tyr Gly Ile Cys Thr Lys Leu Lys
    50                  55                  60

Thr Ser Pro Asn Glu Gly Leu Ser Gly Asn Pro Ala Asp Leu Glu Arg
65                  70                  75                  80

Arg Glu Ala Val Phe Gly Lys Asn Phe Ile Pro Pro Lys Lys Pro Lys
                85                  90                  95

Thr Phe Leu Gln Leu Val Trp Glu Ala Leu Gln Asp Val Thr Leu Ile
            100                 105                 110

Ile Leu Glu Ile Ala Ala Ile Val Ser Leu Gly Leu Ser Phe Tyr Gln
        115                 120                 125

Pro Pro Glu Gly Asp Asn Ala Leu Cys Gly Glu Val Ser Val Gly Glu
    130                 135                 140

Glu Glu Gly Glu Gly Glu Thr Gly Trp Ile Glu Gly Ala Ala Ile Leu
145                 150                 155                 160

Leu Ser Val Val Cys Val Val Leu Val Thr Ala Phe Asn Asp Trp Ser
                165                 170                 175

Lys Glu Lys Gln Phe Arg Gly Leu Gln Ser Arg Ile Glu Gln Glu Gln
            180                 185                 190

Lys Phe Thr Val Ile Arg Gly Gly Gln Val Ile Gln Ile Pro Val Ala
        195                 200                 205

Asp Ile Thr Val Gly Asp Ile Ala Gln Val Lys Tyr Gly Asp Leu Leu
    210                 215                 220

Pro Ala Asp Gly Ile Leu Ile Gln Gly Asn Asp Leu Lys Ile Asp Glu
225                 230                 235                 240

Ser Ser Leu Thr Gly Glu Ser Asp His Val Lys Lys Ser Leu Asp Lys
                245                 250                 255

Asp Pro Leu Leu Leu Ser Gly Thr His Val Met Glu Gly Ser Gly Arg
            260                 265                 270

Met Val Val Thr Ala Val Gly Val Asn Ser Gln Thr Gly Ile Ile Phe
        275                 280                 285

Thr Leu Leu Gly Ala Gly Gly Glu Glu Glu Glu Lys Lys Asp Glu Lys
    290                 295                 300

Lys Lys Glu Lys Lys Asn Lys Lys Gln Asp Gly Ala Ile Glu Asn Arg
305                 310                 315                 320

Asn Lys Ala Lys Ala Gln Asp Gly Ala Ala Met Glu Met Gln Pro Leu
                325                 330                 335

Lys Ser Glu Glu Gly Gly Asp Gly Asp Glu Lys Asp Lys Lys Lys Ala
            340                 345                 350
```

-continued

```
Asn Leu Pro Lys Lys Glu Lys Ser Val Leu Gln Gly Lys Leu Thr Lys
        355                 360                 365

Leu Ala Val Gln Ile Gly Lys Ala Gly Leu Leu Met Ser Ala Ile Thr
    370                 375                 380

Val Ile Ile Leu Val Leu Tyr Phe Val Ile Asp Thr Phe Trp Val Gln
385                 390                 395                 400

Lys Arg Pro Trp Leu Ala Glu Cys Thr Pro Ile Tyr Ile Gln Tyr Phe
                405                 410                 415

Val Lys Phe Phe Ile Ile Gly Val Thr Val Leu Val Val Ala Val Pro
            420                 425                 430

Glu Gly Leu Pro Leu Ala Val Thr Ile Ser Leu Ala Tyr Ser Val Lys
        435                 440                 445

Lys Met Met Lys Asp Asn Asn Leu Val Arg His Leu Asp Ala Cys Glu
    450                 455                 460

Thr Met Gly Asn Ala Thr Ala Ile Cys Ser Asp Lys Thr Gly Thr Leu
465                 470                 475                 480

Thr Met Asn Arg Met Thr Val Val Gln Ala Tyr Ile Asn Glu Lys His
                485                 490                 495

Tyr Lys Lys Val Pro Glu Pro Glu Ala Ile Pro Pro Asn Ile Leu Ser
            500                 505                 510

Tyr Leu Val Thr Gly Ile Ser Val Asn Cys Ala Tyr Thr Ser Lys Ile
        515                 520                 525

Leu Pro Pro Glu Lys Glu Gly Gly Leu Pro Arg His Val Gly Asn Lys
    530                 535                 540

Thr Glu Cys Ala Leu Leu Gly Leu Leu Leu Asp Leu Lys Arg Asp Tyr
545                 550                 555                 560

Gln Asp Val Arg Asn Glu Ile Pro Glu Glu Ala Leu Tyr Lys Val Tyr
                565                 570                 575

Thr Phe Asn Ser Val Arg Lys Ser Met Ser Thr Val Leu Lys Asn Ser
            580                 585                 590

Asp Gly Ser Tyr Arg Ile Phe Ser Lys Gly Ala Ser Glu Ile Ile Leu
        595                 600                 605

Lys Lys Cys Phe Lys Ile Leu Ser Ala Asn Gly Glu Ala Lys Val Phe
    610                 615                 620

Arg Pro Arg Asp Arg Asp Asp Ile Val Lys Thr Val Ile Glu Pro Met
625                 630                 635                 640

Ala Ser Glu Gly Leu Arg Thr Ile Cys Leu Ala Phe Arg Asp Phe Pro
                645                 650                 655

Ala Gly Glu Pro Glu Pro Glu Trp Asp Asn Glu Asn Asp Ile Val Thr
            660                 665                 670

Gly Leu Thr Cys Ile Ala Val Val Gly Ile Glu Asp Pro Val Arg Pro
        675                 680                 685

Glu Val Pro Asp Ala Ile Lys Lys Cys Gln Arg Ala Gly Ile Thr Val
    690                 695                 700

Arg Met Val Thr Gly Asp Asn Ile Asn Thr Ala Arg Ala Ile Ala Thr
705                 710                 715                 720

Lys Cys Gly Ile Leu His Pro Gly Glu Asp Phe Leu Cys Leu Glu Gly
                725                 730                 735

Lys Asp Phe Asn Arg Arg Ile Arg Asn Glu Lys Gly Glu Ile Glu Gln
            740                 745                 750

Glu Arg Ile Asp Lys Ile Trp Pro Lys Leu Arg Val Leu Ala Arg Ser
        755                 760                 765
```

-continued

```
Ser Pro Thr Asp Lys His Thr Leu Val Lys Gly Ile Ile Asp Ser Thr
    770                 775                 780

Val Ser Asp Gln Arg Gln Val Val Ala Val Thr Gly Asp Gly Thr Asn
785                 790                 795                 800

Asp Gly Pro Ala Leu Lys Lys Ala Asp Val Gly Phe Ala Met Gly Ile
                805                 810                 815

Ala Gly Thr Asp Val Ala Lys Glu Ala Ser Asp Ile Ile Leu Thr Asp
            820                 825                 830

Asp Asn Phe Thr Ser Ile Val Lys Ala Val Met Trp Gly Arg Asn Val
        835                 840                 845

Tyr Asp Ser Ile Ser Lys Phe Leu Gln Phe Gln Leu Thr Val Asn Val
    850                 855                 860

Val Ala Val Ile Val Ala Phe Thr Gly Ala Cys Ile Thr Gln Asp Ser
865                 870                 875                 880

Pro Leu Lys Ala Val Gln Met Leu Trp Val Asn Leu Ile Met Asp Thr
                885                 890                 895

Leu Ala Ser Leu Ala Leu Ala Thr Glu Pro Pro Thr Glu Ser Leu Leu
            900                 905                 910

Leu Arg Lys Pro Tyr Gly Arg Asn Lys Pro Leu Ile Ser Arg Thr Met
        915                 920                 925

Met Lys Asn Ile Leu Gly His Ala Phe Tyr Gln Leu Val Val Val Phe
    930                 935                 940

Thr Leu Leu Phe Ala Gly Glu Lys Phe Phe Asp Ile Asp Ser Gly Arg
945                 950                 955                 960

Asn Ala Pro Leu His Ala Pro Pro Ser Glu His Tyr Thr Ile Val Phe
                965                 970                 975

Asn Thr Phe Val Leu Met Gln Leu Phe Asn Glu Ile Asn Ala Arg Lys
            980                 985                 990

Ile His Gly Glu Arg Asn Val Phe  Glu Gly Ile Phe Asn  Asn Ala Ile
        995                 1000                1005

Phe Cys  Thr Ile Val Leu Gly  Thr Phe Val Val Gln  Ile Ile Ile
    1010                 1015                 1020

Val Gln  Phe Gly Gly Lys Pro  Phe Ser Cys Ser Glu  Leu Ser Ile
    1025                 1030                 1035

Glu Gln  Trp Leu Trp Ser Ile  Phe Leu Gly Met Gly  Thr Leu Leu
    1040                 1045                 1050

Trp Gly  Gln Leu Ile Ser Thr  Ile Pro Thr Ser Arg  Leu Lys Phe
    1055                 1060                 1065

Leu Lys  Glu Ala Gly His Gly  Thr Gln Lys Glu Glu  Ile Pro Glu
    1070                 1075                 1080

Glu Glu  Leu Ala Glu Asp Val  Glu Glu Ile Asp His  Ala Glu Arg
    1085                 1090                 1095

Glu Leu  Arg Arg Gly Gln Ile  Leu Trp Phe Arg Gly  Leu Asn Arg
    1100                 1105                 1110

Ile Gln  Thr Gln Met Asp Val  Val Asn Ala Phe Gln  Ser Gly Ser
    1115                 1120                 1125

Ser Ile  Gln Gly Ala Leu Arg  Arg Gln Pro Ser Ile  Ala Ser Gln
    1130                 1135                 1140

His His  Asp Val Thr Asn Ile  Ser Thr Pro Thr His  Ile Arg Val
    1145                 1150                 1155

Val Asn  Ala Phe Arg Ser Ser  Leu Tyr Glu Gly Leu  Glu Lys Pro
    1160                 1165                 1170

Glu Ser  Arg Ser Ser Ile His  Asn Phe Met Thr His  Pro Glu Phe
```

```
    1175                1180                1185

Arg Ile  Glu Asp Ser Glu Pro  His Ile Pro Leu Ile  Asp Asp Thr
    1190                1195                1200

Asp Ala  Glu Asp Asp Ala Pro  Thr Lys Arg Asn Ser  Ser Pro Pro
    1205                1210                1215

Pro Ser  Pro Asn Lys Asn Asn  Asn Ala Val Asp Ser  Gly Ile His
    1220                1225                1230

Leu Thr  Ile Glu Met Asn Lys  Ser Ala Thr Ser Ser  Ser Pro Gly
    1235                1240                1245

Ser Pro  Leu His Ser Leu Glu  Thr Ser Leu
    1250                1255


<210> SEQ ID NO 30
<211> LENGTH: 1272
<212> TYPE: PRT
<213> ORGANISM: Homo sapiens

<400> SEQUENCE: 30

Met Gly Asp Met Thr Asn Ser Asp Phe Tyr Ser Lys Asn Gln Arg Asn
1               5                   10                  15

Glu Ser Ser His Gly Gly Glu Phe Gly Cys Thr Met Glu Glu Leu Arg
            20                  25                  30

Ser Leu Met Glu Leu Arg Gly Thr Glu Ala Val Val Lys Ile Lys Glu
        35                  40                  45

Thr Tyr Gly Asp Thr Glu Ala Ile Cys Arg Arg Leu Lys Thr Ser Pro
    50                  55                  60

Val Glu Gly Leu Pro Gly Thr Ala Pro Asp Leu Glu Lys Arg Lys Gln
65                  70                  75                  80

Ile Phe Gly Gln Asn Phe Ile Pro Pro Lys Lys Pro Lys Thr Phe Leu
                85                  90                  95

Gln Leu Val Trp Glu Ala Leu Gln Asp Val Thr Leu Ile Ile Leu Glu
            100                 105                 110

Ile Ala Ala Ile Ile Ser Leu Gly Leu Ser Phe Tyr His Pro Pro Gly
        115                 120                 125

Glu Gly Asn Glu Gly Cys Ala Thr Ala Gln Gly Gly Ala Glu Asp Glu
    130                 135                 140

Gly Glu Ala Glu Ala Gly Trp Ile Glu Gly Ala Ala Ile Leu Leu Ser
145                 150                 155                 160

Val Ile Cys Val Val Leu Val Thr Ala Phe Asn Asp Trp Ser Lys Glu
                165                 170                 175

Lys Gln Phe Arg Gly Leu Gln Ser Arg Ile Glu Gln Glu Gln Lys Phe
            180                 185                 190

Thr Val Val Arg Ala Gly Gln Val Val Gln Ile Pro Val Ala Glu Ile
        195                 200                 205

Val Val Gly Asp Ile Ala Gln Val Lys Tyr Gly Asp Leu Leu Pro Ala
    210                 215                 220

Asp Gly Leu Phe Ile Gln Gly Asn Asp Leu Lys Ile Asp Glu Ser Ser
225                 230                 235                 240

Leu Thr Gly Glu Ser Asp Gln Val Arg Lys Ser Val Asp Lys Asp Pro
                245                 250                 255

Met Leu Leu Ser Gly Thr His Val Met Glu Gly Ser Gly Arg Met Leu
            260                 265                 270

Val Thr Ala Val Gly Val Asn Ser Gln Thr Gly Ile Ile Phe Thr Leu
        275                 280                 285
```

-continued

```
Leu Gly Ala Gly Gly Glu Glu Glu Glu Lys Lys Asp Lys Lys Gly Val
    290                 295                 300

Lys Lys Gly Asp Gly Leu Gln Leu Pro Ala Ala Asp Gly Ala Ala Ala
305                 310                 315                 320

Ser Asn Ala Ala Asp Ser Ala Asn Ala Ser Leu Val Asn Gly Lys Met
                325                 330                 335

Gln Asp Gly Asn Val Asp Ala Ser Gln Ser Lys Ala Lys Gln Gln Asp
            340                 345                 350

Gly Ala Ala Ala Met Glu Met Gln Pro Leu Lys Ser Ala Glu Gly Gly
        355                 360                 365

Asp Ala Asp Asp Arg Lys Lys Ala Ser Met His Lys Lys Glu Lys Ser
    370                 375                 380

Val Leu Gln Gly Lys Leu Thr Lys Leu Ala Val Gln Ile Gly Lys Ala
385                 390                 395                 400

Gly Leu Val Met Ser Ala Ile Thr Val Ile Ile Leu Val Leu Tyr Phe
                405                 410                 415

Thr Val Asp Thr Phe Val Val Asn Lys Lys Pro Trp Leu Pro Glu Cys
            420                 425                 430

Thr Pro Val Tyr Val Gln Tyr Phe Val Lys Phe Phe Ile Ile Gly Val
        435                 440                 445

Thr Val Leu Val Val Ala Val Pro Glu Gly Leu Pro Leu Ala Val Thr
    450                 455                 460

Ile Ser Leu Ala Tyr Ser Val Lys Lys Met Met Lys Asp Asn Asn Leu
465                 470                 475                 480

Val Arg His Leu Asp Ala Cys Glu Thr Met Gly Asn Ala Thr Ala Ile
                485                 490                 495

Cys Ser Asp Lys Thr Gly Thr Leu Thr Thr Asn Arg Met Thr Val Val
            500                 505                 510

Gln Ala Tyr Val Gly Asp Val His Tyr Lys Glu Ile Pro Asp Pro Ser
        515                 520                 525

Ser Ile Asn Thr Lys Thr Met Glu Leu Leu Ile Asn Ala Ile Ala Ile
    530                 535                 540

Asn Ser Ala Tyr Thr Thr Lys Ile Leu Pro Pro Glu Lys Glu Gly Ala
545                 550                 555                 560

Leu Pro Arg Gln Val Gly Asn Lys Thr Glu Cys Gly Leu Leu Gly Phe
                565                 570                 575

Val Leu Asp Leu Lys Gln Asp Tyr Glu Pro Val Arg Ser Gln Met Pro
            580                 585                 590

Glu Glu Lys Leu Tyr Lys Val Tyr Thr Phe Asn Ser Val Arg Lys Ser
        595                 600                 605

Met Ser Thr Val Ile Lys Leu Pro Asp Glu Ser Phe Arg Met Tyr Ser
    610                 615                 620

Lys Gly Ala Ser Glu Ile Val Leu Lys Lys Cys Cys Lys Ile Leu Asn
625                 630                 635                 640

Gly Ala Gly Glu Pro Arg Val Phe Arg Pro Arg Asp Arg Asp Glu Met
                645                 650                 655

Val Lys Lys Val Ile Glu Pro Met Ala Cys Asp Gly Leu Arg Thr Ile
            660                 665                 670

Cys Val Ala Tyr Arg Asp Phe Pro Ser Ser Pro Glu Pro Asp Trp Asp
        675                 680                 685

Asn Glu Asn Asp Ile Leu Asn Glu Leu Thr Cys Ile Cys Val Val Gly
    690                 695                 700

Ile Glu Asp Pro Val Arg Pro Glu Val Pro Glu Ala Ile Arg Lys Cys
```

-continued 705 710 715 720

Gln Arg Ala Gly Ile Thr Val Arg Met Val Thr Gly Asp Asn Ile Asn
725 730 735

Thr Ala Arg Ala Ile Ala Ile Lys Cys Gly Ile Ile His Pro Gly Glu
740 745 750

Asp Phe Leu Cys Leu Glu Gly Lys Glu Phe Asn Arg Arg Ile Arg Asn
755 760 765

Glu Lys Gly Glu Ile Glu Gln Glu Arg Ile Asp Lys Ile Trp Pro Lys
770 775 780

Leu Arg Val Leu Ala Arg Ser Ser Pro Thr Asp Lys His Thr Leu Val
785 790 795 800

Lys Gly Ile Ile Asp Ser Thr His Thr Glu Gln Arg Gln Val Val Ala
805 810 815

Val Thr Gly Asp Gly Thr Asn Asp Gly Pro Ala Leu Lys Lys Ala Asp
820 825 830

Val Gly Phe Ala Met Gly Ile Ala Gly Thr Asp Val Ala Lys Glu Ala
835 840 845

Ser Asp Ile Ile Leu Thr Asp Asp Asn Phe Ser Ser Ile Val Lys Ala
850 855 860

Val Met Trp Gly Arg Asn Val Tyr Asp Ser Ile Ser Lys Phe Leu Gln
865 870 875 880

Phe Gln Leu Thr Val Asn Val Val Ala Val Ile Val Ala Phe Thr Gly
885 890 895

Ala Cys Ile Thr Gln Asp Ser Pro Leu Lys Ala Val Gln Met Leu Trp
900 905 910

Val Asn Leu Ile Met Asp Thr Phe Ala Ser Leu Ala Leu Ala Thr Glu
915 920 925

Pro Pro Thr Glu Thr Leu Leu Leu Arg Lys Pro Tyr Gly Arg Asn Lys
930 935 940

Pro Leu Ile Ser Arg Thr Met Met Lys Asn Ile Leu Gly His Ala Val
945 950 955 960

Tyr Gln Leu Ala Leu Ile Phe Thr Leu Leu Phe Val Gly Glu Lys Met
965 970 975

Phe Gln Ile Asp Ser Gly Arg Asn Ala Pro Leu His Ser Pro Pro Ser
980 985 990

Glu His Tyr Thr Ile Ile Phe Asn Thr Phe Val Met Met Gln Leu Phe
995 1000 1005

Asn Glu Ile Asn Ala Arg Lys Ile His Gly Glu Arg Asn Val Phe
1010 1015 1020

Asp Gly Ile Phe Arg Asn Pro Ile Phe Cys Thr Ile Val Leu Gly
1025 1030 1035

Thr Phe Ala Ile Gln Ile Val Ile Val Gln Phe Gly Gly Lys Pro
1040 1045 1050

Phe Ser Cys Ser Pro Leu Gln Leu Asp Gln Trp Met Trp Cys Ile
1055 1060 1065

Phe Ile Gly Leu Gly Glu Leu Val Trp Gly Gln Val Ile Ala Thr
1070 1075 1080

Ile Pro Thr Ser Arg Leu Lys Phe Leu Lys Glu Ala Gly Arg Leu
1085 1090 1095

Thr Gln Lys Glu Glu Ile Pro Glu Glu Glu Leu Asn Glu Asp Val
1100 1105 1110

Glu Glu Ile Asp His Ala Glu Arg Glu Leu Arg Arg Gly Gln Ile
1115 1120 1125

```
Leu Trp  Phe Arg Gly Leu Asn  Arg Ile Gln Thr Gln  Ile Glu Val
    1130                 1135                 1140

Val Asn  Thr Phe Lys Ser Gly  Ala Ser Phe Gln Gly  Ala Leu Arg
    1145                 1150                 1155

Arg Gln  Ser Ser Val Thr Ser  Gln Ser Gln Asp Ile  Arg Val Val
    1160                 1165                 1170

Lys Ala  Phe Arg Ser Ser Leu  Tyr Glu Gly Leu Glu  Lys Pro Glu
    1175                 1180                 1185

Ser Arg  Thr Ser Ile His Asn  Phe Met Ala His Pro  Glu Phe Arg
    1190                 1195                 1200

Ile Glu  Asp Ser Gln Pro His  Ile Pro Leu Ile Asp  Asp Thr Asp
    1205                 1210                 1215

Leu Glu  Glu Asp Ala Ala Leu  Lys Gln Asn Ser Ser  Pro Pro Ser
    1220                 1225                 1230

Ser Leu  Asn Lys Asn Asn Ser  Ala Ile Asp Ser Gly  Ile Asn Leu
    1235                 1240                 1245

Thr Thr  Asp Thr Ser Lys Ser  Ala Thr Ser Ser Ser  Pro Gly Ser
    1250                 1255                 1260

Pro Ile  His Ser Leu Glu Thr  Ser Leu
    1265                 1270


<210> SEQ ID NO 31
<211> LENGTH: 1241
<212> TYPE: PRT
<213> ORGANISM: Homo sapiens

<400> SEQUENCE: 31

Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175

Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205

Gly Asp Ile Ala Gln Val Lys Tyr Gly Asp Leu Leu Pro Ala Asp Gly
```

-continued

```
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
                245                 250                 255

Leu Ser Gly Thr His Val Met Glu Gly Ser Gly Arg Met Val Val Thr
            260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Lys Gly Lys Lys Gln
    290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
                325                 330                 335

Lys Asp Lys Lys Ala Val Lys Val Pro Lys Lys Glu Lys Ser Val Leu
            340                 345                 350

Gln Gly Lys Leu Thr Arg Leu Ala Val Gln Ile Gly Lys Ala Gly Leu
        355                 360                 365

Leu Met Ser Ala Leu Thr Val Phe Ile Leu Ile Leu Tyr Phe Val Ile
    370                 375                 380

Asp Asn Phe Val Ile Asn Arg Arg Pro Trp Leu Pro Glu Cys Thr Pro
385                 390                 395                 400

Ile Tyr Ile Gln Tyr Phe Val Lys Phe Phe Ile Ile Gly Ile Thr Val
                405                 410                 415

Leu Val Val Ala Val Pro Glu Gly Leu Pro Leu Ala Val Thr Ile Ser
            420                 425                 430

Leu Ala Tyr Ser Val Lys Lys Met Met Lys Asp Asn Asn Leu Val Arg
        435                 440                 445

His Leu Asp Ala Cys Glu Thr Met Gly Asn Ala Thr Ala Ile Cys Ser
    450                 455                 460

Asp Lys Thr Gly Thr Leu Thr Met Asn Arg Met Thr Val Val Gln Ala
465                 470                 475                 480

Tyr Ile Gly Gly Ile His Tyr Arg Gln Ile Pro Ser Pro Asp Val Phe
                485                 490                 495

Leu Pro Lys Val Leu Asp Leu Ile Val Asn Gly Ile Ser Ile Asn Ser
            500                 505                 510

Ala Tyr Thr Ser Lys Ile Leu Pro Pro Glu Lys Glu Gly Gly Leu Pro
        515                 520                 525

Arg Gln Val Gly Asn Lys Thr Glu Cys Ala Leu Leu Gly Phe Val Thr
    530                 535                 540

Asp Leu Lys Gln Asp Tyr Gln Ala Val Arg Asn Glu Val Pro Glu Glu
545                 550                 555                 560

Lys Leu Tyr Lys Val Tyr Thr Phe Asn Ser Val Arg Lys Ser Met Ser
                565                 570                 575

Thr Val Ile Arg Asn Pro Asn Gly Gly Phe Arg Met Tyr Ser Lys Gly
            580                 585                 590

Ala Ser Glu Ile Ile Leu Arg Lys Cys Asn Arg Ile Leu Asp Arg Lys
        595                 600                 605

Gly Glu Ala Val Pro Phe Lys Asn Lys Asp Arg Asp Asp Met Val Arg
    610                 615                 620

Thr Val Ile Glu Pro Met Ala Cys Asp Gly Leu Arg Thr Ile Cys Ile
625                 630                 635                 640
```

```
Ala Tyr Arg Asp Phe Asp Asp Thr Glu Pro Ser Trp Asp Asn Glu Asn
                645                 650                 655

Glu Ile Leu Thr Glu Leu Thr Cys Ile Ala Val Val Gly Ile Glu Asp
            660                 665                 670

Pro Val Arg Pro Glu Val Pro Asp Ala Ile Ala Lys Cys Lys Gln Ala
        675                 680                 685

Gly Ile Thr Val Arg Met Val Thr Gly Asp Asn Ile Asn Thr Ala Arg
    690                 695                 700

Ala Ile Ala Thr Lys Cys Gly Ile Leu Thr Pro Gly Asp Asp Phe Leu
705                 710                 715                 720

Cys Leu Glu Gly Lys Glu Phe Asn Arg Leu Ile Arg Asn Glu Lys Gly
                725                 730                 735

Glu Val Glu Gln Glu Lys Leu Asp Lys Ile Trp Pro Lys Leu Arg Val
            740                 745                 750

Leu Ala Arg Ser Ser Pro Thr Asp Lys His Thr Leu Val Lys Gly Ile
        755                 760                 765

Ile Asp Ser Thr Val Gly Glu His Arg Gln Val Val Ala Val Thr Gly
    770                 775                 780

Asp Gly Thr Asn Asp Gly Pro Ala Leu Lys Lys Ala Asp Val Gly Phe
785                 790                 795                 800

Ala Met Gly Ile Ala Gly Thr Asp Val Ala Lys Glu Ala Ser Asp Ile
                805                 810                 815

Ile Leu Thr Asp Asp Asn Phe Thr Ser Ile Val Lys Ala Val Met Trp
            820                 825                 830

Gly Arg Asn Val Tyr Asp Ser Ile Ser Lys Phe Leu Gln Phe Gln Leu
        835                 840                 845

Thr Val Asn Val Val Ala Val Ile Val Ala Phe Thr Gly Ala Cys Ile
    850                 855                 860

Thr Gln Asp Ser Pro Leu Lys Ala Val Gln Met Leu Trp Val Asn Leu
865                 870                 875                 880

Ile Met Asp Thr Phe Ala Ser Leu Ala Leu Ala Thr Glu Pro Pro Thr
                885                 890                 895

Glu Ser Leu Leu Lys Arg Arg Pro Tyr Gly Arg Asn Lys Pro Leu Ile
            900                 905                 910

Ser Arg Thr Met Met Lys Asn Ile Leu Gly His Ala Phe Tyr Gln Leu
        915                 920                 925

Ile Val Ile Phe Ile Leu Val Phe Ala Gly Glu Lys Phe Phe Asp Ile
    930                 935                 940

Asp Ser Gly Arg Lys Ala Pro Leu His Ser Pro Pro Ser Gln His Tyr
945                 950                 955                 960

Thr Ile Val Phe Asn Thr Phe Val Leu Met Gln Leu Phe Asn Glu Ile
                965                 970                 975

Asn Ser Arg Lys Ile His Gly Glu Lys Asn Val Phe Ser Gly Ile Tyr
            980                 985                 990

Arg Asn Ile Ile Phe Cys Ser Val  Val Leu Gly Thr Phe  Ile Cys Gln
        995                 1000                1005

Ile Phe  Ile Val Glu Phe Gly  Gly Lys Pro Phe Ser  Cys Thr Ser
    1010                1015                1020

Leu Ser  Leu Ser Gln Trp Leu  Trp Cys Leu Phe Ile  Gly Ile Gly
    1025                1030                1035

Glu Leu  Leu Trp Gly Gln Phe  Ile Ser Ala Ile Pro  Thr Arg Ser
    1040                1045                1050
```

-continued

```
Leu Lys  Phe Leu Lys Glu Ala  Gly His Gly Thr Thr  Lys Glu Glu
    1055                 1060                 1065

Ile Thr  Lys Asp Ala Glu Gly  Leu Asp Glu Ile Asp  His Ala Glu
    1070                 1075                 1080

Met Glu  Leu Arg Arg Gly Gln  Ile Leu Trp Phe Arg  Gly Leu Asn
    1085                 1090                 1095

Arg Ile  Gln Thr Gln Ile Asp  Val Ile Asn Thr Phe  Gln Thr Gly
    1100                 1105                 1110

Ala Ser  Phe Lys Gly Val Leu  Arg Arg Gln Asn Met  Gly Gln His
    1115                 1120                 1125

Leu Asp  Val Lys Leu Val Pro  Ser Ser Ser Tyr Ile  Lys Val Val
    1130                 1135                 1140

Lys Ala  Phe His Ser Ser Leu  His Glu Ser Ile Gln  Lys Pro Tyr
    1145                 1150                 1155

Asn Gln  Lys Ser Ile His Ser  Phe Met Thr His Pro  Glu Phe Ala
    1160                 1165                 1170

Ile Glu  Glu Glu Leu Pro Arg  Thr Pro Leu Leu Asp  Glu Glu Glu
    1175                 1180                 1185

Glu Glu  Asn Pro Asp Lys Ala  Ser Lys Phe Gly Thr  Arg Val Leu
    1190                 1195                 1200

Leu Leu  Asp Gly Glu Val Thr  Pro Tyr Ala Asn Thr  Asn Asn Asn
    1205                 1210                 1215

Ala Val  Asp Cys Asn Gln Val  Gln Leu Pro Gln Ser  Asp Ser Ser
    1220                 1225                 1230

Leu Gln  Ser Leu Glu Thr Ser  Val
    1235                 1240


<210> SEQ ID NO 32
<211> LENGTH: 1241
<212> TYPE: PRT
<213> ORGANISM: homo sapiens

<400> SEQUENCE: 32

Met Thr Asn Pro Ser Asp Arg Val Leu Pro Ala Asn Ser Met Ala Glu
1               5                   10                  15

Ser Arg Glu Gly Asp Phe Gly Cys Thr Val Met Glu Leu Arg Lys Leu
            20                  25                  30

Met Glu Leu Arg Ser Arg Asp Ala Leu Thr Gln Ile Asn Val His Tyr
        35                  40                  45

Gly Gly Val Gln Asn Leu Cys Ser Arg Leu Lys Thr Ser Pro Val Glu
    50                  55                  60

Gly Leu Ser Gly Asn Pro Ala Asp Leu Glu Lys Arg Arg Gln Val Phe
65                  70                  75                  80

Gly His Asn Val Ile Pro Pro Lys Lys Pro Lys Thr Phe Leu Glu Leu
                85                  90                  95

Val Trp Glu Ala Leu Gln Asp Val Thr Leu Ile Ile Leu Glu Ile Ala
            100                 105                 110

Ala Ile Ile Ser Leu Val Leu Ser Phe Tyr Arg Pro Ala Gly Glu Glu
        115                 120                 125

Asn Glu Leu Cys Gly Gln Val Ala Thr Thr Pro Glu Asp Glu Asn Glu
    130                 135                 140

Ala Gln Ala Gly Trp Ile Glu Gly Ala Ala Ile Leu Phe Ser Val Ile
145                 150                 155                 160

Ile Val Val Leu Val Thr Ala Phe Asn Asp Trp Ser Lys Glu Lys Gln
                165                 170                 175
```

```
Phe Arg Gly Leu Gln Cys Arg Ile Glu Gln Glu Gln Lys Phe Ser Ile
            180                 185                 190

Ile Arg Asn Gly Gln Leu Ile Gln Leu Pro Val Ala Glu Ile Val Val
        195                 200                 205

Gly Asp Ile Ala Gln Val Lys Tyr Gly Asp Leu Leu Pro Ala Asp Gly
    210                 215                 220

Ile Leu Ile Gln Gly Asn Asp Leu Lys Ile Asp Glu Ser Ser Leu Thr
225                 230                 235                 240

Gly Glu Ser Asp His Val Lys Lys Ser Leu Asp Lys Asp Pro Met Leu
                245                 250                 255

Leu Ser Gly Thr His Val Met Glu Gly Ser Gly Arg Met Val Val Thr
            260                 265                 270

Ala Val Gly Val Asn Ser Gln Thr Gly Ile Ile Leu Thr Leu Leu Gly
        275                 280                 285

Val Asn Glu Asp Asp Glu Gly Glu Lys Lys Lys Lys Gly Lys Lys Gln
    290                 295                 300

Gly Val Pro Glu Asn Arg Asn Lys Ala Lys Thr Gln Asp Gly Val Ala
305                 310                 315                 320

Leu Glu Ile Gln Pro Leu Asn Ser Gln Glu Gly Ile Asp Asn Glu Glu
                325                 330                 335

Lys Asp Lys Lys Ala Val Lys Val Pro Lys Lys Glu Lys Ser Val Leu
            340                 345                 350

Gln Gly Lys Leu Thr Arg Leu Ala Val Gln Ile Gly Lys Ala Gly Leu
        355                 360                 365

Leu Met Ser Ala Leu Thr Val Phe Ile Leu Ile Leu Tyr Phe Val Ile
    370                 375                 380

Asp Asn Phe Val Ile Asn Arg Arg Pro Trp Leu Pro Glu Cys Thr Pro
385                 390                 395                 400

Ile Tyr Ile Gln Tyr Phe Val Lys Phe Phe Ile Ile Gly Ile Thr Val
                405                 410                 415

Leu Val Val Ala Val Pro Glu Gly Leu Pro Leu Ala Val Thr Ile Ser
            420                 425                 430

Leu Ala Tyr Ser Val Lys Lys Met Met Lys Asp Asn Asn Leu Val Arg
        435                 440                 445

His Leu Asp Ala Cys Glu Thr Met Gly Asn Ala Thr Ala Ile Cys Ser
    450                 455                 460

Asp Lys Thr Gly Thr Leu Thr Met Asn Arg Met Thr Val Val Gln Ala
465                 470                 475                 480

Tyr Ile Gly Gly Ile His Tyr Arg Gln Ile Pro Ser Pro Asp Val Phe
                485                 490                 495

Leu Pro Lys Val Leu Asp Leu Ile Val Asn Gly Ile Ser Ile Asn Ser
            500                 505                 510

Ala Tyr Thr Ser Lys Ile Leu Pro Pro Glu Lys Glu Gly Gly Leu Pro
        515                 520                 525

Arg Gln Val Gly Asn Lys Thr Glu Cys Ala Leu Leu Gly Phe Val Thr
    530                 535                 540

Asp Leu Lys Gln Asp Tyr Gln Ala Val Arg Asn Glu Val Pro Glu Glu
545                 550                 555                 560

Lys Leu Tyr Lys Val Tyr Thr Phe Asn Ser Val Arg Lys Ser Met Ser
                565                 570                 575

Thr Val Ile Arg Asn Pro Asn Gly Gly Phe Arg Met Tyr Ser Lys Gly
            580                 585                 590
```

-continued

```
Ala Ser Glu Ile Ile Leu Arg Lys Cys Asn Arg Ile Leu Asp Arg Lys
        595                 600                 605

Gly Glu Ala Val Pro Phe Lys Asn Lys Asp Arg Asp Asp Met Val Arg
    610                 615                 620

Thr Val Ile Glu Pro Met Ala Cys Asp Gly Leu Arg Thr Ile Cys Ile
625                 630                 635                 640

Ala Tyr Arg Asp Phe Asp Asp Thr Glu Pro Ser Trp Asp Asn Glu Asn
                645                 650                 655

Glu Ile Leu Thr Glu Leu Thr Cys Ile Ala Val Val Gly Ile Glu Asp
            660                 665                 670

Pro Val Arg Pro Glu Val Pro Asp Ala Ile Ala Lys Cys Lys Gln Ala
        675                 680                 685

Gly Ile Thr Val Arg Met Val Thr Gly Asp Asn Ile Asn Thr Ala Arg
    690                 695                 700

Ala Ile Ala Thr Lys Cys Gly Ile Leu Thr Pro Gly Asp Asp Phe Leu
705                 710                 715                 720

Cys Leu Glu Gly Lys Glu Phe Asn Arg Leu Ile Arg Asn Glu Lys Gly
                725                 730                 735

Glu Val Glu Gln Glu Lys Leu Asp Lys Ile Trp Pro Lys Leu Arg Val
            740                 745                 750

Leu Ala Arg Ser Ser Pro Thr Asp Lys His Thr Leu Val Lys Gly Ile
        755                 760                 765

Ile Asp Ser Thr Val Gly Glu His Arg Gln Val Val Ala Val Thr Gly
    770                 775                 780

Asp Gly Thr Asn Asp Gly Pro Ala Leu Lys Lys Ala Asp Val Gly Phe
785                 790                 795                 800

Ala Met Gly Ile Ala Gly Thr Asp Val Ala Lys Glu Ala Ser Asp Ile
                805                 810                 815

Ile Leu Thr Asp Asp Asn Phe Thr Ser Ile Val Lys Ala Val Met Trp
            820                 825                 830

Gly Arg Asn Val Tyr Asp Ser Ile Ser Lys Phe Leu Gln Phe Gln Leu
        835                 840                 845

Thr Val Asn Val Val Ala Val Ile Val Ala Phe Thr Gly Ala Cys Ile
    850                 855                 860

Thr Gln Asp Ser Pro Leu Lys Ala Val Gln Met Leu Trp Val Asn Leu
865                 870                 875                 880

Ile Met Asp Thr Phe Ala Ser Leu Ala Leu Ala Thr Glu Pro Pro Thr
                885                 890                 895

Glu Ser Leu Leu Lys Arg Arg Pro Tyr Gly Arg Asn Lys Pro Leu Ile
            900                 905                 910

Ser Arg Thr Met Met Lys Asn Ile Leu Gly His Ala Phe Tyr Gln Leu
        915                 920                 925

Ile Val Ile Phe Ile Leu Val Phe Ala Gly Glu Lys Phe Phe Asp Ile
    930                 935                 940

Asp Ser Gly Arg Lys Ala Pro Leu His Ser Pro Pro Ser Gln His Tyr
945                 950                 955                 960

Thr Ile Val Phe Asn Thr Phe Val Leu Met Gln Leu Phe Asn Glu Ile
                965                 970                 975

Asn Ser Arg Lys Ile His Gly Glu Lys Asn Val Phe Ser Gly Ile Tyr
            980                 985                 990

Arg Asn Ile Ile Phe Cys Ser Val  Val Leu Gly Thr Phe  Ile Cys Gln
        995                 1000                1005

Ile Phe  Ile Val Glu Phe Gly  Gly Lys Pro Phe Ser  Cys Thr Ser
```

1010 1015 1020

Leu Ser Leu Ser Gln Trp Leu Trp Cys Leu Phe Ile Gly Ile Gly
1025 1030 1035

Glu Leu Leu Trp Gly Gln Phe Ile Ser Ala Ile Pro Thr Arg Ser
1040 1045 1050

Leu Lys Phe Leu Lys Glu Ala Gly His Gly Thr Thr Lys Glu Glu
1055 1060 1065

Ile Thr Lys Asp Ala Glu Gly Leu Asp Glu Ile Asp His Ala Glu
1070 1075 1080

Met Glu Leu Arg Arg Gly Gln Ile Leu Trp Phe Arg Gly Leu Asn
1085 1090 1095

Arg Ile Gln Thr Gln Ile Asp Val Ile Asn Thr Phe Gln Thr Gly
1100 1105 1110

Ala Ser Phe Lys Gly Val Leu Arg Arg Gln Asn Met Gly Gln His
1115 1120 1125

Leu Asp Val Lys Leu Val Pro Ser Ser Ser Tyr Ile Lys Val Val
1130 1135 1140

Lys Ala Phe His Ser Ser Leu His Glu Ser Ile Gln Lys Pro Tyr
1145 1150 1155

Asn Gln Lys Ser Ile His Ser Phe Met Thr His Pro Glu Phe Ala
1160 1165 1170

Ile Glu Glu Glu Leu Pro Arg Thr Pro Leu Leu Asp Glu Glu Glu
1175 1180 1185

Glu Glu Asn Pro Asp Lys Ala Ser Lys Phe Gly Thr Arg Val Leu
1190 1195 1200

Leu Leu Asp Gly Glu Val Thr Pro Tyr Ala Asn Thr Asn Asn Asn
1205 1210 1215

Ala Val Asp Cys Asn Gln Val Gln Leu Pro Gln Ser Asp Ser Ser
1220 1225 1230

Leu Gln Ser Leu Glu Thr Ser Val
1235 1240

<210> SEQ ID NO 33
<211> LENGTH: 193
<212> TYPE: PRT
<213> ORGANISM: homo sapiens

<400> SEQUENCE: 33

Gly Pro Ile Phe Asn Ala Ser Val His Ser Asp Thr Pro Ser Val Ile
1 5 10 15

Arg Gly Asp Leu Ile Lys Leu Phe Cys Ile Ile Thr Val Glu Gly Ala
20 25 30

Ala Leu Asp Pro Asp Asp Met Ala Phe Asp Val Ser Trp Phe Ala Val
35 40 45

His Ser Phe Gly Leu Asp Lys Ala Pro Val Leu Leu Ser Ser Leu Asp
50 55 60

Arg Lys Gly Ile Val Thr Thr Ser Arg Arg Asp Trp Lys Ser Asp Leu
65 70 75 80

Ser Leu Glu Arg Val Ser Val Leu Glu Phe Leu Leu Gln Val His Gly
85 90 95

Ser Glu Asp Gln Asp Phe Gly Asn Tyr Tyr Cys Ser Val Thr Pro Trp
100 105 110

Val Lys Ser Pro Thr Gly Ser Trp Gln Lys Glu Ala Glu Ile His Ser
115 120 125

-continued

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160

Ser Cys Leu Ile Gly Tyr Cys Ser Ser His Trp Cys Cys Lys Lys Glu
                165                 170                 175

Val Gln Glu Thr Arg Arg Glu Arg Arg Arg Leu Met Ser Met Glu Met
            180                 185                 190

Asp

<210> SEQ ID NO 34
<211> LENGTH: 1021
<212> TYPE: PRT
<213> ORGANISM: homo sapiens

<400> SEQUENCE: 34

Met Ala Gly Ile Ser Tyr Val Ala Ser Phe Phe Leu Leu Leu Thr Lys
1               5                   10                  15

Leu Ser Ile Gly Gln Arg Glu Val Thr Val Gln Lys Gly Pro Leu Phe
            20                  25                  30

Arg Ala Glu Gly Tyr Pro Val Ser Ile Gly Cys Asn Val Thr Gly His
        35                  40                  45

Gln Gly Pro Ser Glu Gln His Phe Gln Trp Ser Val Tyr Leu Pro Thr
    50                  55                  60

Asn Pro Thr Gln Glu Val Gln Ile Ile Ser Thr Lys Asp Ala Ala Phe
65                  70                  75                  80

Ser Tyr Ala Val Tyr Thr Gln Arg Val Arg Ser Gly Asp Val Tyr Val
                85                  90                  95

Glu Arg Val Gln Gly Asn Ser Val Leu Leu His Ile Ser Lys Leu Gln
            100                 105                 110

Met Lys Asp Ala Gly Glu Tyr Glu Cys His Thr Pro Asn Thr Asp Glu
        115                 120                 125

Lys Tyr Tyr Gly Ser Tyr Ser Ala Lys Thr Asn Leu Ile Val Ile Pro
    130                 135                 140

Asp Thr Leu Ser Ala Thr Met Ser Ser Gln Thr Leu Gly Lys Glu Glu
145                 150                 155                 160

Gly Glu Pro Leu Ala Leu Thr Cys Glu Ala Ser Lys Ala Thr Ala Gln
                165                 170                 175

His Thr His Leu Ser Val Thr Trp Tyr Leu Thr Gln Asp Gly Gly Gly
            180                 185                 190

Ser Gln Ala Thr Glu Ile Ile Ser Leu Ser Lys Asp Phe Ile Leu Val
        195                 200                 205

Pro Gly Pro Leu Tyr Thr Glu Arg Phe Ala Ala Ser Asp Val Gln Leu
    210                 215                 220

Asn Lys Leu Gly Pro Thr Thr Phe Arg Leu Ser Ile Glu Arg Leu Gln
225                 230                 235                 240

Ser Ser Asp Gln Gly Gln Leu Phe Cys Glu Ala Thr Glu Trp Ile Gln
                245                 250                 255

Asp Pro Asp Glu Thr Trp Met Phe Ile Thr Lys Lys Gln Thr Asp Gln
            260                 265                 270

Thr Thr Leu Arg Ile Gln Pro Ala Val Lys Asp Phe Gln Val Asn Ile
        275                 280                 285

Thr Ala Asp Ser Leu Phe Ala Glu Gly Lys Pro Leu Glu Leu Val Cys
    290                 295                 300

-continued

```
Leu Val Val Ser Ser Gly Arg Asp Pro Gln Leu Gln Gly Ile Trp Phe
305                 310                 315                 320

Phe Asn Gly Thr Glu Ile Ala His Ile Asp Ala Gly Gly Val Leu Gly
                325                 330                 335

Leu Lys Asn Asp Tyr Lys Glu Arg Ala Ser Gln Gly Glu Leu Gln Val
            340                 345                 350

Ser Lys Leu Gly Pro Lys Ala Phe Ser Leu Lys Ile Phe Ser Leu Gly
        355                 360                 365

Pro Glu Asp Glu Gly Ala Tyr Arg Cys Val Val Ala Glu Val Met Lys
    370                 375                 380

Thr Arg Thr Gly Ser Trp Gln Val Leu Gln Arg Lys Gln Ser Pro Asp
385                 390                 395                 400

Ser His Val His Leu Arg Lys Pro Ala Ala Arg Ser Val Val Met Ser
                405                 410                 415

Thr Lys Asn Lys Gln Gln Val Val Trp Glu Gly Glu Thr Leu Ala Phe
            420                 425                 430

Leu Cys Lys Ala Gly Gly Ala Glu Ser Pro Leu Ser Val Ser Trp Trp
        435                 440                 445

His Ile Pro Arg Asp Gln Thr Gln Pro Glu Phe Val Ala Gly Met Gly
    450                 455                 460

Gln Asp Gly Ile Val Gln Leu Gly Ala Ser Tyr Gly Val Pro Ser Tyr
465                 470                 475                 480

His Gly Asn Thr Arg Leu Glu Lys Met Asp Trp Ala Thr Phe Gln Leu
                485                 490                 495

Glu Ile Thr Phe Thr Ala Ile Thr Asp Ser Gly Thr Tyr Glu Cys Arg
            500                 505                 510

Val Ser Glu Lys Ser Arg Asn Gln Ala Arg Asp Leu Ser Trp Thr Gln
        515                 520                 525

Lys Ile Ser Val Thr Val Lys Ser Leu Glu Ser Ser Leu Gln Val Ser
    530                 535                 540

Leu Met Ser Arg Gln Pro Gln Val Met Leu Thr Asn Thr Phe Asp Leu
545                 550                 555                 560

Ser Cys Val Val Arg Ala Gly Tyr Ser Asp Leu Lys Val Pro Leu Thr
                565                 570                 575

Val Thr Trp Gln Phe Gln Pro Ala Ser Ser His Ile Phe His Gln Leu
            580                 585                 590

Ile Arg Ile Thr His Asn Gly Thr Ile Glu Trp Gly Asn Phe Leu Ser
        595                 600                 605

Arg Phe Gln Lys Lys Thr Lys Val Ser Gln Ser Leu Phe Arg Ser Gln
    610                 615                 620

Leu Leu Val His Asp Ala Thr Glu Glu Glu Thr Gly Val Tyr Gln Cys
625                 630                 635                 640

Glu Val Glu Val Tyr Asp Arg Asn Ser Leu Tyr Asn Asn Arg Pro Pro
                645                 650                 655

Arg Ala Ser Ala Ile Ser His Pro Leu Arg Ile Ala Val Thr Leu Pro
            660                 665                 670

Glu Ser Lys Leu Lys Val Asn Ser Arg Ser Gln Val Gln Glu Leu Ser
        675                 680                 685

Ile Asn Ser Asn Thr Asp Ile Glu Cys Ser Ile Leu Ser Arg Ser Asn
    690                 695                 700

Gly Asn Leu Gln Leu Ala Ile Ile Trp Tyr Phe Ser Pro Val Ser Thr
705                 710                 715                 720

Asn Ala Ser Trp Leu Lys Ile Leu Glu Met Asp Gln Thr Asn Val Ile
```

```
                725                 730                 735

Lys Thr Gly Asp Glu Phe His Thr Pro Gln Arg Lys Gln Lys Phe His
            740                 745                 750

Thr Glu Lys Val Ser Gln Asp Leu Phe Gln Leu His Ile Leu Asn Val
        755                 760                 765

Glu Asp Ser Asp Arg Gly Lys Tyr His Cys Ala Val Glu Glu Trp Leu
    770                 775                 780

Leu Ser Thr Asn Gly Thr Trp His Lys Leu Gly Glu Lys Lys Ser Gly
785                 790                 795                 800

Leu Thr Glu Leu Lys Leu Lys Pro Thr Gly Ser Lys Val Arg Val Ser
                805                 810                 815

Lys Val Tyr Trp Thr Glu Asn Val Thr Glu His Arg Glu Val Ala Ile
            820                 825                 830

Arg Cys Ser Leu Glu Ser Val Gly Ser Ser Ala Thr Leu Tyr Ser Val
        835                 840                 845

Met Trp Tyr Trp Asn Arg Glu Asn Ser Gly Ser Lys Leu Leu Val His
    850                 855                 860

Leu Gln His Asp Gly Leu Leu Glu Tyr Gly Glu Glu Gly Leu Arg Arg
865                 870                 875                 880

His Leu His Cys Tyr Arg Ser Ser Ser Thr Asp Phe Val Leu Lys Leu
                885                 890                 895

His Gln Val Glu Met Glu Asp Ala Gly Met Tyr Trp Cys Arg Val Ala
            900                 905                 910

Glu Trp Gln Leu His Gly His Pro Ser Lys Trp Ile Asn Gln Ala Ser
        915                 920                 925

Asp Glu Ser Gln Arg Met Val Leu Thr Val Leu Pro Ser Glu Pro Thr
    930                 935                 940

Leu Pro Ser Arg Ile Cys Ser Ser Ala Pro Leu Leu Tyr Phe Leu Phe
945                 950                 955                 960

Ile Cys Pro Phe Val Leu Leu Leu Leu Leu Leu Ile Ser Leu Leu Cys
                965                 970                 975

Leu Tyr Trp Lys Ala Arg Lys Leu Ser Thr Leu Arg Ser Asn Thr Arg
            980                 985                 990

Lys Glu Lys Ala Leu Trp Val Asp  Leu Lys Glu Ala Gly  Gly Val Thr
        995                 1000                1005

Thr Asn  Arg Arg Glu Asp Glu  Glu Glu Asp Glu Gly  Asn
    1010                 1015                 1020
```

<210> SEQ ID NO 35
<211> LENGTH: 20
<212> TYPE: PRT
<213> ORGANISM: homo sapiens

<400> SEQUENCE: 35

```
Met Ala Gly Ile Ser Tyr Val Ala Ser Phe Phe Leu Leu Leu Thr Lys
1               5                   10                  15

Leu Ser Ile Gly
            20
```

<210> SEQ ID NO 36
<211> LENGTH: 20
<212> TYPE: DNA
<213> ORGANISM: Artificial Sequence
<220> FEATURE:
<223> OTHER INFORMATION: Synthetic  Oligonucleotide

<400> SEQUENCE: 36
cgttggcagt ccgccttaac 20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
catagtcact gacgttgcag 20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ttgtggagct tgcaagcacc 20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gttctttatg tggagctcca 20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
tatcccttgc tgatcggcgt 20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gctgcagtac ccgatgagac 20

<210> SEQ ID NO 42
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 42

```
Glu His Ser Ala Gly Gly Gly Gly Ser Asp Tyr Lys Asp Asp Asp Asp
1               5                   10                  15

Lys Gly Gly Gly Gly Ser Leu Ser Asn Pro Ile Glu Ile Asp Phe Gln
            20                  25                  30
```

Thr Ser Gly Pro Ile Phe
35

<210> SEQ ID NO 43
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 43

Glu His Ser Ala Gly Gly Gly Gly Ser Asp Tyr Lys Asp Asp Asp Asp
1 5 10 15

Lys Gly Gly Gly Gly Ser Ile Glu Ile Asp Phe Gln Thr Ser Gly Pro
20 25 30

Ile Phe

<210> SEQ ID NO 44
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 44

Glu His Ser Ala Gly Gly Gly Gly Ser Asp Tyr Lys Asp Asp Asp Asp
1 5 10 15

Lys Gly Gly Gly Gly Ser Phe Gln Thr Ser Gly Pro Ile Phe
20 25 30

<210> SEQ ID NO 45
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 45

Glu His Ser Ala Gly Gly Gly Gly Ser Asp Tyr Lys Asp Asp Asp Asp
1 5 10 15

Lys Gly Gly Gly Gly Ser Gly Pro Ile Phe
20 25

<210> SEQ ID NO 46
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 46

Phe Ile Thr Val Lys Met Asp Thr Leu Asp Pro Arg Ser Phe Leu Leu
1 5 10 15

Arg Asn Pro Asn Asp Lys Tyr Glu Pro Phe Trp Glu Asp Glu Glu Lys
20 25 30

Asn Glu Ser Gly Ser Asp Lys Thr His Thr
35 40

<210> SEQ ID NO 47
<211> LENGTH: 332
<212> TYPE: PRT
<213> ORGANISM: Homo sapiens

<400> SEQUENCE: 47

```
Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Ala Gly Ser Gly Ala Ala
65                  70                  75                  80

Ser Pro Ser Ala Ala Glu Lys Gly Glu Pro Ala Ala Ala Ala Ala Pro
                85                  90                  95

Glu Ala Gly Ala Ser Pro Val Glu Lys Glu Ala Pro Ala Glu Gly Glu
            100                 105                 110

Ala Ala Glu Pro Gly Ser Pro Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Ala Glu Ala Gly
        195                 200                 205

Ala Ala Ser Gly Glu Gln Ala Ala Ala Pro Gly Glu Glu Ala Ala Ala
    210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Pro Gly
        275                 280                 285

Ala Pro Pro Glu Gln Glu Ala Ala Pro Ala Glu Glu Pro Ala Ala Ala
    290                 295                 300

Ala Ala Ser Ser Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330
```

<210> SEQ ID NO 48
<211> LENGTH: 195
<212> TYPE: PRT
<213> ORGANISM: Homo sapiens

<400> SEQUENCE: 48

```
Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
            20                  25                  30

His Val Lys Ser Asn Gly Asp Leu Ser Pro Lys Gly Glu Gly Glu Ser
```

```
        35                  40                  45

Pro Pro Val Asn Gly Thr Asp Glu Ala Ala Gly Ala Thr Gly Asp Ala
    50                  55                  60

Ile Glu Pro Ala Pro Pro Ser Gln Gly Ala Glu Ala Lys Gly Glu Val
65                  70                  75                  80

Pro Pro Lys Glu Thr Pro Lys Lys Lys Lys Lys Phe Ser Phe Lys Lys
                85                  90                  95

Pro Phe Lys Leu Ser Gly Leu Ser Phe Lys Arg Asn Arg Lys Glu Gly
            100                 105                 110

Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
    130                 135                 140

Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195


<210> SEQ ID NO 49
<211> LENGTH: 227
<212> TYPE: PRT
<213> ORGANISM: Homo sapiens

<400> SEQUENCE: 49

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala Ala
        115                 120                 125

Pro Ala Glu Ser Ala Ala Pro Ala Ala Gly Glu Glu Pro Ser Lys Glu
    130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205
```

-continued

Pro Lys Pro Val Glu Ala Pro Ala Ala Asn Ser Asp Gln Thr Val Thr
    210                 215                 220

Val Lys Glu
225

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu
            20                  25

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met Gly Gly Lys Leu Ser Lys Lys Lys Lys Gly Tyr Asn Val Asn Asp
1               5                   10                  15

Glu Lys Ala Lys Glu Lys Asp Lys
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Gly Gly Lys Leu Ser Lys Lys Lys Lys Gly Tyr Asn Val Asn Asp
1               5                   10                  15

Glu Lys Ala Lys Glu
            20

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Met Gly Gly Lys Leu Ser Lys Lys Lys Lys Gly Tyr Asn Val Asn Asp
1 5 10 15

Glu Lys

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Met Gly Gly Lys Leu Ser Lys Lys Lys Lys Gly Tyr Asn Val Asn
1 5 10 15

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Met Gly Gly Lys Leu Ser Lys Lys Lys Lys Gly Tyr
1 5 10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Met Gly Gly Lys Leu Ser Lys Lys Lys Lys Gly
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Met Gly Gly Lys Leu Ser Lys Lys Lys Lys
1 5 10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Met Gly Gly Lys Leu Ser Lys Lys Lys 1 5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Met Gly Gly Lys Leu Ser Lys Lys
1 5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Met Gly Gly Lys Leu Ser Lys
1 5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Met Gly Gly Lys Leu Ala Lys Lys
1 5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Met Gly Gly Lys Phe Ser Lys Lys
1 5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Met Gly Gly Lys Phe Ala Lys Lys
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Met Gly Gly Lys Ser Ser Lys Lys
1 5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Met Gly Gly Lys Ser Ala Lys Lys
1 5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Met Gly Gly Lys Gln Ser Lys Lys
1 5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Met Gly Gly Lys Gln Ala Lys Lys
1 5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Met Gly Gly Gln Leu Ser Lys Lys
1 5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Met Gly Gly Gln Leu Ala Lys Lys
1 5

<210> SEQ ID NO 71

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Met Gly Gly Gln Phe Ser Lys Lys
1 5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Met Gly Gly Gln Phe Ala Lys Lys
1 5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Met Gly Gly Gln Ser Ser Lys Lys
1 5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Met Gly Gly Gln Ser Ala Lys Lys
1 5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Met Gly Gly Gln Gln Ser Lys Lys
1 5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Met Gly Gly Gln Gln Ala Lys Lys
1 5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Met Gly Ala Lys Leu Ser Lys Lys
1 5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Met Gly Ala Lys Leu Ala Lys Lys
1 5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Met Gly Ala Lys Phe Ser Lys Lys
1 5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Met Gly Ala Lys Phe Ala Lys Lys
1 5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Met Gly Ala Lys Ser Ser Lys Lys
1 5

<210> SEQ ID NO 82
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 82

Met Gly Ala Lys Ser Ala Lys Lys
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Gly Ala Lys Gln Ser Lys Lys
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Gly Ala Lys Gln Ala Lys Lys
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Gly Ala Gln Leu Ser Lys Lys
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Gly Ala Gln Leu Ala Lys Lys
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met Gly Ala Gln Phe Ser Lys Lys
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Met Gly Ala Gln Phe Ala Lys Lys
1 5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Met Gly Ala Gln Ser Ser Lys Lys
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Met Gly Ala Gln Ser Ala Lys Lys
1 5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Met Gly Ala Gln Gln Ser Lys Lys
1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Met Gly Ala Gln Gln Ala Lys Lys
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Met Gly Ser Lys Leu Ser Lys Lys
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Gly Ser Lys Leu Ala Lys Lys
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Met Gly Ser Lys Phe Ser Lys Lys
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met Gly Ser Lys Phe Ala Lys Lys
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met Gly Ser Lys Ser Ser Lys Lys
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Gly Ser Lys Ser Ala Lys Lys
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Met Gly Ser Lys Gln Ser Lys Lys
1 5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Met Gly Ser Lys Gln Ala Lys Lys
1 5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Met Gly Ser Gln Leu Ser Lys Lys
1 5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Met Gly Ser Gln Leu Ala Lys Lys
1 5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Met Gly Ser Gln Phe Ser Lys Lys
1 5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Met Gly Ser Gln Phe Ala Lys Lys
1 5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Met Gly Ser Gln Ser Ser Lys Lys
1 5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Met Gly Ser Gln Ser Ala Lys Lys
1 5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Met Gly Ser Gln Gln Ser Lys Lys
1 5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Met Gly Ser Gln Gln Ala Lys Lys
1 5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Met Gly Gly Lys Leu Ala Lys
1 5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Met Gly Gly Lys Phe Ser Lys
1 5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Met Gly Gly Lys Phe Ala Lys
1 5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Met Gly Gly Lys Ser Ser Lys
1 5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Met Gly Gly Lys Ser Ala Lys
1 5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Met Gly Gly Lys Gln Ser Lys
1 5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Met Gly Gly Lys Gln Ala Lys
1 5

<210> SEQ ID NO 116
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 116

Met Gly Gly Gln Leu Ser Lys
1 5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Met Gly Gly Gln Leu Ala Lys
1 5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Met Gly Gly Gln Phe Ser Lys
1 5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Met Gly Gly Gln Phe Ala Lys
1 5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Met Gly Gly Gln Ser Ser Lys
1 5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Met Gly Gly Gln Ser Ala Lys
1 5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Met Gly Gly Gln Gln Ser Lys
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Met Gly Gly Gln Gln Ala Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Met Gly Ala Lys Leu Ser Lys
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Met Gly Ala Lys Leu Ala Lys
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Met Gly Ala Lys Phe Ser Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Met Gly Ala Lys Phe Ala Lys
1 5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Met Gly Ala Lys Ser Ser Lys
1 5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Met Gly Ala Lys Ser Ala Lys
1 5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Met Gly Ala Lys Gln Ser Lys
1 5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Met Gly Ala Lys Gln Ala Lys
1 5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Met Gly Ala Gln Leu Ser Lys
1 5

<210> SEQ ID NO 133
<211> LENGTH: 7

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Met Gly Ala Gln Leu Ala Lys
1 5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Met Gly Ala Gln Phe Ser Lys
1 5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Met Gly Ala Gln Phe Ala Lys
1 5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Met Gly Ala Gln Ser Ser Lys
1 5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Met Gly Ala Gln Ser Ala Lys
1 5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Met Gly Ala Gln Gln Ser Lys 1 5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Met Gly Ala Gln Gln Ala Lys
1 5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Met Gly Ser Lys Leu Ser Lys
1 5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Met Gly Ser Lys Leu Ala Lys
1 5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Met Gly Ser Lys Phe Ser Lys
1 5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Met Gly Ser Lys Phe Ala Lys
1 5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Met Gly Ser Lys Ser Ser Lys
1 5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Met Gly Ser Lys Ser Ala Lys
1 5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Met Gly Ser Lys Gln Ser Lys
1 5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Met Gly Ser Lys Gln Ala Lys
1 5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Met Gly Ser Gln Leu Ser Lys
1 5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Met Gly Ser Gln Leu Ala Lys
1 5

<210> SEQ ID NO 150

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Met Gly Ser Gln Phe Ser Lys
1 5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Met Gly Ser Gln Phe Ala Lys
1 5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Met Gly Ser Gln Ser Ser Lys
1 5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Met Gly Ser Gln Ser Ala Lys
1 5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Met Gly Ser Gln Gln Ser Lys
1 5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Met Gly Ser Gln Gln Ala Lys
1 5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Met Gly Ala Lys Leu Ser Lys Lys Lys
1 5

<210> SEQ ID NO 157
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Gly
20 25 30

Gly Ser Gly Gly Ser Asp Tyr Lys Asp Asp Asp Asp Lys Gly Gly Gly
35 40 45

Ser Gly Met Ala Ser Asn Phe Thr Gln Phe Val Leu Val Asp Asn Gly
50 55 60

Gly Thr Gly Asp Val Thr Val Ala Pro Ser Asn Phe Ala Asn Gly Ile
65 70 75 80

Ala Glu Trp Ile Ser Ser Asn Ser Arg Ser Gln Ala Tyr Lys Val Thr
85 90 95

Cys Ser Val Arg Gln Ser Ser Ala Gln Asn Arg Lys Tyr Thr Ile Lys
100 105 110

Val Glu Val Pro Lys Gly Ala Trp Arg Ser Tyr Leu Asn Met Glu Leu
115 120 125

Thr Ile Pro Ile Phe Ala Thr Asn Ser Asp Cys Glu Leu Ile Val Lys
130 135 140

Ala Met Gln Gly Leu Leu Lys Asp Gly Asn Pro Ile Pro Ser Ala Ile
145 150 155 160

Ala Ala Asn Ser Gly Ile Tyr
165

<210> SEQ ID NO 158
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Gly
20 25 30

Gly Ser Gly Gly Ser Asp Tyr Lys Asp Asp Asp Asp Lys Gly Gly Gly

```
        35                  40                  45

Ser Gly Met Ala Ser Asn Phe Thr Gln Phe Val Leu Val Asp Asn Gly
    50                  55                  60

Gly Thr Gly Asp Val Thr Val Ala Pro Ser Asn Phe Ala Asn Gly Ile
65                  70                  75                  80

Ala Glu Trp Ile Ser Ser Asn Ser Arg Ser Gln Ala Tyr Lys Val Thr
                85                  90                  95

Cys Ser Val Arg Gln Ser Ser Ala Gln Lys Arg Lys Tyr Thr Ile Lys
            100                 105                 110

Val Glu Val Pro Lys Gly Ala Trp Arg Ser Tyr Leu Asn Met Glu Leu
        115                 120                 125

Thr Ile Pro Ile Phe Ala Thr Asn Ser Asp Cys Glu Leu Ile Val Lys
    130                 135                 140

Ala Met Gln Gly Leu Leu Lys Asp Gly Asn Pro Ile Pro Ser Ala Ile
145                 150                 155                 160

Ala Ala Asn Ser Gly Ile Tyr
                165


<210> SEQ ID NO 159
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Ser Gly
            20                  25                  30

Gly Ser Gly Gly Ser Asp Tyr Lys Asp Asp Asp Asp Lys Gly Gly Gly
        35                  40                  45

Ser Gly Met Ala Ser Asn Phe Thr Gln Phe Val Leu Val Asp Asn Gly
    50                  55                  60

Gly Thr Gly Asp Val Thr Val Ala Pro Ser Asn Phe Ala Asn Gly Ile
65                  70                  75                  80

Ala Glu Trp Ile Ser Ser Asn Ser Arg Ser Gln Ala Tyr Lys Val Thr
                85                  90                  95

Cys Ser Val Arg Gln Ser Ser Ala Gln Asn Arg Lys Tyr Thr Ile Lys
            100                 105                 110

Val Glu Val Pro Lys Gly Ala Trp Arg Ser Tyr Leu Asn Met Glu Leu
        115                 120                 125

Thr Ile Pro Ile Phe Ala Thr Asn Ser Asp Cys Glu Leu Ile Val Lys
    130                 135                 140

Ala Met Gln Gly Leu Leu Lys Asp Gly Asn Pro Ile Pro Ser Ala Ile
145                 150                 155                 160

Ala Ala Asn Ser Gly Ile Tyr Gly Ser Gly Gly Ser Gly Gly Ser Gly
                165                 170                 175

Gly Ser Gly Met Ala Ser Asn Phe Thr Gln Phe Val Leu Val Asp Asn
            180                 185                 190

Gly Gly Thr Gly Asp Val Thr Val Ala Pro Ser Asn Phe Ala Asn Gly
        195                 200                 205

Ile Ala Glu Trp Ile Ser Ser Asn Ser Arg Ser Gln Ala Tyr Lys Val
    210                 215                 220
```

Thr Cys Ser Val Arg Gln Ser Ser Ala Gln Asn Arg Lys Tyr Thr Ile
225 230 235 240

Lys Val Glu Val Pro Lys Gly Ala Trp Arg Ser Tyr Leu Asn Met Glu
245 250 255

Leu Thr Ile Pro Ile Phe Ala Thr Asn Ser Asp Cys Glu Leu Ile Val
260 265 270

Lys Ala Met Gln Gly Leu Leu Lys Asp Gly Asn Pro Ile Pro Ser Ala
275 280 285

Ile Ala Ala Asn Ser Gly Ile Tyr
290 295

<210> SEQ ID NO 160
<211> LENGTH: 296
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Gly
20 25 30

Gly Ser Gly Gly Ser Asp Tyr Lys Asp Asp Asp Asp Lys Gly Gly Gly
35 40 45

Ser Gly Met Ala Ser Asn Phe Thr Gln Phe Val Leu Val Asp Asn Gly
50 55 60

Gly Thr Gly Asp Val Thr Val Ala Pro Ser Asn Phe Ala Asn Gly Ile
65 70 75 80

Ala Glu Trp Ile Ser Ser Asn Ser Arg Ser Gln Ala Tyr Lys Val Thr
85 90 95

Cys Ser Val Arg Gln Ser Ser Ala Gln Lys Arg Lys Tyr Thr Ile Lys
100 105 110

Val Glu Val Pro Lys Gly Ala Trp Arg Ser Tyr Leu Asn Met Glu Leu
115 120 125

Thr Ile Pro Ile Phe Ala Thr Asn Ser Asp Cys Glu Leu Ile Val Lys
130 135 140

Ala Met Gln Gly Leu Leu Lys Asp Gly Asn Pro Ile Pro Ser Ala Ile
145 150 155 160

Ala Ala Asn Ser Gly Ile Tyr Gly Ser Gly Gly Ser Gly Gly Ser Gly
165 170 175

Gly Ser Gly Met Ala Ser Asn Phe Thr Gln Phe Val Leu Val Asp Asn
180 185 190

Gly Gly Thr Gly Asp Val Thr Val Ala Pro Ser Asn Phe Ala Asn Gly
195 200 205

Ile Ala Glu Trp Ile Ser Ser Asn Ser Arg Ser Gln Ala Tyr Lys Val
210 215 220

Thr Cys Ser Val Arg Gln Ser Ser Ala Gln Lys Arg Lys Tyr Thr Ile
225 230 235 240

Lys Val Glu Val Pro Lys Gly Ala Trp Arg Ser Tyr Leu Asn Met Glu
245 250 255

Leu Thr Ile Pro Ile Phe Ala Thr Asn Ser Asp Cys Glu Leu Ile Val
260 265 270

Lys Ala Met Gln Gly Leu Leu Lys Asp Gly Asn Pro Ile Pro Ser Ala
275 280 285

Ile Ala Ala Asn Ser Gly Ile Tyr
    290                 295

<210> SEQ ID NO 161
<211> LENGTH: 680
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 161
augaagccca ccgagaacaa cgaagacuuc aacaucgugg ccguggccag caacuucgcg 60
accacggauc ucgaugcuga ccgcgggaag uugcccggca agaagcugcc gcuggaggug 120
cucaaagagu uggaagccaa ugcccggaaa gcuggcugca ccaggggcug ucugaucugc 180
cugucccaca ucaagugcac gcccaagaug aagaaguuca ucccaggacg cugccacacc 240
uacgaaggcg acaaagaguc cgcacagggc ggcauaggcg aggcgaucgu cgacauuccu 300
gagauuccug gguucaagga cuuggagccc uuggagcagu ucaucgcaca ggucgaucug 360
uguguggacu gcacaacugg cugccucaaa gggcuugcca acgugcagug uucugaccug 420
cucaagaagu ggcugccgca acgcugugcg accuuugcca gcaagaucca gggccaggug 480
gacaagauca agggggccgg uggugacuaa ggauccaucg auaagcuuca ucgaaacaug 540
aggaucaccc auaucugcag ucgacaucga aacaugagga ucacccaugu cugcagucga 600
caucgaaaca ugaggaucac ccaugucugc agucgacauc gaaacaugag gaucacccau 660
gucugcaguc gacaucgaaa 680

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any Naturally Occuring Amino Acid

<400> SEQUENCE: 162

Met Gly Xaa Lys Leu Ser Lys Lys Lys
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Xaa is any amino acid

<400> SEQUENCE: 163

Met Gly Xaa Lys Leu Ser Lys Lys Lys
1               5

<210> SEQ ID NO 164
<211> LENGTH: 8
<212> TYPE: PRT

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Gly, Ala, or Ser
<220> FEATURE:
<221> NAME/KEY: MOD_RES
<222> LOCATION: (4)..(4)
<223> OTHER INFORMATION: Lys or Gln
<220> FEATURE:
<221> NAME/KEY: MOD_RES
<222> LOCATION: (5)..(5)
<223> OTHER INFORMATION: Leu, Phe, Ser, or Gln
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (6)..(6)
<223> OTHER INFORMATION: Ser or Ala, See specification as filed for detailed description of substitutions and preferred embodiments

<400> SEQUENCE: 164

```
Met Gly Xaa Xaa Xaa Xaa Lys Lys
1               5
```

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
tggaggtgct caaagagttg 20

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
ttgggcgtgc acttgat 17

<210> SEQ ID NO 167
<211> LENGTH: 13
<212> TYPE: DNA
<213> ORGANISM: Artificial Sequence
<220> FEATURE:
<223> OTHER INFORMATION: Description of Artificial Sequence: Synthetic probe

<400> SEQUENCE: 167
gggcattggc ttc 13

<210> SEQ ID NO 168
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 169
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

Met Ala Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 170
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Met Gly Ala Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
50 55 60

<210> SEQ ID NO 171
<211> LENGTH: 60
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Met Ala Ala Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly Glu Glu Leu Phe Thr Gly
    50                  55                  60

<210> SEQ ID NO 172
<211> LENGTH: 57
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Ser Ala Gly Gly Gly
            20                  25                  30

Gly Ser Asp Tyr Lys Asp Asp Asp Asp Lys Gly Gly Gly Gly Ser Val
        35                  40                  45

Ser Lys Gly Glu Glu Leu Phe Thr Gly
    50                  55

<210> SEQ ID NO 173
<211> LENGTH: 54
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Met Gly Gly Lys Leu Ser Lys Lys Lys Lys Gly Tyr Asn Val Asn Asp
1               5                   10                  15

Glu Lys Ala Lys Glu Lys Asp Lys Ser Ala Gly Gly Gly Gly Ser Asp
            20                  25                  30

Tyr Lys Asp Asp Asp Asp Lys Gly Gly Gly Gly Ser Val Ser Lys Gly
        35                  40                  45

Glu Glu Leu Phe Thr Gly
    50

<210> SEQ ID NO 174
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Met Gly Gly Lys Leu Ser Lys Lys Lys Lys Gly Tyr Asn Val Asn Asp
1               5                   10                  15

Glu Lys Ala Lys Glu Ser Ala Gly Gly Gly Gly Ser Asp Tyr Lys Asp
            20                  25                  30

Asp Asp Asp Lys Gly Gly Gly Gly Ser Val Ser Lys Gly Glu Glu Leu
        35                  40                  45

Phe Thr Gly
    50

<210> SEQ ID NO 175
<211> LENGTH: 48
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 175

Met Gly Gly Lys Leu Ser Lys Lys Lys Lys Gly Tyr Asn Val Asn Asp
1 5 10 15

Glu Lys Ser Ala Gly Gly Gly Gly Ser Asp Tyr Lys Asp Asp Asp Asp
20 25 30

Lys Gly Gly Gly Gly Ser Val Ser Lys Gly Glu Glu Leu Phe Thr Gly
35 40 45

<210> SEQ ID NO 176
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 176

Met Gly Gly Lys Leu Ser Lys Lys Lys Lys Gly Tyr Asn Val Asn Ser
1 5 10 15

Ala Gly Gly Gly Gly Ser Asp Tyr Lys Asp Asp Asp Asp Lys Gly Gly
20 25 30

Gly Gly Ser Val Ser Lys Gly Glu Glu Leu Phe Thr Gly
35 40 45

<210> SEQ ID NO 177
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 177

Met Gly Gly Lys Leu Ser Lys Lys Lys Lys Gly Tyr Ser Ala Gly Gly
1 5 10 15

Gly Gly Ser Asp Tyr Lys Asp Asp Asp Asp Lys Gly Gly Gly Gly Ser
20 25 30

Val Ser Lys Gly Glu Glu Leu Phe Thr Gly
35 40

<210> SEQ ID NO 178
<211> LENGTH: 39
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 178

Met Gly Gly Lys Leu Ser Lys Lys Lys Ser Ala Gly Gly Gly Gly Ser
1 5 10 15

Asp Tyr Lys Asp Asp Asp Asp Lys Gly Gly Gly Gly Ser Val Ser Lys
20 25 30

Gly Glu Glu Leu Phe Thr Gly
35

<210> SEQ ID NO 179
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 179

Met Gly Gly Lys Leu Ser Ser Ala Gly Gly Gly Gly Ser Asp Tyr Lys
1 5 10 15

Asp Asp Asp Asp Lys Gly Gly Gly Gly Ser Val Ser Lys Gly Glu Glu
20 25 30

Leu Phe Thr Gly
35

<210> SEQ ID NO 180
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 180

Met Gly Gly Ser Ala Gly Gly Gly Gly Ser Asp Tyr Lys Asp Asp Asp
1 5 10 15

Asp Lys Gly Gly Gly Gly Ser Val Ser Lys Gly Glu Glu Leu Phe Thr
20 25 30

Gly

<210> SEQ ID NO 181
<211> LENGTH: 54
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 181

Met Gly Gly Lys Leu Ser Lys Lys Lys Lys Gly Tyr Asn Val Asn Asp
1 5 10 15

Glu Lys Ala Lys Glu Lys Asp Lys Lys Ala Glu Gly Ala Ala Ser Ala
20 25 30

Gly Gly Gly Gly Ser Asp Tyr Lys Asp Asp Asp Asp Lys Gly Gly Gly
35 40 45

Gly Ser Val Ser Lys Gly
50

<210> SEQ ID NO 182
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 182

Met Gly Gly Lys Leu Ser Lys Lys Lys Lys Gly Tyr Ser Ala Gly Gly
1 5 10 15

Gly Gly Ser Asp Tyr Lys Asp Asp Asp Asp Lys Gly Gly Gly Gly Ser
20 25 30

Val Ser Lys Gly
35

<210> SEQ ID NO 183

<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

```
Met Gly Gly Lys Leu Ser Lys Lys Lys Lys Gly Ser Ala Gly Gly Gly
1               5                   10                  15

Gly Ser Asp Tyr Lys Asp Asp Asp Asp Lys Gly Gly Gly Gly Ser Val
            20                  25                  30

Ser Lys Gly
        35
```

<210> SEQ ID NO 184
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Met Gly Gly Lys Leu Ser Lys Lys Lys Lys Ser Ala Gly Gly Gly Gly
1               5                   10                  15

Ser Asp Tyr Lys Asp Asp Asp Asp Lys Gly Gly Gly Gly Ser Val Ser
            20                  25                  30

Lys Gly
```

<210> SEQ ID NO 185
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Met Gly Gly Lys Leu Ser Lys Lys Lys Ser Ala Gly Gly Gly Gly Ser
1               5                   10                  15

Asp Tyr Lys Asp Asp Asp Asp Lys Gly Gly Gly Gly Ser Val Ser Lys
            20                  25                  30

Gly
```

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

```
Met Gly Gly Lys Leu Ser Lys Lys Ser Ala Gly Gly Gly Gly Ser Asp
1               5                   10                  15

Tyr Lys Asp Asp Asp Asp Lys Gly Gly Gly Gly Ser Val Ser Lys Gly
            20                  25                  30
```

<210> SEQ ID NO 187
<211> LENGTH: 31
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 187

Met Gly Gly Lys Leu Ser Lys Ser Ala Gly Gly Gly Gly Ser Asp Tyr
1               5                   10                  15

Lys Asp Asp Asp Asp Lys Gly Gly Gly Gly Ser Val Ser Lys Gly
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Gly Gly Lys Leu Ser Ser Ala Gly Gly Gly Gly Ser Asp Tyr Lys
1               5                   10                  15

Asp Asp Asp Asp Lys Gly Gly Gly Gly Ser Val Ser Lys Gly
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Gly Gly Lys Leu Asp Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Gly Gly Lys Leu Ala Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Gly Gly Lys Gln Ser Lys Lys Lys Lys Gly Tyr Asn Val Asn Asp
1               5                   10                  15

Glu Lys Ala Lys Glu Lys Asp Lys Lys Ala Glu Gly Ala Ala
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

Met Gly Ala Lys Lys Lys Lys Lys Arg Phe Ser Phe Lys Lys Ser Phe
1               5                   10                  15

Lys Leu Ser Gly Phe Ser Phe Lys Lys Asn Lys Lys Glu Ala
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

Met Ala Ala Lys Lys Lys Lys Lys Arg Phe Ser Phe Lys Lys Ser Phe
1               5                   10                  15

Lys Leu Ser Gly Phe Ser Phe Lys Lys Asn Lys Lys Glu Ala
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Met Gly Ala Lys Lys Ser Lys Lys Arg Phe Ser Phe Lys Lys Ser Phe
1               5                   10                  15

Lys Leu Ser Gly Phe Ser Phe Lys Lys Asn Lys Lys Glu Ala
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

Met Gly Ala Lys Lys Ala Lys Lys Arg Phe Ser Phe Lys Lys Pro Phe
1               5                   10                  15

Lys Leu Ser Gly Phe Ser Phe Lys Lys Asn Lys Lys Glu Ala
            20                  25                  30

<210> SEQ ID NO 196
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 196

-continued

```
Met Gly Gly Lys Leu Ser Lys Lys Lys Lys Ser Ala Gly Gly Ser Gly
1               5                   10                  15

Gly Ser Thr Ser Gly Ser Gly Asp Tyr Lys Asp Asp Asp Asp Lys Gly
            20                  25                  30

Ser Gly Phe Glu Met Asp Gln Val Gln Leu Val Glu Ser Gly Gly Ala
        35                  40                  45

Leu Val Gln Pro Gly Gly Ser Leu Arg Leu Ser Cys Ala Ala Ser Gly
    50                  55                  60

Phe Pro Val Asn Arg Tyr Ser Met Arg Trp Tyr Arg Gln Ala Pro Gly
65                  70                  75                  80

Lys Glu Arg Glu Trp Val Ala Gly Met Ser Ser Ala Gly Asp Arg Ser
                85                  90                  95

Ser Tyr Glu Asp Ser Val Lys Gly Arg Phe Thr Ile Ser Arg Asp Asp
            100                 105                 110

Ala Arg Asn Thr Val Tyr Leu Gln Met Asn Ser Leu Lys Pro Glu Asp
        115                 120                 125

Thr Ala Val Tyr Tyr Cys Asn Val Asn Val Gly Phe Glu Tyr Trp Gly
    130                 135                 140

Gln Gly Thr Gln Val Thr Val Ser Ser
145                 150


<210> SEQ ID NO 197
<211> LENGTH: 4
<212> TYPE: PRT
<213> ORGANISM: Artificial Sequence
<220> FEATURE:
<223> OTHER INFORMATION: Peptide Linker

<400> SEQUENCE: 197

Gly Gly Gly Gly
1


<210> SEQ ID NO 198
<211> LENGTH: 7
<212> TYPE: PRT
<213> ORGANISM: Artificial Sequence
<220> FEATURE:
<223> OTHER INFORMATION: Peptide Linker

<400> SEQUENCE: 198

Ser Gly Gly Ser Gly Gly Ser
1               5


<210> SEQ ID NO 199
<211> LENGTH: 15
<212> TYPE: PRT
<213> ORGANISM: Artificial Sequence
<220> FEATURE:
<223> OTHER INFORMATION: Peptide Linker

<400> SEQUENCE: 199

Gly Gly Ser Gly Gly Ser Gly Gly Ser Gly Gly Ser Gly Gly Gly
1               5                   10                  15


<210> SEQ ID NO 200
<211> LENGTH: 16
<212> TYPE: PRT
<213> ORGANISM: Artificial Sequence
<220> FEATURE:
<223> OTHER INFORMATION: Peptide Linker

<400> SEQUENCE: 200
```

-continued

```
Gly Gly Ser Gly Gly Ser Gly Gly Gly Gly Ser Gly Gly Gly Gly Ser
1               5                   10                  15


<210> SEQ ID NO 201
<211> LENGTH: 18
<212> TYPE: PRT
<213> ORGANISM: Artificial Sequence
<220> FEATURE:
<223> OTHER INFORMATION: Peptide Linker

<400> SEQUENCE: 201

Gly Gly Ser Gly Gly Ser Gly Gly Ser Gly Gly Ser Gly Gly Ser Gly
1               5                   10                  15

Gly Ser


<210> SEQ ID NO 202
<211> LENGTH: 15
<212> TYPE: PRT
<213> ORGANISM: Artificial Sequence
<220> FEATURE:
<223> OTHER INFORMATION: Peptide Linker

<400> SEQUENCE: 202

Gly Gly Gly Gly Ser Gly Gly Gly Gly Ser Gly Gly Gly Gly Ser
1               5                   10                  15
```

EXTRACELLULAR VESICLES COMPRISING STING-AGONIST

CROSS-REFERENCE TO RELATED APPLICATIONS

This application claims the benefit of, and priority to, U.S. provisional application Ser. No. 62/647,491, filed Mar. 23, 2018; 62/680,501, filed Jun. 4, 2018; 62/688,600, filed Jun. 22, 2018; 62/756,247, filed Nov. 6, 2018; and 62/822,019, filed Mar. 21, 2019; the contents of each of which are hereby incorporated by reference herein in their entirety.

REFERENCE TO SEQUENCE LISTING SUBMITTED ELECTRONICALLY VIA EFS-WEB

The content of the electronically submitted sequence listing in ASCII text file (Name: 4000_0210005_Seqlisting_ST25.txt; Size: 237,415 bytes; and Date of Creation: Jan. 25, 2021) filed with the application is herein incorporated by reference in its entirety.

BACKGROUND OF THE DISCLOSURE

Stimulator of Interferon Genes (STING) is a cytosolic sensor of cyclic dinucleotides that is typically produced by bacteria. Upon activation, it leads to the production of type I interferons and initiates an immune response. Agonism of STING has been shown as a promising approach for generating an immune response against tumors pre-clinically. Unfortunately, given the broad expression profile of STING, systemic delivery of STING agonists leads to systemic inflammation. This limits the dose that can be given which in turn limits the therapeutic efficacy. An alternative approach to systemic delivery is to inject the STING agonist directly into the tumor. Intra-tumoral injections are quite effective; however, they are limited to solid tumors that can be reached with a needle and lead to tissue damage. Improved methods of delivering STING agonists are therefore needed.

SUMMARY OF THE DISCLOSURE

Provided herein are compositions comprising exosomes encapsulating or associated with a STING agonist that can, upon administration to a subject in need, modulate the human immune system. Such compositions can be used to treat a plurality of diseases or conditions wherein a modulation of the STING signaling pathway is of beneficial effect. For example, treatment of tumors or cancerous lesions in human subjects. Encapsulation of a STING agonist inside exosomes allows for selective activation of immune cells and provide a narrower biodistribution profile, thereby allowing for systemic delivery without the associated toxicities of administering the agonist alone.

In some embodiments, the composition comprises a cyclic dinucleotide STING agonist or a non-cyclic dinucleotide STING agonist.

In one embodiment, the composition comprises an extracellular vesicle and a STING agonist wherein the extracellular vesicle is an exosome, a nanovesicle, an apoptotic body, a microvesicle, a lysosome, an endosome, a liposome, a lipid nanoparticle, a micelle, a multilamellar structure, a revesiculated vesicle, or an extruded cell.

In some embodiments, the exosome overexpresses the protein PTGFRN. In one embodiment, the exosome is produced by a cell that overexpresses PTGFRN.

In some embodiments, the exosome overexpresses an IgV domain-containing protein. In one embodiment, the exosome is produced by a cell that overexpresses an IgV domain-containing protein. In some embodiments, the IgV-containing protein is Basigin, IGSF2, IGSF3, or IGSF8. In another embodiment, the exosome or the exosome producing cell overexpresses an exosome surface protein described in detail in U.S. Patent Application 62/656,956, which is incorporated herein by reference in its entirety. In some embodiments, the exosome is glycan modified. In one embodiment, the glycan modification comprises enzymatic or chemical modification. In another embodiment, the exosome is derived from a glycan modified producer cell. In one embodiment, the glycan modification of the producer cell comprises an enzymatic or a chemical modification. In one embodiment, the glycan modification of the producer cell comprises treatment with kifunensine. In another embodiment, the glycan modification of the producer cell comprises knockout of a sialyltransferase or cytidylyltransferase gene. In one embodiment, the glycan modification of the producer cell comprises CRISPR knockout of a sialyltransferase or cytidylyltransferase gene. In one embodiment, the gene is Cytidine Monophosphate N-Acetylneuraminic Acid Synthetase (CMAS). In other embodiments, the exosome is desialylated or deglycosylated.

In some embodiments, the exosome overexpressing PTGFRN or IgV domain-containing protein is a glycan modified exosome. In one embodiment, the exosome overexpressing PTGFRN or IgV domain-containing protein is desialylated. In one embodiment, the exosome overexpressing PTGFRN or IgV domain-containing protein is deglycosylated. In some embodiments, the exosome or producer cell is deglycosylated or desialylated about or more than 95%, 90-95%, 85-90%, 80-85%, 75-80%, 70-75%, 65-70%, 60-65%, 50-60%, 40-50%, 30-40%, 20-30%, 10-20% or 0-10%.

In some embodiments, the exosome further comprises an exosome that expresses a ligand, a cytokine, or an antibody. In one embodiment, the ligand comprises CD40L, OX40L, or CD27L. In another embodiment, the cytokine comprises IL-7, IL-12, or IL-15. In one embodiment, the antibody comprises an antagonistic antibody or an agonistic antibody.

In one embodiment, the STING agonist comprises a cyclic dinucleotide STING agonist or a non-cyclic dinucleotide STING agonist comprising a lipid-binding tag. In another embodiment, the STING agonist comprises a cyclic dinucleotide STING agonist or a non-cyclic dinucleotide STING agonist physically or chemically modified, the modifications comprising altering the agonist polarity or charge. In another embodiment, the STING agonist comprises a cyclic dinucleotide STING agonist or a non-cyclic dinucleotide STING agonist physically and/or chemically modified. In other embodiments, the STING agonist has a polarity and/or a charge different from the STING agonist prior to the modification (i.e., corresponding unmodified STING agonist).

The concentration of the STING agonist associated with the exosome can be about 0.01 μM to 100 μM. In one embodiment, wherein the concentration of the STING agonist associated with the exosome is about 0.01 μM to 0.1 μM, 0.1 μM to 1 μM, 1 μM to 10 μM, 10 μM to 50 μM, or 50 μM to 100 μM. In another embodiment, the concentration of the STING agonist associated with the exosome is about 1 μM to 10 μM.

Provided herein is also a kit comprising the composition of any of the above claims and instructions for use.

Also provided herein are methods of producing an exosome comprising a STING agonist, the steps comprising obtaining an exosome, mixing the exosome with a STING agonist in a solution, incubating the mixture of the exosome and the STING agonist in a solution comprising a buffer, and purifying the exosome comprising the STING agonist.

In some embodiments, the incubating step comprises incubating the exosome and the STING agonist for about 2-24 hours. In one embodiment, the incubating step comprises incubating the exosome and the STING agonist for about 6-12 hours. In one embodiment, the incubating step comprises incubating the exosome and the STING agonist for about 12-20 hours. In one embodiment, the incubating step comprises incubating the exosome and the STING agonist for about 14-18 hours. In one embodiment, the incubating step comprises incubating the exosome and the STING agonist for about 16 hours.

In some embodiments, the incubating step comprises incubating the exosome and the STING agonist at about 15-90° C. In one embodiment, the incubating step comprises incubating the exosome and the STING agonist at about 37° C. In one embodiment, the incubating step comprises incubating the exosome and the STING agonist at about 15-30° C. In one embodiment, the incubating step comprises incubating the exosome and the STING agonist at about 30-50° C. In one embodiment, the incubating step comprises incubating the exosome and the STING agonist at about 50-90° C.

In some embodiments, the incubating step comprises at least 0.01 mM to 100 mM STING agonist. In one embodiment, the incubating step comprises at least 1 mM to 10 mM STING agonist.

In some embodiments, the incubating step comprises at least about $10^8$ to at least about $10^{16}$ total particles of purified exosomes. In one embodiment, the incubating step comprises at least about $10^{12}$ total particles of purified exosomes.

In some embodiments, the buffer comprises phosphate buffered saline (PBS).

In some embodiments, the purification step comprises size exclusion chromatography or ion chromatography. In one embodiment, the purification step comprises anion exchange chromatography. In some embodiments, the purification step comprises desalting, dialysis, tangential flow filtration, ultrafiltration, or diafiltration. In one embodiment, the purification step comprises one or more centrifugation steps. In one embodiment, the purification step comprises one or more centrifugation steps at about 100,000×g.

Also provided herein are methods of inducing or modulating an immune or inflammatory response in a subject, the method comprising administering to the subject in need thereof a pharmaceutically effective amount of a composition comprising an exosome comprising a STING agonist, thereby inducing or modulating the immune or inflammatory response in the subject.

In some embodiments, the method activates Dendritic Cells. In one embodiment, the method activates myeloid Dendritic Cells. In some embodiments, the method results in reduced monocyte cell activation compared to administration of similar or identical levels of free STING agonist. In one embodiment, the method does not induce monocyte cell activation.

In some embodiments, the method induces interferon-β (IFN-β) production.

In one embodiment, the method results in reduced systemic inflammation compared to administration of similar or identical levels of free STING agonist. In some embodiments, the method results in insubstantial amounts of systemic inflammation.

In some embodiments, the administration is, parenterally, orally, intravenously, intramuscularly, intra-tumorally, intraperitoneally, or via any other appropriate administration route. In one embodiment, the administration is intravenous. In some embodiments, the immune response is an anti-tumor response.

Also provided here in are methods of inducing or modulating an immune or inflammatory response in a subject, the method comprising administering to the subject in need thereof a composition comprising an exosome comprising a STING agonist, in an amount sufficient to induce IFN-β or activate dendritic cells, thereby inducing or modulating the immune or inflammatory response in the subject. In one embodiment, the method activates myeloid dendritic cells. In some embodiments, the method results in reduced monocyte cell activation compared to administration of similar or identical levels of free STING agonist. In one embodiment, wherein the method does not induce monocyte cell activation. In one embodiment, the method results in reduced systemic inflammation compared to administration of similar or identical levels of free STING agonist. In some embodiments, the method results in insubstantial amounts of systemic inflammation.

In another aspect, also provided herein are methods of treating cancer in a subject, the method comprising administering to the subject in need thereof a composition comprising a therapeutically effective amount of an exosome comprising a STING agonist, thereby inducing or modulating an anti-tumor immune response in the subject.

In one embodiment, the method induces interferon-β (IFN-β) production.

In some embodiments, the administration is parenterally, orally, intravenously, intramuscularly, intra-tumorally, intraperitoneally, or via any other appropriate administration route.

In various embodiments, the method further comprises administering an additional therapeutic agent. In some embodiments, the additional therapeutic agent is an immunomodulating agent. In one embodiment, the additional therapeutic agent is an antibody or antigen-binding fragment thereof. In one embodiment, the therapeutic antibody or antigen-binding fragment thereof is an inhibitor of CTLA-4, PD-1, PD-L1, PD-L2, TIM-3, or LAG3.

In another aspect, also provided herein are methods of preventing metastasis of cancer in a subject, the method comprising administering to the subject in need thereof a composition comprising a therapeutically effective amount of an exosome comprising a STING agonist.

In some embodiments, the therapeutically effective amount of the exosome comprising a STING agonist is capable of preventing one or more tumors at one location in the subject from promoting the growth of one or more tumors at another location in the subject.

In one embodiment, the method induces interferon-β (IFN-β) production.

In various embodiments, the administration is parenterally, orally, intravenously, intramuscularly, intra-tumorally, intraperitoneally, or via any other appropriate administration route.

In some embodiments, the composition is administered intratumorally in a first tumor in one location, and wherein the composition administered in the first tumor prevents metastasis of one or more tumors at a second location.

In various embodiments, the method further comprises administering an additional therapeutic agent. In some embodiments, the additional therapeutic agent is an immunomodulating agent. In one embodiment, the additional therapeutic agent is an antibody or antigen-binding fragment thereof. In one embodiment, the therapeutic antibody or antigen-binding fragment thereof is an inhibitor of CTLA-4, PD-1, PD-L1, PD-L2, TIM-3, or LAG3.

Provided herein is a composition comprising an extracellular vesicle and a stimulator of interferon genes protein (STING) agonist. In some embodiments, the extracellular vesicle is an exosome, a nanovesicle, an apoptotic body, a microvesicle, a lysosome, an endosome, a liposome, a lipid nanoparticle, a micelle, a multilamellar structure, a revesiculated vesicle, or an extruded cell. In certain embodiments, the extracellular vesicle is an exosome.

In some embodiments, the STING agonist is associated with the extracellular vesicle. In some embodiments, the STING agonist is encapsulated within the extracellular vesicle. In certain embodiments, the STING agonist is linked to a lipid bilayer of the extracellular vesicle, optionally by a linker.

In some embodiments, the extracellular vesicle of the present disclosure overexpresses a PTGFRN protein. In certain embodiments, the STING agonist is linked to the PTGFRN protein, optionally by a linker.

In some embodiments, the extracellular vesicle is produced by a cell that overexpresses a PTGFRN protein. In some embodiments, the extracellular vesicle is glycan modified. In certain embodiments, the extracellular vesicle is desialylated. In further embodiments, the extracellular vesicle is deglycosylated.

In some embodiments, the extracellular vesicle further comprises a protein that binds to or enzymatically reacts with the STING agonist. In certain embodiments, the extracellular vesicle further comprises a ligand, a cytokine, or an antibody. In some embodiments, the ligand comprises CD40L, OX40L, and/or CD27L. In some embodiments, the cytokine comprises IL-7, IL-12, and/or IL-15. In certain embodiments, the antibody comprises an antagonistic antibody and/or an agonistic antibody.

In some embodiments, the STING agonist is a cyclic dinucleotide. In other embodiments, the STING agonist is a non-cyclic dinucleotide. In certain embodiments, the STING agonist comprises a lipid-binding tag. In some embodiments, the STING agonist is physically and/or chemically modified. In certain embodiments, the modified STING agonist has a polarity and/or a charge different from the corresponding unmodified STING agonist.

In some embodiments, the concentration of the STING agonist associated with the extracellular vesicle is about 0.01 μM to 100 μM. In certain embodiments, the concentration of the STING agonist associated with the extracellular vesicle is about 0.01 μM to 0.1 μM, 0.1 μM to 1 μM, 1 μM to 10 μM, 10 μM to 50 μM, or 50 μM to 100 μM. In further embodiments, the concentration of the STING agonist associated with the extracellular vesicle is about 1 μM to 10 μM.

In some embodiments, the STING agonist comprises:

Formula 1

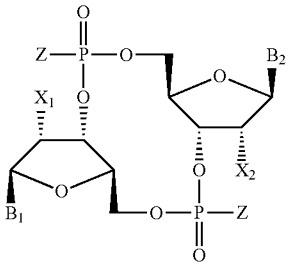

or

Formula 2

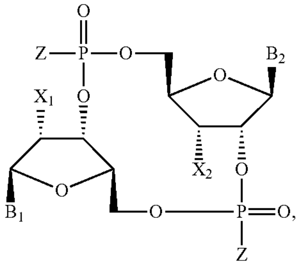

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

$B_1$ and $B_2$ are bases chosen from:

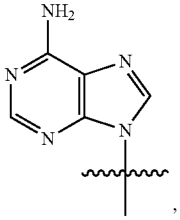

,

Adenine

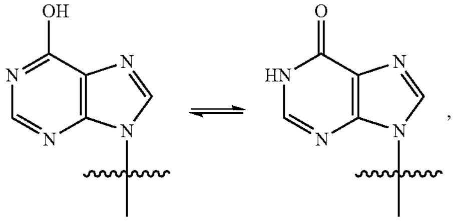

, or

Hypoxanthine

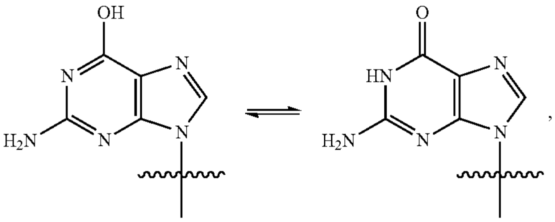

,

Guanine with the proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH, or a pharmaceutically acceptable salt thereof.

In some embodiments, the STING agonist is selected from the group consisting of:

CL606

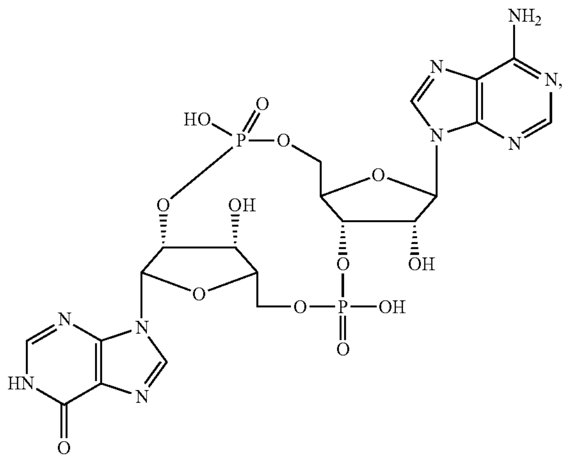

(3′,2′)c-AIMP

CL611

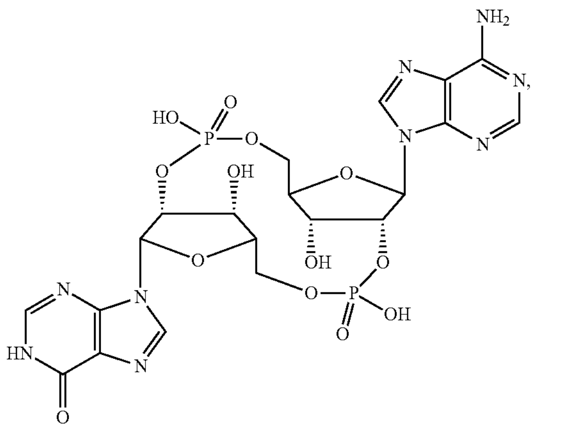

(2′,2′)c-AIMP

-continued

CL602

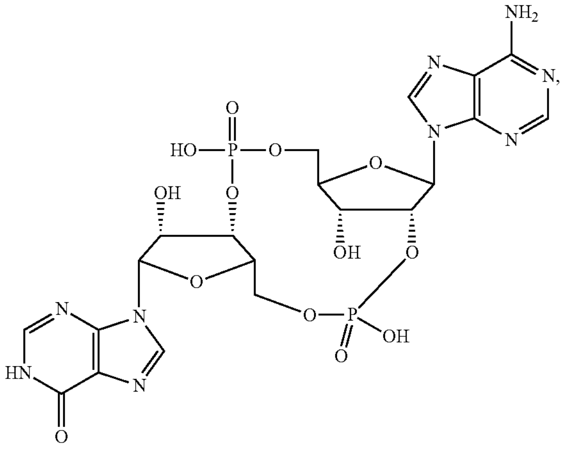

(2′,3′)c-AIMP

CL655

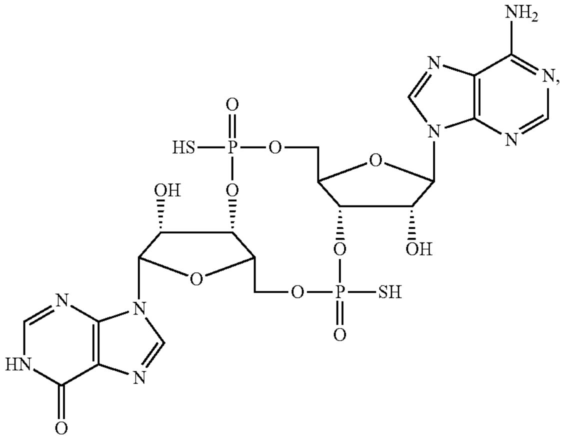

c-AIMP(S)

CL604

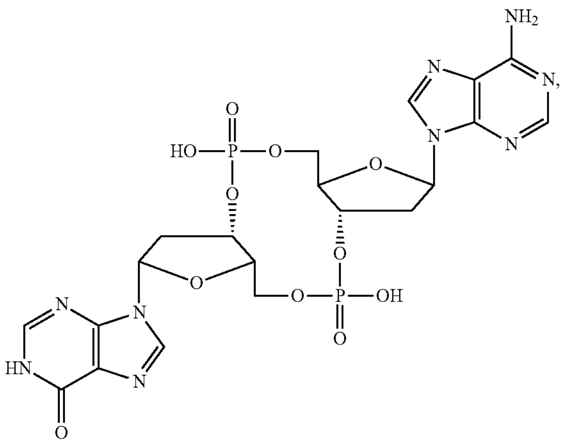

c-(dAMP-dIMP)

-continued
CL609
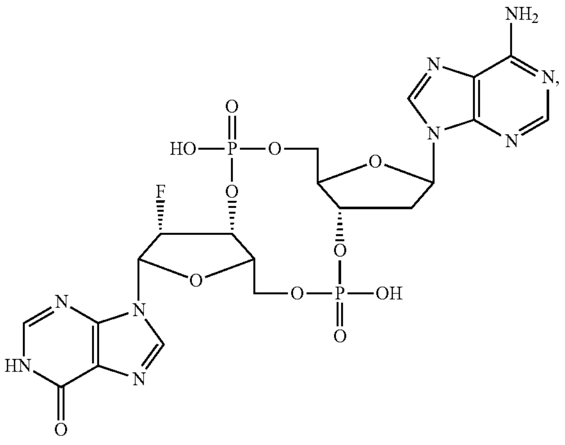
c-(dAMP-2′FdIMP)
CL614
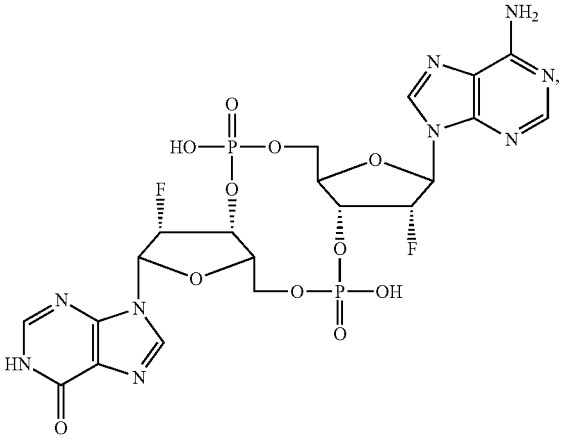
c-(2′FdAMP-2′FdIMP)
CL656
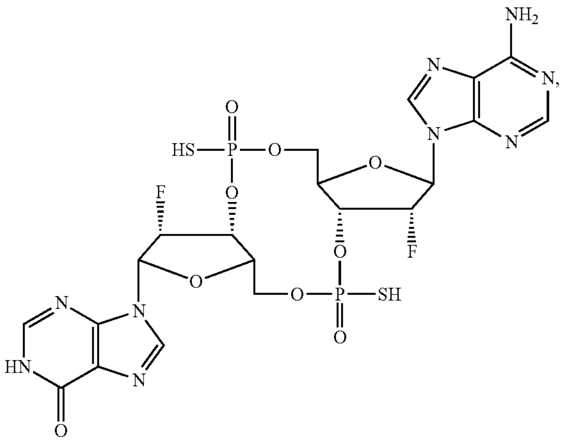
c-[2′FdAMP(S)-2′FdIMP(S)]
-continued
CL647
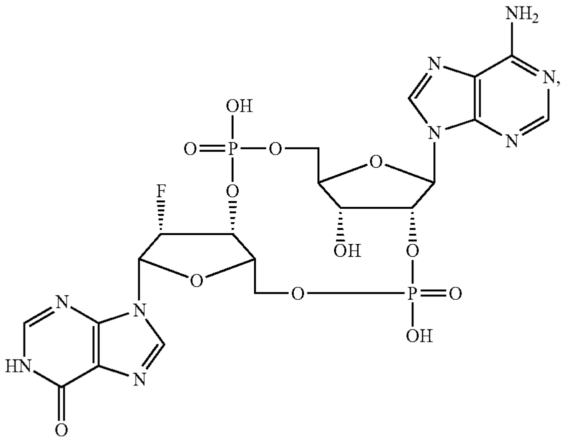
(2′,3′)c-(AMP-2′FdIMP)
CL626
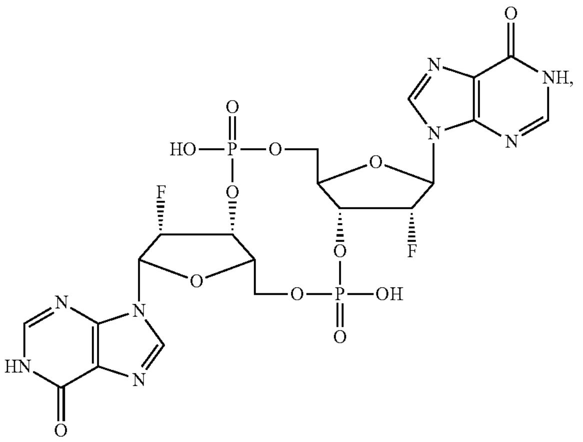
c-di(2′FdIMP)
CL629
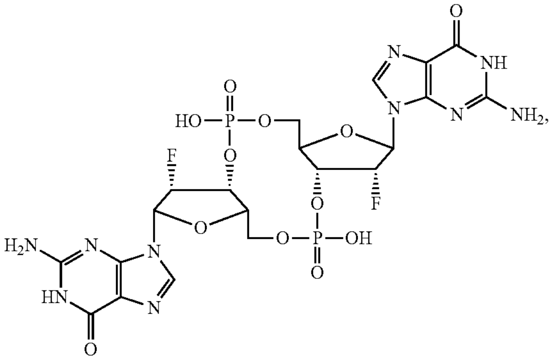
c-di(2′FdIMP)

-continued

CL603

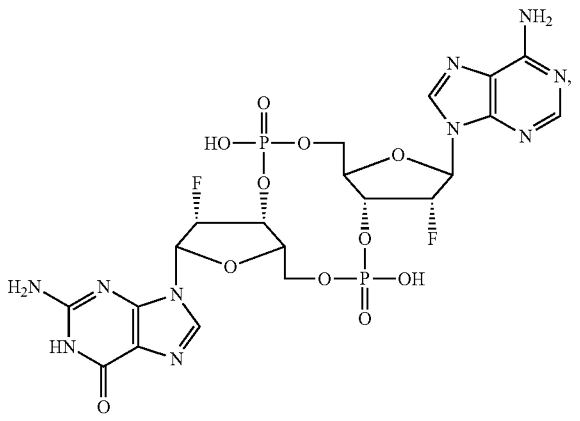

c-(2′FdGMP-2′FdAMP)

CL632

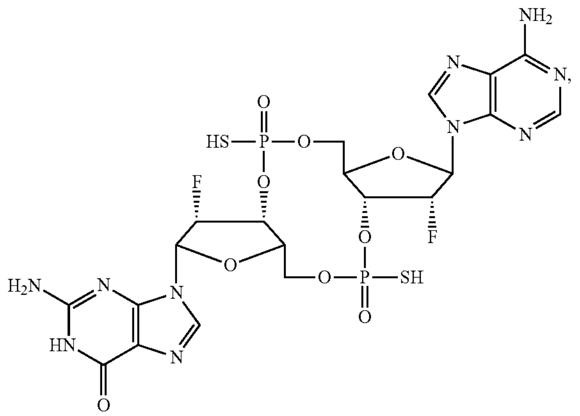

c-[2′FdGMP(S)-2′FdAMP(S)]

CL633

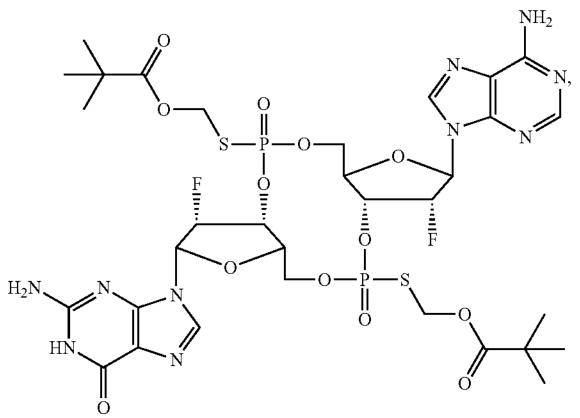

c-[2′FdGMP(S)-2′FdAMP(S)](POM)$_2$

-continued

CL659

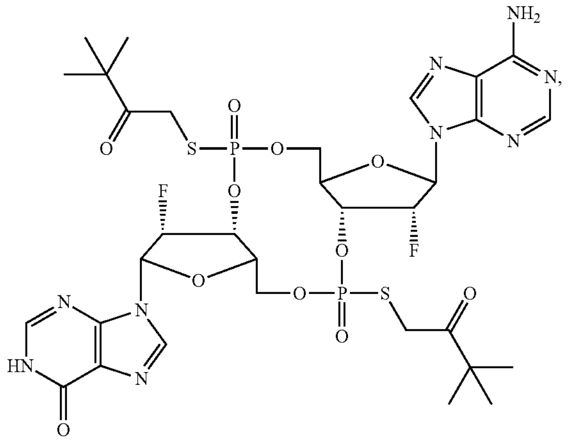

c-[2′FdAMP(S)-2′FdIMP(S)](POM)$_2$ and a pharmaceutically acceptable salt thereof.

In some embodiments, the extracellular vesicle associated with the STING agonist exhibits one or more of the following characteristics: (i) activates dendritic cells, e.g., myeloid dendritic cells; (ii) activates monocyte cells at a lesser degree than the STING agonist alone ("free STING agonist"); (iii) does not activate monocyte cells; (iv) has a wider therapeutic index compared to the free STING agonist; (v) has less systemic toxicity than the free STING agonist; (vi) has less immune cell killing than the free STING agonist; (vii) has higher cell selectivity than the free STING agonist; (viii) provides tumor protective immunity at a dose lower than the free STING agonist; (ix) induce a specific cellular response in vivo in antigen-presenting cells, e.g., dendritic cells; (x) is capable of inducing an immune response at a distal region after a local administration; and (xi) is capable of being dosed at a lower level than the free STING agonist.

In some embodiments, the extracellular vesicle associated with the STING agonist, when administered to a mammal, does not deplete T cells and/or macrophages in the mammal. In other embodiments, the extracellular vesicle associated with the STING agonist, when administered to a mammal, depletes T cells and/or macrophages in the mammal at a lesser degree than the free STING agonist.

Disclosed herein is a pharmaceutical composition comprising a composition (e.g., comprising an extracellular vesicle described herein) and a pharmaceutically acceptable carrier.

Disclosed herein is a kit comprising a composition (e.g., comprising an extracellular vesicle described herein) and instructions for use.

Also provided herein is a method of producing an extracellular vesicle (EV) (e.g., exosome) comprising a STING agonist, the method comprising: (a) obtaining an EV, e.g., exosome; (b) mixing the EV, e.g., exosome, with a STING agonist in a solution; (c) incubating the mixture of the EV, e.g., exosome, and the STING agonist in a solution comprising a buffer under suitable conditions; and (d) purifying the EV, e.g., exosome, comprising the STING agonist.

In some embodiments, the suitable conditions comprise incubating the EV, e.g., exosome and the STING agonist for about 2-24 hours. In certain embodiments, the suitable conditions comprise incubating the EV, e.g., exosome and the STING agonist at about 15-90° C. In some embodiments, the suitable conditions comprise incubating the EV, e.g., exosome and the STING agonist at about 37° C.

In some embodiments, the amount of the STING agonist in the mixing step comprises at least 0.01 mM to 100 mM. In certain embodiments, the amount of the STING agonist in the mixing step comprises at least 1 mM to 10 mM. In further embodiments, the amount of the exosome in the mixing step comprises at least about $10^8$ to at least about $10^{16}$ total particles. In some embodiments, the amount of the EV, e.g., exosome in the mixing step comprises at least about $10^{12}$ total particles.

In some embodiments, the buffer for producing EVs disclosed herein, e.g., exosomes, comprises phosphate buffered saline (PBS).

In some embodiments, purifying the EVs, e.g., exosomes, comprises one or more centrifugation steps. In certain embodiments, the one or more centrifugation steps are at about 100,000×g.

Present disclosure also provides a method of inducing or modulating an immune response and/or an inflammatory response in a subject in need thereof, the method comprising administering to the subject a pharmaceutically effective amount of the composition or pharmaceutical composition disclosed herein.

Also provided is a method treating a tumor in a subject in need thereof, the method comprising administering to the subject the composition or pharmaceutical composition disclosed herein.

In some embodiments, the administering induces or modulates the immune response and/or the inflammatory response in the subject. In certain embodiments, the administering activates dendritic cells. In some embodiments, the administering results in reduced monocyte cell activation compared to the free STING agonist. In further embodiments, the administering does not induce monocyte cell activation. In some embodiments, the administering induces interferon-β (IFN-β) production. In some embodiments, the administering results in reduced systemic inflammation compared to the free STING agonist. In some embodiments, the administering results in insubstantial amounts of systemic inflammation.

In some embodiments, the administration is parenterally, orally, intravenously, intramuscularly, intra-tumorally, intraperitoneally, or via any other appropriate administration route. In certain embodiments, the administration is intravenous.

In some embodiments, the immune response (e.g., that can be induced or modulated by administering a composition or pharmaceutical composition disclosed herein) is an anti-tumor immune response.

In some embodiments, the composition (e.g., disclosed herein) is in an amount sufficient to induce IFN-β and/or to activate dendritic cells. In some embodiments, the composition is administered intratumorally in a first tumor in one location, and wherein the composition administered in the first tumor prevents metastasis of one or more tumors at a second location.

In some embodiments, the method of inducing or modulating an immune response and/or an inflammatory response in a subject or the method of treating a tumor in a subject, further comprises administering an additional therapeutic agent. In certain embodiments, the additional therapeutic agent is an immunomodulating agent. In some embodiments, the additional therapeutic agent is an antibody or antigen-binding fragment thereof. In certain embodiments, the antibody or antigen-binding fragment thereof is an inhibitor of CTLA-4, PD-1, PD-L1, PD-L2, TIM-3, or LAG3.

In some embodiments, administering the composition or pharmaceutical composition disclosed herein prevents metastasis of the tumor in the subject.

Embodiments

Embodiment 1. A composition comprising an extracellular vesicle and a stimulator of interferon genes protein (STING) agonist.

Embodiment 2. The composition of Embodiment 1, wherein the extracellular vesicle is an exosome, a nanovesicle, an apoptotic body, a microvesicle, a lysosome, an endosome, a liposome, a lipid nanoparticle, a micelle, a multilamellar structure, a revesiculated vesicle, or an extruded cell.

Embodiment 3. The composition of Embodiment 2, wherein the extracellular vesicle is an exosome.

Embodiment 4. The composition of any of the above Embodiments, wherein the STING agonist is associated with the exosome.

Embodiment 5. The composition of any of the above Embodiments, wherein the STING agonist is associated with a lipid bilayer of the exosome or encapsulated within the exosome.

Embodiment 6. The composition of any of the above Embodiments, wherein the exosome overexpresses the protein PTGFRN.

Embodiment 7. The composition of any of the above Embodiments, wherein the exosome is produced by a cell that overexpresses PTGFRN.

Embodiment 8. The composition of any of the above Embodiments, wherein the exosome is glycan modified.

Embodiment 9. The composition of Embodiment 8, wherein the glycan modification comprises enzymatic or chemical modification.

Embodiment 10. The composition of any of Embodiments 1-8, wherein the exosome is derived from a glycan modified producer cell.

The composition of Embodiment 10, wherein the glycan modification of the producer cell comprises an enzymatic or a chemical modification.

Embodiment 12. The composition of Embodiment 10, wherein the glycan modification of the producer cell comprises treatment with kifunensine.

Embodiment 13. The composition of Embodiment 10, wherein the glycan modification of the producer cell comprises knockout of a sialyltransferase or cytidylyltransferase gene.

Embodiment 14. The composition of Embodiment 13, wherein the glycan modification of the producer cell comprises CRISPR knockout of a sialyltransferase or cytidylyltransferase gene.

Embodiment 15. The composition of Embodiment 13 or 14, wherein said gene is Cytidine Monophosphate N-Acetylneuraminic Acid Synthetase (CMAS).

Embodiment 16. The composition of any of the above Embodiments, wherein the exosome is desialylated.

Embodiment 17. The composition of any of the above Embodiments, wherein the exosome is deglycosylated.

Embodiment 18. The composition of any of the above Embodiments, wherein the exosome overexpressing PTGFRN is a glycan modified exosome.

Embodiment 19. The composition of any of the above Embodiments, wherein the exosome overexpressing PTGFRN is desialylated.

Embodiment 20. The composition of any of the above Embodiments, wherein the exosome overexpressing PTGFRN is deglycosylated.

Embodiment 21. The composition of any of the above Embodiments, wherein the exosome or producer cell is deglycosylated or desialylated about or more than 95%, 90-95%, 85-90%, 80-85%, 75-80%, 70-75%, 65-70%, 60-65%, 50-60%, 40-50%, 30-40%, 20-30%, 10-20% or 0-10%.

Embodiment 22. The composition of any of the above Embodiments, wherein the exosome further comprises a protein that binds to or enzymatically reacts with a cyclic dinucleotide STING agonist or a non-cyclic dinucleotide STING agonist.

Embodiment 23. The composition of any of the above Embodiments, wherein the exosome further comprises an exosome that expresses a ligand, a cytokine, or an antibody.

Embodiment 24. The composition of Embodiment 23, wherein in the ligand comprises CD40L, OX40L, or CD27L.

Embodiment 25. The composition of Embodiment 23, wherein the cytokine comprises IL-7, IL-12, or IL-15.

Embodiment 26. The composition of Embodiment 23, wherein the antibody comprises an antagonistic antibody or an agonistic antibody.

Embodiment 27. The composition of any of the above Embodiments, wherein the STING agonist comprises a cyclic dinucleotide STING agonist or a non-cyclic dinucleotide STING agonist.

Embodiment 28. The composition of any of the above Embodiments, wherein the STING agonist comprises a cyclic dinucleotide STING agonist or a non-cyclic dinucleotide STING agonist comprising a lipid-binding tag.

Embodiment 29. The composition of any of the above Embodiments, wherein the STING agonist comprises a cyclic dinucleotide STING agonist or a non-cyclic dinucleotide STING agonist that is physically or chemically modified, the modifications comprising altering the agonist polarity or charge.

Embodiment 30. The composition of any of the above Embodiments, wherein the concentration of the STING agonist associated with the exosome is about 0.01 μM to 100 μM.

Embodiment 31. The composition of any of the above Embodiments, wherein the concentration of the STING agonist associated with the exosome is about 0.01 μM to 0.1 μM, 0.1 μM to 1 μM, 1 μM to 10 μM, 10 μM to 50 μM, or 50 μM to 100 μM.

Embodiment 32. The composition of any of the above Embodiments, wherein the concentration of the STING agonist associated with the exosome is about 1 μM to 10 μM.

Embodiment 33. A kit comprising the composition of any of the above Embodiments and instructions for use.

Embodiment 34. A method of producing an exosome comprising a STING agonist, the method comprising:

a. Obtaining an exosome;

b. Mixing said exosome with a STING agonist in a solution;

c. Incubating the mixture of the exosome and the STING agonist in a solution comprising a buffer; and d. Purifying the exosome comprising the STING agonist.

Embodiment 35. The method of Embodiment 34, wherein the incubating step comprising incubating the exosome and the STING agonist for about 2-24 hours.

Embodiment 36. The method of Embodiment 34, wherein the incubating step comprises incubating the exosome and the STING agonist for about 6-12 hours.

Embodiment 37. The method of Embodiment 34, wherein the incubating step comprises incubating the exosome and the STING agonist for about 12-20 hours.

Embodiment 38. The method of Embodiment 34, wherein the incubating step comprises incubating the exosome and the STING agonist for about 14-18 hours.

Embodiment 39. The method of Embodiment 34, wherein the incubating step comprises incubating the exosome and the STING agonist for about 16 hours.

Embodiment 40. The method of any of Embodiments 34-39, wherein the incubating step comprises incubating the exosome and the STING agonist at about 15-90° C.

Embodiment 41. The method of any of Embodiments 34-39, wherein the incubating step comprises incubating the exosome and the STING agonist at about 37° C.

Embodiment 42. The method of any of Embodiments 34-39, wherein the incubating step comprises incubating the exosome and the STING agonist at about 15-30° C.

Embodiment 43. The method of any of Embodiments 34-39, wherein the incubating step comprises incubating the exosome and the STING agonist at about 30-50° C.

Embodiment 44. The method of any of Embodiments 34-39, wherein the incubating step comprises incubating the exosome and the STING agonist at about 50-90° C.

Embodiment 45. The method of any of Embodiments 34-44, wherein the incubating step comprises at least 0.01 mM to 100 mM STING agonist.

Embodiment 46. The method of any of Embodiments 34-44, wherein the incubating step comprises at least 1 mM to 10 mM STING agonist.

Embodiment 47. The method of any of Embodiments 34-46, wherein the incubating step comprises at least about 108 to at least about 1016 total particles of purified exosomes.

Embodiment 48. The method of any of Embodiments 34-46, wherein the incubating step comprises at least about 1012 total particles of purified exosomes.

Embodiment 49. The method of any of Embodiments 34-47, wherein the buffer comprises phosphate buffered saline (PBS).

Embodiment 50. The method of any of Embodiments 34-49, wherein the purification step comprises size exclusion chromatography or ion chromatography.

Embodiment 51. The method of any of Embodiments 34-50, wherein the purification step comprises anion exchange chromatography.

Embodiment 52. The method of any of Embodiments 34-51, wherein the purification step comprises desalting, dialysis, tangential flow filtration, ultrafiltration, or diafiltration.

Embodiment 53. The method of any of Embodiments 34-49, wherein the purification step comprises one or more centrifugation steps.

Embodiment 54. The method of Embodiment 53, wherein the purification step comprises one or more centrifugation steps at about 100,000×g.

Embodiment 55. A method of inducing or modulating an immune or inflammatory response in a subject, the method comprising administering to the subject in need thereof a pharmaceutically effective amount of a composition comprising an exosome comprising a STING agonist, thereby inducing or modulating the immune or inflammatory response in the subject.

Embodiment 56. The method of Embodiment 55, wherein the method activates Dendritic Cells.

Embodiment 57. The method of any of Embodiments 55-56, wherein the method activates myeloid Dendritic Cells.

Embodiment 58. The method of any of Embodiments 55-57, wherein the method results in reduced monocyte cell activation compared to administration of similar or identical levels of free STING agonist.

Embodiment 59. The method of any of Embodiments 55-58, wherein the method does not induce monocyte cell activation.

Embodiment 60. The method of any of Embodiments 55-59, wherein the method induces interferon-β (IFN-β) production.

Embodiment 61. The method of any of Embodiments 55-60, wherein the method results in reduced systemic inflammation compared to administration of similar or identical levels of free STING agonist.

Embodiment 62. The method of any of Embodiments 55-60, wherein the method results in insubstantial amounts of systemic inflammation.

Embodiment 63. The method of any of Embodiments 55-62, wherein the administration is parenterally, orally, intravenously, intramuscularly, intra-tumorally, intraperitoneally, or via any other appropriate administration route.

Embodiment 64. The method of any of Embodiments 55-63, wherein the administration is intravenous.

Embodiment 65. The method of any of Embodiments 55-64, wherein the immune response is an anti-tumor response.

Embodiment 66. A method of inducing or modulating an immune or inflammatory response in a subject, the method comprising administering to the subject in need thereof a composition comprising an exosome comprising a STING agonist, in an amount sufficient to induce IFN-β or activate dendritic cells, thereby inducing or modulating the immune or inflammatory response in the subject.

Embodiment 67. The method of Embodiment 66, wherein the method activates myeloid Dendritic Cells.

Embodiment 68. The method of any of Embodiments 66-67, wherein the method results in reduced monocyte cell activation compared to administration of similar or identical levels of free STING agonist.

Embodiment 69. The method of any of Embodiments 66-67, wherein the method does not induce monocyte cell activation.

Embodiment 70. The method of any of Embodiments 66-69, wherein the method results in reduced systemic inflammation compared to administration of similar or identical levels of free STING agonist.

Embodiment 71. The method of any of Embodiments 66-69, wherein the method does not induce significant systemic inflammation.

Embodiment 72. The method of any of Embodiments 66-71, wherein the administration is parenterally, orally, intravenously, intramuscularly, intra-tumorally, intraperitoneally, or via any other appropriate administration route.

Embodiment 73. The method of any of Embodiments 66-71, wherein the administration is intravenous.

Embodiment 74. The method of any of Embodiments 66-73, wherein the immune response is an anti-tumor response.

Embodiment 75. A method of treating cancer in a subject, the method comprising administering to the subject in need thereof a composition comprising a therapeutically effective amount of an exosome comprising a STING agonist, thereby inducing or modulating an anti-tumor immune response in the subject.

Embodiment 76. The method of Embodiment 75, wherein the method induces interferon-β (IFN-β) production.

Embodiment 77. The method of Embodiment 75 or 76, wherein the administration is parenterally, orally, intravenously, intramuscularly, intra-tumorally, intraperitoneally, or via any other appropriate administration route.

Embodiment 78. The method of any one of Embodiments 75-77, further comprising administering an additional therapeutic agent.

Embodiment 79. The method of any one of Embodiments 75-78, wherein the additional therapeutic agent is an immunomodulating agent.

Embodiment 80. The method of Embodiment 79, wherein the additional therapeutic agent is an antibody or antigen-binding fragment thereof.

Embodiment 81. The method of any one of Embodiments 80, wherein the therapeutic antibody or antigen-binding fragment thereof is an inhibitor of CTLA-4, PD-1, PD-L1, PD-L2, TIM-3, or LAG3.

Embodiment 82. A method of preventing metastasis of cancer in a subject, the method comprising administering to the subject in need thereof a composition comprising a therapeutically effective amount of an exosome comprising a STING agonist.

Embodiment 83. The method of Embodiment 81, wherein the therapeutically effective amount of the exosome comprising a STING agonist is capable of preventing one or more tumors at one location in the subject from promoting the growth of one or more tumors at another location in the subject.

Embodiment 84. The method of Embodiment 82 or 83, wherein the method induces interferon-β (IFN-β) production.

Embodiment 85. The method of any one of Embodiments 81-84, wherein the administration is parenterally, orally, intravenously, intramuscularly, intra-tumorally, intraperitoneally, or via any other appropriate administration route.

Embodiment 86. The method of any one of Embodiments 81-85, wherein the composition is administered intratumorally in a first tumor in one location, and wherein the composition administered in the first tumor prevents metastasis of one or more tumors at a second location.

Embodiment 87. The method of any one of Embodiments 81-86, further comprising administering an additional therapeutic agent.

Embodiment 88. The method of Embodiment 87, wherein the additional therapeutic agent is an immunomodulating agent.

Embodiment 89. The method of Embodiment 88, wherein the additional therapeutic agent is an antibody or antigen-binding fragment thereof.

Embodiment 90. The method of Embodiment 89, wherein the additional therapeutic agent is a therapeutic antibody or antigen-binding fragment thereof that is an inhibitor of CTLA-4, PD-1, PD-L1, PD-L2, TIM-3, or LAG3.

BRIEF DESCRIPTION OF THE DRAWINGS

FIG. 9 shows a comparison of the IFN-β production $EC_{50}$ for the free STING agonist and the exosome-encapsulated STING agonists tested in FIG. 8.

FIG. 11 shows a comparison of the monocyte activation $EC_{50}$ for the free STING agonist and the exosome-encapsulated STING agonists tested in FIG. 10.

FIG. 13 shows a comparison of the mDC activation $EC_{50}$ for the free STING agonist and the exosome-encapsulated STING agonists tested in FIG. 12.

FIGS. 45A and 45B shows the results for freshly prepared exosomes from two separate donors (donors 1 and 2, respectively). FIGS. 45C and 45D show the results for exosomes after storage from two separate donors (donors 5 and 6, respectively).

FIG. 52C-D show radial response analysis of IFNβ (FIG. 52C) or CXCL10 (FIG. 52D) transcripts after injected with microdoses of free 3-3 cAIMPdFSH or 3-3 cAIMPdFSH-loaded exosomes.

FIG. 53A shows the results for exosomes loaded with STING agonists ML RR-S2 CDA ("ExoML RR-S2") or 2-3 cGAMP ("Exo2-3 cGAMP"). The corresponding free STING agonists are noted as "Free ML RR-S2" and "Free 2-3 cGAMP," respectively. FIG. 53B shows the results for exosomes loaded with STING agonists 3-3 cAIMPdFSH ("exo3-3 cAIMPdFSH") or 3-3 cAIM(PS)2 ("exo3-3 cAIM (PS)2"). "Free 3-3 cAIMPdFSH" and "Free 3-3 cAIM(PS) 2" represent the free form of the corresponding agonists, respectively. FIG. 53C shows the results for exosomes loaded with 3-3 cAIMP ("exo3-3 cAIMP") and 3-3 cAIMPdF ("exo3-3 cAIMPdF"). The corresponding free STING agonists are shown as "Free 3-3 cAIMP" and "Free 3-3 cAIMPdF," respectively. FIG. 53D shows the results for exosome loaded with STING agonist 3-3 cAIMPmFSH ("exo3-3 cAIMPmFSH") and free STING agonist 3-3 cAIMPmFSH ("Free 3-3 cAIMPmFSH"). FIG. 53E shows the results for exosome loaded with STING agonist CP214 ("Exo-CP214"; open diamond) and free CP214 STING agonist ("CP214"; closed diamond). FIG. 53F shows the results for exosome loaded with STING agonist CP201 ("Exo-CP201"; open square) and free form of the CP201 STING agonist ("CP201"; closed square). FIG. 53G shows the results for exosome loaded with STING agonist CP204 ("Exo-CP204"; open triangle) and free CP204 STING agonist ("CP204"; closed triangle). The 3-3 cAIMPdFSH, 3-3 cAIM(PS)2, cAIMPdF, cAIMP are corresponded to compound 53, 13, 52, and 51 from a paper (J Med Chem. 2016 Nov. 23; 59(22):10253-10267), respectively. The CP214 is 2-3 cAMPmFSH. The CP201 and CP204 are analogues of compounds from patent WO2017/175156 and WO2017/175147, respectively.

Figure 61A:
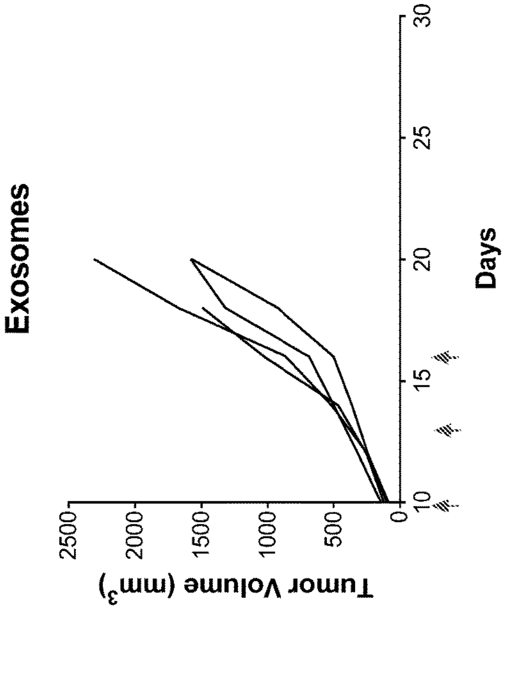
FIGS. 61A-61E shows the tumor growth curves for each animal in the different groups shown in FIG. 60 and Example 21. The different groups include: exosomes (FIG.
Figure 61B:
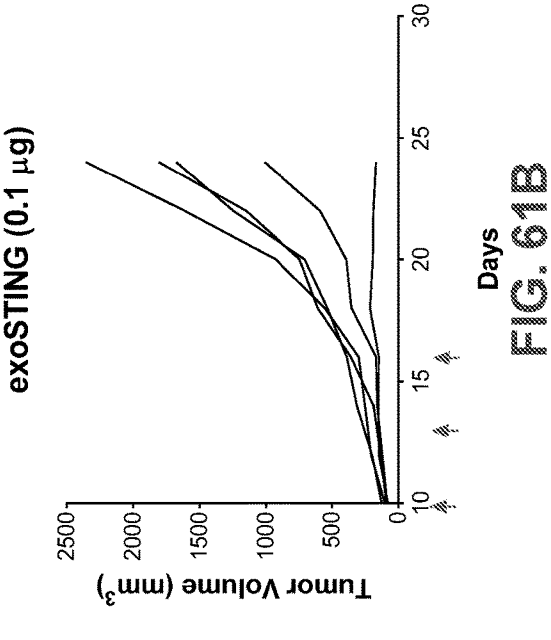
Figure 61C:
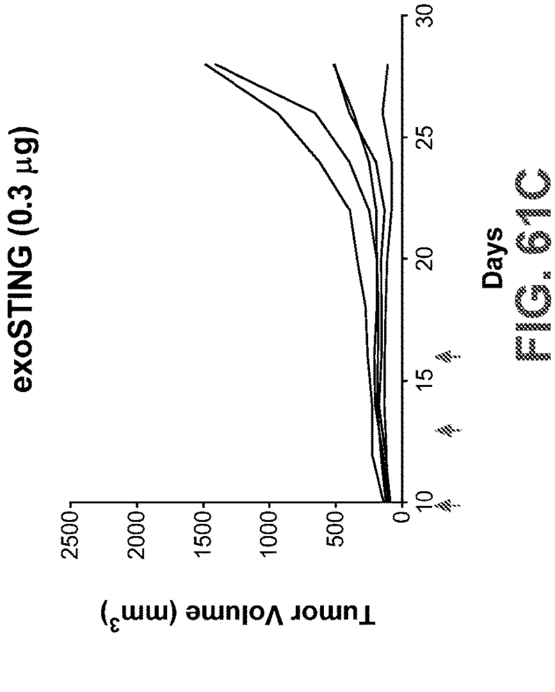
Figure 61D:
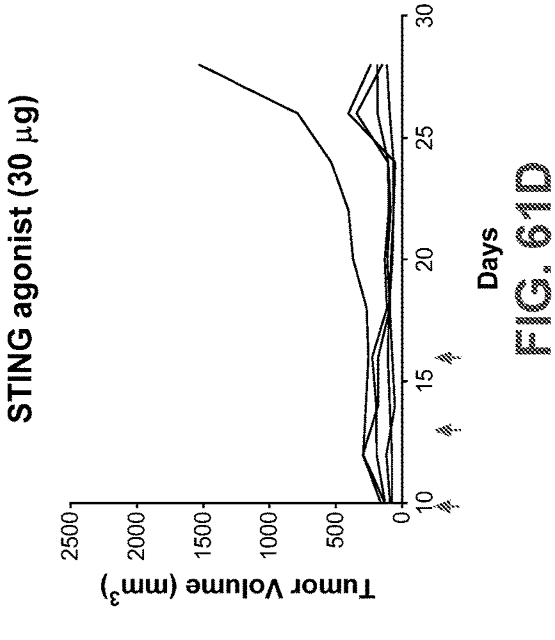
Figure 61E:
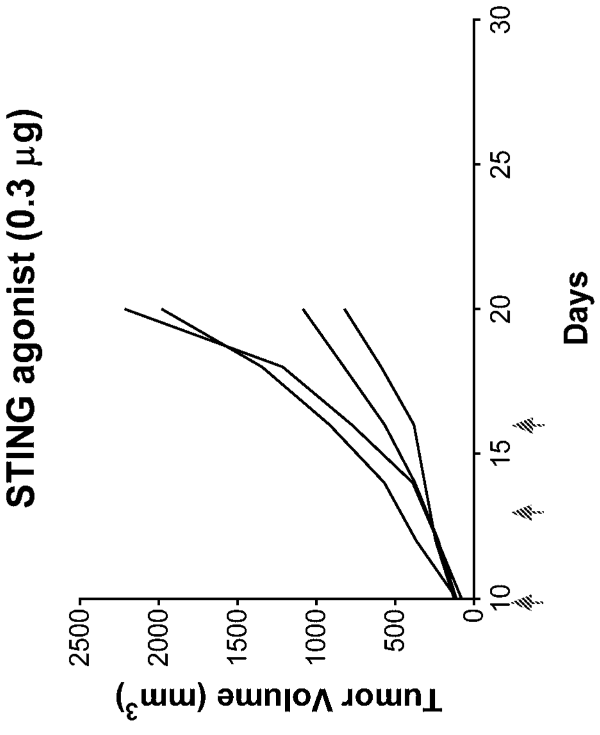

61A), exoSTING (0.1 μg) (FIG. 61B), exoSTING (0.3 μg) (FIG. 61C), STING agonist (30 μg) (FIG. 61D), and STING agonist (0.3 μg) (FIG. 61E).

Figure 62:
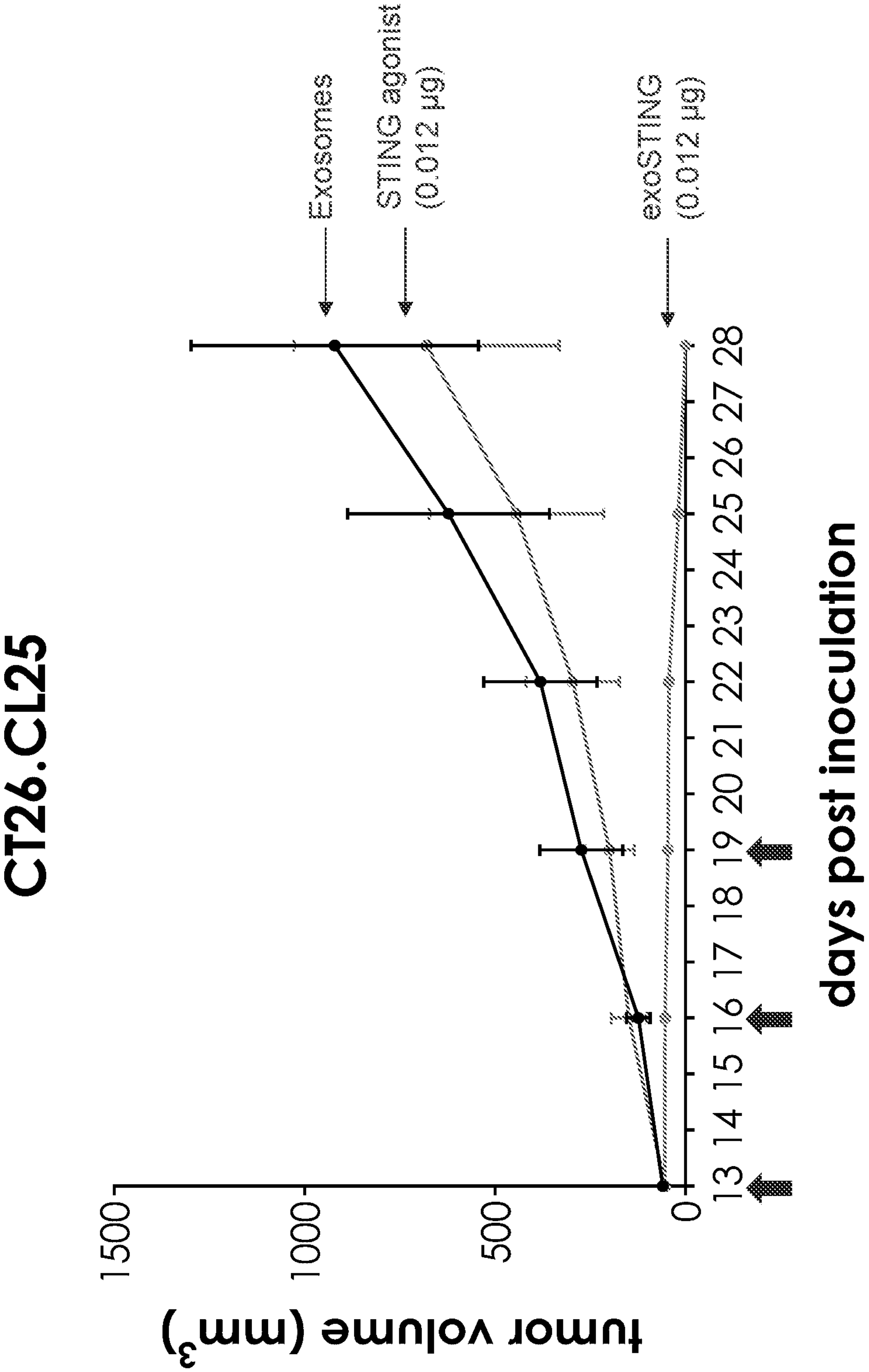

FIG. 62 shows tumor growth curves in CT26.CT25 tumor-bearing BALB/c mice over the course of the study described in Example 22.

Figure 63:
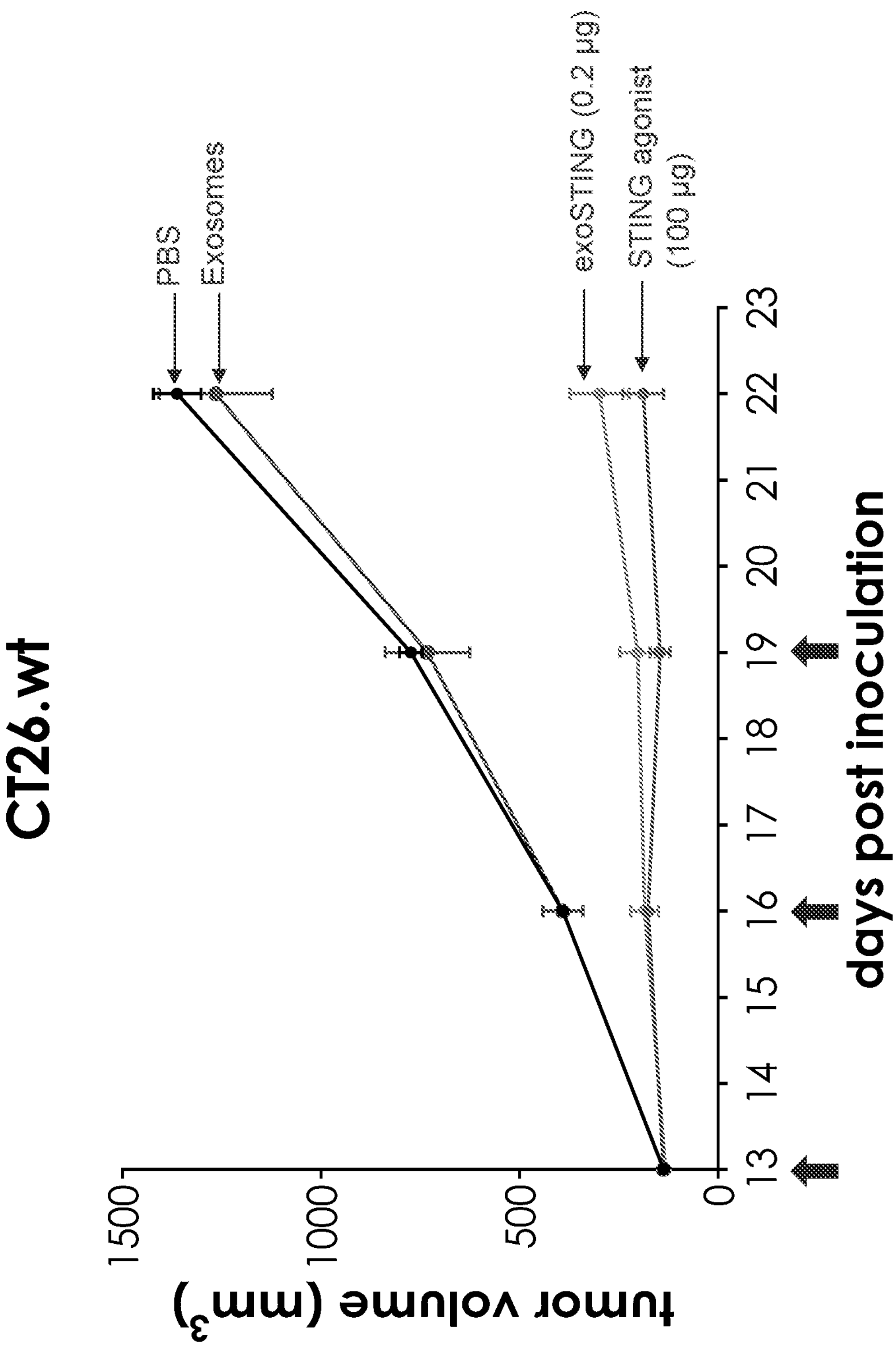

FIG. 63 shows tumor growth curves in CT26.wt tumor-bearing BALB/c mice over the course of the study described in Example 22.

Figure 64:
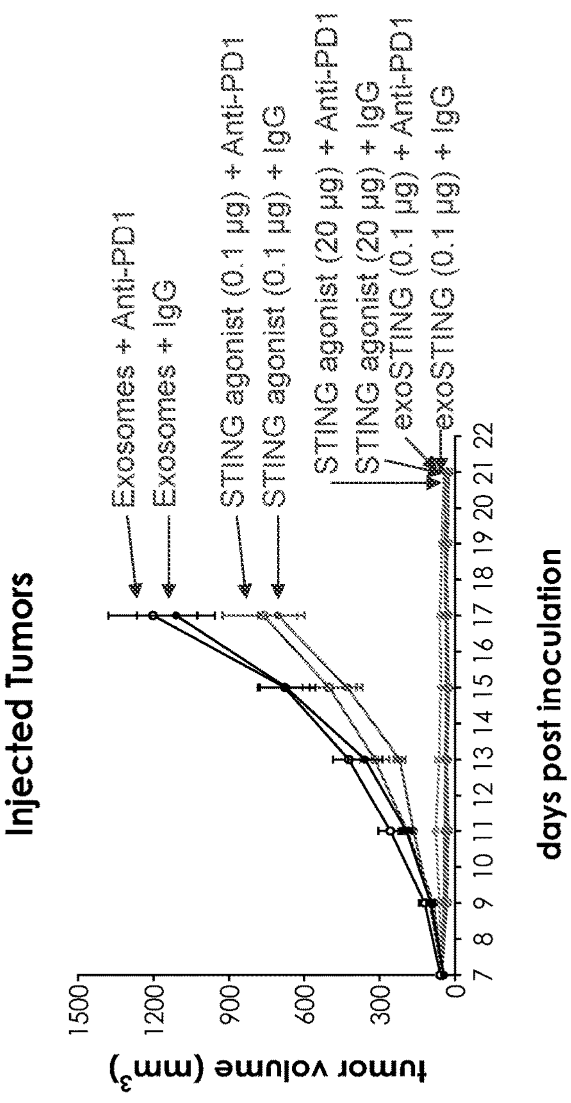

FIG. 64 shows the tumor growth curves of injected B16F10 tumor over the course of the study described in Example 23.

Figure 65:
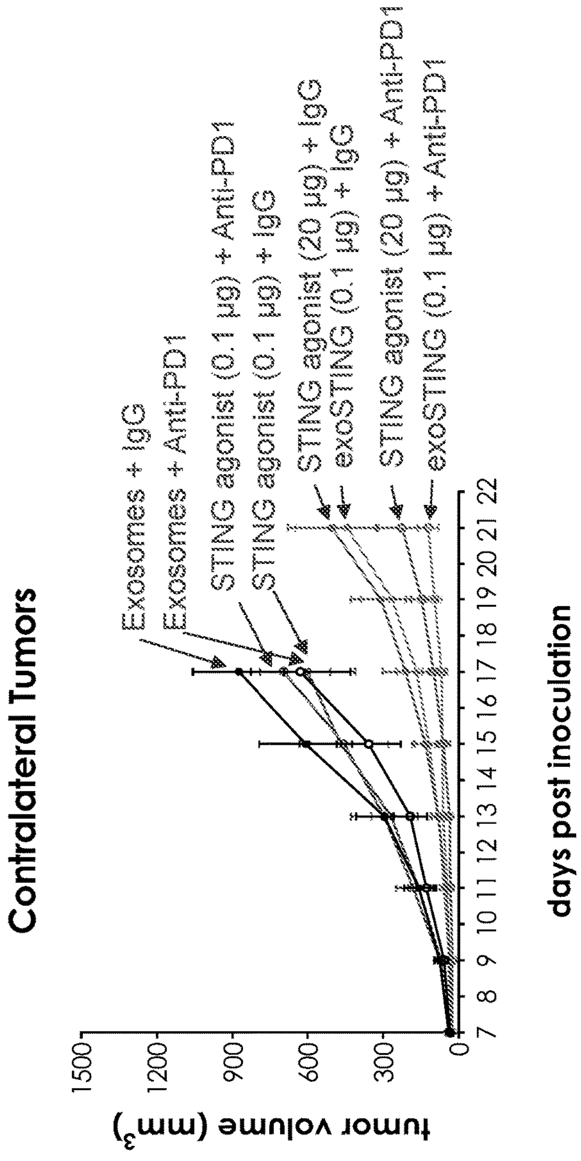

FIG. 65 shows the tumor growth curves of contralateral B16F10 tumor, which was not injected, over the course of the study described in Example 23.

Figure 66:
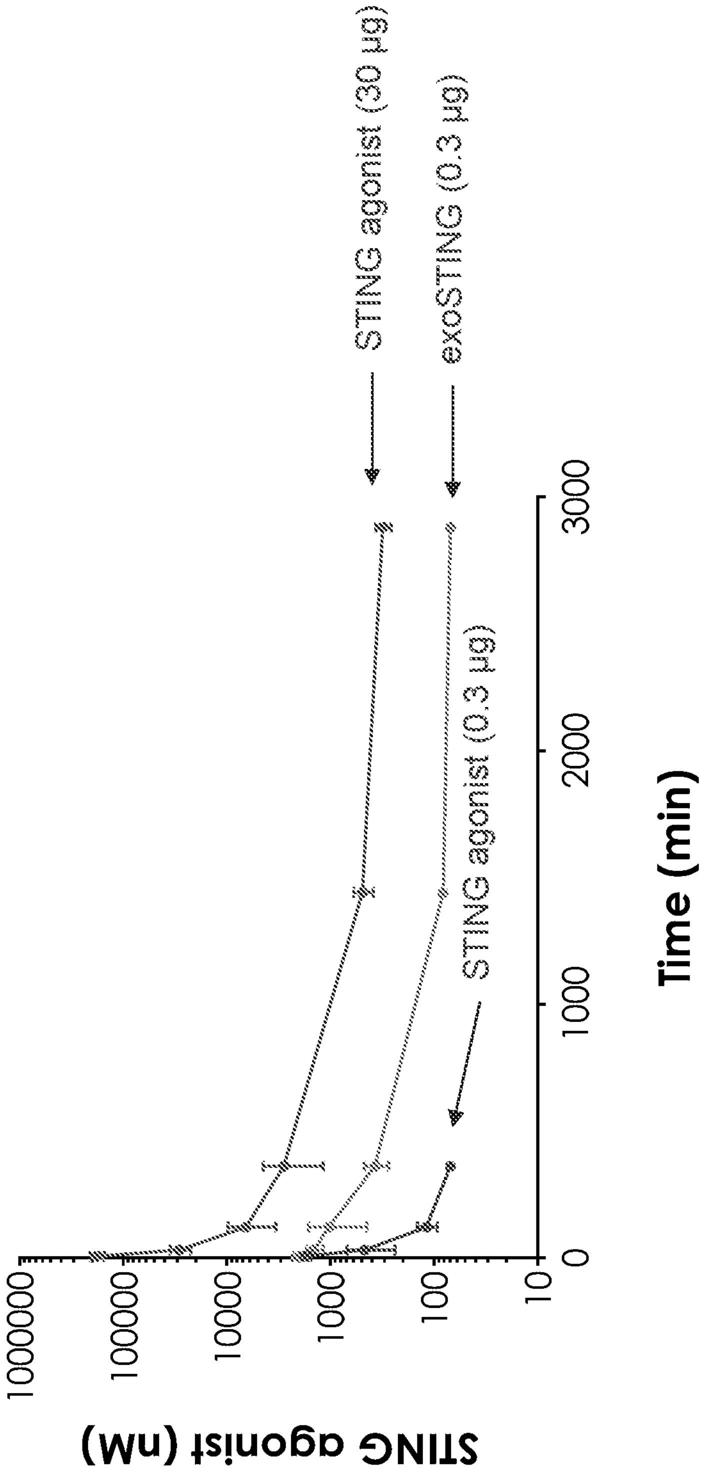

FIG. 66 shows a tumoral pharmacokinetics of 3-3 cAIMPdFSH after intratumoral injection of 30 μg free 3-3 cAIMPdFSH, 0.2 μg free 3-3 cAIMPdFSH, and 0.2 μg exosome-encapsulated 3-3 cAIMPdFSH in B16F10 tumor. Table shows half-life of each samples.

Figure 67:
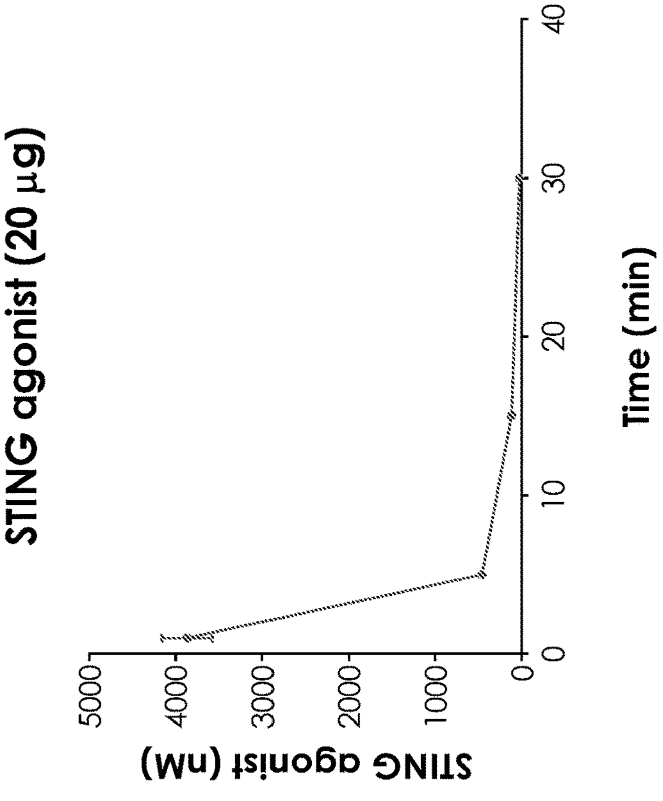

FIG. 67 shows a plasma pharmacokinetics of 3-3 cAIMPdFSH after intravenous injection of 20 μg free 3-3 cAIMPdFSH in naïve C57BL/6 mice.

Figure 68:
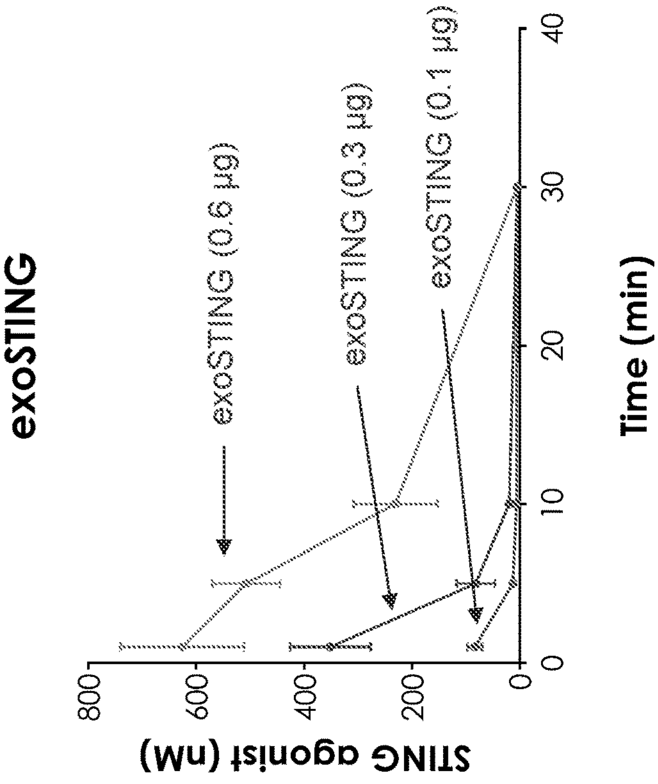
Figure 69A:
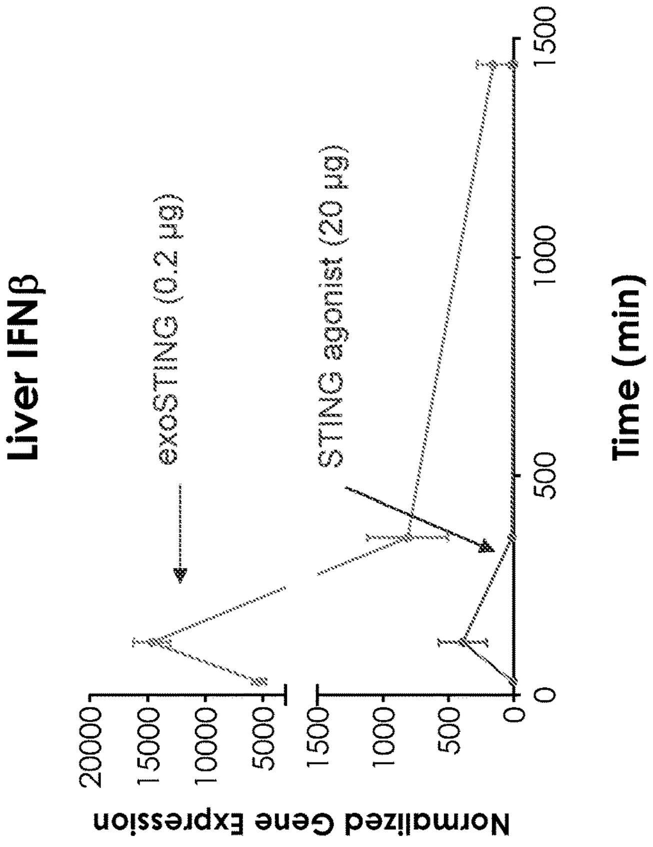
Figure 69B:
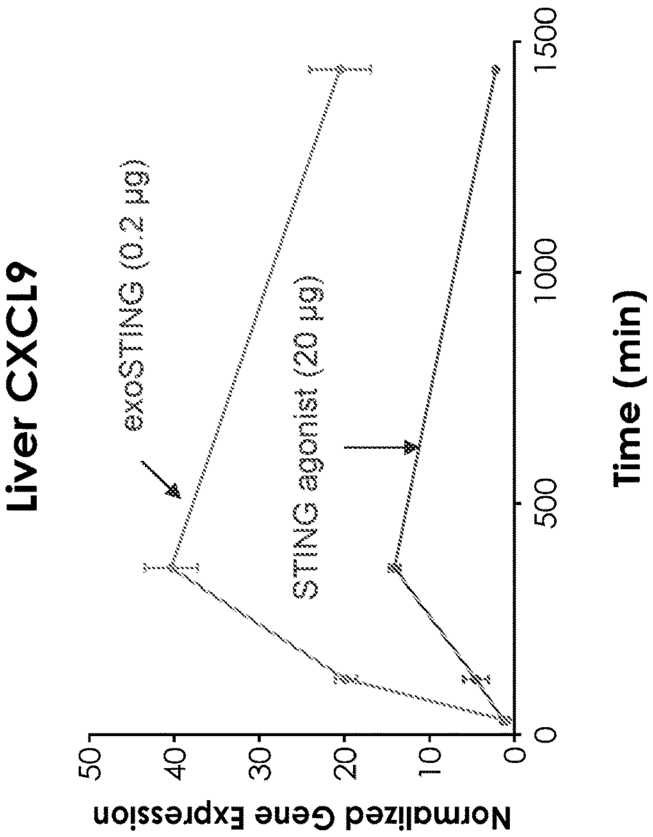
Figure 69D:
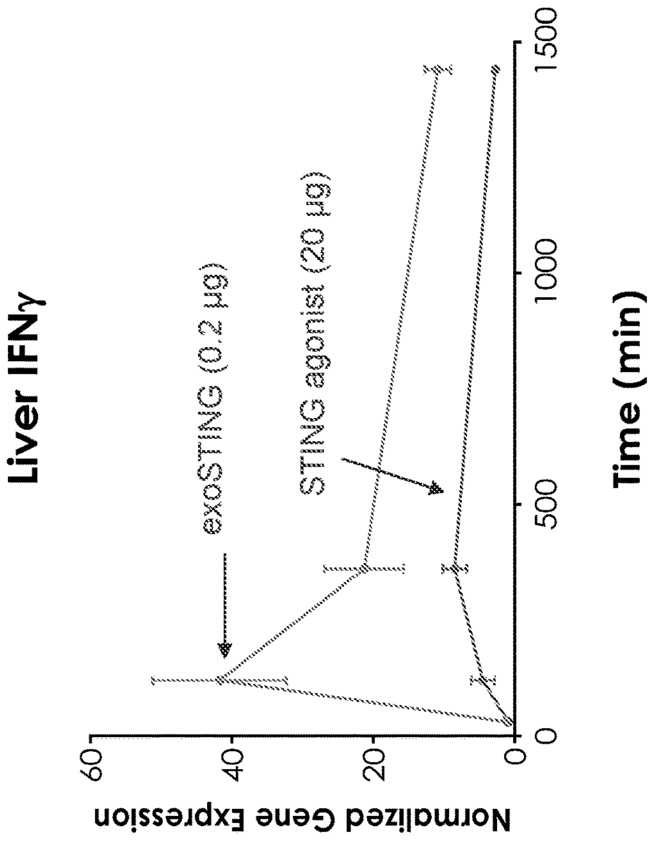
Figure 69C:
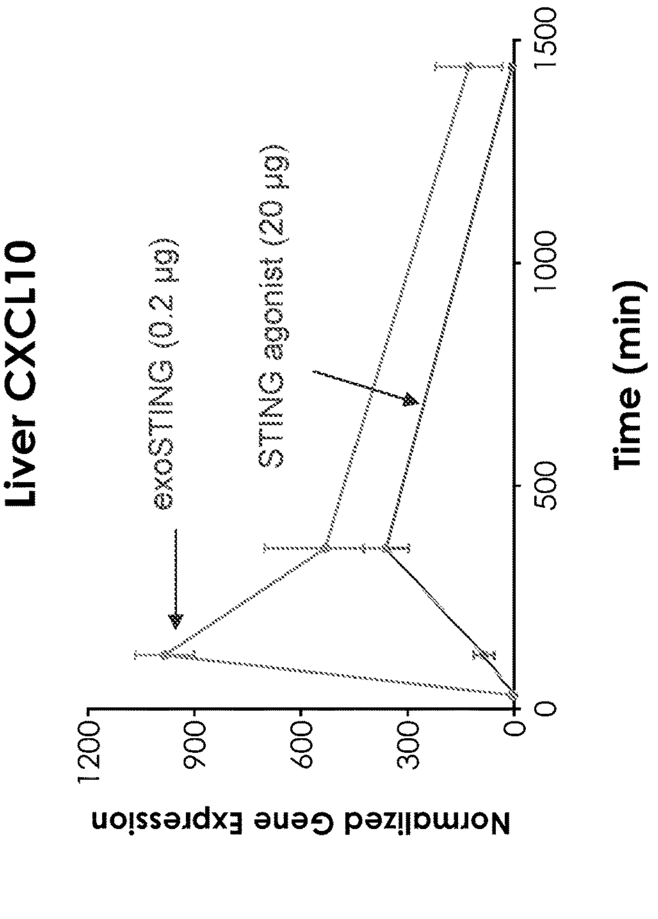
Figure 70A:
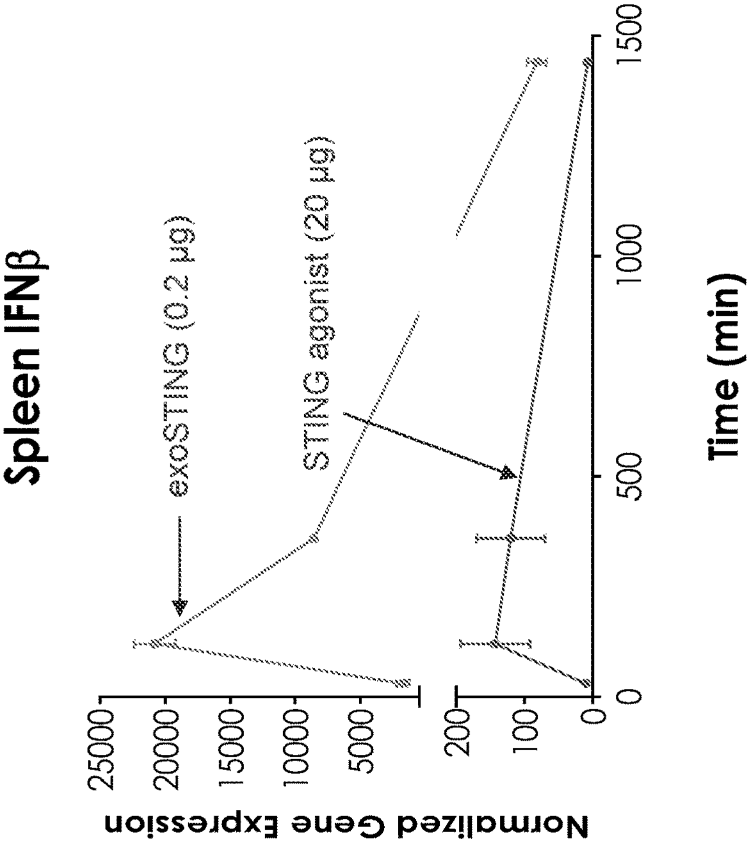
Figure 70B:
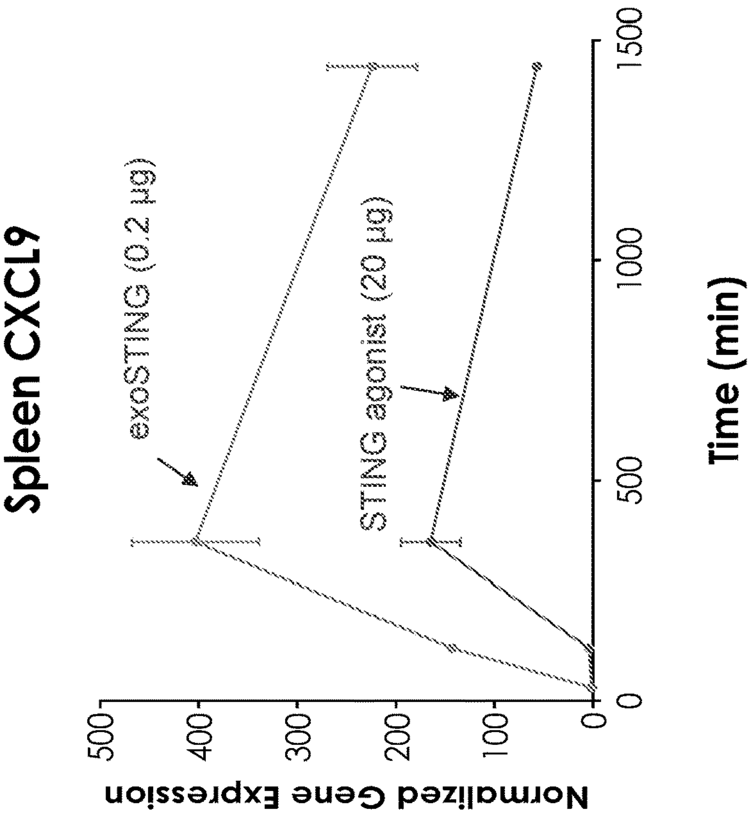
Figure 70C:
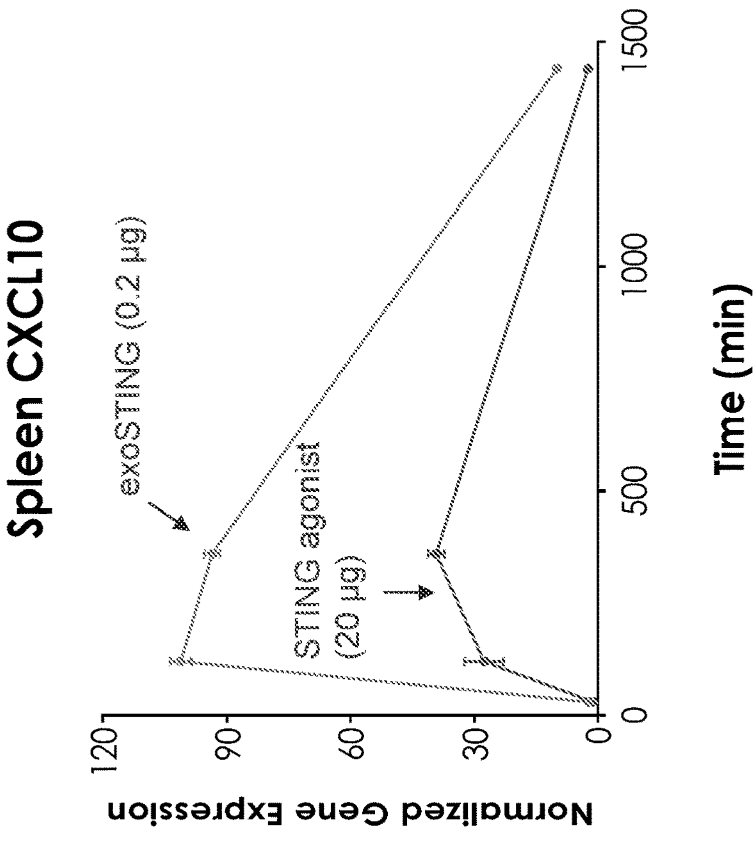
Figure 70D:
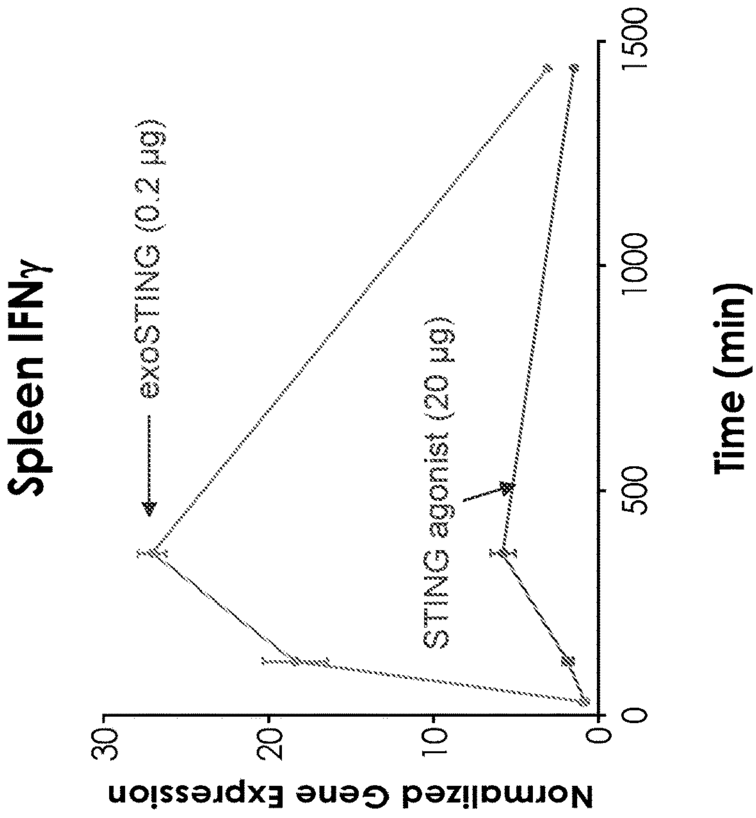
Figure 71B:
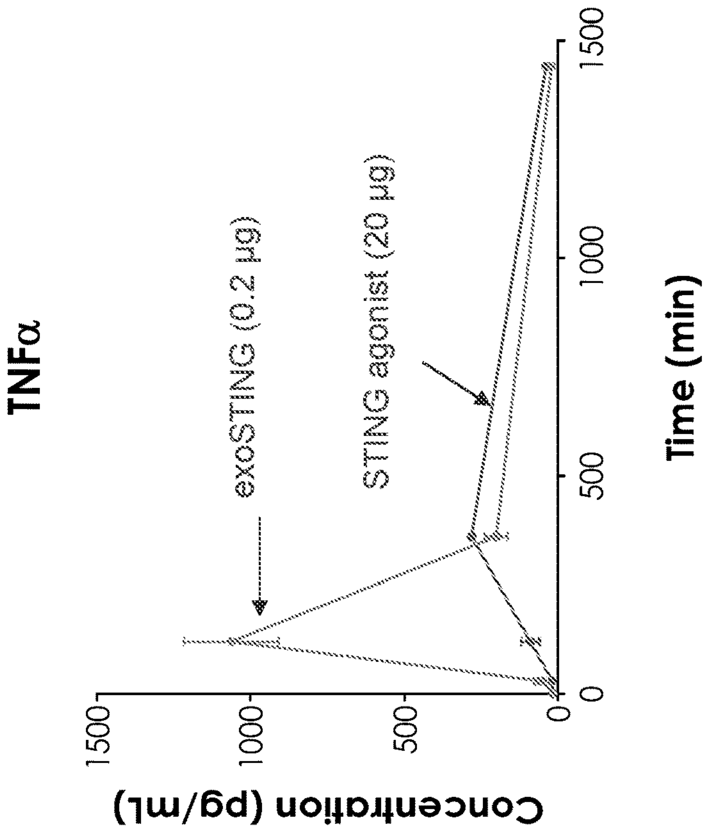
Figure 71A:
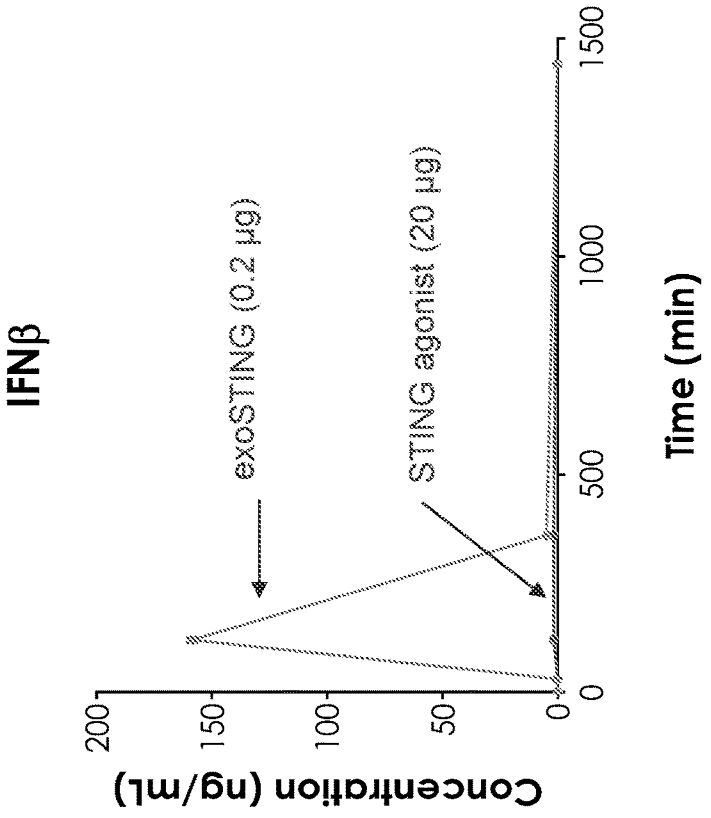
Figures 71C, 71D:
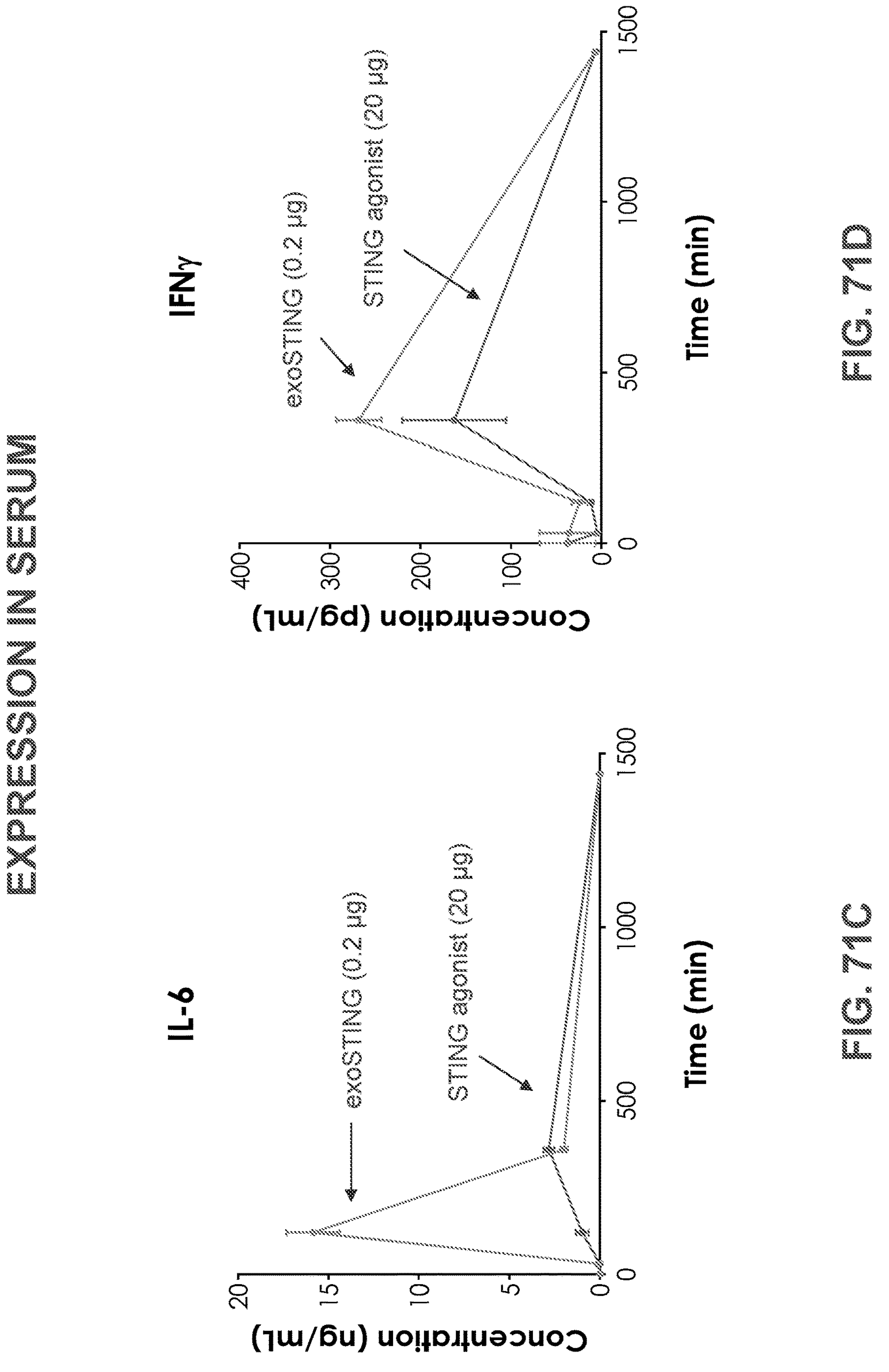
Figure 71E:
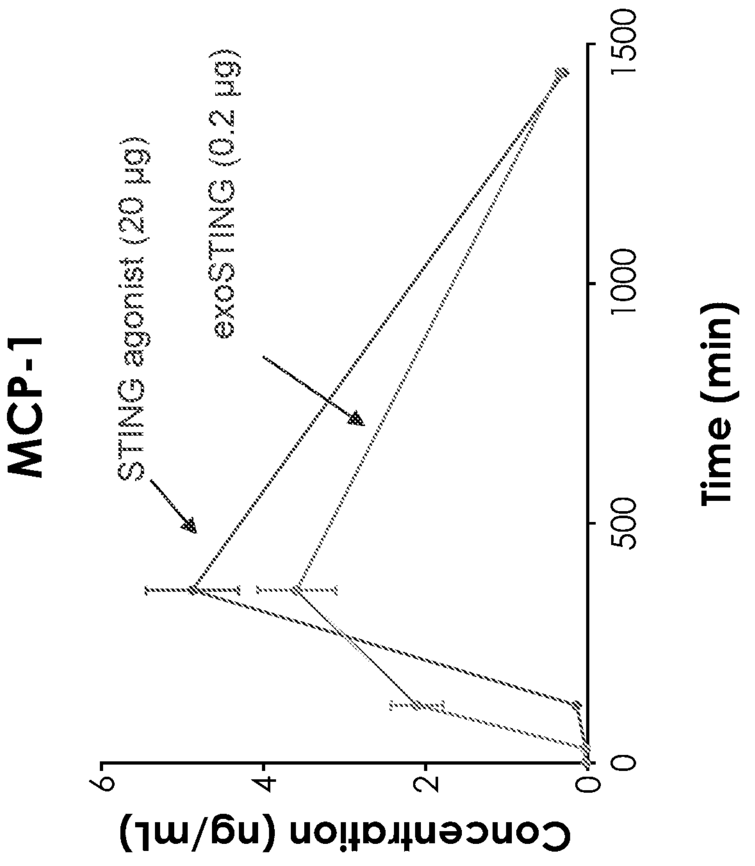

FIG. 68 shows a plasma pharmacokinetics of 3-3 cAIMPdFSH after intravenous injection of 0.1 μg, 0.3 μg, and 0.6 μg exosome-encapsulated 3-3 cAIMPdFSH in naïve C57BL/6 mice. Table shows half-life of each samples.

FIGS. 69A-69D show cytokine expression profiles (IFN-β, CXCL9, CXCL10, and IFN-γ, respectively) over the time in liver of naïve C57BL/6 mice after a single intravenous injection of 20 μg free 3-3 cAIMPdFSH or 0.2 μg exosome-encapsulated 3-3 cAIMPdFSH.

FIGS. 70A-70D show cytokine expression profiles (IFN-β, CXCL9, CXCL10, and IFN-γ, respectively) over time in spleen of naïve C57BL/6 mice after a single intravenous injection of 20 μg free 3-3 cAIMPdFSH or 0.2 μg exosome-encapsulated 3-3 cAIMPdFSH.

FIGS. 71A-71E show serum cytokine expression profiles (IFN-β, TNF-α, IL-6, IFN-γ, and MCP-1, respectively) over the time after a single intravenous injection of 20 μg free 3-3 cAIMPdFSH or 0.2 μg exosome-encapsulated 3-3 cAIMPdFSH in naïve C57BL/6 mice.

Figures 72A, 72B, 72C:
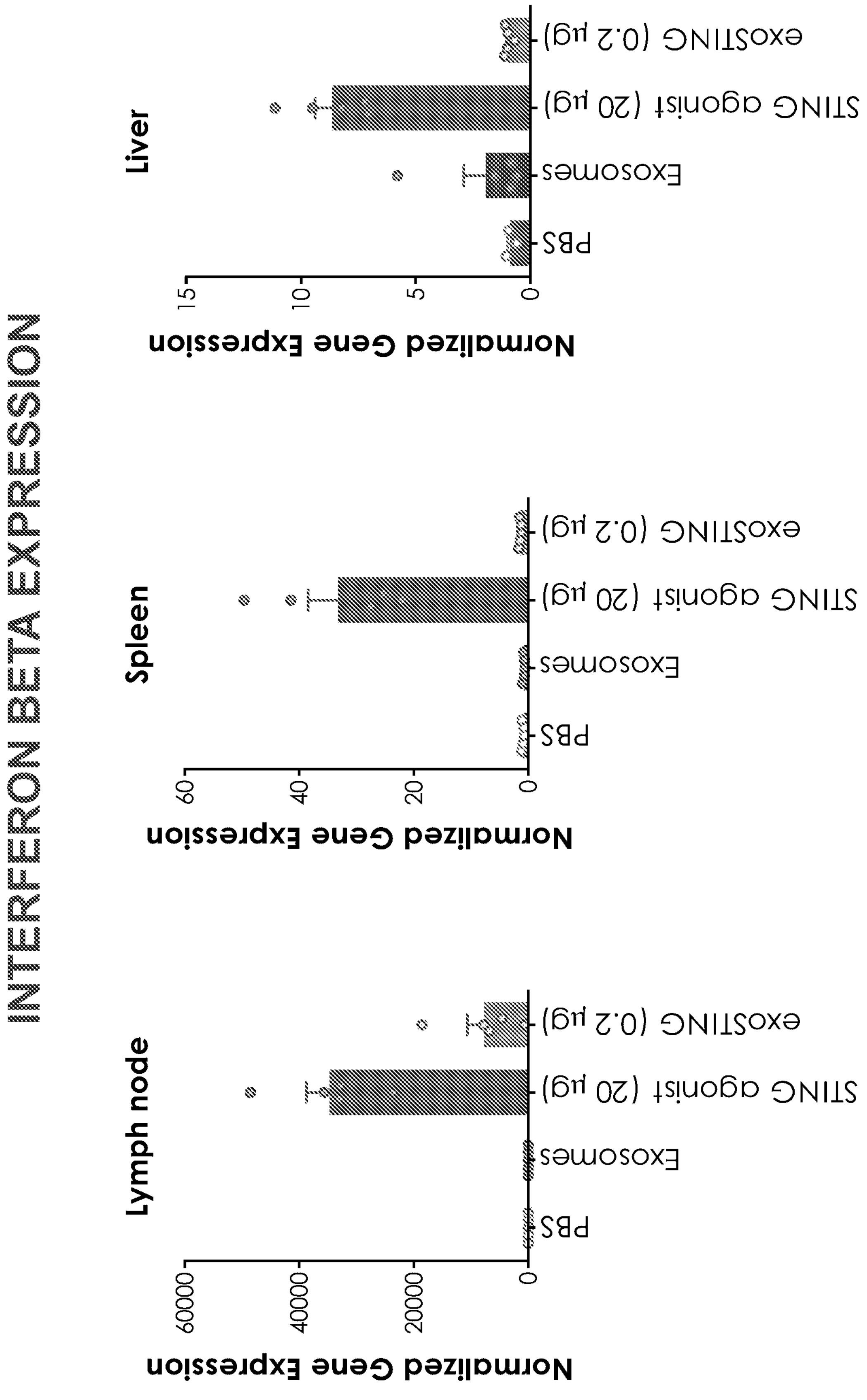

FIGS. 72A-72C show IFNβ expression profiles in tissues (lymph node, spleen, and liver, respectively) from naïve C57BL/6 mice after a single subcutaneous injection of PBS, exosomes, 20 μg free 3-3 cAIMPdFSH, or 0.2 μg exosome-encapsulated 3-3 cAIMPdFSH.

Figure 73A:
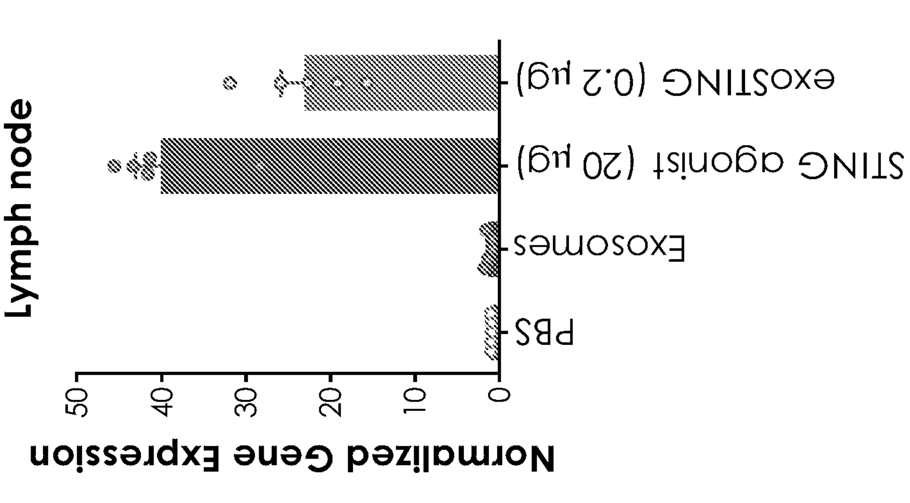
Figure 73B:
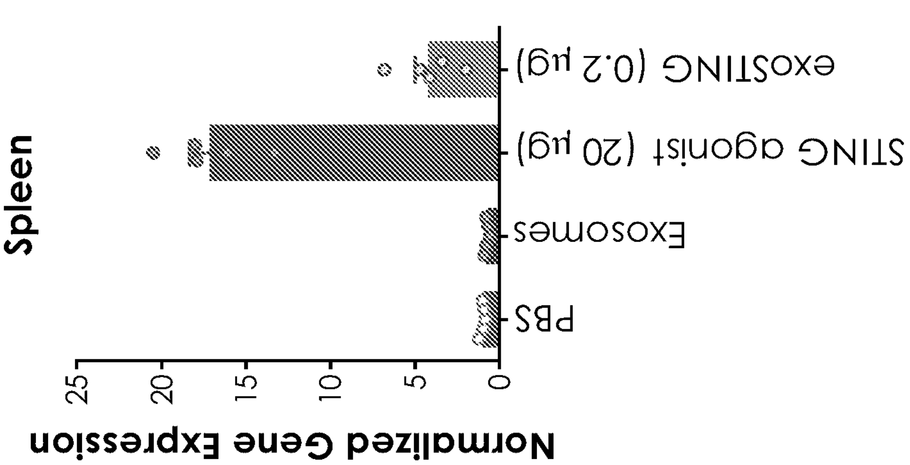
Figure 73C:
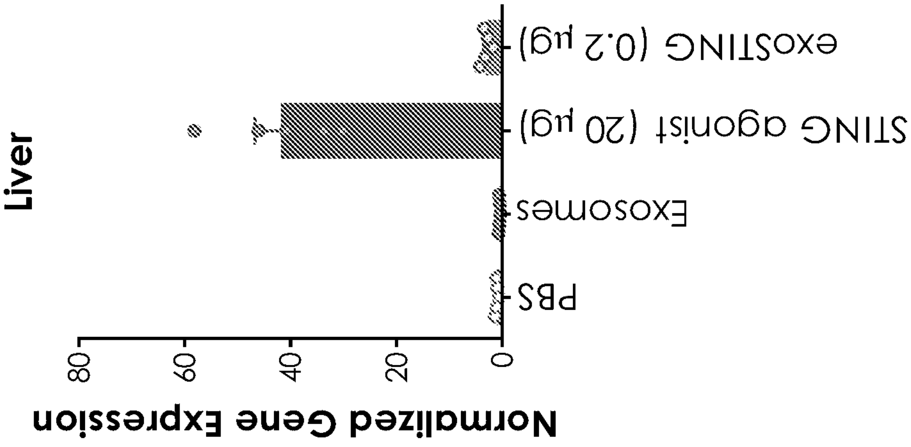

FIGS. 73A-73C show CXCL9 expression profiles in tissues (lymph node, spleen, and liver, respectively) from naïve C57BL/6 mice after a single subcutaneous injection of PBS, exosomes, 20 μg free 3-3 cAIMPdFSH, or 0.2 μg exosome-encapsulated 3-3 cAIMPdFSH.

Figures 74A, 74B, 74C:
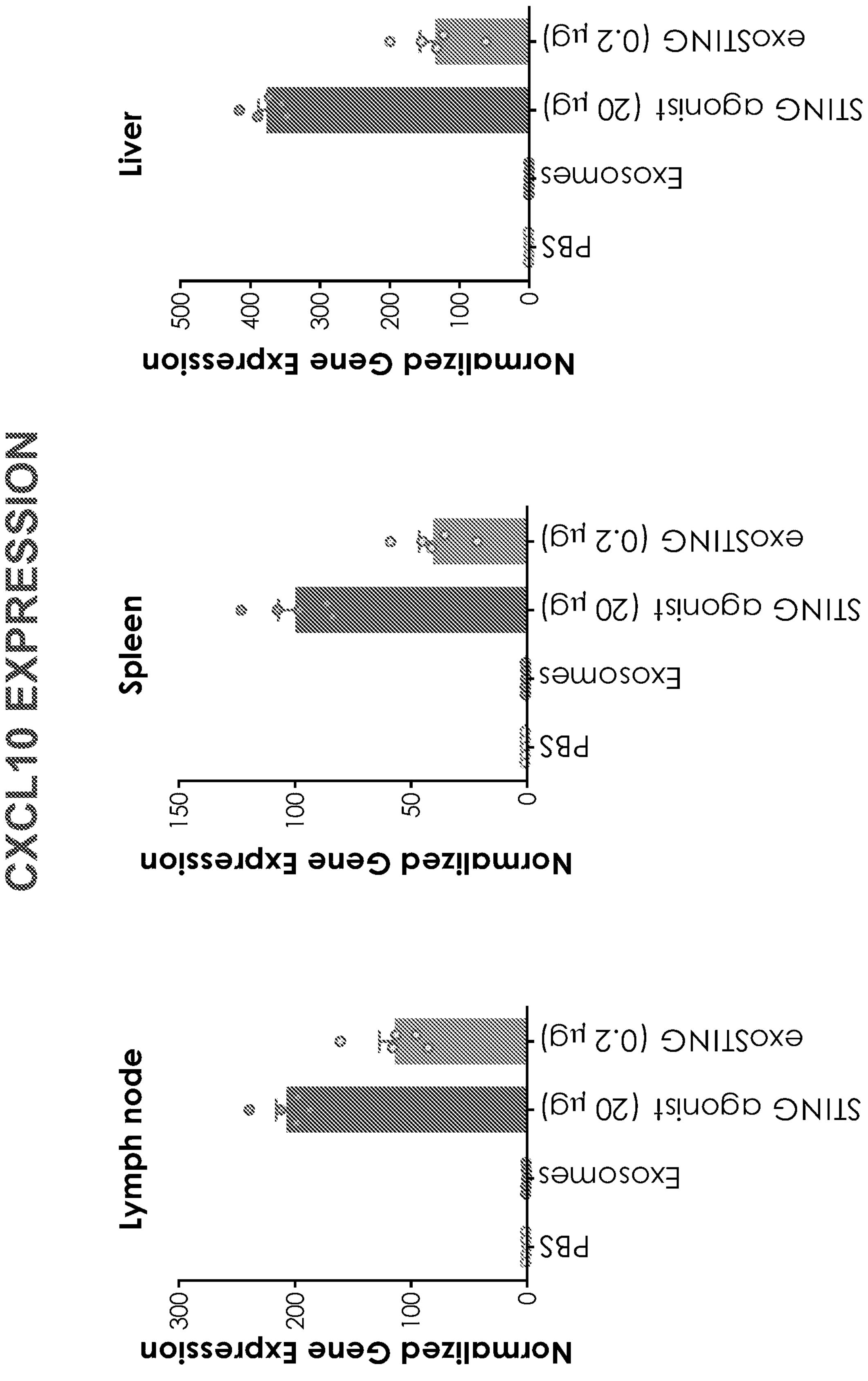

FIGS. 74A-74C show CXCL10 expression profiles in tissues (lymph node, spleen, and liver, respectively) from naïve C57BL/6 mice after a single subcutaneous injection of PBS, exosomes, 20 μg free 3-3 cAIMPdFSH, or 0.2 μg exosome-encapsulated 3-3 cAIMPdFSH.

Figure 75A:
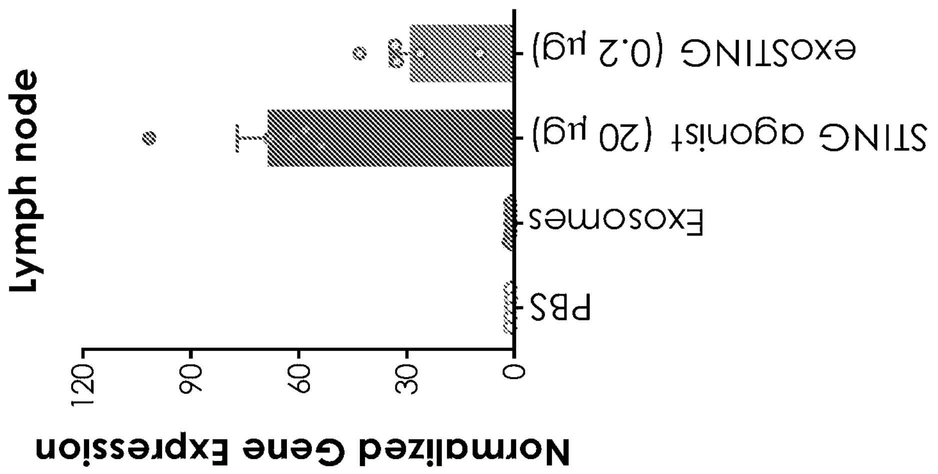
Figure 75B:
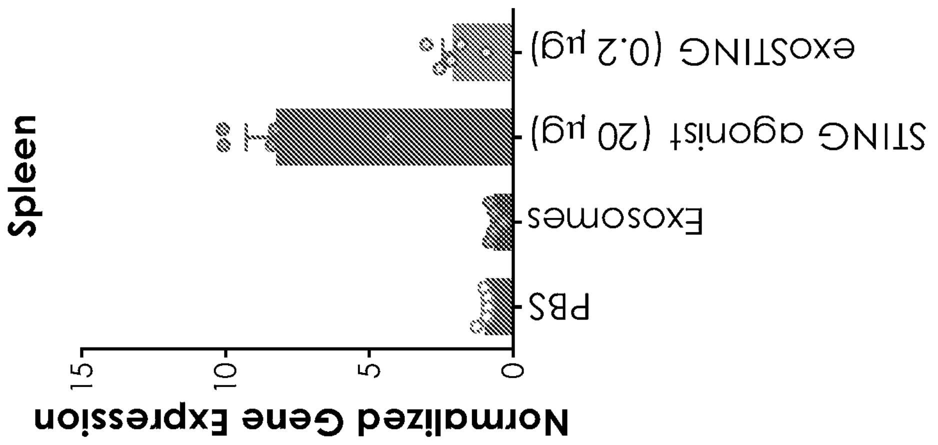
Figure 75C:
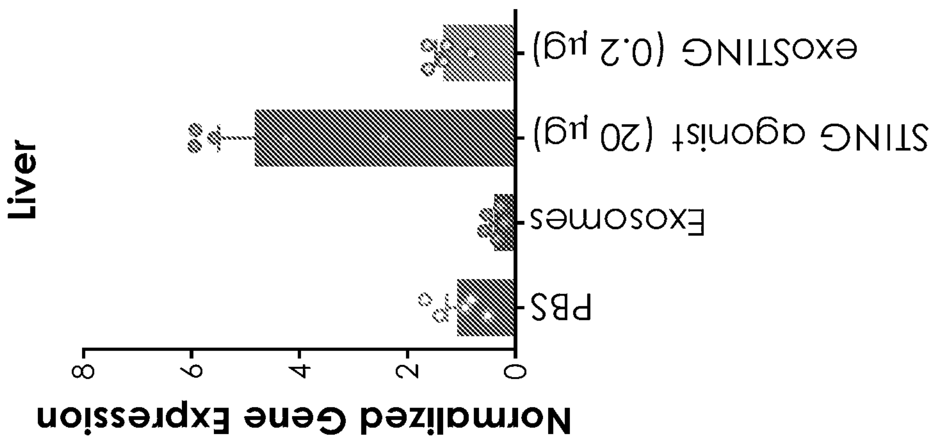
Figure 76A:
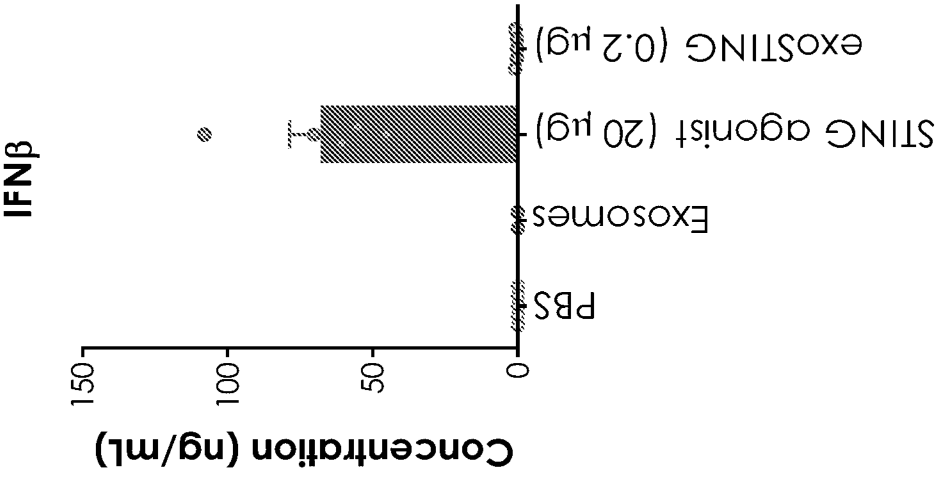
Figure 76B:
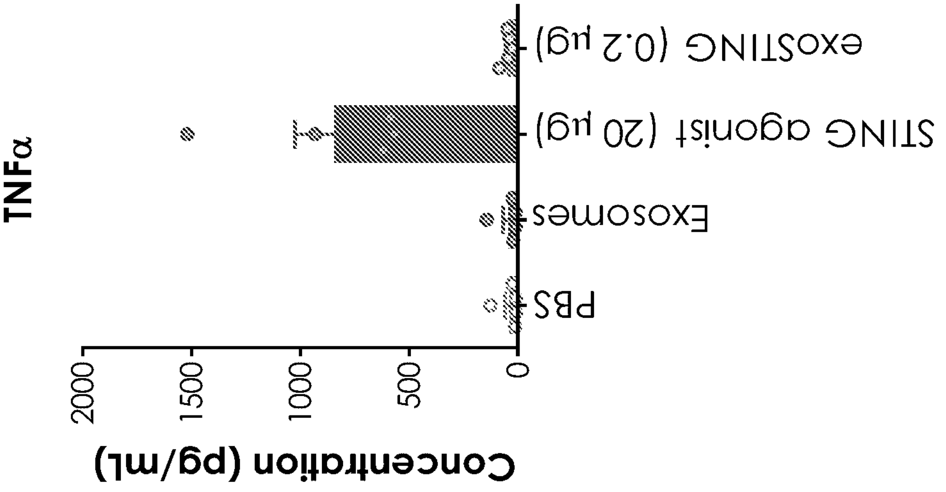
Figure 76C:
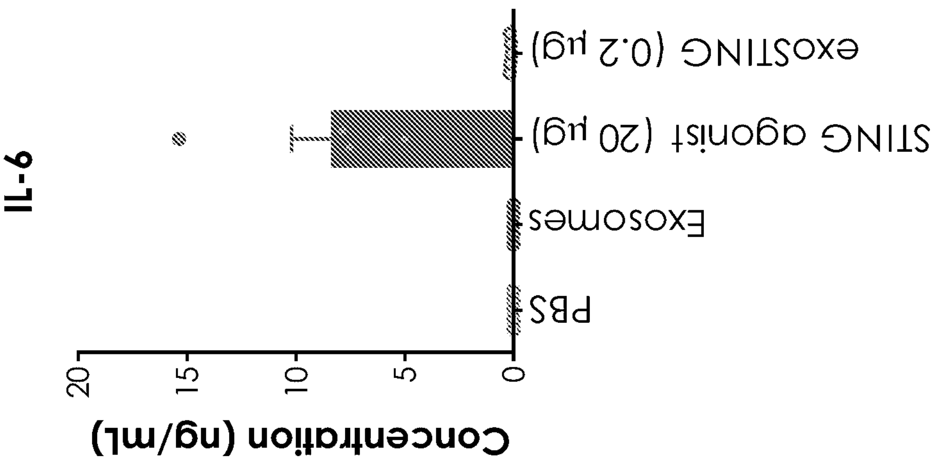
Figure 76E:
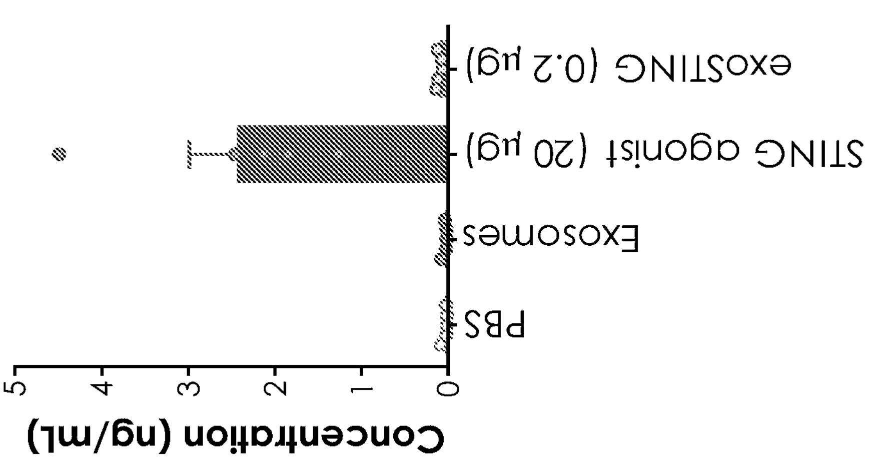
Figure 76D:
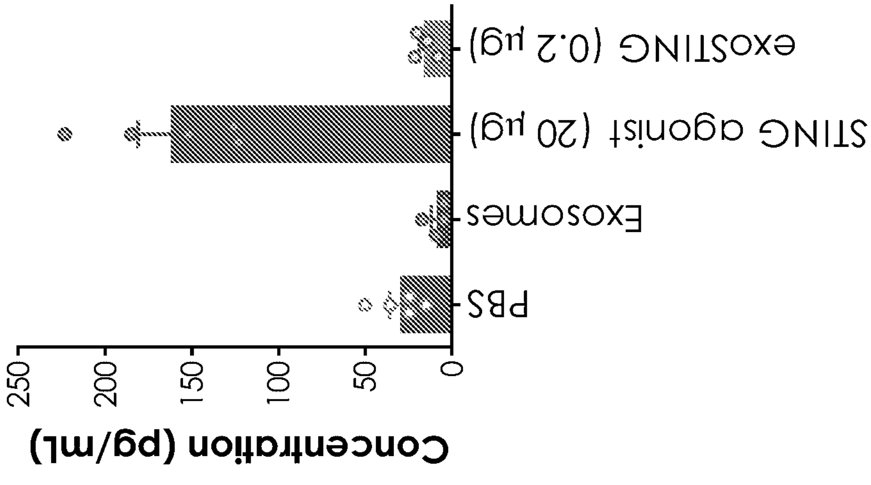

FIGS. 75A-75C show IFN-γ expression profiles in tissues (lymph node, spleen, and liver, respectively) from naïve C57BL/6 mice after a single subcutaneous injection of PBS, exosomes, 20 μg free 3-3 cAIMPdFSH, or 0.2 μg exosome-encapsulated 3-3 cAIMPdFSH.

FIGS. 76A-76E show serum cytokine expression profiles (IFNβ, TNFα, IL-6, IFN-γ, and MCP-1, respectively) in naïve C57BL/6 mice after a single subcutaneous injection of PBS, exosomes, 20 μg free 3-3 cAIMPdFSH, or 0.2 μg exosome-encapsulated 3-3 cAIMPdFSH.

Figure 77A:
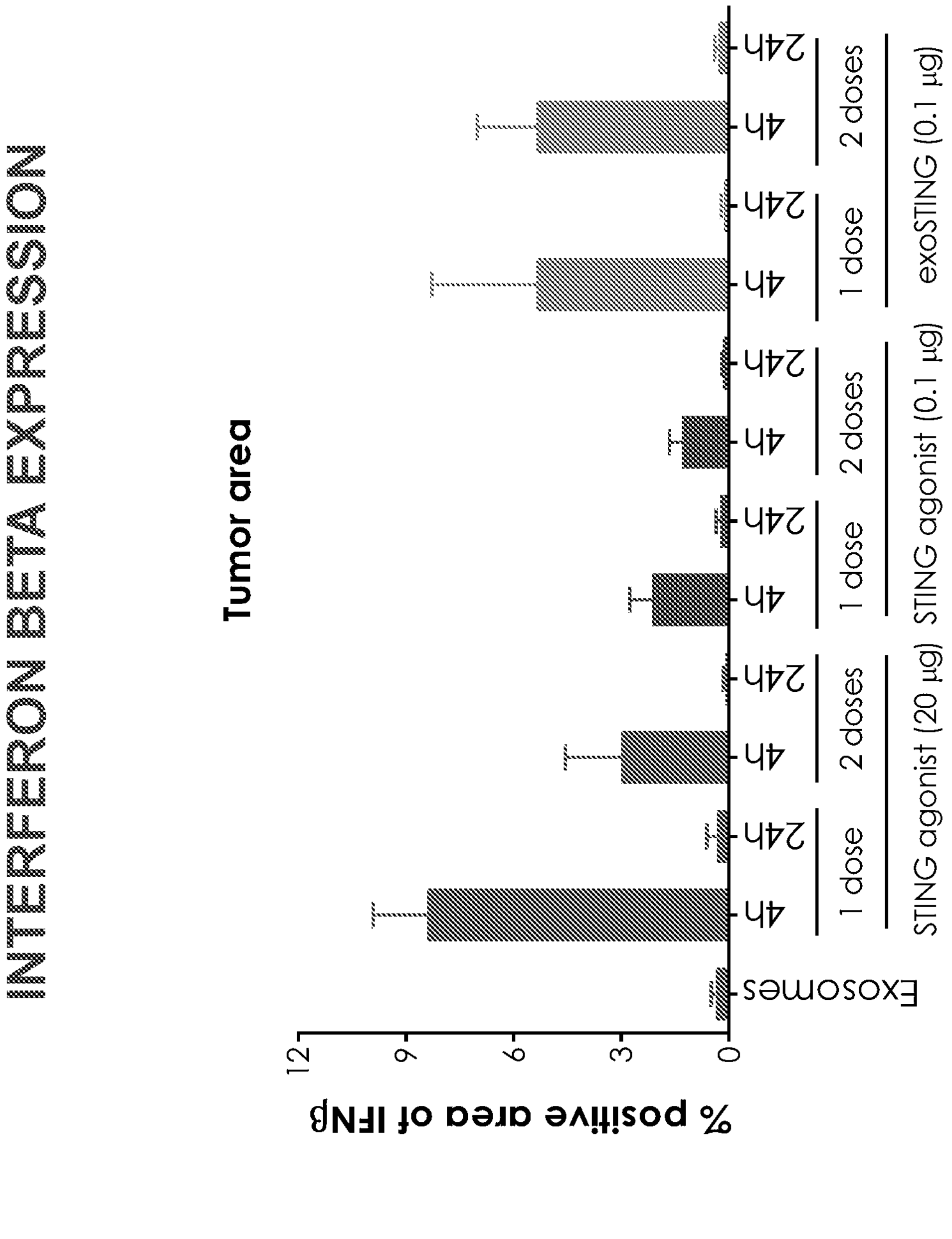
Figure 77B:
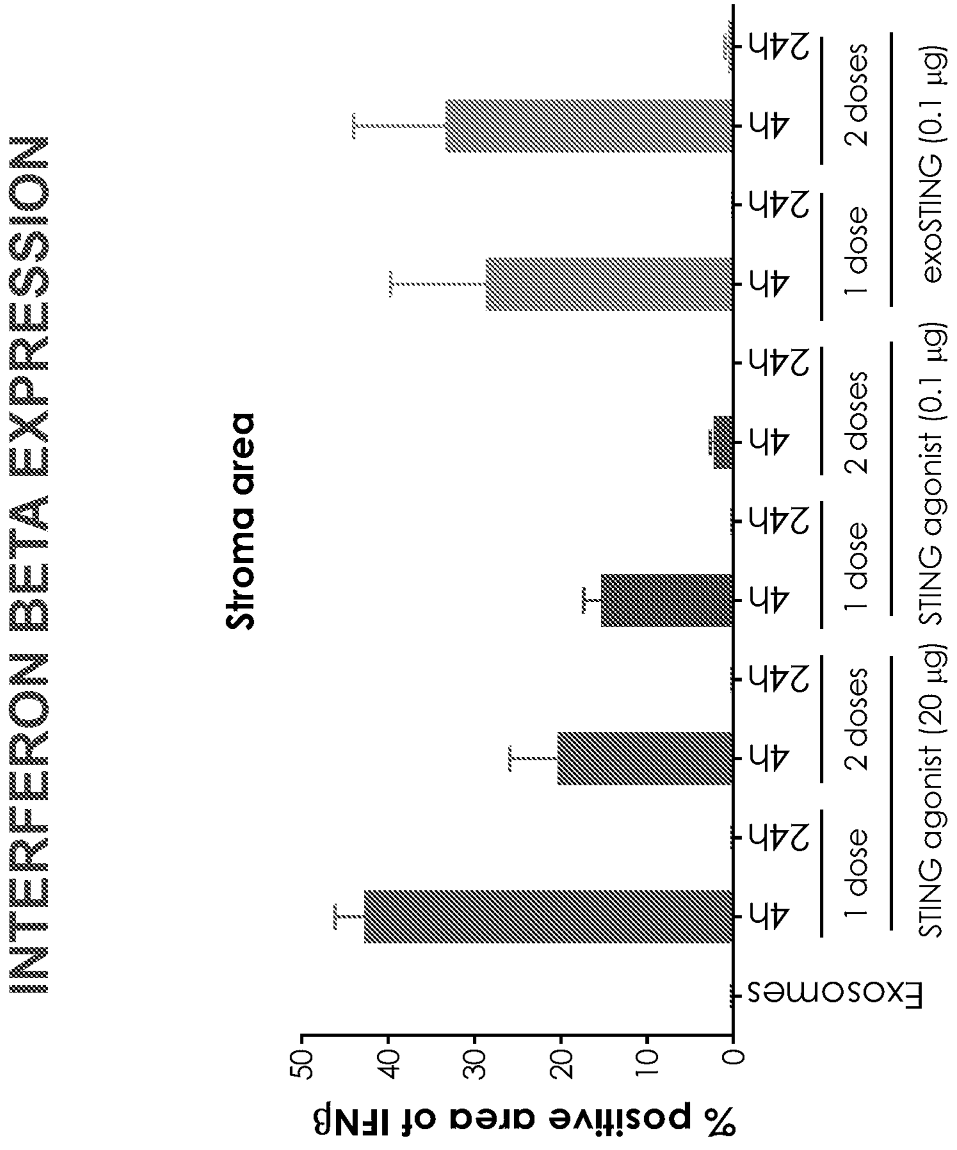

FIGS. 77A and 77B show quantitative IFNβ expression profiles in tumor (FIG. 77A) or stromal area (FIG. 77B) from B16F10 tumor section after intratumoral injection of exosomes, 20 μg free 3-3 cAIMPdFSH, 0.1 μg free 3-3 cAIMPdFSH, or 0.1 μg exosome-encapsulated 3-3 cAIMPdFSH as described in Example 28.

Figure 78A:
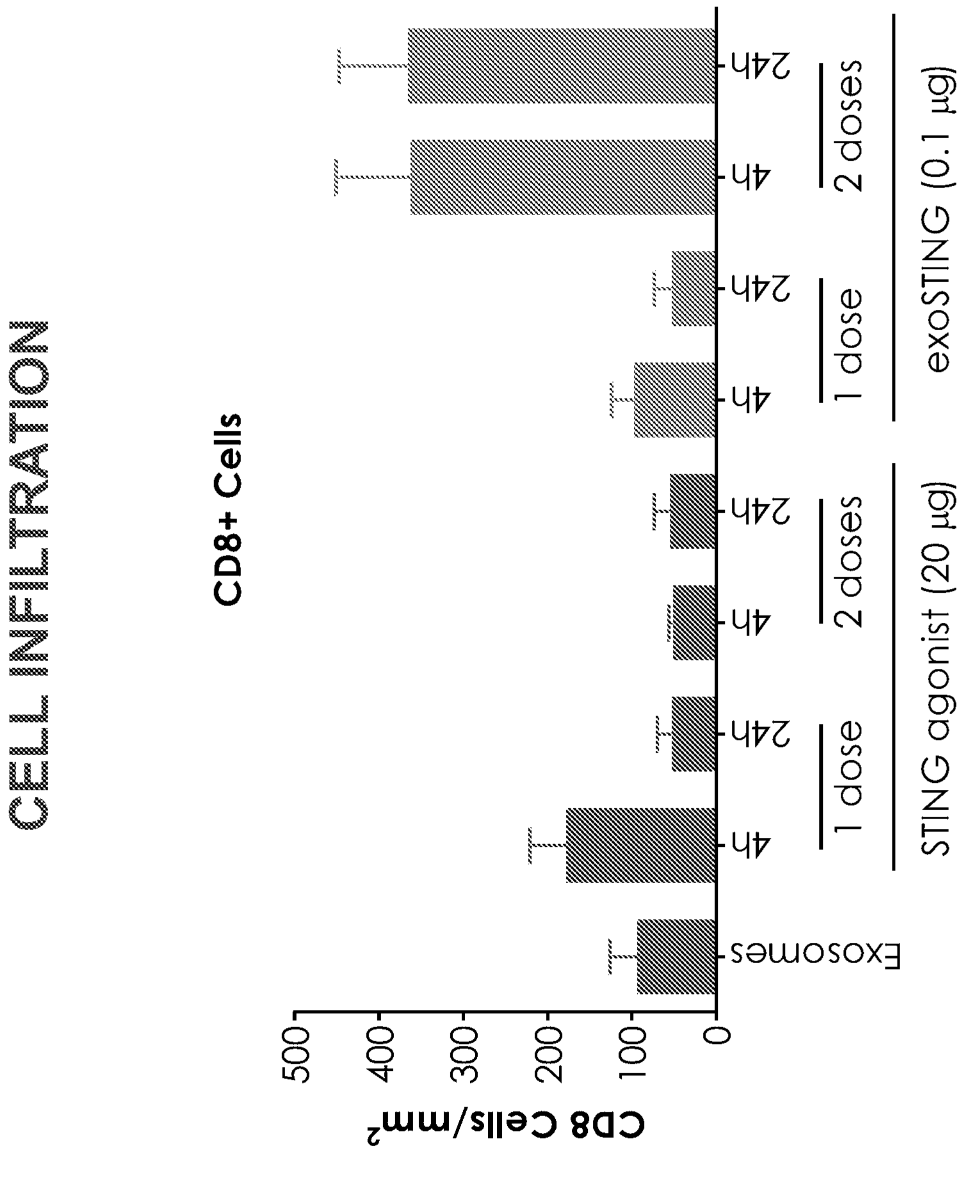
Figure 78B:
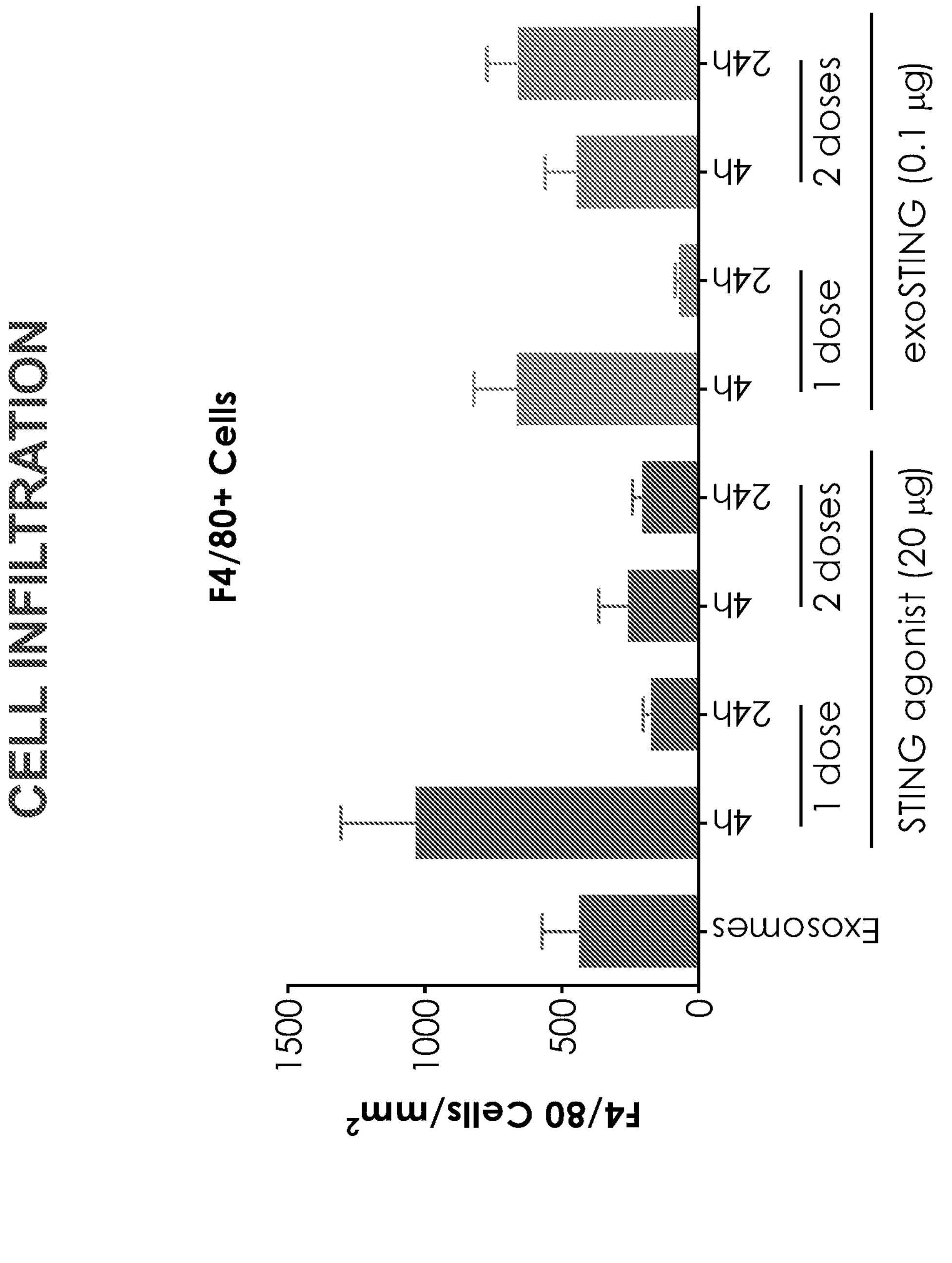

FIGS. 78A and 78B show a number of CD8 positive cells (FIG. 78A) and F4/80 positive cells (FIG. 78B) in the tumor sections after intratumoral injection of exosomes, 20 μg free 3-3 cAIMPdFSH, or 0.1 μg exosome-encapsulated 3-3 cAIMPdFSH as described in Example 28.

Figure 79A:
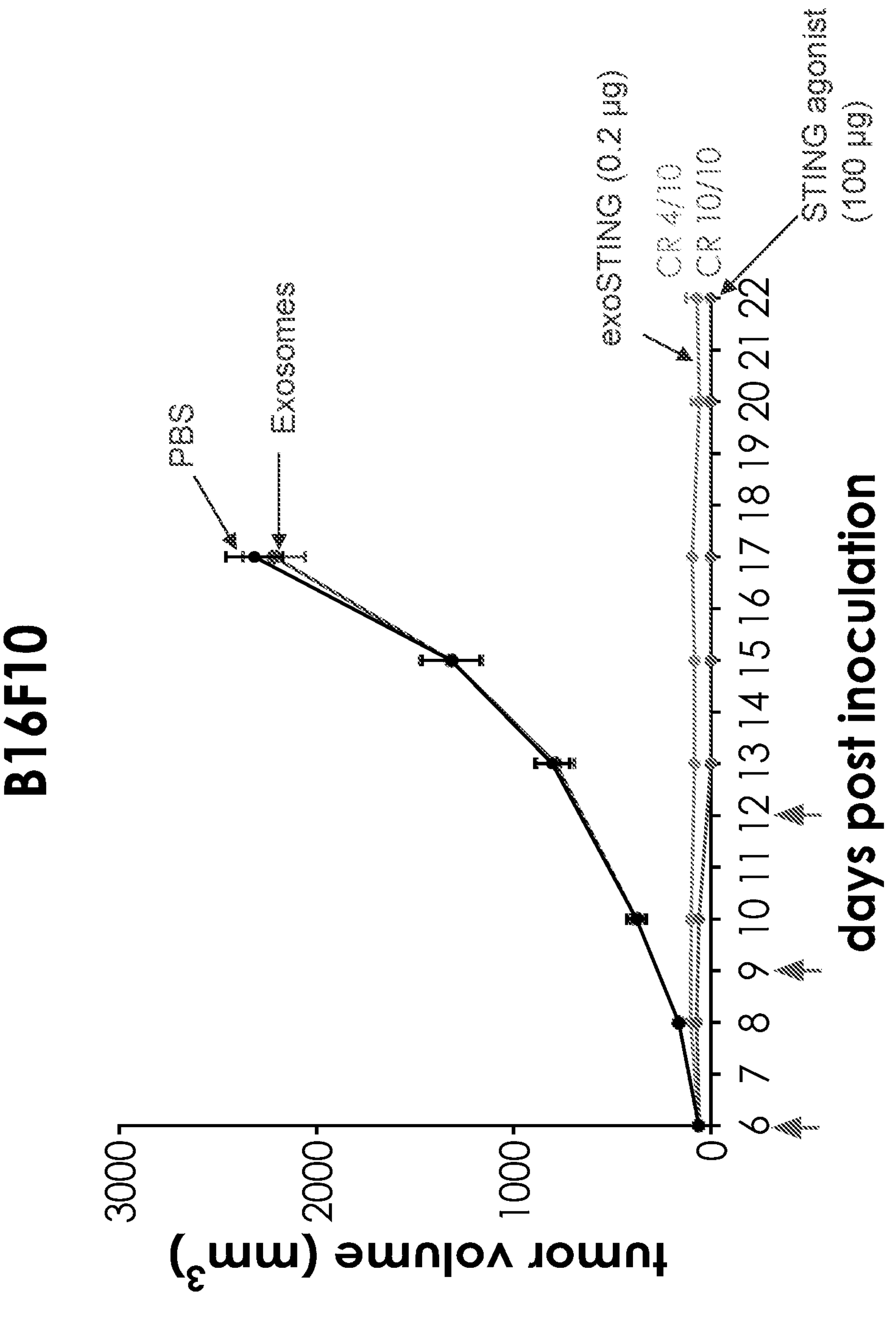
Figure 79B:
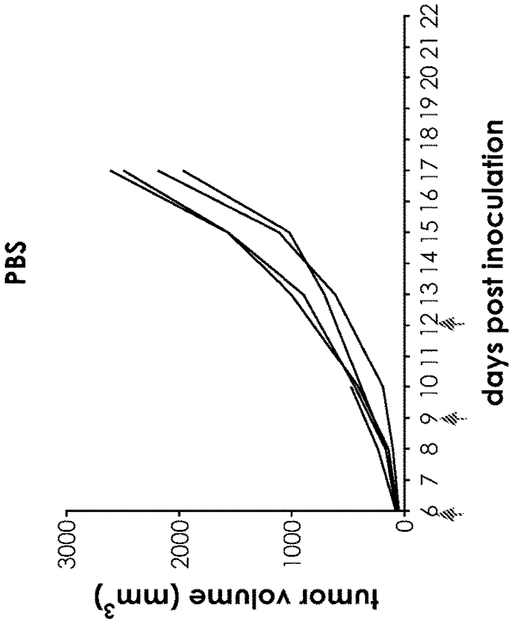
Figure 79C:
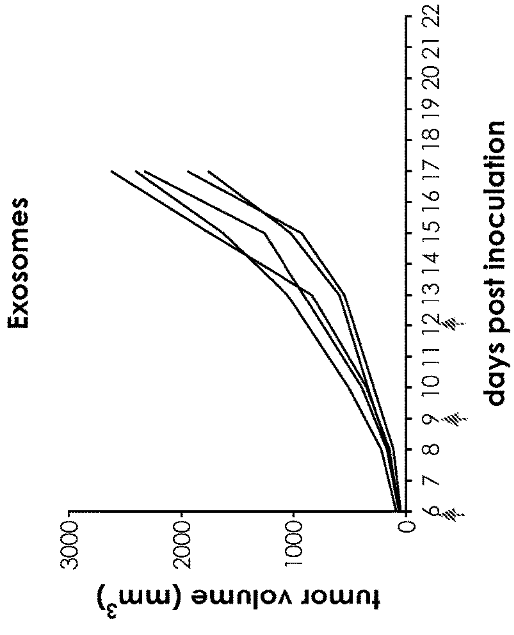
Figure 79D:
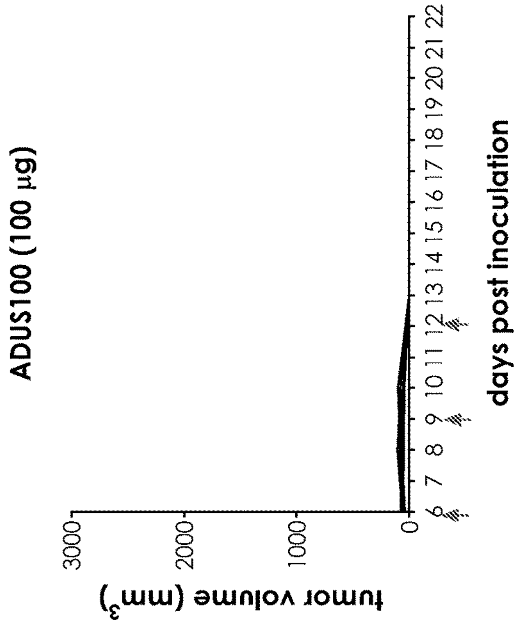
Figure 79E:
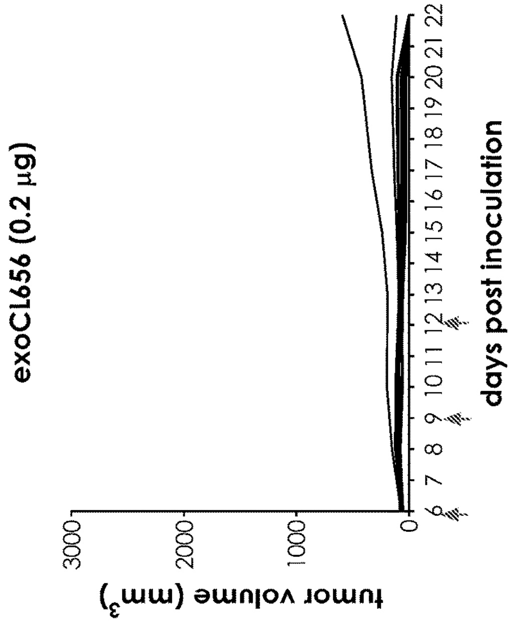

FIG. 79A shows the primary tumor growth curves in B16F10 tumor-bearing mice over the course of the study described in Example 29. FIGS. 79B-79E show the tumor growth curves for each animal in the different groups (i.e., PBS, exosomes, ADUS100, and exoCL656, respectively)

Figure 80A:
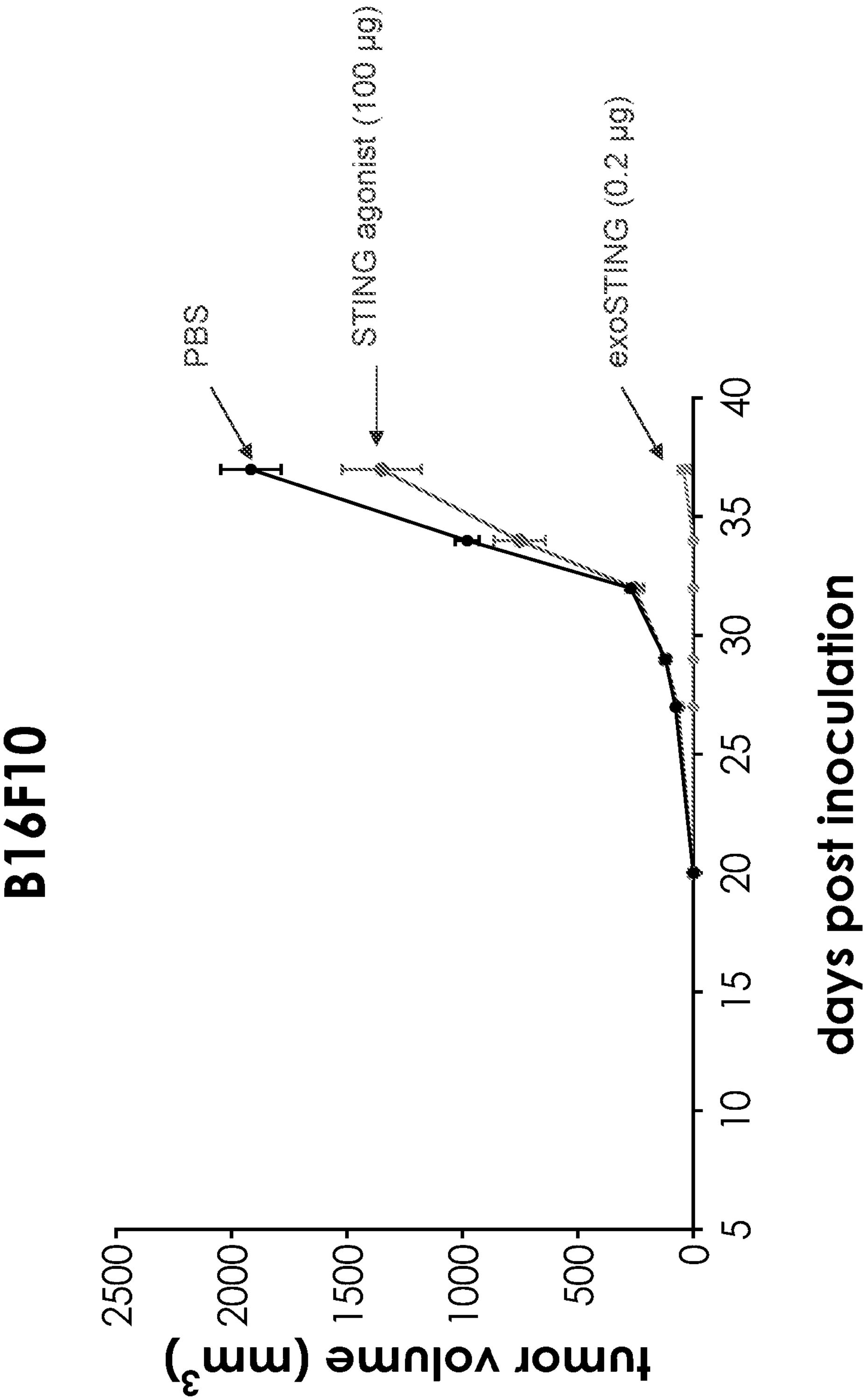
Figure 80B:
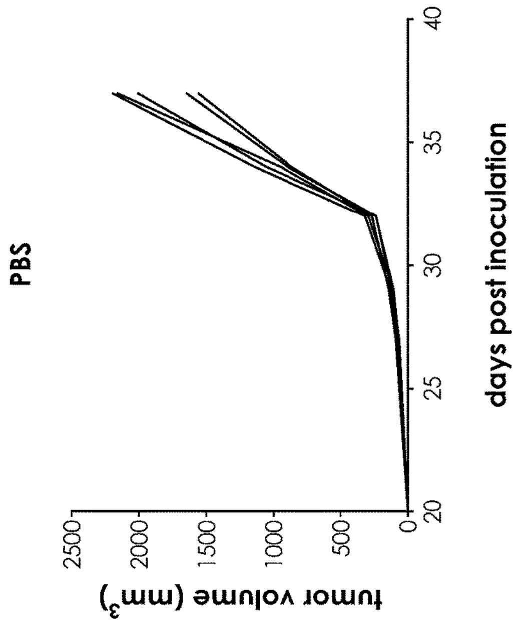
Figure 80C:
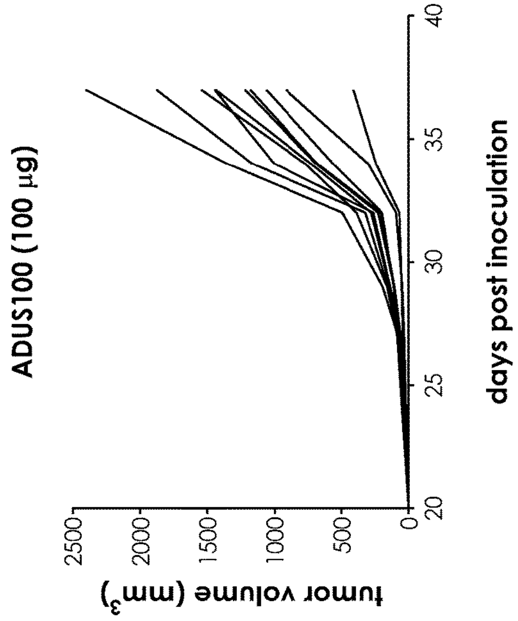
Figure 80D:
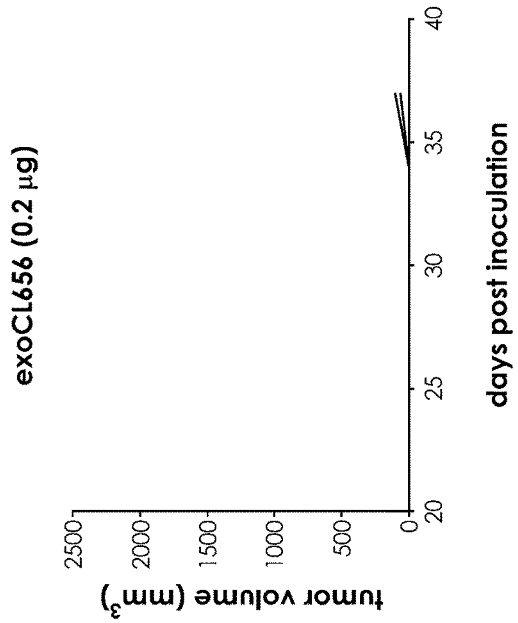

FIG. 80A shows the re-challenged tumor growth curves in B16F10 tumor-bearing mice over the course of the study described in Example 29. FIGS. 80B-80D show the tumor growth curves for each animal in the different groups (i.e., PBS, ADUS100, and exoCL656, respectively).

DETAILED DESCRIPTION OF THE DISCLOSURE

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

I. Definitions

It is noted that, as used herein and in the appended claims, the singular forms “a,” “an,” and “the” include plural referents unless the context clearly dictates otherwise. As such, the terms “a” (or “an”), “one or more,” and “at least one” can be used interchangeably herein. It is further noted that the claims can be drafted to exclude any optional element. As such, this statement is intended to serve as antecedent basis for use of such exclusive terminology as “solely,” “only” and the like in connection with the recitation of claim elements, or use of a negative limitation.

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

It is understood that wherever aspects are described herein with the language “comprising,” otherwise analogous aspects described in terms of “consisting of” and/or “consisting essentially of” are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term “about” or “approximately” is used herein to mean approximately roughly, around, or in the region of. When the term “about” is used in conjunction with a numerical range, it modifies that range by extending the boundaries above and below the numerical values set forth. The term used herein means within 5% of the referenced amount, e.g., about 50% is understood to encompass a range of values from 47.5% to 52.5%.

As used herein, the term “extracellular vesicle” or “EV” refers to a cell-derived vesicle comprising a membrane that encloses an internal space. Extracellular vesicles comprise all membrane-bound vesicles (e.g., exosomes, nanovesicles) that have a smaller diameter than the cell from which they are derived. Generally extracellular vesicles range in diameter from 20 nm to 1000 nm, and can comprise various macromolecular payload either within the internal space (i.e., lumen), displayed on the external surface of the extracellular vesicle, and/or spanning the membrane. Said payload can comprise nucleic acids, proteins, carbohydrates, lipids, small molecules, and/or combinations thereof. In some embodiments, an extracellular vesicle comprises a scaffold moiety. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some embodiments, extracellular vesicles are produced by cells that express one or more transgene products.

As used herein the term “exosome” refers to a cell-derived small (between 20-300 nm in diameter, more preferably 40-200 nm in diameter) vesicle comprising a membrane that encloses an internal space (i.e., lumen), and which is generated from said cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some embodiments, an exosome comprises a scaffold moiety. The exosome can be derived from a producer cell, and isolated from the producer cell based on its size, density, biochemical parameters, or a combination thereof. In some embodiments, the exosomes of the present disclosure are produced by cells that express one or more transgene products.

As used herein, the term “nanovesicle” refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some embodiments, a nanovesicle comprises a scaffold moiety. The nanovesicle, once it is derived from a producer cell according to said manipulation, may be isolated from the producer cell based on its size, density, biochemical parameters, or a combination thereof.

The term "modified," when used in the context of exosomes described herein, refers to an alteration or engineering of an EV, such that the modified EV is different from a naturally-occurring EV. In some embodiments, a modified EV described herein comprises a membrane that differs in composition of a protein, a lipid, a small molecular, a carbohydrate, etc. compared to the membrane of a naturally-occurring EV (e.g., membrane comprises higher density or number of natural EV proteins and/or membrane comprises proteins that are not naturally found in EVs. In certain embodiments, such modifications to the membrane changes the exterior surface of the EV. In certain embodiments, such modifications to the membrane changes the lumen of the EV.

As used herein, the term "scaffold moiety" refers to a molecule that can be used to anchor STING agonists disclosed herein or any other compound of interest (e.g., payload) to the EV either on the luminal surface or on the exterior surface of the EV. In certain embodiments, a scaffold moiety comprises a synthetic molecule. In some embodiments, a scaffold moiety comprises a non-polypeptide moiety. In other embodiments, a scaffold moiety comprises a lipid, carbohydrate, or protein that naturally exists in the EV. In some embodiments, a scaffold moiety comprises a lipid, carbohydrate, or protein that does not naturally exist in the exosome. In certain embodiments, a scaffold moiety is Scaffold X. In some embodiments, a scaffold moiety is Scaffold Y. In further embodiments, a scaffold moiety comprises both Scaffold X and Scaffold Y.

As used herein, the term "Scaffold X" refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some embodiments, a Scaffold X protein can be a whole protein or a fragment thereof (e.g., functional fragment, e.g., the smallest fragment that is capable of anchoring another moiety on the exterior surface or on the luminal surface of the EV, e.g., exosome,). In some embodiments, a Scaffold X can anchor a moiety (e.g., STING agonist) to the external surface or the luminal surface of the EVs, e.g., exosomes.

As used herein, the term "Scaffold Y" refers to exosome proteins that were newly identified within the luminal surface of exosomes. See, e.g., International Appl. No. PCT/US2018/061679, which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some embodiments, a Scaffold Y protein can be a whole protein or a fragment thereof (e.g., functional fragment, e.g., the smallest fragment that is capable of anchoring a moiety on the luminal surface of the EVs, e.g., exosomes,). In some embodiments, a Scaffold Y can anchor a moiety (e.g., STING agonist) to the lumen of the EVs, e.g., exosomes.

As used herein, the term "fragment" of a protein (e.g., therapeutic protein, Scaffold X, or Scaffold Y) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some embodiments, a functional fragment of a Scaffold X protein retains the ability to anchor a moiety on the luminal surface and/or on the exterior surface of the EV. Similarly, in certain embodiments, a functional fragment of a Scaffold Y protein retains the ability to anchor a moiety on the luminal surface of the EV. Whether a fragment is a functional fragment can be assessed by any art known methods to determine the protein content of EVs including Western Blots, FACS analysis and fusions of the fragments with autofluorescent proteins like, e.g., GFP. In certain embodiments, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein. In some embodiments, a functional fragment of a Scaffold Y protein retains at least about 50%, at least about 60%, at least about 70%, at least about 80%, at least about 90% or at least about 100% of the ability, e.g., an ability to anchor another molecule, of the naturally occurring Scaffold Y protein.

As used herein, the term "variant" of a molecule (e.g., functional molecule, antigen, Scaffold X and/or Scaffold Y) refers to a molecule that shares certain structural and functional identities with another molecule upon comparison by a method known in the art. For example, a variant of a protein can include a substitution, insertion, deletion, frameshift or rearrangement in another protein.

In some embodiments, a variant of a Scaffold X comprises a variant having at least about 70% identity to the full-length, mature PTGFRN, BSG, IGSF2, IGSF3, IGSF8, ITGB1, ITGA4, SLC3A2, or ATP transporter proteins or a fragment (e.g., functional fragment) of the PTGFRN, BSG, IGSF2, IGSF3, IGSF8, ITGB1, ITGA4, SLC3A2, or ATP transporter proteins. In some embodiments, variants or variants of fragments of PTGFRN share at least about 70%, at least about 80%, at least about 85%, at least about 90%, at least about 95%, at least about 96%, at least about 97%, at least about 98%, or at least about 99% sequence identity with PTGFRN according to SEQ ID NO: 1 or with a functional fragment thereof. In some embodiments variants or variants of fragments of BSG share at least about 70%, at least about 80%, at least about 85%, at least about 90%, at least about 95%, at least about 96%, at least about 97%, at least about 98%, or at least about 99% sequence identity with BSG according to SEQ ID NO: 9 or with a functional fragment thereof. In some embodiments, variants or variants of fragments of IGSF2 share at least about 70%, at least about 80%, at least about 85%, at least about 90%, at least about 95%, at least about 96%, at least about 97%, at least about 98%, or at least about 99% sequence identity with IGSF2 according to SEQ ID NO: 34 or with a functional fragment thereof. In some embodiments variants or variants of fragments of IGSF3 share at least about 70%, at least about 80%, at least about 85%, at least about 90%, at least about 95%, at least about 96%, at least about 97%, at least about 98%, or at least about 99% sequence identity with IGSF3 according to SEQ ID NO: 20 or with a functional fragment thereof. In some embodiments variants or variants of fragments of IGSF8 share at least about 70%, at least about 80%, at least about 85%, at least about 90%, at least about 95%, at least about 96%, at least about 97%, at least about 98%, or at least about 99% sequence identity with IGSF8 according to SEQ ID NO: 14 or with a functional fragment thereof. In some embodiments variants or variants of fragments of ITGB1 share at least about 70%, at least about 80%, at least about 85%, at least about 90%, at least about 95%, at least about 96%, at least about 97%, at least about 98%, or at least about 99% sequence identity with ITGB1 according to SEQ ID NO: 21 or with a functional fragment thereof. In some embodiments variants or variants of fragments of ITGA4 share at least about 70%, at least about 80%, at least about 85%, at least about 90%, at least about 95%, at least about 96%, at least about 97%, at least about 98%, or at least about 99% sequence identity with ITGA4 according to SEQ ID NO: 22 or with a functional fragment thereof. In some embodiments variants or variants of fragments of SLC3A2 share at least about 70%, at least about 80%, at least about 85%, at least about 90%, at least about 95%, at least about 96%, at least about 97%, at least about 98%, or at least about 99% sequence identity with SLC3A2 according to SEQ ID NO: 23 or with a functional fragment thereof. In some embodiments variants or variants of fragments of ATP1A1 share at least about 70%, at least about 80%, at least about 85%, at least about 90%, at least about 95%, at least about 96%, at least about 97%, at least about 98%, or at least about 99% sequence identity with ATP1A1 according to SEQ ID NO: 24 or with a functional fragment thereof. In some embodiments variants or variants of fragments of ATP1A2 share at least about 70%, at least about 80%, at least about 85%, at least about 90%, at least about 95%, at least about 96%, at least about 97%, at least about 98%, or at least about 99% sequence identity with ATP1A2 according to SEQ ID NO: 25 or with a functional fragment thereof. In some embodiments variants or variants of fragments of ATP1A3 share at least about 70%, at least about 80%, at least about 85%, at least about 90%, at least about 95%, at least about 96%, at least about 97%, at least about 98%, or at least about 99% sequence identity with ATP1A3 according to SEQ ID NO: 26 or with a functional fragment thereof. In some embodiments variants or variants of fragments of ATP1A4 share at least about 70%, at least about 80%, at least about 85%, at least about 90%, at least about 95%, at least about 96%, at least about 97%, at least about 98%, or at least about 99% sequence identity with ATP1A4 according to SEQ ID NO: 27 or with a functional fragment thereof. In some embodiments variants or variants of fragments of ATP1B3 share at least about 70%, at least about 80%, at least about 85%, at least about 90%, at least about 95%, at least about 96%, at least about 97%, at least about 98%, or at least about 99% sequence identity with ATP1B3 according to SEQ ID NO: 28 or with a functional fragment thereof. In some embodiments variants or variants of fragments of ATP2B1 share at least about 70%, at least about 80%, at least about 85%, at least about 90%, at least about 95%, at least about 96%, at least about 97%, at least about 98%, or at least about 99% sequence identity with ATP2B1 according to SEQ ID NO: 29 or with a functional fragment thereof. In some embodiments variants or variants of fragments of ATP2B2 share at least about 70%, at least about 80%, at least about 85%, at least about 90%, at least about 95%, at least about 96%, at least about 97%, at least about 98%, or at least about 99% sequence identity with ATP2B2 according to SEQ ID NO: 30 or with a functional fragment thereof. In some embodiments variants or variants of fragments of ATP2B3 share at least about 70%, at least about 80%, at least about 85%, at least about 90%, at least about 95%, at least about 96%, at least about 97%, at least about 98%, or at least about 99% sequence identity with ATP2B3 according to SEQ ID NO: 31 or with a functional fragment thereof. In some embodiments variants or variants of fragments of ATP2B4 share at least about 70%, at least about 80%, at least about 85%, at least about 90%, at least about 95%, at least about 96%, at least about 97%, at least about 98%, or at least about 99% sequence identity with ATP2B4 according to SEQ ID NO: 32 or with a functional fragment thereof. In some embodiments, the variant or variant of a fragment of Scaffold X protein disclosed herein retains the ability to be specifically targeted to EVs. In some embodiments, the Scaffold X includes one or more mutations, for example, conservative amino acid substitutions.

In some embodiments, a variant of a Scaffold Y comprises a variant having at least 70% identity to MARCKS, MARCKSL1, BASP1 or a fragment of MARCKS, MARCKSL1, or BASP1. In some embodiments variants or variants of fragments of MARCKS share at least about 70%, at least about 80%, at least about 85%, at least about 90%, at least about 95%, at least about 96%, at least about 97%, at least about 98%, or at least about 99% sequence identity with MARCKS according to SEQ ID NO: 47 or with a functional fragment thereof. In some embodiments variants or variants of fragments of MARCKSL1 share at least about 70%, at least about 80%, at least about 85%, at least about 90%, at least about 95%, at least about 96%, at least about 97%, at least about 98%, or at least about 99% sequence identity with MARCKSL1 according to SEQ ID NO: 48 or with a functional fragment thereof. In some embodiments variants or variants of fragments of BASP1 share at least about 70%, at least about 80%, at least about 85%, at least about 90%, at least about 95%, at least about 96%, at least about 97%, at least about 98%, or at least about 99% sequence identity with BASP1 according to SEQ ID NO: 49 or with a functional fragment thereof. In some embodiments, the variant or variant of a fragment of Scaffold Y protein retains the ability to be specifically targeted to the lumen of EVs. In some embodiments, the Scaffold Y includes one or more mutations, e.g., conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity may be curated either automatically or manually.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, Scaffold X and/or Scaffold Y is modified at any convenient location.

As used herein the term "producer cell" refers to a cell used for generating an EV. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, s9f cells, fHDF fibroblast cells, AGE.HN® neuronal precursor cells, CAP® amniocyte cells, adipose mesenchymal stem cells, and RPTEC/TERT1 cells. In certain embodiments, a producer cell is an antigen-presenting cell. In some embodiments, the producer cell is a bacterial cell. In some embodiments, a producer cell is a dendritic cell, a B cell, a mast cell, a macrophage, a neutrophil, a Kupffer-Browicz cell, or a cell derived from any of these cells, or any combination thereof. In some embodiments, the producer cell is not a bacterial cell. In other embodiments, the producer cell is not an antigen-presenting cell.

As used herein the term "associated with" refers to encapsulation of a first moiety, e.g., a STING agonist, into a second moiety, e.g., extracellular vesicle, or to a covalent or non-covalent bond formed between a first moiety and a second moiety, e.g., a STING agonist and an extracellular vesicle, respectively, e.g., a scaffold moiety expressed in or on the extracellular vesicle and a STING agonist, e.g., Scaffold X (e.g., a PTGFRN protein), respectively, on the luminal surface of or on the external surface of the extracellular vesicle. In one embodiment, the term "associated with" means a covalent, non-peptide bond or a non-covalent bond. For example, the amino acid cysteine comprises a thiol group that can form a disulfide bond or bridge with a thiol group on a second cysteine residue. Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity. In other embodiments, the term "associated with" means that a state of encapsulation by a first moiety, e.g., extracellular vesicle of a second moiety, e.g., a STING agonist. In the encapsulation state, the first moiety and the second moiety can be linked to each other. In other embodiments, the encapsulation means that the first moiety and the second moiety are not physically and/or chemically linked to each other.

As used herein the term "linked to" or "conjugated to" are used interchangeably and refer to a covalent or non-covalent bond formed between a first moiety and a second moiety, e.g., a STING agonist and an extracellular vesicle, respectively, e.g., a scaffold moiety expressed in or on the extracellular vesicle and a STING agonist, e.g., Scaffold X (e.g., a PTGFRN protein), respectively, on the luminal surface of or on the external surface of the extracellular vesicle.

The term "encapsulated", or grammatically different forms of the term (e.g., encapsulation, or encapsulating), refers to a status or process of having a first moiety (e.g., STING agonist) inside a second moiety (e.g., an EV, e.g., exosome) without chemically or physically linking the two moieties. In some embodiments, the term "encapsulated" can be used interchangeably with "in the lumen of". Non-limiting examples of encapsulating a first moiety (e.g., STING agonist) into a second moiety (e.g., EVs, e.g., exosomes) are disclosed elsewhere herein.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some embodiments, isolating or purifying as used herein is the process of removing, partially removing (e.g., a fraction) of the EVs from a sample containing producer cells. In some embodiments, an isolated EV composition has no detectable undesired activity or, alternatively, the level or amount of the undesired activity is at or below an acceptable level or amount. In other embodiments, an isolated EV composition has an amount and/or concentration of desired EVs at or above an acceptable amount and/or concentration. In other embodiments, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated EV preparations are substantially free of residual biological products. In some embodiments, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "agonist" refers to a molecule that binds to a receptor and activates the receptor to produce a biological response. Receptors can be activated by either an endogenous or an exogenous agonist. Non-limiting examples of endogenous agonist include hormones, neurotransmitters, and cyclic dinucleotides. Non-limiting examples of exogenous agonist include drugs, small molecules, and cyclic dinucleotides. The agonist can be a full, partial, or inverse agonist.

As used herein, the term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

The term "free STING agonist" as used herein means a STING agonist not associated with an extracellular vesicle, but otherwise identical to the STING agonist associated with the extracellular vesicle. Especially when compared to an extracellular vesicle associated with a STING agonist, the free STING agonist is the same STING agonist associated with the extracellular vesicle. In some embodiments, when a free STING agonist is compared to an extracellular vesicle comprising the STING agonist in its efficacy, toxicity, and/or any other characteristics, the amount of the free STING agonist compared to the STING agonist associated with the extracellular vesicle is the same as the amount of the STING agonist associated with the EV.

As used herein, the term "ligand" refers to a molecule that binds to a receptor and modulates the receptor to produce a biological response. Modulation can be activation, deactivation, blocking, or damping of the biological response mediated by the receptor. Receptors can be modulated by either an endogenous or an exogenous ligand. Non-limiting examples of endogenous ligands include antibodies and peptides. Non-limiting examples of exogenous agonist include drugs, small molecules, and cyclic dinucleotides. The ligand can be a full, partial, or inverse ligand.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab1)_2$, Fv, dAb, and Fd fragments, diabodies, and antibody-related polypeptides. Antibody includes bispecific antibodies and multispecific antibodies so long as they exhibit the desired biological activity or function.

As used herein the term "therapeutically effective amount" is the amount of reagent or pharmaceutical compound that is sufficient to a produce a desired therapeutic effect, pharmacologic and/or physiologic effect on a subject in need thereof. A therapeutically effective amount can be a "prophylactically effective amount" as prophylaxis can be considered therapy.

As used herein, the term "pharmaceutical composition" refers to one or more of the compounds described herein, such as, e.g., an EV mixed or intermingled with, or suspended in one or more other chemical components, such as pharmaceutically-acceptable carriers and excipients. One purpose of a pharmaceutical composition is to facilitate administration of preparations of EVs to a subject. The term "excipient" or "carrier" refers to an inert substance added to a pharmaceutical composition to further facilitate administration of a compound. The term "pharmaceutically-acceptable carrier" or "pharmaceutically-acceptable excipient" and grammatical variations thereof, encompasses any of the agents approved by a regulatory agency of the US Federal government or listed in the US Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV. Payloads that can be introduced into an EV and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins).

The terms "administration," "administering" and variants thereof refer to introducing a composition, such as an EV, or agent into a subject and includes concurrent and sequential introduction of a composition or agent. The introduction of a composition or agent into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

The term "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one embodiment, the term "treating" or "treatment" means inducing an immune response in a subject against an antigen.

The term "prevent" or "preventing," as used herein, refers to decreasing or reducing the occurrence or severity of a particular outcome. In some embodiments, preventing an outcome is achieved through prophylactic treatment.

As used herein, the term "modulate," "modulating", "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, the term "substantially free" means that the sample comprising EVs comprise less than 10% of macromolecules by mass/volume (m/v) percentage concentration. Some fractions may contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, exogenous proteins, lipids, carbohydrates, metabolites, or a combination thereof.

As used herein, the term "insubstantial," "reduced," or "negligible" refers to the presence, level, or amount of an inflammation response in a subject after administration of the sample comprising EVs encapsulating a STING agonist relative to the baseline inflammation response in the subject or compared to the subject inflammation response to the administration of a free STING agonist. For example, a negligible or insubstantial presence, level or amount of systemic inflammation may be less than 0.001%, less than 0.01%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, less than 10%, less than 12%, less than 15%, less than 17%, less than 20%, or less than 25% of systemic inflammation as relative to the baseline inflammation in the subject or compared to the subject immune response to the administration of a free STING agonist. A level or amount of a systemic inflammation may be less than 0.1-fold, less than 0.5-fold, less than 0.5-fold, less than 1-fold, less than 1.5-fold, less than 2-fold relative to the baseline or compared to the inflammation response to the administration of a free STING agonist.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

II. Compositions (Vesicles) with STING Agonist

The innate immune system recognizes pathogen associated molecular patterns (PAMPs) via pattern recognition receptors (PRRs) that induce an immune response. PRRs recognize a variety of pathogen molecules including single and double stranded RNA and DNA. PRRS such as retinoic acid-inducible gene-I (RIG-I)-like receptors (RLRs) and some toll-like receptors (TLRs) recognize RNA ligands. DNA ligands are recognized by cyclic GMP-AMP synthase (cGAS), AIM2 and other TLRs. The TLRs, RLRs, and AIM2 directly interact with other signal cascade adaptor proteins to activate transcription factors, while cGAS produces cGAMP, a cyclic dinucleotide molecule that activates the stimulator of interferon gene (STING) receptor. Both STING and the RLRs activate the adaptor kinase TBK1 which induces activation of transcription factors IRF3, and NF-κB, and result in the production of type I IFNs and pro-inflammatory cytokines.

Cyclic dinucleotides (CDNs) were first identified as bacterial signaling molecules characterized by two 3', 5' phosphodiester bonds, such as in the molecule c-di-GMP. While STING can be activated by bacterial CDNs, the innate immune response in mammalian cells is also mediated by the CDN signaling molecule cGAMP which is produced by cGAS. cGAMP is characterized by a mixed 2', 5' and 3', 5' phosphodiester linkage. Both bacterial and mammalian CDNs directly interact with STING to induce the pro-inflammatory signaling cascade that results in the production of type I IFNs, such as IFNα and IFN-β.

II.A. STING Agonists

STING agonists used in this disclosure can be cyclic dinucleotides (CDNs) or non-cyclic dinucleotide agonists. Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, are known to stimulate or enhance an immune or inflammation response in a patient. The CDNs may have 2'2', 2'3', 2'5', 3'3', or 3'5' bonds linking the cyclic dinucleotides, or any combination thereof.

Cyclic purine dinucleotides may be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides may be modified analogues. Any suitable modification known in the art may be used, including, but not limited to, phosphorothioate, biphosphorothioate, fluorinate, and difluorinate modifications.

Non cyclic dinucleotide agonists may also be used, such as 5,6-Dimethylxanthenone-4-acetic acid (DMXAA), or any other non-cyclic dinucleotide agonist known in the art.

It is contemplated that any STING agonist may be used. Among the STING agonists are DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, c-di-AMP, 2'3'-c-di-AMP, 2'3'-c-di-AM(PS)2, c-di-GMP, 2'3'-c-di-GMP, c-di-IMP, c-di-UMP or any combination thereof. In a preferred embodiment, the STING agonist is 3'3'-cAIMPdFSH, alternatively named 3-3 cAIMPdFSH. Additional STING agonists known in the art may also be used.

In some embodiments, the STING agonist useful for the present disclosure comprises a compound having the following formula:

Formula 1

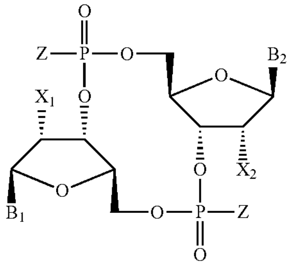

or

Formula 2

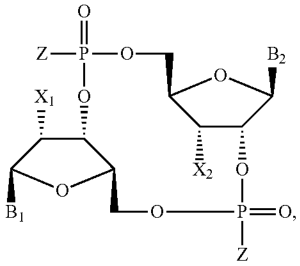

wherein:

$X_1$ is H, OH, or F;

$X_2$ is H, OH, or F;

Z is OH, $OR_1$, SH or $SR_1$, wherein:

i) $R_1$ is Na or $NH_4$, or ii) $R_1$ is an enzyme-labile group which provides OH or SH in vivo such as pivaloyloxymethyl;

$B_1$ and $B_2$ are bases chosen from:

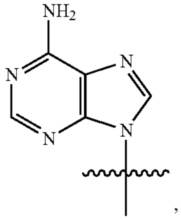

,

Adenine

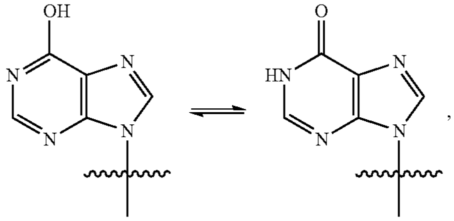

, or

Hypoxanthine

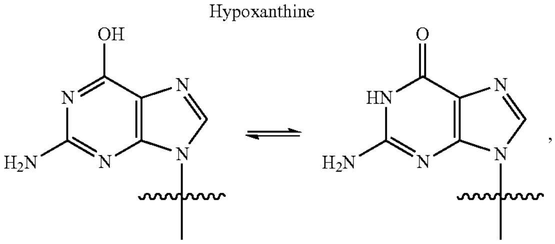

,

Guanine

With proviso that:

in Formula (I): $X_1$ and $X_2$ are not OH, in Formula (II): when $X_1$ and $X_2$ are OH, $B_1$ is not Adenine and $B_2$ is not Guanine, and in Formula (III): when $X_1$ and $X_2$ are OH, $B_1$ is not Adenine, $B_2$ is not Guanine and Z is not OH. See WO 2016/096174, the content of which is incorporated herein by reference in its entirety.

In some embodiments, the STING agonist useful for the present disclosure comprises:

ADU-S100

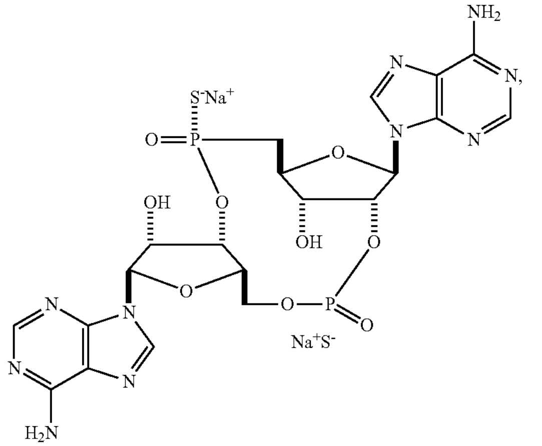

CL-592

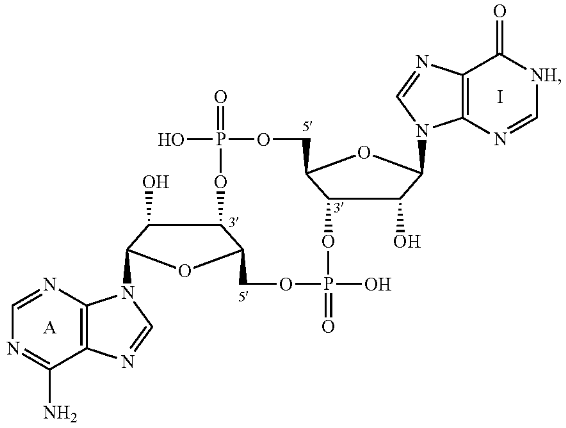

cAIMP

CL656

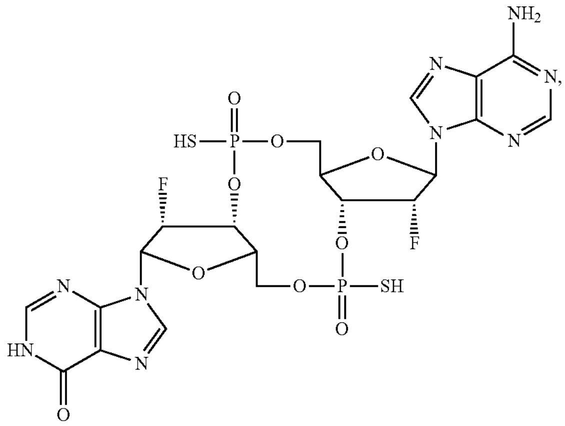

c-[2'FdAMP(S)-2'FdIMP(S)]

-continued
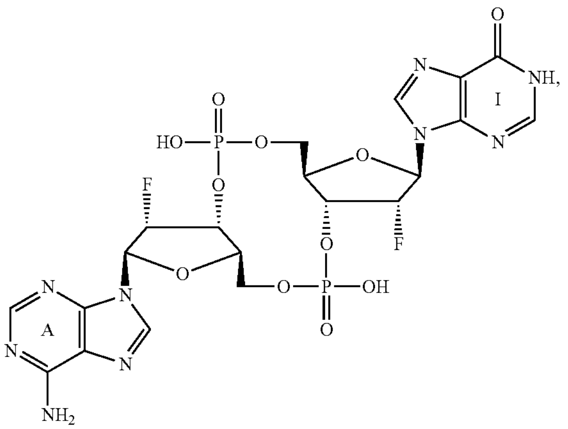
c-[2FdAMP-2FdIMP]
CL659
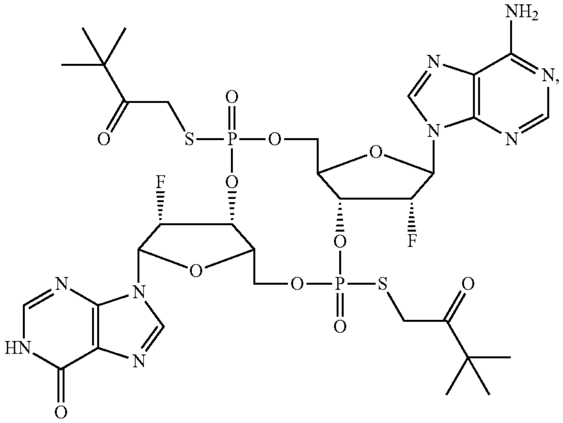
c-[2′FdAMP(S)-2′FdIMP(S)](POM)$_2$
CL-655
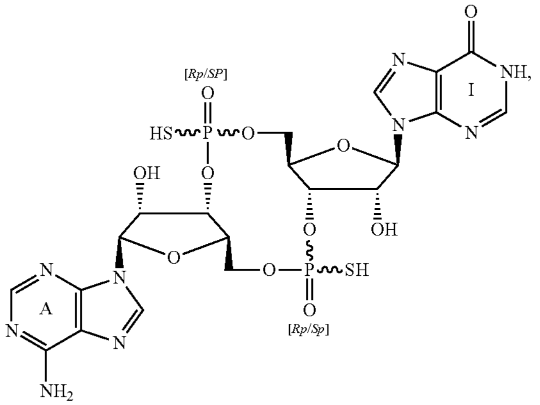
and
c-[AMP(S)-IMP(S)]
a pharmaceutically acceptable salt thereof. See WO 2016/096174A1.
and a pharmaceutically acceptable salt thereof. See WO 2016/096174A1.
In other embodiments, the STING agonist useful for the present disclosure comprises a compound having the following formula:
CL606
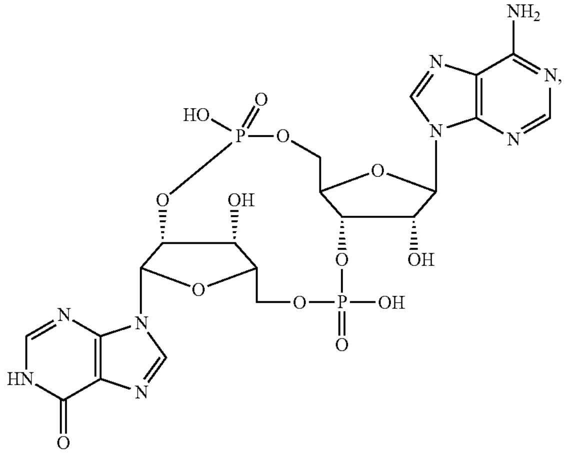
(3′,2′)c-AIMP
CL611
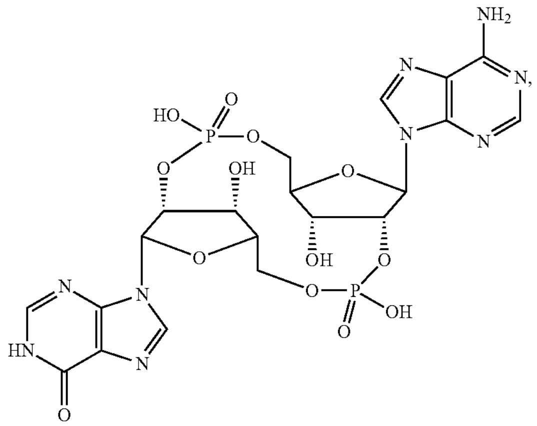
(2′,2′)c-AIMP
CL602
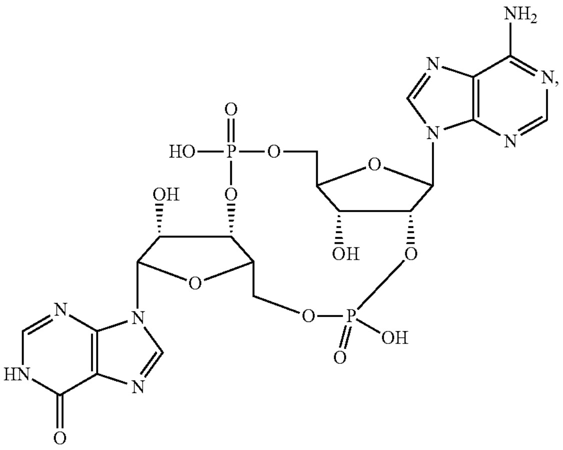
(2′,3′)c-AIMP -continued
CL655
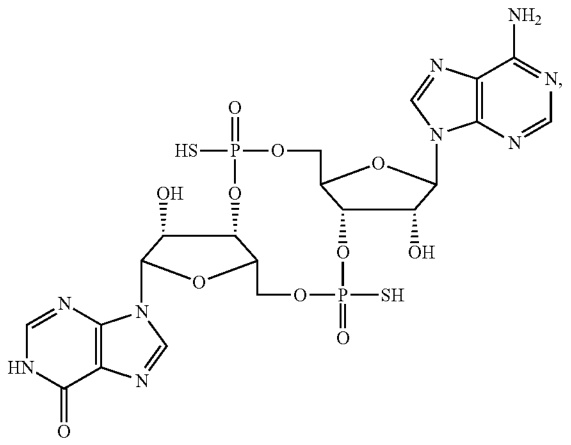
c-AIMP(S)
CL604
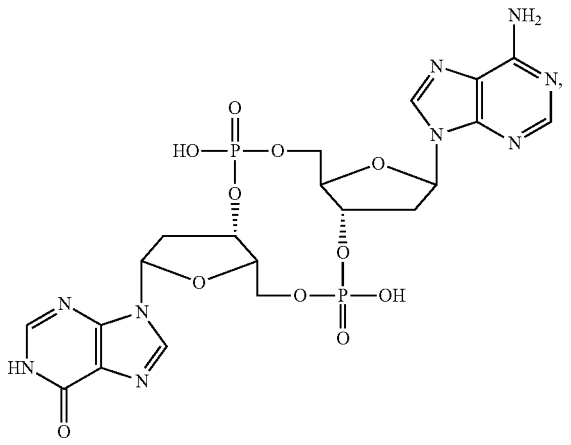
c-(dAMP-dIMP)
CL609
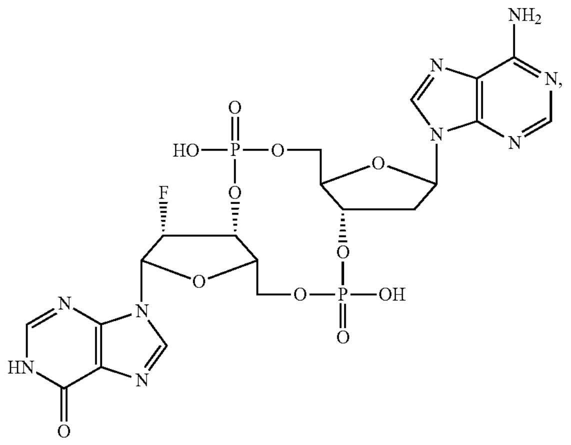
c-(dAMP-2′FdIMP)
-continued
CL614
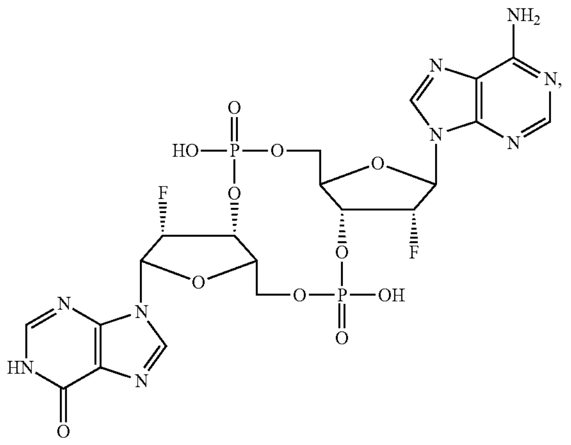
c-(2′FdAMP-2′FdIMP)
CL656
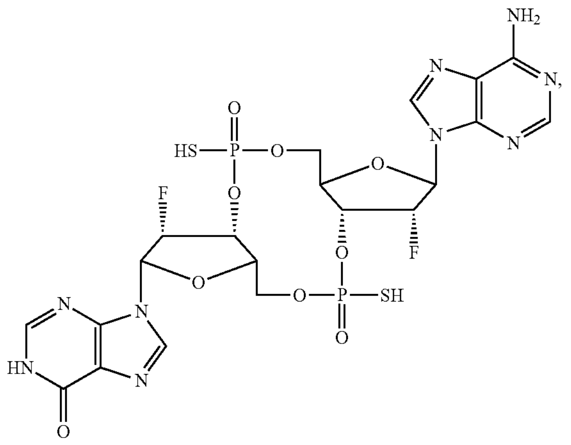
c-[2′FdAMP(S)-2′FdIMP(S)]
CL647
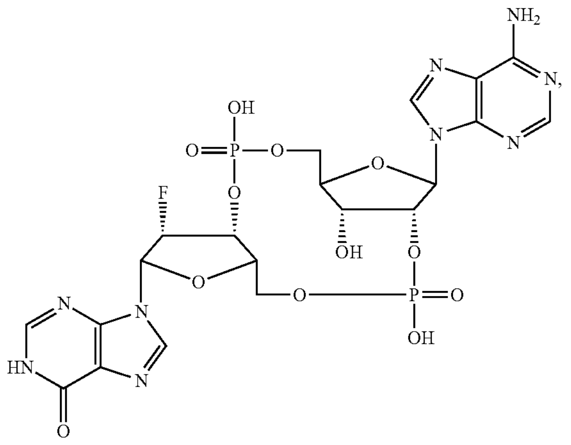
(2′,3′)c-(AMP-2′FdIMP)

-continued
CL626
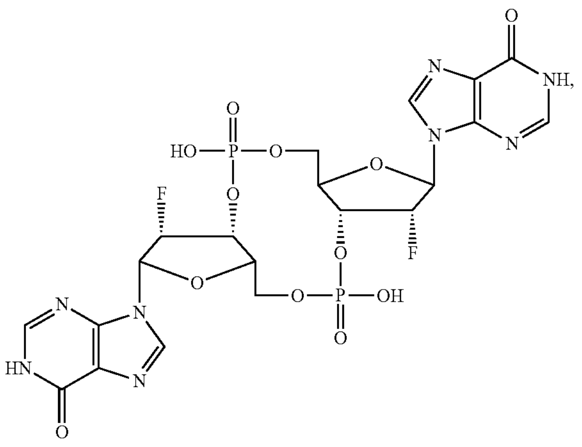
c-di(2′FdIMP)
CL629
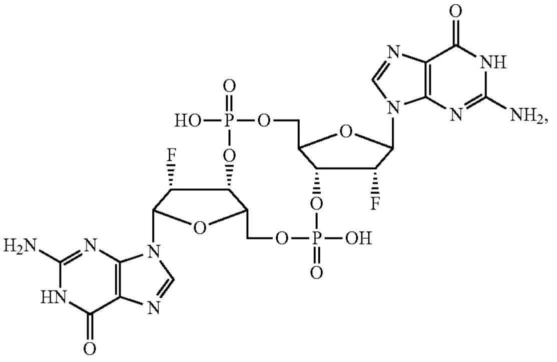
c-di(2′FdIMP)
CL603
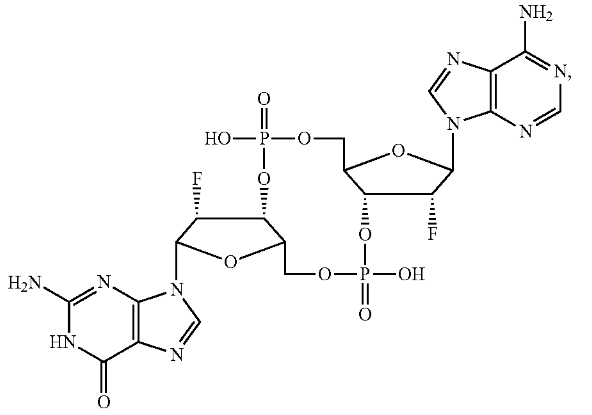
c-(2′FdGMP-2′FdAMP)
-continued
CL632
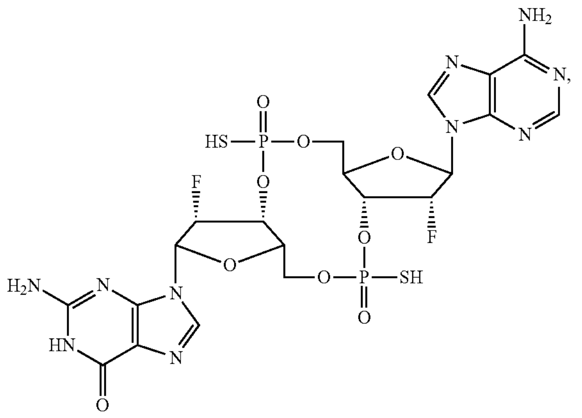
c-[2′FdGMP(S)-2′FdAMP(S)]
CL633
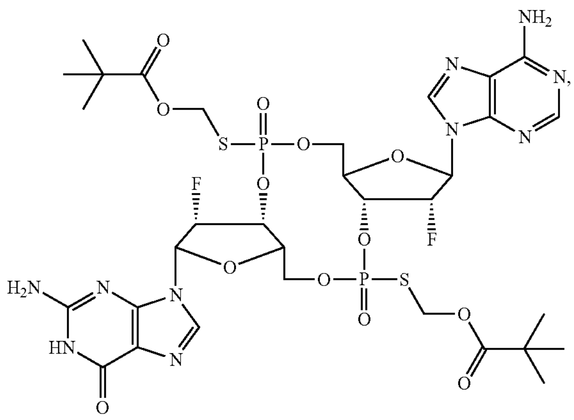
c-[2′FdGMP(S)-2′FdAMP(S)](POM)$_2$
CL659
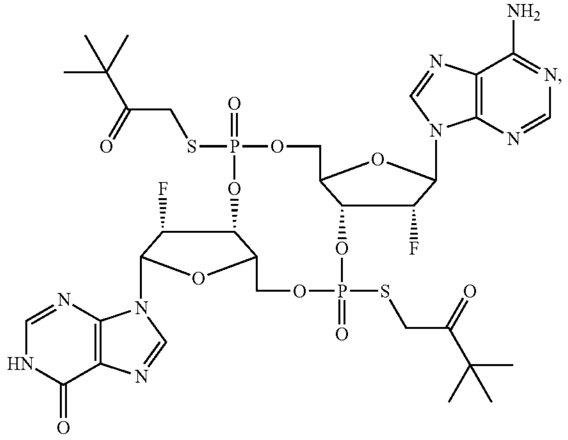
c-[2′FdAMP(S)-2′FdIMP(S)](POM)$_2$
or any pharmaceutically acceptable salts thereof.
In some embodiments, the STING agonist useful for the present disclosure comprises a compound having the following formula:

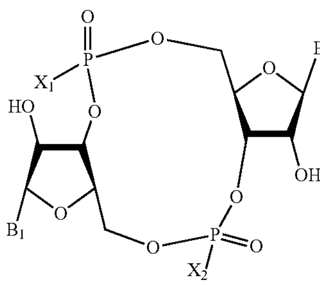

wherein each symbol is defined in WO 2014/093936, the content of which is incorporated herein by reference in its entirety.

In some embodiments, the STING agonist useful for the present disclosure comprises a compound having the following formula:

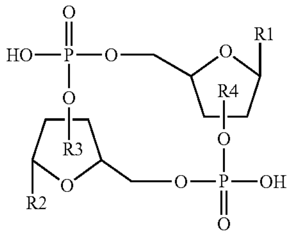

and

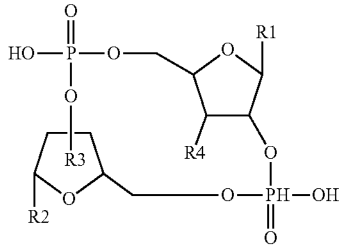

wherein each symbol is defined in WO 2014/189805, the content of which is incorporated herein by reference in its entirety.

In some embodiments, the STING agonist useful for the present disclosure comprises a compound having the following formula:

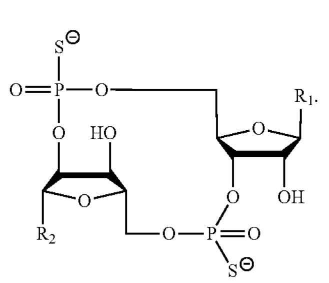

wherein each symbol is defined in WO 2015/077354, the content of which is incorporated herein by reference in its entirety. See also Cell reports 11, 1018-1030 (2015).

In some embodiments, the STING agonist useful for the present disclosure comprises c-di-AMP, c-di-GMP, c-di-IMP, c-AMP-GMP, c-AMP-IMP, and c-GMP-IMP, described in WO 2013/185052 and Sci. Transl. Med. 283, 283ra52 (2015), which are incorporated herein by reference in their entireties.

In some embodiments, the STING agonist useful for the present disclosure comprises a compound having the following formula:

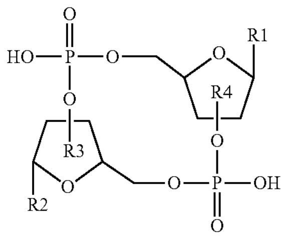

and

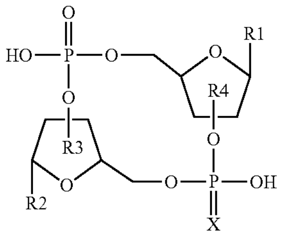

wherein each symbol is defined in WO 2014/189806, the content of which is incorporated herein by reference in its entirety.

In some embodiments, the STING agonist useful for the present disclosure comprises a compound having the following formula:

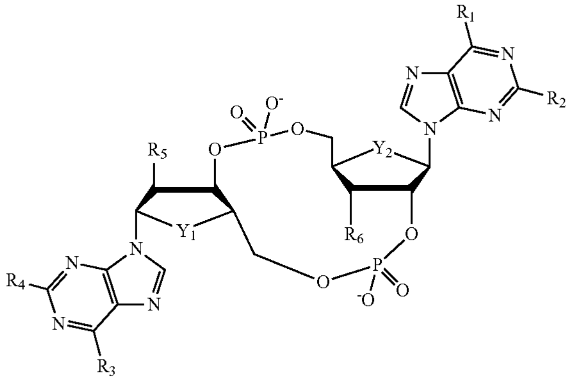

wherein each symbol is defined in WO 2015/185565, the content of which is incorporated herein by reference in its entirety.

In some embodiments, the STING agonist useful for the present disclosure comprises a compound having the following formula:

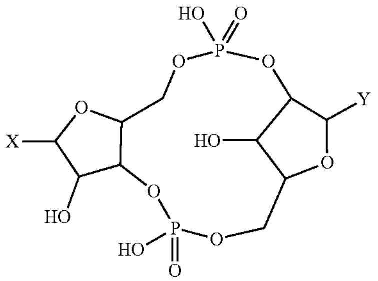
or
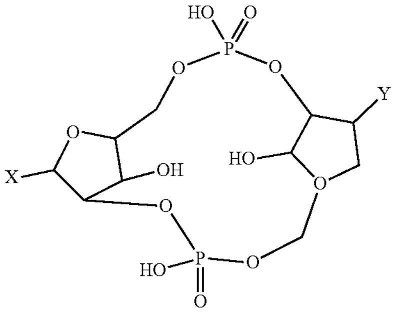
wherein each symbol is defined in WO 2014/179760, the content of which is incorporated herein by reference in its entirety.
In some embodiments, the STING agonist useful for the present disclosure comprises a compound having the following formula:
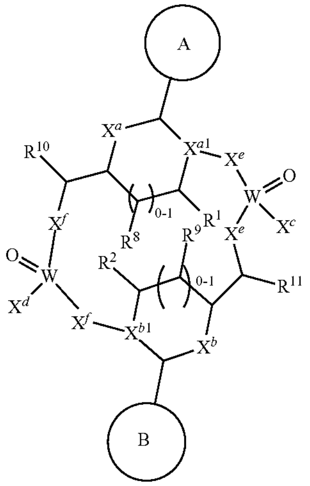
-continued
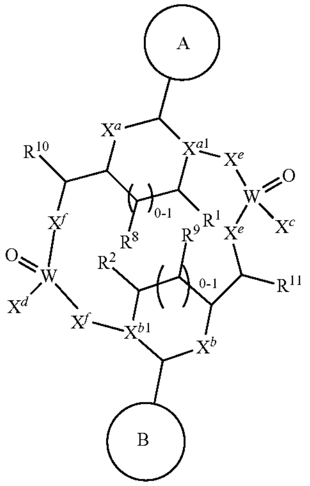
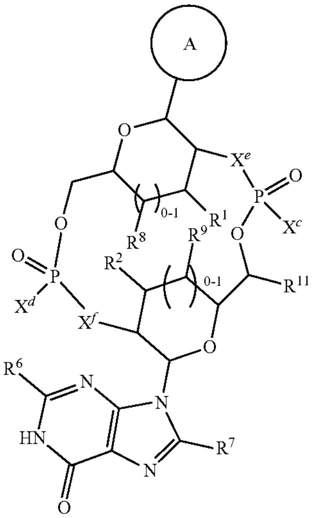
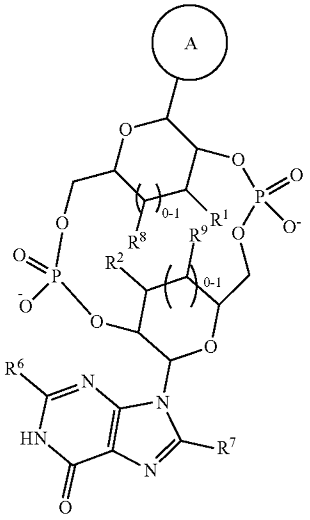

-continued

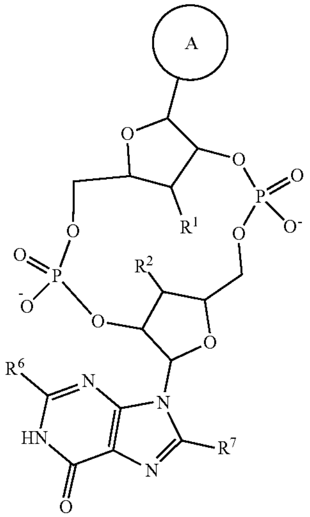

wherein each symbol is defined in WO 2014/179335, the content of which is incorporated herein by reference in its entirety.

In some embodiments, the STING agonist useful for the present disclosure comprises a compound having the following formula:

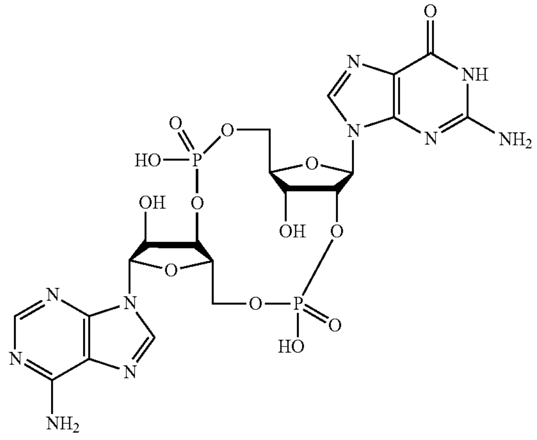

described in WO 2015/017652, the content of which is incorporated herein by reference in its entirety.

In some embodiments, the STING agonist useful for the present disclosure comprises a compound having the following formula:

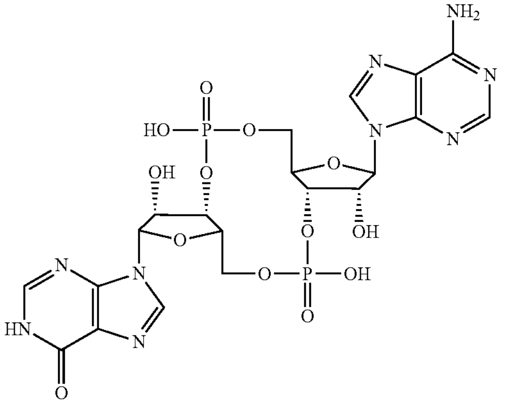 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

described in WO 2016/096577, the content of which is incorporated herein by reference in its entirety.

In some embodiments, the STING agonist useful for the present disclosure comprises a compound having the following formula:

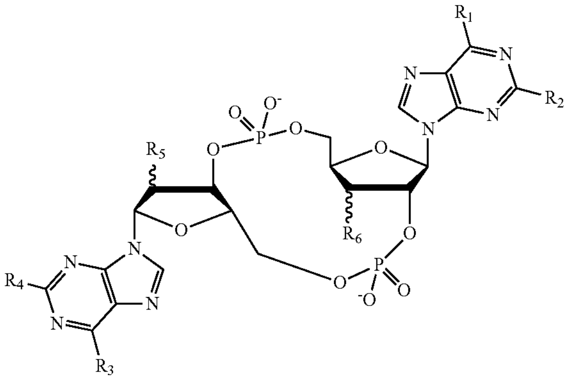

wherein each symbol is defined in WO 2016/120305, the content of which is incorporated herein by reference in its entirety.

In some embodiments, the STING agonist useful for the present disclosure comprises a compound having the following formula:

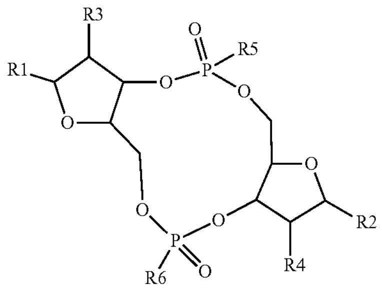

wherein each symbol is defined in WO 2016/145102, the content of which is incorporated herein by reference in its entirety.

In some embodiments, the STING agonist useful for the present disclosure comprises a compound having the following formula:

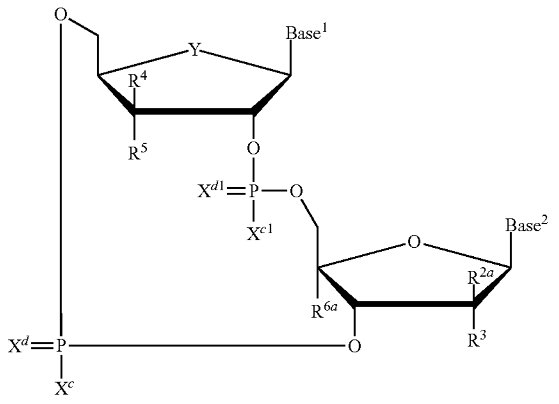

wherein each symbol is defined in WO 2017/027646, the content of which is incorporated herein by reference in its entirety.

In some embodiments, the STING agonist useful for the present disclosure comprises a compound having the following formula:

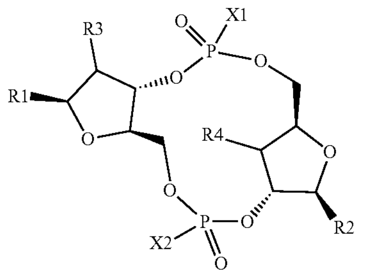

wherein each symbol is defined in WO 2017/075477, the content of which is incorporated herein by reference in its entirety.

In some embodiments, the STING agonist useful for the present disclosure comprises a compound having the following formula:

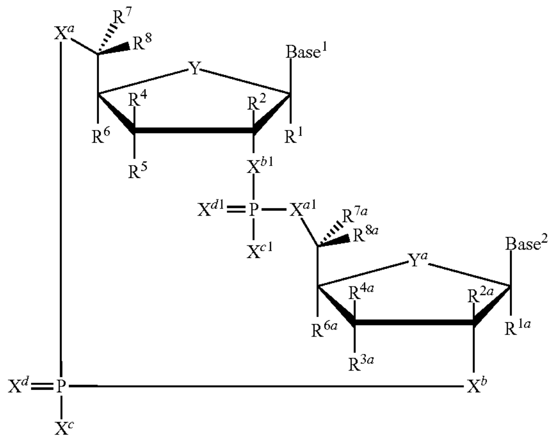

wherein each symbol is defined in WO 2017/027645, the content of which is incorporated herein by reference in its entirety.

In some embodiments, the STING agonist useful for the present disclosure comprises a compound having the following formula:

(I)

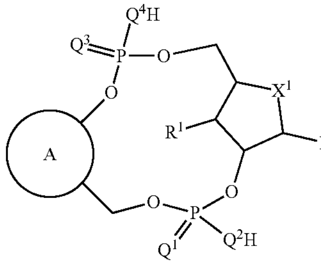

wherein each symbol is defined in WO 2018/100558, the content of which is incorporated herein by reference in its entirety.

In some embodiments, the STING agonist useful for the present disclosure comprises a compound having the following formula:

(I-N)

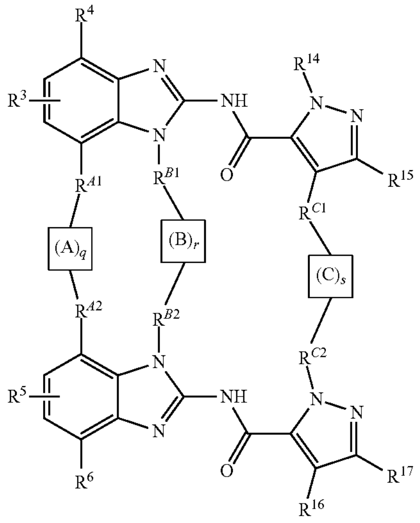

wherein each symbol is defined in WO 2017/175147, the content of which is incorporated herein by reference in its entirety.

In some embodiments, the STING agonist useful for the present disclosure comprises a compound having the following formula:

(I)

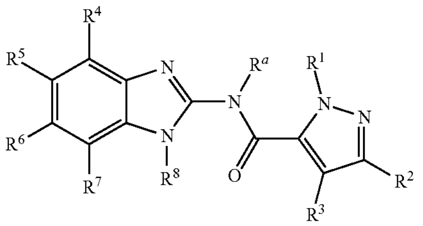

or

-continued

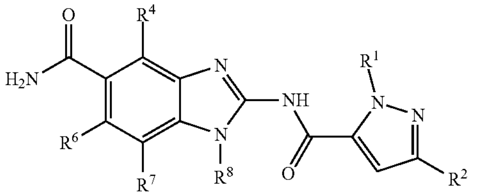

wherein each symbol is defined in WO 2017/175156, the content of which is incorporated herein by reference in its entirety.

In some aspects, the STING agonist useful for the present disclosure is CL606, CL611, CL602, CL655, CL604, CL609, CL614, CL656, CL647, CL626, CL629, CL603, CL632, CL633, CL659, or a pharmaceutically acceptable salt thereof. In some aspects, the STING agonist useful for the present disclosure is CL606 or a pharmaceutically acceptable salt thereof. In some aspects, the STING agonist useful for the present disclosure is CL611 or a pharmaceutically acceptable salt thereof. In some aspects, the STING agonist useful for the present disclosure is CL602 or a pharmaceutically acceptable salt thereof. In some aspects, the STING agonist useful for the present disclosure is CL655 or a pharmaceutically acceptable salt thereof. In some aspects, the STING agonist useful for the present disclosure is CL604 or a pharmaceutically acceptable salt thereof. In some aspects, the STING agonist useful for the present disclosure is CL609 or a pharmaceutically acceptable salt thereof. In some aspects, the STING agonist useful for the present disclosure is CL614 or a pharmaceutically acceptable salt thereof. In some aspects, the STING agonist useful for the present disclosure is CL656 or a pharmaceutically acceptable salt thereof. In some aspects, the STING agonist useful for the present disclosure is CL647 or a pharmaceutically acceptable salt thereof. In some aspects, the STING agonist useful for the present disclosure is CL626 or a pharmaceutically acceptable salt thereof. In some aspects, the STING agonist useful for the present disclosure is CL629 or a pharmaceutically acceptable salt thereof. In some aspects, the STING agonist useful for the present disclosure is CL603 or a pharmaceutically acceptable salt thereof. In some aspects, the STING agonist useful for the present disclosure is CL632 or a pharmaceutically acceptable salt thereof. In some aspects, the STING agonist useful for the present disclosure is CL633 or a pharmaceutically acceptable salt thereof. In some aspects, the STING agonist useful for the present disclosure is CL659 or a pharmaceutically acceptable salt thereof.

In some aspects, the EV, e.g., exosome, comprises a cyclic dinucleotide STING agonist and/or a non-cyclic dinucleotide STING agonist. In some aspects, when several cyclic dinucleotide STING agonist are present on an EV, e.g., exosome, disclosed herein, such STING agonists can be the same or they can be different. In some aspects, when several non-cyclic dinucleotide STING agonist are present, such STING agonists can be the same or they can be different. In some aspects, an EV, e.g., exosome, composition of the present disclosure can comprise two or more populations of EVs, e.g., exosomes, wherein each population of EVs, e.g., exosomes, comprises a different STING agonist or combination thereof.

The STING agonists can also be modified to increase encapsulation of the agonist in an extracellular vesicle or EV (e.g., either unbound in the lumen). In some embodiments, the STING agonists are linked to a scaffold moiety, e.g., Scaffold Y. In certain embodiments, the modification allows better expression of the STING agonist on the exterior surface of the EV, e.g., exosome, (e.g., linked to a scaffold moiety disclosed herein, e.g., Scaffold X). This modification can include the addition of a lipid binding tag by treating the agonist with a chemical or enzyme, or by physically or chemically altering the polarity or charge of the STING agonist. The STING agonist may be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications may be practiced. The modification may increase encapsulation of the agonist in the EV by between 2-fold and 10,000 fold, between 10-fold and 1,000 fold, or between 100-fold and 500-fold compared to encapsulation of an unmodified agonist. The modification may increase encapsulation of the agonist in the EV by at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, or 10,000-fold compared to encapsulation of an unmodified agonist.

In some embodiments, STING agonists can be modified to allow for better expression of the agonists on the exterior surface of the EV, e.g., exosome, (e.g., linked to a scaffold moiety disclosed herein, e.g., Scaffold X). Any of the modifications described above can be used. The modification may increase encapsulation of the agonist in the EV, e.g., exosome, by about between 2-fold and 10,000 fold, about between 10-fold and 1,000 fold, or about between 100-fold and 500-fold compared to encapsulation of an unmodified agonist. The modification can increase expression of the agonist on the exterior surface of the EV, e.g., exosome, by at least about 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, or 10,000-fold compared to expression of an unmodified agonist.

The concentration of the STING agonist associated with the EV may be about 0.01 μM to 1000 μM. The concentration of the associated STING agonist may be between about 0.01-0.05 μM, 0.05-0.1 μM, 0.1-0.5 μM, 0.5-1 μM, 1-5 μM, 5-10 μM, 10-15 μM, 15-20 μM, 20-25 μM, 25-30 μM, 30-35 μM, 35-40 μM, 45-50 μM, 55-60 μM, 65-70 μM, 70-75 μM, 75-80 μM, 80-85 μM, 85-90 μM, 90-95 μM, 95-100 μM, 100-150 μM, 150-200 μM, 200-250 μM, 250-300 μM, 300-350 μM, 250-400 μM, 400-450 μM, 450-500 μM, 500-550 μM, 550-600 μM, 600-650 μM, 650-700 μM, 700-750 μM, 750-800 μM, 800-850 μM, 805-900 μM, 900-950 μM, or 950-1000 μM. The concentration of the associated STING agonist may be equal to or greater than about 0.01 μM, 0.1 μM, 0.5 μM, 1 μM, 5 μM, 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 150 μM, 200 μM, 250 μM, 300 μM, 350 μM, 400 μM, 450 μM, 500 μM, 550 μM, 600 μM, 650 μM, 700 μM, 750 μM, 800 μM, 850 μM, 900 μM, 950 μM, or 1000 μM.

II.B. Scaffold-X-Engineered EVs, e.g., Exosomes

In some embodiments, EVs of the present disclosure comprise a membrane modified in its composition. For example, their membrane compositions can be modified by changing the protein, lipid, or glycan content of the membrane.

In some embodiments, the surface-engineered EVs are generated by chemical and/or physical methods, such as PEG-induced fusion and/or ultrasonic fusion. In other embodiments, the surface-engineered EVs, e.g., exosomes, are generated by genetic engineering. EVs produced from a genetically-modified producer cell or a progeny of the genetically-modified cell can contain modified membrane compositions. In some embodiments, surface-engineered EVs, e.g., exosomes, have scaffold moiety (e.g., exosome protein, e.g., Scaffold X) at a higher or lower density (e.g., higher number) or include a variant or a fragment of the scaffold moiety.

For example, surface-engineered EVs (e.g., Scaffold X-engineered EVs) can be produced from a cell (e.g., HEK293 cells) transformed with an exogenous sequence encoding a scaffold moiety (e.g., exosome proteins, e.g., Scaffold X) or a variant or a fragment thereof. EVs including scaffold moiety expressed from the exogenous sequence can include modified membrane compositions.

Various modifications or fragments of the scaffold moiety can be used for the embodiments of the present disclosure. For example, scaffold moiety modified to have enhanced affinity to a binding agent can be used for generating surface-engineered EVs that can be purified using the binding agent. Scaffold moieties modified to be more effectively targeted to EVs, e.g., exosomes, and/or membranes can be used. Scaffold moieties modified to comprise a minimal fragment required for specific and effective targeting to EVs, e.g., exosomes, membranes can be also used.

In some embodiments, a STING agonist disclosed herein is expressed on the surface of an EV, e.g., exosome, as a fusion protein, e.g., fusion protein of a STING agonist to a Scaffold X. For example, the fusion protein can comprise a STING agonist disclosed herein linked to a scaffold moiety (e.g., Scaffold X). In certain embodiments, Scaffold X comprises the PTGFRN protein, BSG protein, IGSF2 protein, IGSF3 protein, IGSF8 protein, ITGB1 protein, ITGA4 protein, SLC3A2 protein, ATP transporter protein, or a fragment or a variant thereof.

In some embodiments, the surface-engineered EVs, e.g., exosomes (e.g., Scaffold X-engineered EVs, e.g., exosomes) described herein demonstrate superior characteristics compared to EVs, e.g., exosomes, known in the art. For example, surface (e.g., Scaffold X)-engineered contain modified proteins more highly enriched on their surface than naturally occurring EVs, e.g., exosomes, or the EVs, e.g., exosomes, produced using conventional exosome proteins. Moreover, the surface-engineered EVs, e.g., exosomes, (e.g., Scaffold X-engineered EVs, e.g., exosomes) of the present invention can have greater, more specific, or more controlled biological activity compared to naturally occurring EVs, e.g., exosomes, or the EVs, e.g., exosomes, produced using conventional exosome proteins.

In other embodiments, the EVs, e.g., exosomes, of the present disclosure contains a STING agonist and a Scaffold X, wherein the STING agonist is linked to the Scaffold X. In some embodiments, the EVs, e.g., exosomes, of the present disclosure comprises a STING agonist and a Scaffold X, wherein the STING agonist is not linked to the Scaffold X.

In some embodiments, Scaffold X useful for the present disclosure comprises Prostaglandin F2 receptor negative regulator (the PTGFRN polypeptide). The PTGFRN protein can be also referred to as CD9 partner 1 (CD9P-1), Glu-Trp-Ile EWI motif-containing protein F (EWI-F), Prostaglandin F2-alpha receptor regulatory protein, Prostaglandin F2-alpha receptor-associated protein, or CD315. The full length amino acid sequence of the human PTGFRN protein (Uniprot Accession No. Q9P2B2) is shown at Table 1 as SEQ ID NO: 1. The PTGFRN polypeptide contains a signal peptide (amino acids 1 to 25 of SEQ ID NO: 1), the extracellular domain (amino acids 26 to 832 of SEQ ID NO: 1), a transmembrane domain (amino acids 833 to 853 of SEQ ID NO: 1), and a cytoplasmic domain (amino acids 854 to 879 of SEQ ID NO: 1). The mature PTGFRN polypeptide consists of SEQ ID NO: 1 without the signal peptide, i.e., amino acids 26 to 879 of SEQ ID NO: 1. In some embodiments, a PTGFRN polypeptide fragment useful for the present disclosure comprises a transmembrane domain of the PTGFRN polypeptide. In other embodiments, a PTGFRN polypeptide fragment useful for the present disclosure comprises the transmembrane domain of the PTGFRN polypeptide and (i) at least five, at least 10, at least 15, at least 20, at least 25, at least 30, at least 40, at least 50, at least 70, at least 80, at least 90, at least 100, at least 110, at least 120, at least 130, at least 140, at least 150 amino acids at the N terminus of the transmembrane domain, (ii) at least five, at least 10, at least 15, at least 20, or at least 25 amino acids at the C terminus of the transmembrane domain, or both (i) and (ii).

In some embodiments, the fragments of PTGFRN polypeptide lack one or more functional or structural domains, such as IgV.

In other embodiments, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 26 to 879 of SEQ ID NO: 1. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 33. In other embodiments, the Scaffold X comprises the amino acid sequence of SEQ ID NO: 33, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of SEQ ID NO: 33 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 33.

In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 2, 3, 4, 5, 6, or 7. In other embodiments, the Scaffold X comprises the amino acid sequence of SEQ ID NO: 2, 3, 4, 5, 6, or 7, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of SEQ ID NO: 2, 3, 4, 5, 6, or 7 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 2, 3, 4, 5, 6, or 7.

TABLE 1

| Protein | Sequence |
|---|---|
| The PTGFRN Protein (SEQ ID NO: 1) | MGRLASRPLLLALLSLALCRGRVVRVPTATLVRVVGTELVIPCNVSDYDGPSEQN<br>FDWSF<br>SSLGSSFVELASTWEVGFPAQLYQERLQRGEILLRRTANDAVELHIKNVQPSDQG<br>HYKCS<br>TPSTDATVQGNYEDTVQVKVLADSLHVGPSARPPPSLSLREGEPFELRCTAASASP<br>LHTH<br>LALLWEVHRGPARRSVLALTHEGRFHPGLGYEQRYHSGDVRLDTVGSDAYRLSV<br>SRALSA<br>DQGSYRCIVSEWIAEQGNWQEIQEKAVEVATVVIQPSVLRAAVPKNVSVAEGKE<br>LDLTCN<br>ITTDRADDVRPEVTWSFSRMPDSTLPGSRVLARLDRDSLVHSSPHVALSHVDARS<br>YHLLV<br>RDVSKENSGYYYCHVSLWAPGHNRSWHKVAEAVSSPAGVGVTWLEPDYQVYL<br>NASKVPGF<br>ADDPTELACRVVDTKSGEANVRFTVSWYYRMNRRSDNVVTSELLAVMDGDWT<br>LKYGERSK<br>QRAQDGDFIFSKEHTDTFNFRIQRTTEEDRGNYYCVVSAWTKQRNNSWVKSKDV<br>FSKPVN<br>IFWALEDSVLVVKARQPKPFFAAGNTFEMTCKVSSKNIKSPRYSVLIMAEKPVGD<br>LSSPN<br>ETKYIISLDQDSVVKLENWTDASRVDGVVLEKVQEDEFRYRMYQTQVSDAGLYR<br>CMVTAW<br>SPVRGSLWREAATSLSNPIEIDFQTSGPIFNASVHSDTPSVIRGDLIKLFCIITVEGAA<br>L<br>DPDDMAFDVSWFAVHSFGLDKAPVLLSSLDRKGIVTTSRRDWKSDLSLERVSVL<br>EFLLQV<br>HGSEDQDFGNYYCSVTPWVKSPTGSWQKEAEIHSKPVFITVKMDVLNAFKYPLLI<br>GVGLS<br>TVIGLLSCLIGYCSSHWCCKKEVQETRRERRRLMSMEMD |
| The PTGFRN protein Fragment (SEQ ID NO: 33) | GPIFNASVHSDTPSVIRGDLIKLFCIITVEGAALDPDDMAFDVSWFAVHSFGLDKA<br>PVLL<br>SSLDRKGIVTTSRRDWKSDLSLERVSVLEFLLQVHGSEDQDFGNYYCSVTPWVKS<br>PTGSW<br>QKEAEIHSKPVFITVKMDVLNAFKYPLLIGVGLSTVIGLLSCLIGYCSSHWCCKKE<br>VQET<br>RRERRRLMSMEM<br>687-878 of SEQ ID NO: 1 |
| The BSG protein (SEQ ID NO: 9) | MAAALFVLLG FALLGTHGAS GAAGFVQAPL SQQRWVGGSV ELHCEAVGSP<br>VPEIQWWFEG QGPNDTCSQL WDGARLDRVH IHATYHQHAA STISIDTLVE<br>EDTGTYECRA SNDPDRNHLT RAPRVKWVRA QAVVLVLEPG TVFTTVEDLG<br>SKILLTCSLN DSATEVTGHR WLKGGVVLKE DALPGQKTEF KVDSDDQWGE<br>YSCVFLPEPM GTANIQLHGP PRVKAVKSSE HINEGETAML VCKSESVPPV<br>TDWAWYKITD SEDKALMNGS ESRFFVSSSQ GRSELHIENL NMEADPGQYR<br>CNGTSSKGSD QAIITLRVRS HLAALWPFLG IVAEVLVLVT IIFIYEKRRK<br>PEDVLDDDDA GSAPLKSSGQ HQNDKGKNVR QRNSS |
| The IGSF8 protein (SEQ ID NO: 14) | MGALRPTLLP PSLPLLLLLM LGMGCWAREV LVPEGPLYRV AGTAVSISCN<br>VTGYEGPAQQ NFEWFLYRPE APDTALGIVS TKDTQFSYAV FKSRVVAGEV<br>QVQRLQGDAV VLKIARLQAQ DAGIYECHTP STDTRYLGSY SGKVELRVLP<br>DVLQVSAAPP GPRGRQAPTS PPRMTVHEGQ ELALGCLART STQKHTHLAV<br>SFGRSVPEAP VGRSTLQEVV GIRSDLAVEA GAPYAERLAA GELRLGKEGT<br>DRYRMVVGGA QAGDAGTYHC TAAEWIQDPD GSWAQIAEKR AVLAHVDVQT<br>LSSQLAVTVG PGERRIGPGE PLELLCNVSG ALPPAGRHAA YSVGWEMAPA<br>GAPGPGRLVA QLDlEGVGSL GPGYEGRHIA MEKVASRTYR LRLEAARPGD<br>AGTYRCLAKA YVRGSGTRLR EAASARSRPL PVHVREEGVV LEAVAWLAGG<br>TVYRGETASL LCNISVRGGP PGLRLAASWW VERPEDGELS SVPAQLVGGV<br>GQDGVAELGV RPGGGPVSVE LVGPRSHRLR LHSLGPEDEG VYHCAPSAWV<br>QHADYSWYQA GSARSGPVTV YPYMHALDTL FVPLLVGTGV ALVTGATVLG<br>TITCCFMKRL RKR |
| The ITGB1 protein (SEQ ID NO: 21) | MNLQPIFWIG LISSVCCVFA QTDENRCLKA NAKSCGECIQ AGPNCGWCTN<br>STFLQEGMPT SARCDDLEAL KKKGCPPDDI ENPRGSKDIK KNKNVTNRSK<br>GTAEKLKPED ITQIQPQQLV LRLRSGEPQT FTLKFKRAED YPIDLYYLMD<br>LSYSMKDDLE NVKSLGTDLM NEMRRITSDF RIGFGSFVEK TVMPYISTTP<br>AKLRNPCTSE QNCTSPFSYK NVLSLTNKGE VFNELVGKQR ISGNLDSPEG<br>GFDAIMQVAV CGSLIGWRNV TRLLVFSTDA GFHFAGDGKL GGIVLPNDGQ<br>CHLENNMYTM SHYYDYPSIA HLVQKLSENN IQTIFAVTEE FQPVYKELKN<br>LIPKSAVGTL SANSSNVIQL IIDAYNSLSS EVILENGKLS EGVTISYKSY |

TABLE 1-continued

| Protein | Sequence |
|---|---|
| | CKNGVNGTGE NGRKCSNISI GDEVQFEISI TSNKCPKKDS DSFKIRPLGF<br>TEEVEVILQY ICECECQSEG IPESPKCHEG NGTFECGACR CNEGRVGRHC<br>ECSTDEVNSE DMDAYCRKEN SSEICSNNGE CVCGQCVCRK RDNTNEIYSG<br>ASNGQICNGR GICECGVCKC TDPKFQGQTC EMCQTCLGVC AEHKECVQCR<br>AFNKGEKKDT CTQECSYFNI TKVESRDKLP QPVQPDPVSH CKEKDVDDCW<br>FYFTYSVNGN NEVMVHVVEN PECPTGPDII PIVAGVVAGI VLIGLALLLI<br>WKLLMIIHDR REFAKFEKEK MNAKWDTGEN PIYKSAVTTV VNPKYEGK |
| The ITGA4 protein (SEQ ID NO: 22) | MAWEARREPG PRRAAVRETV MLLLCLGVPT GRPYNVDTES ALLYQGPHNT<br>LFGYSVVLHS HGANRWLLVG APTANWLANA SVINPGAIYR CRIGKNPGQT<br>CEQLQLGSPN GEPCGKTCLE ERDNQWLGVT LSRQPGENGS IVTCGHRWKN<br>IFYIKNENKL PTGGCYGVPP DLR1ELSKRI APCYQDYVKK FGENFASCQA<br>GISSFYTKDL IVMGAPGSSY WTGSLFVYNI TTNKYKAFLD KQNQVKFGSY<br>LGYSVGAGHF RSQHTTEVVG GAPQHEQIGK AYIFSIDEKE LNILHEMKGK<br>KLGSYFGASV CAVDLNADGF SDLLVGAPMQ STIREEGRVF VYINSGSGAV<br>MNAMETNLVG SDKYAARFGE SIVNLGDIDN DGFEDVAIGA PQEDDLQGAI<br>YIYNGRADGI SSTFSQRIEG LQISKSLSMF GQSISGQIDA DNNGYVDVAV<br>GAFRSDSAVL LRTRPVVIVD ASLSHPESVN RTKFDCVENG WPSVCIDLTL<br>CFSYKGKEVP GYIVLFYNMS LDVNRKAESP PRFYFSSNGT SDVITGSIQV<br>SSREANCRTH QAFMRKDVRD ILTPIQIEAA YHLGPHVISK RSTEEFPPLQ<br>PILQQKKEKD IMKKTINFAR FCAHENCSAD LQVSAKIGFL KPHENKTYLA<br>VGSMKTLMLN VSLFNAGDDA YETTLHVKLP VGLYFIKILE LEEKQINCEV<br>TDNSGVVQLD CSIGYIYVDH LSRIDISFLL DVSSLSRAEE DLSITVHATC<br>ENEEEMDNLK HSRVTVAIPL KYEVKLTVHG FVNPTSFVYG SNDENEPETC<br>MVEKMNLTFH VINTGNSMAP NVSVEIMVPN SFSPQTDKLF NILDVQTTTG<br>ECHFENYQRV CALEQQKSAM QTLKGIVRFL SKTDKRLLYC IKADPHCLNF<br>LCNFGKMESG KEASVHIQLE GRPSILEMDE TSALKFEIRA TGFPEPNPRV<br>IELNKDENVA HVLLEGLHHQ RPKRYFTIVI ISSSLLLGLI VLLLISYVMW<br>KAGFFKRQYK SILQEENRRD SWSYINSKSN DD |
| The SLC3A2 Protein, where the first Met is processed. (SEQ ID NO: 23) | MELQPPEASI AVVSIPRQLP GSHSEAGVQG LSAGDDSELG SHCVAQTGLE<br>LLASGDPLPS ASQNAEMIET GSDCVTQAGL QLLASSDPPA LASKNAEVTG<br>TMSQDTEVDM KEVELNELEP EKQPMNAASG AAMSLAGAEK NGLVKIKVAE<br>DEAEAAAAAK FTGLSKEELL KVAGSPGWVR TRWALLLLFW LGWLGMLAGA<br>VVIIVRAPRC RELPAQKWWH TGALYRIGDL QAFQGHGAGN LAGLKGRLDY<br>LSSLKVKGLV LGPIHKNQKD DVAQTDLLQI DPNFGSKEDF DSLLQSAKKK<br>SIRVILDLTP NYRGENSWFS TQVDTVATKV KDALEFWLQA GVDGFQVRDI<br>ENLKDASSFL AEWQNITKGF SEDRLLIAGT NSSDLQQILS LLESNKDLLL<br>TSSYLSDSGS TGEHTKSLVT QYLNATGNRW CSWSLSQARL LTSFLPAQLL<br>RLYQLMLFTL PGTPVFSYGD EIGLDAAALP GQPMEAPVML WDESSFPDIP<br>GAVSANMTVK GQSEDPGSLL SLFRRLSDQR SKERSLLHGD FHAFSAGPGL<br>FSYIRHWDQN ERFLVVLNFG DVGLSAGLQA SDLPASASLP AKADLLLSTQ<br>PGREEGSPLE LERLKLEPHE GLLLRFPYAA |

In some embodiments, a Scaffold X useful for the present disclosure comprises Basigin (the BSG protein), represented by SEQ ID NO: 9. The BSG protein is also known as 5F7, Collagenase stimulatory factor, Extracellular matrix metalloproteinase inducer (EMMPRIN), Leukocyte activation antigen M6, OK blood group antigen, Tumor cell-derived collagenase stimulatory factor (TCSF), or CD147. The Uniprot number for the human BSG protein is P35613. The signal peptide of the BSG protein is amino acid 1 to 21 of SEQ ID NO: 9. Amino acids 138-323 of SEQ ID NO: 9 is the extracellular domain, amino acids 324 to 344 is the transmembrane domain, and amino acids 345 to 385 of SEQ ID NO: 9 is the cytoplasmic domain.

In other embodiments, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 22 to 385 of SEQ ID NO: 9. In some embodiments, the fragments of Basigin polypeptide lack one or more functional or structural domains, such as IgV, e.g., amino acids 221 to 315 of SEQ ID NO: 9. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 10, 11, or 12. In other embodiments, the Scaffold X comprises the amino acid sequence of SEQ ID NO: 10, 11, or 12, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of SEQ ID NO: 10, 11, or 12 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 10, 11, or 12.

In some embodiments, a Scaffold X useful for the present disclosure comprises Immunoglobulin superfamily member 8 (IgSF8 or the IGSF8 protein), which is also known as CD81 partner 3, Glu-Trp-Ile EWI motif-containing protein 2 (EWI-2), Keratinocytes-associated transmembrane protein 4 (KCT-4), LIR-D1, Prostaglandin regulatory-like protein (PGRL) or CD316. The full length human IGSF8 protein is accession no. Q969P0 in Uniprot and is shown as SEQ ID NO: 14 herein. The human IGSF8 protein has a signal peptide (amino acids 1 to 27 of SEQ ID NO: 14), an extracellular domain (amino acids 28 to 579 of SEQ ID NO: 14), a transmembrane domain (amino acids 580 to 600 of SEQ ID NO: 14), and a cytoplasmic domain (amino acids 601 to 613 of SEQ ID NO: 14).

In other embodiments, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 14. In some embodiments, the IGSF8 protein lack one or more functional or structural domains, such as IgV. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 15, 16, 17, or 18. In other embodiments, the Scaffold X comprises the amino acid sequence of SEQ ID NO: 15, 16, 17, or 18, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of SEQ ID 15, 16, 17, or 18 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 15, 16, 17, or 18.

In some embodiments, a Scaffold X that can be used with STING agonists disclosed herein comprises Immunoglobulin superfamily member 3 (IgSF3 or the IGSF3 protein), which is also known as Glu-Trp-Ile EWI motif-containing protein 3 (EWI-3), and is shown as the amino acid sequence of SEQ ID NO: 20. The human IGSF3 protein has a signal peptide (amino acids 1 to 19 of SEQ ID NO: 20), an extracellular domain (amino acids 20 to 1124 of SEQ ID NO: 20), a transmembrane domain (amino acids 1125 to 1145 of SEQ ID NO: 20), and a cytoplasmic domain (amino acids 1146 to 1194 of SEQ ID NO: 20).

In other embodiments, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 28 to 613 of SEQ ID NO: 20. In some embodiments, the IGSF3 protein lack one or more functional or structural domains, such as IgV.

In some embodiments, a Scaffold X useful for the present disclosure comprises Integrin beta-1 (the ITGB1 protein), which is also known as Fibronectin receptor subunit beta, Glycoprotein IIa (GPIIA), VLA-4 subunit beta, or CD29, and is shown as the amino acid sequence of SEQ ID NO: 21. The human ITGB1 protein has a signal peptide (amino acids 1 to 20 of SEQ ID NO: 21), an extracellular domain (amino acids 21 to 728 of SEQ ID NO: 21), a transmembrane domain (amino acids 729 to 751 of SEQ ID NO: 21), and a cytoplasmic domain (amino acids 752 to 798 of SEQ ID NO: 21).

In other embodiments, a Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 21 to 798 of SEQ ID NO: 21. In some embodiments, the ITGB1 protein lack one or more functional or structural domains, such as IgV.

In other embodiments, a Scaffold X comprises the ITGA4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 22 without the signal peptide (amino acids 1 to 33 of SEQ ID NO: 22). In some embodiments, the ITGA4 protein lacks one or more functional or structural domains, such as IgV.

In other embodiments, a Scaffold X comprises the SLC3A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 23 without the signal peptide. In some embodiments, the SLC3A2 protein lacks one or more functional or structural domains, such as IgV.

In other embodiments, a Scaffold X comprises the ATP1A1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 24 without the signal peptide. In some embodiments, the ATP1A1 protein lacks one or more functional or structural domains, such as IgV.

In other embodiments, a Scaffold X comprises the ATP1A2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 25 without the signal peptide. In some embodiments, the ATP1A2 protein lacks one or more functional or structural domains, such as IgV.

In other embodiments, a Scaffold X comprises the ATP1A3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 26 without the signal peptide. In some embodiments, the ATP1A3 protein lacks one or more functional or structural domains, such as IgV.

In other embodiments, a Scaffold X comprises the ATP1A4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 27 without the signal peptide. In some embodiments, the ATP1A4 protein lacks one or more functional or structural domains, such as IgV.

In other embodiments, a Scaffold X comprises the ATP1A5 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 28 without the signal peptide. In some embodiments, the ATP1A5 protein lacks one or more functional or structural domains, such as IgV.

In other embodiments, a Scaffold X comprises the ATP2B1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 29 without the signal peptide. In some embodiments, the ATP2B1 protein lacks one or more functional or structural domains, such as IgV.

In other embodiments, a Scaffold X comprises the ATP2B2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 30 without the signal peptide. In some embodiments, the ATP2B2 protein lacks one or more functional or structural domains, such as IgV.

In other embodiments, a Scaffold X comprises the ATP2B3 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 31 without the signal peptide. In some embodiments, the ATP2B3 protein lacks one or more functional or structural domains, such as IgV.

In other embodiments, a Scaffold X comprises the ATP2B4 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 32 without the signal peptide. In some embodiments, the ATP2B4 protein lacks one or more functional or structural domains, such as IgV.

In other embodiments, a Scaffold X comprises the IGSF2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 34 without the signal peptide. In some embodiments, the IGSF2 protein lacks one or more functional or structural domains, such as IgV.

Non-limiting examples of other Scaffold X proteins that can be used to link a STING agonist to the surface of EVs, e.g., exosomes, can be found at U.S. Pat. No. 10,195,290 B1, issued Feb. 5, 2019, which is incorporated by reference in its entirety.

In some embodiments, a Scaffold X protein useful for the present disclosure lacks at least 5, 10, 50, 100, 200, 300, 400, 500, 600, 700, or 800 amino acids from the N-terminus of the native protein. In some embodiments, a Scaffold X lacks at least 5, 10, 50, 100, 200, 300, 400, 500, 600, 700, or 800 amino acids from the C-terminus of the native protein. In some embodiments, a Scaffold X lacks at least 5, 10, 50, 100, 200, 300, 400, 500, 600, 700, or 800 amino acids from both the N-terminus and C-terminus of the native protein. In some embodiments, a Scaffold X lacks one or more functional or structural domains of the native protein.

In some embodiments, Scaffold X described herein can also be used to link a STING agonist on the luminal surface and/or on the exterior surface of the EVs, e.g., exosomes, at the same time. For example, the PTGFRN polypeptide can be used to link a STING agonist inside the lumen in addition to the surface of the EV, e.g., exosome. In some embodiments, a Scaffold X can be used to link a STING agonist and an additional therapeutic agent to the EVs, e.g., exosomes, (e.g., payload). Therefore, in certain embodiments, Scaffold X disclosed herein can be used for dual purposes.

Scaffold-Y-Engineered EVs, e.g., Exosomes

In some embodiments, EVs, e.g., exosomes, of the present disclosure comprise an internal space (i.e., lumen) that is different from that of the naturally occurring EVs, e.g., exosomes. For example, the EV, e.g., exosome, can be changed such that the composition in the luminal side of the EV, e.g., exosome, has the protein, lipid, or glycan content different from that of the naturally-occurring EVs, e.g., exosomes.

In some embodiments, engineered EVs, e.g., exosomes, can be produced from a cell transformed with an exogenous sequence encoding a scaffold moiety (e.g., exosome proteins, e.g., Scaffold Y) or a modification or a fragment of the scaffold moiety that changes the composition or content of the luminal side of the EV, e.g., exosome. Various modifications or fragments of the exosome protein that can be expressed in the luminal side of the EV, e.g., exosome, can be used for the embodiments of the present disclosure.

In some embodiments, a STING agonist disclosed herein is in the lumen of the EV, e.g., exosome (i.e., encapsulated). In some embodiments, a STING agonist is linked to the luminal surface of the EV, e.g., exosome. As used herein, when a molecule (e.g., antigen or adjuvant) is described as "in the lumen" of the EV, e.g., exosome, it means that the molecule is located within the EV, e.g., exosome (e.g., associated), but is not linked to any molecule on the luminal surface of EVs. In other embodiments, a STING agonist is expressed on the luminal surface of the EV, e.g., exosome as a fusion molecule, e.g., fusion molecule of a STING agonist to a scaffold moiety (e.g., Scaffold Y). In certain embodiments, Scaffold Y comprises the MARCKS protein, MARCKSL1 protein, BASP1 protein, or any combination thereof.

In other embodiments, the EVs, e.g., exosomes, of the present disclosure contain a STING agonist and a Scaffold Y, wherein the STING agonist is linked to Scaffold Y. In some embodiments, the EVs, e.g., exosomes, of the present disclosure comprise a STING agonist and a Scaffold Y, wherein the STING agonist is not linked to Scaffold Y.

In some embodiments, scaffold moieties (e.g., Scaffold Y) that can change the luminal side of the EVs, e.g., exosomes, include, but are not limited to the MARCKS protein, MARCKSL1 protein, BASP1 protein, or any combination thereof. In some embodiments, Scaffold Y comprises Brain Acid Soluble Protein 1 (the BASP1 protein). The BASP1 protein is also known as 22 kDa neuronal tissue-enriched acidic protein or neuronal axonal membrane protein NAP-22. The full-length human BASP1 protein sequence (isomer 1) is shown in Table 2. An isomer produced by an alternative splicing is missing amino acids 88 to 141 from SEQ ID NO: XX (isomer 1).

TABLE 2

| Protein | Sequence |
|---|---|
| The BASP1 protein (SEQ ID NO: 49) | MGGKLSKKKK GYNVNDEKAK EKDKKAEGAA TEEEGTPKES EPQAAAEPAE AKEGKEKPDQ DAEGKAEEKE GEKDAAAAKE EAPKAEPEKT |

TABLE 2-continued

| Protein | Sequence |
|---|---|
| | EGAAEAKAEP PKAPEQEQAA PGPAAGGEAP KAAEAAAAPA ESAAPAAGEE PSKEEGEPKK TEAPAAPAAQ ETKSDGAPAS DSKPGSSEAA PSSKETPAAT EAPSSTPKAQ GPAASAEEPK PVEAPAANSD QTVTVKE |

The mature BASP1 protein sequence is missing the first Met from SEQ ID NO: 49 and thus contains amino acids 2 to 227 of SEQ ID NO: 49.

In other embodiments, Scaffold Y useful for the present disclosure comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 2 to 227 of SEQ ID NO: 49. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 50-155. In other embodiments, a Scaffold Y useful for the present disclosure comprises the amino acid sequence of SEQ ID NO: 50-155, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, a Scaffold Y useful for the present disclosure comprises the amino acid sequence of SEQ ID NO: 50-155 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 50-155.

In some embodiments, a Scaffold Y useful for the present disclosure is the MARCKS protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 47 without the signal peptide. In certain embodiments, the MARCKS protein lacks one or more functional or structural domains.

In some embodiments, a Scaffold Y comprises the MARCKSL1 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 48 without the signal peptide. In certain embodiments, the MARCKS protein lacks one or more functional or structural domains.

In some embodiments, a Scaffold Y useful for the present disclosure comprises a peptide with the MGXKLSKKK, where X is alanine or any other amino acid (SEQ ID NO: 163). In some embodiments, an EV, e.g., exosome, comprises a peptide with sequence of (M)(G)(π)(ξ)(Φ/π)(S/A/G/N)(+)(+), wherein each parenthetical position represents an amino acid, and wherein π is any amino acid selected from the group consisting of (Pro, Gly, Ala, Ser), ξ is any amino acid selected from the group consisting of (Asn, Gln, Ser, Thr, Asp, Glu, Lys, His, Arg), Φ is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). In further embodiments, an EV, e.g., exosome, described herein (e.g., engineered EVs, e.g., exosomes) comprises a peptide with sequence of (M)(G)(π)(X)(Φ/π)(π)(+)(+), wherein each parenthetical position represents an amino acid, and wherein π is any amino acid selected from the group consisting of (Pro, Gly, Ala, Ser), X is any amino acid, D is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu).

In some embodiments, a Scaffold Y that can be used to express a STING agonist on the luminal surface of an EV, e.g., exosome, comprises an amino acid sequence at least about 70%, at least about 75%, at least about 80%, at least about 85%, at least about 90%, at least about 95%, at least about 96%, at least about 97%, at least about 98%, at least about 99%, or about 100% identical to any one of SEQ ID NO: 7-155.

Scaffold Y-engineered EVs, e.g., exosomes, described herein can be produced from a cell transformed with a sequence set forth in SEQ ID NOs: 47-155.

II.C. Linker

The EVs of the present disclosure can comprises one or more linkers that link the STING agonist to EVs or to a scaffold moiety, e.g., Scaffold X on the exterior surface of the EVs. In some embodiments, the STING agonist is linked to the EVs directly or in a scaffold moiety on the EVs by a linker. The linker can be any chemical moiety known in the art.

In some embodiments, the term "linker" refers to a peptide or polypeptide sequence (e.g., a synthetic peptide or polypeptide sequence) or to a non-polypeptide. In some aspects, two or more linkers can be linked in tandem. Generally, linkers provide flexibility or prevent/ameliorate steric hindrances. Linkers are not typically cleaved; however in certain aspects, such cleavage can be desirable. Accordingly, in some aspects a linker can comprise one or more protease-cleavable sites, which can be located within the sequence of the linker or flanking the linker at either end of the linker sequence.

In some embodiments, the linker is a peptide linker. In some embodiments, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some embodiments, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion).

Linkers may be susceptible to cleavage ("cleavable linker") thereby facilitating release of the STING Agonist or other payloads. In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof. In some aspects, the linker comprises a non-cleavable liker.

II.D. Producer Cells and Modifications

EVs, e.g., exosomes, can be produced from a cell grown in vitro or a body fluid of a subject. When EVs, e.g., exosomes, are produced from in vitro cell culture, various producer cells, e.g., HEK293 cells, can be used. Additional cell types that can be used for the production of the lumen-engineered EVs, e.g., exosomes, described herein include, without limitation, mesenchymal stem cells, T-cells, B-cells, dendritic cells, macrophages, and cancer cell lines. Further examples include: Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, and RPTEC/TERT1 cells. In certain embodiments, a producer cell is not a dendritic cell, macrophage, B cell, mast cell, neutrophil, Kupffer-Browicz cell, cell derived from any of these cells, or any combination thereof.

Some embodiments may also include genetically modifying the EV, e.g., exosome, to comprise one or more exogenous sequences to produce modified EVs that express exogenous proteins on the vesicle surface. The exogenous sequences can comprise a sequence encoding the EV, e.g., exosome, protein or a modification or a fragment of the EV protein. An extra copy of the sequence encoding the EV, e.g., exosome, protein can be introduced to produce a surface-engineered EV having a higher density of the EV protein. An exogenous sequence encoding a modification or a fragment of the EV, e.g., exosome, protein can be introduced to produce a modified EV containing the modification or the fragment of the EV protein. An exogenous sequence encoding an affinity tag can be introduced to produce a modified EV, e.g., exosome, containing a fusion protein comprising the affinity tag attached to the EV protein.

In some embodiments, the exogenous sequence encodes for Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In some embodiments the modified EV, e.g., exosome, overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In other embodiments, the EV, e.g., exosome, is produced by a cell that overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof).

In some embodiments, the exogenous sequence encodes for Scaffold Y (e.g., the MARCKS protein, MARCKSL1 protein, BASP1 protein, or a fragment or variant thereof). In some embodiments, the modified EV, e.g., exosome, overexpresses Scaffold Y (e.g., the MARCKS protein, MARCKSL1 protein, BASP1 protein, or a fragment or variant thereof). In other embodiments, the EV, e.g., exosome, is produced by a cell that overexpresses Scaffold Y (e.g., the MARCKS protein, MARCKSL1 protein, BASP1 protein, or a fragment or variant thereof).

The exogenous sequence may be transiently or stabled expressed in the producer cell or cell line via transfection, transformation, transduction, electroporation, or any other appropriate method of gene delivery or combination thereof known in the art. The exogenous sequence may be integrated into the producer cell genome, or remain extra chromosomal. The exogenous sequence can be transformed as a plasmid. The exogenous sequences can be stably integrated into a genomic sequence of the producer cell, at a targeted site or in a random site. The exogenous sequences can be inserted into a genomic sequence of the producer cell, located within, upstream (5'-end) or downstream (3'-end) of an endogenous sequence encoding the EV, e.g., exosome, protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 CRISPR/Cfp1, CRISPR/C2c1, C2c2, or C2c3, CRISPR/CasY or CasX, TAL-effector nuclease or TALEN, or zinc finger nuclease (ZFN) systems) are within the scope of various embodiments.

In some embodiments, the producer cell is further modified to comprise an additional exogenous sequence. For example, an additional exogenous sequence can be included to modulate endogenous gene expression, modulate the immune response or immune signaling, or produce an EV, e.g., exosome, including a certain polypeptide as a payload or additional surface expressed ligand. In some embodiments, the producer cell can be further modified to comprise an additional exogenous sequence conferring additional functionalities to EVs, e.g., exosomes, for example, specific targeting capabilities, delivery functions, enzymatic functions, increased or decreased half-life in vivo, etc. In some embodiments, the producer cell is modified to comprise two exogenous sequences, one encoding the exosome protein or a modification or a fragment of the exosome protein, and the other encoding a protein conferring the additional functionalities to exosomes.

More specifically, the EV, e.g., exosome, of the present can be produced from a cell transformed with a sequence encoding one or more additional exogenous proteins including, but not limited to ligands, cytokines, or antibodies, or any combination thereof. These additional exogenous proteins may enable activation or modulation of additional immune stimulatory signals in combination with the STING agonist. Exemplary additional exogenous proteins contemplated for use include the proteins, ligands, and other molecules described in detail in U.S. Patent Application 62/611,140, which is incorporated herein by reference in its entirety. In some embodiments, the EV, e.g., exosome, is further modified with a ligand comprising CD40L, OX40L, or CD27L. In some embodiments, the EV, e.g., exosome, is further modified with a cytokine comprising IL-7, IL-12, or IL-15. Any of the one or more exosome proteins described herein can be expressed from a plasmid, an exogenous sequence inserted into the genome or other exogenous nucleic acid such as a synthetic messenger RNA (mRNA).

In some embodiments, the EV, e.g., exosome, is further modified to display an antagonistic antibody or an agonistic antibody or a fragment thereof on the EV, e.g., exosome, surface to direct EV uptake, activate, or block cellular pathways to enhance the combinatorial effect of the STING agonist. In some specific embodiments, the antibody or fragment thereof is an antibody against DEC205, CLEC9A, CLEC6, DCIR, DC-SIGN, LOX-1, or Langerin. The producer cell may be modified to comprise an additional exogenous sequence encoding for an antagonistic antibody or an agonistic antibody. Alternatively, the antagonistic antibody or agonistic antibody may be covalently linked or conjugated to the EV, e.g., exosome, via any appropriate linking chemistry known in the art. Non-limiting examples of appropriate linking chemistry include amine-reactive groups, carboxyl-reactive groups, sulfhydryl-reactive groups, aldehyde-reactive groups, photoreactive groups, ClickIT chemistry, biotin-streptavidin or other avidin conjugation, or any combination thereof.

II.D.1. Glycan Modification of Producer Cells or EVs, e.g., Exosomes

In some embodiments the EV, e.g., exosome, is glycan modified via enzymatic or chemical treatment. In one embodiment, the EV, e.g., exosome, is derived from a glycan modified producer cell. In another embodiment, the glycan modification of the producer cell comprises an enzymatic or a chemical modification. In various embodiments, the glycan modification of the producer cell is treatment with kifunensine or knockout of a sialyltransferase or cytidylyltransferase gene. In one embodiment, the glycan modification of the producer cell comprises knockout of the cytidylyltransferase gene Cytidine Monophosphate N-Acetylneuraminic Acid Synthetase (CMAS). In one embodiment, the glycan modification of the producer cell comprises knockout of the mannose biosynthesis gene Mannosidase Alpha Class 1A Member 1 (MAN1A1). In one embodiment, the glycan modification of the producer cell comprises knockout of the mannose biosynthesis gene Mannosidase Alpha Class 2A Member 1 (MAN2A1).

Glycan modification may be deglycosylation or desialylation of the producer cell or of the isolated or purified EVs, e.g., exosomes. The EVs, e.g., exosomes, may be glycan modified before encapsulation of the STING agonist or after encapsulation of the STING agonist. The producer cell or EV, e.g., exosome, may be glycan modified (e.g. deglycosylated or desialylated) about or more than 99%, 95%, 90%, 85%, 80%, 75%, 70%, 65%, 60%, 55%, 50%, 45%, 40%, 35%, 30%, 25%, 20%, 15%, 10%, or 5% relative to an unmodified producer cell or EV, e.g., exosome. The producer cell or EV, e.g., exosome, may be glycan modified between 95-100%, 90-95%, 85-95%, 80-85%, 75-80%, 70-75%, 65-70%, 60-65%, 55-60%, 50-55%, 45-50%, 40-45%, 35-40%, 30-35%, 25-30%, 20-25%, 15-20%, 10-15%, or 5-10% relative to an unmodified producer cell or EV, e.g., exosome.

The producer cell or EV, e.g., exosome, may be glycan modified via chemical, enzymatic, or genetic editing techniques. Glycan modification may include treating producer cells with chemicals, small molecules, or enzymes that alter or inhibit glycosyltransferases, galactosyltransferases, sialyltransferase, or cytidylyltransferase enzymes in the producer cell, resulting in EVs, e.g., exosomes, derived from the producer cell that are glycan modified. Glycan modification may also include treating EVs, e.g., exosomes, with chemicals or enzymes that alter the glycans on the EV surface, such as small molecule inhibitors or glycoside hydrolases such as sialidase or neuraminidase enzymes, as well as any other appropriate chemical or enzyme glycan modification treatments.

In some embodiments, the producer cell or EVs, e.g., exosomes, is glycan modified via treatment with kifunensine. Kifunensine is a mannosidase I inhibitor that inhibits mannosidase I from removing mannose residues from precursor glycoproteins. Treatment of cells with kifunensine results in glycoproteins with terminal mannose residues. Another mannosidase I inhibitor that may be used is 1-deoxymannojirimycin. Other small molecules that inhibit alpha-mannosidase I or II or beta-mannosidase enzymes may also be used, such as swainsonine.

Some embodiments may also include treatment of producer cells or EVs, e.g., exosomes, with glycoside hydrolases such as sialidases, neuraminidases, or mannosidases. Any glycoside hydrolase known in the art may be used, including but not limited to, exo-α-sialidases, endo-α-sialidases, N-acetylneuraminidase, sialidase 1, sialidase 2, sialidase, 3, or sialidase 4, any other appropriate sialidase, α-mannosidases, β-mannosidases, or any combination thereof.

In addition, glycan modification may include genetically altering the producer cell via an appropriate genome editing technique to have altered glycan enzyme expression, such as knockout or knock down of glycosyltransferases, galactosyltransferases, sialyltransferase or cytidylyltransferase enzymes in the producer cell. Any genome editing technique known in the art may be used, including, but not limited to, CRISPR/Cas9, CRISPR/Cfp1, CRISPR/C2c1, C2c2, or C2c3, CRISPR/CasY or CasX, TAL-effector nuclease or TALEN, or zinc finger nuclease (ZFN) systems, or any combination thereof.

Exemplary genes that may be altered include Cytidine Monophosphate N-Acetylneuraminic Acid Synthetase (CMAS), and the mannose biosynthesis genes Mannosidase Alpha Class 1A Member 1 (MANIA1) and Mannosidase Alpha Class 2A Member 1 (MAN2A1).

The glycan modified EVs, e.g., exosomes, may also be derived from a PTGFRN overexpressing producer cell line that has also ben glycan modified. In such an example, the producer cell line may be transformed, transfected, transduced, or otherwise genetically modified to express the PTGFRN gene and gene product and to have altered glycan transferase enzyme expression. In one embodiment, the producer cell is altered to overexpress the PTGFRN gene and gene product and knockdown or knock out of the cytidylyltransferase gene CMAS. Alternatively, the producer cell line may be genetically modified to express the PTGFRN gene and gene product and treated with kifunensine or other mannosidase, glycosyltransferase, galactosyltransferase, sialyltransferase or cytidylyltransferase inhibitors known in the art, or any combination thereof, thereby resulting in a producer cell that both overexpresses the PTGFRN gene and gene product, and has altered glycan expression.

III. Method of Producing EVs with STING Agonists

III.A. Methods for Encapsulating STING Agonists in EVs

STING agonists can be encapsulated in EVs, e.g., exosomes, via any appropriate technique known in the art. It is contemplated that all known manners of loading biomolecules into EVs, e.g., exosomes, are deemed suitable for use herein. Such techniques include passive diffusion, electroporation, chemical or polymeric transfection, viral transduction, mechanical membrane disruption or mechanical shear, or any combination thereof. The STING agonist and an EV, e.g., exosome, may be incubated in an appropriate buffer during encapsulation.

In one embodiment, a STING agonist is encapsulated by an EV, e.g., exosome, by passive diffusion. The STING agonist and the EV, e.g., exosome, may be mixed together and incubated for a time period sufficient for the STING agonist to diffuse through the vesicle lipid bilayer, thereby becoming encapsulated in the EV, e.g., exosome. The STING agonist and the EV, e.g., exosome, may be incubated together for between about 1 to 30 hours, 2 to 24 hours, 4 to 18 hours, 6 to 16 hours, 8 to 14 hours, 10 to 12 hours, 6 to 12 hours, 12 to 20 hours, 14 to 18 hours, or 20 to 30 hours. The STING agonist and the EV, e.g., exosome, may be incubated together for about 2 hours, 4 hours, 6, hours, 8, hours, 10, hours, 12 hours, 14 hours, 16 hours, 18 hours, 20 hours, 22 hours, 24 hours, 26 hours, or 30 hours.

The buffer conditions of the solution of EVs, e.g., exosomes, may also be altered to optimize encapsulation of the STING agonist. In one embodiment, the buffer may be a phosphate buffered saline (PBS) with sucrose. PBS is a well-known buffer to those skilled in the art. Additional buffer modifications may also be used, such as shear protectants, viscosity modifiers, and/or solutes that affect vesicle structural properties. Excipients may also be added to improve the efficiency of the STING agonist encapsulation such as membrane softening materials and molecular crowding agents. Other modifications to the buffer may include specific pH ranges and/or concentrations of salts, organic solvents, small molecules, detergents, zwitterions, amino acids, polymers, and/or any combination of the above including multiple concentrations.

The temperature of the solution of EVs, e.g., exosomes, and STING agonists during incubation may be changed to optimize encapsulation of the STING agonist. The temperature may be room temperature. The temperature may be between about 15° C. to 90° C., 15-30° C., 30-50° C., 50-90° C. The temperature may be about 15° C., 20° C., 35° C., 30° C., 35° C., 37° C., 40° C., 45° C., 50° C., 55° C., 60° C., 65° C., 70° C., 75° C., 80° C., 85° C., or 90° C.

The concentration of STING agonist during the incubation of the agonist with the EVs, e.g., exosomes, may also be altered to optimize encapsulation of the STING agonist. The concentration of agonist may be between at least 0.01 mM and 100 mM STING agonist. The concentration of the agonist may be at least 0.01-1 mM, 1-10 mM, 10-50 mM, or 50-100 mM. The concentration of the agonist may be at least 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 15 mM, 20 mM 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM.

The number of extracellular particles incubated with the STING agonist may also be altered to optimize encapsulation of the STING agonist. The number of purified EV, e.g., exosome, particles may be between at least about $10^6$ to at least about $10^{20}$ total particles of purified vesicles. The number of purified particles may be between about $10^8$ to $10^{18}$, $10^{10}$ to $10^{16}$, $10^8$ to $10^{14}$, or $10^{10}$ to $10^{12}$ total particles of purified vesicles. The number of purified particles may be at least about $10^6$, $10^8$, $10^{10}$, $10^2$, $10^{14}$, $10^{16}$, $10^{18}$, or $10^{20}$ total particles of purified vesicles.

In some embodiments, the one or more moieties can be introduced into suitable producer cells using synthetic macromolecules, such as cationic lipids and polymers (Papapetrou et al., *Gene Therapy* 12: S118-S130 (2005)). In some embodiments, the cationic lipids form complexes with the one or more moieties through charge interactions. In some of these embodiments, the positively charged complexes bind to the negatively charged cell surface and are taken up by the cell by endocytosis. In some other embodiments, a cationic polymer can be used to transfect producer cells. In some of these embodiments, the cationic polymer is polyethylenimine (PEI). In certain embodiments, chemicals such as calcium phosphate, cyclodextrin, or polybrene, can be used to introduce the one or more moieties to the producer cells. The one or more moieties can also be introduced into a producer cell using a physical method such as particle-mediated transfection, "gene gun", biolistics, or particle bombardment technology (Papapetrou et al., *Gene Therapy* 12: S118-S130 (2005)). A reporter gene such as, for example, beta-galactosidase, chloramphenicol acetyltransferase, luciferase, or green fluorescent protein can be used to assess the transfection efficiency of the producer cell.

In some embodiments, the one or more moieties are introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In some embodiments, the one or more moieties are introduced to the producer cell by electroporation. Electroporation creates transient pores in the cell membrane, allowing for the introduction of various molecules into the cell. In some embodiments, DNA and RNA as well as polypeptides and non-polypeptide therapeutic agents can be introduced into the producer cell by electroporation.

In some embodiments, the one or more moieties are introduced to the producer cell by microinjection. In some embodiments, a glass micropipette can be used to inject the one or more moieties into the producer cell at the microscopic level.

In some embodiments, the one or more moieties are introduced to the producer cell by extrusion.

In some embodiments, the one or more moieties are introduced to the producer cell by sonication. In some embodiments, the producer cell is exposed to high intensity sound waves, causing transient disruption of the cell membrane allowing loading of the one or more moieties.

In some embodiments, the one or more moieties are introduced to the producer cell by cell fusion. In some embodiments, the one or more moieties are introduced by electrical cell fusion. In other embodiments, polyethylene glycol (PEG) is used to fuse the producer cells. In further embodiments, sendai virus is used to fuse the producer cells.

In some embodiments, the one or more moieties are introduced to the producer cell by hypotonic lysis. In such embodiments, the producer cell can be exposed to low ionic strength buffer causing them to burst allowing loading of the one or more moieties. In other embodiments, controlled dialysis against a hypotonic solution can be used to swell the producer cell and to create pores in the producer cell membrane. The producer cell is subsequently exposed to conditions that allow resealing of the membrane.

In some embodiments, the one or more moieties are introduced to the producer cell by detergent treatment. In certain embodiments, producer cell is treated with a mild detergent which transiently compromises the producer cell membrane by creating pores allowing loading of the one or more moieties. After producer cells are loaded, the detergent is washed away thereby resealing the membrane.

In some embodiments, the one or more moieties introduced to the producer cell by receptor mediated endocytosis. In certain embodiments, producer cells have a surface receptor which upon binding of the one or more moieties induces internalization of the receptor and the associated moieties.

In some embodiments, the one or more moieties are introduced to the producer cell by filtration. In certain embodiments, the producer cells and the one or more moieties can be forced through a filter of pore size smaller than the producer cell causing transient disruption of the producer cell membrane and allowing the one or more moieties to enter the producer cell.

In some embodiments, the producer cell is subjected to several freeze thaw cycles, resulting in cell membrane disruption allowing loading of the one or more moieties.

IV. EV Purification

The EVs, e.g., exosomes, prepared for the present disclosure can be isolated from the producer cells. It is contemplated that all known manners of isolation of EVs, e.g., exosomes, are deemed suitable for use herein. For example, physical properties of EVs, e.g., exosomes, may be employed to separate them from a medium or other source material, including separation on the basis of electrical charge (e.g., electrophoretic separation), size (e.g., filtration, molecular sieving, etc), density (e.g., regular or gradient centrifugation), Svedberg constant (e.g., sedimentation with or without external force, etc). Alternatively, or additionally, isolation may be based on one or more biological properties, and include methods that may employ surface markers (e.g., for precipitation, reversible binding to solid phase, FACS separation, specific ligand binding, non-specific ligand binding, etc.). In yet further contemplated methods, the EVs, e.g., exosomes, may also be fused using chemical and/or physical methods, including PEG-induced fusion and/or ultrasonic fusion.

The EVs, e.g., exosomes, may also be purified after incubation with the STING agonist to remove free, unencapsulated STING agonist from the composition. All manners of previously disclosed methods are also deemed suitable for use herein, including separation on the basis of physical or biological properties of EVs, e.g., exosomes.

Isolation, purification, and enrichment can be done in a general and non-selective manner (typically including serial centrifugation). Alternatively, isolation, purification, and enrichment can be done in a more specific and selective manner (e.g., using producer cell-specific surface markers). For example, specific surface markers may be used in immunoprecipitation, FACS sorting, affinity purification, bead-bound ligands for magnetic separation etc.

In some embodiments, size exclusion chromatography can be utilized to isolate or purify the EVs, e.g., exosomes. Size exclusion chromatography techniques are known in the art. Exemplary, non-limiting techniques are provided herein. In some embodiments, a void volume fraction is isolated and comprises the EVs, e.g., exosomes, of interest. In some embodiments, for example, density gradient centrifugation can be utilized to further isolate the EVs, e.g., exosomes. Still further, in some embodiments, it can be desirable to further separate the producer cell-derived EVs, e.g., exosomes, from EVs of other origin. For example, the producer cell-derived EVs, e.g., exosomes, can be separated from non-producer cell-derived EVs, e.g., exosomes, by immunosorbent capture using an antigen antibody specific for the producer cell.

In some embodiments, the isolation of EVs, e.g., exosomes, may involve size exclusion chromatography or ion chromatography, such as anion exchange, cation exchange, or mixed mode chromatography. In some embodiments, the isolation of EVs, e.g., exosomes, may involve desalting, dialysis, tangential flow filtration, ultrafiltration, or diafiltration, or any combination thereof. In some embodiments, the isolation of EVs, e.g., exosomes, may involve combinations of methods that include, but are not limited to, differential centrifugation, size-based membrane filtration, concentration and/or rate zonal centrifugation. In some embodiments, the isolation of EVs, e.g., exosomes, may involve one or more centrifugation steps. The centrifugation may be performed at about 50,000 to 150,000×g. The centrifugation may be performed at about 50,000×g, 75,000×g, 100,000×g, 125,000×g, or 150,000×g.

V. Therapeutic Administration

V.A. Immune Modulation and Dosage

Provided herein are methods for inducing and/or modulating an immune or inflammatory response in a subject by administering a pharmaceutically effective amount of an EV, e.g., exosome, comprising a STING agonist.

Dendritic cells (DCs) are a population of antigen present cells derived from a hematopoietic cell lineage that link the innate and adaptive immune systems. DCs share a common myeloid precursor with monocytes and macrophages and are generally separated into two major groups: plasmacytoid DCs (pDCs) and myeloid DCs (mDCs), which are also known as conventional DCs (cDCs). mDCs are further classified based on their development from myeloid or lymphoid precursors and expression levels of CD8a, CD4, and C11b. A third population of DCs are monocyte-derived DCs (moDCs) which arise from a monocyte precursor, not a DC progenitor like pDCs and cDCs. moDCs develop after receiving inflammatory cues. Immature DCs reside in peripheral tissue before maturation. Several signaling pathways lead to DC maturation, including the signaling cascades induced by pattern recognition receptors (PRRs). Each subset of immature DCs varies in the protein expression patterns of PRRs which allows the immature DC populations to respond differently upon activation of the same PRR. This results in modulation of the immune response mediated by DCs. PRRs present in DCs include Toll-like receptors (TLRs), C-type lectin receptors, retinoic-acid inducible gene (RIG)-I-like receptors (RLRs), NOD-like receptors (NLRs), and STING.

The STING pathway is the dominant DNA sensing pathway in both mDCs and pDCs. Activation of the STING pathway in DCs results in Type I IFN and pro inflammatory cytokine production via TBK1, IRF3, and NF-κB signaling. Binding of IFN to their receptors on cells results in activation of IFN-stimulated response elements and the transcription of IFN-sensitive genes that result in the immune and inflammatory response. IFN signaling also cross-primes DCs to promote antigen persistence, alters the antigen repertoire available for MHCI presentation, enhances MHCI presentation of antigens, and increases the overall surface expression of MHCI, MHCII, and co-stimulatory molecules CD40, CD80, and CD86. These actions result in increased priming of tumor specific CD8+ T cells and initiation of the adaptive immune response.

In some embodiments, the method of administering an EV, e.g., exosome, encapsulating a STING agonist and/or expressing a STING agonist on the surface to a subject in need thereof activates or induces dendritic cells, thereby inducing or modulating an immune or inflammatory response in the subject. In some embodiments, the dendritic cells activated are myeloid dendritic cells. In some embodiments, the dendritic cells are plasmacytoid dendritic cells.

In some embodiments, the method induces interferon (IFN)-β production. Administration of EVs, e.g., exosomes, comprising a STING agonist (e.g., encapsulated or expressed on the luminal or exterior surface) may result in between 2-fold and 10,000-fold greater IFN-β induction compared to administration of a STING agonist alone. Administration of EVs, e.g., exosomes, comprising a STING agonist (e.g., encapsulated or expressed on the surface) may result in between about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, or 9000-10,000 fold greater IFN-β induction compared to administration of a STING agonist alone. Administration of EVs, e.g., exosomes, comprising a STING agonist (e.g., encapsulated or expressed on the luminal or exterior surface) may result in greater than about 2-fold, >5 fold, >10-fold, >20-fold, >30-fold, >40-fold, >50-fold, >60-fold, >70-fold, >80-fold, >90-fold, >100-fold, >200-fold, >300-fold, >400-fold, >500-fold, >600-fold, >700-fold, >800-fold, >900-fold, >1000-fold, >2000-fold, >3000-fold, >4000-fold, >5000-fold, >6000-fold, >7000-fold, >8000-fold, >9000-fold, or >10,000-fold IFN-β induction compared to administration of a STING agonist alone. Administration of EVs, e.g., exosomes, comprising a STING agonist (e.g., encapsulated or expressed on the luminal or exterior surface) may result in between 2-fold and 10,000-fold greater IFN-β induction compared to the subject's baseline IFN-β production. Administration of EVs, e.g., exosomes, comprising a STING agonist (e.g., encapsulated or expressed on the luminal or exterior surface) may result in between about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, or 9000-10,000 fold greater IFN-β induction compared to the subject's baseline IFN-β production. Administration of EVs, e.g., exosomes, comprising a STING agonist may result in greater than about 2-fold, >5 fold, >10-fold, >20-fold, >30-fold, >40-fold, >50-fold, >60-fold, >70-fold, >80-fold, >90-fold, >100-fold, >200-fold, >300-fold, >400-fold, >500-fold, >600-fold, >700-fold, >800-fold, >900-fold, >1000-fold, >2000-fold, >3000-fold, >4000-fold, >5000-fold, >6000-fold, >7000-fold, >8000-fold, >9000-fold, or >10,000-fold IFN-β induction compared to the subject's baseline IFN-β production.

In some embodiments, administering an EV, e.g., exosome, disclosed herein to a subject can also regulate the levels of other immune modulators (e.g., cytokines or chemokines). In certain embodiments, the method disclosed herein can increase the level of IFN-γ, CXCL9, and/or CXCL10. In some embodiments, administration of EVs, e.g., exosomes, described herein (can result in between about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, or 9000-10,000 fold greater amount of IFN-γ, CXCL9, and/or CXCL10 compared to a free STING agonist.

In some embodiments, the method induces myeloid dendritic cell (mDC) activation. Administration of EVs, e.g., exosomes, comprising a STING agonist (e.g., encapsulated or expressed on the luminal or exterior surface) may result in between 2-fold and 50,000-fold greater mDC activation compared to administration of a STING agonist alone. Administration of EVs, e.g., exosomes, comprising a STING agonist (e.g., encapsulated or expressed on the luminal or exterior surface) may result in between about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold greater mDC activation compared to administration of a STING agonist alone. Administration of EVs, e.g., exosomes, comprising a STING agonist (e.g., encapsulated or expressed on the luminal or exterior surface) may result in greater than about 2-fold, >5 fold, >10-fold, >20-fold, >30-fold, >40-fold, >50-fold, >60-fold, >70-fold, >80-fold, >90-fold, >100-fold, >200-fold, >300-fold, >400-fold, >500-fold, >600-fold, >700-fold, >800-fold, >900-fold, >1000-fold, >2000-fold, >3000-fold, >4000-fold, >5000-fold, >6000-fold, >7000-fold, >8000-fold, >9000-fold, >10,000-fold, >15,000-fold, >20,000-fold, >25,000-fold, >30,000-fold, >35,000-fold, >40,000-fold, >45,000-fold, or >50,000-fold mDC activation compared to administration of a STING agonist alone.

Administration of EVs, e.g., exosomes, comprising a STING agonist (e.g., encapsulated or expressed on the luminal or exterior surface) may result in between 2-fold and 10,000-fold greater mDC activation compared to the subject's baseline mDC activation. Administration of EVs, e.g., exosomes, comprising a STING agonist (e.g., encapsulated or expressed on the luminal or exterior surface) may result in between about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold greater mDC activation compared to the subject's baseline mDC activation. Administration of EVs, e.g., exosomes, comprising a STING agonist (e.g., encapsulated or expressed on the luminal or exterior surface) may result in greater than about 2-fold, >5 fold, >10-fold, >20-fold, >30-fold, >40-fold, >50-fold, >60-fold, >70-fold, >80-fold, >90-fold, >100-fold, >200-fold, >300-fold, >400-fold, >500-fold, >600-fold, >700-fold, >800-fold, >900-fold, >1000-fold, >2000-fold, >3000-fold, >4000-fold, >5000-fold, >6000-fold, >7000-fold, >8000-fold, >9000-fold, >10,000-fold, >15,000-fold, >20,000-fold, >25,000-fold, >30, 000-fold, >35,000-fold, >40,000-fold, >45,000-fold, or >50,000-fold mDC activation compared to the subject's baseline mDC activation.

In some embodiments, the method of administering an EV, e.g., exosome, comprising a STING agonist (e.g., encapsulated or expressed on the luminal or exterior surface) does not induce monocyte activation as compared to the subject's baseline monocyte activation. In some embodiments, the administration of an EV, e.g., exosome, comprising a STING agonist (e.g., encapsulated or expressed on the luminal or exterior surface) results in less than less than about 2-fold, <5 fold, <10-fold, <20-fold, <30-fold, <40-fold, <50-fold, <60-fold, <70-fold, <80-fold, <90-fold, <100-fold, <200-fold, <300-fold, <400-fold, <500-fold, <600-fold, <700-fold, <800-fold, <900-fold, <1000-fold, <2000-fold, <3000-fold, <4000-fold, <5000-fold, <6000-fold, <7000-fold, <8000-fold, <9000-fold, <10,000-fold, <15,000-fold, <20,000-fold, <25,000-fold, <30,000-fold, <35,000-fold, <40,000-fold, <45,000-fold, <50,000-fold, <55,000-fold, <60,000-fold, <65,000-fold, <70,000-fold, <75,000-fold, <80,000-fold, <85,000-fold, <90,000-fold, <95,000-fold, <100,000-fold, <200,000-fold, <300,000-fold, <400,000-fold, <500,000-fold, <600,000-fold, <700,000-fold, <800,000-fold, <900,000-fold, or <1,000,000-fold induction of monocyte activation relative to the subject's baseline monocyte activation. In some embodiments, the administration of an EV, e.g., exosome, comprising a STING agonist (e.g., encapsulated or expressed on the luminal or exterior surface) to a subject results in less than about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, 45,000-50,000 fold, 55,000-60,000 fold, 60,000-65,000 fold, 65,000-70,000 fold, 70,000-75,000 fold, 75,000-80,000 fold, 80,000-85,000 fold, 85,000-90,000 fold, 90,000-95,000 fold, 95,000-100,000 fold, 100,000-200,000 fold, 200,000-300,000 fold, 300,000-400,000 fold, 400,000-500,000 fold, 500,000-600,000 fold, 600,000-700,000 fold, 700,000-800,000 fold, 800,000-900,000 fold, or 900,000-1,000,000 fold induction of monocyte activation relative to the subject's baseline monocyte activation.

In some embodiments, the method of administering an EV, e.g., exosome, comprising a STING agonist (e.g., encapsulated or expressed on the luminal or exterior surface) to a subject does not induce monocyte activation as compared to administration of the STING agonist alone. In some embodiments, the administration of an EV, e.g., exosome, comprising a STING agonist (e.g., encapsulated or expressed on the luminal or exterior surface) results in less than less than about 2-fold, <5 fold, <10-fold, <20-fold, <30-fold, <40-fold, <50-fold, <60-fold, <70-fold, <80-fold, <90-fold, <100-fold, <200-fold, <300-fold, <400-fold, <500-fold, <600-fold, <700-fold, <800-fold, <900-fold, <1000-fold, <2000-fold, <3000-fold, <4000-fold, <5000-fold, <6000-fold, <7000-fold, <8000-fold, <9000-fold, <10,000-fold, <15,000-fold, <20,000-fold, <25,000-fold, <30,000-fold, <35,000-fold, <40,000-fold, <45,000-fold, or <50,000-fold induction of monocyte activation relative to the amount of monocyte activation after administration of the free STING agonist. In some embodiments, the administration of an EV, e.g., exosome, comprising a STING agonist (e.g., encapsulated or expressed on the luminal or exterior surface) to a subject results in less than about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold induction of monocyte activation relative to the amount of monocyte activation after administration of the free STING agonist. Monocyte activation may be measured by the surface expression of CD86 on the monocyte, or by any other appropriate monocyte activation marker known in the art.

Because of the improved therapeutic effects associated with EVs, e.g., exosomes, described herein, in some embodiments, lower dosages of the EV, e.g., exosome, comprising a STING agonist (e.g., encapsulated or expressed on the luminal or exterior surface) can be delivered compared to the free STING agonist. Moreover, non-selective delivery of high doses of STING agonists can attenuate desirable immune stimulatory responses. Accordingly, because the EVs, e.g., exosomes, described herein can be administered at lower doses, in some embodiments, they can operate in a wider therapeutic window and reduce the liabilities (e.g., systemic toxicity, immune cell killing, lack of cell selectivity) observed with free STING agonists.

The compositions described herein may be administered in a dosage sufficient to ameliorate the disease, disorder, condition, or symptom of the subject in need thereof. In some embodiments, the dosage of the EV, e.g., exosome, comprising a STING agonist administered to a subject in need is between about 0.01 to 0.1 μM, 0.1 to 1 μM, 1 to 10 μM, 10 to 100 μM, or 100 to 1000 μM. In certain embodiments, the dosage of the EV, e.g., exosome, comprising a STING agonist administered to a subject in need is about 0.01 μM, 0.05 μM, 0.1 μM, 0.2 μM, 0.3 μM, 0.4 μM, 0.5 μM, 0.6 μM, 0.7 μM, 0.8 μM, 0.9 μM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 40 μM, 55 μM, 60 μM, 65 μM, 70 μM, 75 μM, 80 μM, 85 μM, 90 μM, 95 μM, 100 μM, 150 μM, 200 μM, 250 μM, 300 μM, 350 μM, 400 μM, 450 μM, 500 μM, 550 μM, 600 μM, 650 μM, 700 μM, 750 μM, 800 μM, 850 μM, 900 μM, 950 μM, or 1000 μM.

In some embodiments, the amount of the EV, e.g., exosome, comprising a STING agonist (e.g., encapsulated or expressed on the luminal or exterior surface) administered to a subject in need is less than 2-fold, <5 fold, <10-fold, <20-fold, <30-fold, <40-fold, <50-fold, <60-fold, <70-fold, <80-fold, <90-fold, <100-fold, <200-fold, <300-fold, <400-fold, <500-fold, <600-fold, <700-fold, <800-fold, <900-fold, <1000-fold, <2000-fold, <3000-fold, <4000-fold, <5000-fold, <6000-fold, <7000-fold, <8000-fold, <9000-fold, <10,000-fold, <15,000-fold, <20,000-fold, <25,000-fold, <30,000-fold, <35,000-fold, <40,000-fold, <45,000-fold, or <50,000-fold relative to the amount of a free STING agonist required to effect the same ameliorative results in a subject in need. In some embodiments, the amount of the EV, e.g., exosome, comprising a STING agonist (e.g., encapsulated or expressed on the luminal or exterior surface) administered to a subject in need is between less than about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold less relative to the amount of a free STING agonist required to effect the same ameliorative results in a subject in need.

In some embodiments, the method of administering an EV, e.g., exosome, comprising a STING agonist does not induce systemic inflammation as compared to the subject's baseline systemic inflammation. In some embodiments, the administration of an EV, e.g., exosome, comprising a STING agonist results in less than less than about 2-fold, <5 fold, <10-fold, <20-fold, <30-fold, <40-fold, <50-fold, <60-fold, <70-fold, <80-fold, <90-fold, <100-fold, <200-fold, <300-fold, <400-fold, <500-fold, <600-fold, <700-fold, <800-fold, <900-fold, <1000-fold, <2000-fold, <3000-fold, <4000-fold, <5000-fold, <6000-fold, <7000-fold, <8000-fold, <9000-fold, <10,000-fold, <15,000-fold, <20,000-fold, <25,000-fold, <30,000-fold, <35,000-fold, <40,000-fold, <45,000-fold, or <50,000-fold induction of systemic inflammation relative to the subject's baseline systemic inflammation. In some embodiments, the administration of an EV, e.g., exosome, comprising a STING agonist to a subject results in less than about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold induction of systemic inflammation relative to the subject's baseline systemic inflammation.

In some embodiments, the method of administering an EV, e.g., exosome, comprising a STING agonist (e.g., encapsulated or expressed on the luminal or exterior surface) to a subject does not induce systemic inflammation as compared to administration of the STING agonist alone. In some embodiments, the administration of an EV, e.g., exosome, comprising a STING agonist (e.g., encapsulated or expressed on the luminal or exterior surface) results in less than less than about 2-fold, <5 fold, <10-fold, <20-fold, <30-fold, <40-fold, <50-fold, <60-fold, <70-fold, <80-fold, <90-fold, <100-fold, <200-fold, <300-fold, <400-fold, <500-fold, <600-fold, <700-fold, <800-fold, <900-fold, <1000-fold, <2000-fold, <3000-fold, <4000-fold, <5000-fold, <6000-fold, <7000-fold, <8000-fold, <9000-fold, <10,000-fold, <15,000-fold, <20,000-fold, <25,000-fold, <30,000-fold, <35,000-fold, <40,000-fold, <45,000-fold, or <50,000-fold induction of systemic inflammation relative to the amount of systemic inflammation after administration of the free STING agonist. In some embodiments, the administration of an EV, e.g., exosome, comprising a STING agonist (e.g., encapsulated or expressed on the luminal or exterior surface) to subject results in less than about 2-5 fold, 5-10 fold, 10-20 fold, 20-30 fold, 30-40 fold, 40-50 fold, 50-60 fold, 60-70 fold, 70-80 fold, 80-90 fold, 90-100 fold, 100-200 fold, 200-300 fold, 300-400 fold, 400-500 fold, 500-600 fold, 600-700 fold, 700-800 fold, 800-900 fold, 900-1000 fold, 1000-2000 fold, 2000-3000 fold, 3000-4000 fold, 4000-5000 fold, 5000-6000 fold, 6000-7000 fold, 7000-8000 fold, 8000-9000 fold, 9000-10,000 fold, 10,000-15,000 fold, 15,000-20,000 fold, 20,000-25,000 fold, 25,000-30,000 fold, 30,000-35,000 fold, 35,000-40,000 fold, 40,000-45,000 fold, or 45,000-50,000 fold induction of systemic inflammation relative to the amount of systemic inflammation after administration of the free STING agonist. Systemic inflammation may be quantified or measured by any appropriate method known in the art.

In some embodiments, the method of administering an EV, e.g., exosome, comprising a STING agonist (e.g., encapsulated or expressed on the luminal or exterior surface) to a subject additionally comprises administering an additional therapeutic agent. In some embodiments, the additional therapeutic agent is an immunomodulating agent. In some embodiments, the immunomodulating component is an inhibitor for a negative checkpoint regulator or an inhibitor for a binding partner of a negative checkpoint regulator. In some of these embodiments, the negative checkpoint regulator is selected from the group consisting of: cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, and CD73. In various embodiments, the additional therapeutic agent is an antibody or antigen-binding fragment thereof. In some embodiments, the antibody or antigen-binding fragment thereof is one or more whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)2, Fab, Fab', and F(ab')2, F(ab1)2, Fv, dAb, and Fd fragments, diabodies, and antibody-related polypeptides. The term antibody includes bispecific antibodies and multispecific antibodies so long as they exhibit the desired biological activity or function. In some embodiments, the additional therapeutic agent is a therapeutic antibody or antigen-binding fragment thereof that is an inhibitor of CTLA-4, PD-1, PD-L1, PD-L2, TIM-3, or LAG3.

In some embodiments, the additional therapeutic agent is an agent that prevents or treats T cell exhaustion. Such agents may increase, decrease, or modulate the expression of genes associated with T cell exhaustion, including Prdm1, Bhlhe40, Irf4, Ikzj2, Zeb2, Lass6, Egr2, Tox, Eomes, Nfatc1, Nfatc2, Zbtb32, Rbpj, Hif1a, Lag3, Tnfrsf9, Ptger2, Havcr2, Alcam, Tigit, Ctla4, Ptger4, Tnfrsflb, Ccl4, CD109, CD200, Tnfsf9, Nrpl, Sema4c, Ptprj, Il21, Tspan2, Rgs16, Sh2d2a, Nucb1, Plscr1, Ptpn11, Prkca, Plscr4, Casp3, Gpd2, Gas2, Sh3rf1, Nhedc2, Plek, Tnfaip2, and Ctsb, or any combination thereof. Therapeutic agents may also increase, decrease, or modulate a protein associated with T cell exhaustion, including NFAT-1 or NFAT-2.

V.B. Method of Treating Cancer

Provided herein are methods of treating cancer in a subject. The method comprises administering to the subject a therapeutically effective amount of the compositions disclosed herein, wherein the composition is capable of up-regulating a STING-mediated immune response in the subject, thereby enhancing the tumor targeting of the subject's immune system. In some embodiments, the composition is administered intra-tumorally to the subject. In some embodiments, the composition is administered parenterally, orally, intravenously, intramuscularly, intraperitoneally, or via any other appropriate administration route.

Also provided herein are methods of preventing metastasis of cancer in a subject. The method comprises administering to the subject a therapeutically effective amount of the compositions disclosed herein, wherein the composition is capable of preventing one or more tumors at one location in the subject from promoting the growth of one or more tumors at another location in the subject. In some embodiments, the composition is administered intratumorally in a first tumor in one location, and the composition administered in a first tumor prevents metastasis of one or more tumors at a second location.

In some embodiments, administering an EV, e.g., exosome, disclosed herein inhibits and/or reduces tumor growth in a subject. In some embodiments, the tumor growth (e.g., tumor volume or weight) is reduced by at least about 5%, at least about 10%, at least about 20%, at least about 30%, at least about 40%, at least about 50%, at least about 60%, at least about 70%, at least about 80%, at least about 90%, or about 100% compared to a reference (e.g., tumor volume in a corresponding subject after administration of free STING agonist or an EV, e.g., exosome, without the STING agonist).

In some embodiments, the cancer being treated is characterized by infiltration of leukocytes (T-cells, B-cells, macrophages, dendritic cells, monocytes) into the tumor microenvironment, or so-called "hot tumors" or "inflammatory tumors". In some embodiments, the cancer being treated is characterized by low levels or undetectable levels of leukocyte infiltration into the tumor microenvironment, or so-called "cold tumors" or "non-inflammatory tumors". In some embodiments, an EV, e.g., exosome, is administered in an amount and for a time sufficient to convert a "cold tumor" into a "hot tumor", i.e., said administering results in the infiltration of leukocytes (such as T-cells) into the tumor microenvironment. In certain embodiments, cancer comprises bladder cancer, cervical cancer, renal cell cancer, testicular cancer, colorectal cancer, lung cancer, head and neck cancer, and ovarian, lymphoma, liver cancer, glioblastoma, melanoma, myeloma, leukemia, pancreatic cancers, or combinations thereof. The term "distal tumor" or "distant tumor" as used herein refers to a tumor that has spread from the original (or primary) tumor to distant organs or distant tissues, e.g., lymph nodes. In some embodiments, the EVs, e.g., exosomes, of the disclosure treats a tumor after the metastatic spread.

Non-limiting examples of cancers (or tumors) that can be treated with methods disclosed herein include squamous cell carcinoma, small-cell lung cancer (SCLC), non-small cell lung cancer, squamous non-small cell lung cancer (NSCLC), nonsquamous NSCLC, gastrointestinal cancer, renal cancer (e.g., clear cell carcinoma), ovarian cancer, liver cancer (e.g., hepatocellular carcinoma), colorectal cancer, endometrial cancer, kidney cancer (e.g., renal cell carcinoma (RCC)), prostate cancer (e.g., hormone refractory prostate adenocarcinoma), thyroid cancer, pancreatic cancer, cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus (e.g., gastroesophageal junction cancer), cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, tumor angiogenesis, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., $Ki1^{+}$) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, and any combinations thereof.

In some embodiments, a cancer (or tumor) that can be treated comprises a breast cancer, head and neck cancer, uterine cancer, brain cancer, skin cancer, renal cancer, lung cancer, colorectal cancer, prostate cancer, liver cancer, bladder cancer, kidney cancer, peritoneal cancer, pancreatic cancer, thyroid cancer, esophageal cancer, eye cancer, stomach (gastric) cancer, gastrointestinal cancer, carcinoma, sarcoma, leukemia, lymphoma, myeloma, or a combination thereof. In certain embodiments, a cancer that can be treated with the present disclosure is a pancreatic cancer and/or a peritoneal cancer.

In some embodiments, the methods described herein can also be used for treatment of metastatic cancers, unresectable, refractory cancers (e.g., cancers refractory to previous cancer therapy), and/or recurrent cancers.

In some embodiments, EVs, e.g., exosomes, disclosed herein can be used in combination with one or more additional anti-cancer and/or immunomodulating agents. Such agents can include, for example, chemotherapy drugs, small molecule drugs, or antibodies that stimulate the immune response to a given cancer. In some embodiments, the methods described herein are used in combination with a standard of care treatment (e.g., surgery, radiation, and chemotherapy).

In some embodiments, a method for treating a cancer disclosed herein can comprise administering an EV, e.g., exosome, comprising a STING agonist (e.g., encapsulated or expressed on the luminal or exterior surface) with one or more immuno-oncology agents, such that multiple elements of the immune pathway can be targeted. Non-limiting of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

In some embodiments, an immuno-oncology agent that can be used in combination with EVs, e.g., exosomes, disclosed herein comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof.

In some embodiments, an immuno-oncology agent comprises an immune checkpoint activator (i.e., promotes signaling through the particular immune checkpoint pathway). In certain embodiments, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), or any combination thereof.

In some embodiments, a combination of an EV, e.g., exosome, disclosed herein and a second agent discussed herein (e.g., immune checkpoint inhibitor) can be administered concurrently as a single composition in a pharmaceutically acceptable carrier. In other embodiments, a combination of an EV, e.g., exosome, and a second agent discussed herein (e.g., immune checkpoint inhibitor) can be administered concurrently as separate compositions. In further embodiments, a combination of an EV, e.g., exosome, and a second agent discussed herein (e.g., immune checkpoint inhibitor) can be administered sequentially. In some embodiments, an EV, e.g., exosome, is administered prior to the administration of a second agent (e.g., immune checkpoint inhibitor).

V.C. Pharmaceutical Compositions

Provided herein are pharmaceutical compositions comprising EVs, e.g., exosomes, that are suitable for administration to a subject. The pharmaceutical compositions generally comprise a plurality of EVs, e.g., exosomes, comprising a STING agonist (e.g., encapsulated or expressed on the luminal or exterior surface) and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of EVs, e.g., exosomes. (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration.

In some embodiments, the pharmaceutical composition comprises one or more STING agonist and the EVs, e.g., exosomes, described herein.

Pharmaceutically-acceptable excipients include excipients that are generally safe (GRAS), non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the EVs, e.g., exosomes, described herein, use thereof in the compositions is contemplated. Supplementary therapeutic agents may also be incorporated into the compositions. Typically, a pharmaceutical composition is formulated to be compatible with its intended route of administration. The EVs, e.g., exosomes, can be administered by intratumoral, parenteral, topical, intravenous, oral, subcutaneous, intraarterial, intradermal, transdermal, rectal, intracranial, intraperitoneal, intranasal; intramuscular route or as inhalants. In one embodiment, the pharmaceutical composition comprising EVs, e.g., exosomes, is administered intravenously, e.g. by injection. The EVs, e.g., exosomes, can optionally be administered in combination with other therapeutic agents that are at least partly effective in treating the disease, disorder or condition for which the EVs, e.g., exosomes, are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the EVs, e.g., exosomes, in an effective amount and in an appropriate solvent with one or a combination of ingredients enumerated herein, as desired. Generally, dispersions are prepared by incorporating the EVs, e.g., exosomes, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The EVs, e.g., exosomes, can be administered in the form of a depot injection or implant preparation which can be formulated in such a manner to permit a sustained or pulsatile release of the EVs, e.g., exosomes.

Systemic administration of compositions comprising EVs, e.g., exosomes, can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified EVs, e.g., exosomes, are formulated into ointments, salves, gels, or creams as generally known in the art.

This PCT application claims the priority benefit of U.S. Provisional Application Nos. 62/647,491, filed Mar. 23, 2018; 62/680,501, filed Jun. 4, 2018; 62/688,600, filed Jun. 22, 2018; and 62/756,247, filed Nov. 6, 2018, each of which is incorporated herein by reference in its entirety.

EXAMPLES

The following examples are provided for illustrative purposes only, and are not to be construed as limiting the scope or content of the invention in any way. The practice of the current invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); Green & Sambrook et al., Molecular Cloning: A Laboratory Manual, 4th Edition (Cold Spring Harbor Laboratory Press, 2012); Colowick & Kaplan, Methods In Enzymology (Academic Press); Remington: The Science and Practice of Pharmacy, 22nd Edition (Pharmaceutical Press, 2012); Sundberg & Carey, Advanced Organic Chemistry: Parts A and B, 5th Edition (Springer, 2007).

Methods

Exosome Purification

HEK293SF cells were grown to high density in chemically defined medium for 7 days. Conditioned cell culture media was collected and centrifuged at 300-800×g for 5 minutes at room temperature to remove cells and large debris. Media supernatant was then supplemented with 1000 U/L BENZONASE® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and any residual media was aspirated from the bottom of the tube. The pellet was resuspended in 200-1000 μL PBS (—Ca—Mg).

To further enrich exosome populations, the pellet was processed via density gradient purification (sucrose or OPTIPREP™). For sucrose gradient purification, the exosome pellet was layered on top of a sucrose gradient as defined in Table 3 below.

TABLE 3

| WORKING PERCENTAGE (%) | 65% STOCK VOL. (ML) | MILLI-Q VOL. (ML) |
|---|---|---|
| 50 | 3.85 | 1.15 |
| 40 | 3.08 | 1.92 |
| 25 | 1.92 | 3.08 |
| 10 | 0.46 | 2.54 |

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 μL) and stored at 4° C.

For OPTIPREP™ gradient, a 3-tier sterile gradient is prepared with equal volumes of 10%, 30%, and 45% OPTIPREP™ in a 12 mL Ultra-Clear (344059) tube for a SW 41 Ti rotor. The pellet was added to the OPTIPREP™ gradient and ultracentrifuged at 200,000×g for 16 hours at 4° C. to separate the exosome fraction. The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 μL) and store at 4° C.

In Vivo Intratumoral Microinjection Studies with CIVO®

Tumor Cell Culture

A20 cells (ATCC Lot #70006082) were cultured in RPMI 1640 with L-Glutamine (ThermoFisher), 10% fetal bovine serum (Thermofisher) and 50 nanomolar BME at 37 degrees Celsius, 5% $CO_2$. IMPACT III testing (IDEXX Bioresearch) was carried out to confirm mycoplasma- and pathogen-free status. Cells were expanded and cryopreserved following 2-3 passages after obtaining from vendor. After thawing, cells were maintained for a maximum of 8 weeks by sub-culturing 3 times a week and replenished from a fresh frozen stock thereafter.

In Vivo Studies

All experiments in mice were approved by IACUC Board of Presage Biosciences, Seattle, WA (Protocol number PR-001) and were performed at Presage in accordance with relevant guidelines and regulations. All relevant procedures were performed under anesthesia and all efforts were made to minimize pain and suffering. Female BALB/cAnNHsd mice (Envigo) with an average weight of 18 gm were used for experiments at 5-7 weeks of age. For generating A20 allografts, mice were inoculated with 1 million A20 cells in 100 μl inoculation volume.

CIVO® Intra-Tumoral Microinjections

CIVO intra-tumoral microinjections were performed as described in Klinghoffer et al. (2016) Science Translational Medicine. Briefly, mice (n=6 per time point, 4 and 24 hours) were enrolled in microinjection studies when implanted tumors reached the following approximate dimensions: 14 mm (length), 10 mm (width) and 7 mm (depth). The CIVO device was configured with 6 thirty-gauge injection needles with a total volume delivery of 2.0 μl. Presage's fluorescent tracking marker (FTM, 5% by volume) was added to the injection contents for spatial orientation. Agents microinjected were as follows: control PTGFRN++ GFP exosomes, ML RR-S2 CDA loaded PTGFRN++ GFP Exosomes, ML RR-S2 CDA loaded PTGFRN++ GFP Desialylated exosomes, ML RR-S2 CDA loaded native exosomes, all at 10 ng/μl ML RR-S2 CDA such that the total amount delivered was 20 ng. Free ML RR-S2 CDA was microinjected at both 20 ng and 2 μg. At 4 and 24 hours following CIVO microinjections, mice were euthanized using $CO_2$ inhalation for biomarker analyses.

Histology, Immunohistochemistry and In Situ Hybridization

Resected tumors were cut into 2 mm thick sections perpendicular to the injection columns, fixed in 10% buffered formalin for 48 hours. UV imaging was used to confirm CIVO microinjections based on signal from the FTM injected at each CIVO site. 2 mm-thick tissue sections were then processed for standard paraffin embedding. 4 μm thick sections were for used for all histological assays as described below. Hematoxylin-Eosin (H&E) staining was performed using standard methods.

Immunohistochemistry

Formalin-fixed, paraffin embedded tumors were cut onto slides with a thickness of 4 μm. Slides were baked for 1 hour at 60° C., deparaffinized in xylene, and rehydrated via graded alcohols.

Slides underwent a 20-minute target retrieval solution incubation at 100° C., followed by a 20-minute cool down to room temperature. Serum Block (5% Normal Goat Serum in TBST) was performed for 1 hr at room temperature. Primary antibody staining was carried out with appropriate primary antibody in 5% NGS TBS diluent overnight at room temperature. Corresponding isotype controls were included in each batch. Secondary antibody staining was carried out with appropriate secondary antibody in 5% NGS TBS diluent overnight at room temperature. The slides were counterstained with DAPI for 10 minutes and coverslipped with Prolong Gold mounting medium (Invitrogen). Stained slides were imaged using a digital, automated, high resolution scanner.

In situ hybridization was completed using the RNAscope multiplex fluorescent reagent kit v2 (Advanced Cell Diagnostics). Formalin-fixed, paraffin embedded tumors were cut onto slides with a thickness of 4 μm. Slides were baked for 1 hour at 60° C., deparaffinized in xylene, and rehydrated via graded alcohols. Hydrogen peroxide was added for 10 minutes to quench endogenous peroxidase activity. Slides underwent a 15-minute target retrieval solution incubation at 100° C., followed by a 15-minute protease digestion at 40° C. The RNAscope ISH assay was completed with a mouse Ifnb1 probe (Advanced Cell Diagnostics) and TSA Plus Cyanine 5 detection (Perkin Elmer). The slides were counterstained with DAPI for 10 minutes and coverslipped with Prolong Gold mounting medium (Invitrogen). Stained slides were imaged using a digital, automated, high resolution scanner.

Whole-Slide Scanning and Image Analysis

Images of every cell from each tissue section stained were captured by digital, automated, high-resolution whole-tissue scanning (3D Histech Panoramic 250 Flash). Tumor responses were quantified from image files from each tissue section using Presage's custom CIVO Analyzer image analysis platform. Whole-tissue section images captured by the slide scanners were automatically processed by CIVO Analyzer. Each cell from each tissue section was segmented based on the nuclear (DAPI) signal and classified as biomarker-negative or -positive using Cell Profiler (Broad Institute). Following cellular segmentation and classification, circular regions of interest (ROI) were localized around each microinjection site in each image around the FTM at each position, with the largest ROI no greater than 2000 μm in radius. In order to mitigate the influence of pre-existing necrosis on biomarker measurements, injection sites that fall within largely acellular tumor regions are excluded prior to quantitative analysis.

Example 1: Exosome-Encapsulated STING Agonists

Figure 1:
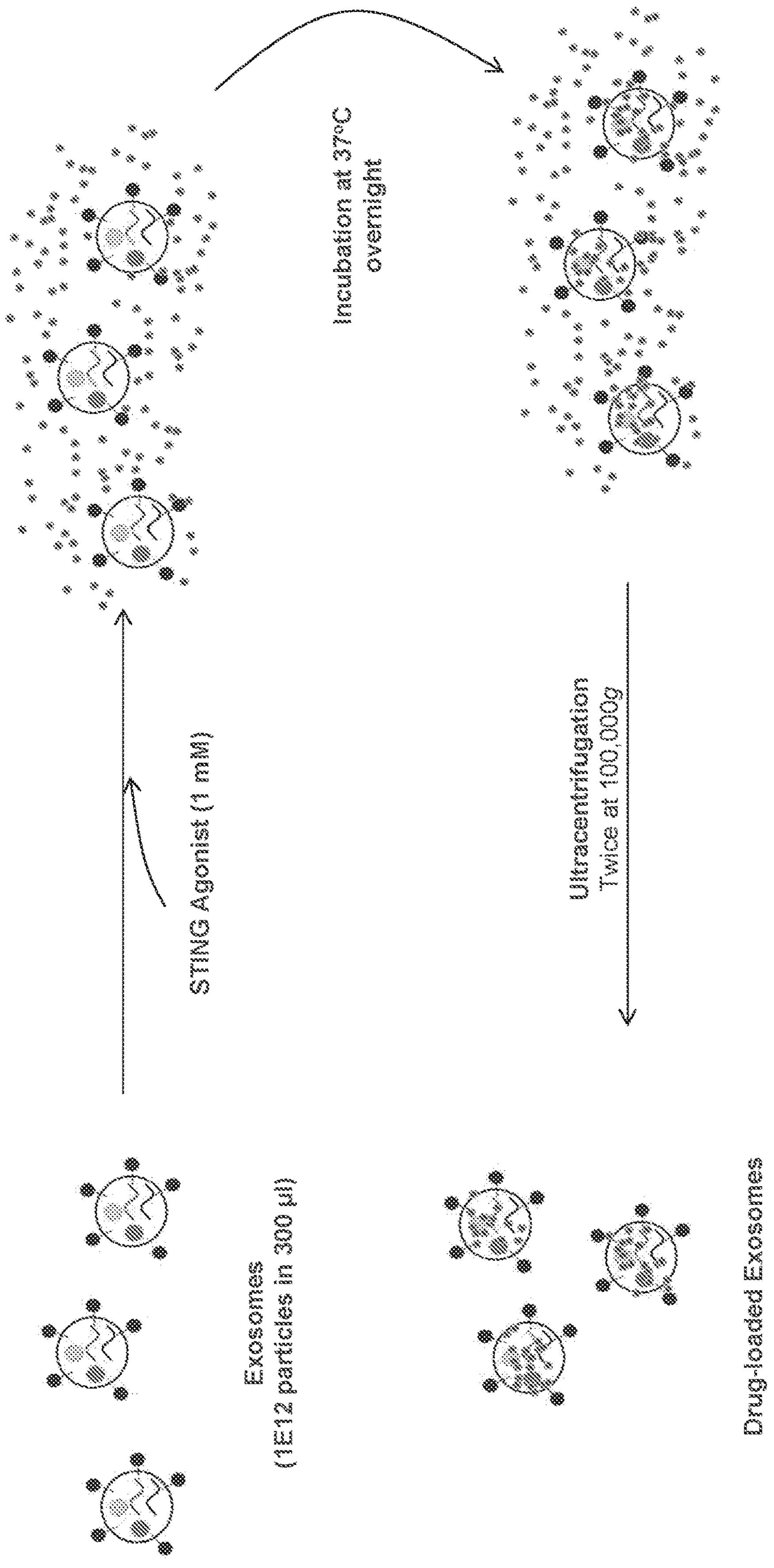
FIG. 1 shows a diagram of the method of loading exosomes with a STING agonist.

Encapsulation of STING Agonist 1 mM STING agonist including ML RR-S2 CDA ammonium salt (MedChem Express, Cat. No. HY-12885B) and (3-3 cAIMPdFSH; InvivoGen, Cat. No. tlrl-nacairs) was incubated with purified exosomes (1E12 total particles) in 300 ul of PBS at 37° C. overnight. The mixture was then washed twice in PBS and purified by ultra-centrifugation at 100,000×g (FIG. 1).

Quantification of the Cyclic Dinucleotide STING Agonist

Sample Preparation for LC-MS Analysis

All samples were received in either phosphate-buffered saline (PBS) buffer or PBS and 5% sucrose. Prior to analysis, the particle concentration (P/mL) was measured by Nanoparticle Tracking Analysis (NTA) on the NanoSight NS300. All standards and samples were prepared such that each injection contained a virtually identical number of particles. This was achieved through a combination of diluting samples and spiking exosomes into standards to reach a final concentration of 1.0-4.0E+11 P/mL, depending on the initial particle concentrations of the samples.

Standard curves were prepared by spiking a known concentration of STING agonist into PBS buffer, then preparing additional standards through serial dilution. Separate standards were typically prepared such that the final concentrations (after all sample preparation steps) were 25, 50, 250, 500, 1250, 2500, and 5000 nM STING agonist. First, 75.0 μL of each appropriately diluted sample and each matrix-matched standard was prepared in a separate 1.5 mL microcentrifuge tube. Next, 25.0 μL of exosome lysis buffer (60 mM Tris, 400 mM GdmCl, 100 mM EDTA, 20 mM TCEP, 1.0% Triton X-100) was added to each tube, then all tubes were vortexed to mix and briefly centrifuged to settle. Finally, 1.0 μL of concentrated Proteinase K enzyme solution (Dako, reference S3004) was added to each tube, and again all tubes were vortexed and then briefly centrifuged, followed by incubation at 55° C. for 60 minutes. Prior to injection on the LC-MS, samples were allowed to cool to room temperature and were transferred to HPLC vials.

LC-MS Analysis 20.0 μL of standards and samples were injected neat into an UltiMate 3000 RSCLnano (Thermo Fisher Scientific) low flow chromatography system without cleanup. Separation of analytes was performed using a Phenomenex Kinetex EVO C18 core-shell analytical column (50×2.1 mm, 2.6 μm particle size, 100 Å pore size) and the loading pumps delivering a gradient of mobile phase A (MPA: water, 0.1% formic acid) and mobile phase B (MPB: acetonitrile, 0.1% formic acid) at a flowrate of 500 μL/min. The gradient began at 2% MPB, which was held for 2 minutes to load and desalt the STING agonist analyte. The percentage MPB then increased from 2-30% over 3 minutes to elute the STING agonist analyte. The percentage MPB then increased from 30-95% over 1 minute, held at 95% for 3 minutes, decreased from 95-2% over 1 minute, and then held at 2% for another 3 minutes to re-equilibrate the column. The total runtime for the method was 13 minutes, and LC flow was only directed into the MS between 2.5-4.5 minutes. Typical carry-over was less than 0.05% of the peak area of the previous injection, therefore blank injections were not performed between analytical injections.

Mass analyses were performed with a Q Exactive Basic (Thermo Fisher Scientific) mass spectrometer with the Ion Max source and a HESI-II probe operating in negative ion mode, and mass spectra were collected using Full MS-SIM mode scanning from 500-800 Da with an AGC target of 1E+6 ions, a maximum injection time of 200 ms, and a resolution of 35,000. STING agonist quantitation was performed using the monoisotopic-1 STING agonist peak by selectively extracting all ions within the m/z range from 688.97-689.13 Da, and then integrating the resulting peak at a retention time between 3.80-3.90 minutes. The concentration of STING agonist in a given sample was determined by comparing the STING agonist peak area in that sample to STING agonist peak areas generated by standards, which is typical of relative quantitation.

Example 2: Increased Potency of STING Agonist Loaded in Exosomes

Figure 2:
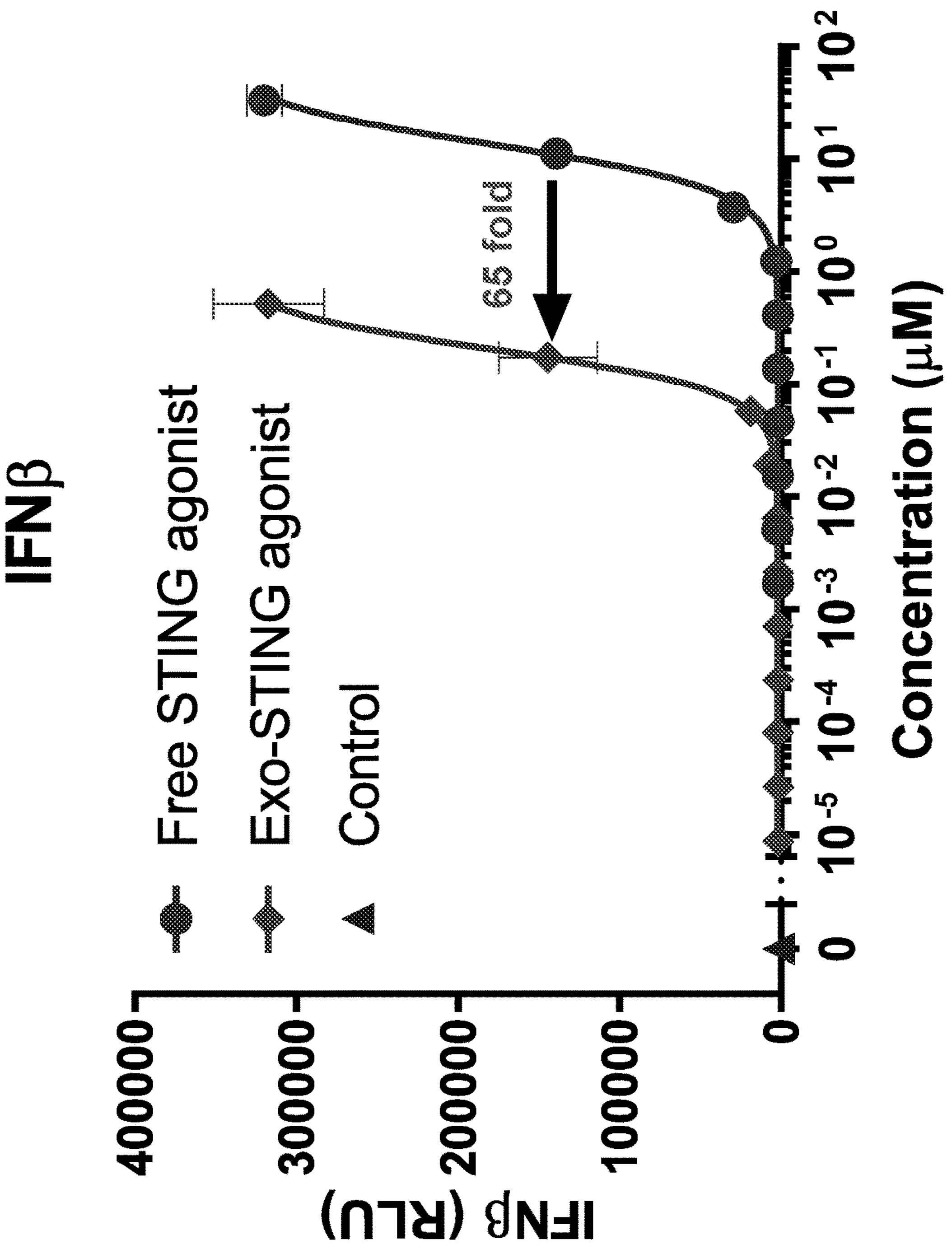
FIG. 2 shows a comparison of the IFNβ response in peripheral blood mononuclear cells (PBMCs) treated with exosome-encapsulated STING agonist and free STING agonist, as determined by relative luminescence (RLU).
Figure 3:
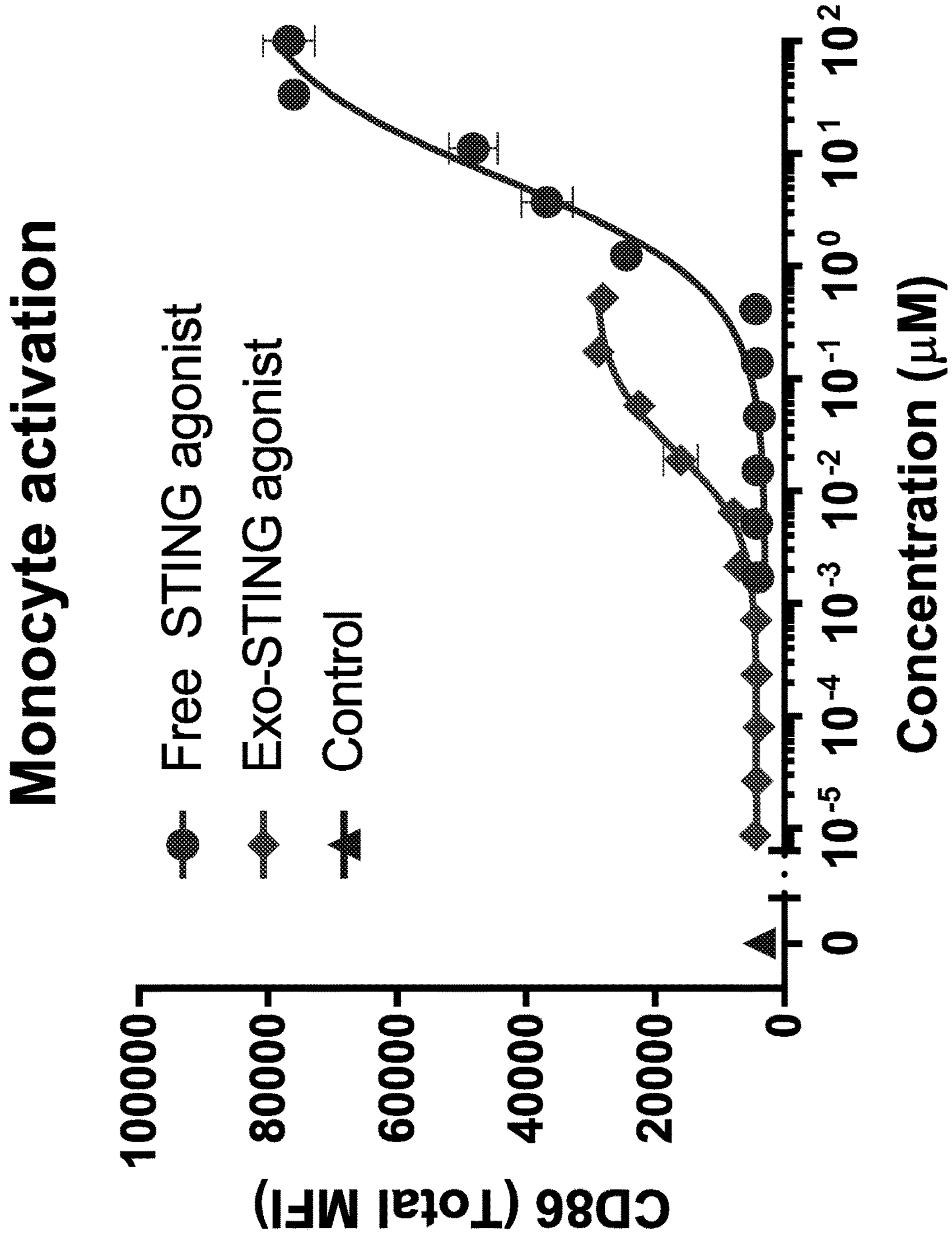
FIG. 3 shows comparison of the monocyte activation in cells treated with exosome-encapsulated STING agonist and free STING agonist, as determined by CD86 mean fluorescence intensity (MFI).
Figure 4:
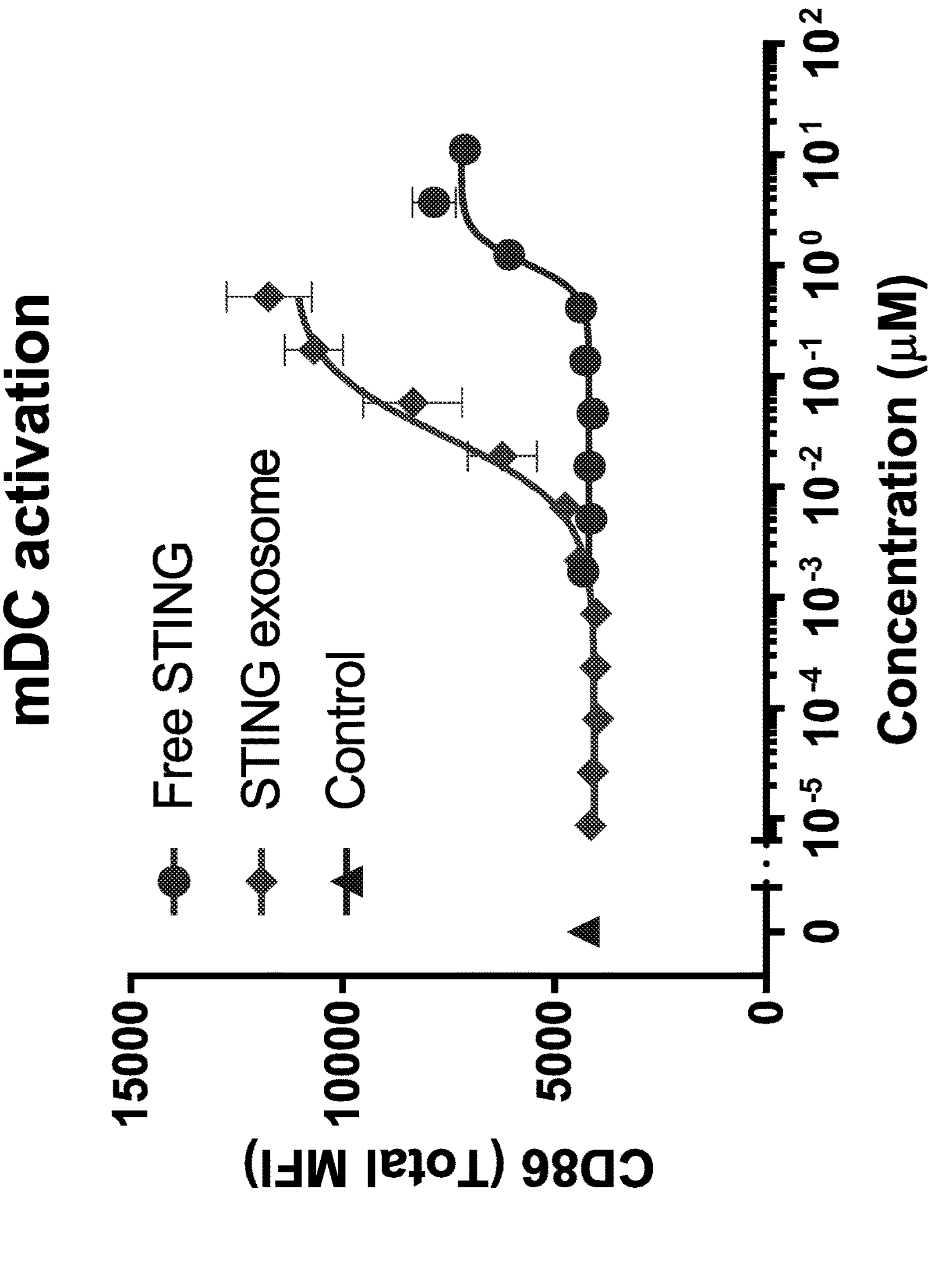
FIG. 4 shows comparison of the mDC activation in cells treated with exosome-encapsulated STING agonist and free STING agonist, as determined by CD86 mean fluorescence intensity (MFI).
Figure 5A:
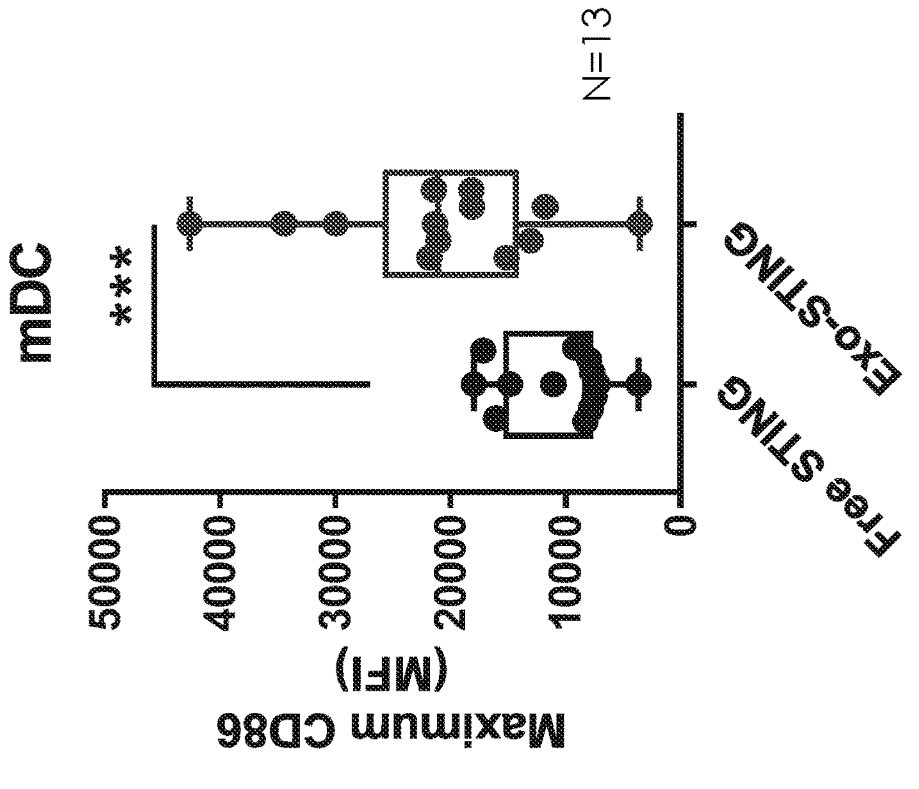
FIG. 5A shows mDC activation in samples treated with exosome-encapsulated STING agonist (Exo-STING) or free STING agonist, as determined by CD86 staining
Figure 5B:
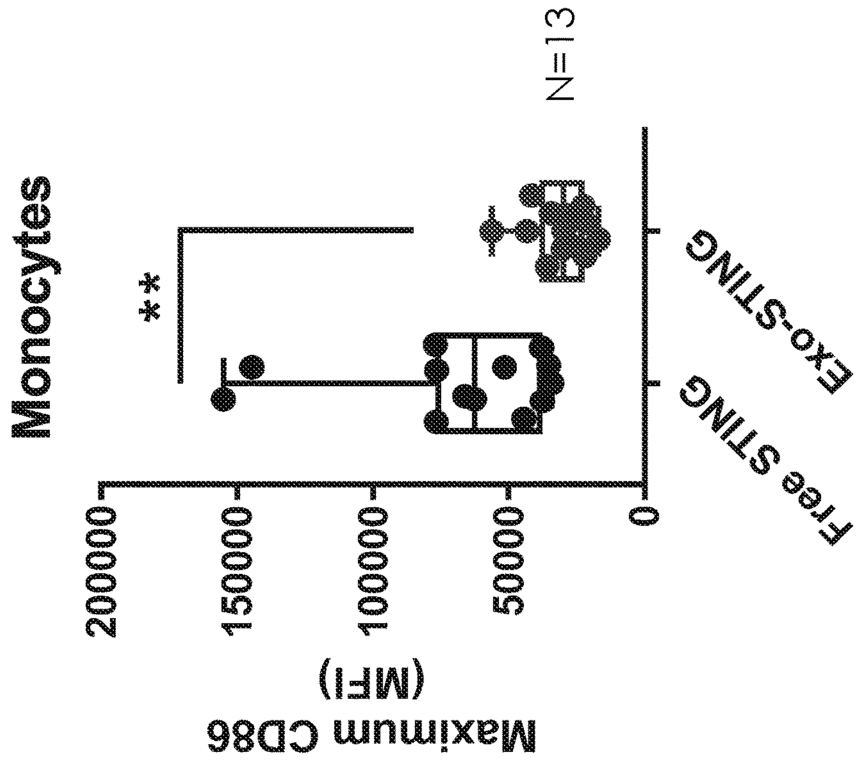
FIG. 5B shows monocyte activation in samples treated with exosome-encapsulated STING agonist (Exo-STING) or free STING agonist, as determined by CD86 staining.

Exosome-encapsulated STING agonist and free STING agonist were tested for activity in human peripheral blood mononuclear cells (PBMCs). PBMCs were isolated from fresh human blood by centrifugation over a layer of Lymphoprep at 1000×g for 15 minutes. The resulting buffy coat was washed in PBS and counted. PBMCs were plated in 96-well U-bottom plates. Titrations of the exosome-encapsulated (Exo-STING agonist) or free STING agonist were prepared in a separate U-bottom plate to perform dose-response studies. The exosome-encapsulated or free STING agonist was added to the PBMCs and incubated at 37° C. overnight. General activation of PBMCs by the STING agonist was detected by measuring the amount of IFNβ in the supernatant. As shown in FIG. 2, both free STING agonist and Exo-STING agonist induced maximal IFNβ to a similar extent. Interestingly, the $EC_{50}$ of Exo-STING agonist was ~65-fold lower than for free STING agonist, suggesting that exosomes may increase the potency of STING agonist activity. To understand which cell types in PBMCs are differentially affected by Exo-STING agonist, monocyte and dendritic cell activation was measured. As shown in FIG. 3, maximal monocyte activation was attenuated in Exo-STING agonist treated cells, while the $EC_{50}$ was improved compared free STING agonist. In contrast, the maximal activation of myeloid dendritic cells (mDCs) was higher while also experiencing improved potency of $EC_{50}$ (FIG. 4). mDC and monocyte activation were measured in PBMCs from 13 donors after treatment with free STING agonist or Exo-STING agonists, and maximal mDC activation was significantly higher while maximal monocyte activation was significantly attenuated with Exo-STING agonist compared to free STING agonist (FIG. 5). These results demonstrate that in the context of PBMCs, only a fraction of the myeloid dendritic cells was activated. This result is saturable and exemplifies the limitations of the STING agonist alone as adding additional compound does not increase the amount of activation. In contrast, the exosome-encapsulated STING agonist activated a significantly larger proportion of myeloid dendritic cells. Monocytes were robustly activated by the STING agonist alone with over 90% becoming activated at micromolar concentrations of the agonist. However, exosome-encapsulated STING agonist resulted in a significantly smaller proportion of monocytes becoming activated. Given that monocytes are much more abundant than myeloid dendritic cells in the circulation, the lower activation profile of monocytes by exosome-encapsulated STING agonists may result in reduced systemic inflammation as compared to an equal amount of the free compound. Furthermore, initiation of adaptive immune responses against tumors is largely dependent upon dendritic cell activation; therefore, exosome-encapsulated STING agonists will likely lead to increased anti-tumor immune responses with reduced toxicities as compared to the compound alone.

Figure 6A:
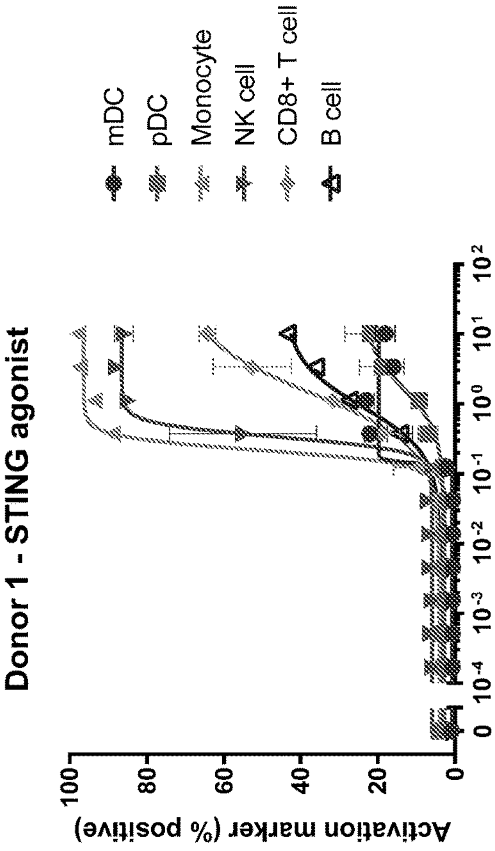
FIGS. 6A and 6B show the percentage of activation marker positive cells of different populations of cell types (mDC, pDC, monocytes, NK cells, CD8+ T cells, and B cells) after treatment with a free STING agonist (STING Agonist).
Figure 6B:
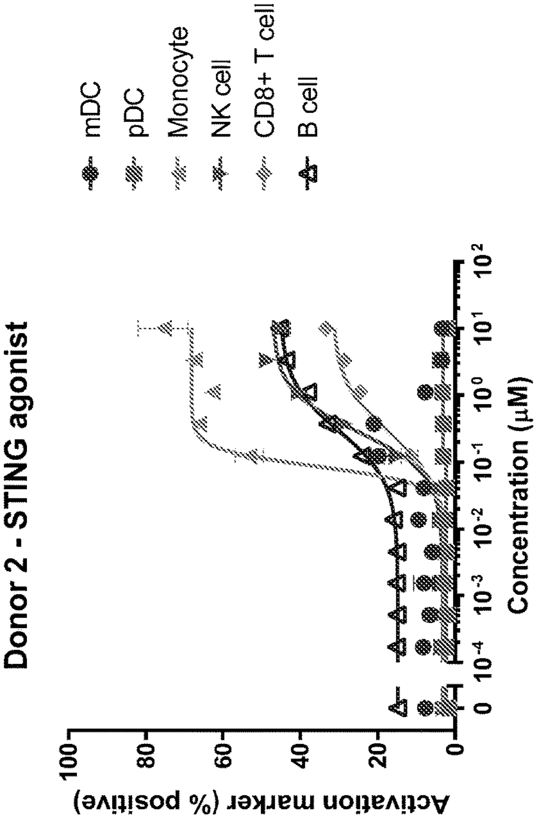
Figure 7A:
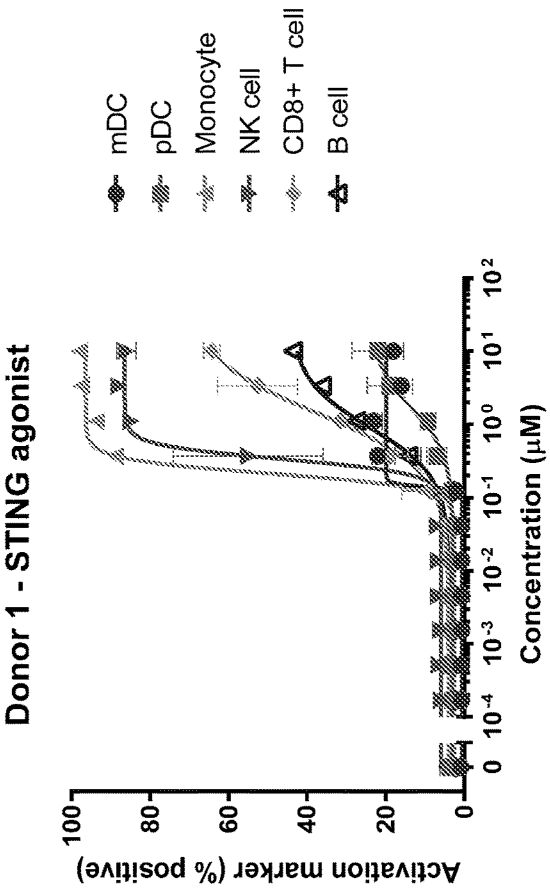
FIG. 7A shows the percentage of activation marker positive cells of different populations of cell types (mDC, pDC, monocytes, NK cells, CD8+ T cells, and B cells) after treatment with a free STING agonist (STING Agonist).
Figure 7B:
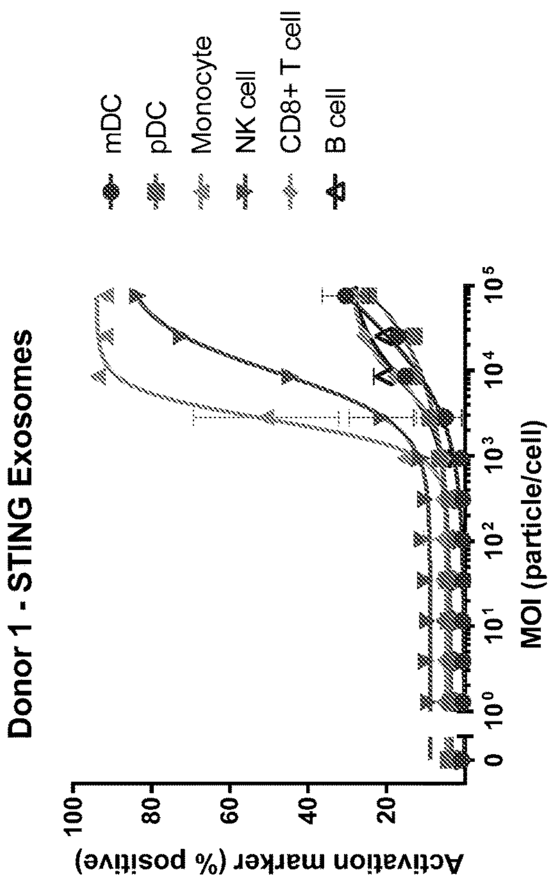
FIG. 7B shows the percentage of activation marker positive cells of different populations of cell types (mDC, pDC, monocytes, NK cells, CD8+ T cells, and B cells) after treatment with an exosome-encapsulated STING agonist (STING Exosomes).

To understand the extent that different immune cell types are activated by STING agonists, specific activation of T cells, B cells, and NK cells was assessed by measuring the amount of CD69 on the cell surface by flow cytometry. Activation of antigen-presenting cells (APCs) including monocytes, myeloid dendritic cells, plasmacytoid dendritic cells, and B cells was assessed by measuring the amount of CD80, CD86, HLA-DR, or CD83 on the cell surface by flow cytometry. As shown in FIG. 6, free STING agonist readily activated monocytes, NK cells, B cells, and CD8 T cells from two different donors. In contrast, Exo-STING agonist reduced the activation of B cells and T cells, while retaining activation of antigen presenting cells (FIGS. 7A and 7B). These results suggest that antigen presenting cells can be specifically activated by STING agonist loaded exosomes while reducing the activation of T cells and B cells, which may limit systemic toxicity.

Figure 8A:
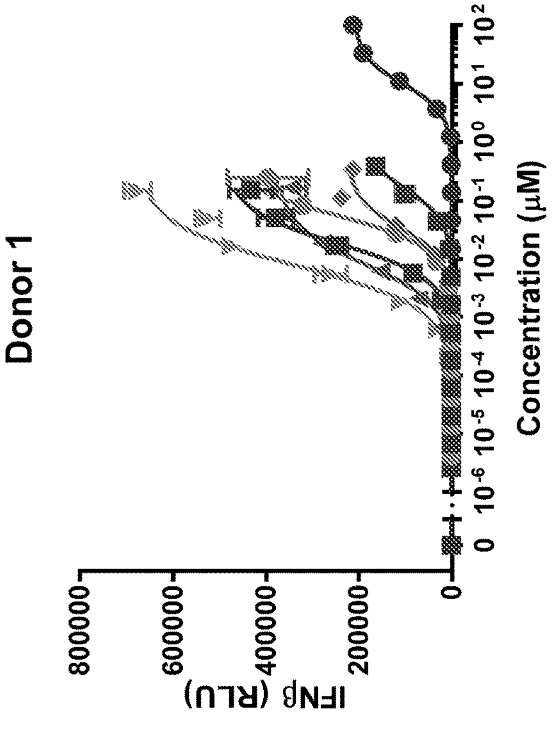
FIGS. 8A and 8B show a dose-dependent IFN-0 response in PBMCs from two donors after treatment with free STING agonist, exosome-encapsulated STING agonist (STING Exo), or STING agonist encapsulated glycan modified or protein-overexpressing exosomes (deglycosylated [Degly], desialylated [Desialy], PTGFRN-over expressing [PTGFRN], deglycosylated and PTGFRN-over expressing [PTGFRN Degly] or desialylated and PTGFRN-over expressing [PTGFRN Desialy]).
Figure 8B:
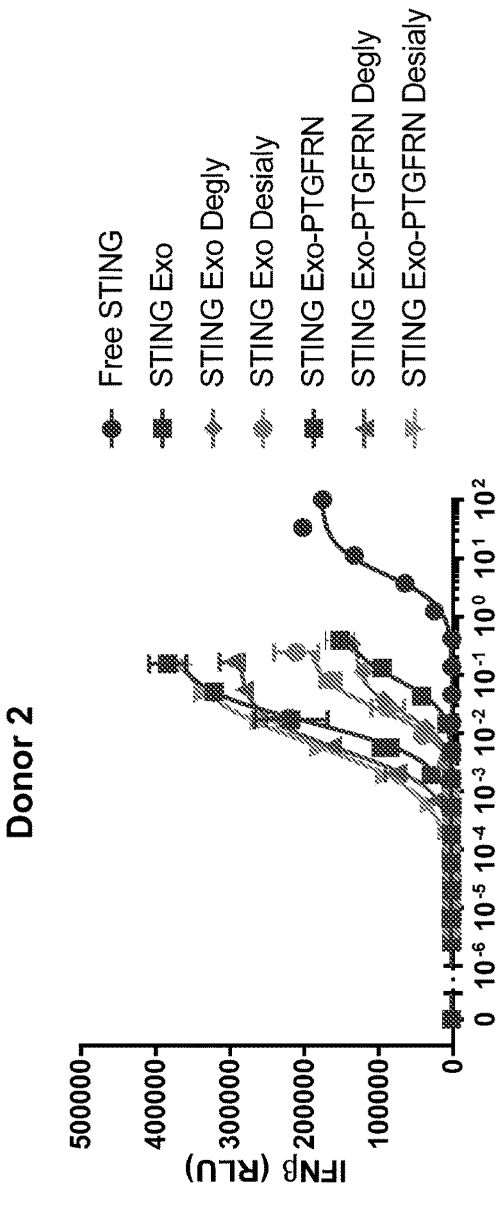

Example 3: Enhancing STING Exosome Activity by PTGFRN Overexpression and Exosome Glycan Modification The results in Examples 1 and 2 suggest that exosome surface molecules may mediate the increased potency of Exo-STING agonist compared to free STING agonist. Previous results have demonstrated that prostaglandin F2 receptor negative regulator (PTGFRN) is an abundant glycoprotein on the luminal or exterior surface of exosomes. When PTGFRN is overexpressed in a producer cell, PTGFRN is the predominant glycoprotein on the luminal or exterior surface of exosomes. To determine whether PTGFRN played a role in mediating Exo-STING agonist activation of immune cells, exosomes with modified glycan profiles or engineered to express higher levels of PTGFRN were compared to free STING agonist. Similar to the results in FIG. 2, Exo-STING agonist was more potent in inducing IFNβ production than free STING agonist without altering the maximal level of IFNβ production in PBMCs. STING loaded into exosomes that were first deglycosylated by PNGase F further enhanced this potency shift, while delivery of STING agonist in exosomes that were first desialylated with sialidase resulted in a further enhancement of potency and higher maximal level of IFNβ production, indicating that glycan modification of exosomes can alter the delivery of STING agonist molecules to immune cells. Surprisingly, exosomes overexpressing PTGFRN and loaded with STING agonist further enhanced the potency and maximal production of IFNβ compared to the unmodified or glycan engineered exosomes containing endogenous levels of PTGFRN. Deglycosylating or desialylating the PTGFRN Exo-STING samples further enhanced potency beyond the effect of exosomes overexpressing PTGFRN alone (FIGS. 8A and 8B in two donors). Quantifying the level of IFNβ as a result of STING agonist delivery demonstrates that glycan modified PTGFRN overexpressing exosomes can enhance the potency of a STING agonist more than 1000-fold over free STING agonist, and ~50-fold over STING agonist loaded in unmodified exosomes (FIG. 9).

Figures 10A, 10B:
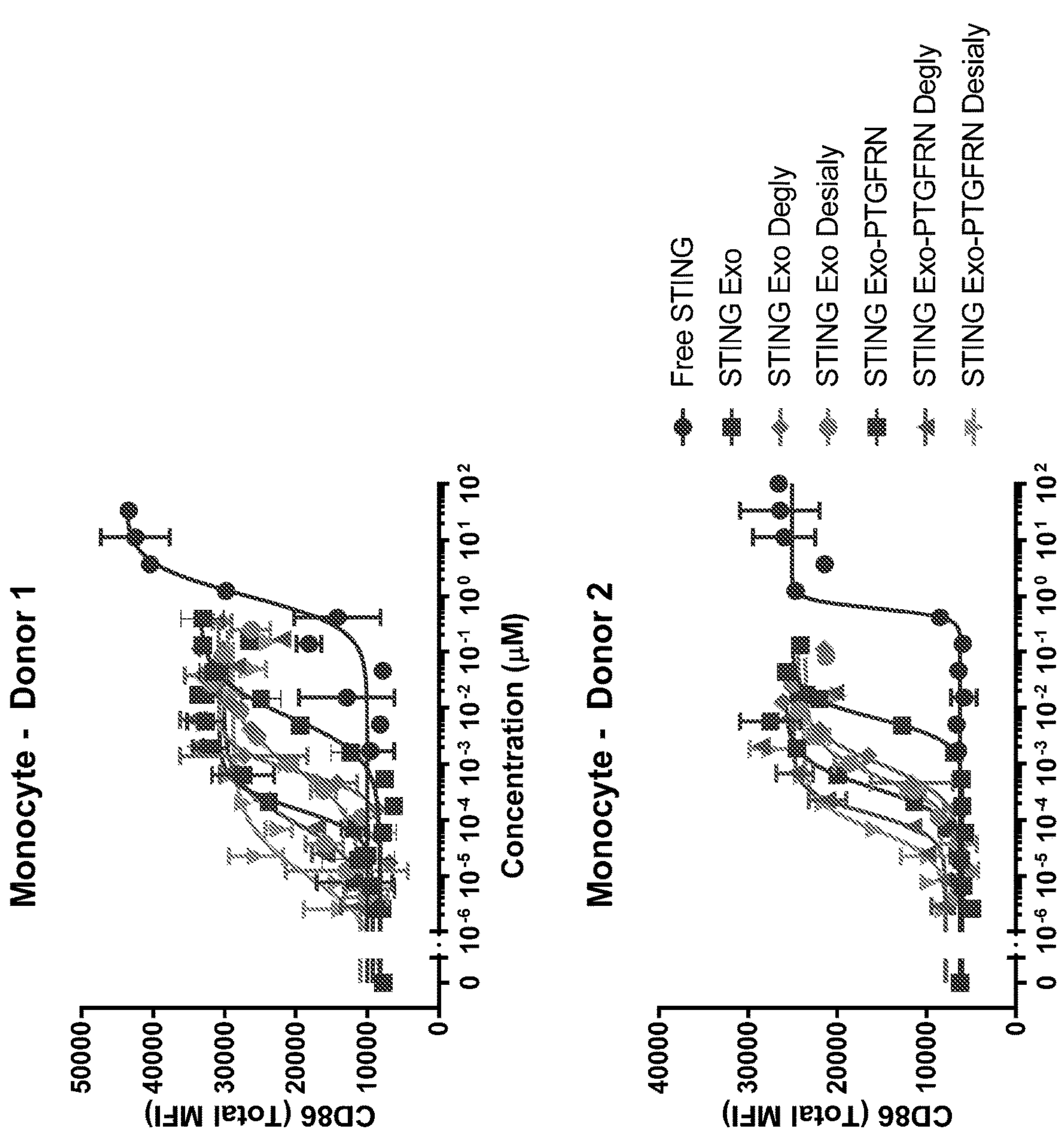
FIGS. 10A and 10B show a dose-dependent CD86 expression response in monocytes from two donors after treatment with free STING agonist, exosome-encapsulated STING agonist (STING Exo), or STING agonist encapsulated glycan modified or protein-overexpressing exosomes, as in FIGS. 8A and 8B.
Figure 12A:
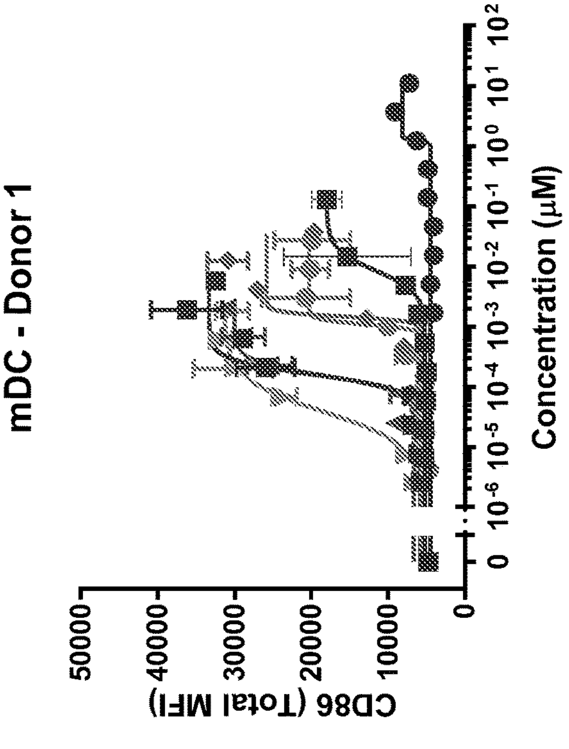
FIGS. 12A and 12B show a dose-dependent CD86 expression response in mDCs after treatment with free STING agonist, exosome-encapsulated STING agonist (STING Exo), or STING agonist encapsulated glycan modified or protein-overexpressing exosomes, as in FIGS. 8A and 8B.
Figure 12B:
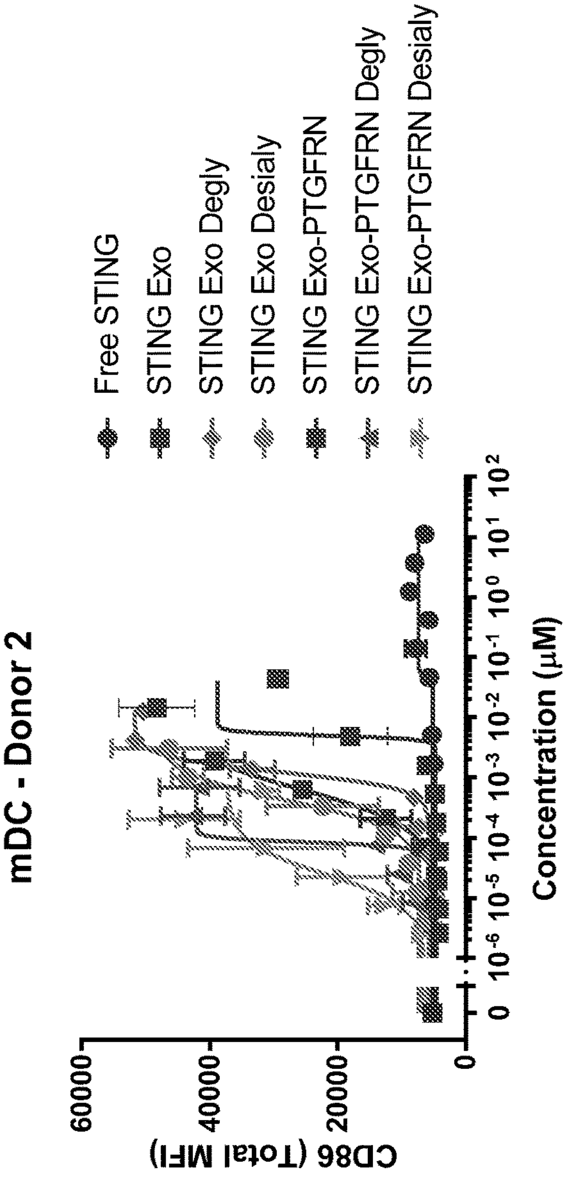
Figure 14:
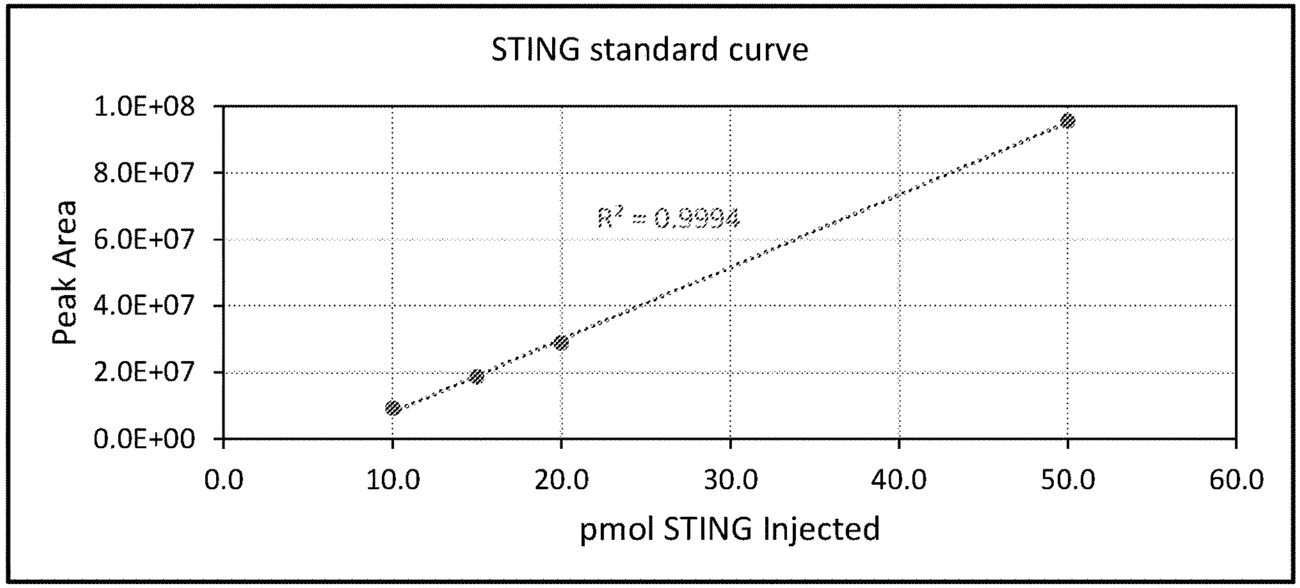
FIG. 14 shows a quantification of the concentration of the STING agonist in exosomes.

The results in FIG. 9 demonstrate that a combination of glycan engineering and PTGFRN overexpression on exosomes could enhance the delivery of a STING agonist molecule to immune cells. To understand the impact that these modifications have on the activation of specific cell types in PBMCs, the STING agonist loaded exosome preparations shown in FIG. 9 were tested in their activation of monocytes and dendritic cells. FIG. 10 demonstrated that glycan modification and/or PTGFRN overexpression of STING agonist loaded exosomes results in increased potency of monocyte activation as measured by $EC_{50}$ but a reduced or unchanged level of maximal activation in two donors (FIG. 10). The change in $EC_{50}$ of monocyte activation was up to 54,000-fold for desialylated PTGFRN overexpressing exosomes compared to free STING agonist (FIG. 11). In contrast, free STING agonist poorly activated mDCs in two donors, while the glycan engineered and/or PTGFRN overexpressing exosomes dramatically enhanced the $EC_{50}$ and maximal activation of mDCs (FIG. 12). The shift in $EC_{50}$ for mDCs was >16,000-fold (FIG. 13), while the maximal activation was ~4-10-fold greater for desialylated PTGFRN overexpressing STING agonist exosomes. Importantly, the effects observed in these experiments were not due to enhanced loading efficiency for the PTGFRN overexpressing or glycan engineered exosomes, because STING agonist quantitation as determined by the LC-MS described above allowed for normalization of the STING agonist across exosome preparations. Indeed, PTGFRN overexpressing and/or glycan engineered exosomes are loaded less efficiently on a per-particle basis than unmodified exosomes (FIG. 14). Together, these results demonstrate that specific glycan modifications and/or overexpression of a single exosome surface protein can dramatically enhance the potency of STING agonist loaded exosomes and enhance the selectivity of cargo delivery to dendritic cells.

Kifunensine Pre-Treatment to Modulate STING Activation

Figure 15A:
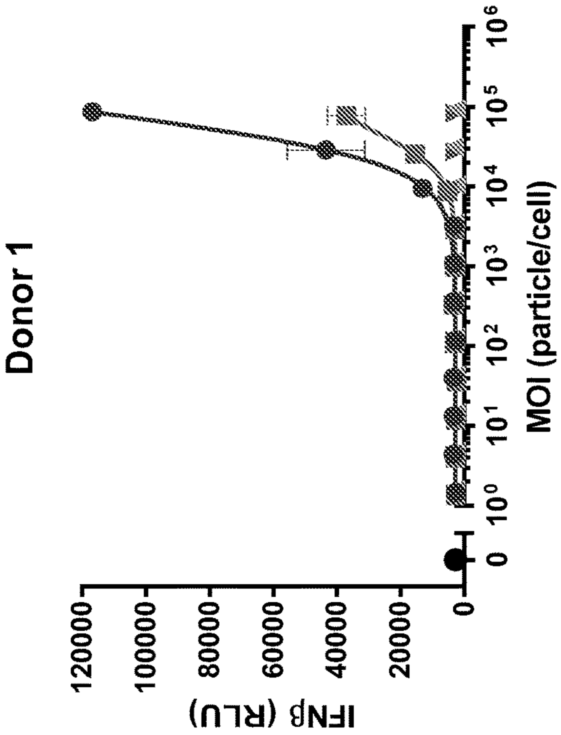
FIGS. 15A and 15B show a dose-dependent IFNβ response in two different donor samples after treatment with kifunensine treated (Exo+Kif) or untreated (Exo) exosomes with or without encapsulated STING agonist.
Figure 15B:
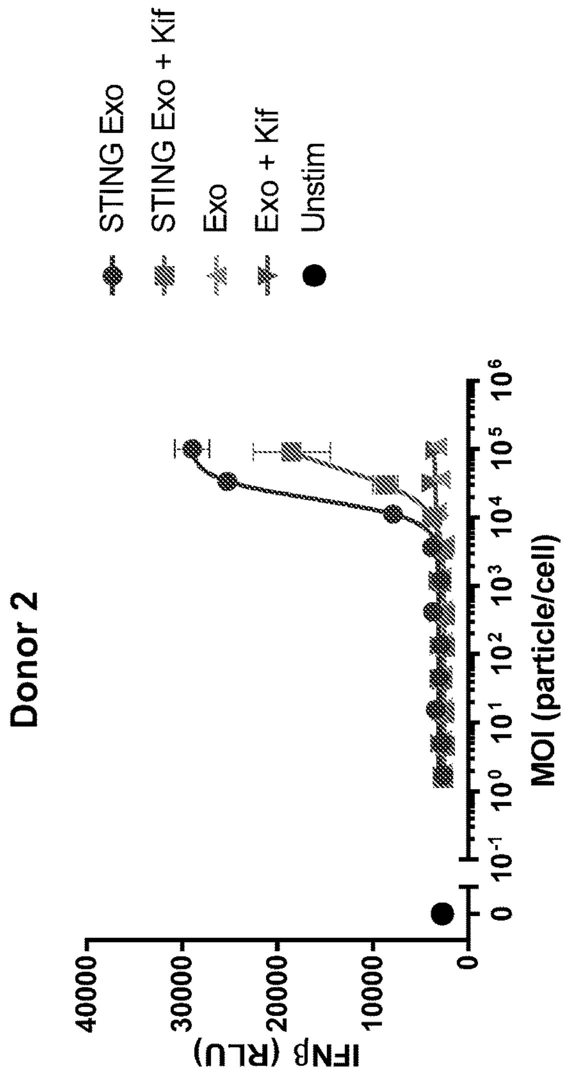
Figure 16A:
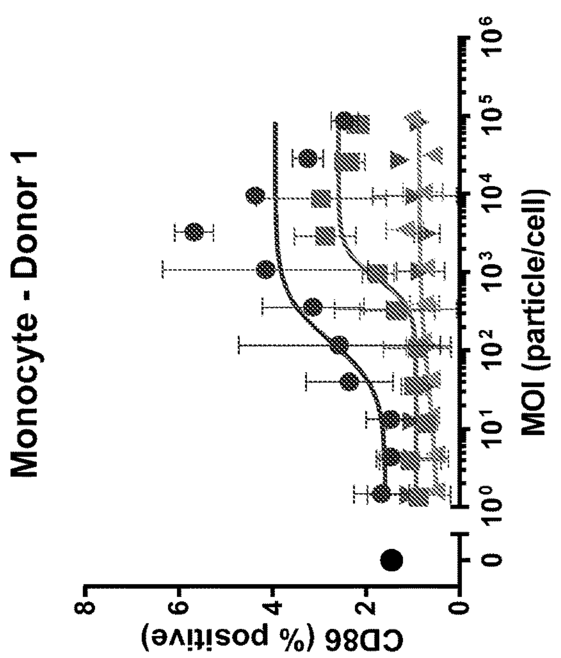
FIGS. 16A and 16B show a dose-dependent activation of monocytes as measured by CD86 signal in two different donor samples after treatment with kifunensine treated (Exo+Kif) or untreated (Exo) exosomes with or without encapsulated STING agonist.
Figure 16B:
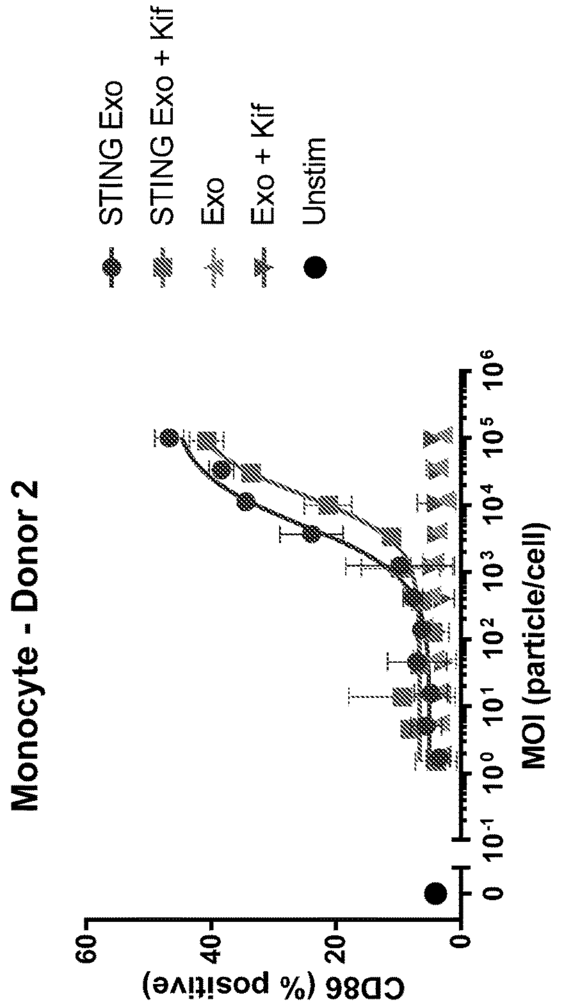
Figure 17A:
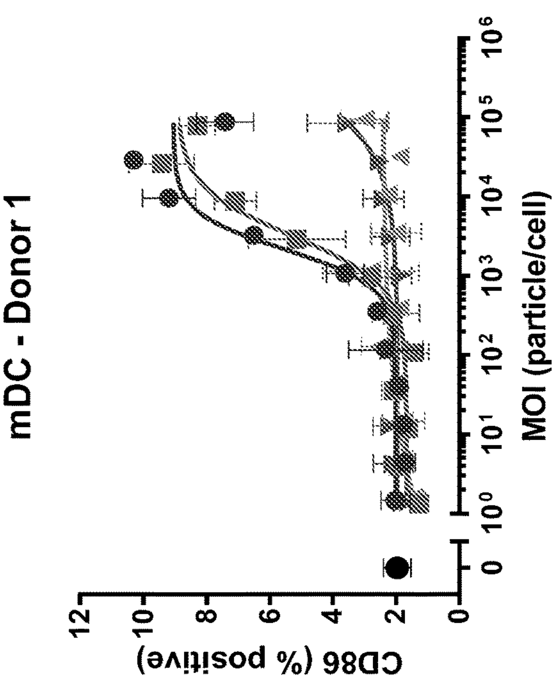
FIGS. 17A and 17B show a dose-dependent activation of mDCs as measured by CD86 signal in two different donor samples after treatment with kifunensine treated (Exo+Kif) or untreated (Exo) exosomes with or without encapsulated STING agonist.
Figure 17B:
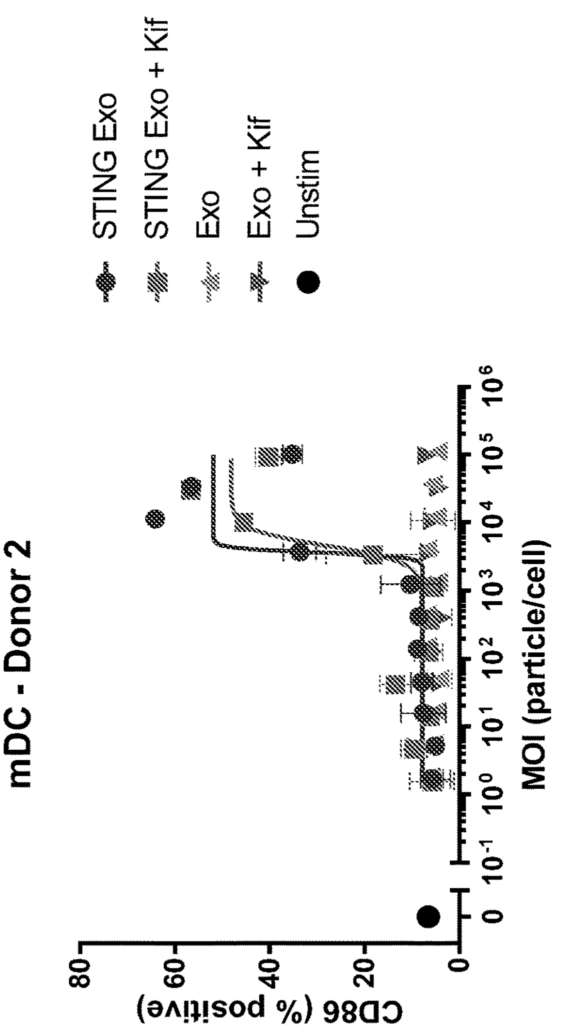

To determine whether any perturbation of exosomal surface glycans can alter immune cell uptake, producer cell lines were treated with the alkaloid agent kifunensine, which prevents the trimming of high mannose sugar residues during protein glycosylation, and prevents complete glycosylation. The resulting exosomes from kifunensine-treated cells have altered glycosylation status and are enriched in high mannose. Kifunensine-treated exosomes were loaded with STING agonist and administered to PBMCs from two donors. This resulted in a partial attenuation of STING agonistic activity compared to wild-type exosomes. Specifically, monocyte and mDC activation were largely unchanged (FIGS. 16 and 17, respectively), while IFNβ production was dramatically reduced (FIG. 15). These results suggest that specific glycosylation patterns at least partially mediate the uptake of exosomes in immune cells, and that not all modifications of the surface glycoproteins can enhance the activation of immune cells during exosome-mediated delivery of STING agonist molecules.

Example 4: Optimizing Loading of Exosomes with STING Agonist

Figure 18A:
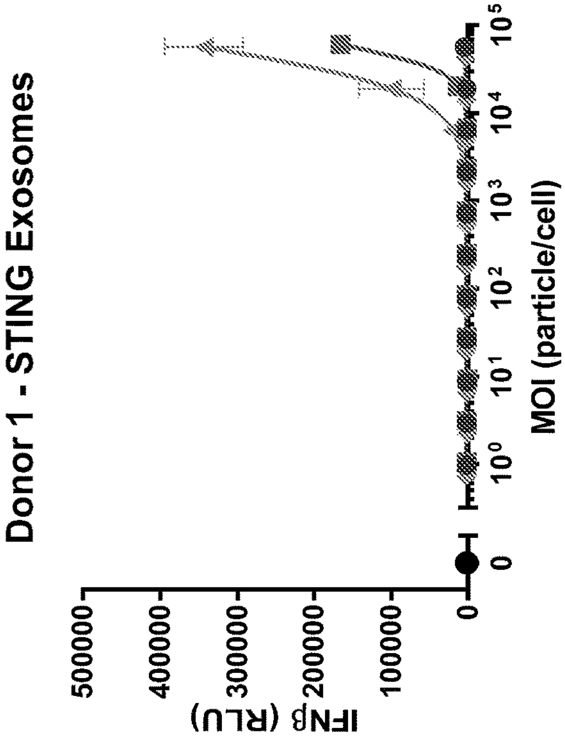
FIGS. 18A and 18B show a dose-dependent IFNβ response in two different donor samples after treatment with exosomes that had been incubated with STING agonist for different amounts of time (2 h, 6 h, overnight (0/N)) or no STING agonist (exo).
Figure 18B:
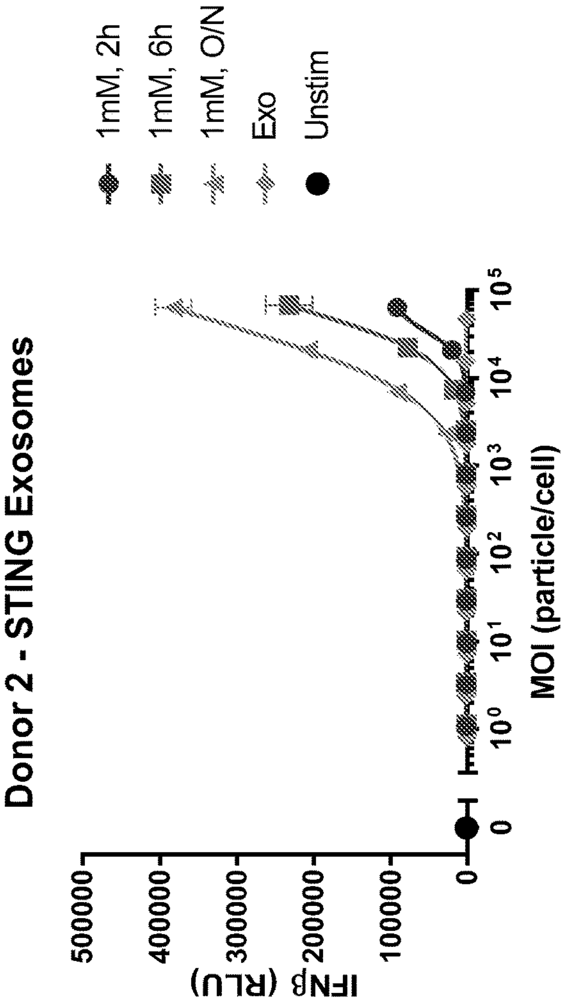

In the previous examples, the exosomes were loaded with STING agonist by incubating at 37° C. overnight. To determine the kinetics of STING agonist loading, exosomes were incubated with 1 mM STING agonist for 2 hours, 6 hours, or overnight, and added to PBMCs to measure IFNβ production. As shown in FIGS. 18A and 18B, unloaded exosomes failed to induce IFNβ production, while exosomes incubated in STING agonist for 2 hours either failed to induce IFNβ production or resulted in relatively low levels. Samples loaded for 6 hours resulted in intermediate IFNβ production, while overnight loading resulted in the highest levels of IFNβ production in two donors. These results indicate that STING agonist loading into exosomes can be enhanced by increasing incubation time.

Figure 19:
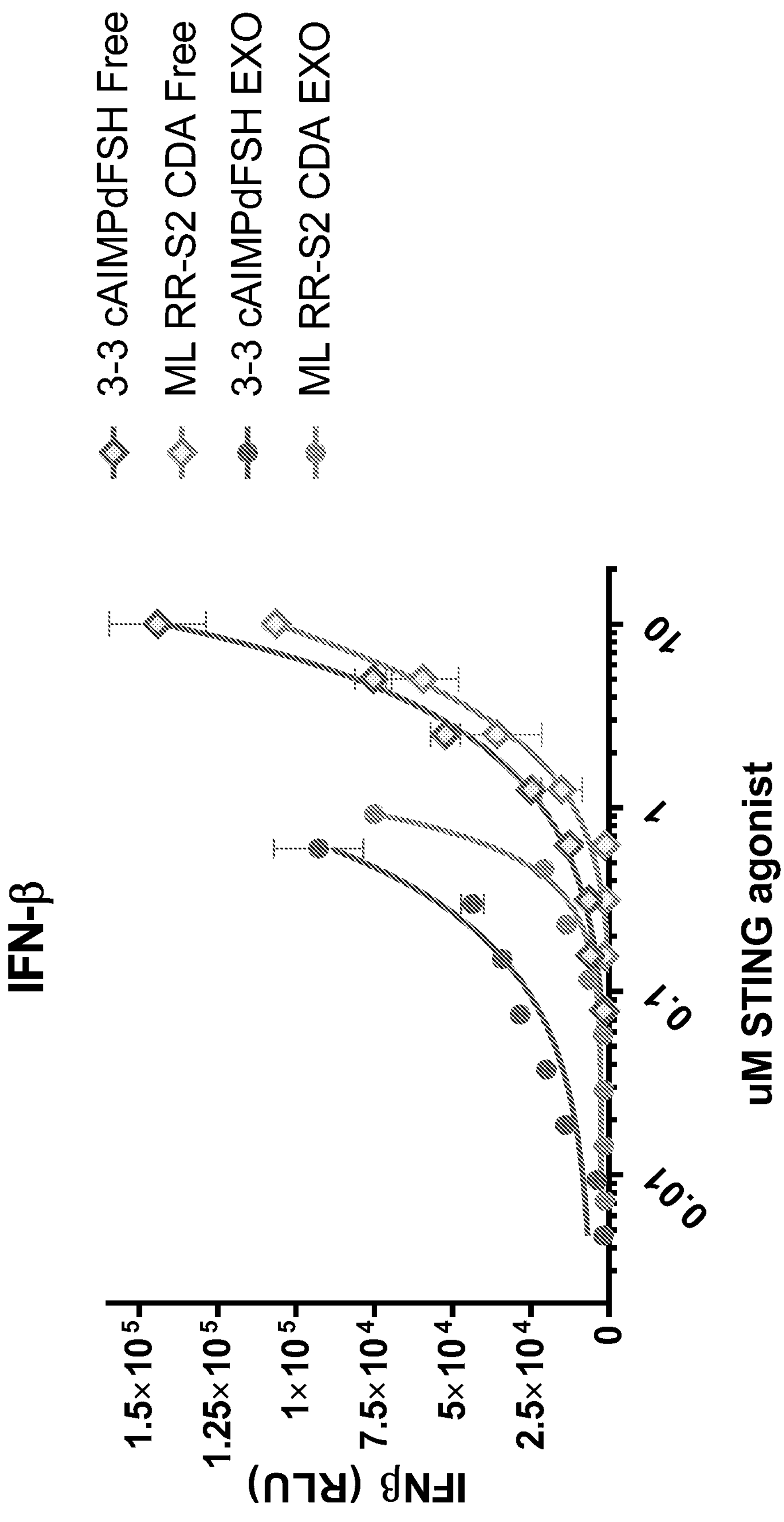
FIG. 19 shows a dose-dependent IFNβ response in human PBMCs treated with two different exosome-encapsulated STING agonists and free STING agonists (ML RR-S2 CDA and 3-3 cAIMPdFSH), as determined by relative luminescence (RLU).

Example 5: Comparative Potency of Different Exosome-Encapsulated STING Agonist Cyclic Dinucleotides HEK293SF cells overexpressing PTGFRN were grown in shake flasks and the resulting exosomes were purified by Optiprep™ density gradient ultracentrifugation as described in the Methods. The purified exosomes were loaded with either of the STING agonists ML RR-S2 CDA (MedChem Express, Cat. No. HY-12885B) or 3-3 cAIMPdFSH (InvivoGen, Cat. No. tlrl-nacairs) according to the methods in Example 1. Loading was quantified as described in Example 1. The exosome-encapsulated or free STING agonists were added to human PBMCs and incubated at 37° C. overnight. Activation of PBMCs by the STING agonists was detected by measuring the amount of IFNβ in the supernatant. As shown in FIG. 19, both free STING agonists induced IFNβ to a similar extent, while both exosome-encapsulated STING agonists resulted in a potency shift as shown in Example 2. Exosome-encapsulated 3-3 cAIMPdFSH was more potent than exosome-encapsulated ML RR-S2 CDA, however, suggesting that fluorinated STING agonists may provide a potency advantage when delivered in an exosome formulation.

Figure 20A:
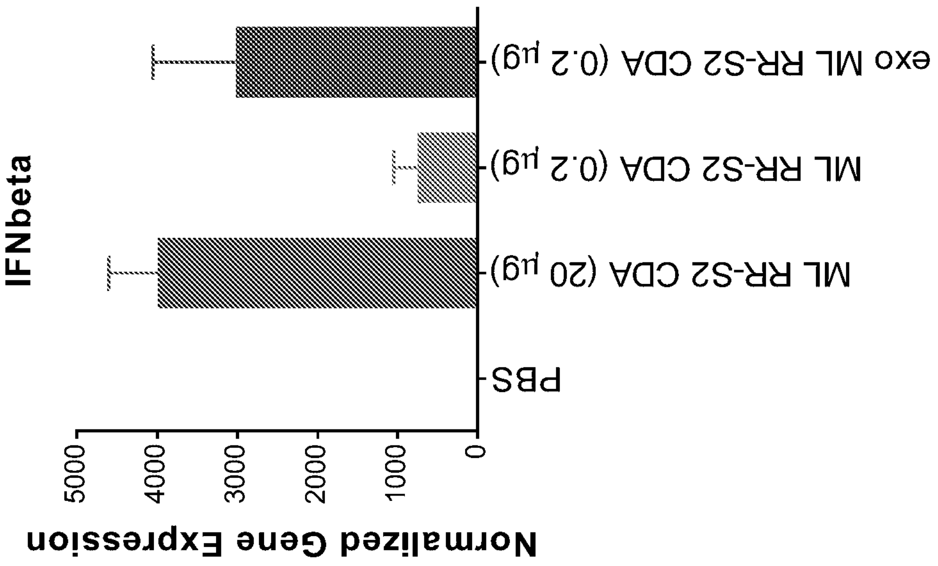
FIGS. 20A-20D show cytokine expression profiles (IFNβ, CXCL9, CXCL10, and IFN-γ, respectively) in the tumor of B16F10 tumor-bearing mice after a single intratumoral injection of PBS, 20 μg free ML RR-S2 CDA, 0.2 μg free ML RR-S2 CDA, or 0.2 μg exosome-encapsulated ML RR-S2 CDA.
Figure 20B:
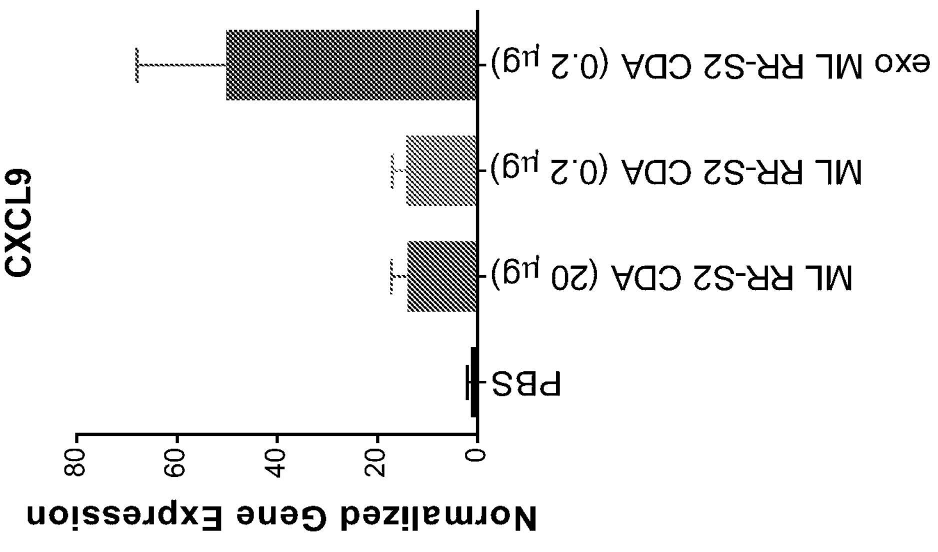
Figure 20C:
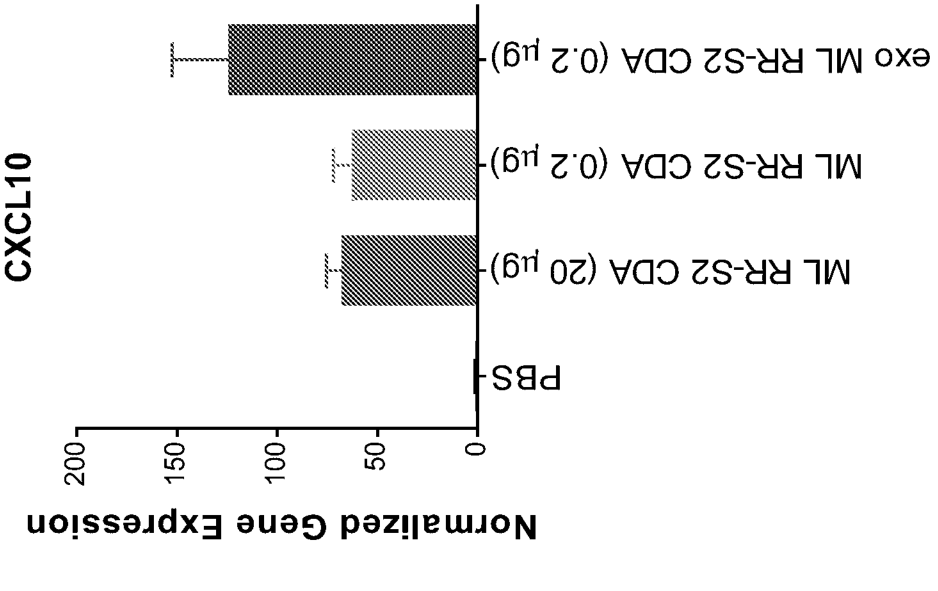
Figure 20D:
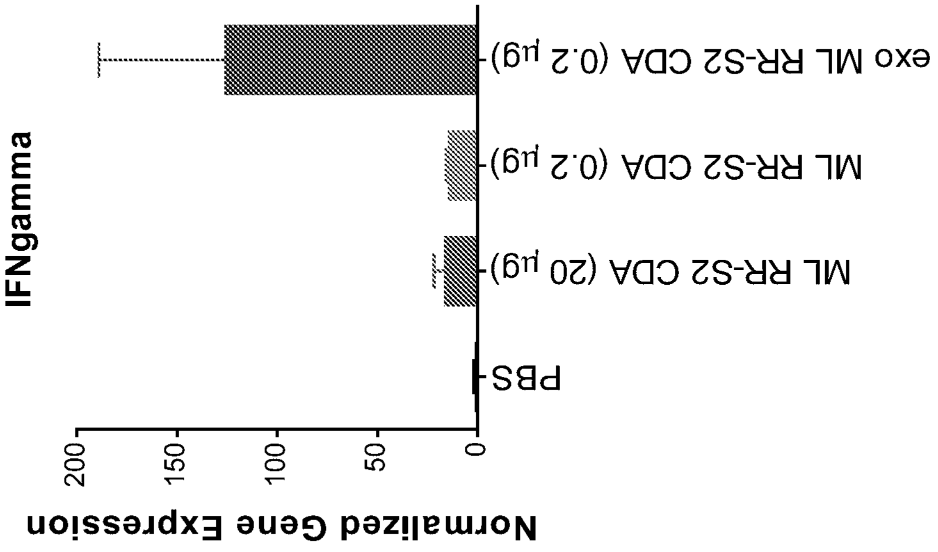

Example 6: In Vivo Potency and Systemic Effects of Free STING Agonists Compared to Exosome-Encapsulated STING Agonists in Tumor-Bearing Mice Four groups of C57BL/6 mice (3-4 mice per group) were inoculated subcutaneously with $5\times10^5$ B16F10 tumor cells. Eight days post-inoculation the mice were injected with a single intratumoral dose of PBS, 20 μg of free ML RR-S2 CDA, 0.2 μg of free ML RR-S2 CDA, or 0.2 μg of ML RR-S2 CDA loaded in PTGFN-overexpressing exosomes (exo ML RR-S2 CDA). Four hours post-injection the tumors, draining lymph nodes, spleens, and serum were collected and cytokine levels were measured. IFNβ gene expression levels in the tumor were comparable in the 20 μg free STING agonist and 0.2 μg exosome-STING agonist groups, which were both higher than the 0.2 μg free STING agonist and PBS groups (FIG. 20A). Additionally, the levels of IFNγ and the T-cell chemoattractants CXCL9 and CXCL10 were all higher in the exosome-STING agonist group (FIGS. 20B, 20C, and 20D). These data demonstrate that 100-fold less STING agonist can induce a comparable induction of an IFN gene expression signature in a tumor when the STING agonist is encapsulated in exosomes.

Figure 21A:
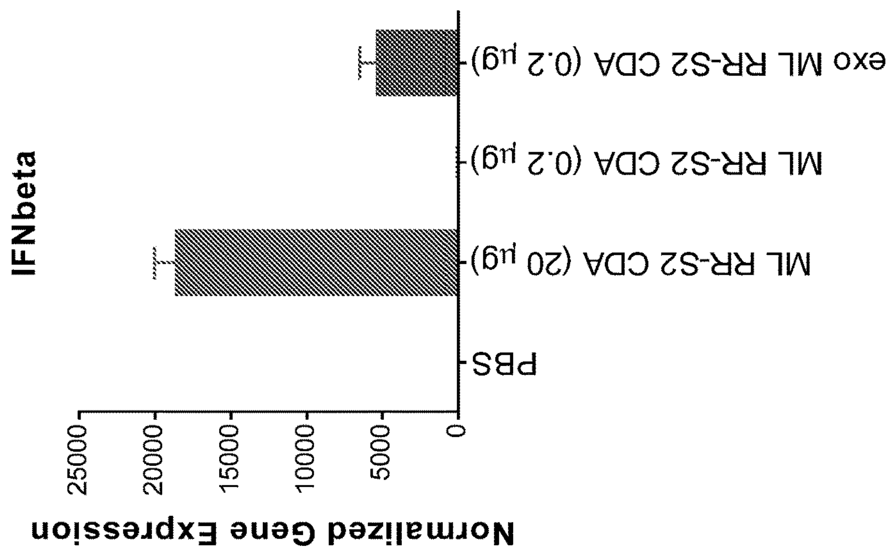
FIGS. 21A-21C show cytokine expression profiles (IFNβ, CXCL9, and CXCL10, respectively) in the draining lymph node of B16F10 tumor-bearing mice after a single intratumoral injection of PBS, 20 μg free ML RR-S2 CDA, 0.2 μg free ML RR-S2 CDA, or 0.2 μg exosome-encapsulated ML RR-S2 CDA.
Figure 21B:
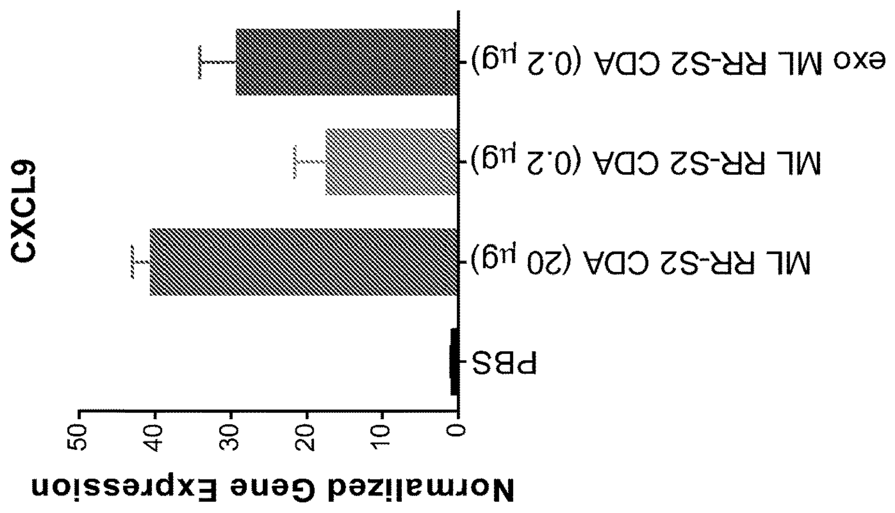
Figure 21C:
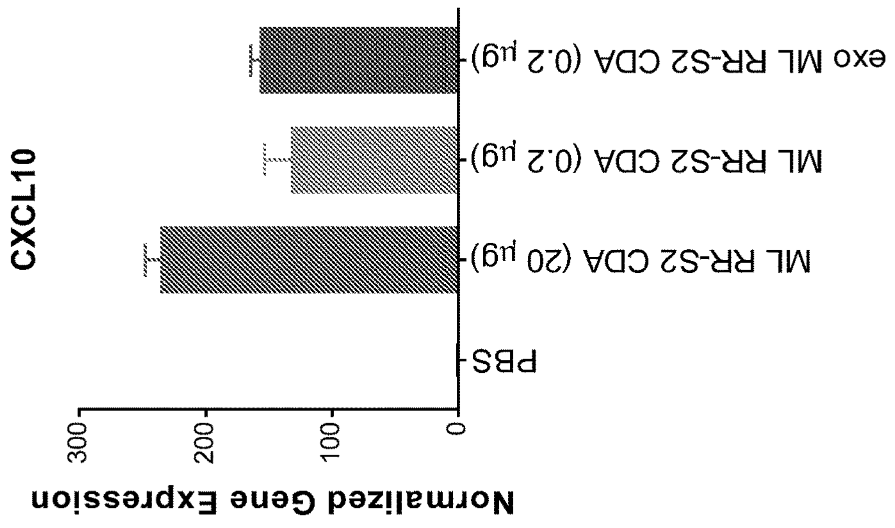
Figure 22A:
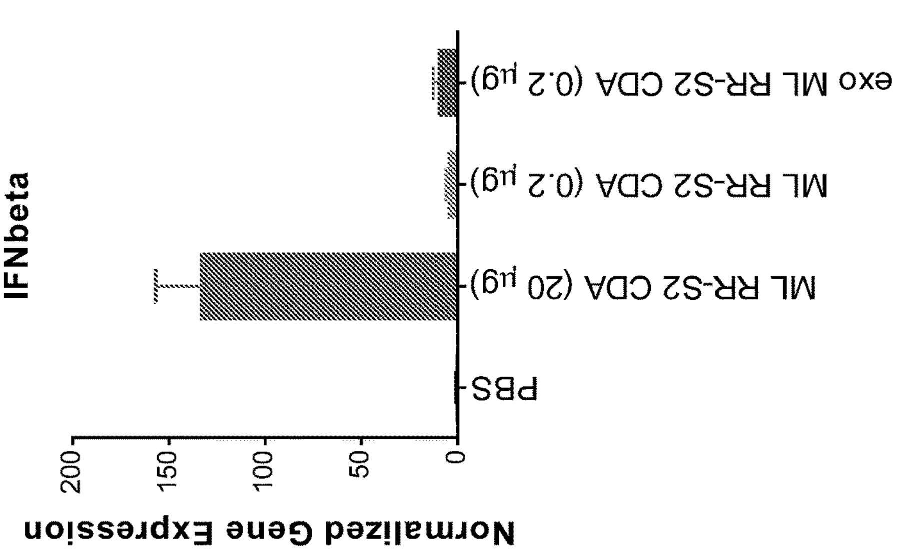
FIGS. 22A-22C show cytokine expression profiles (IFNβ, CXCL9, and CXCL10, respectively) in the spleen of B16F10 tumor-bearing mice after a single intratumoral injection of PBS, 20 μg free ML RR-S2 CDA, 0.2 μg free ML RR-S2 CDA, or 0.2 μg exosome-encapsulated ML RR-S2 CDA.
Figure 22B:
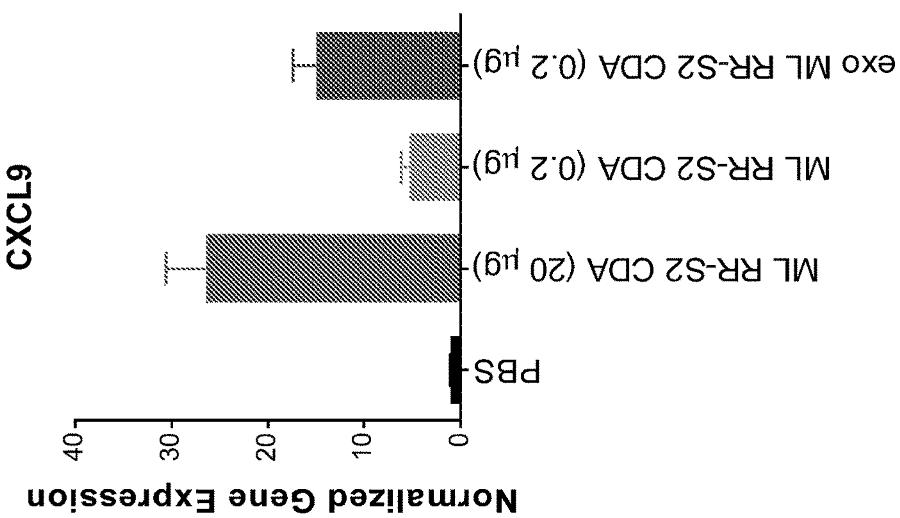
Figure 22C:
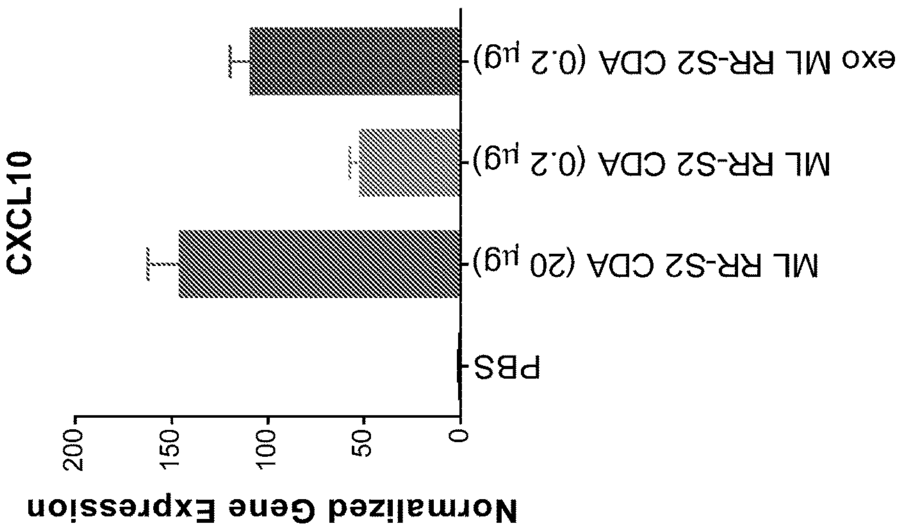
Figures 23A, 23B, 23C:
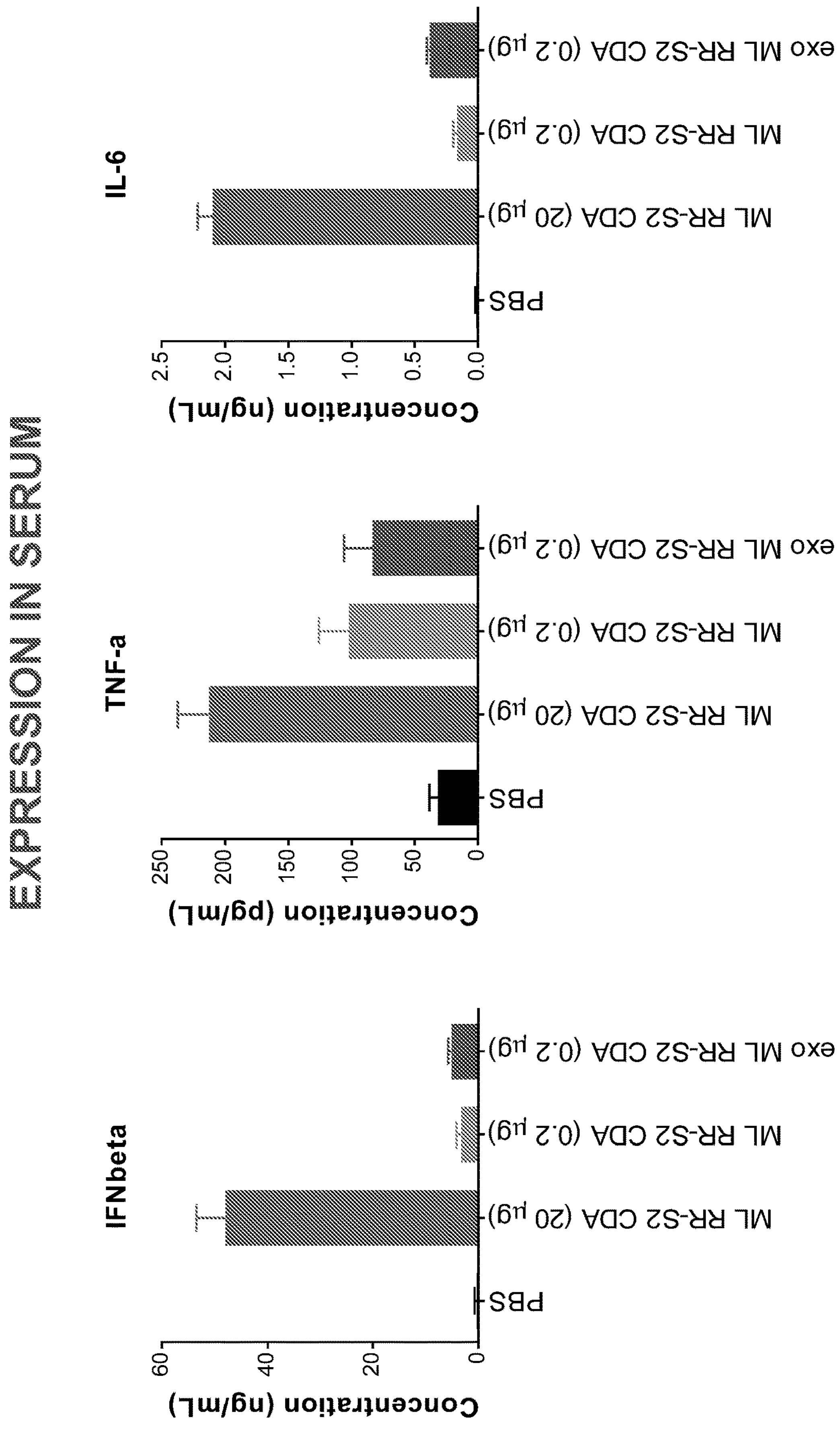
FIGS. 23A-23E show cytokine expression profiles (IFNβ, TNF-α, IL-6, MCP-1, and IFN-γ, respectively) in the serum of B16F10 tumor-bearing mice after a single intratumoral injection of PBS, 20 μg free ML RR-S2 CDA, 0.2 μg free ML RR-S2 CDA, or 0.2 μg exosome-encapsulated ML RR-S2 CDA.
Figure 23E:
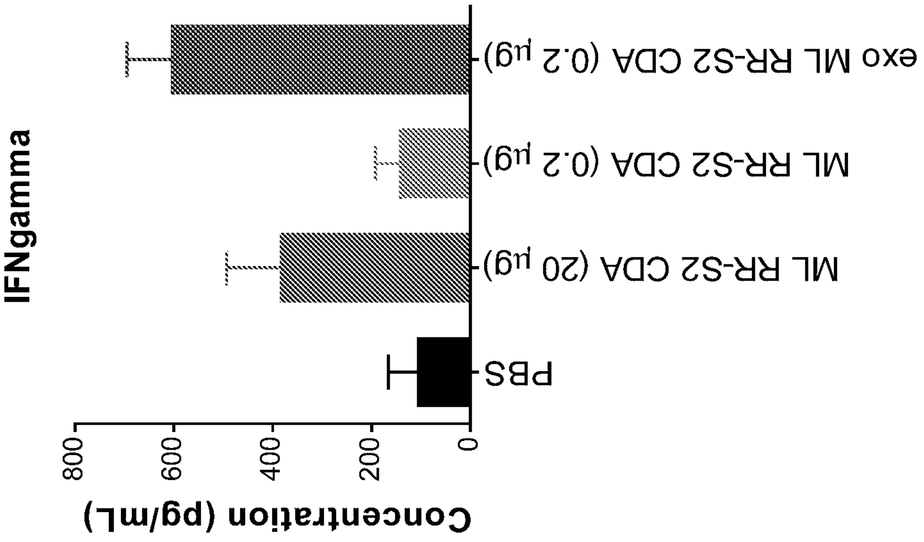
Figure 23D:
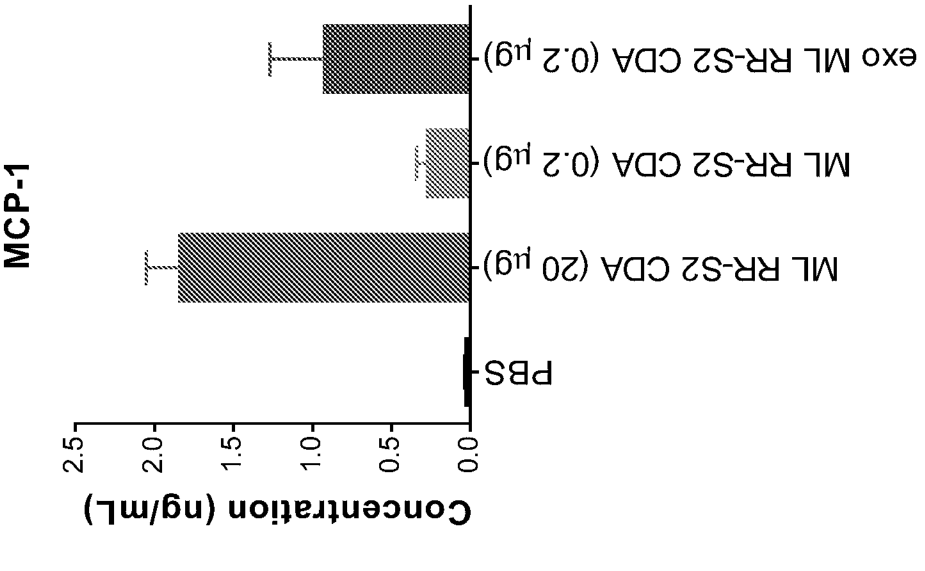
Figure 24A:
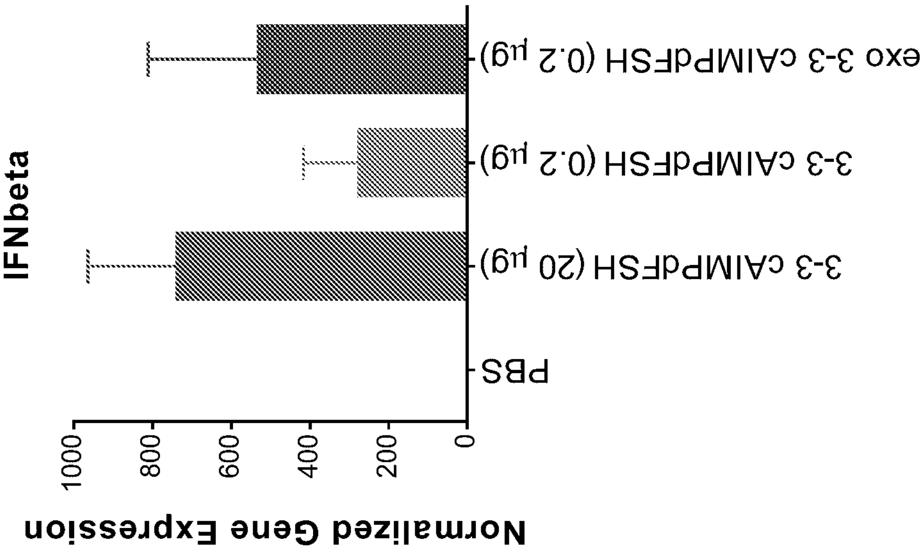
FIGS. 24A-24D show cytokine expression profiles (IFNβ, CXCL9, CXCL10, and IFN-γ, respectively) in the tumor of B16F10 tumor-bearing mice after a single intratumoral injection of PBS, 20 μg free 3-3 cAIMPdFSH, 0.2 μg free 3-3 cAIMPdFSH, or 0.2 μg exosome-encapsulated 3-3 cAIMPdFSH.
Figure 24B:
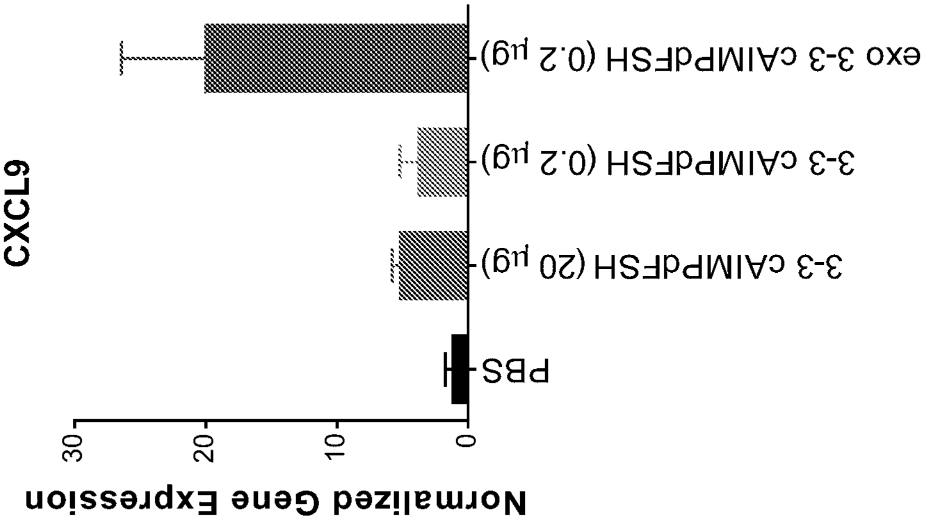
Figure 24C:
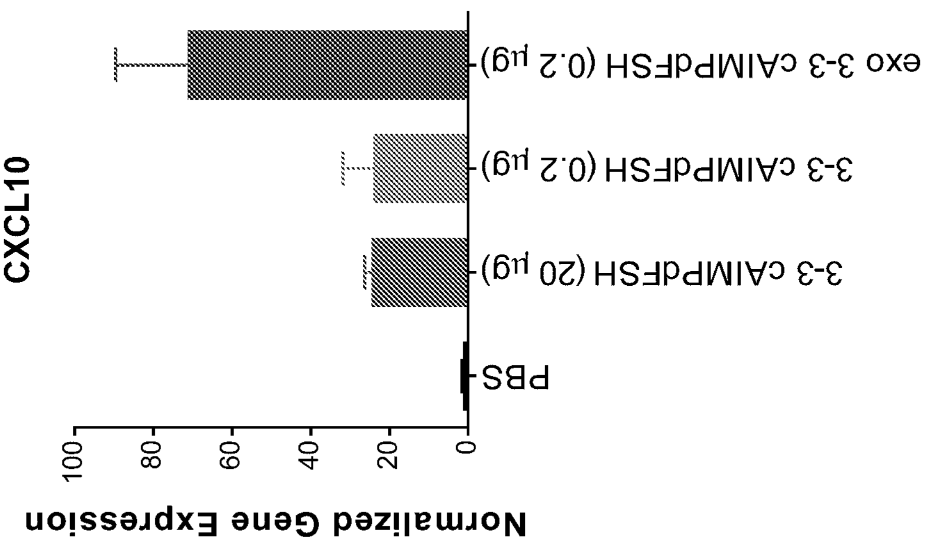
Figure 24D:
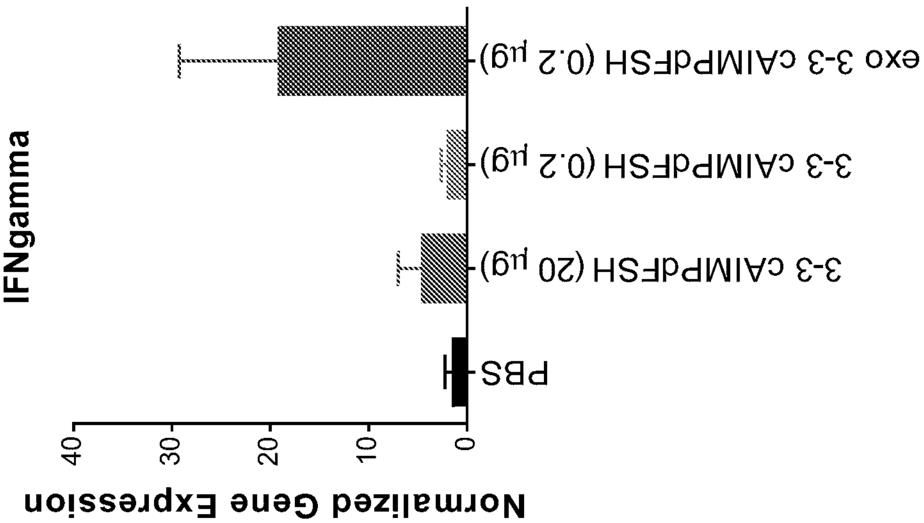
Figure 25A:
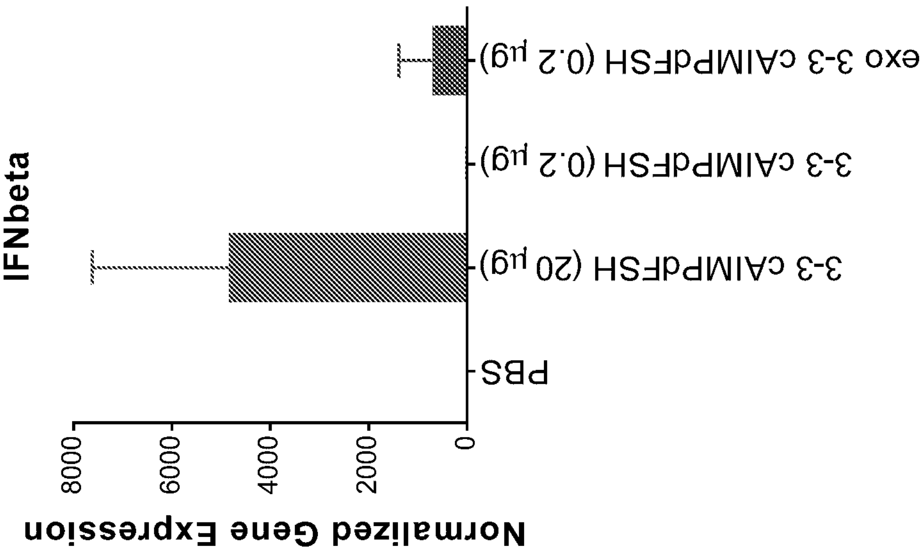
FIGS. 25A-25D show cytokine expression profiles (IFNβ, CXCL9, CXCL10, and IFN-γ, respectively) in the draining lymph node of B16F10 tumor-bearing mice after a single intratumoral injection of PBS, 20 μg free 3-3 cAIMPdFSH, 0.2 μg free 3-3 cAIMPdFSH, or 0.2 μg exosome-encapsulated 3-3 cAIMPdFSH.
Figure 25B:
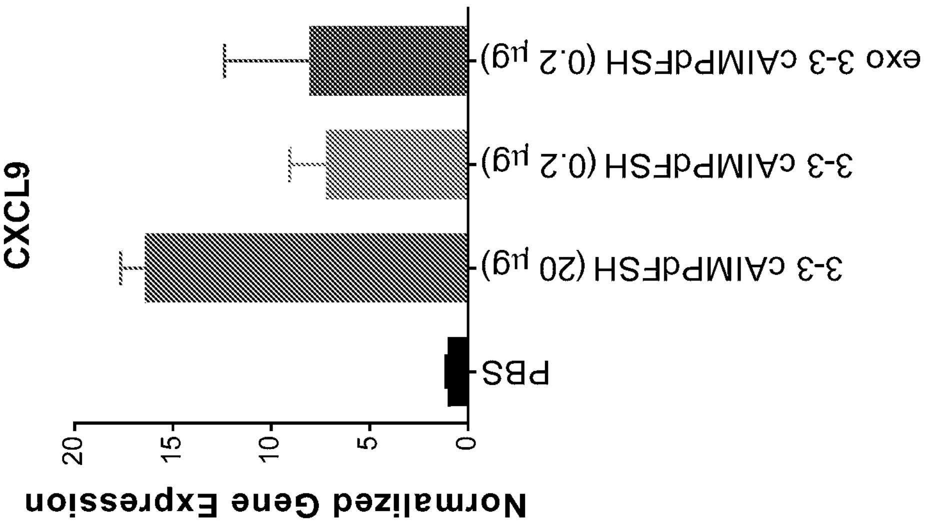
Figure 25D:
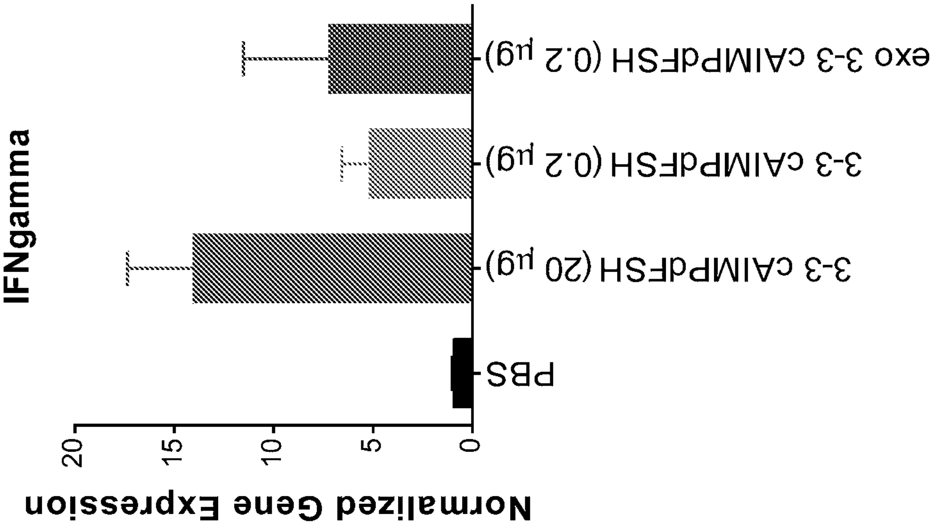
Figure 25C:
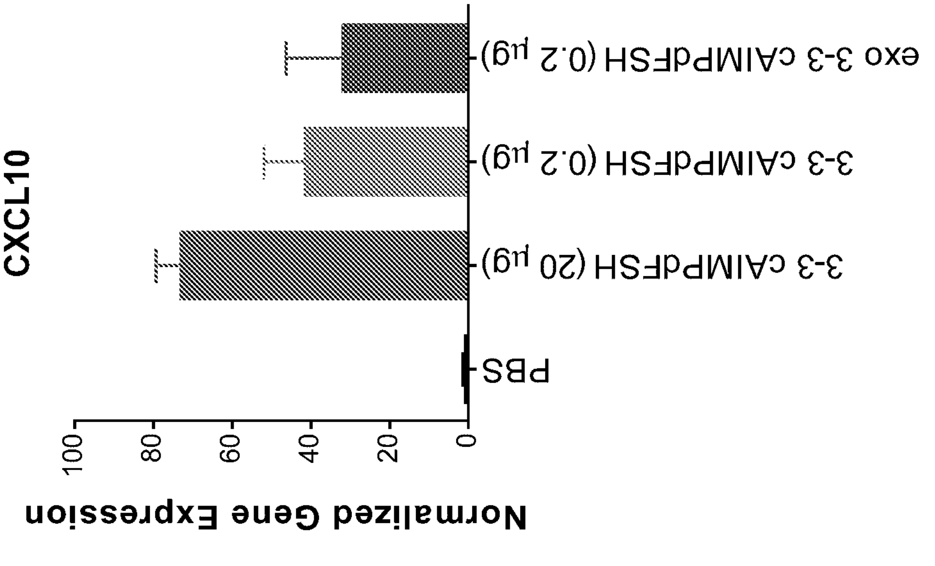
Figures 26A, 26B:
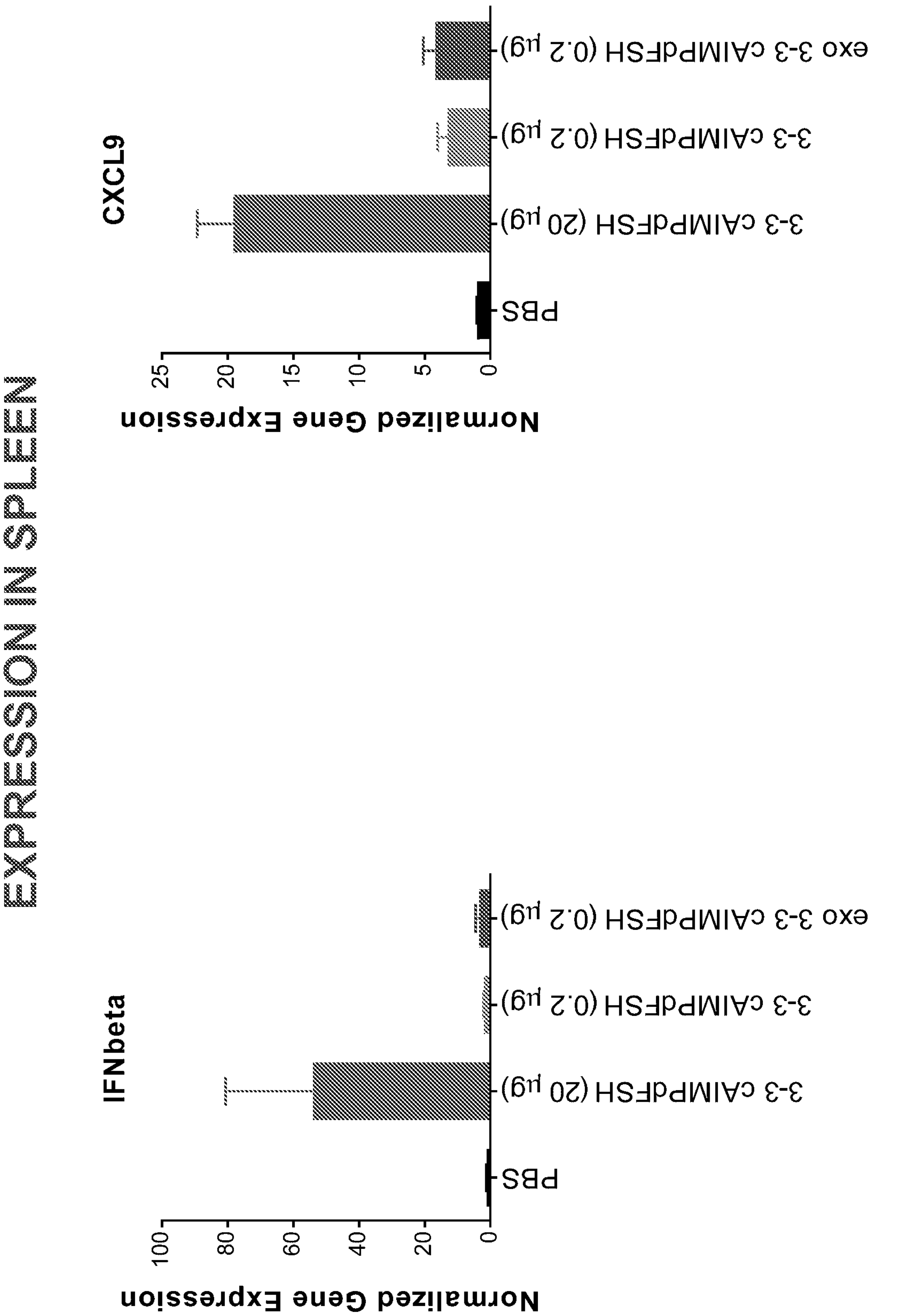
FIGS. 26A-26D show cytokine expression profiles (IFNβ, CXCL9, CXCL10, and IFN-γ, respectively) in the spleen of B16F10 tumor-bearing mice after a single intratumoral injection of PBS, 20 μg free 3-3 cAIMPdFSH, 0.2 μg free 3-3 cAIMPdFSH, or 0.2 μg exosome-encapsulated 3-3 cAIMPdFSH.
Figure 26D:
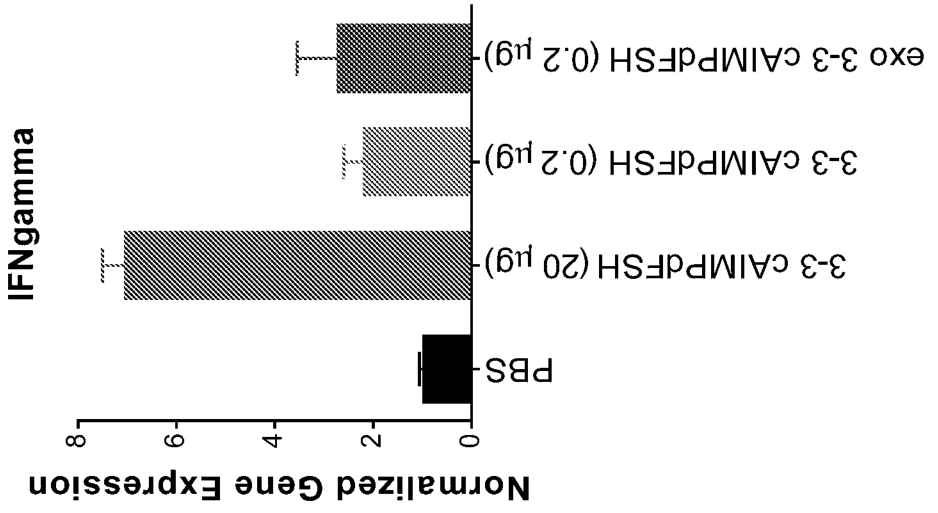
Figure 26C:
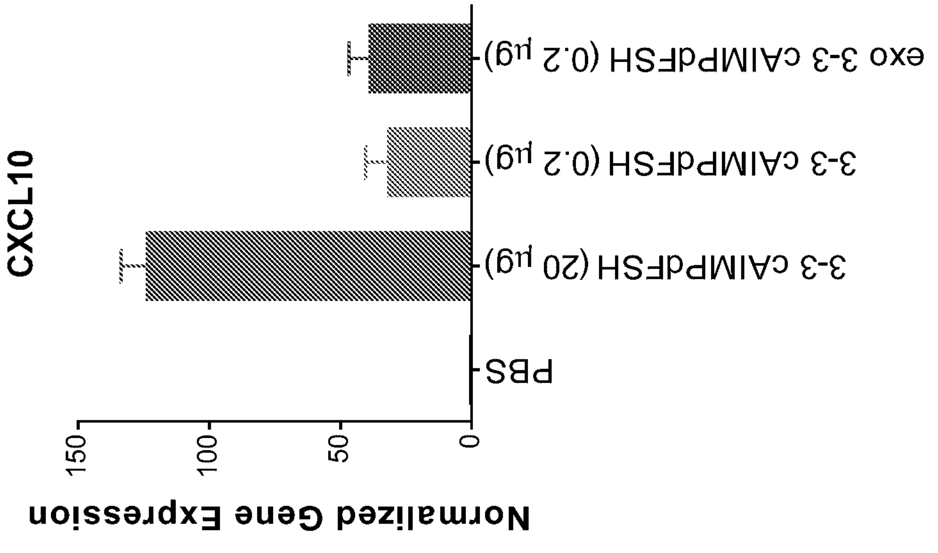
Figure 27A:
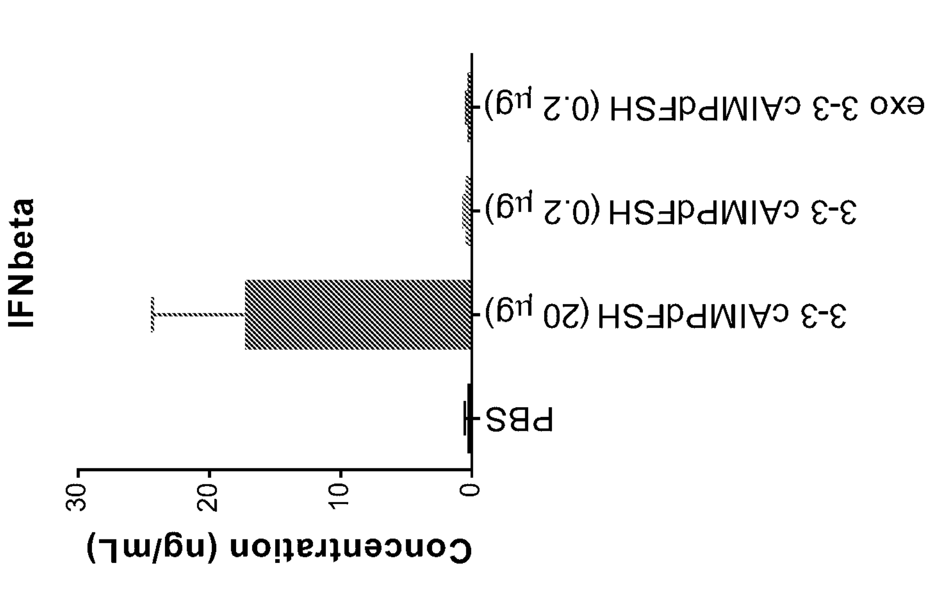
FIGS. 27A-27D show cytokine expression profiles (IFNβ, TNF-α, IL-6, and MCP-1, respectively) in the serum of B16F10 tumor-bearing mice after a single intratumoral injection of PBS, 20 μg free 3-3 cAIMPdFSH, 0.2 μg free 3-3 cAIMPdFSH, or 0.2 μg exosome-encapsulated 3-3 cAIMPdFSH.
Figure 27B:
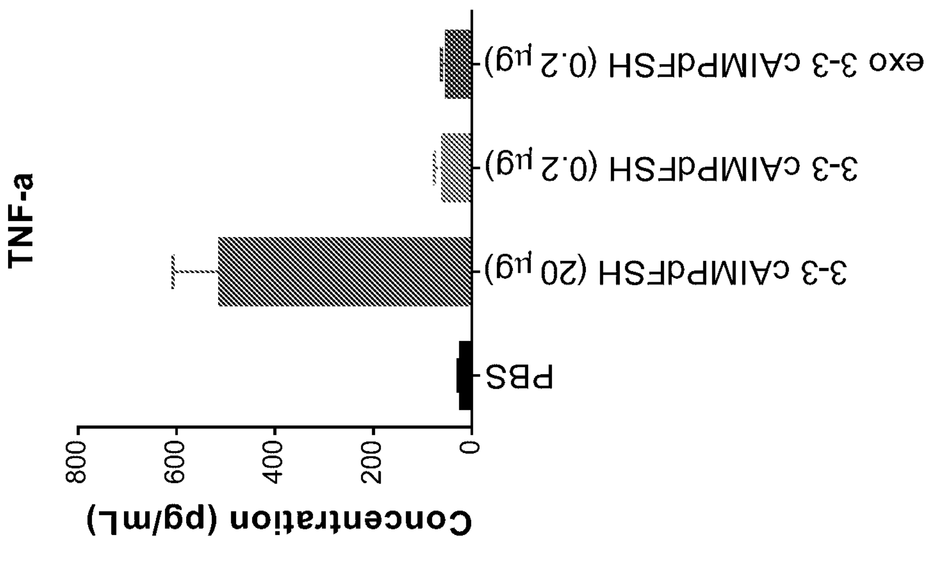
Figure 27C:
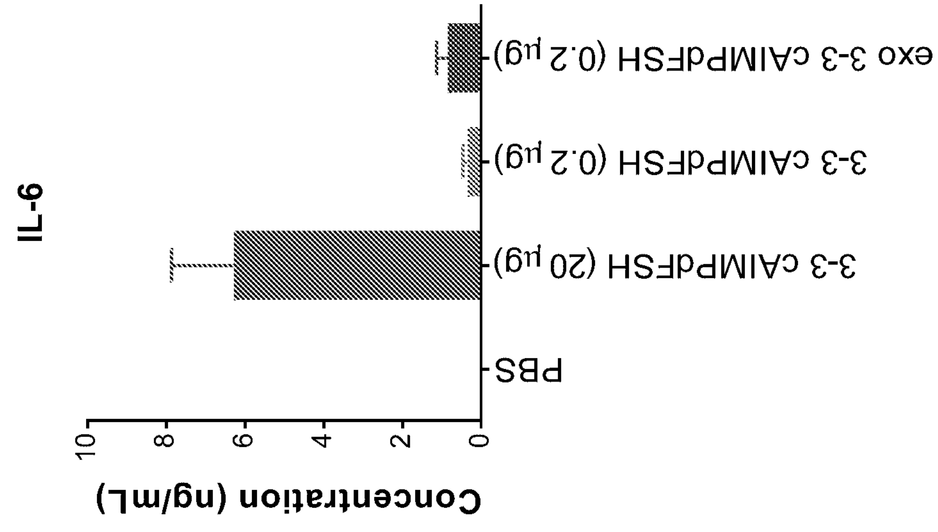
Figure 27D:
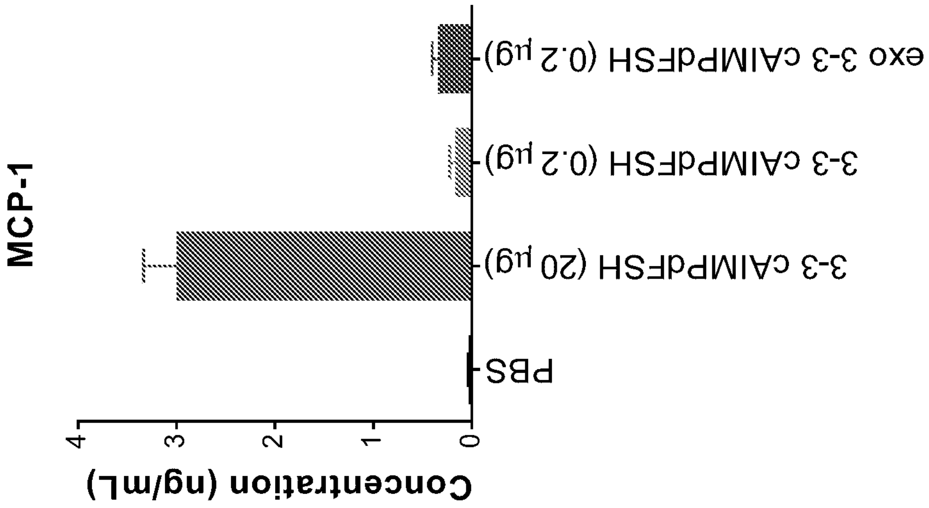

STING agonists are very potent pro-inflammatory molecules, and one potential clinical liability of these compounds is their induction of systemic toxicity due to free compound escaping the tumor injection site and diffusing into circulation. The draining lymph nodes of the exosome-STING agonist-treated tumor bearing mice showed comparable or slightly elevated IFNβ (FIG. 21A), CXCL9 (FIG. 21B), and CXCL10 (FIG. 21C) gene expression compared to the concentration-matched free STING agonist group, but dramatically reduced expression levels compared to the 100-fold higher free STING agonist treatment group. These results were more dramatic in the spleen (FIGS. 22A, 22B, and 22C) and the serum (FIG. 23A-23E), with the serum showing marked decreases in the pro-inflammatory cytokines IFNβ (FIG. 23A), TNF-α (FIG. 23B), and IL-6 (FIG. 23C) in the exosome-STING agonist group compared to either of the free STING agonist groups.

To confirm that the effects observed in FIGS. 20-23 were applicable to other STING agonists, B16F10 subcutaneous tumor-bearing mice were injected with 20 μg of free 3-3 cAIMPdFSH, 0.2 μg of free 3-3 cAIMPdFSH, or 0.2 μg of 3-3 cAIMPdFSH loaded in PTGFRN-overexpressing exosomes (exo 3-3 cAIMPdFSH). The cytokine levels in the tumor (FIGS. 24A-24D), draining lymph node (FIGS. 25A-25D), spleen (FIGS. 26A-26D), and serum (FIGS. 27A-27D) were measured and showed an expression pattern similar to the results shown in FIGS. 20-23 for ML RR-S2 CDA. Together these results demonstrate that exosome-encapsulated STING agonists can induce a potent IFN gene expression signature comparable to 100-fold greater free STING agonist after an intratumoral injection in vivo, and that this comparable gene expression pattern is largely limited to the tumor microenvironment and does not result in systemic inflammatory signals as is observed with the free STING agonist. Additionally, these effects were observed with two different STING agonists, demonstrating the broad applicability of using exosomes to deliver STING agonists to a tumor.

Figures 28A, 28B, 28C:
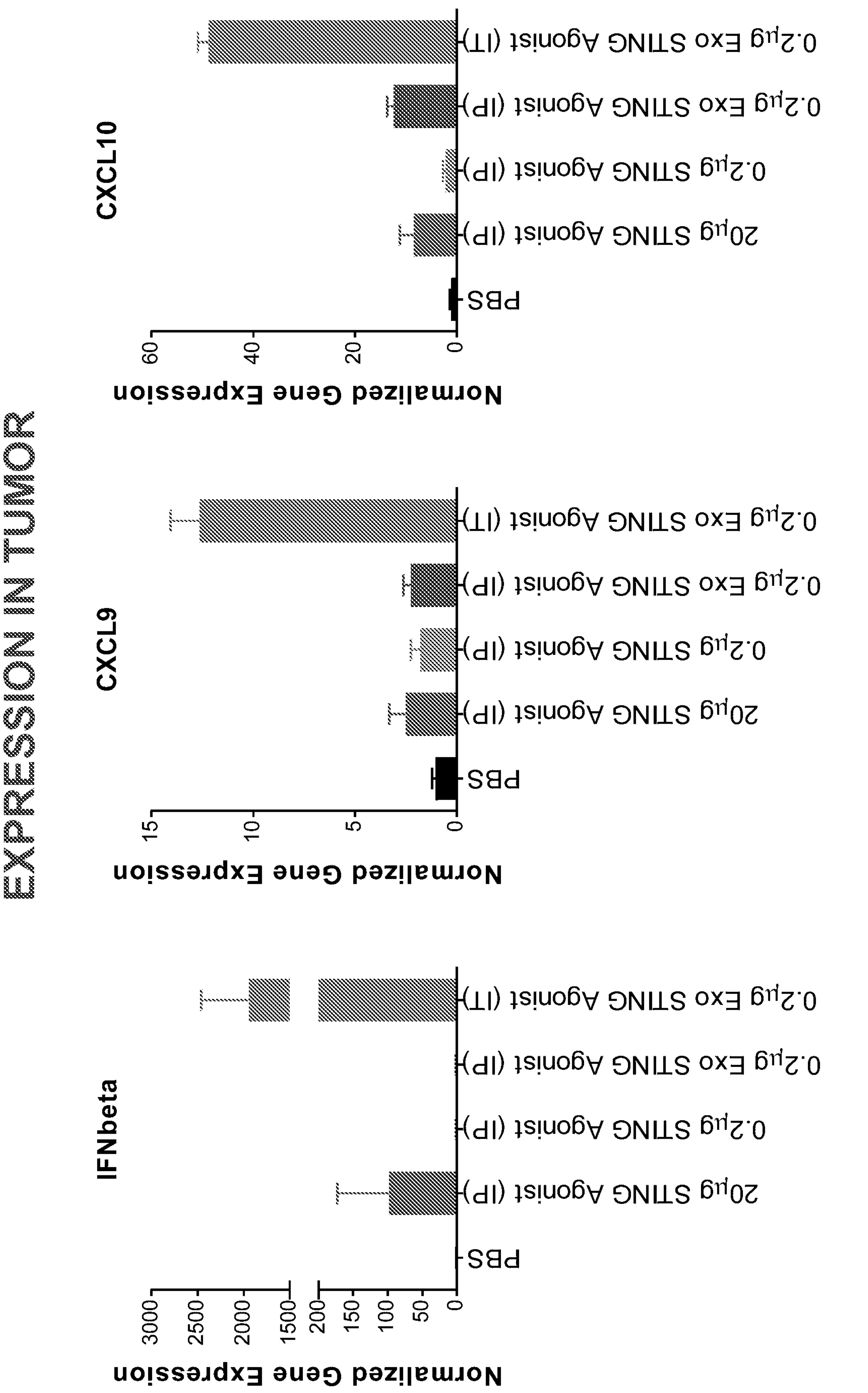
FIGS. 28A-C show cytokine expression profiles (IFNβ, CXCL9, and CXCL10, respectively) in the tumor of B16F10 tumor-bearing mice after a single intraperitoneal injection of PBS, 20 μg free ML RR-S2 CDA, 0.2 μg free ML RR-S2 CDA, or 0.2 μg exosome-encapsulated ML RR-S2 CDA, or a single intratumoral injection of 0.2 μg exosome-encapsulated ML RR-S2 CDA.
Figures 29A, 29B, 29C:
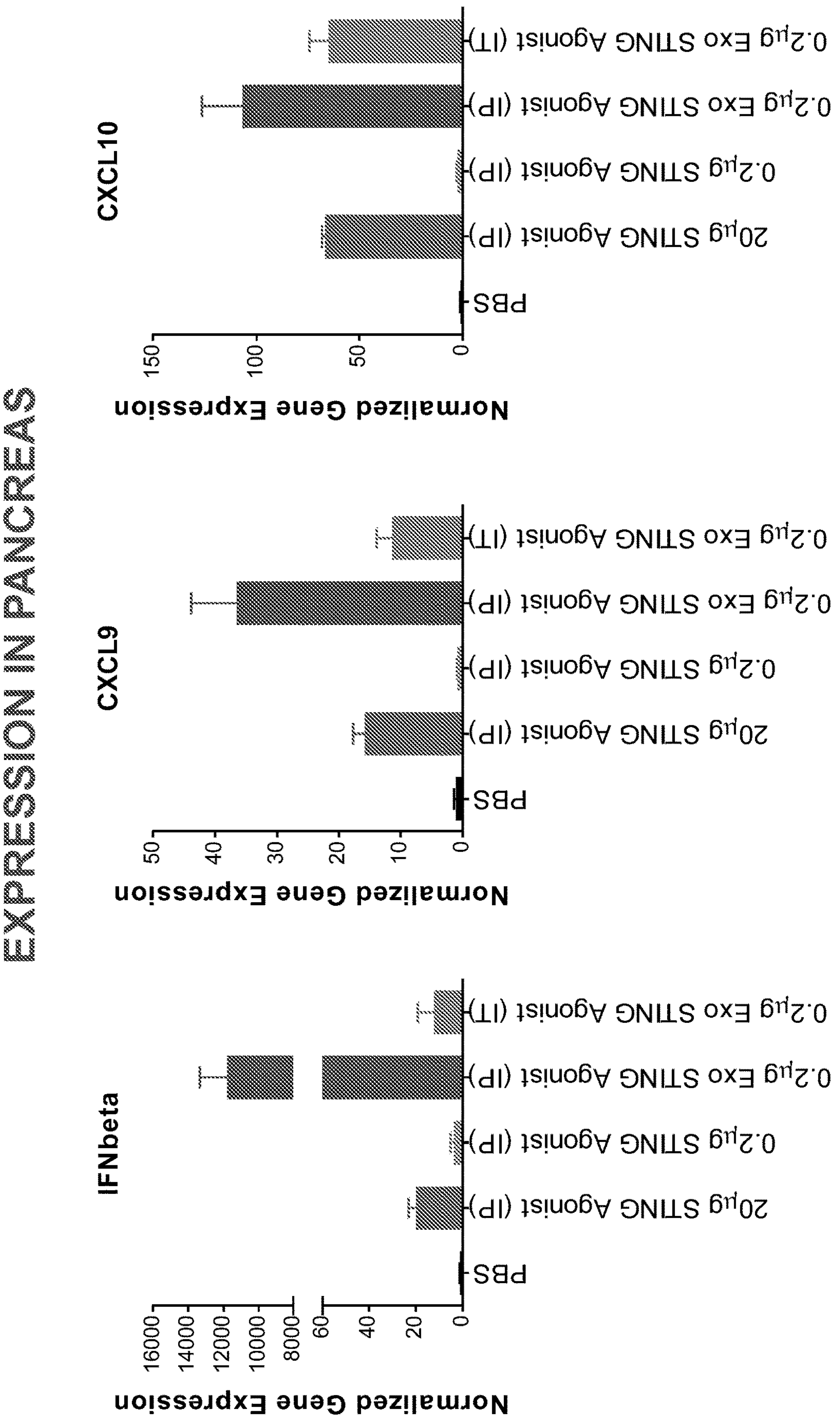
FIGS. 29A-C show cytokine expression profiles (IFNβ, CXCL9, and CXCL10, respectively) in the pancreas of B16F10 tumor-bearing mice after a single intraperitoneal injection of PBS, 20 μg free ML RR-S2 CDA, 0.2 μg free ML RR-S2 CDA, or 0.2 μg exosome-encapsulated ML RR-S2 CDA, or a single intratumoral injection of 0.2 μg exosome-encapsulated ML RR-S2 CDA.
Figures 30A, 30B, 30C:
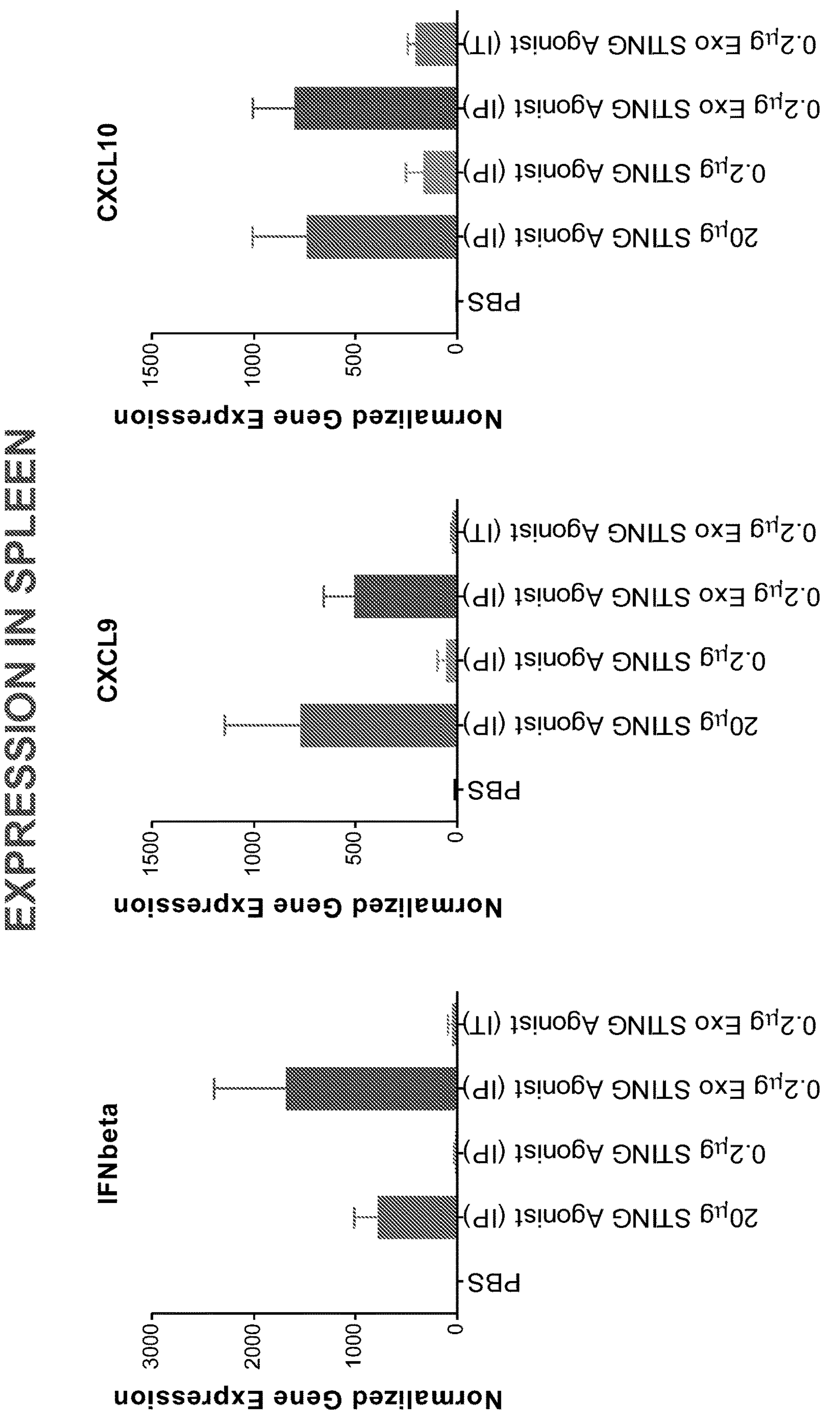
FIGS. 30A-30C show cytokine expression profiles (IFNβ, CXCL9, and CXCL10, respectively) in the spleen of B16F10 tumor-bearing mice after a single intraperitoneal injection of PBS, 20 μg free ML RR-S2 CDA, 0.2 μg free ML RR-S2 CDA, or 0.2 μg exosome-encapsulated ML RR-S2 CDA, or a single intratumoral injection of 0.2 μg exosome-encapsulated ML RR-S2 CDA.

Example 7: Comparative Local and Systemic Activation of STING Pathway after Intratumoral and Intraperitoneal Administration of Free STING Agonist and Exosome-Encapsulated STING Agonist in Tumor-Bearing Mice Five groups of C57BL/6 mice (n=4 mice per group) were inoculated subcutaneously with $5\times10^5$ B16F10 murine melanoma cells. Eight days post-inoculation the mice were injected intraperitoneally (IP) with a single dose of either PBS, 20 μg ML RR-S2, 0.2 μg ML RR-S2, 0.2 μg ML RR-S2 loaded in PTGFRN-overexpressing exosomes (Exo STING IP), or intratumorally (IT) with a single dose of 0.2 μg ML RR-S2 loaded in PTGFRN-overexpressing exosomes (Exo STING IT). The exosome-encapsulated STING agonist formulations were loaded and quantitated as described in Example 1. High-dose free STING agonist injected IP induced IFNβ expression in the tumor, pancreas, and spleen above the PBS-treated group. Exo STING IP, at a 100-fold lower dose, led to superior IFNβ expression in the pancreas (FIG. 29A) and spleen (FIG. 30A) and reduced IFNβ expression in the tumor (FIG. 28A) compared to high-dose free STING. CXCL9 and CXCL10 expression were similar in the tumor (FIGS. 28B-C) and spleen (FIGS. 30B-C) between these two groups but enhanced in the pancreas (FIGS. 29B-C) in the Exo STING IP group. Exo STING IT showed much greater STING pathway activation in the tumor compared to other groups but did not lead to robust expression changes in the spleen compared to the Exo STING IP or high-dose free STING agonist groups, and showed similar expression in the pancreas compared to high-dose free STING agonist. In the pancreas and spleen, STING pathway activation was consistently enhanced by Exo STING IP compared to concentration-matched low-dose free STING agonist, confirming an increase in potency for exosome encapsulated STING agonist. Importantly, Exo STING IP led to a comparable or, in some cases, enhanced potency compared to a 100-fold greater dose of free STING agonist in the pancreas and spleen. These results suggest that regional IP administration of STING agonist-loaded exosomes at a low dose can induce a potent immune response in tissues including the pancreas, presenting an opportunity for regional administration to treat pancreatic and other peritoneal cancers.

Figure 31A:
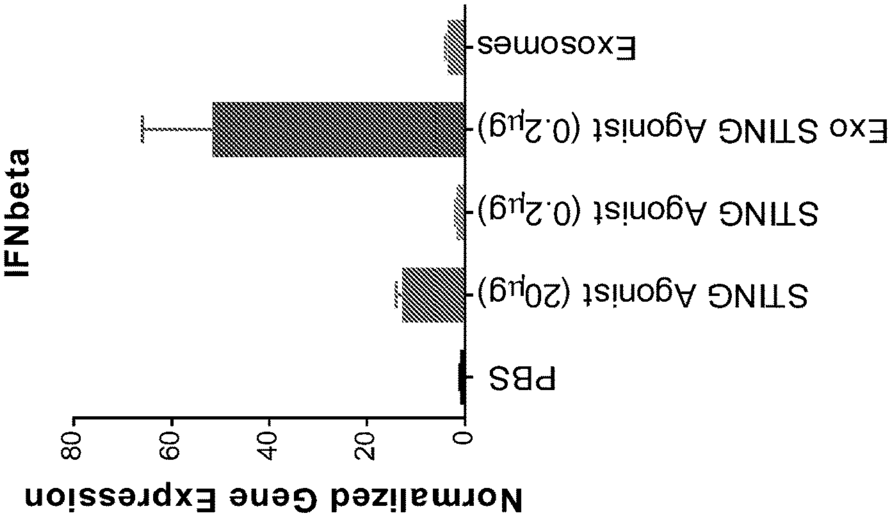
FIGS. 31A-31C show cytokine expression profiles (IFNβ, CXCL9, and CXCL10, respectively) in the lung of naïve mice after a single intraperitoneal injection of PBS, 20 μg free ML RR-S2 CDA, 0.2 μg free ML RR-S2 CDA, 0.2 μg exosome-encapsulated ML RR-S2 CDA, or an equal number of exosomes.
Figure 31B:
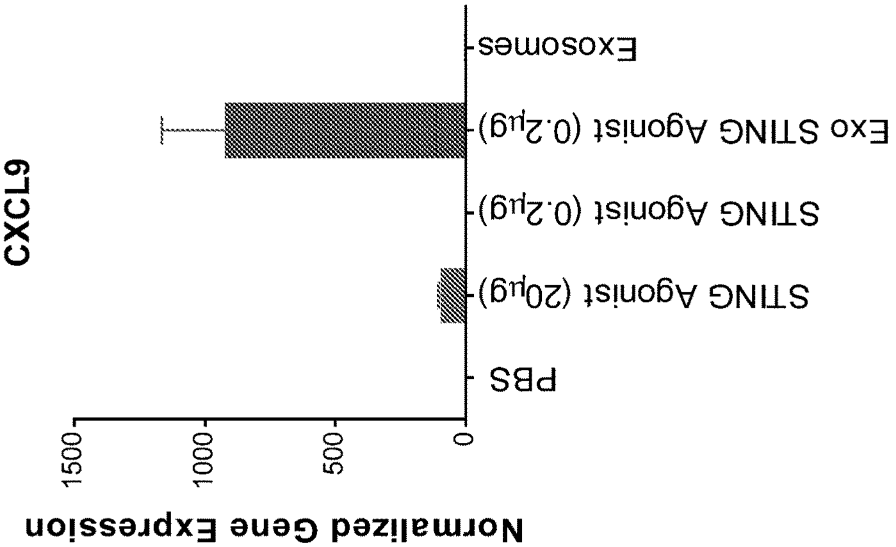
Figure 31C:
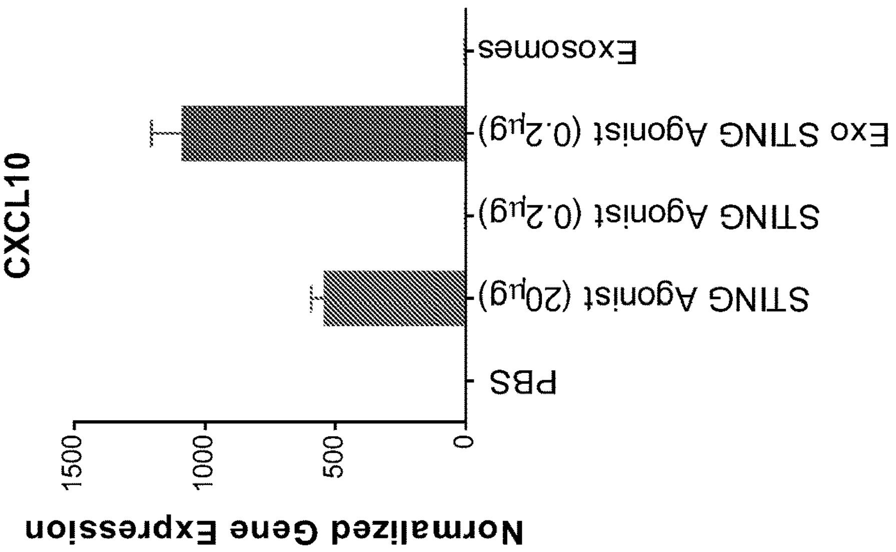
Figure 32A:
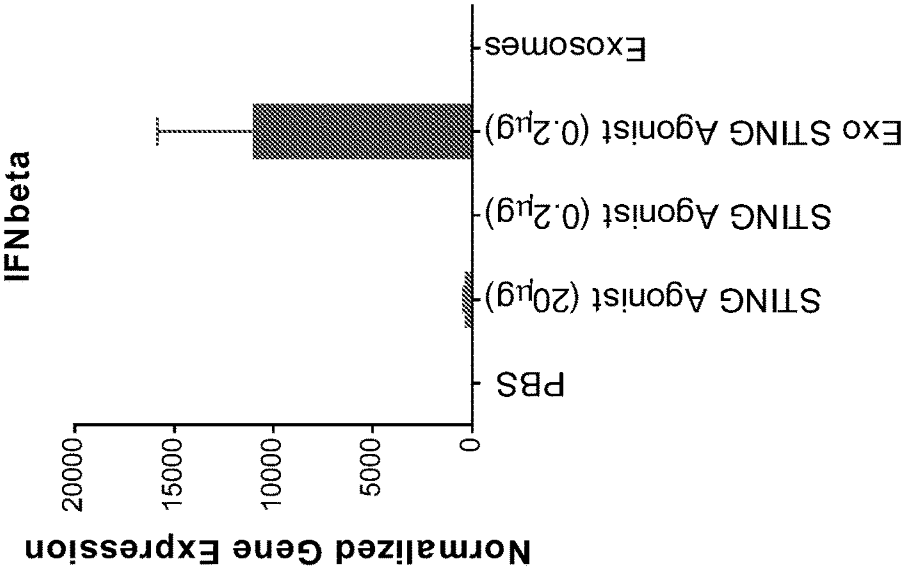
FIGS. 32A-32C show cytokine expression profiles (IFNβ, CXCL9, and CXCL10, respectively) in the spleen of naïve mice after a single intraperitoneal injection of PBS, 20 μg free ML RR-S2 CDA, 0.2 μg free ML RR-S2 CDA, 0.2 μg exosome-encapsulated ML RR-S2 CDA, or an equal number of exosomes.
Figure 32B:
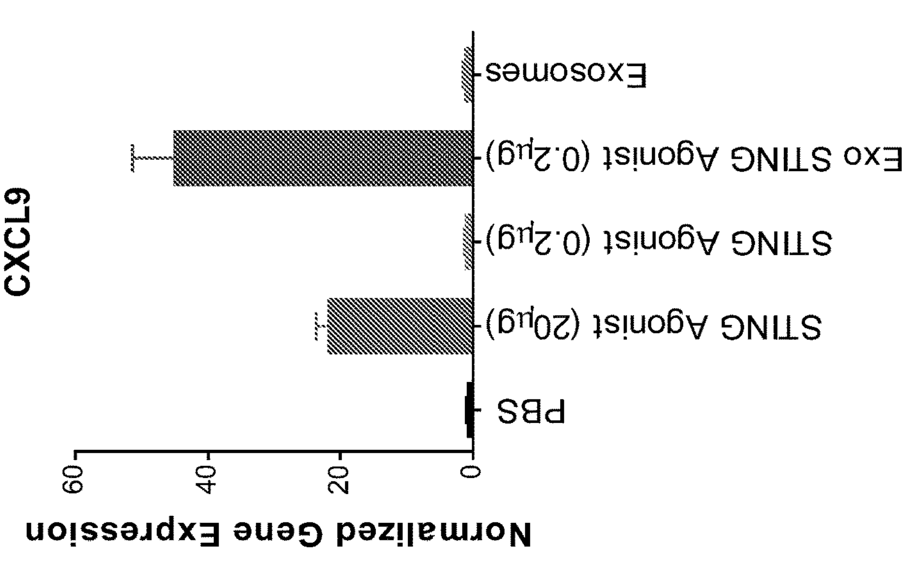
Figure 32C:
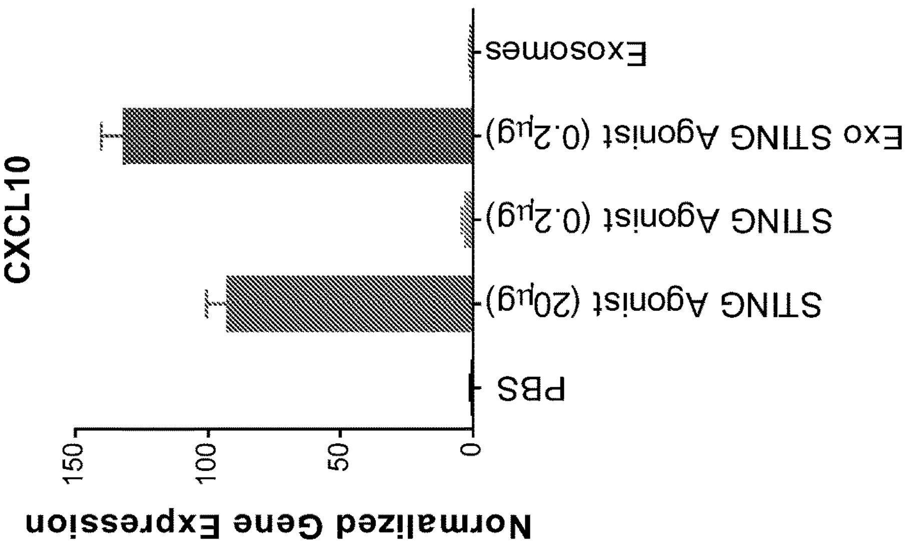
Figures 33A, 33B, 33C:
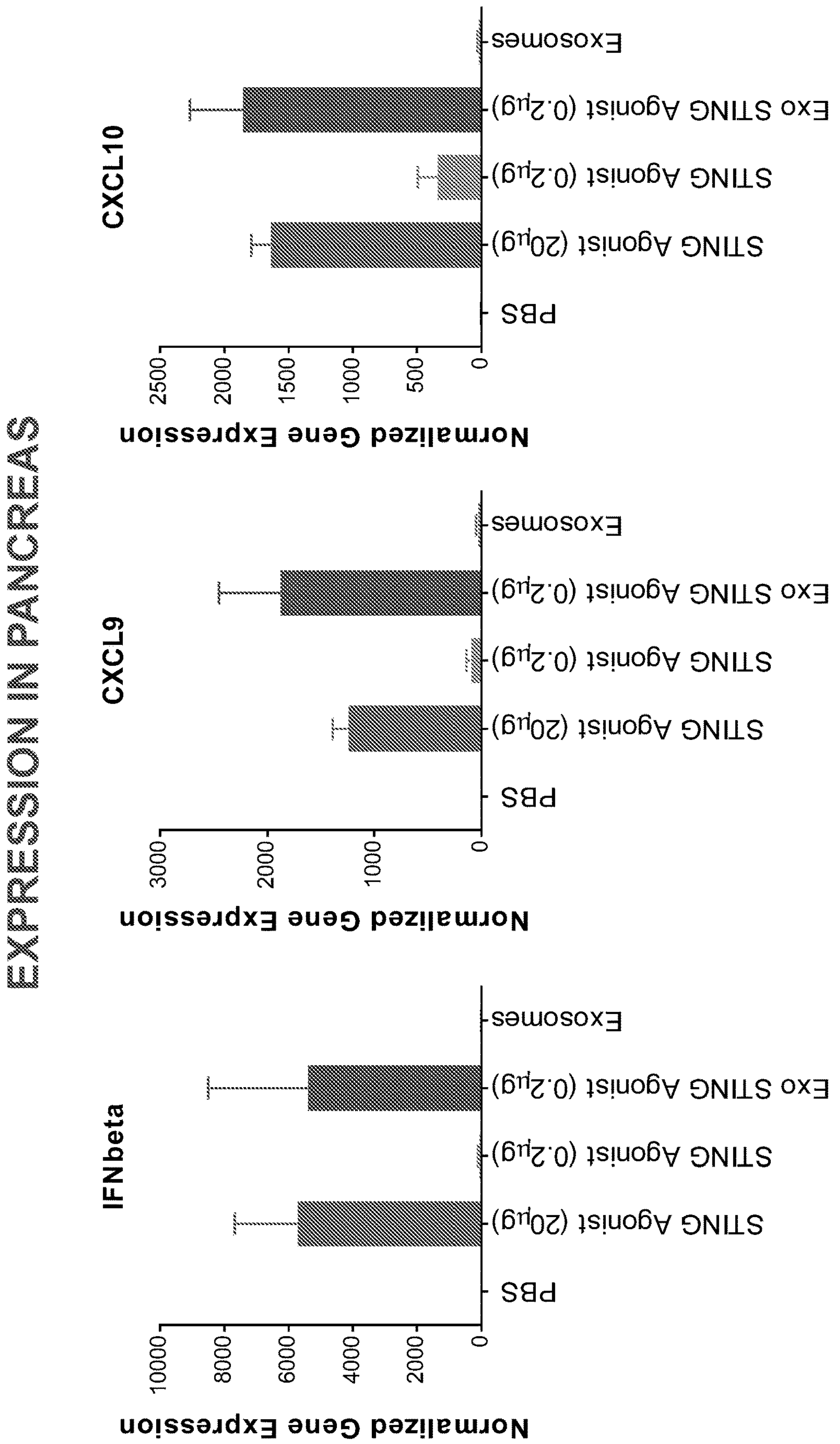
FIGS. 33A-33C show cytokine expression profiles (IFNβ, CXCL9, and CXCL10, respectively) in the pancreas of naïve mice after a single intraperitoneal injection of PBS, 20 μg free ML RR-S2 CDA, 0.2 μg free ML RR-S2 CDA, 0.2 μg exosome-encapsulated ML RR-S2 CDA, or an equal number of exosomes.
Figures 34A, 34B:
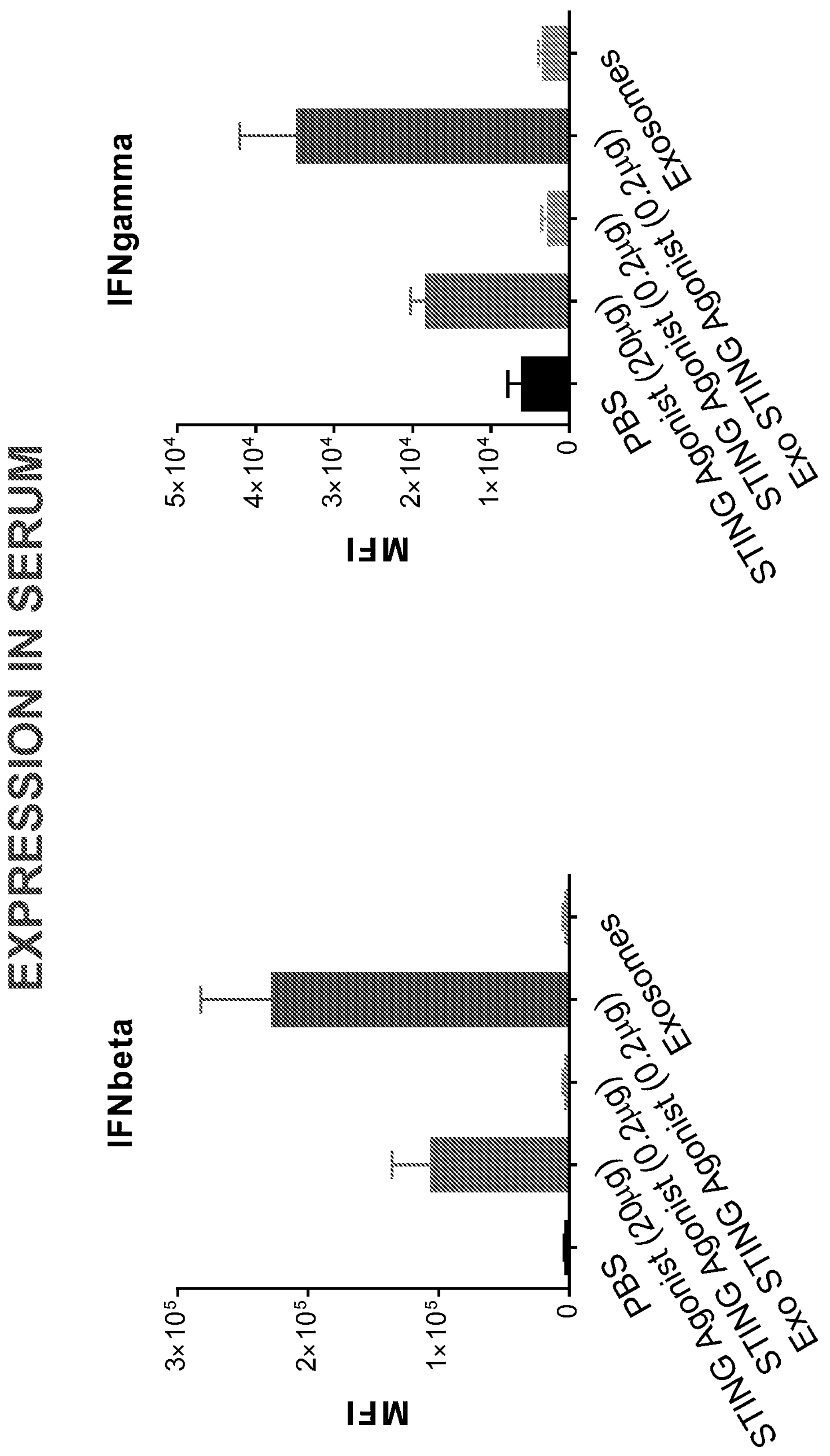
FIGS. 34A-34G show cytokine expression profiles (IFN-β, IFN-γ, TNF-α, IL-6, MCP-1, IL-1a, and IL-27 respectively) in the serum of naïve mice after a single intraperitoneal injection of PBS, 20 μg free ML RR-S2 CDA, 0.2 μg free ML RR-S2 CDA, 0.2 μg exosome-encapsulated ML RR-S2 CDA, or an equal number of exosomes.
Figures 34C, 34D:
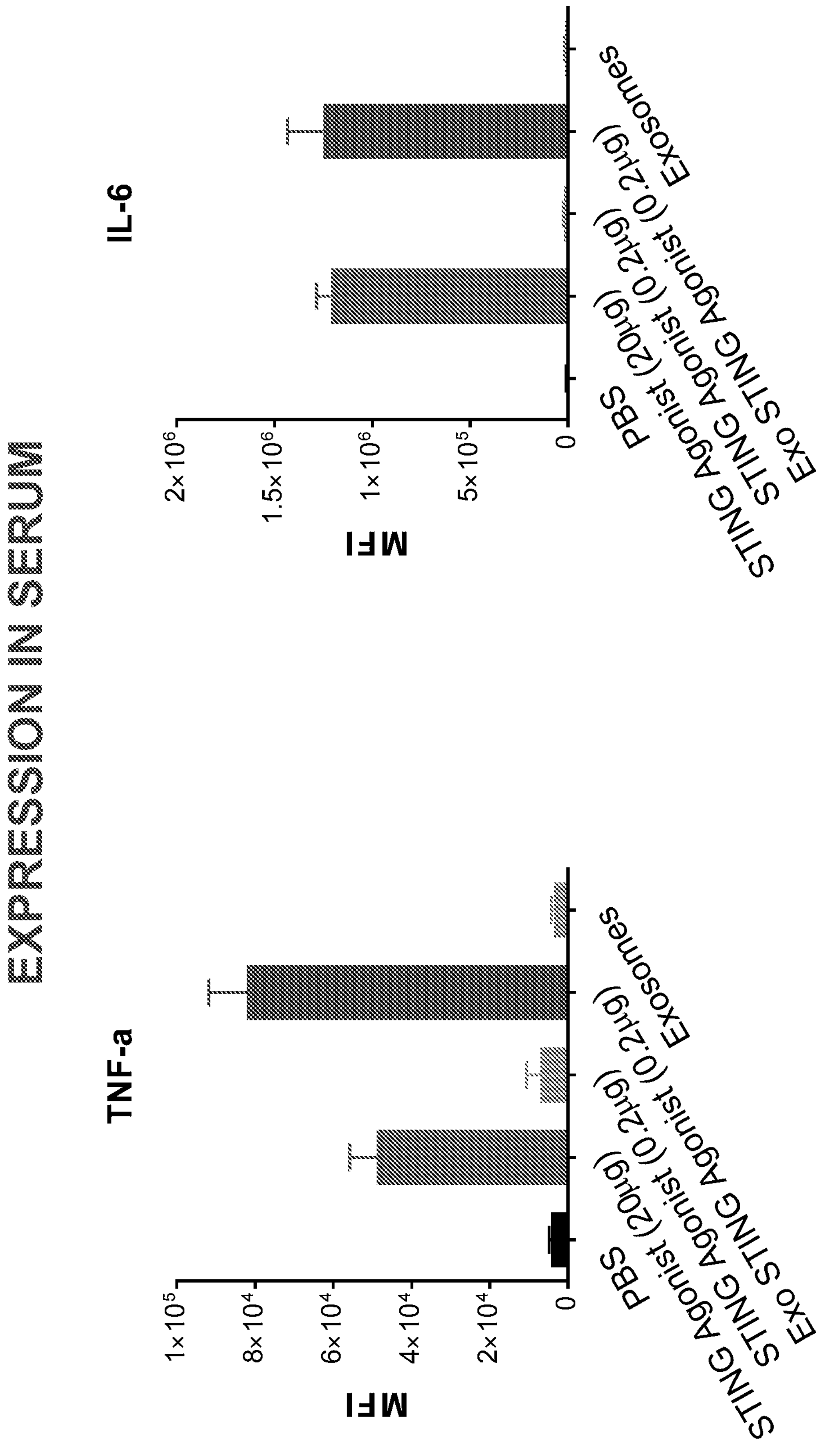
Figure 34F:
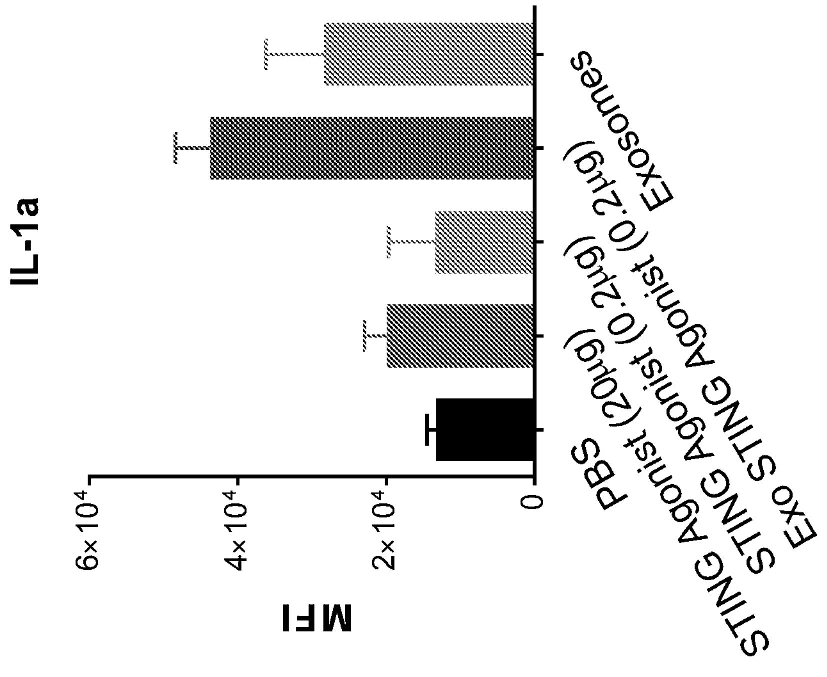
Figure 34E:
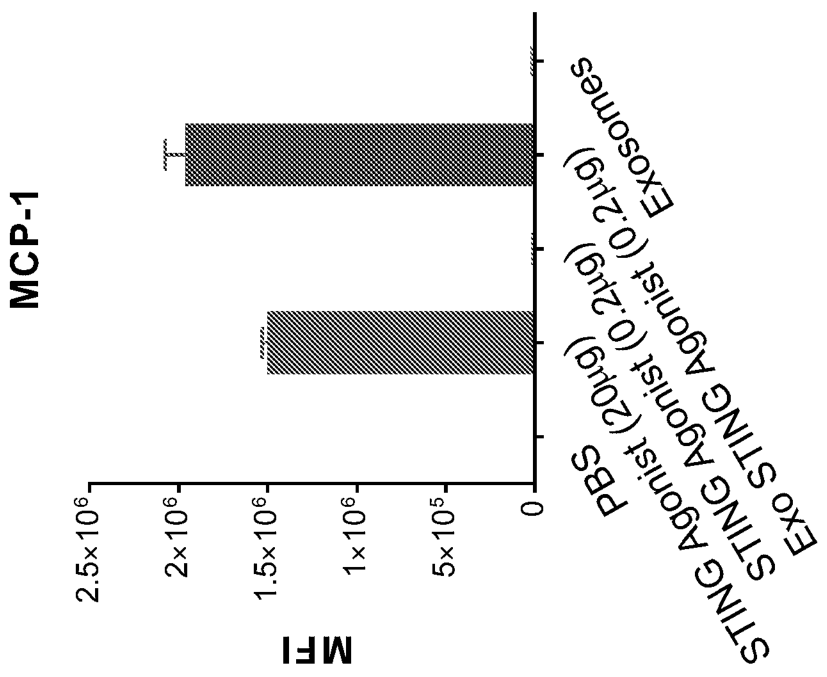
Figure 34G:
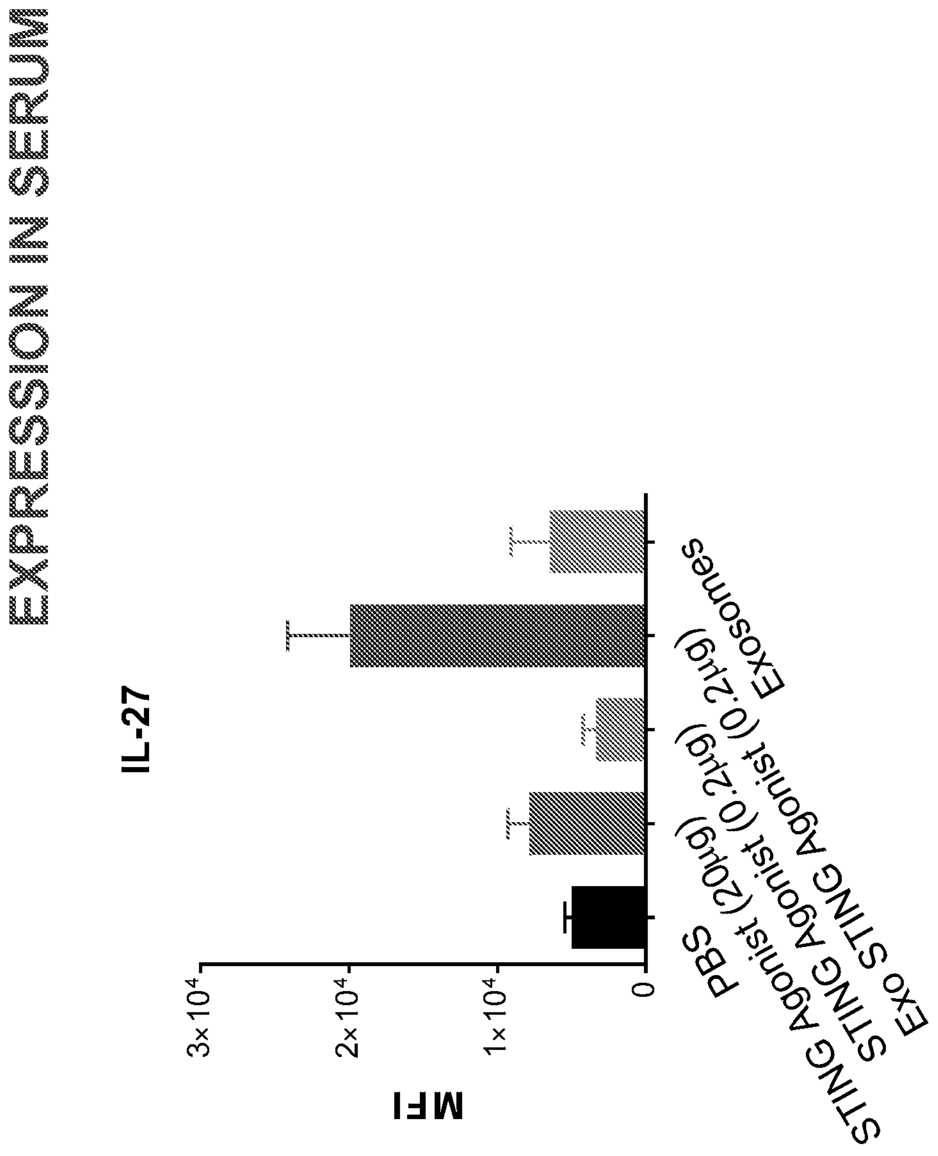

Example 8: Differential STING Pathway Signaling in Naïve Mice In Vivo with Exosome-Encapsulated STING Agonists and Free STING Agonists Naïve C57BL/6 mice were injected intraperitoneally (IP) with a single dose of either PBS, 20 μg ML RR-S2, 0.2 μg ML RR-S2, or 0.2 μg ML RR-S2 loaded in PTGFRN-overexpressing exosomes (Exo STING), which were formulated and quantitated as described in Example 1 (n=5 mice per group). Lung, spleen, pancreas, and serum were isolated four hours post-injection and analyzed for gene expression and cytokine production. IFNβ, CXCL9, and CXCL10 expression were dramatically higher in the lungs (FIGS. 31A-C) and spleens (FIGS. 32A-C) of Exo STING-treated mice compared to mice receiving a 100-fold higher dose of free STING agonist, while pancreatic gene expression profiles were similar between these two groups (FIGS. 33A-C). Similarly, serum cytokine levels in Exo STING-treated mice were greater than or equal to mice treated with a 100-fold higher dose of free STING agonist (FIGS. 34A-G). Together, these results demonstrate that exosomes loaded with a STING agonist are significantly more potent activators of the STING pathway in vivo compared to equal amounts of free STING agonists, and that exosome-loaded STING agonists therefore may provide a differentiated therapeutic application, especially in the context of reducing systemic toxicity of high doses of free STING agonists and enhancing expression of T-cell chemoattractants.

Figure 35:
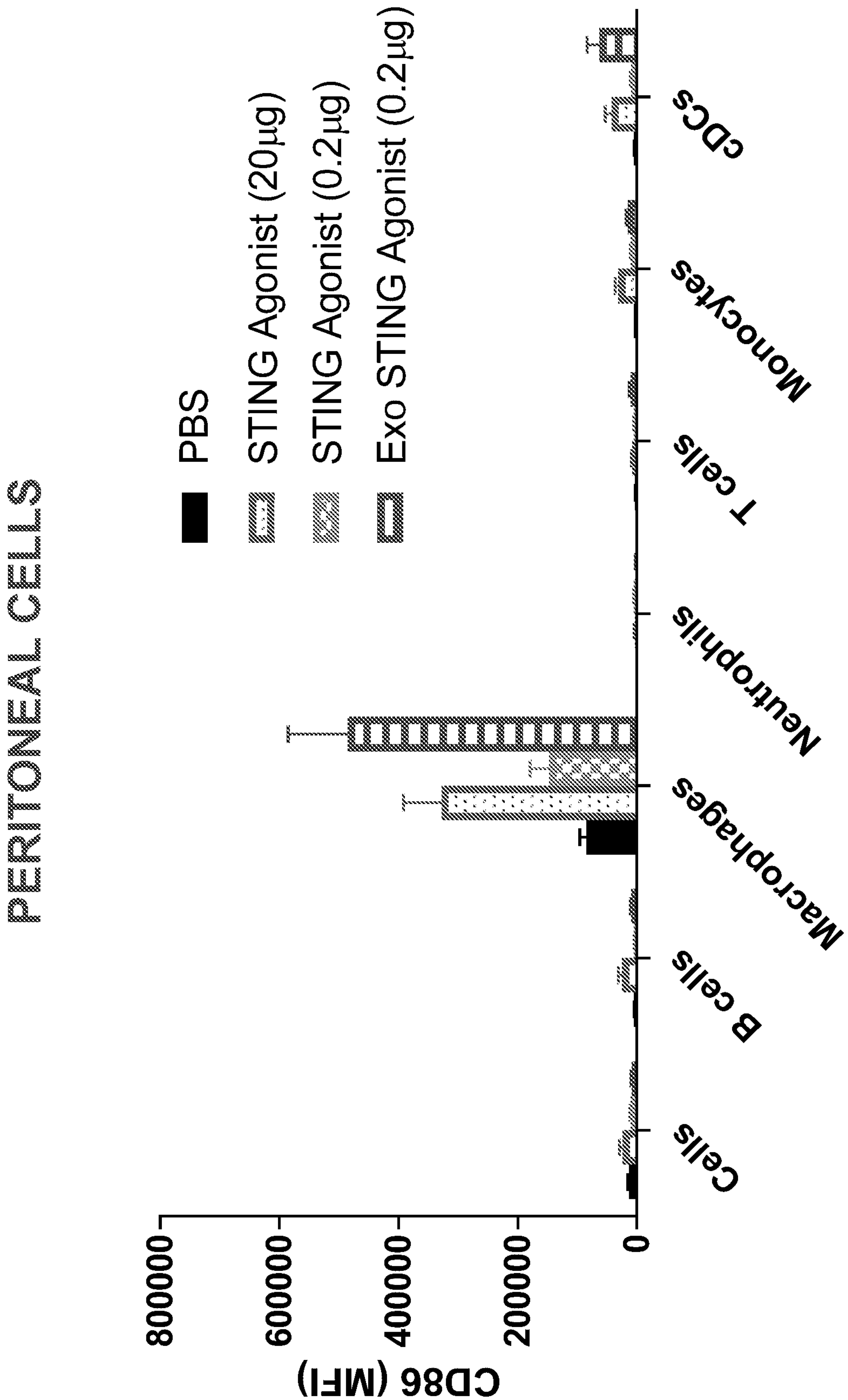
FIG. 35 shows immune cell activation profiles in the peritoneum 24 hours after a single intraperitoneal injection of PBS, 20 μg free ML RR-S2 CDA, 0.2 μg free ML RR-S2 CDA, 0.2 μg exosome-encapsulated ML RR-S2 CDA.
Figure 36:
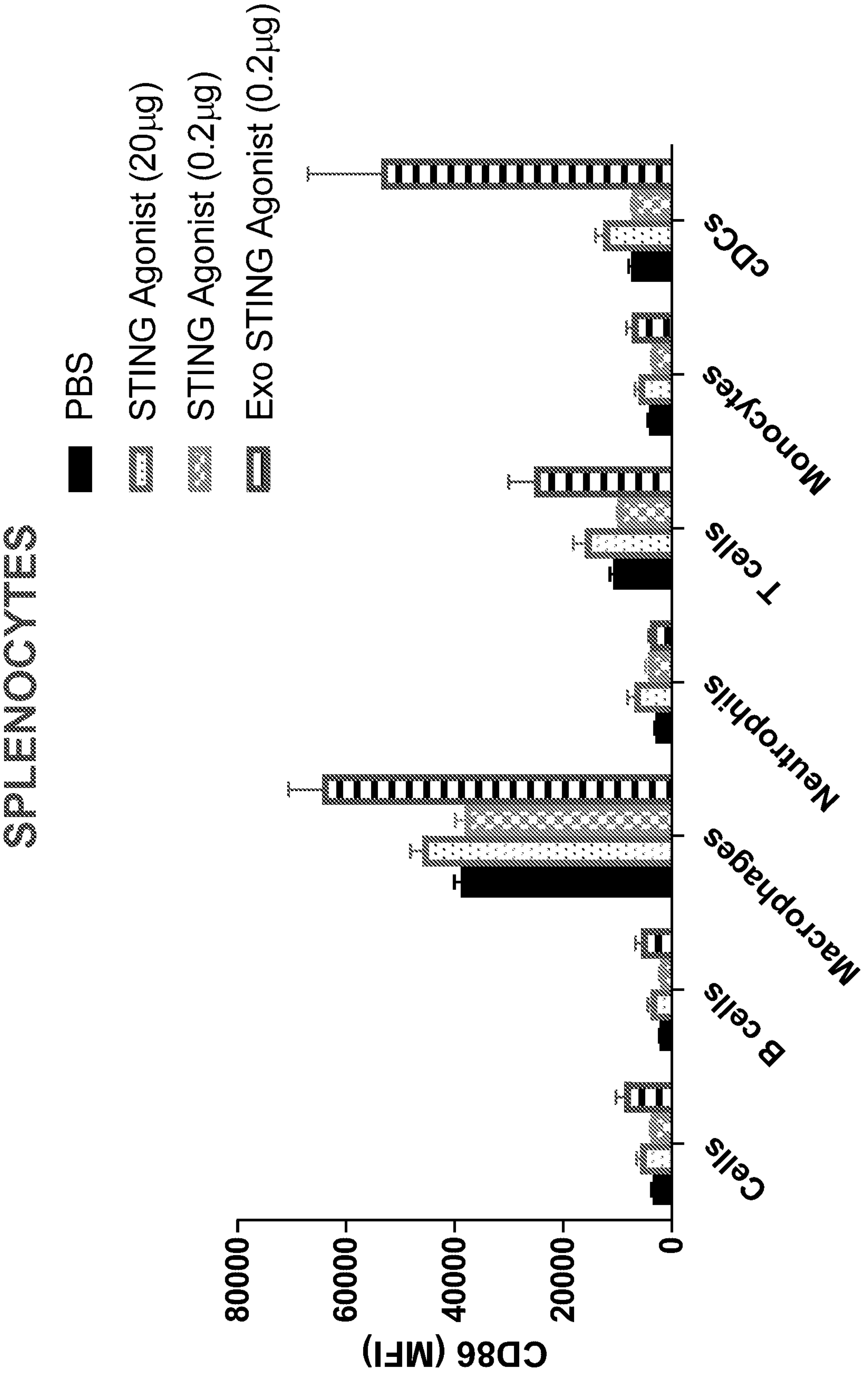
FIG. 36 shows immune cell activation profiles in the spleen 24 hours after a single intraperitoneal injection of PBS, 20 μg free ML RR-S2 CDA, 0.2 μg free ML RR-S2 CDA, 0.2 μg exosome-encapsulated ML RR-S2 CDA.

A second experiment similar to the previous study was carried out with single-dose IP administration, and extended to 24 hours. Peritoneal cells and splenocytes were isolated from treated mice, and cell activation was measured by detection of CD86. High doses of free STING agonist resulted in activation of peritoneal B cells, macrophages, monocytes and conventional dendritic cells (cDCs), while Exo STING at a 100-fold lower dose induced greater activation of macrophages, similar activation of cDCs, and attenuated activation of B-cells and monocytes (FIG. 35). In the spleen, high dose STING agonist induced moderate levels of immune cell activation, while Exo STING at a 100-fold lower dose induced greater macrophage and T-cell activation, and dramatically greater cDC activation, suggesting a cell-type uptake/delivery preference for exosomes in cDCs and macrophages in vivo (FIG. 36). These results demonstrate that exosomes loaded with a STING agonist can induce a specific cellular response in vivo in antigen presenting cells, which are the primary mediators of STING pathway-induced anti-tumor and anti-pathogenic responses.

Figure 37A:
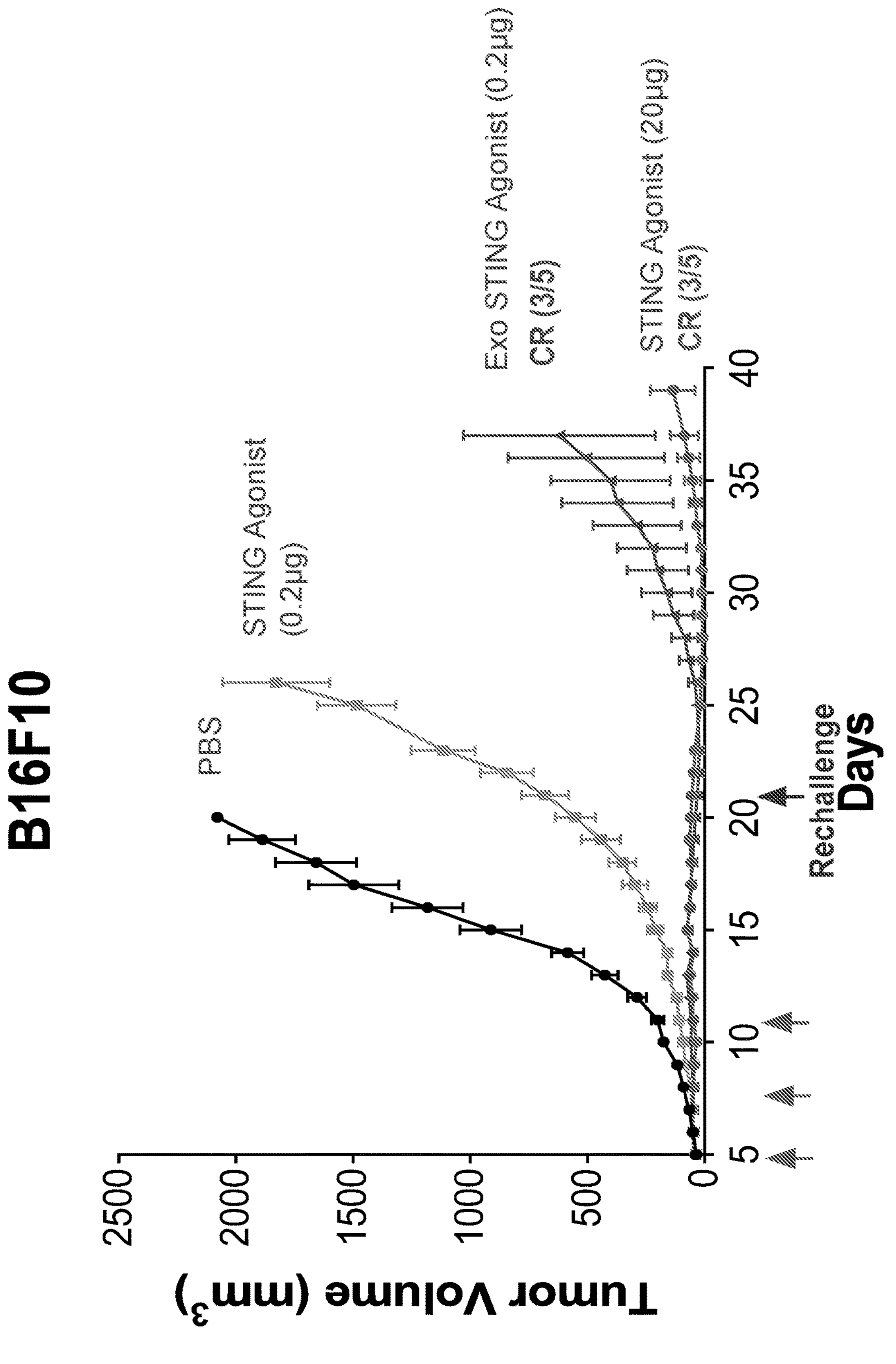
FIG. 37A shows tumor growth curves in B16F10 tumor-bearing mice over the course of the study described in Example 9 (i.e., an intratumoral injection study comparing the efficacy of PBS, 20 μg free ML RR-S2 CDA, 0.2 μg free ML RR-S2 CDA, 0.2 μg exosome-encapsulated ML RR-S2 CDA).
Figure 37B:
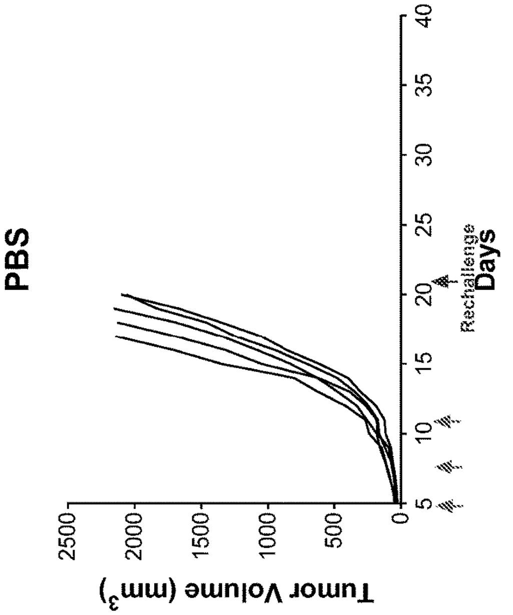
FIGS. 37B-37E show the tumor growth curves for each animal in the different groups (i.e., PBS, STING agonist (20 μg), STING agonist (0.2 μg), and Exo STING agonist (0.2 μg), respectively).
Figure 37C:
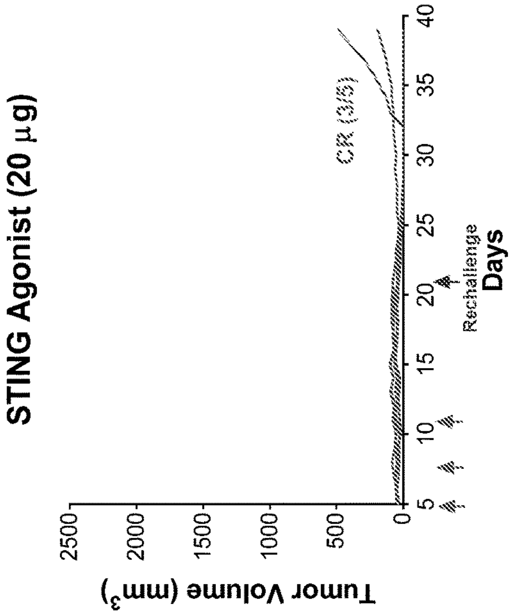
Figure 37D:
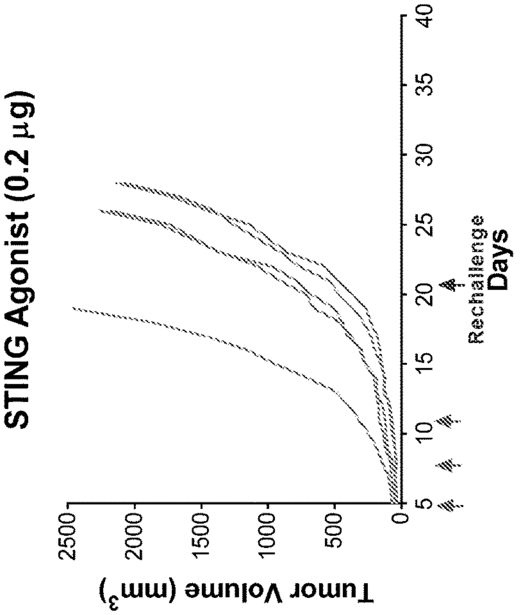
Figure 37E:
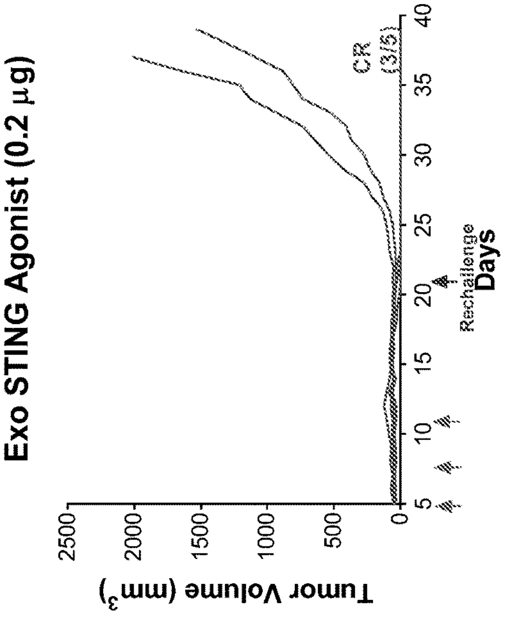

Example 9: Comparative In Vivo Efficacy of STING Agonist-Loaded Exosomes and Free STING Agonist in a Murine Model of Melanoma The results of the previous Examples suggest that Exo STING may be a more potent anti-tumor formulation than equal or greater amounts of soluble STING agonist. To test this hypothesis, C57BL/6 mice were inoculated subcutaneously with $5\times10^5$ B16F10 murine melanoma cells (n=5 mice per group). Five, eight, and eleven days post-inoculation the mice were injected intratumorally with PBS, 20 μg ML RR-S2, 0.2 μg ML RR-S2, or 0.2 μg ML RR-S2 loaded in PTGFRN-overexpressing exosomes Tumor volumes were measured daily until day 39, and animals were sacrificed when tumor volume reached 2000 $mm^3$. Compared to the PBS control group, tumor growth was moderately potentiated after treatment with 0.2 μg free STING agonist and almost completely eliminated upon treatment with 20 μg free STING agonist at day 25. Surprisingly, treatment with 0.2 μg of Exo STING resulted in dramatically improved tumor regression compared to the concentration-matched free STING agonist group and to a similar extent as the high-dose free STING agonist group at day 25. Notably, treatment with Exo STING and high dose free STING agonist led to a complete response (defined as undetectable tumors at the site of inoculation; CR) in three out of five animals in each group (FIGS. 37A-E). FIG. 37A shows the average tumor growth in the animal groups and FIGS. 37B-D shows the tumor growth in individual mice in each treatment group.

Figure 38A:
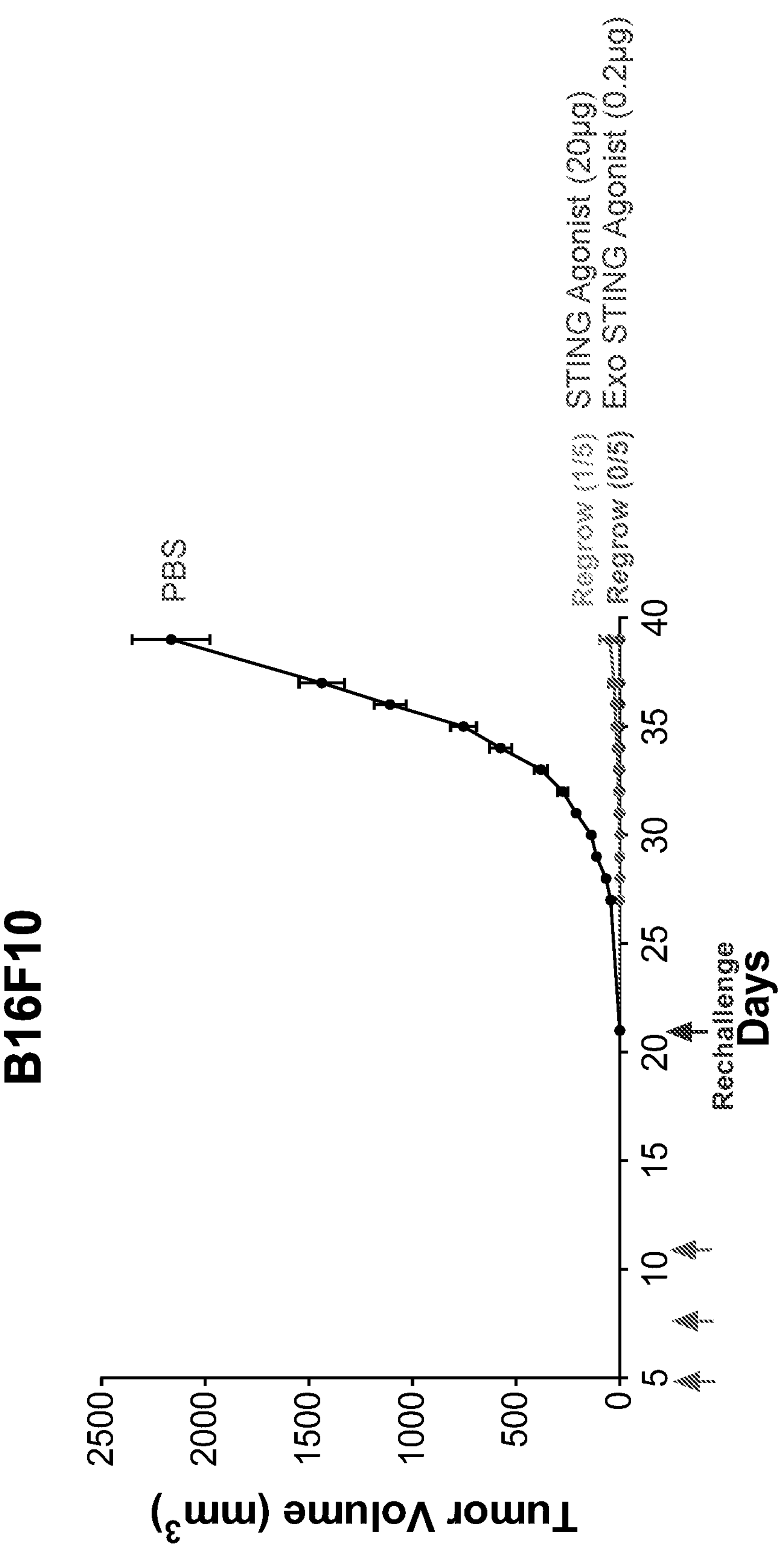
FIG. 38A shows the tumor growth curves in B16F10 tumor-bearing mice previously treated with STING agonists as described in FIG. 37A after re-challenge with a second tumor cell inoculation.
Figure 38B:
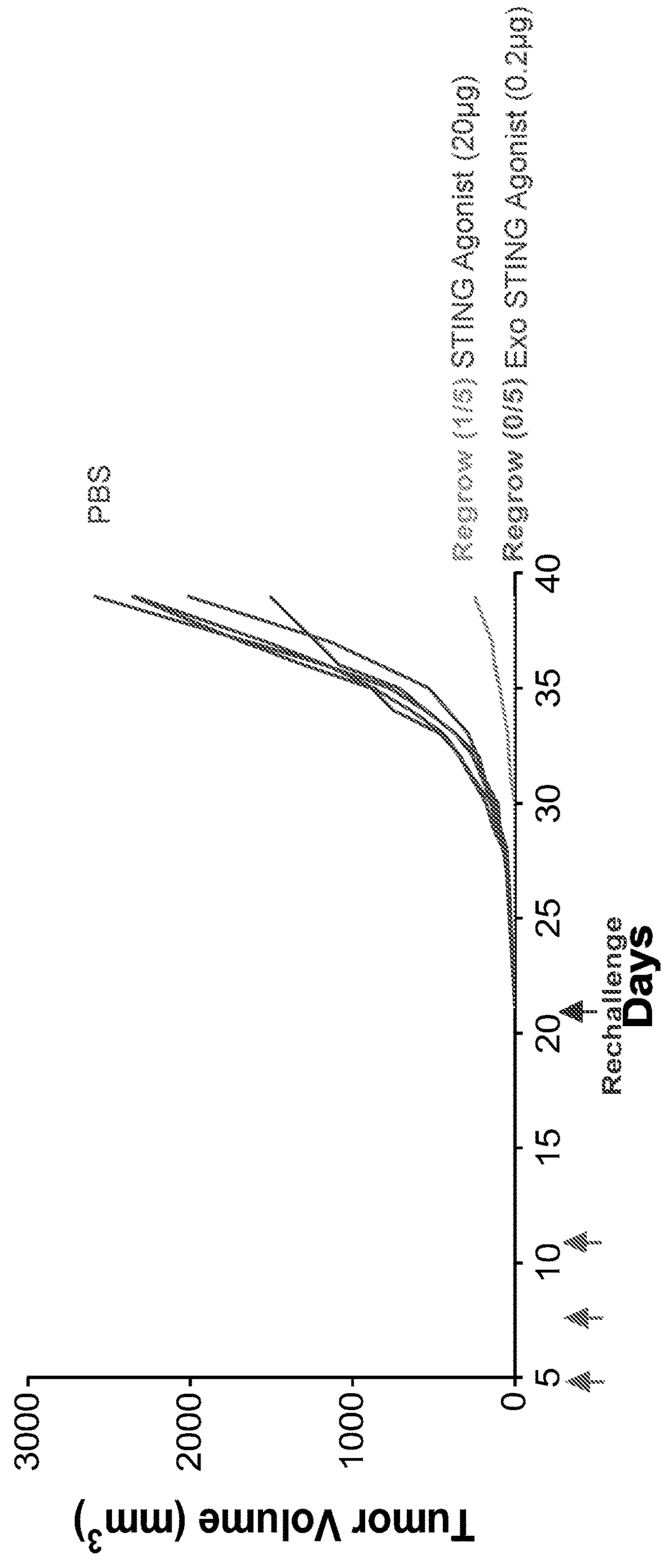
FIG. 38B shows the tumor growth curves for each animal in the different groups.
Figure 38C:
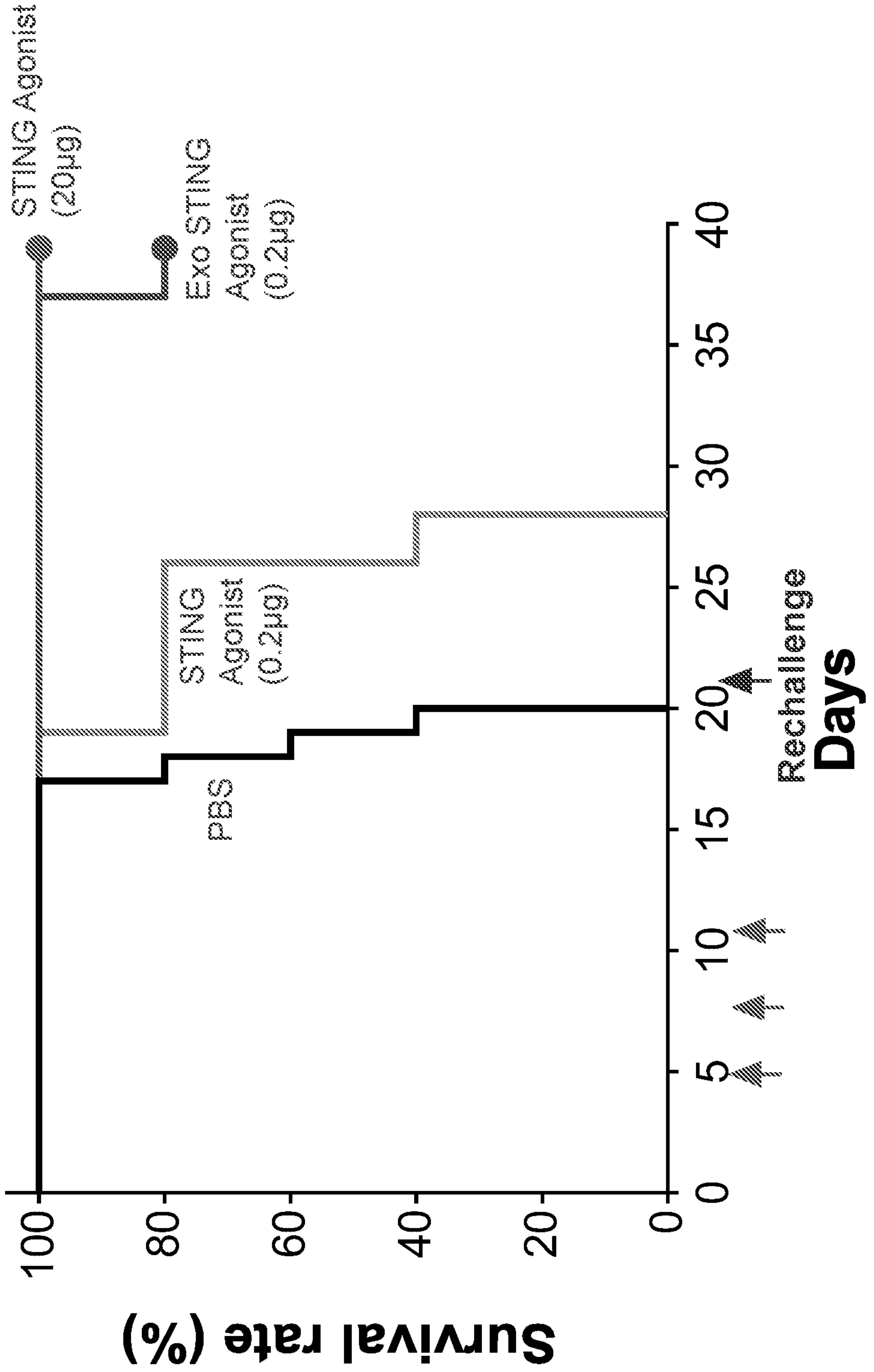
FIG. 38C shows the viability of the animals in the study described in FIG. 37A.

STING pathway activation leads to memory T-cell recruitment and ultimately a durable adaptive immune response. To determine whether the anti-tumor effects in this study led to an immune response, the five animals in the high dose STING agonist and Exo STING groups were re-challenged on day 21 by transplantation of $5\times10^5$ B16F10 cells on the opposite flank. Five additional naïve mice were inoculated with the same tumor cell preparation and treated daily with PBS to ensure cell viability and growth kinetics. By day 39 (18 days post-challenge) all mice in the PBS group were sacrificed. Tumors in animals from the high-dose free STING agonist group failed to grow in four out of 5 animals, while remarkably, tumor growth was undetectable in all five mice in the Exo STING group (FIGS. 38A-D). FIG. 38A shows the average tumor growth in the animal groups and FIG. 38B shows the tumor growth in individual mice. FIG. 38C shows the survival rate of each treatment group. Notably, although two animals in the Exo STING group were refractory to treatment in the primary tumors, these animals did not exhibit tumor growth at the sites of re-challenge, demonstrating the robustness of the immune response mediated by STING agonists loaded in exosomes (FIGS. 37A-E and 38A-C).

Figure 39:
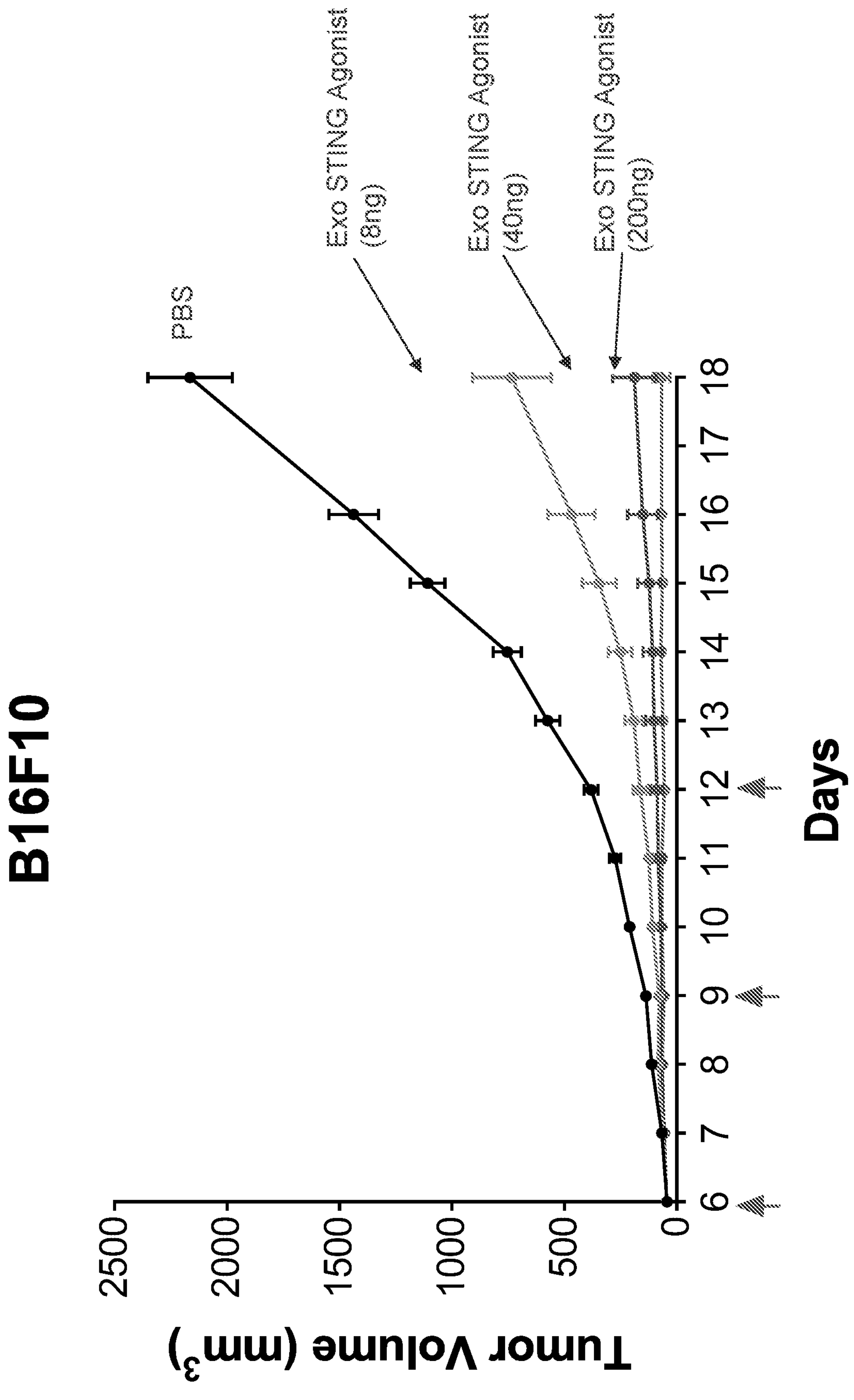
FIG. 39 shows the tumor growth curves during the course of the study described in Example 10 (an intratumoral injection dose-titration study comparing the efficacy of 8 ng, 40 ng, and 200 ng of exosome-encapsulated ML RR-S2 CDA in B16F10 tumor-bearing mice).
Figure 40A:
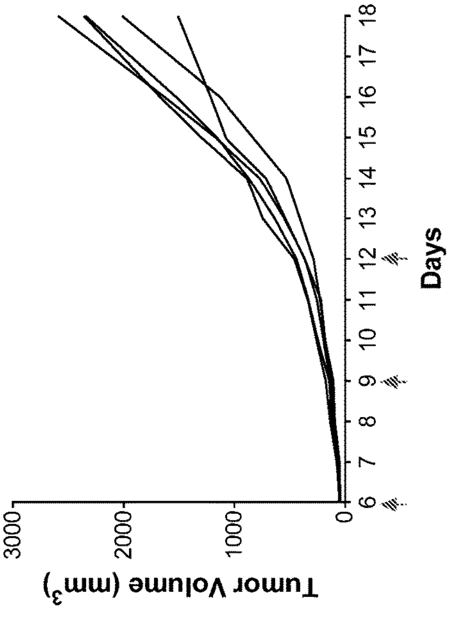
FIGS. 40A-40D show the tumor growth curves for each animal in the different groups described in FIG. 39 (i.e., PBS, Exo STING agonist (8 ng), Exo STING agonist (40 ng), and Exo STING agonist (200 ng), respectively).
Figure 40B:
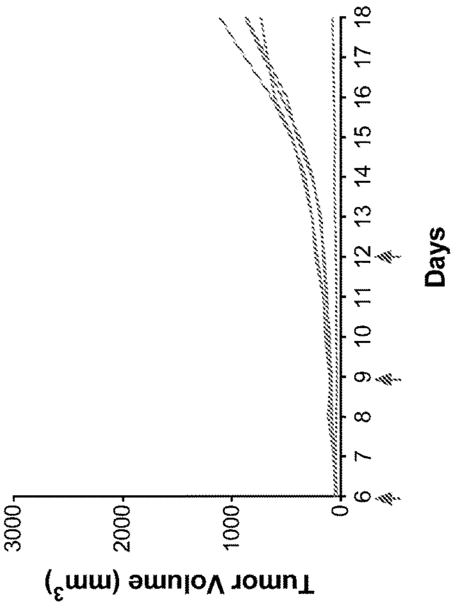
Figure 40C:
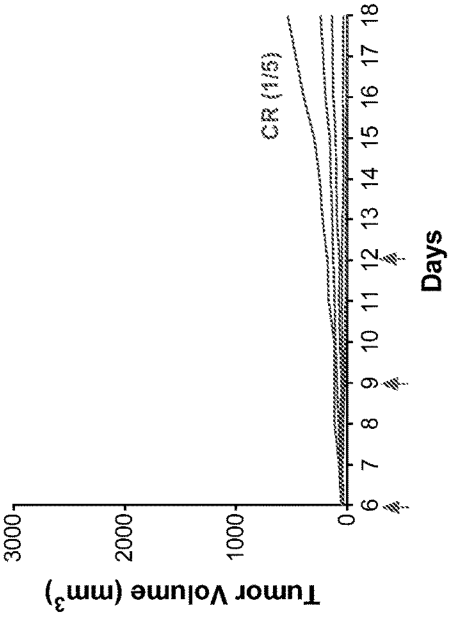
Figure 40D:
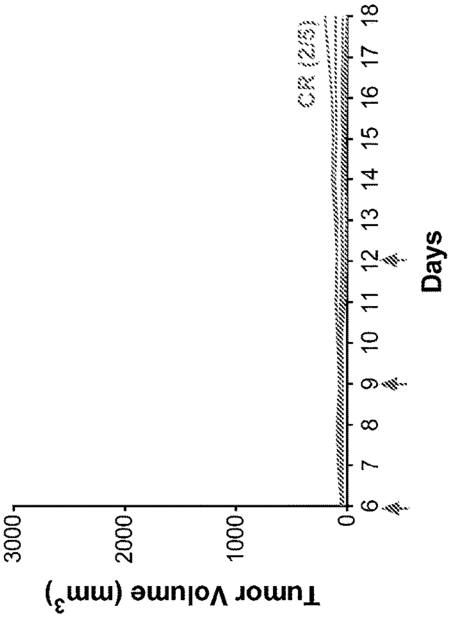

Example 10: Dose-Dependent Anti-Tumor Response of STING Agonist-Loaded Exosomes in a Murine Model of Melanoma The results in Example 9 demonstrate that Exo STING can induce an anti-tumor effect in vivo to a similar extent as a 100-fold greater dose of free STING agonist. To determine the relationship between injected dose of Exo STING and tumor growth, an in vivo dose-titration experiment was carried out. C57BL/6 mice were inoculated subcutaneously with $5\times10^5$ B16F10 murine melanoma cells (n=5 mice per group). Six, nine, and twelve days post-inoculation the mice were injected intratumorally with PBS and either 200 ng, 40 ng, or 8 ng of ML RR-S2 loaded in PTGFRN-overexpressing exosomes). Tumor volumes were measured daily until day 18, and animals were sacrificed when tumor volume reached 2000 $mm^3$. Four out of five mice in the PBS control group were sacrificed by day 18, while none of the Exo STING-treated mice in any group were sacrificed during the course of the study. There were two complete responses in the 200 ng Exo STING group and one complete response in the 40 ng Exo STING group. Surprisingly, there was a substantial reduction in tumor growth in the 8 ng Exo STING group compared to the PBS group, demonstrating that a very low dose of Exo STING can have a measurable pharmacological impact in an aggressive tumor model (FIGS. 39 and 40A-D). FIG. 39 shows the average tumor growth in the animal groups and FIGS. 40A-D shows the tumor growth in individual mice in each treatment group. A low nanogram dose of STING agonist is unlikely to induce harmful systemic toxicity that is observed with higher doses (10-100 micrograms), and thus may be an attractive opportunity for combination therapies with other oncology or immuno-oncology agents (e.g., therapeutic antibodies against PD-1, PD-L1, and/or CTLA-4). Notably, the tumor growth curves for 200 ng and 40 ng Exo STING groups were comparable, suggesting that an intermediate dose may be sufficient to induce a durable immune response, and that Exo STING may present a therapeutic opportunity for reducing the dose of STING agonist by 100-1,000-fold for intratumoral injections.

Figure 41A:
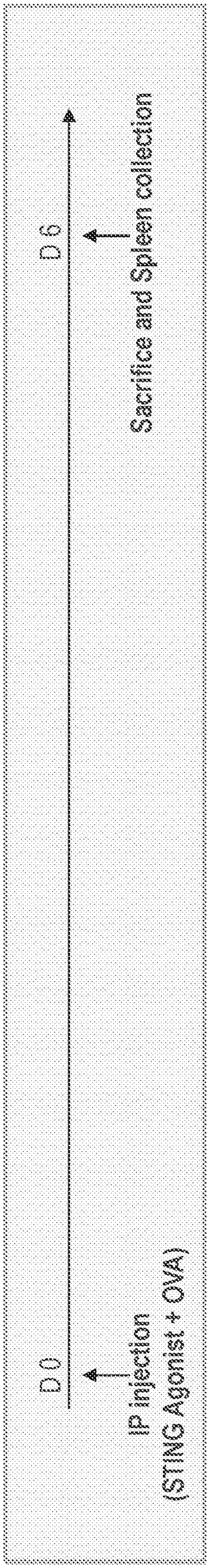
FIGS. 41A-41E show an experimental plan and results from an antigen-specific T-cell induction experiment using ovalbumin as the antigen in naïve mice injected with 200 μg ovalbumin mixed with either PBS, 20 μg free ML RR-S2 CDA, 0.2 μg free ML RR-S2 CDA, or 0.2 μg exosome-encapsulated ML RR-S2 CDA. Percentages of ovalbumin-reactive T-cells and number of IFN-γ producing splenocytes were measured.
Figure 41B:
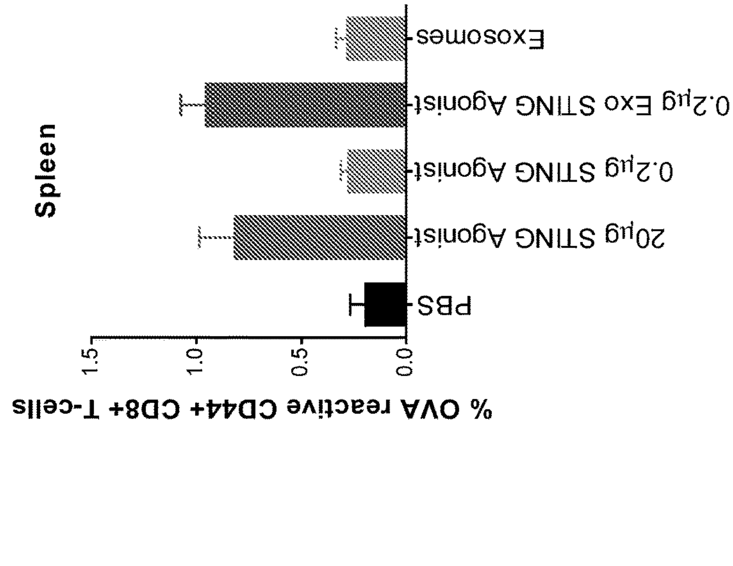
Figure 41C:
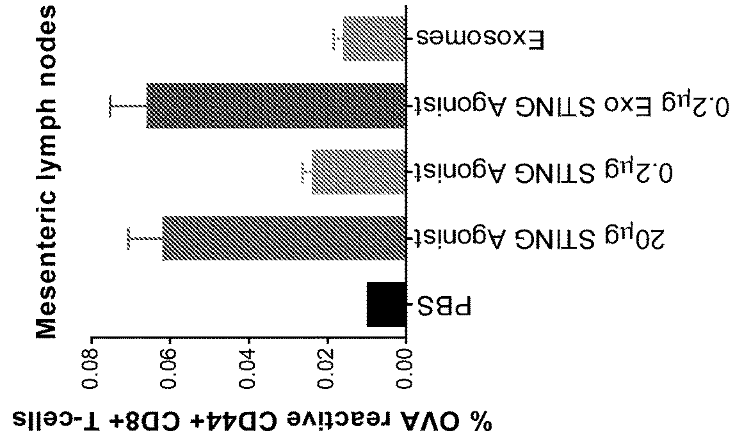

Example 11: Induction of an Antigen-Specific T-Cell Response by Free STING Agonist and STING Agonist-Loaded Exosomes STING pathway agonism in dendritic cells enhances antigen presentation, IFNβ production, and recruits CD8+ memory T-cells to elicit a durable adaptive immune response. To determine whether Exo STING could induce a memory T-cell response to a defined antigen, an antigen-specific T-cell response study was carried out using purified ovalbumin (OVA). A diagram of the experimental overview is shown in FIG. 41A. C57BL/6 mice were injected intraperitoneally with 200 μg OVA mixed with either PBS, 20 μg ML RR-S2, 0.2 μg ML RR-S2, or 0.2 μg ML RR-S2 loaded in PTGFRN-overexpressing exosomes (n=4-10 mice per group). Six days post-injection, spleens and mesenteric lymph nodes were collected, homogenized to a single-cell suspension, and live lymphocytes were enriched by density centrifugation. Isolated lymphocytes were analyzed by flow cytometry by measuring binding to immobilized tetrameric MHC class I bound to the OVA peptide SIINFEKL and phycoerythrin (PE) (iTAg Tetramer/PE—H-2 OVA; MBL®, Code #T03000). OVA-reactive memory T-cells were quantified by gating on PE, CD44, and CD8 positivity. A greater proportion of OVA-reactive T-cells in the spleen (FIG. 41B) and mesenteric lymph nodes (FIG. 41C) were detected in the high-dose free STING agonist and Exo STING groups compared to the PBS, low-dose free STING and native exosome. The low-dose STING agonist, which was concentration-matched to Exo STING, showed no activity in the spleen and only a modest response in mesenteric lymph nodes demonstrating a clear increase in potency for STING agonists loaded in exosomes. Mice treated with unmodified exosomes did not exhibit an immune response, demonstrating that the exosomes alone are non-immunogenic over the time course of the experiment.

Figure 41E:
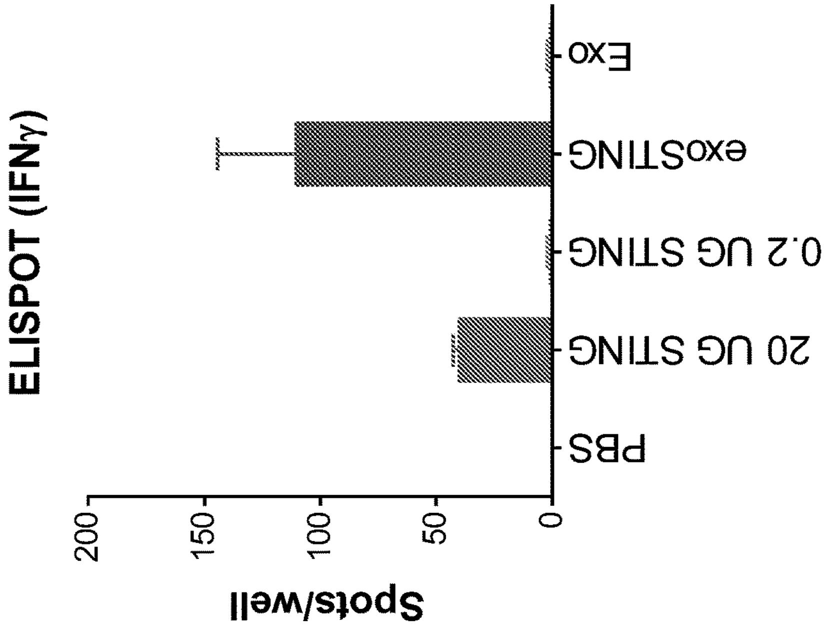
Figure 41D:
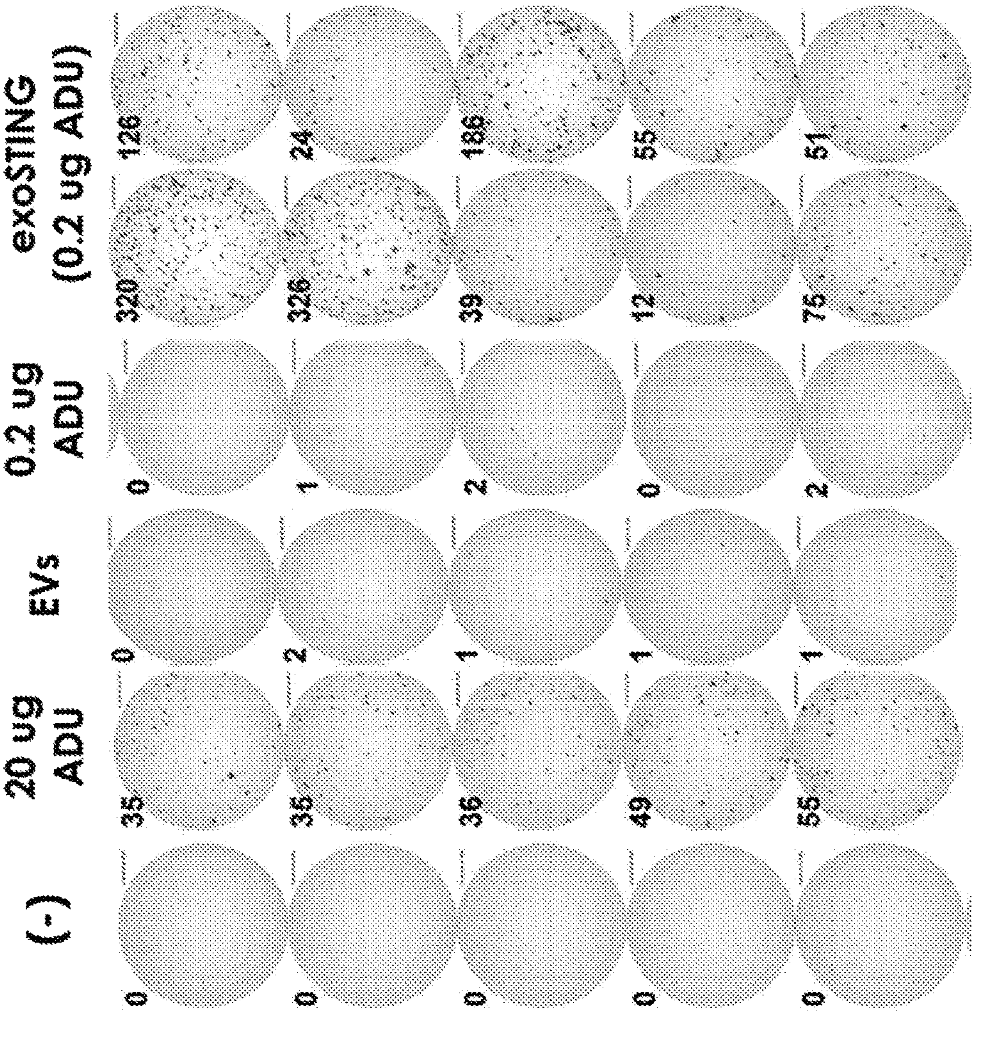

As an orthogonal method to measure antigen-specific immunity, IFNγ-expression was measured by ELISpot according to standard protocols (ImmunoSpot®; Cellular Technology Limited). Splenocytes were homogenized to a single-cell suspension and plated (200,000 cells/well) in a plate coated with an anti-IFNγ antibody. The OVA peptide SIINFEKL was added to the cells for 18 hours to induce IFNγ production, cells were washed from the plate, and plate-bound IFNγ was detected using an orthogonal antibody (FIG. 41D). The total number of reactive spots per plate were counted and compared across groups using ImmunoSpot® software (Cellular Technology Limited). PBS, exosome alone (EVs), and low-dose STING agonist groups exhibited very low levels of OVA-reactivity. Both high-dose STING agonist and Exo STING groups were highly reactive, with greater reactivity in the Exo STING group despite a 100-fold lower dose of STING agonist in this group (FIG. 41E). These results demonstrate that Exo STING may be a differentiated therapeutic opportunity in eliciting an immune response for applications in oncology and infectious disease.

Figure 42:
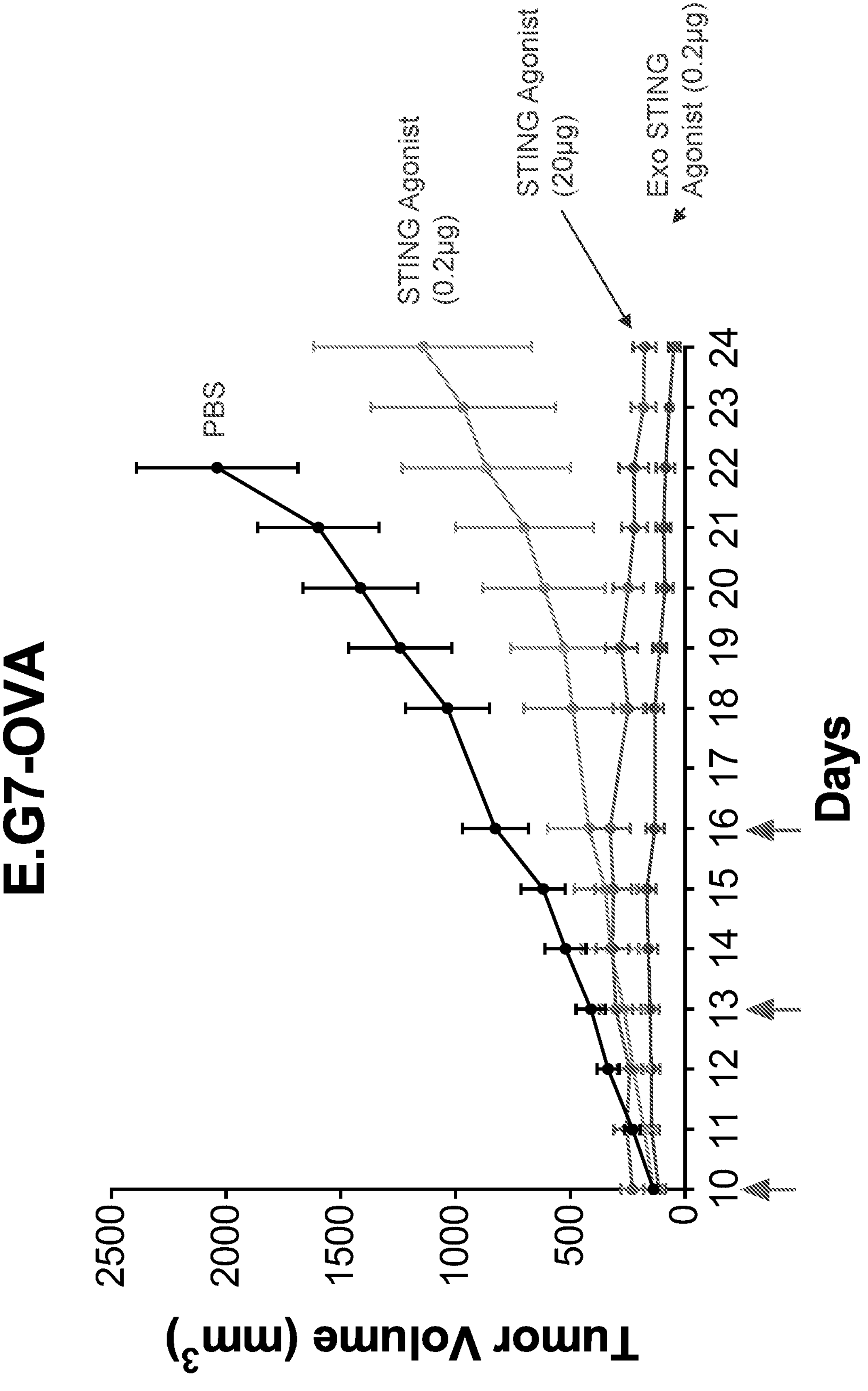
FIG. 42 shows the tumor growth curves during the course of the study described in Example 12 (i.e., an intratumoral injection study comparing anti-tumorigenic effects and immune memory response induction in E.G7-OVA tumor-bearing mice treated with PBS, 20 μg free ML RR-S2 CDA, 0.2 μg free ML RR-S2 CDA, or 0.2 μg exosome-encapsulated ML RR-S2 CDA).
Figure 43A:
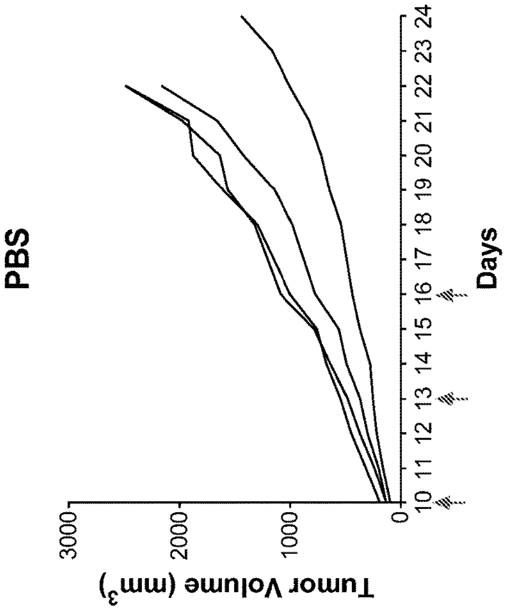
FIGS. 43A-43D show the tumor growth curves for each animal in the different groups (i.e., PBS, STING agonist (20 μg), STING agonist (0.2 μg), and Exo STING agonist (0.2 μg), respectively).
Figure 43B:
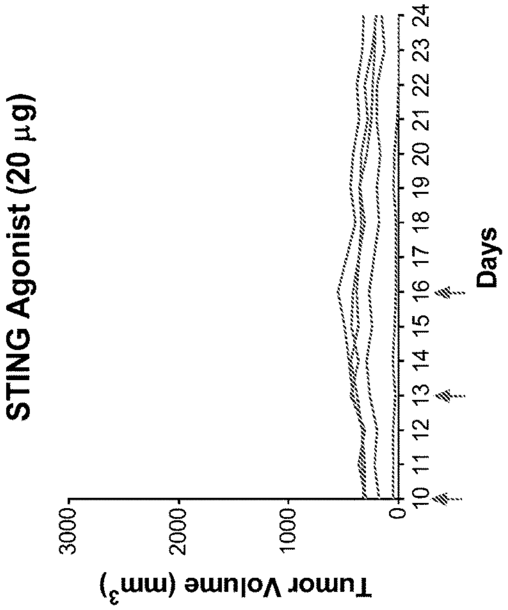
Figure 43C:
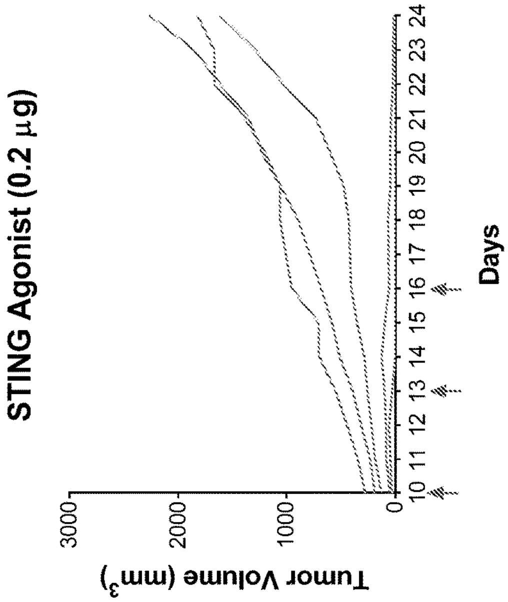
Figure 43D:
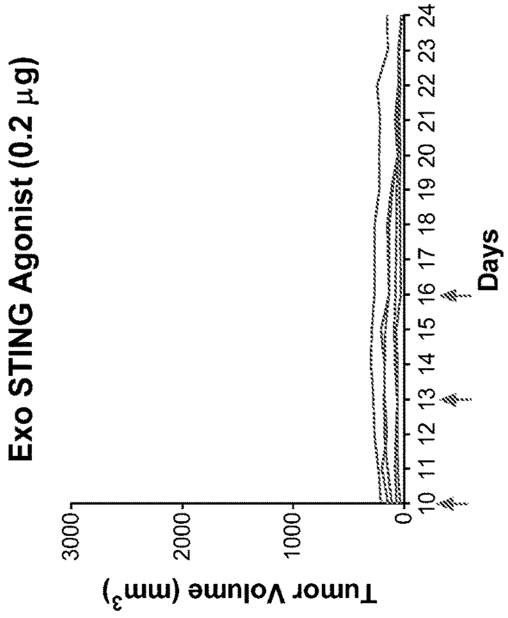
Figure 43E:
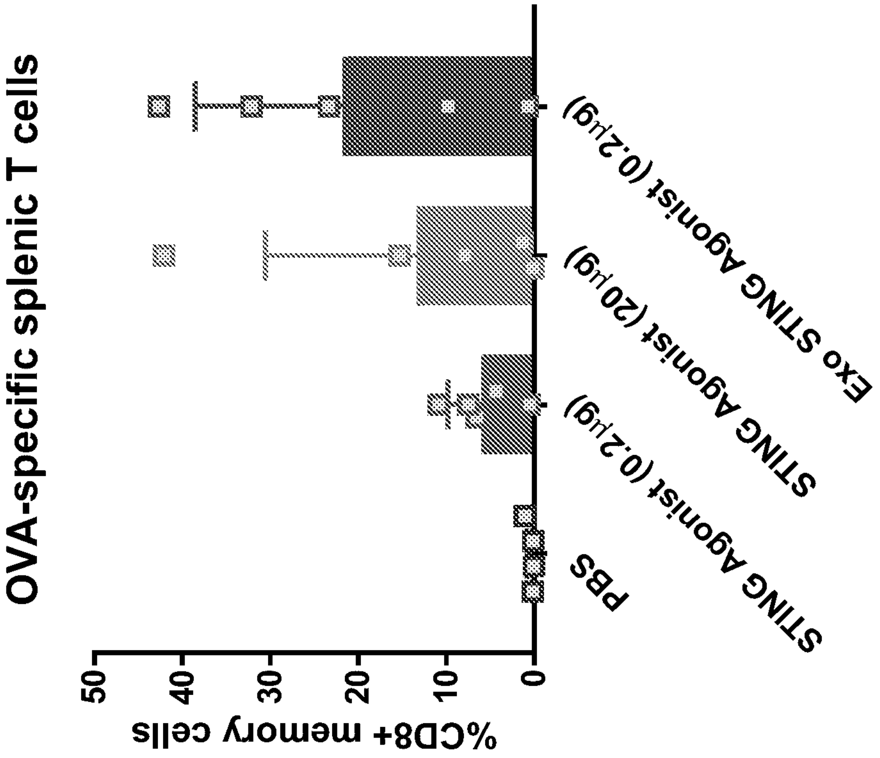
FIG. 43E shows the percentage of ovalbumin-reactive memory T-cells isolated from the spleens of the animals in each group.

Example 12: Anti-Tumor Efficacy and Antigen-Specific Immune Response in a Model of Murine T-Cell Lymphoma The in vivo efficacy results shown in Examples 9 and 10 and the immune response induction shown in Example 11 suggest that Exo STING may be sufficient to induce an antigen-specific tumor-killing response and subsequent immune response in vivo. To test this hypothesis, C57BL/6 mice were inoculated subcutaneously with $1\times10^6$ E.G7-OVA cells (ATCC®; CRL-2113™), a murine T-cell lymphoma cell line engineered to stably express OVA and allow for modeling antigen-specific T-cell responses in mice (n=5 mice per group). Ten, 13, and 16 days post-inoculation the mice were injected intratumorally with PBS, 20 μg ML RR-S2, 0.2 μg ML RR-S2, or 0.2 μg ML RR-S2 loaded in PTGFRN-overexpressing exosomes). Similar to the effects observed in the B16F10 model (FIGS. 37-38, Example 9), low-dose free STING agonist moderately attenuated tumor growth, while high-dose free STING agonist and Exo STING dramatically prevented tumor growth compared to the PBS group (FIGS. 42 and 43A-D). FIG. 42 shows the average tumor growth in the animal groups and FIGS. 43A-D shows the tumor growth in individual mice in each treatment group. Splenic T-cells from all groups were isolated and measured for OVA-specific reactivity as described in Example 11. Low-dose free STING agonist induced a modest memory T-cell response, while high-dose free STING agonist and Exo STING both induced a potent memory T-cell response (FIG. 43E). These data demonstrate that a STING agonist loaded in exosomes can simultaneously induce comparable anti-tumorigenic and memory T-cell responses in vivo compared with 100-fold greater free compound.

Figure 44A:
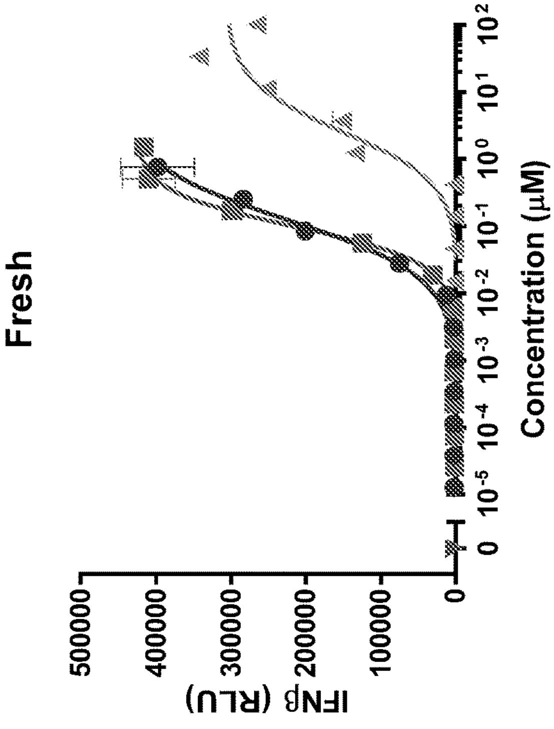
FIGS. 44A-44B show the potency of STING agonist loaded into native exosomes or PTGFRN-overexpressing exosomes in PBMCs either freshly prepared (FIG. 44A) or frozen at −80° C. for seven days (FIG. 44B). Potency is measured by IFNβ production.
Figure 44B:
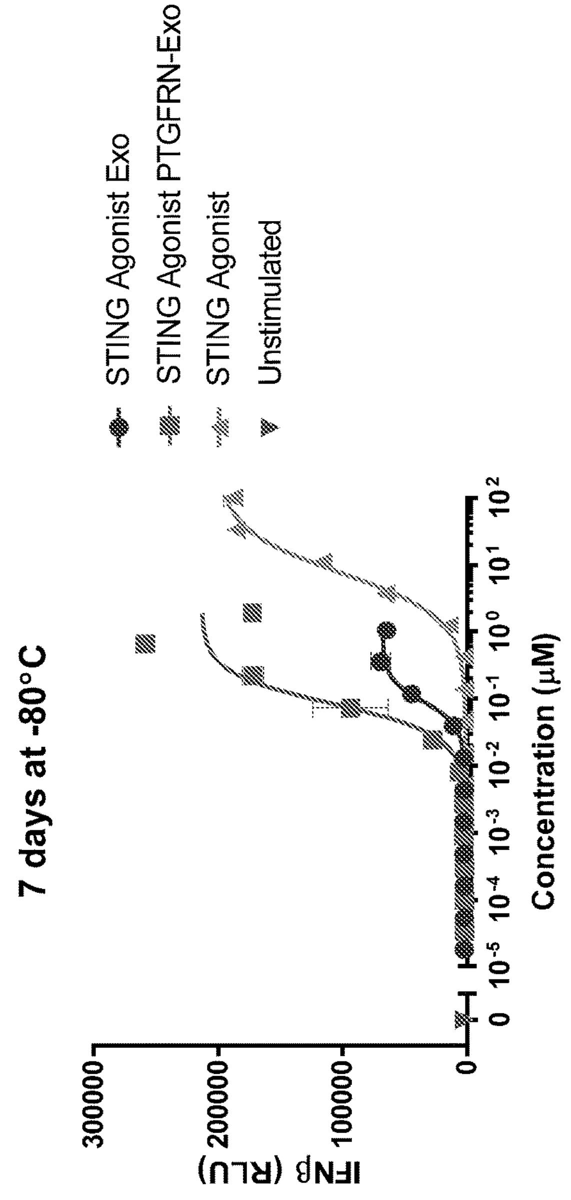
Figure 44C:
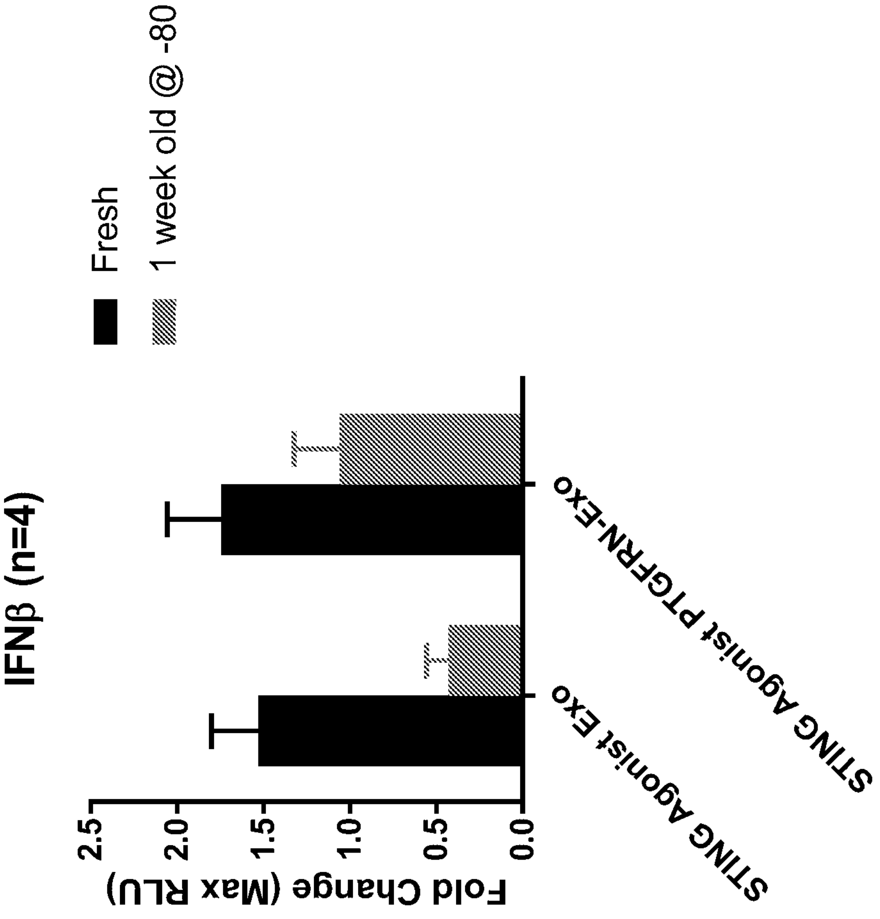
FIG. 44C shows the reduction in potency of STING loaded into native exosomes or PTGFRN-overexpressing exosomes after storage at −80° C. for seven days compared to freshly prepared exosomes.

Example 13: PTGFRN-Overexpressing Exosomes Enhance Stability of STING Agonist Compared to Native Exosomes Exosomes from HEK293SF cells (native exo STING) and from HEK293SF cells overexpressing PTGFRN-GFP (PTGFRN exo STING) were loaded with ML RR-S2, purified, and quantitated as described in Example 1. Fresh samples of native exo STING and PTGFRN exo STING induced similar IFNβ levels in PBMCs from a single donor, and both provided a potency enhancement over free STING agonist (FIG. 44A). Aliquots of the exosome-STING agonist formulations were frozen at −80 C for seven days, thawed, and added to PBMCs. PTGFRN exo STING induced an IFNβ production profile similar to the fresh preparation, while native exo STING induced a blunted IFNβ expression profile, with a dramatically reduced $C_{max}$ compared to free STING agonist or PTGFRN exo STING (FIG. 44B). The loss of potency for PTGFRN exo STING was moderate compared to the loss of potency for native exo STING (FIG. 44C).

Figures 45A, 45B, 45C, 45D:
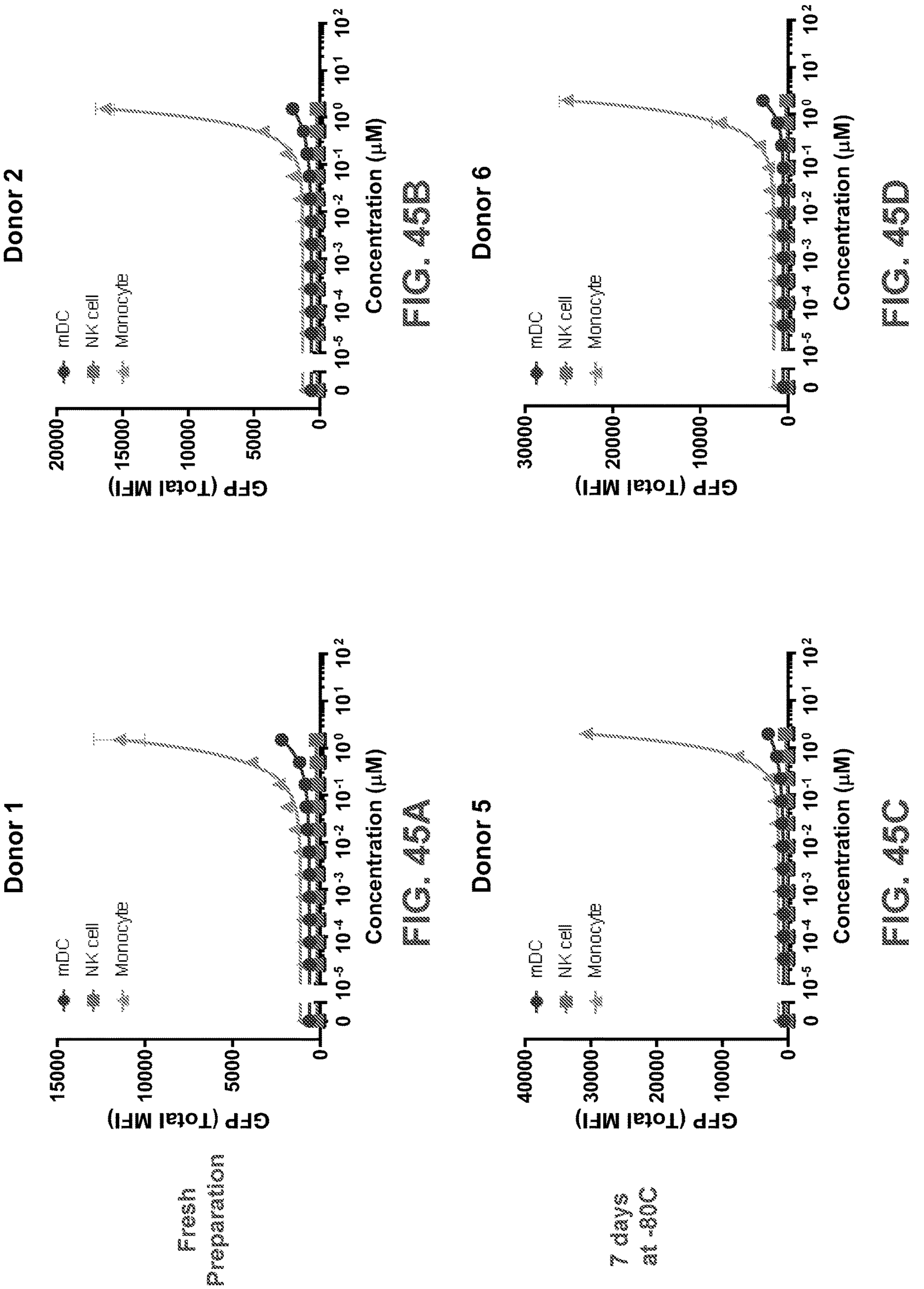
FIG. 45A-45D shows the retention of uptake kinetics in PTGFRN-overexpressing exosomes after storage at −80° C. for seven days compared to freshly prepared exosomes.

Fresh and frozen preparations of PTGFRN exo STING were incubated with PBMCs, and cellular uptake profiles for DCs, NK cells, and monocytes were measured by cell-specific surface markers and GFP positivity. There was no difference in uptake profile between fresh (FIGS. 45A-45B) and frozen (FIGS. 45C-45D) PTGFRN exo STING, indicating that one cycle of freeze-thaw does not disrupt exosome uptake. These results demonstrate that PTGFRN overexpression may be more suitable for long-term storage and formulation of therapeutic exosomes loaded with STING agonists.

Figure 46A:
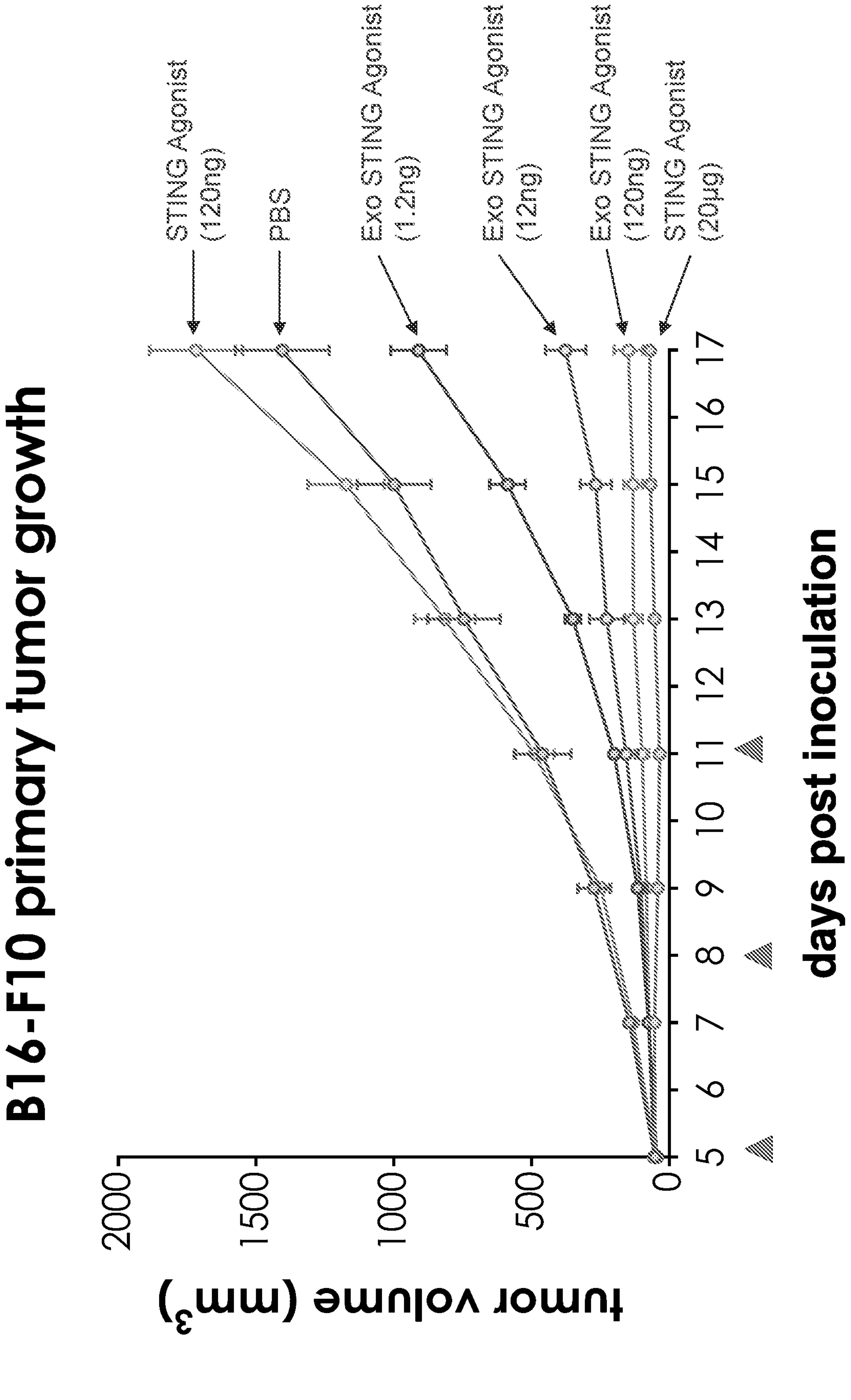
FIG. 46A shows the tumor growth curves during the course of the study described in Example 14 (i.e., an intratumoral injection study followed by lung metastasis challenge comparing the anti-tumorigenic effects in B16F10 tumor-bearing mice treated with PBS, high or low doses of free 3-3 cAIMPdFSH, or one of three doses of 3-3 cAIMPdFSH loaded into PTGFRN-overexpressing exosomes).
Figure 46B:
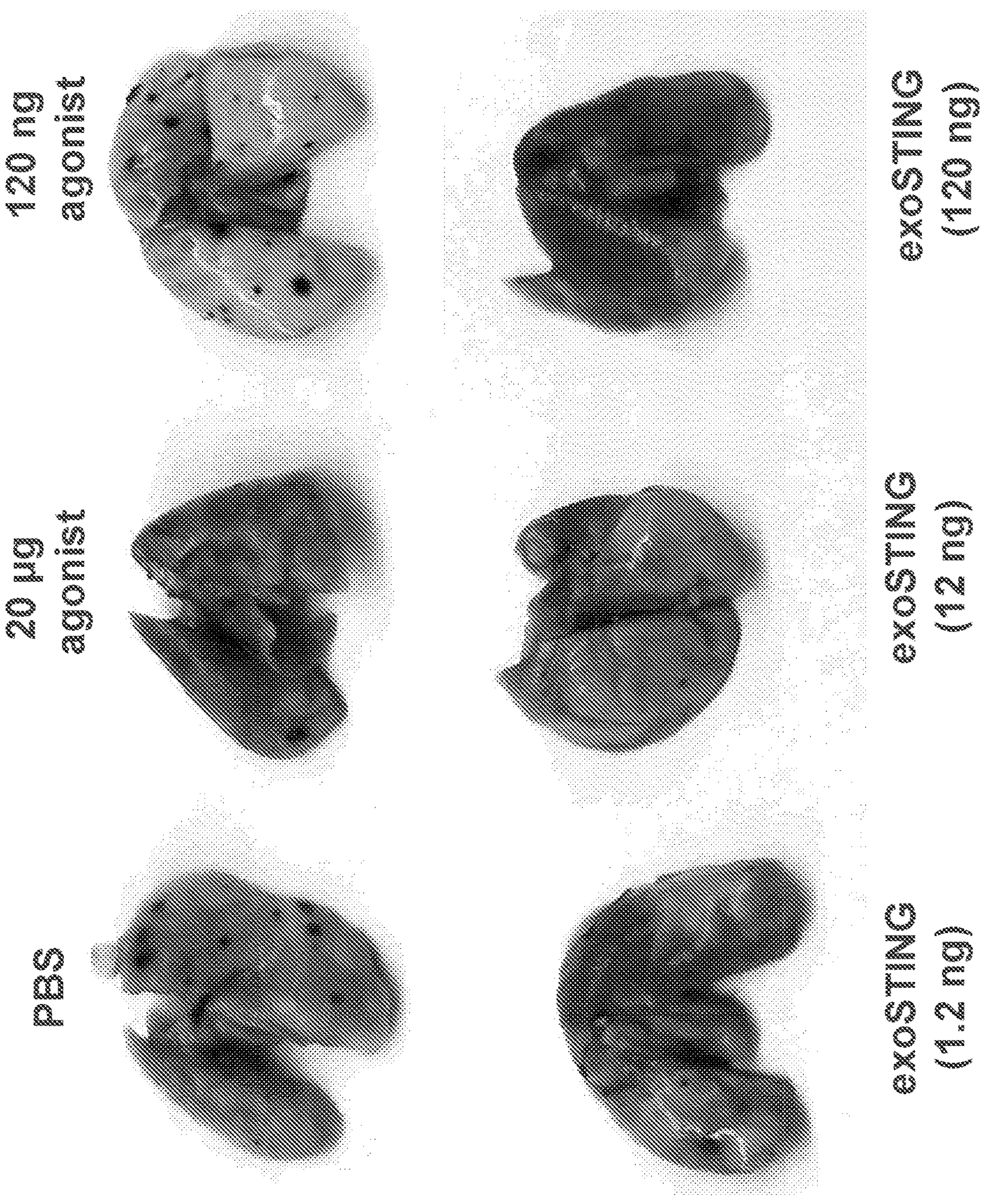
FIG. 46B shows images of representative lungs from animals in each group after the completion of the study.
Figure 47:
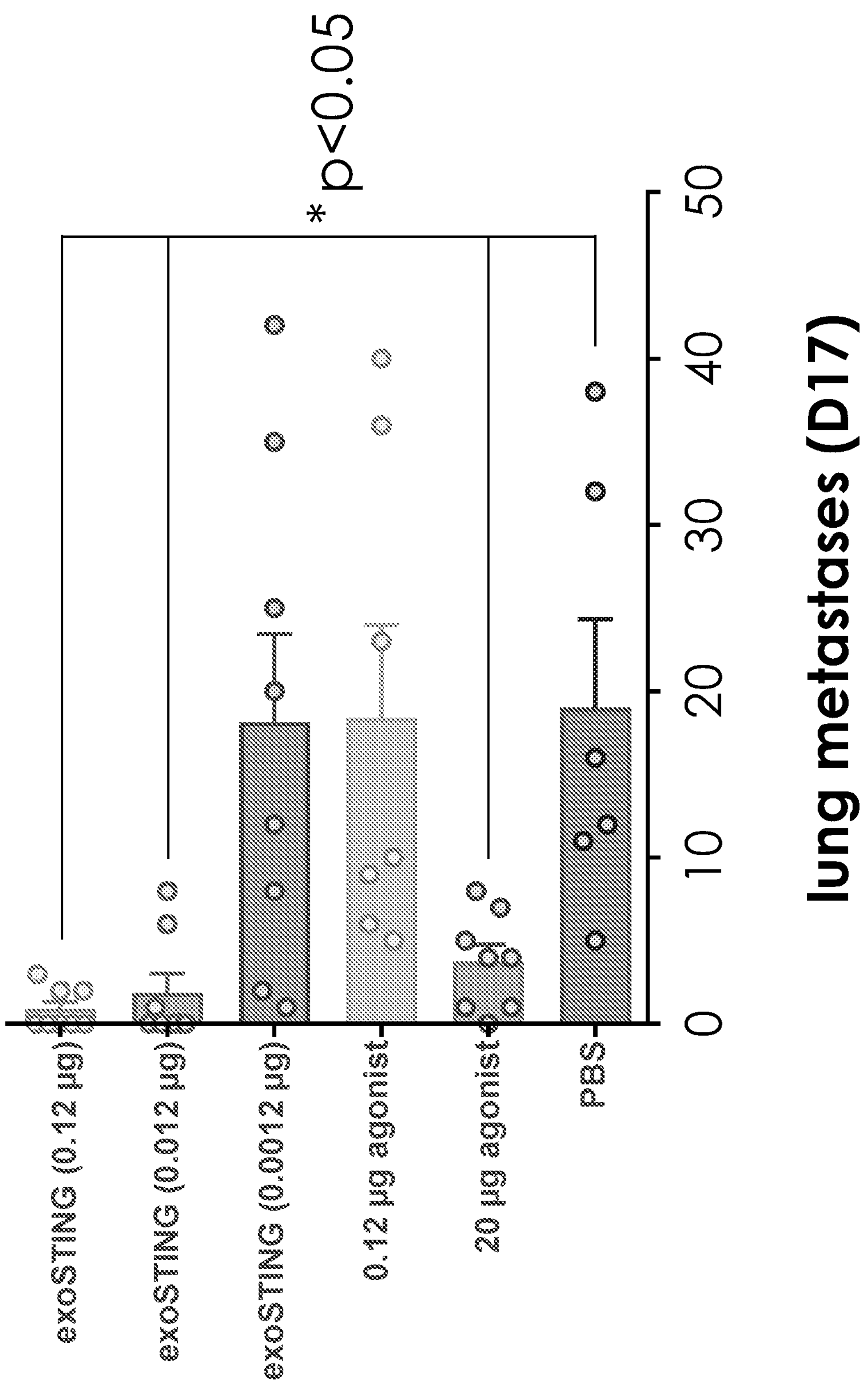
FIG. 47 is a microscopic quantitation of lung metastases of the animals in the study shown in FIGS. 46A and 46B.
Figure 48:
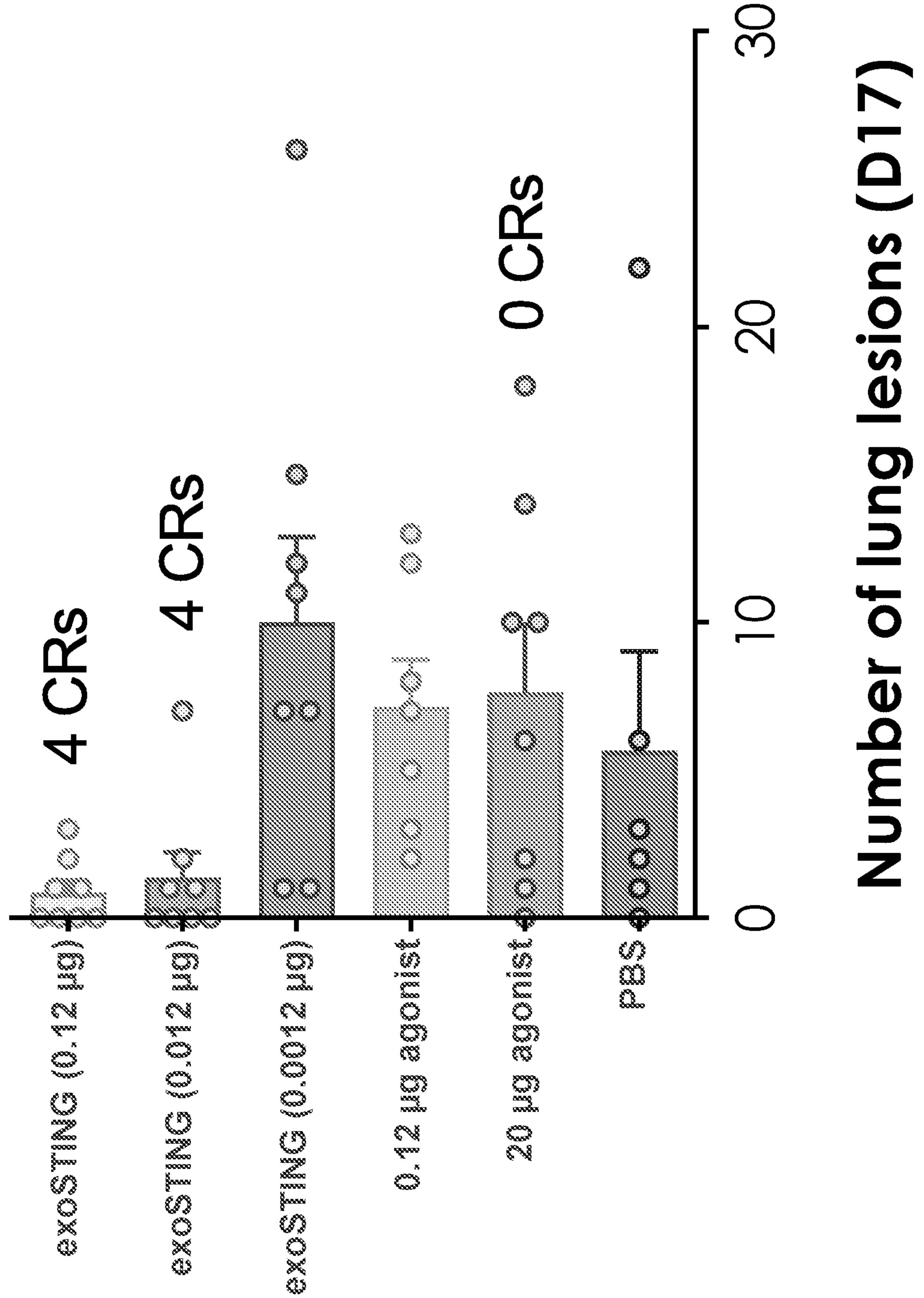
FIG. 48 is a histological quantitation of lung metastases of the animals in the study shown in FIGS. 46A and 46B.

Example 14: Induction of Protective Immunity and Reduction of Metastasis by Intratumoral Administration of STING Agonist-Loaded Exosomes Activation of the STING pathway promotes antigen presentation and induces a durable T-cell response, as shown in Examples 11 and 12. Thus, the immune memory response induced by EXOSTING™ may be sufficient to prevent tumor metastasis after a local administration in a primary tumor. To test this hypothesis, exosomes purified from HEK293SF cells overexpressing PTGFRN were loaded with the cyclic dinucleotide 3-3 cAIMPdFSH as described in Example 1. C57BL/6 mice were inoculated subcutaneously with $1\times10^6$ B16F10 melanoma cells on day zero and challenged with an additional tail vein injection of $1\times10^5$ B16F10 melanoma cells to seed lung metastases (n=8 mice per group). Five, eight, and eleven days post-inoculation the mice were injected intratumorally at the subcutaneous tumor with PBS, 20 μg 3-3 cAIMPdFSH, 120 ng 3-3 cAIMPdFSH, or either 120 ng, 12 ng, or 1.2 ng 3-3 cAIMPdFSH loaded in PTGFRN-overexpressing exosomes (Exo STING Agonist). By day 17, the primary tumors in the 20 μg STING Agonist and 120 ng Exo STING Agonist groups did not grow. There was a dose-response relationship in the 12 ng and 1.2 ng Exo STING Agonist groups, but no tumor regression observed in the PBS or 120 ng STING Agonist groups (FIG. 46A). Lungs from all mice were harvested, imaged, and counted for metastases. Compared to the PBS-injected group, lung metastases were dramatically reduced in the 120 ng and 12 ng Exo STING Agonist groups and the 20 μg STING Agonist group. As little as 12 ng of Exo STING Agonist prevented lung metastasis to the same extent as 20 μg STING Agonist (FIGS. 46B and 47). Interestingly, 20 μg STING Agonist treated groups had significant amount of lung lesions inside of lung when assessed by histology, whereas 120 ng and 12 ng Exo STING Agonist groups had 4 complete responses each (FIG. 48). These data demonstrate that exosome-encapsulated STING agonists can induce tumor-protective immunity at a much lower dose (~1,000-fold) compared to free STING agonists.

Figure 49A:
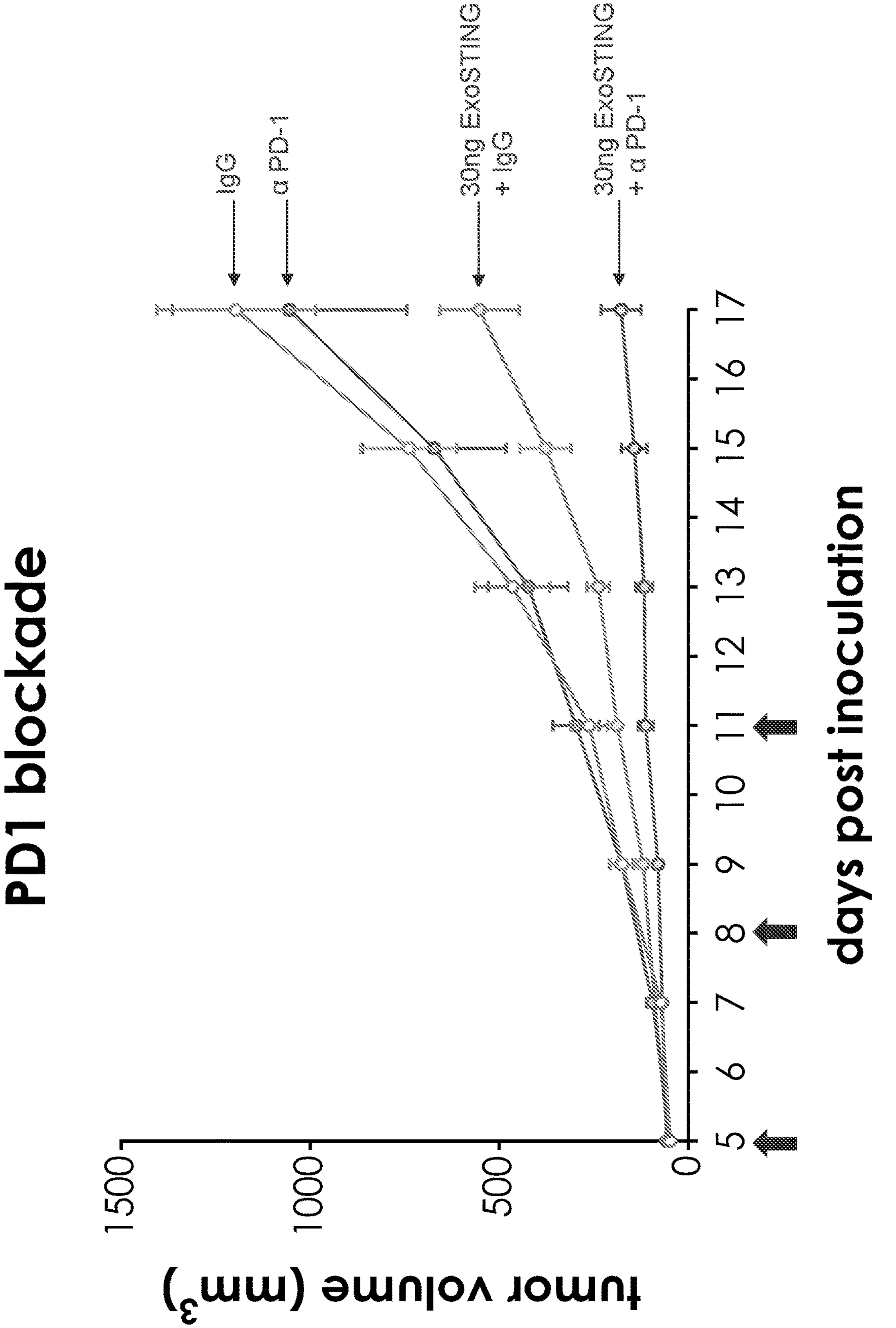
FIG. 49A shows tumor growth curves during the course of the checkpoint blockade study described in Example 15 (i.e., an intratumoral injection study in combination with systemic immune checkpoint inhibition (treatment with an anti-PD-1 antibody) in B16F10 tumor-bearing mice treated with three doses of 30 ng ML RR-S2 CDA loaded into PTGFRN-overexpressing exosomes).

Example 15: Exosome-Mediated Delivery of STING Agonists Synergizes with Immune Checkpoint Blockade Immunotherapy and Relies on T-Cell-Mediated Tumor Killing Activation of the STING pathway induces the upregulation of immune pathway checkpoints, which subsequently reduce T-cell-mediated cell killing, and thus moderate the effects of STING pathway agonism as a therapeutic rationale (Cell Rep. 2015 May 19; 11(7):1018-30). Therefore, it may be beneficial to combine inhibitors of immune checkpoint regulation to further improve immune-mediated clearance of tumor cells. To test this hypothesis, exosomes purified from HEK293SF cells overexpressing PTGFRN were loaded with the cyclic dinucleotide ML RR-S2 CDA as described in Example 1. C57BL/6 mice were inoculated subcutaneously with $1\times10^6$ B16F10 melanoma cells (n=6 mice per group). Five, eight, and eleven days post-inoculation the mice were injected intraperitoneally with a control antibody (α-IgG; 10 mg/kg; BioLegend, Catalog #400559, Clone RTK3758) or an antagonistic antibody against PD-1 (a PD-1; 10 mg/kg; BioLegend, Catalog #114111, Clone RMPI-14) with or without an intratumoral injection of 30 ng ML RR-S2 CDA loaded in PTGFRN-overexpressing exosomes (EXOSTING™). B16F10 tumors are poorly immune cell infiltrated and refractory to checkpoint blockade. The suboptimal dose of 30 ng of EXOSTING™ led to partial tumor reduction, which was amplified by treatment with a PD-1, but not a IgG (FIG. 49A).

In a separate study, C57BL/6 mice were inoculated subcutaneously with $1\times10^6$ B16F10 melanoma cells (n=6 mice per group). Five, eight, 11, and 14 days post-inoculation the mice were injected intraperitoneally with IgG (10 mg/kg) or anti-CD8 antibody (10 mg/kg). Six, nine, and 12 days after the IP administration of the antibodies, the mice were intratumorally treated with Exosomes or ExoSTING (3-3 cAIMPdFSH, 100 ng).

Figure 49B:
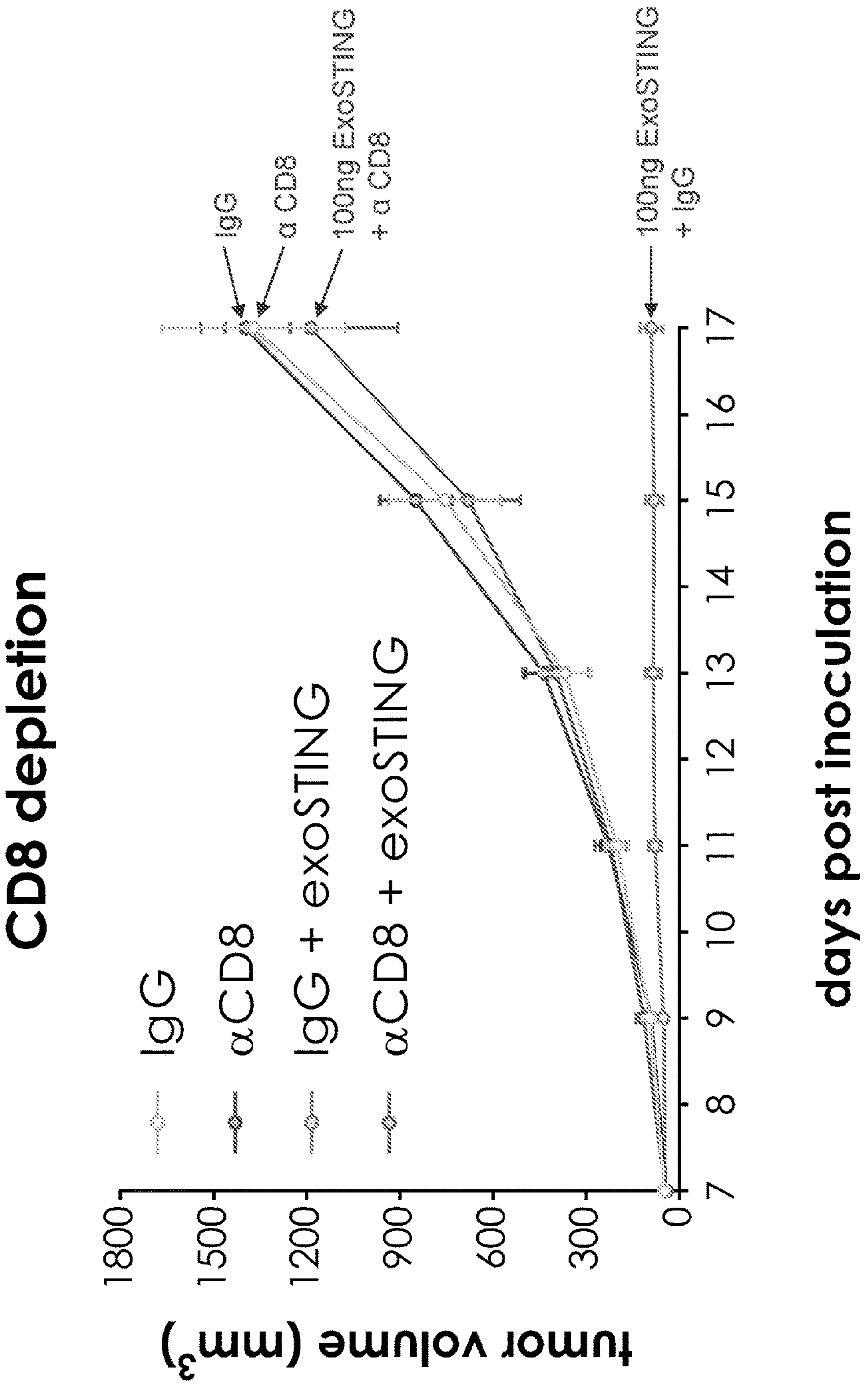
FIG. 49B shows the tumor growth curves during the course of the T-cell depletion study described in Example 15 (i.e., an intratumoral injection study in combination with T-cell depletion (treatment with an anti-CD-8 antibody) in B16F10 tumor-bearing mice treated with three doses of 100 ng of 3-3 cAIMPdFSH loaded into PTGFRN-overexpressing exosomes).

The mice were treated with a T-cell-depleting a CD8 antibody (10 mg/kg; BioLegend, Catalog #100769, Clone 53-6.7) prior to intratumoral administration of EXOSTING™ (3_3 cAIMPdFSH) according to the schematic shown in FIG. 49B. The systemic depletion of T-cells completely abrogated the effects of EXOSTING™, demonstrating the critical role of $CD8^+$ T-cells in mediating the STING agonist-induced antitumor effects of EXOSTING™ (FIG. 49B).

Figure 49C:
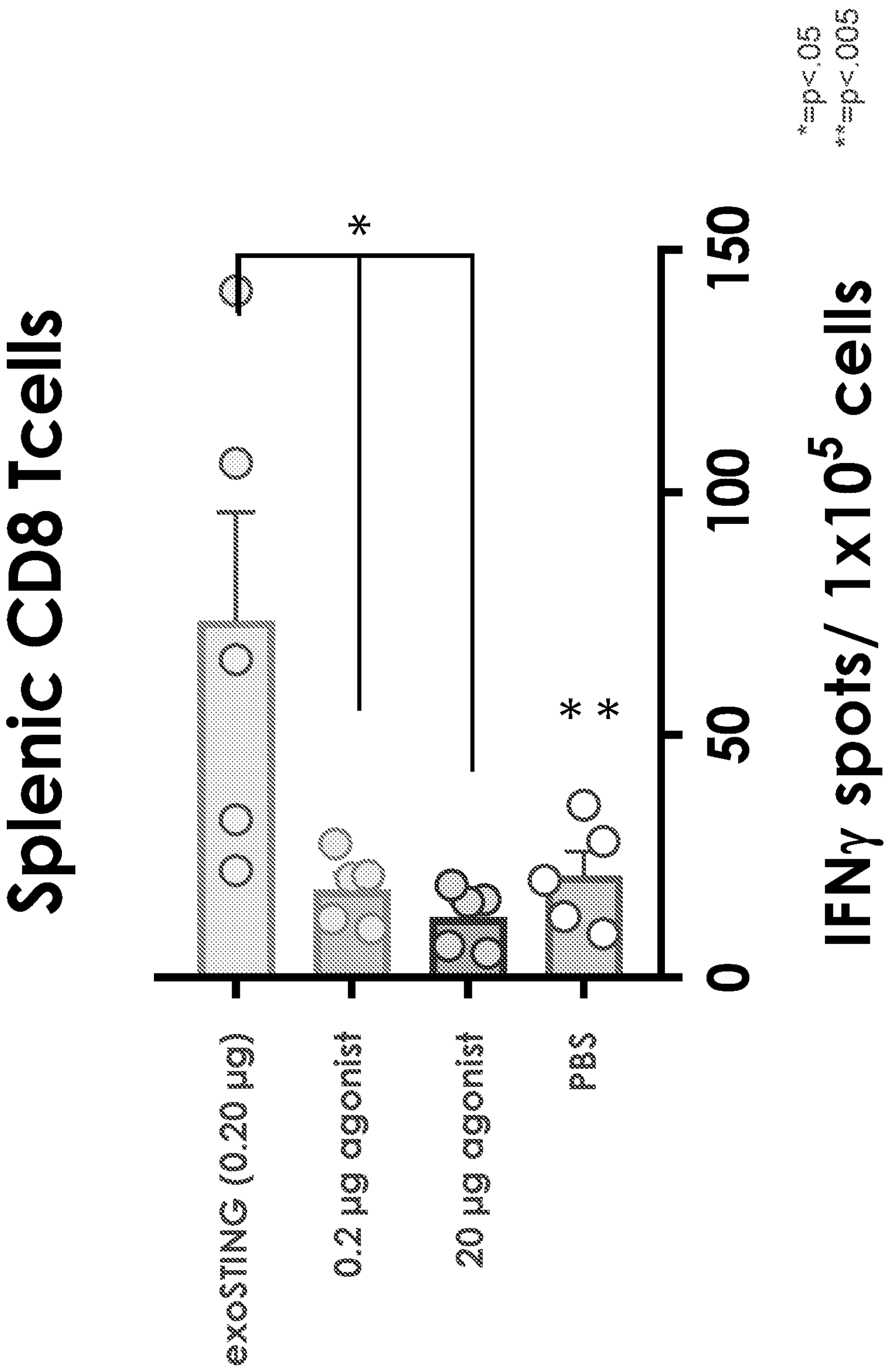
FIG. 49C shows the ELISPOT results from the study described in Example 15 (i.e., an intratumoral injection study in combination in B16F10 tumor-bearing mice treated with three injections of high or low dose free ML RR-S2 CDA, or low dose ML RR-S2 CDA loaded into PTGFRN-overexpressing exosomes, followed by tumor cell-specific ELISPOT to measure T-cell reactivity towards tumor antigens).

In a separate study, C57BL/6 mice Groups (n=5 for each time point) were treated intratumorally with PBS (day 8 only), 0.2 μg ML RR-S2 CDA (days 5 and 8), 20 μg ML RR-S2 CDA (days 5 and 8), and 0.2 μg exoSTING (days 5 and 8). 48 hours after the injection on day 8, tumors and spleens were isolated and dissociated into single cell suspensions utilizing Miltenyi mouse digestions kits (CAT #130-096-730 and 130-095-926, respectively) following the manufacturer's suggested protocol on a gentleMACS instrument. Cells were filtered, washed twice, and then subjected to flow cytometry analysis or culture for ELISPOT to detect specific reactivity against antigens from the B16F10 tumor cells. ELISPOT was carried out using the Mabtech Mouse IFNγ ELISpot PLUS (HRP) according to the manufacturer's protocol. Briefly, $5\times10^5$ splenocytes were incubated with 10 g/ml of three B16F10 peptides, namely GP100 amino acids 25-33 (AnaSpec, Catalog #AS-62589), Tyrosinase amino acids 368-376 (AnaSpec, Catalog #AS-61456), and TRP2 amino acids 180-188 (AnaSpec, Catalog #AS-61058). As shown in FIG. 49C, EXOSTING™ at 200 ng induced significantly more IFNγ-positive spots against the B16F10 peptides compared to high or low dose free STING agonist. Together, these data demonstrate that T-cells are critical mediators of anti-tumor immunity induced by STING agonists and that EXOSTING™ provides superior activity as a single agent or in combination with checkpoint blockade than free STING agonists.

Figure 50A:
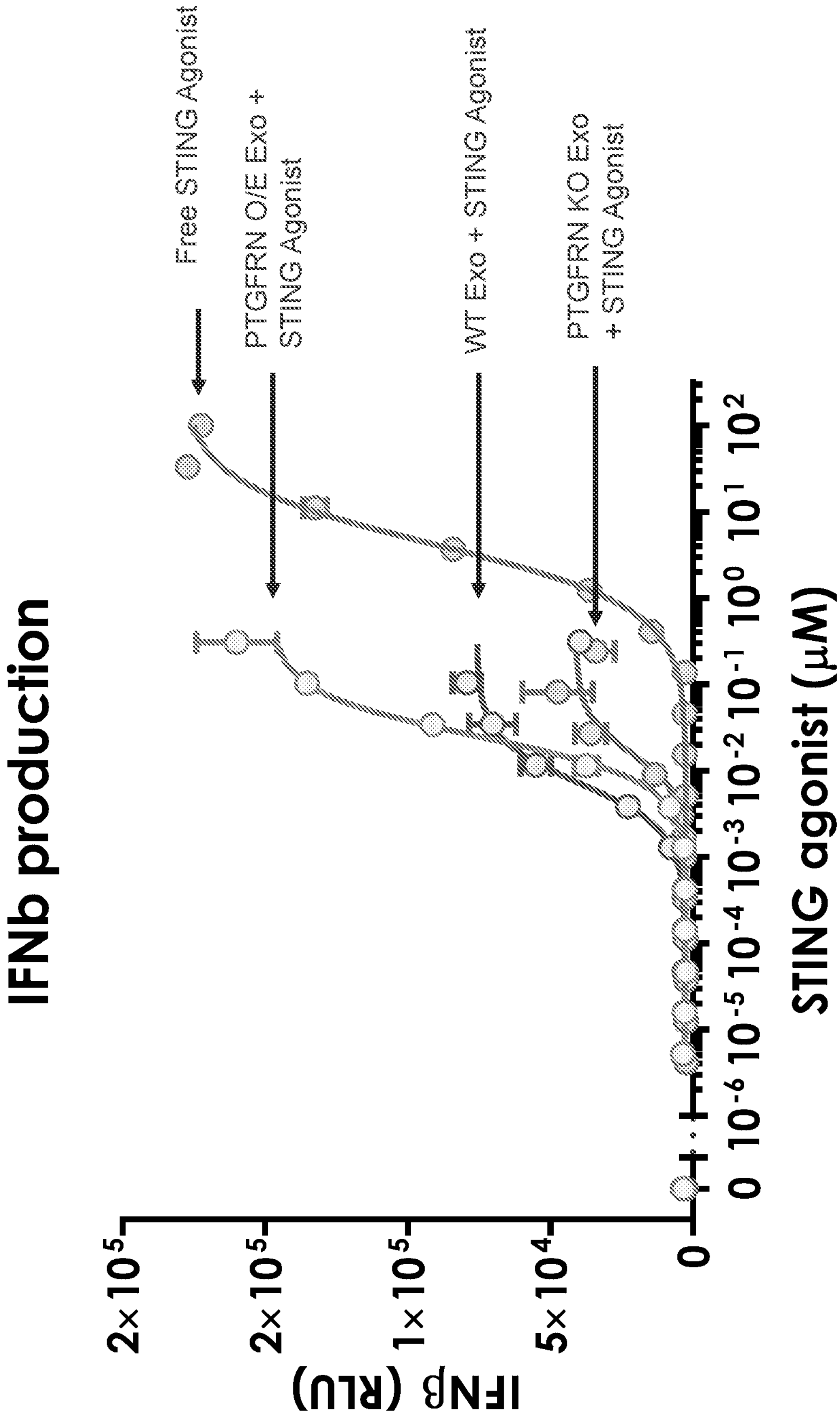
FIG. 50A shows a comparison of the IFNβ response in PBMCs treated with 3-3 cAIMPdFSH, exosome-encapsulated 3-3 cAIMPdFSH from wild-type exosomes, PTGFRN overexpressing exosomes, or PTGFRN knockout exosomes, as determined by relative luminescence (RLU).
Figure 50B:
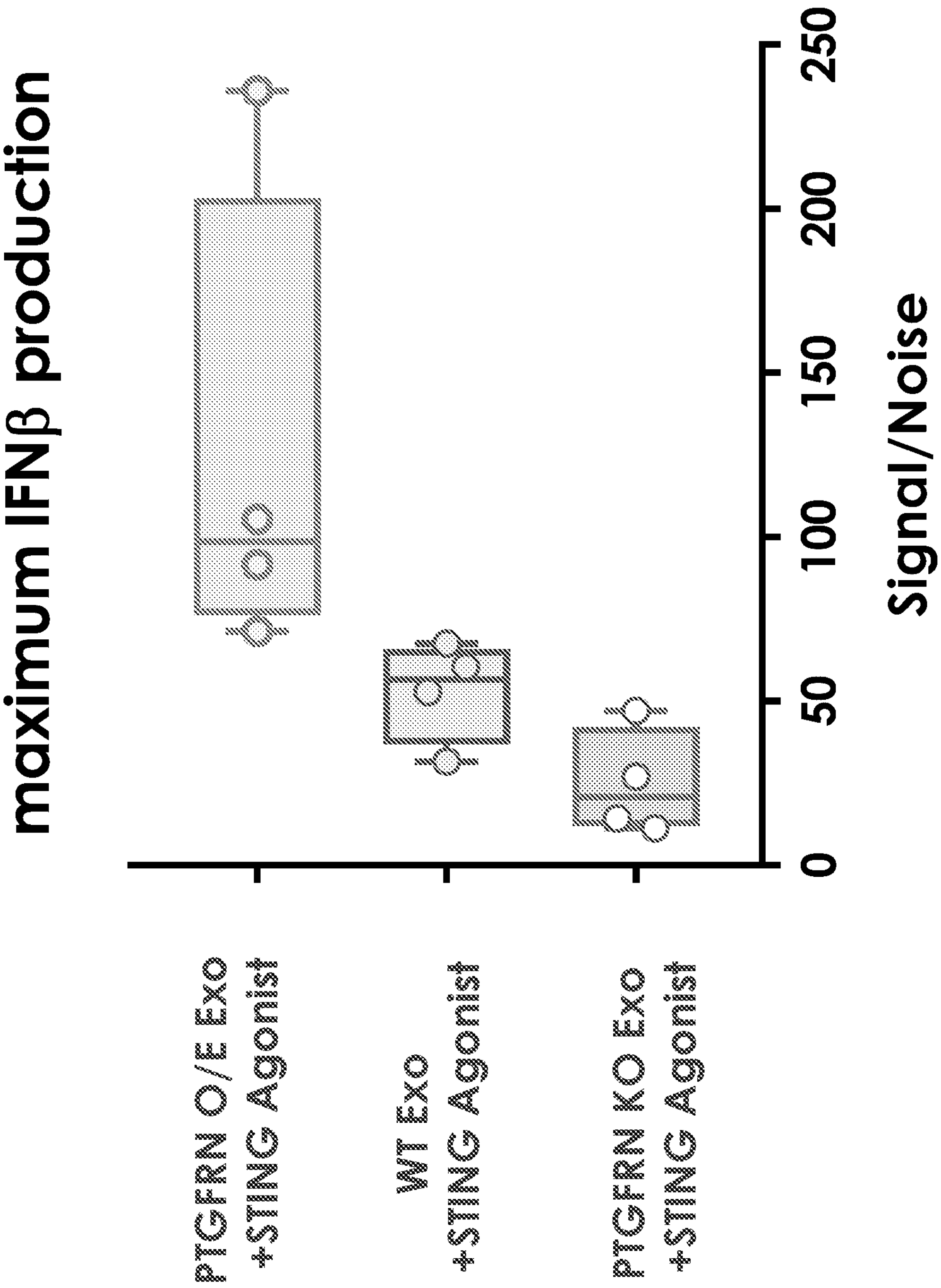
FIG. 50B shows a comparison of the maximal IFNβ signal from PBMCs treated with the exosomes in FIG. 50A.
Figure 50C:
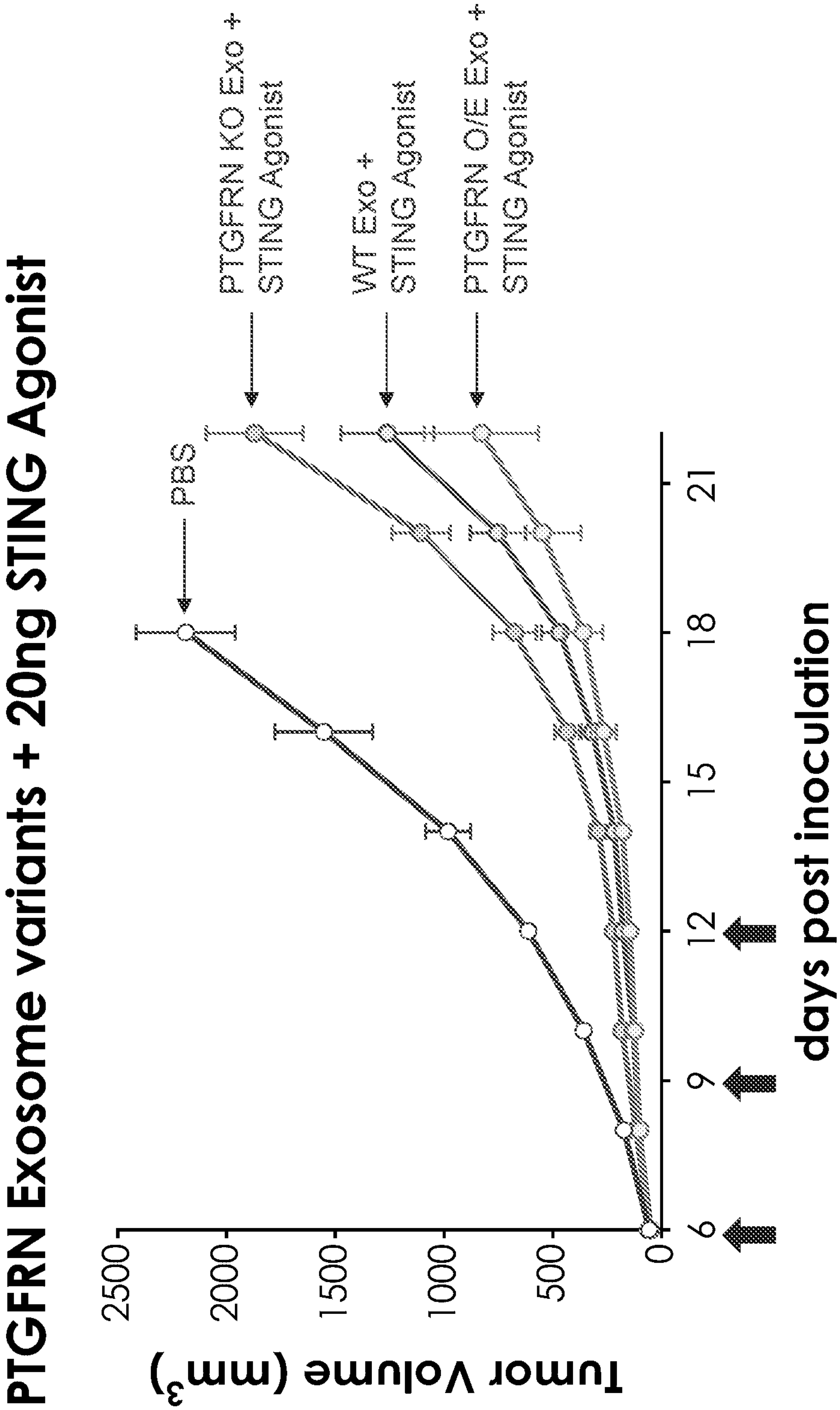
FIG. 50C shows growth curves of B16F10 melanoma tumors implanted subcutaneously in mice after three intratumoral injections (days 6, 9, and 12 post-implantation) of PBS or 20 ng of 3-3 cAIMPdFSH loaded into wild-type exosomes, PTGFRN overexpressing exosomes, or PTGFRN knockout exosomes.

Example 16: Exosomal PTGFRN Levels Correlate with the Potency of Exosomes Loaded with STING Agonists The results in Examples 3 and 13 suggest that PTGFRN overexpression enhances the activity of STING Agonist-loaded exosomes. To determine if PTGFRN levels correlate with EXOSTING™ activity, HEK293SF cells were genetically engineered by CRISPR/Cas9 to delete the endogenous PTGFRN loci (as described in International Patent Application No. PCT/US2018/048026). Exosomes were purified from WT HEK293SF cells (WT Exo), PTGFRN overexpressing HEK293SF cells (PTGFRN O/E Exo) and PTGFRN knockout cells (PTGFRN KO Exo) and loaded with 3-3 cAIMPdFSH as described above. Compared to soluble 3-3 cAIMPdFSH, all EXOSTING™ formulations were more potent activators of IFNβ production in PBMC cultures (n=2 replicates). Interestingly, PTGFRN O/E EXOSTING™ was the most potent activator of IFNβ and resulted in the greatest $C_{max}$ of the EXOSTING™ formulations. WT EXOSTING™ was attenuated compared to PTGFRN O/E EXOSTING™, and PTGFRN KO EXOSTING™ resulted in the mildest IFNβ response (FIG. 50A). Maximal IFNβ signal also correlated with PTGFRN levels (FIG. 50B). To determine whether this potency difference was consistent in an in vivo tumor setting, B16F10 subcutaneous tumors were injected with PBS or 20 ng of WT EXOSTING™, PTGFRN O/E EXOSTING™, or PTGFRN KO EXOSTING™ (injected on days 6, 9, and 12). The degree to which EXOSTING™ treatments attenuated tumor growth also correlated with PTGFRN expression levels, indicating that increased levels of PTGFRN can induce a more favorable anti-tumor immune response, and thus EXOSTING™ therapeutic formulations may be optimized by increasing the expression of PTGFRN on the exosome surface (FIG. 50C).

Figure 51A:
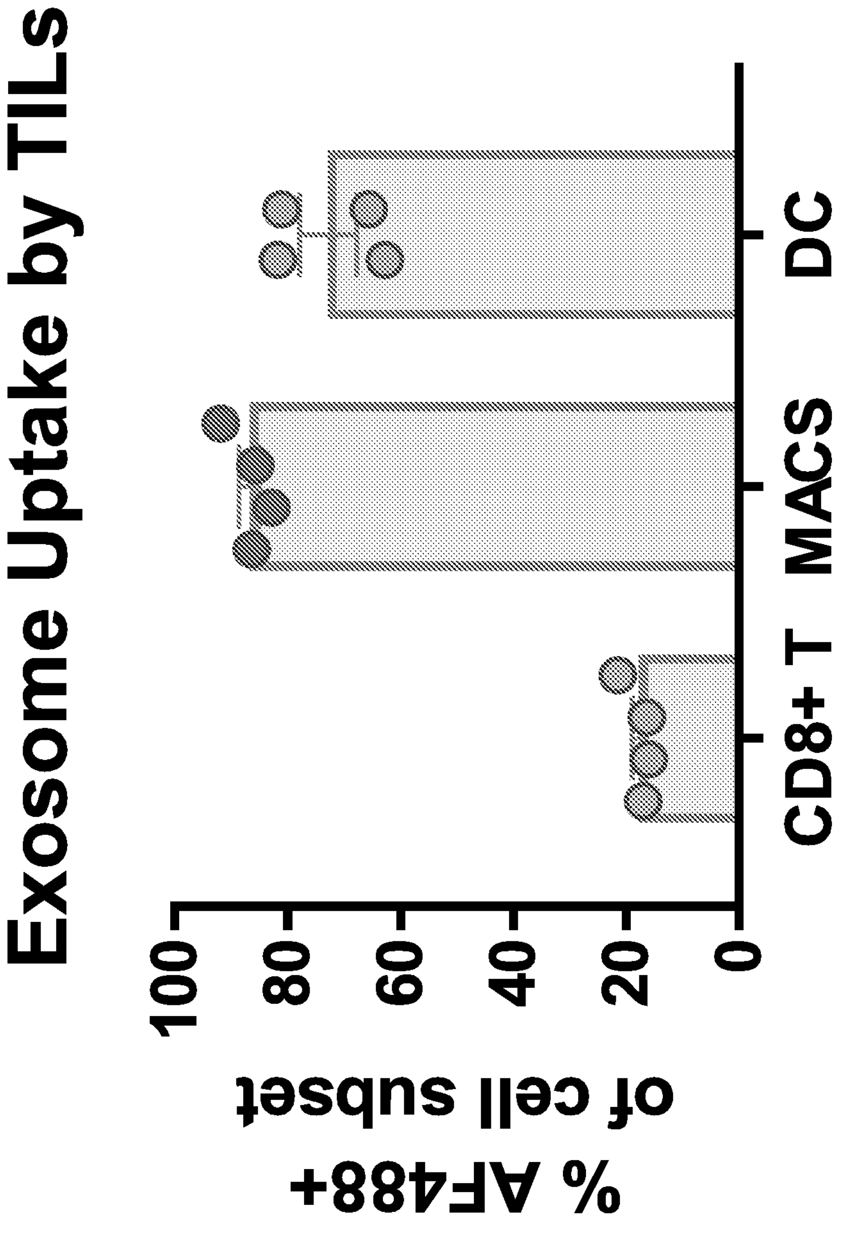
FIG. 51A shows the percent-positive population of different classes of tumor-infiltrating lymphocytes isolated from subcutaneous tumors injected with Alexa Fluor™ 488-labeled exosomes.
Figure 51B:
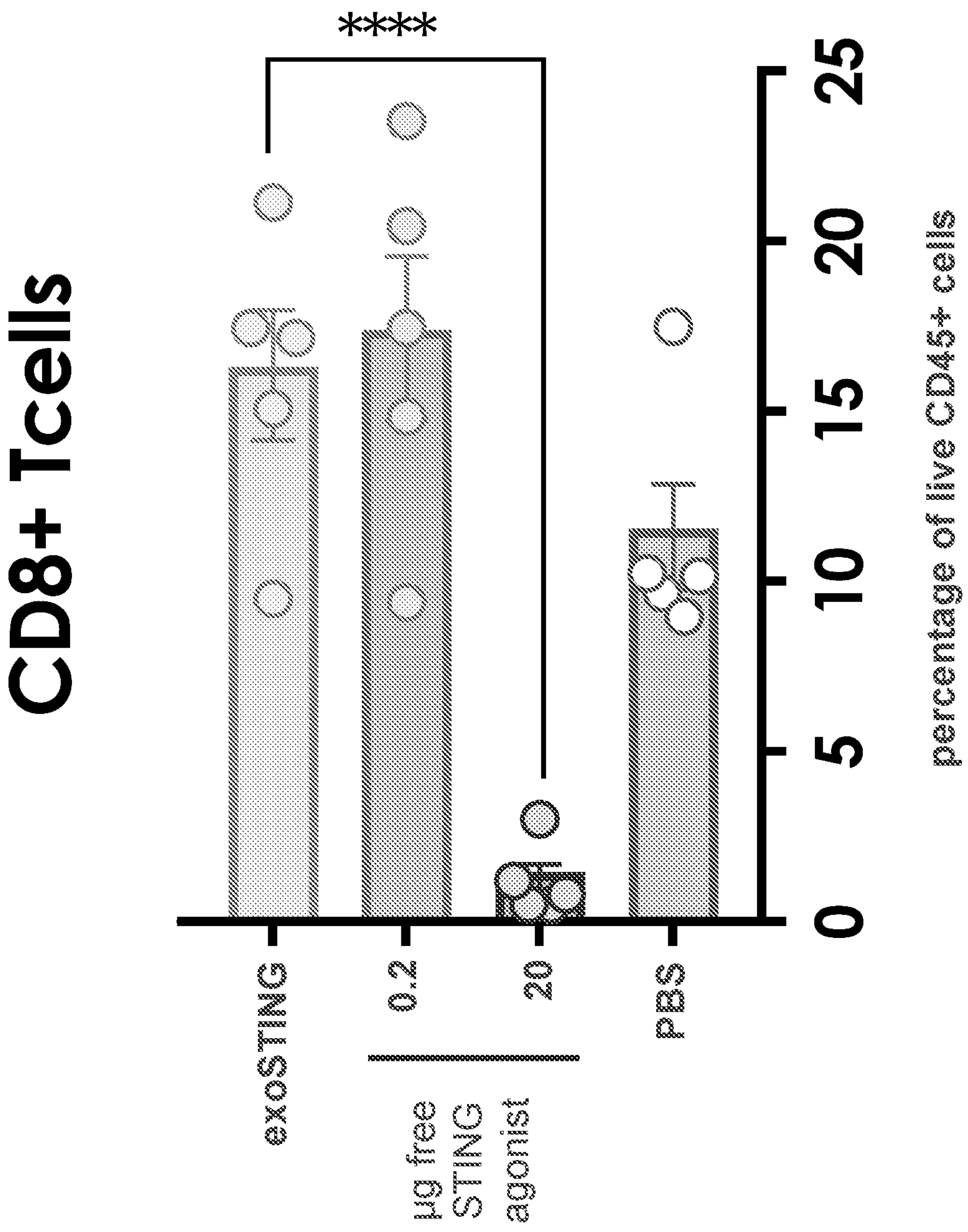
FIG. 51B shows the relative population of $CD8^+$ T-cells isolated from subcutaneous tumors injected with PBS, 200 ng of ML RR-S2 CDA loaded in PTGFRN overexpressing exosomes (EXOSTING™), 200 ng of ML RR-S2 CDA, or 20 μg of ML RR-S2 CDA.
Figure 51C:
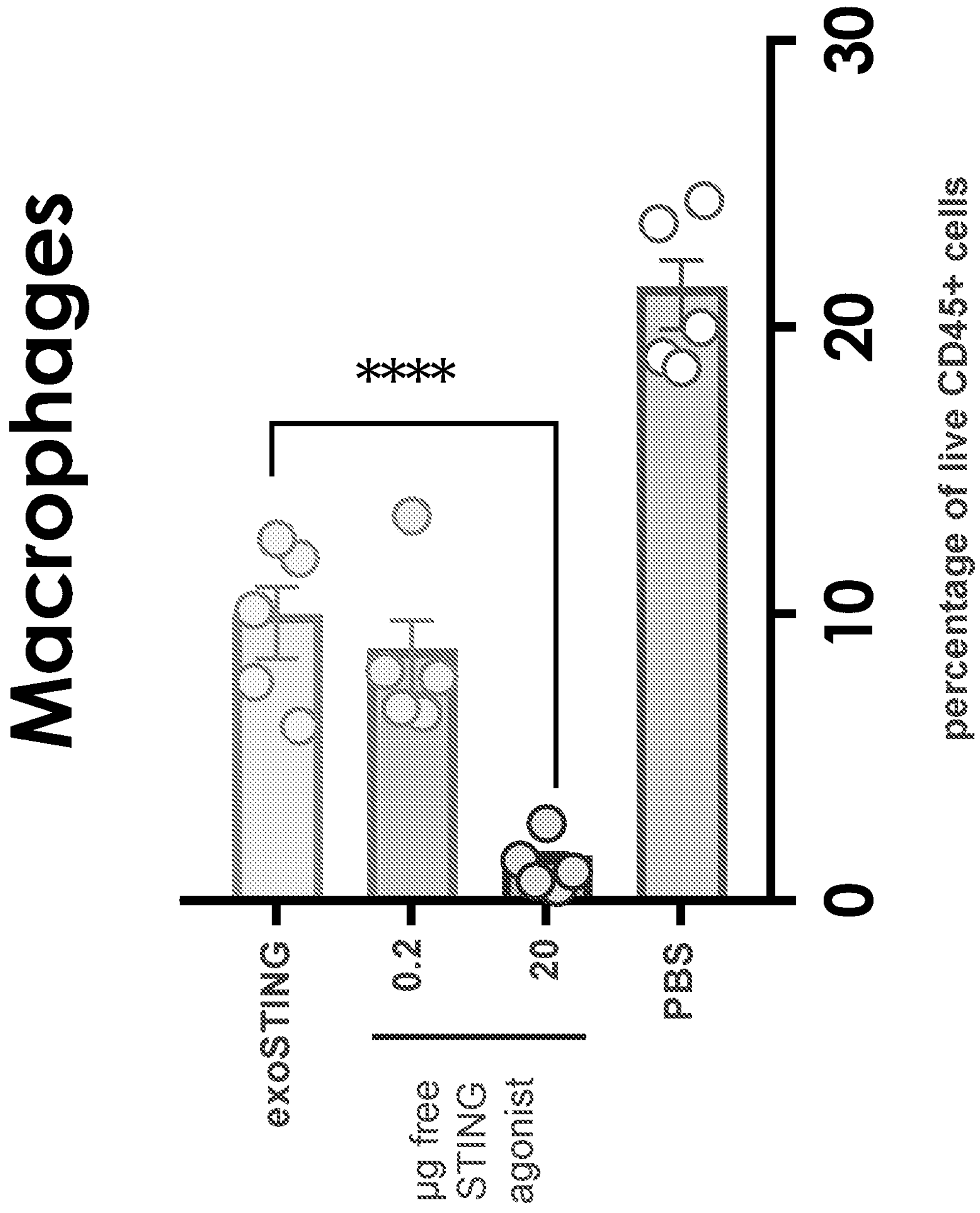
FIG. 51C shows the relative population of macrophages isolated from subcutaneous tumors injected with PBS, 200 ng of ML RR-S2 CDA loaded in PTGFRN overexpressing exosomes (EXOSTING™), 200 ng of ML RR-S2 CDA, or 20 μg of ML RR-S2 CDA.
Figure 51D:
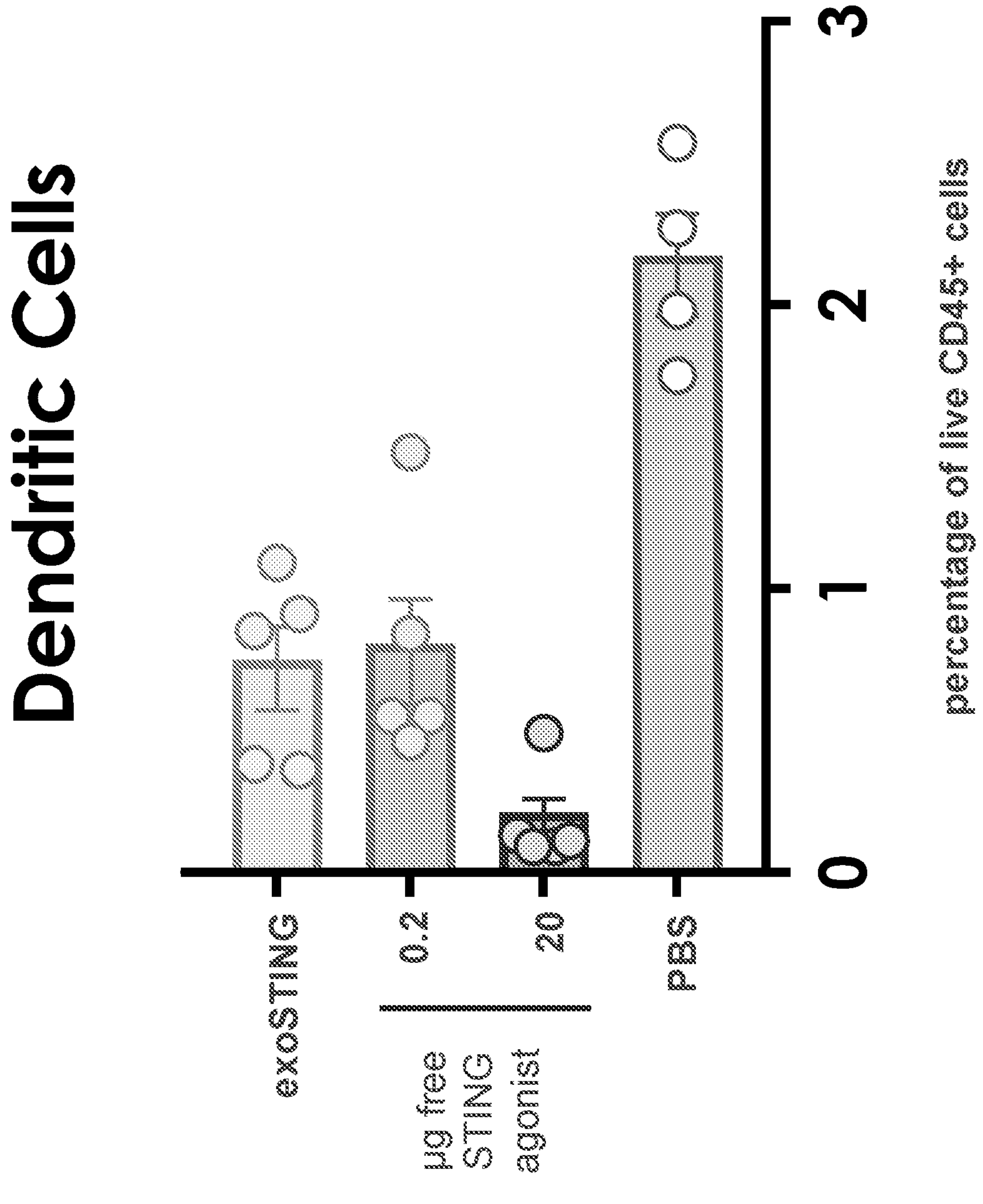
FIG. 51D shows the relative population of dendritic cells isolated from subcutaneous tumors injected with PBS, 200 ng of ML RR-S2 CDA loaded in PTGFRN overexpressing exosomes (EXOSTING™) 200 ng of ML RR-S2 CDA, or 20 μg of ML RR-S2 CDA.

Example 17: Exosomes Loaded with STING Agonists Are Engulfed by Antigen Presenting Cells and Are Not Toxic to Tumor-Resident Immune Effector Cells Constitutive activation of the STING pathway results in robust pro-inflammatory signaling and may be toxic to cells and tissues (N Engl J Med. 2014 Aug. 7; 371(6): 507-518). Non-selective delivery of STING agonists in a tumor microenvironment may result in a robust IFNβ response, but if response is too strong or originates in undesired cell populations, effector cells such as $CD8^+$ T-cells may be killed or otherwise attenuated. B16F10 melanoma tumors were injected with PTGFRN-overexpressing exosomes labeled with Alexa Fluor™ 488 and removed one hour post-injection. Tumor-infiltrating lymphocytes were purified and measured for fluorescence at 488 nm to track exosome uptake. Only ~20% of T-cells engulfed exosomes, while ~90% and ~70% of macrophages and dendritic cells, respectively, engulfed exosomes (FIG. 51A). These data suggest that antigen presenting cells in the tumor microenvironment are natural target cells of human exosomes. To determine whether the cell-specific uptake of exosomes resulted in differential STING pathway activation for EXOSTING™ versus free STING agonists, the B16F10 melanoma tumors from above were injected a second time with PBS, 20 μg free ML RR-S2 CDA, 0.2 μg free ML RR-S2 CDA, or 200 ng ML RR-S2 CDA loaded in PTGFRN-overexpressing exosomes. 24 hours post-injection, the tumors were isolated, homogenized, and live $CD45^+$ cell populations were counted. In the 20 μg ML RR-S2 CDA group, $CD8^+$ T-cells, macrophages, and dendritic cells were dramatically reduced compared to the other groups (FIGS. 51B-D). These data indicate that high doses of free STING agonists may be toxic to the antigen presenting cells and T-cells in the tumor microenvironment, the very cells required for antigen presentation and tumor cell killing. Non-selective delivery of high doses of STING agonists therefore may attenuate desirable immune stimulatory responses. EXOSTING™, due to lower required dose for comparable therapeutic response, therefore operates in a wider therapeutic window and reduces the liabilities (e.g., systemic toxicity, immune cell killing, lack of cell selectivity) observed with free STING agonists.

Figure 52B:
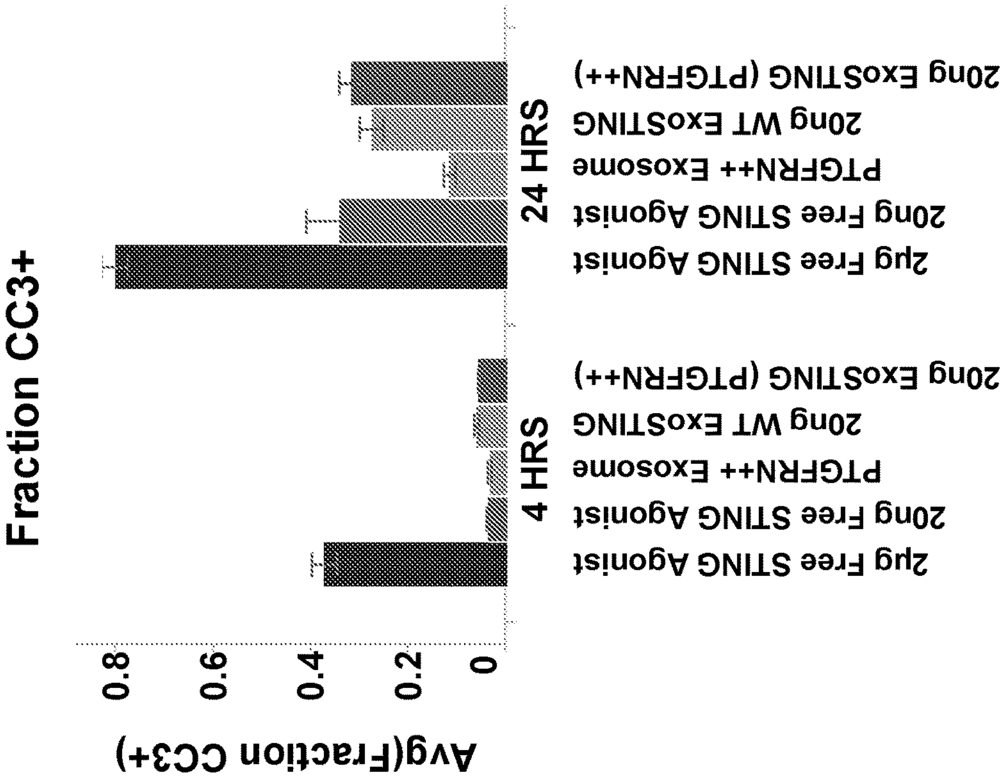
FIGS. 52A-52D show quantitative imaging results of IFNβ transcripts (FIG. 52A) or cleaved caspase 3 protein (FIG. 52B) in murine sarcoma cells directly injected with microdoses of free ML RR-S2 CDA or the indicated exosomes, with or without ML RR-S2 CDA.
Figure 52A:
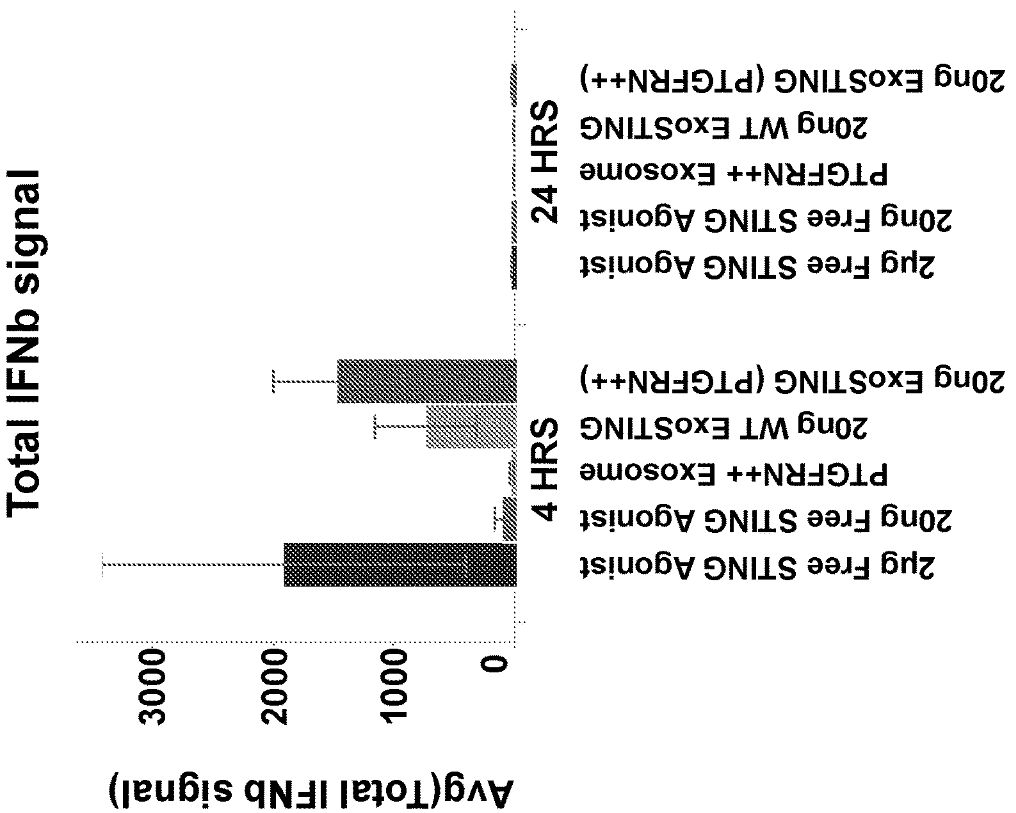

Example 18: High-Resolution Imaging of Intratumorally Administered STING Agonist-Loaded Exosomes Demonstrate Increased Potency and Reduced Toxicity Compared to Free STING Agonist The measurements of EXOSTING™ activity shown in the previous examples demonstrate that exosomes, particularly PTGFRN-overexpressing exosomes, can enhance the activity of STING agonist molecules. The bulk measurements, from homogenized tissues or isolated serum, provide meaningful data on the potency and selectivity of EXOSTING™ in various applications, but do not allow for direct comparison between samples in the same tumor or to the local effects at the site of injection. To answer this question a microdosing intratumoral injection study was completed using a multi-injector apparatus (CIVO®; Presage Biosciences, Seattle, WA). As described in the Methods above, A20 lymphoma cells were implanted subcutaneously in mice and injected simultaneously with up to six different agents. Single dose injections were done with 2 g free ML RR-S2 CDA, 200 ng ML RR-S2 CDA, PTGFRN overexpressing exosomes, wild-type exosomes containing 20 ng ML RR-S2 CDA, or PTGFRN overexpressing exosomes containing 20 ng of ML RR-S2 CDA. Tumors were collected at four hours and 24 hours post-injection, processed, and stained for the presence of IFNβ mRNA (by in situ hybridization) and cleaved caspase 3 protein (Jackson Immunoresearch, antibody #111-605-144). At four hours post-injection, IFNβ levels were comparable between the high dose STING agonist and the PTGFRN O/E EXOSTING™ groups, and much higher than the low dose free STING agonist or empty exosome groups (FIG. 52A). The IFNβ signal returned to baseline by 24 hours post-treatment. Cleaved caspase 3 (CC3), a marker for apoptosis, was dramatically increased at four and 24 hours for high dose free STING agonist compared to all other groups, and modest for the EXOSTING™ and low dose free STING agonist groups, indicating that high doses of free STING agonist led to greater apoptosis with no enhanced benefit for IFNβ production compared to EXOSTING™ (FIG. 52B). These data, combined with the selective cell-type uptake described in Example 17 suggest that EXOSTING™ IS Selectively targeting immune cells leading to enhanced IFNβ secretion without non-selective cell killing observed with the free STING agonist.

Figure 52C:
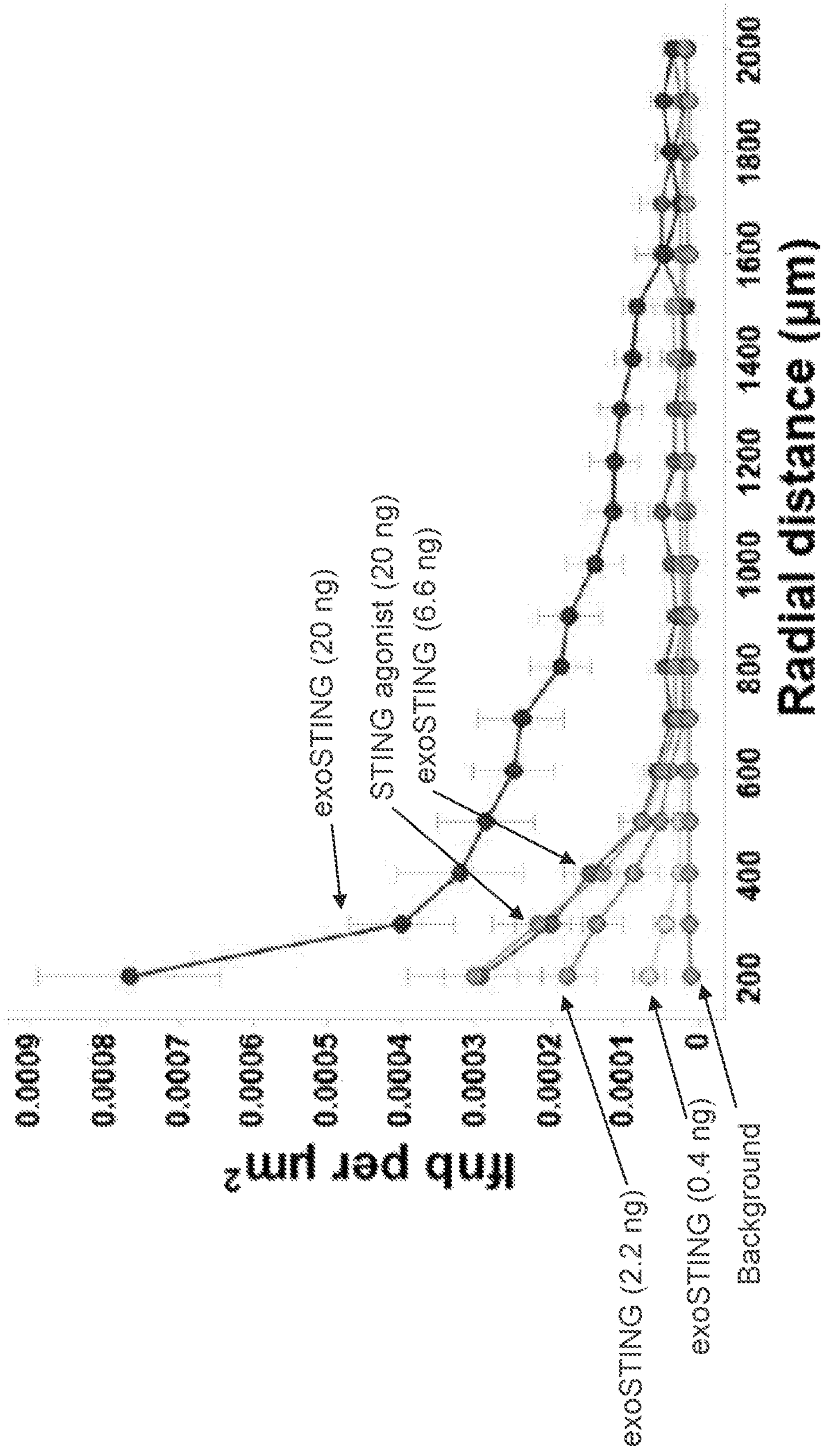
Figure 52D:
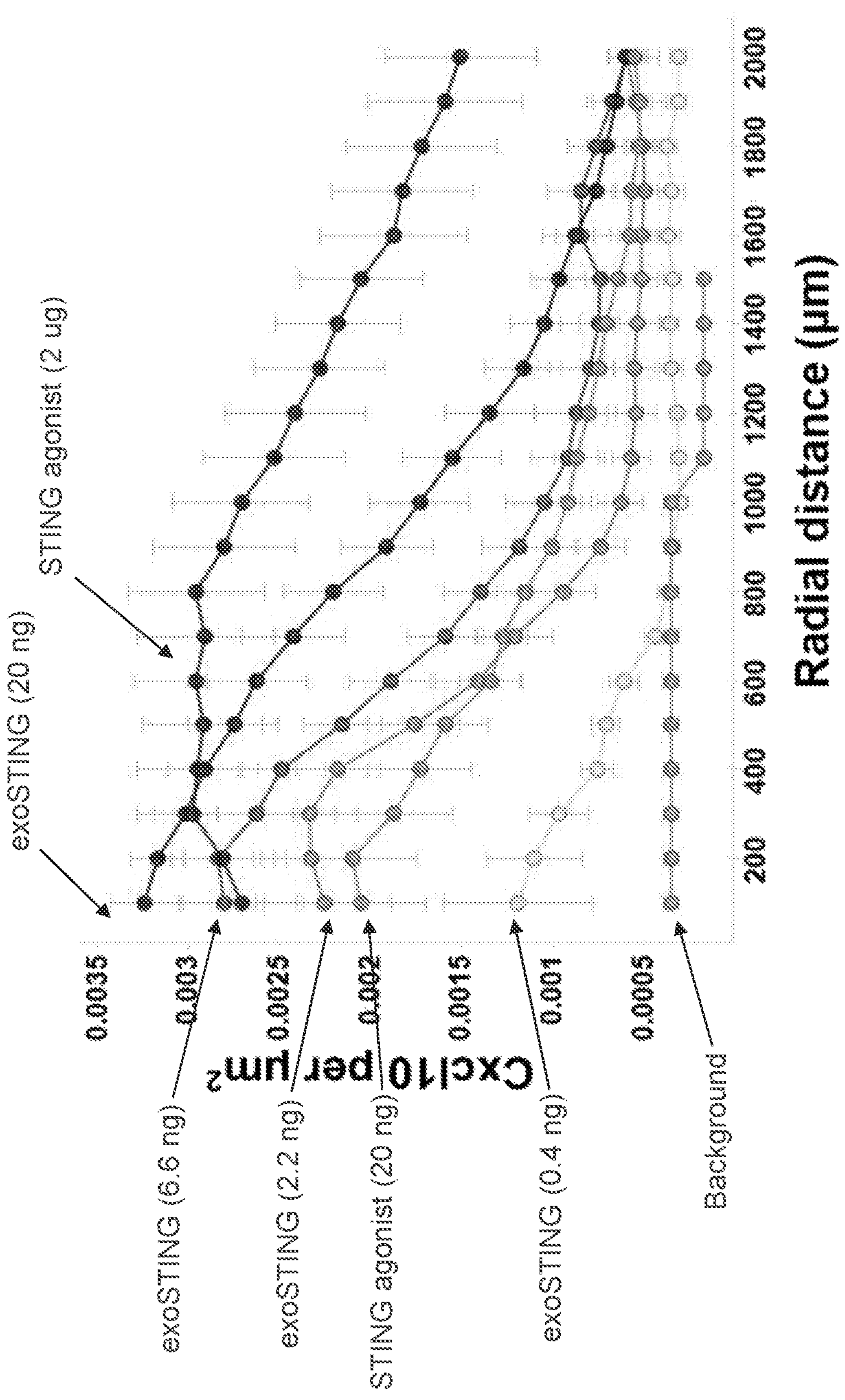
Figures 53A, 53B, 53C, 53D:
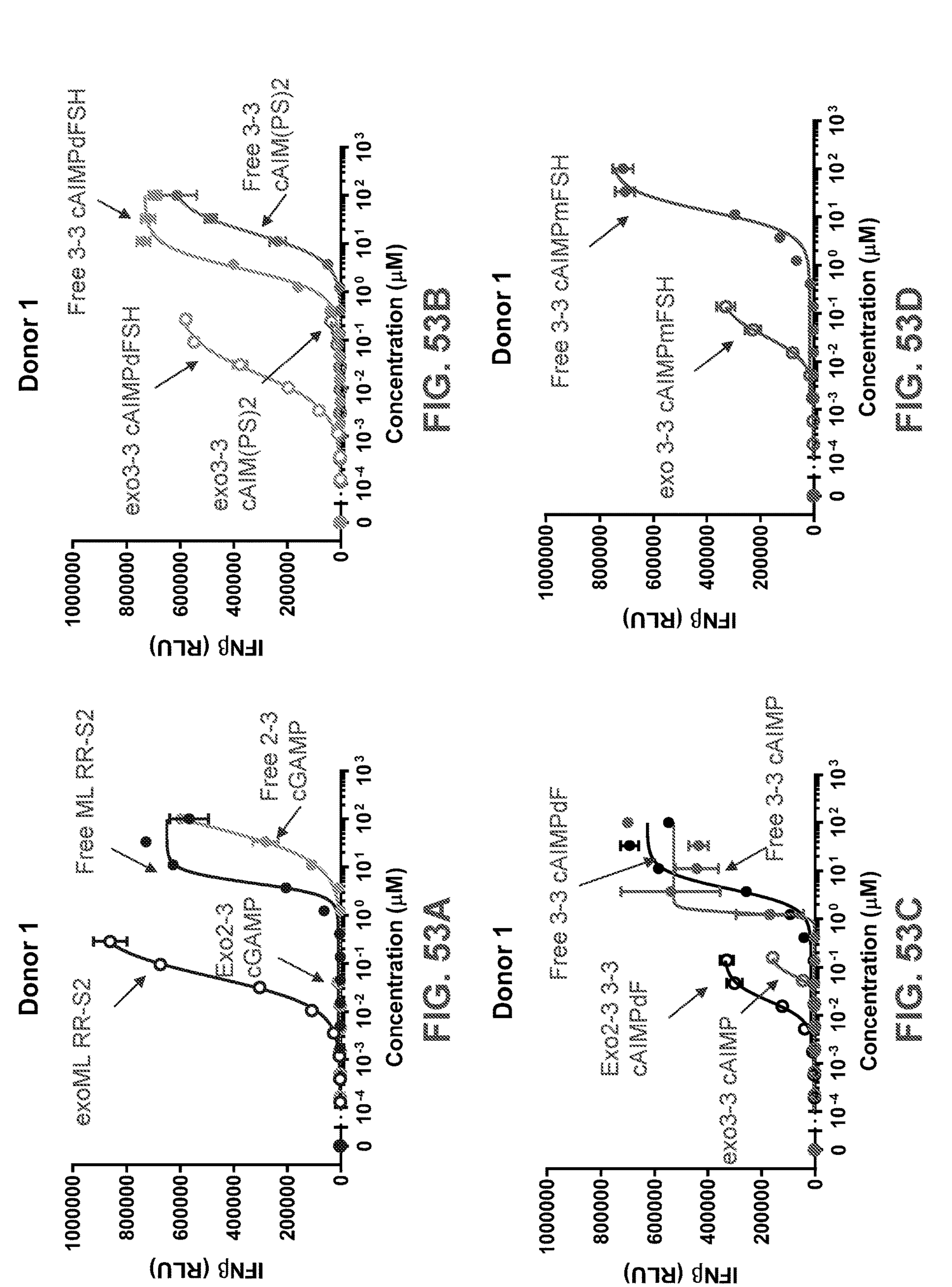
FIGS. 53A-53G shows a comparison of the IFNβ response in peripheral blood mononuclear cells (PBMCs) treated with exosome-encapsulated STING agonist and free STING agonist, as determined by relative luminescence (RLU).
Figure 53F:
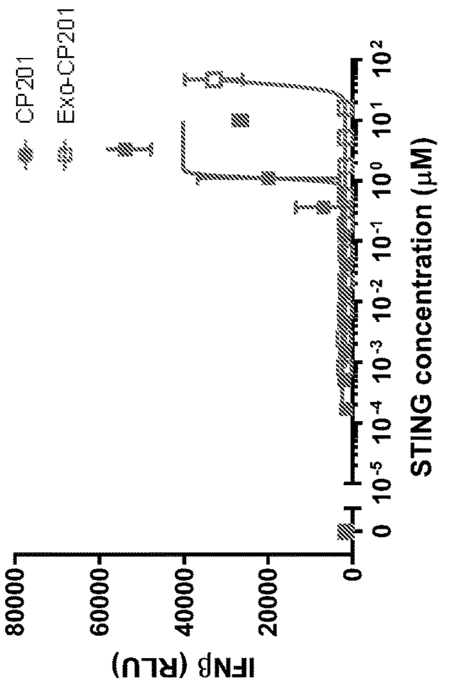
Figure 53E:
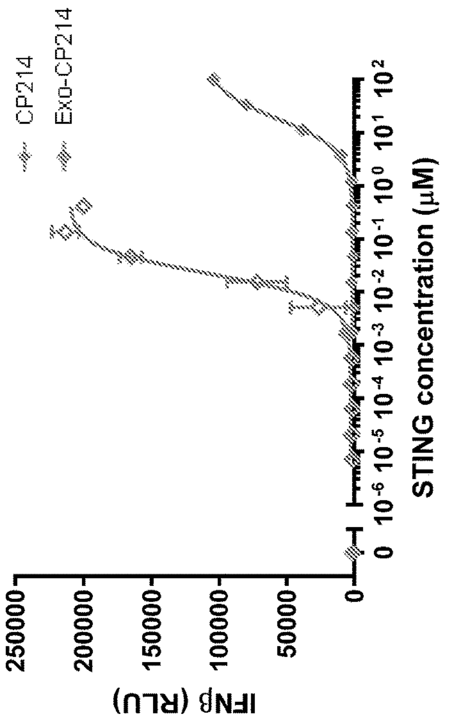
Figure 53G:
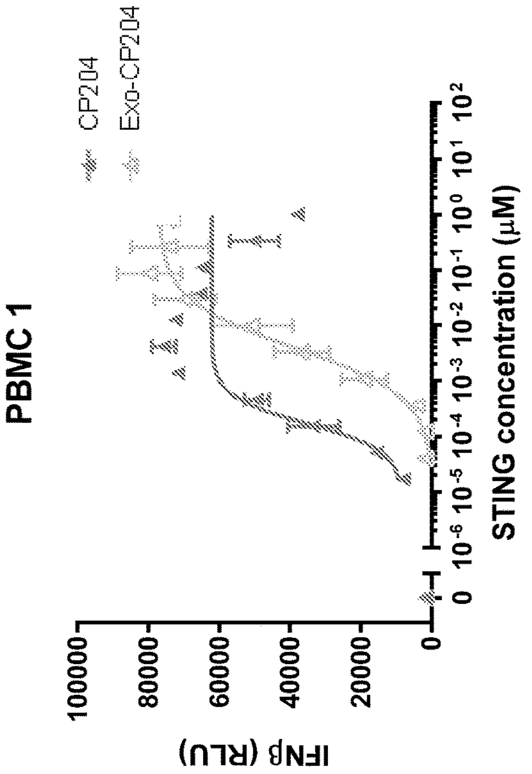

In another study, single dose injections were done with 2 g free 3-3 cAIMPdFSH, 20 ng free 3-3 cAIMPdFSH, 0.4 ng, 2.2 ng, 6.6 ng, or 20 ng of 3-3 cAIMPdFSH loaded in PTGFN-overexpressing exosomes into A20 tumors. Tumors were collected at four hours post-injection, processed, stained for the presence of IFNβ or CXCL10 mRNA (by in situ hybridization), and radial response analysis was conducted. IFNβ (FIG. 52C) or CXCL10 (FIG. 52D) mRNA expression were highest where at samples were injected and were gradually decreased as radial distance was increased.

Example 19: Comparative Potency of Different Exosome-Encapsulated Cyclic Dinucleotides or Non-Cyclic Dinucleotides STING Agonist HEK293SF cells overexpressing PTGFRN were grown in shake flasks and the resulting exosomes were purified by Optiprep™ density gradient ultracentrifugation as described in the Methods. The purified exosomes were loaded with STING agonists including ML RR-S2 CDA, 2-3 cGAMP, 3-3 cAIMPdFSH, 3-3 cAIM(PS)2, cAIMPmFSH, cAIMPdF, cAIMP, CP214, CP201, and CP204 according to the methods in Example 1. The 3-3 cAIMPdFSH, 3-3 cAIM (PS)2, cAIMPdF, cAIMP correspond to compound 53, 13, 52, and 51 from a paper (J Med Chem. 2016 Nov. 23; 59(22):10253-10267), respectively. The CP214 is 2-3 cAMPmFSH. The CP201 and CP204 are analogues of compounds from patent WO2017/175156 and WO2017/175147, respectively. Loading was quantified as described in Example 1. The exosome-encapsulated or free STING agonists were added to human PBMCs and incubated at 37° C. overnight. Activation of PBMCs by the STING agonists was detected by measuring the amount of IFNβ in the supernatant. As shown in FIG. 53A-G, all exosome-encapsulated STING agonists resulted in a potency shift compared to free STING agonists, as shown in Example 2.

Example 20: In Vivo Potency of Free STING Agonists Compared to Exosome-Encapsulated STING Agonists in Tumor-Bearing Mice (C57BL/6) and STING Knock-Out Mice (C57BL/6-Tmem173$^{gt}$)

Figure 54A:
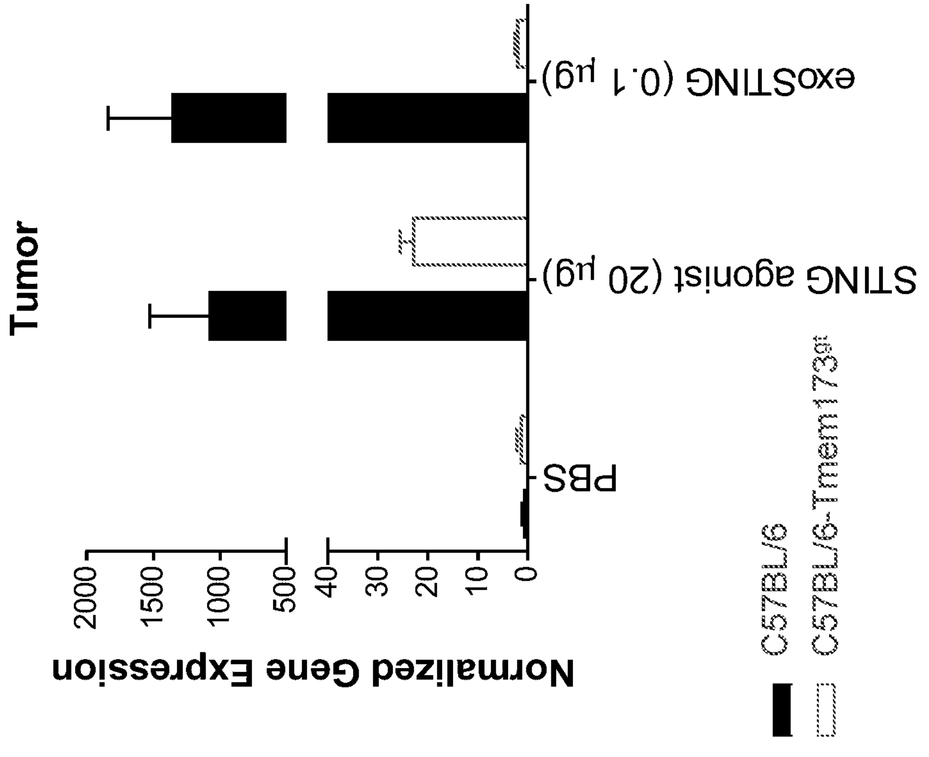
FIGS. 54A-54C show IFNβ expression profiles in tissues (tumor, draining lymph node, and spleen, respectively) from B16F10 tumor-bearing C57BL/6 mice (filled bars) or C57BL/6-Tmem173$^{gt}$ mice (empty bars) after a single intratumoral injection of PBS, 20 μg free 3-3 cAIMPdFSH, or 0.1 μg exosome-encapsulated 3-3 cAIMPdFSH.
Figure 54B:
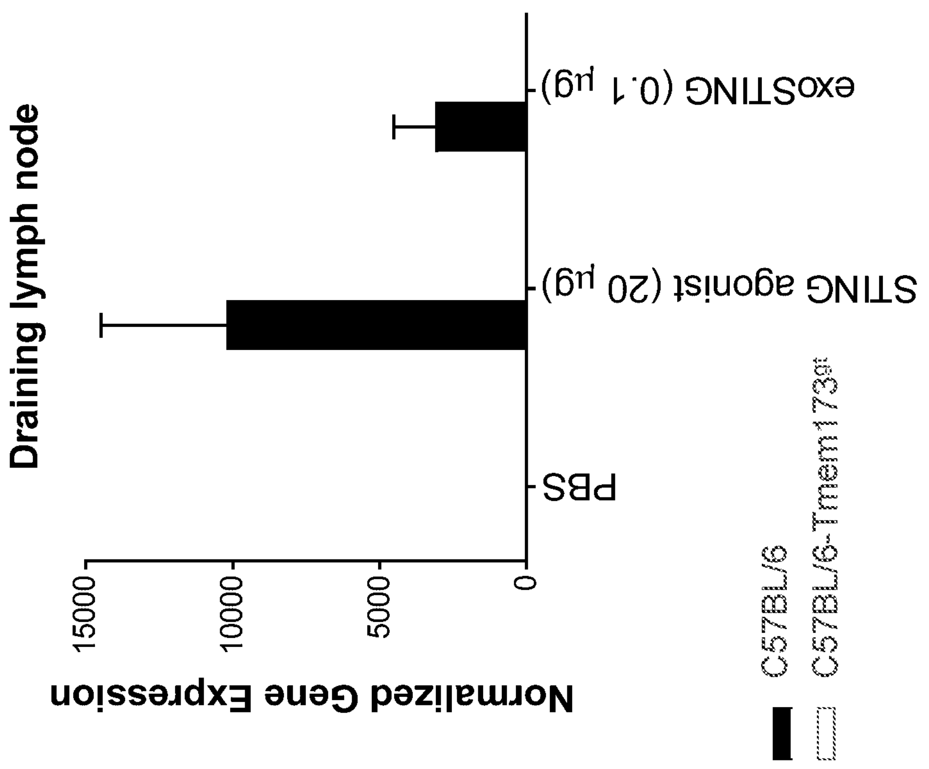
Figure 54C:
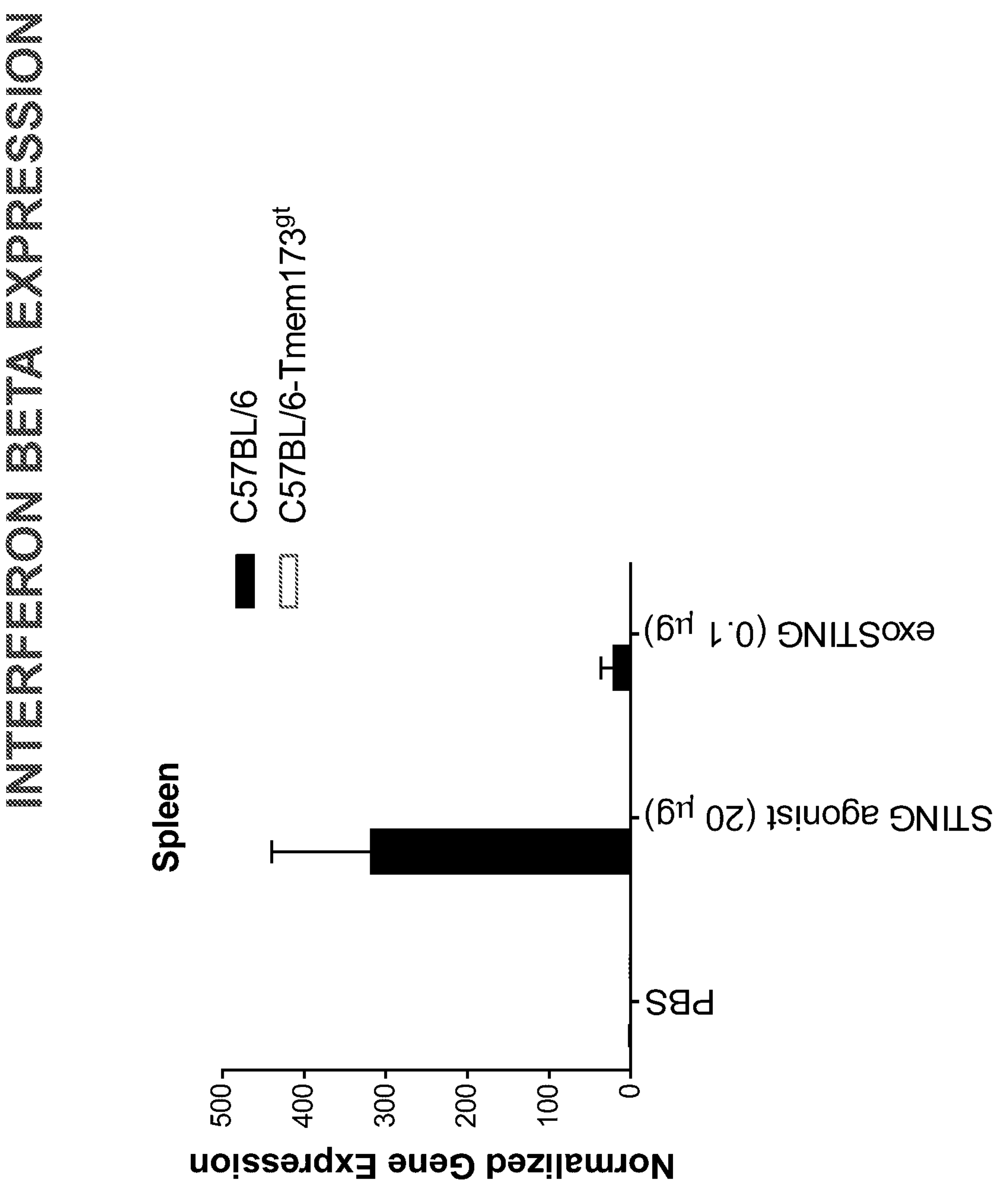
Figures 55A, 55B:
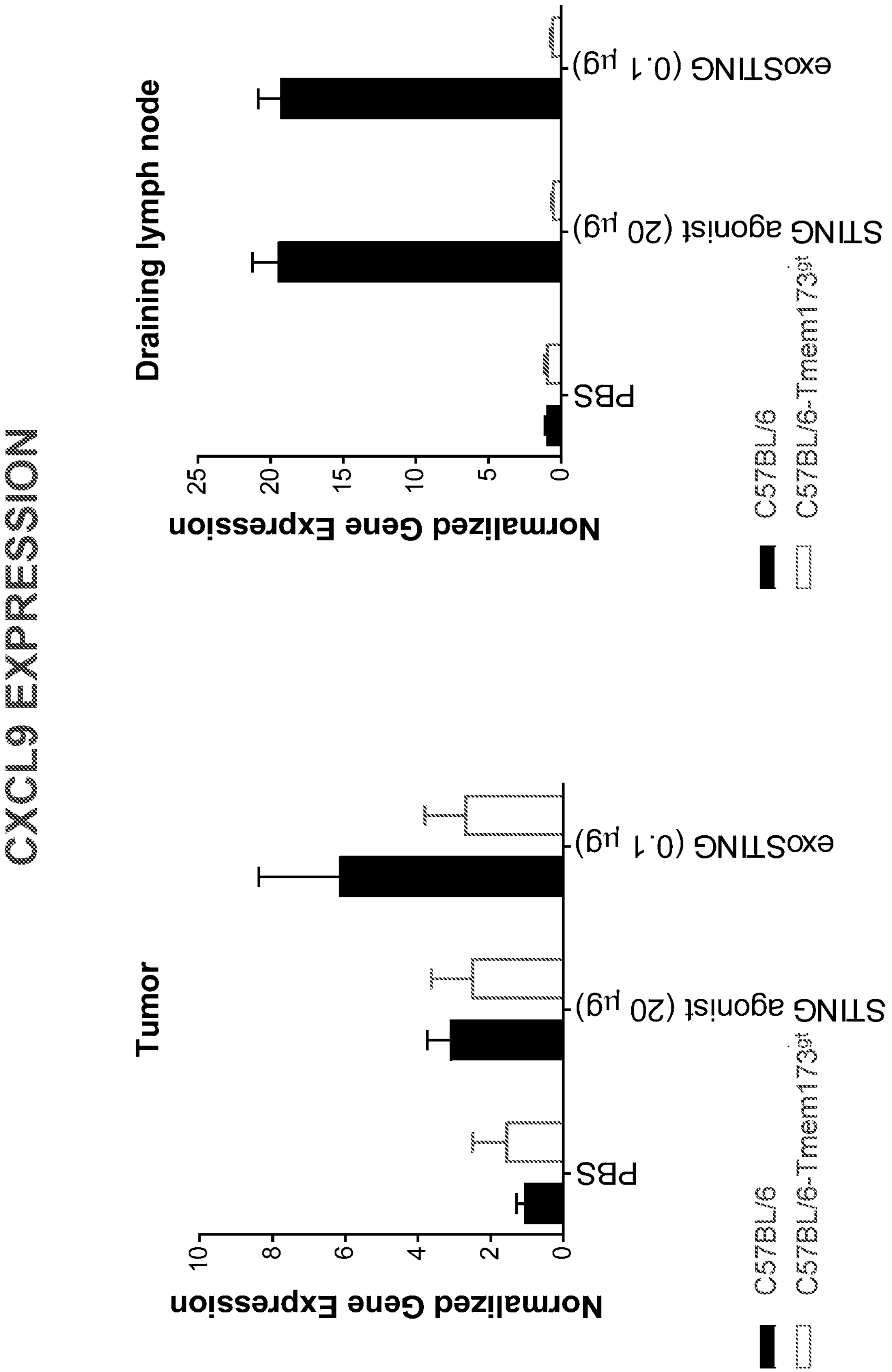
FIGS. 55A-55C show CXCL9 expression profiles in tissues (tumor, draining lymph node, and spleen, respectively) from B16F10 tumor-bearing C57BL/6 mice (filled bars) or C57BL/6-Tmem173$^{gt}$ mice (empty bars) after a single intratumoral injection of PBS, 20 μg free 3-3 cAIMPdFSH, or 0.1 μg exosome-encapsulated 3-3 cAIMPdFSH.
Figure 55C:
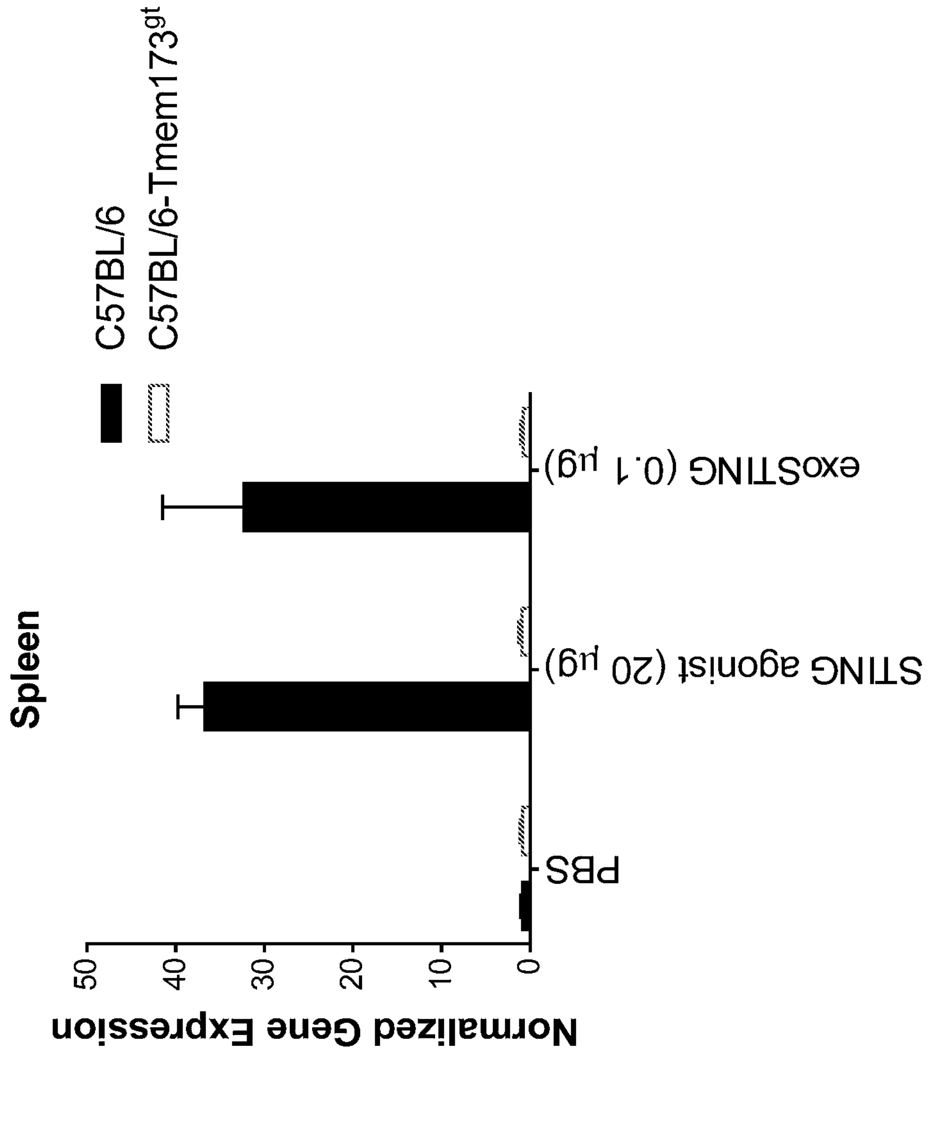
Figure 56A:
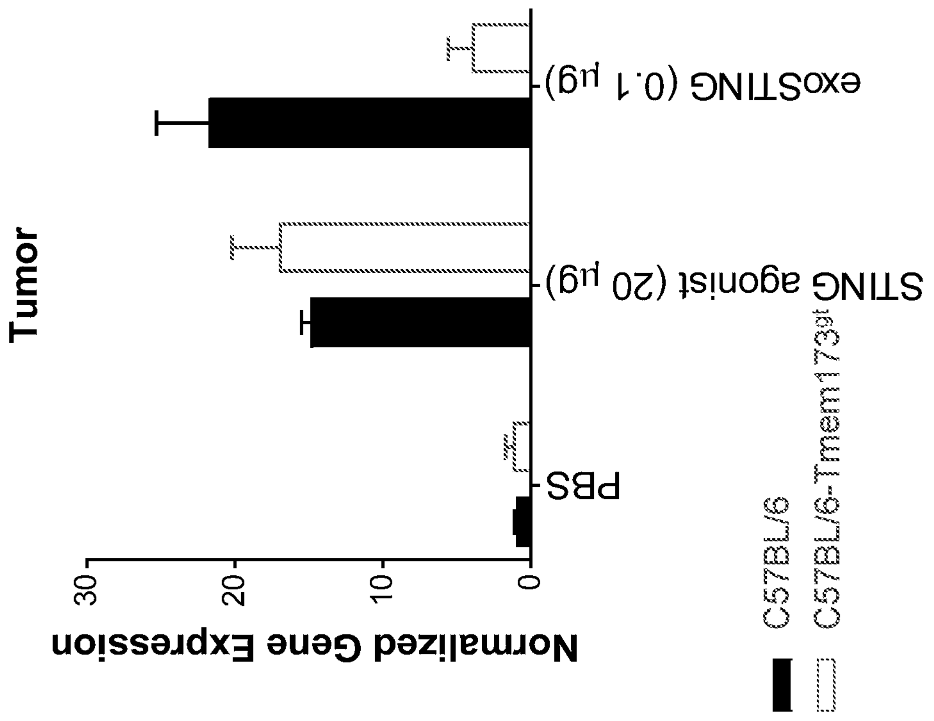
FIGS. 56A-56C show CXCL10 expression profiles in tissues (tumor, draining lymph node, and spleen, respectively) from B16F10 tumor-bearing C57BL/6 mice (filled bars) or C57BL/6-Tmem173$^{gt}$ mice (empty bars) after a single intratumoral injection of PBS, 20 μg free 3-3 cAIMPdFSH, or 0.1 μg exosome-encapsulated 3-3 cAIMPdFSH.
Figure 56B:
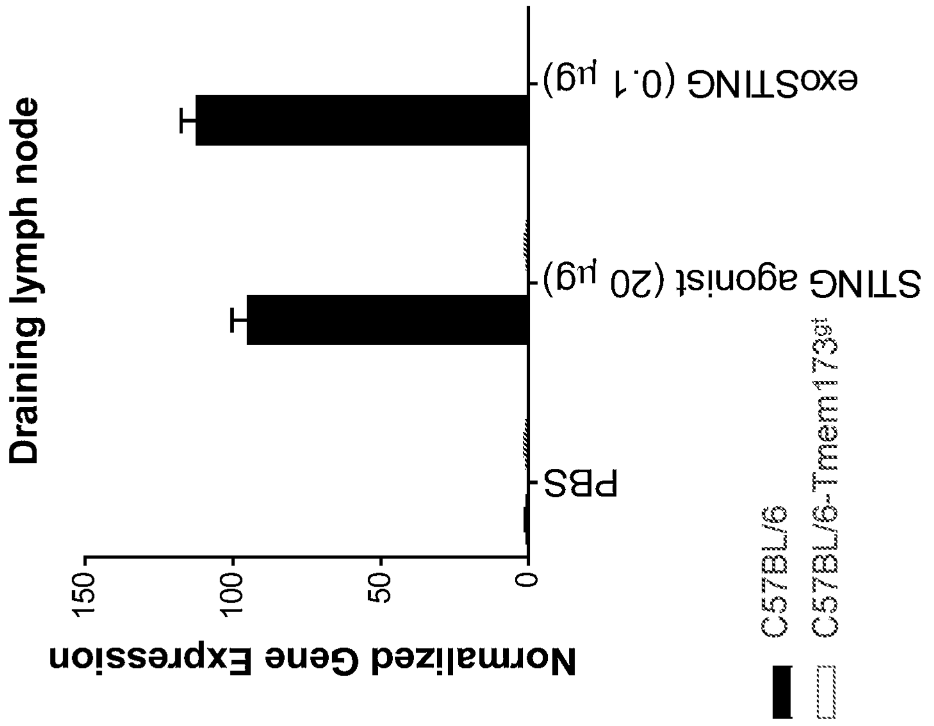
Figure 56C:
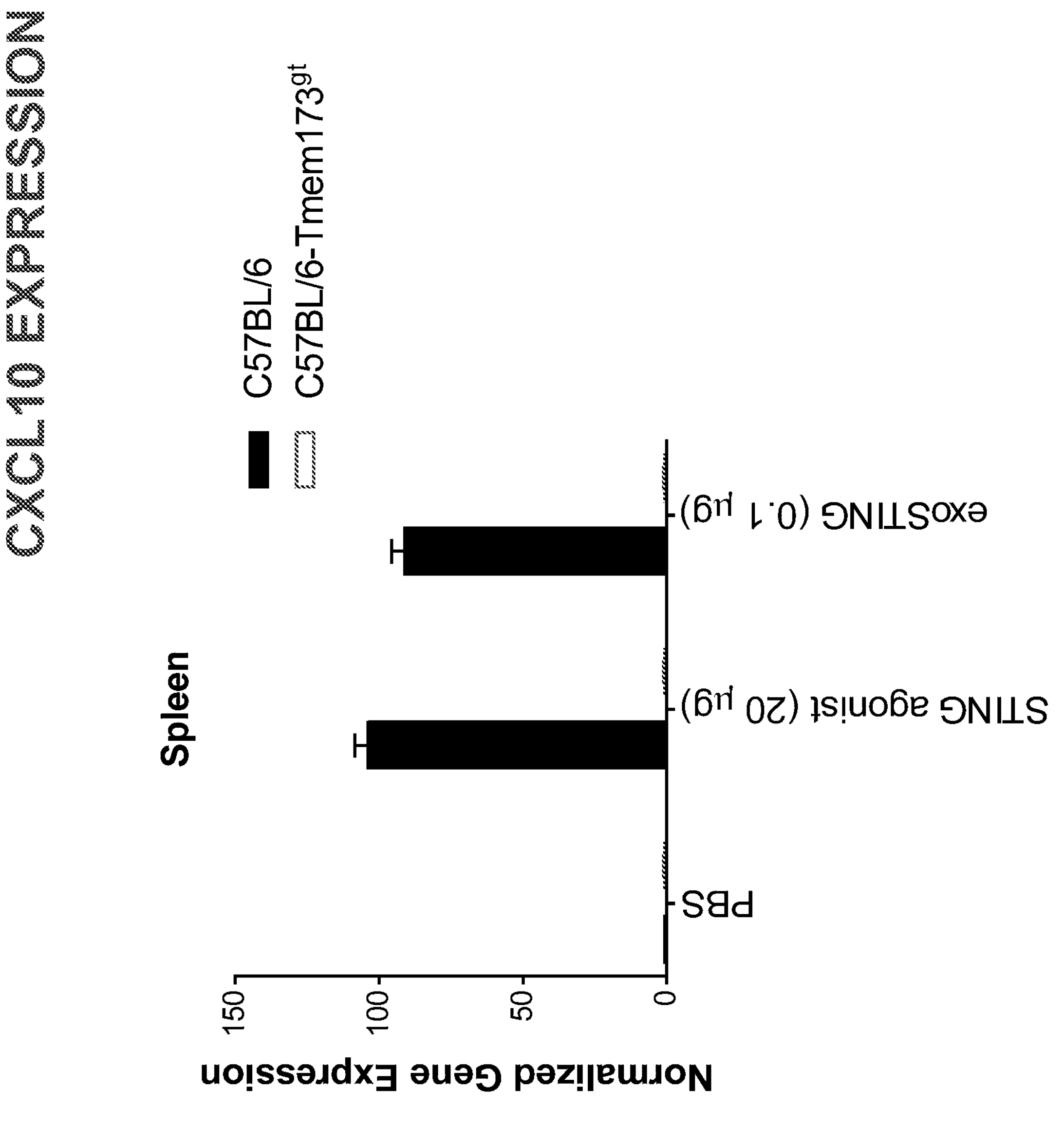
Figure 57B:
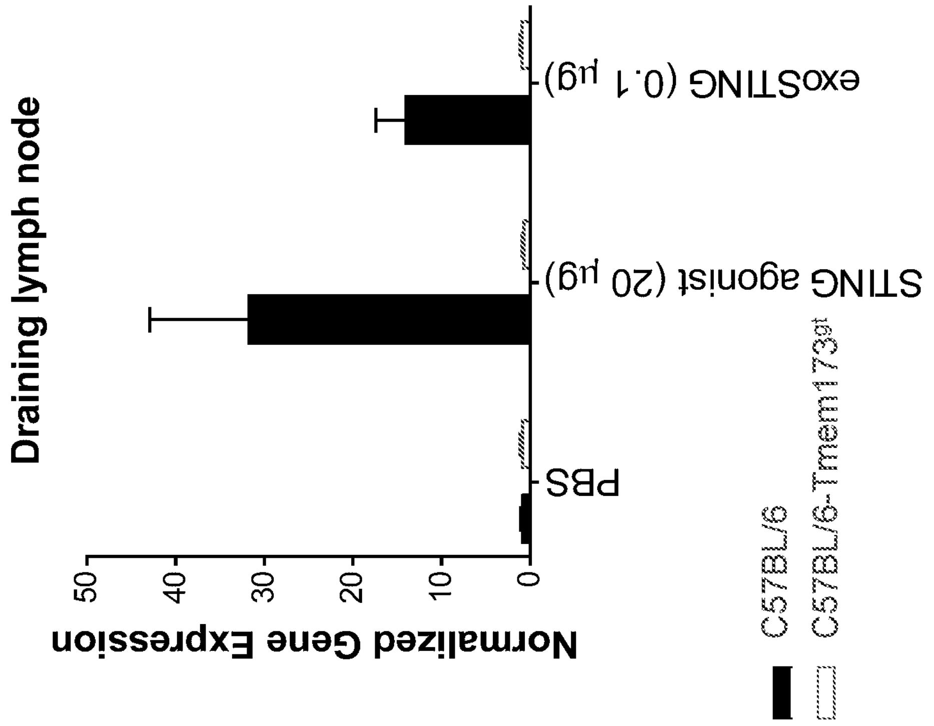
FIGS. 57A-57C show IFN-γ expression profiles in tissues (tumor, draining lymph node, and spleen, respectively) from B16F10 tumor-bearing C57BL/6 mice (filled bars) or C57BL/6-Tmem173$^{gt}$ mice (empty bars) after a single intratumoral injection of PBS, 20 μg free 3-3 cAIMPdFSH, or 0.1 μg exosome-encapsulated 3-3 cAIMPdFSH.
Figure 57A:
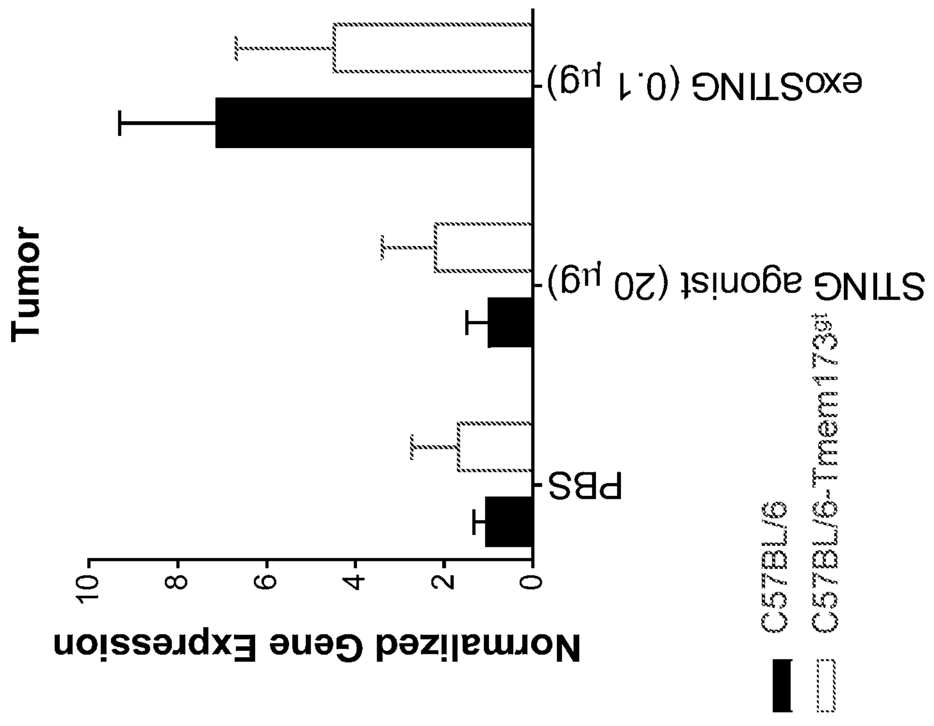
Figure 57C:
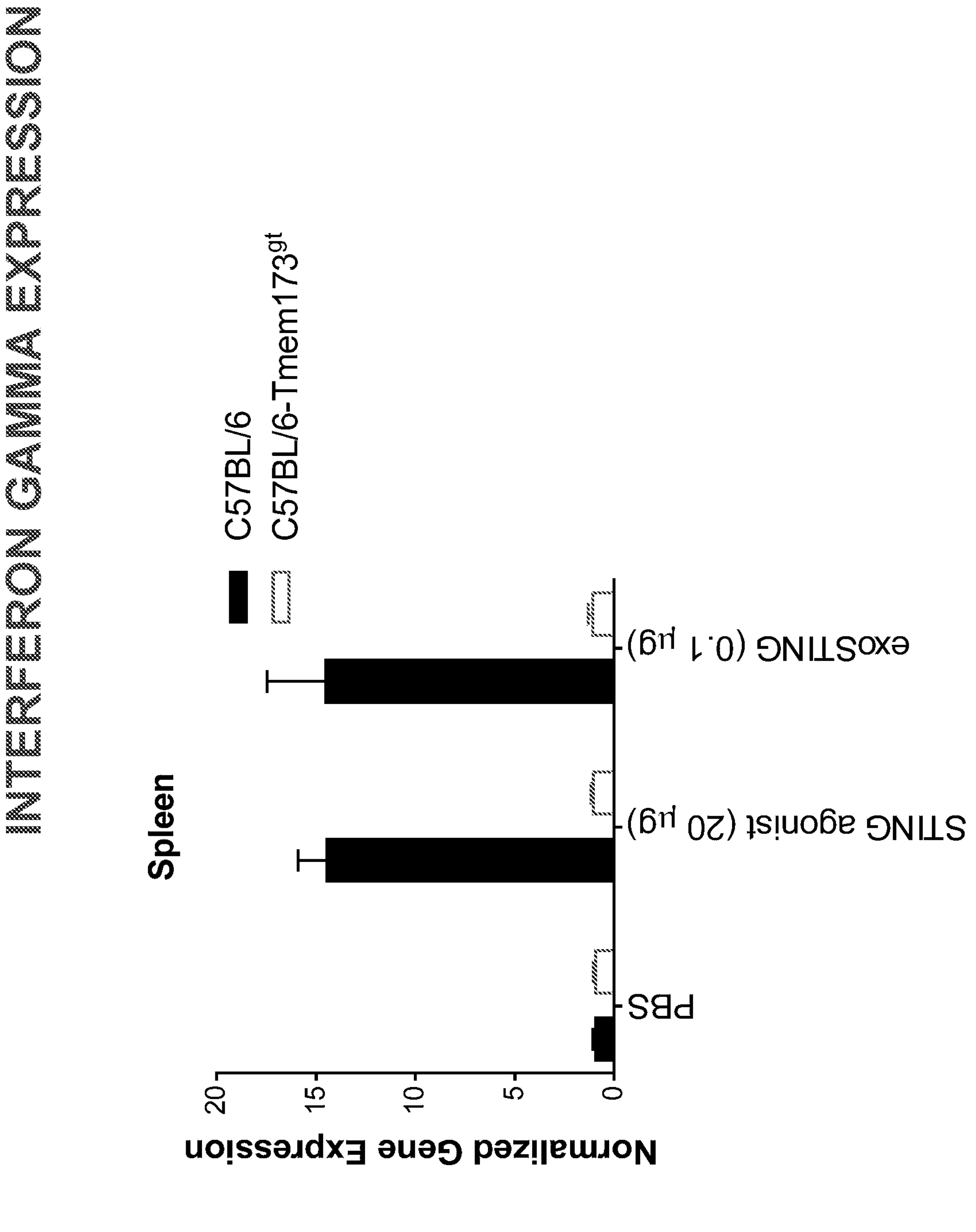
Figure 58B:
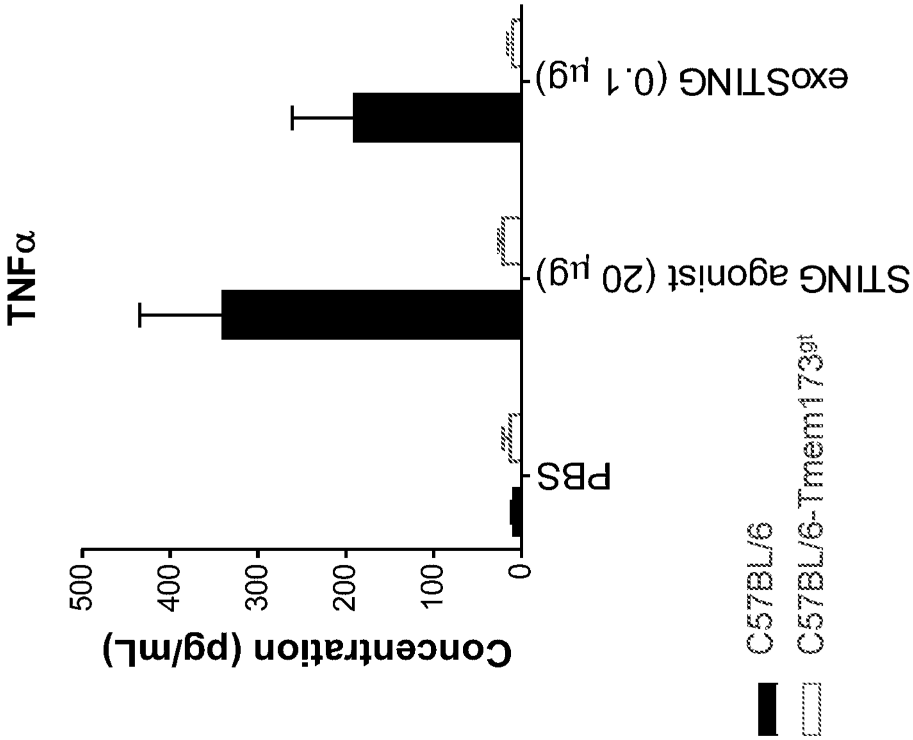
FIGS. 58A-58D show serum cytokine expression profiles (IFN-β, TNF-α, IL-6, and MCP-1, respectively) in B16F10 tumor-bearing C57BL/6 mice (filled bars) or C57BL/6-Tmem173$^{gt}$ mice (empty bars) after a single intratumoral injection of PBS, 20 μg free 3-3 cAIMPdFSH, or 0.1 μg exosome-encapsulated 3-3 cAIMPdFSH.
Figure 58A:
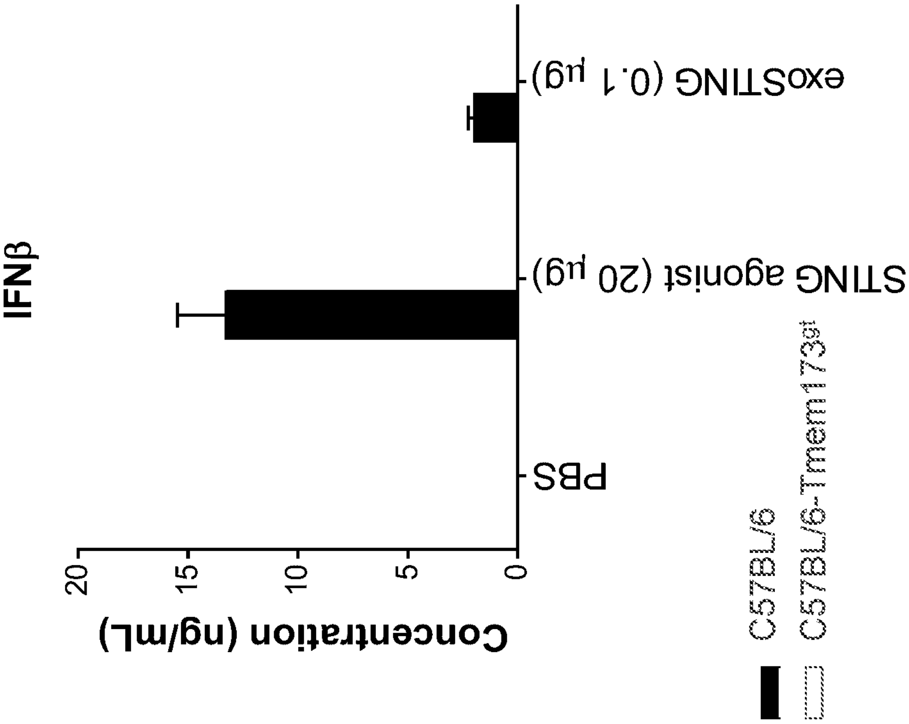
Figure 58C:
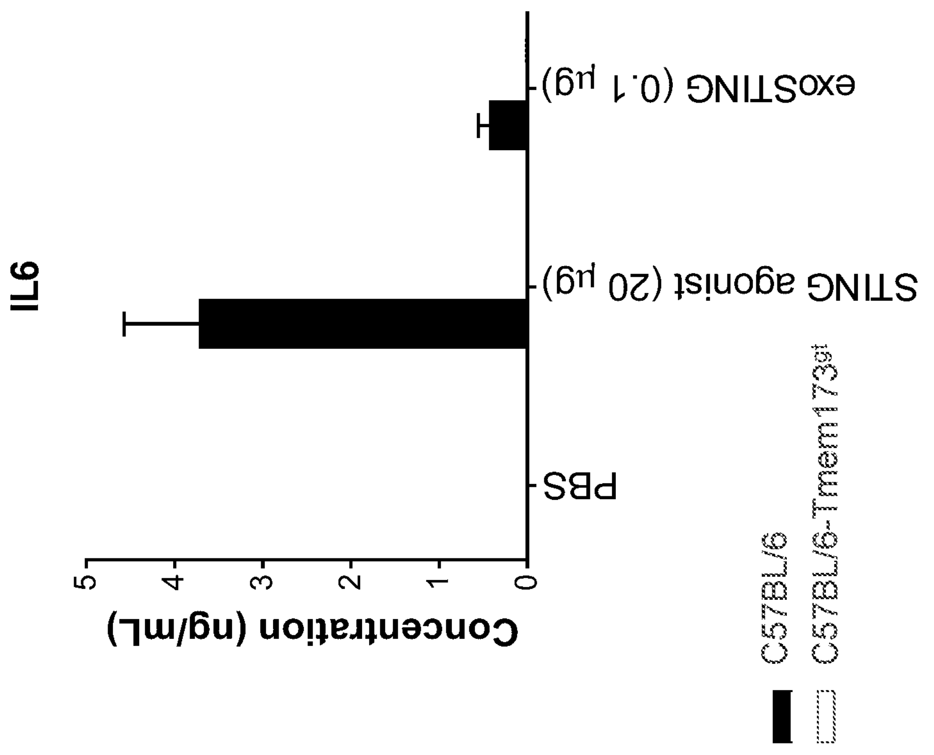
Figure 58D:
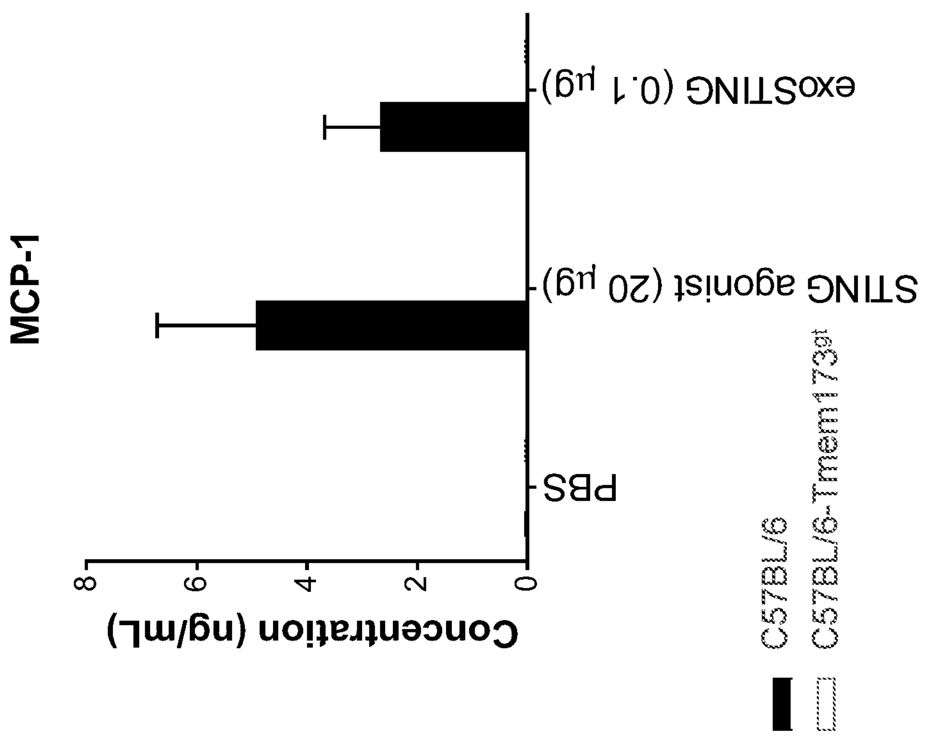

Three groups of C57BL/6 mice and C57BL/6-Tmem173$^{gt}$ mice (4-5 mice per group) were inoculated subcutaneously with 1×10$^6$ B16F10 tumor cells. Eight days post-inoculation the mice were injected with a single intratumoral dose of PBS, 20 μg of free 3-3 cAIMPdFSH, or 0.1 μg of 3-3 cAIMPdFSH loaded in PTGFN-overexpressing exosomes (exeSTING). Four hours post-injection the tumors, draining lymph nodes, spleens, and serum were collected and cytokine levels were measured. IFNβ gene expression levels in the tumors (FIG. 54A), draining lymph node (FIG. 54B), and spleen (FIG. 54C) from C57BL/6 mice (filled bars) were comparable in the 20 μg free STING agonist and 0.1 μg exosome-STING agonist groups, whereas IFNβ gene expression levels in the tumors (FIG. 54A), draining lymph node (FIG. 54B), and spleen (FIG. 54C) from C57BL/6-Tmem173$^{gt}$ mice (empty bars) were similar as control group. Additionally, the levels of IFNγ and the T-cell chemoattractants CXCL9 and CXCL10 were all higher in the exosome-STING agonist group from C57BL/6 mice (filled bars), but were not induced in the exosome-STING agonist group from C57BL/6-Tmem173$^{gt}$ mice (empty bars) (FIGS. 55, 56, and 57). In addition to gene expression, serum cytokine profiles are showing same trend (FIG. 58).

Figure 59:
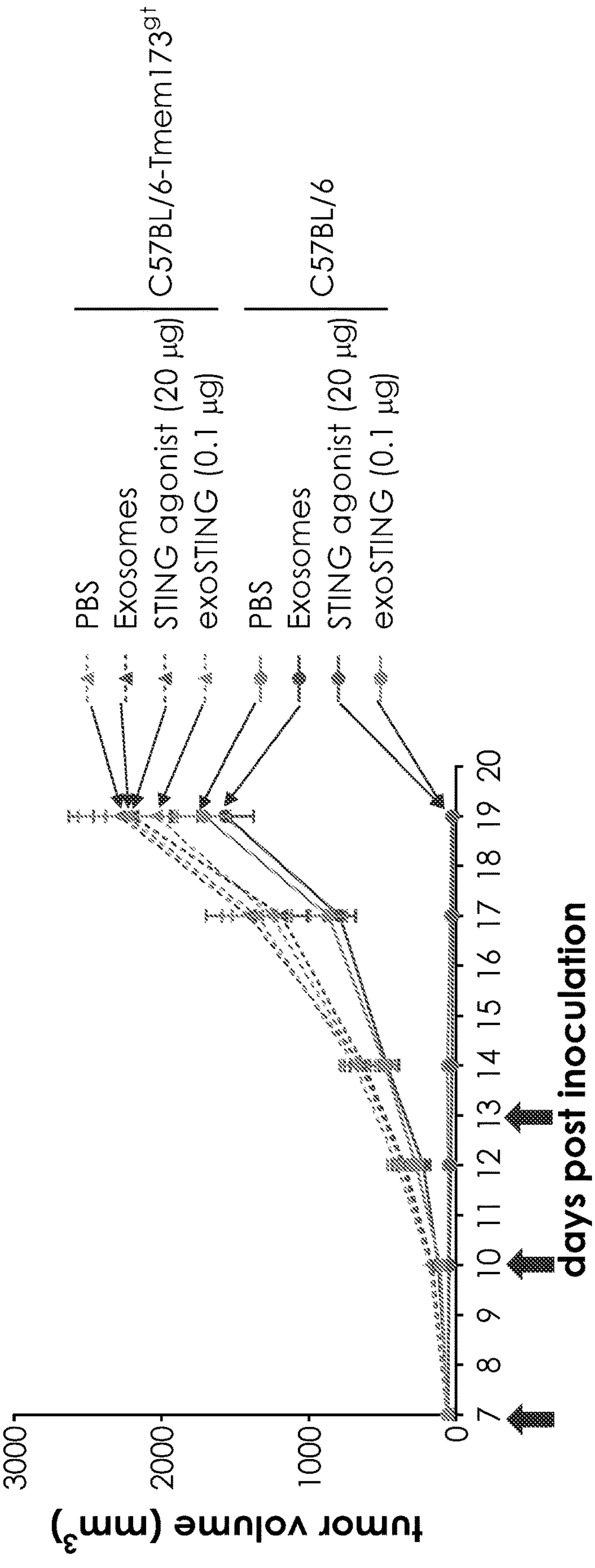
FIG. 59 shows tumor growth curves in B16F10 tumor-bearing C57BL/6 mice or C57BL/6-Tmem173$^{gt}$ mice over the course of the study described in Example 20 (i.e., an intratumoral injection study comparing the efficacy of PBS, 20 μg free 3-3 cAIMPdFSH, 0.2 μg exosome-encapsulated 3-3 cAIMPdFSH in B16F10 tumor-bearing C57BL/6 mice or C57BL/6-Tmem173$^{gt}$ mice).

To confirm that the effects observed in FIGS. 54-58 were translated to anti-tumor activity, C57BL/6 mice and C57BL/6-Tmem173$^{gt}$ mice were inoculated subcutaneously with 1×10$^6$ B16F10 murine melanoma cells (n=5 mice per group). Seven, ten, and thirteen days post-inoculation, the mice were injected intratumorally with PBS, exosomes, 20 μg of free 3-3 cAIMPdFSH, or 0.1 μg of 3-3 cAIMPdFSH loaded in PTGFRN-overexpressing exosomes. Tumor volumes were measured daily until day 19, and animals were sacrificed when tumor volume reached 2000 mm$^3$. As expected, treatment with 0.1 μg of EXOSTING™ and 20 g of free 3-3 cAIMPdFSH resulted in dramatically improved tumor regression in C57BL/6 mice (FIG. 59). However, no tumor regression was observed in C57BL/6-Tmem173$^{gt}$ mice from any treatment (FIG. 59). Collectively, these data demonstrate that activity of exosome-STING agonist is mediated by STING pathway.

Figure 60:
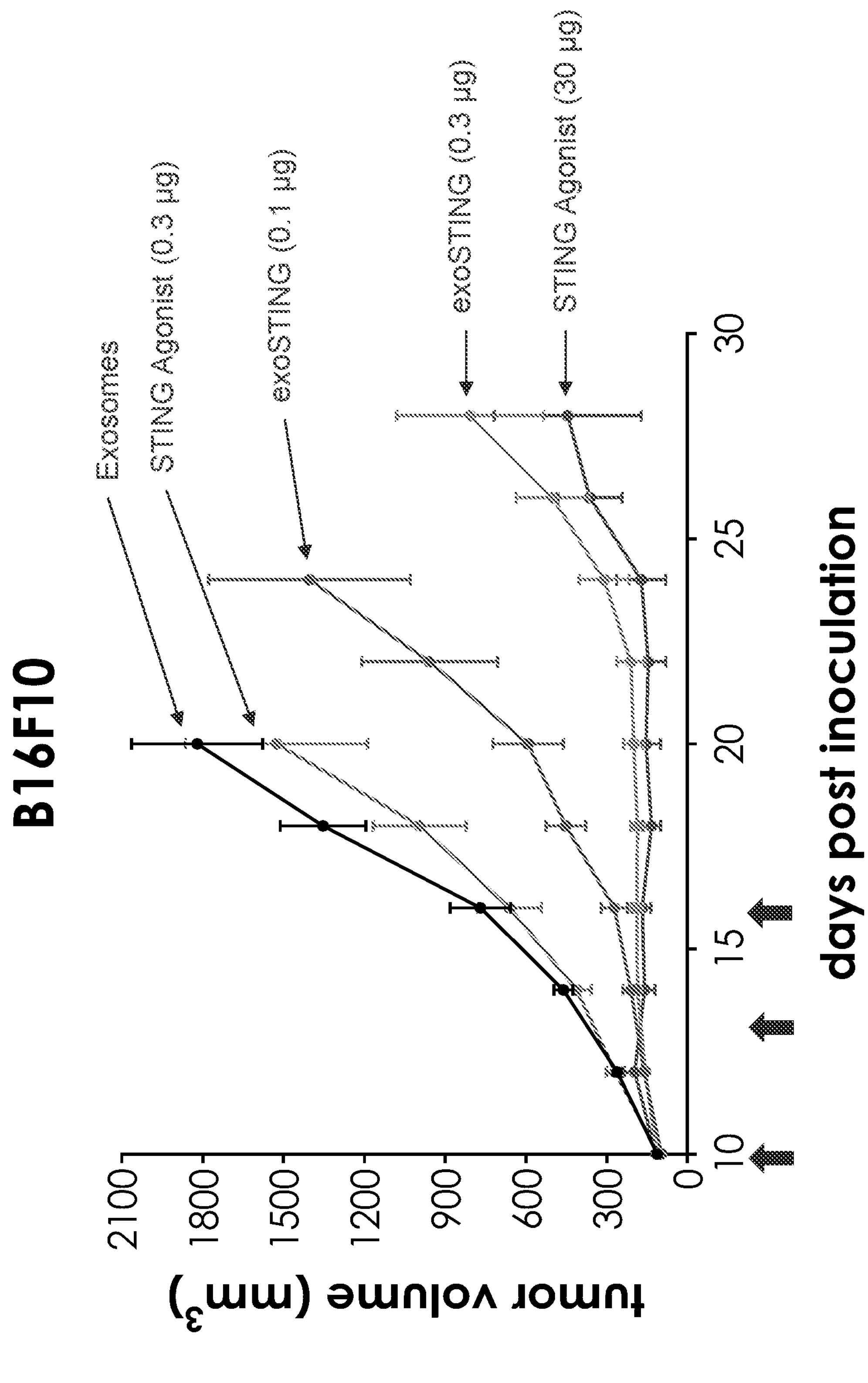
FIG. 60 shows the tumor growth curves in B16F10 tumor-bearing mice over the course of the study described in Example 21.

Example 21: Comparative In Vivo Efficacy of STING Agonist-Loaded Exosomes and Free STING Agonist in an Advanced Murine Model of Melanoma Previous data (FIGS. 37, 40, 47, 49, 50, and 60) with B16F10 tumor showed enhanced anti-tumoral activity of STING agonist-loaded exosomes. Treatment was started when tumor volume reached ~50 mm$^3$. To test the activity in advanced tumor, C57BL/6 mice were inoculated subcutaneously with 1×10$^6$ B16F10 murine melanoma cells (n=5 mice per group) and waited until tumor volume reached ~100 mm$^3$. Ten, thirteen, and sixteen days post-inoculation, the mice were injected intratumorally with exosomes, 30 μg of free 3-3 cAIMPdFSH, 0.3 μg of free 3-3 cAIMPdFSH, 0.1 μg of 3-3 cAIMPdFSH loaded in PTGFRN-overexpressing exosomes, or 0.3 μg of 3-3 cAIMPdFSH loaded in PTGFRN-overexpressing exosomes. Tumor volumes were measured daily until day 28, and animals were sacrificed when tumor volume reached 2000 mm$^3$. Compared to the exosomes control group, tumor growth was not affected after treatment with 0.3 μg of free STING agonist, but great reduction of tumor burden upon treatment with 30 μg free STING agonist. Surprisingly, treatment with 0.1 μg of EXOSTING™ resulted in moderately potentiated tumor growth and with 0.3 μg of EXOSTING™ dramatically improved tumor regression compared to the concentration-matched free STING agonist group and to a similar extent as the high-dose free STING agonist group. FIG. 60 shows the average tumor growth in the animal groups and FIGS. 61A-61E shows the tumor growth in individual mice in each treatment group.

Example 22: Anti-Tumor Efficacy in a Model of Murine Colorectal Cancer Model

To test and expand in vivo efficacy to other types of tumors, BALB/c mice were inoculated subcutaneously with 5×10$^5$ CT26.CL25 cells (ATCC®; CRL-2639™), a murine colorectal cancer cell line engineered to stably express beta-galactosidase, or 5×10$^5$ CT26.WT cells (ATCC®; CRL-2638™) (n=5-7 mice per group). Thirteen, sixteen, and nineteen days post-inoculation the mice were injected intratumorally into CT26.CL25 tumor with exosomes, 0.012 μg of free 3-3 cAIMPdFSH, or 0.012 μg-3 cAIMPdFSH loaded in PTGFRN-overexpressing exosomes and into CT26.WT tumor with PBS, exosomes, 100 μg of free ML RR-S2 CDA, or 0.2 μg-3 cAIMPdFSH loaded in PTGFRN-overexpressing exosomes. Similar to the effects observed in the B16F10 model (FIGS. 37, 39, 40, 46, 47, 48, 49, 50, and 59), low-dose free STING agonist moderately attenuated tumor growth, EXOSTING™ dramatically prevented tumor growth of both CT26.CL25 (FIG. 62) and CT26.WT tumors (FIG. 63) compared to the control group.

Example 23: Comparative In Vivo Abscopal Efficacy of STING Agonist-Loaded Exosomes and Free STING Agonist in a Dual Flank Murine Model of Melanoma Model STING pathway activation leads to induce systemic tumor specific T-cell responses, which resulted in abscopal anti-tumor activity (Cell Rep. 2018 Dec. 11; 25(11):3074-3085). In addition, activation of the STING pathway induces the upregulation of immune pathway checkpoints, which subsequently reduce T-cell-mediated cell killing, and thus moderate the effects of STING pathway agonism as a therapeutic rationale (Cell Rep. 2015 May 19; 11(7):1018-30). To test both hypotheses, C57BL/6 mice were inoculated subcutaneously with 1×10$^6$ and 5×10$^5$ B16F10 murine melanoma cells into right and left flank of mice, respectively (n=5 mice per group). Seven, ten, and thirteen days post-inoculation, the tumor at right flank were injected intratumorally with exosomes, 20 μg of free 3-3 cAIMPdFSH, 0.1 μg of free 3-3 cAIMPdFSH, or 0.1 μg 3-3 cAIMPdFSH loaded in PTGFRN-overexpressing exosomes, with a control antibody (α-IgG; 10 mg/kg; BioLegend, Catalog #400559, Clone RTK3758) or an antagonistic antibody against PD-1 (a PD-1; 10 mg/kg; BioLegend, Catalog #114111, Clone RMPI-14). Antibodies were injected intraperitoneally. Tumor volumes were measured daily until day 21, and animals were sacrificed when tumor volume reached 2000 mm$^3$. In the injected tumor, compared to exosomes control group (both with IgG or Anti-PD1), tumor growth was moderately potentiated after treatment with both 0.1 μg free STING agonist+IgG and 0.1 μg free STING agonist+ Anti-PD1. Almost completely eliminated upon treatment with 20 μg free STING agonist and 0.1 μg of EXOSTING™ was observed regardless of anti-PD1 (FIG. 64). Surprisingly, significant tumor reduction was observed in contralateral tumors, which were not injected tumors, upon treatment with 20 μg free STING agonist and 0.1 μg of EXOSTING™. In addition, this tumor reduction was more strengthened with anti-PD1 combination (FIG. 65). These data demonstrated the induction of systemic tumor specific T cell responses by EXOSTING™.

Example 24: Tumor Pharmacokinetics Analysis of STING Agonist-Loaded Exosomes and Free STING Agonist in a Murine Model of Melanoma To examine the tumor pharmacokinetics of STING agonist, C57BL/6 mice were inoculated subcutaneously with $1\times10^6$ B16F10 murine melanoma cells (n=3 mice per group and time). Eight days post-inoculation, the tumors were injected intratumorally with 30 μg of free 3-3 cAIMPdFSH, 0.3 μg of free 3-3 cAIMPdFSH, or 0.3 μg 3-3 cAIMPdFSH loaded in PTGFRN-overexpressing exosomes. Five minutes, thirty minutes, two hours, 6 hours, 24 hours, and 48 hours after injection, tumors were excised and lysed with 6 volume of plasma. The concentration of 3-3 cAIMPdFSH was measured by LC-MS/MS, as described in Example 1. Free 3-3 cAIMPdFSH in both 30 μg and 0.3 μg was disappeared quickly from tumor, having half-life of around 10 minutes. Surprisingly, half-life of 3-3 cAIMPdFSH was greatly enhanced (~120 minutes) when delivered by exosomes (FIG. 66). This data suggests that after intratumoral injection of high dose of free STING agonist, STING agonist is leaked into systemic circulation quickly and finally leads systemic responses including increase of serum cytokines as described in example 6. However, EXOSTING™ had tumor-retained pharmacology and activated the responses at local, not systemic, which eventually reduced the toxicity of STING agonist.

Example 25: Pharmacokinetics Analysis of STING Agonist-Loaded Exosomes and Free STING Agonist in Mouse Plasma To examine the pharmacokinetics of STING agonist in mouse plasma, naïve C57BL/6 mice were injected intravenously with 20 μg of free 3-3 cAIMPdFSH, or 0.1 μg, 0.3 μg, 0.6 μg 3-3 cAIMPdFSH loaded in PTGFRN-overexpressing exosomes. One, five, ten, and thirty minutes injection, blood was taken, and plasma were prepared. The concentration of 3-3 cAIMPdFSH was measured by LC-MS/MS, as described in Example 1. Free 3-3 cAIMPdFSH was disappeared quickly from circulation, having half-life of 1.2 minutes (FIG. 67). 0.1 μg and 0.3 μg 3-3 cAIMPdFSH loaded exosomes showed similar half-life (1.2 and 1.8 minutes, respectively) as free 3-3 cAIMPdFSH, but 0.6 μg 3-3 cAIMPdFSH loaded exosomes showed enhanced half-life (8.5 minutes) (FIG. 68).

Example 26: Comparative In Vivo Activity of STING Agonist-Loaded Exosomes and Free STING Agonist in Mouse after Intravenous Injection To compare in vivo activity of free STING agonist and STING agonist-loaded exosomes beyond intratumoral dosing, naïve C57BL/6 mice were injected intravenously with 20 μg of free 3-3 cAIMPdFSH or 0.2 μg 3-3 cAIMPdFSH loaded in PTGFRN-overexpressing exosomes. Thirty minutes, two hours, six hours, and twenty-four hours after injection, livers, spleens and serum were collected and cytokine levels were measured. Surprisingly, all cytokine gene expression levels that have been tested here including IFNβ, CXCL9, CXCL10, IFNγ were significantly higher in 0.2 μg EXOSTING™, compared to 20 g free STING agonist, in liver (FIGS. 69A-D), spleen (FIGS. 70A-D) and serum (FIGS. 71A-E), across all time points, although injected amount of −3 cAIMPdFSH was 100-fold less in EXOSTING™ group. This may be due to the selective uptake mechanism of exosomes to liver and spleen (J Extracell Vesicles. 2015 Apr. 20; 4:26316), which allows delivery of STING agonist to these organs. These data demonstrate that 100-fold less STING agonist can induce a significant higher induction of an IFN gene expression after intravenous injection by exosomes due to changing pharmacokinetics and pharmacodynamics of STING agonist.

Example 27: Comparative In Vivo Activity of STING Agonist-Loaded Exosomes and Free STING Agonist in Mouse after Subcutaneous Injection To compare in vivo activity of free STING agonist and STING agonist-loaded exosomes beyond intratumoral dosing, naïve C57BL/6 mice were injected subcutaneously with PBS, exosomes, 20 μg of free 3-3 cAIMPdFSH or 0.2 μg 3-3 cAIMPdFSH loaded in PTGFRN-overexpressing exosomes. Four hours post-injection, lymph nodes, spleens, livers, and serum were collected and cytokine levels were measured. IFNβ gene expression levels in the lymph nodes (FIG. 72A), spleens (FIG. 72B), and livers (FIG. 72C) were significantly elevated after 20 μg of free STING agonist treatment, but IFNβ gene expression levels were dramatically reduced after EXOSTING™, compared to the higher free STING agonist treatment group. Additionally, the levels of IFNγ and the T-cell chemo-attractants CXCL9 and CXCL10 showed similar trend as IFNβ (FIGS. 73, 74, and 75). These results were more dramatic in serum cytokines showing marked decreases in the pro-inflammatory cytokines IFNβ (FIG. 76A), TNF-α (FIG. 76B), IL-6 (FIG. 76C), IFNγ (FIG. 76D), and MCP-1 (FIG. 76E) in the exosome-STING agonist group compared to free STING agonist groups.

Example 28: In Vivo Potency and Systemic Effects of Free STING Agonists Compared to Exosome-Encapsulated STING Agonists in Tumor-Bearing Mice Four groups of C57BL/6 mice (5 mice per group) were inoculated subcutaneously with $1\times10^6$ B16F10 tumor cells. Eight days post-inoculation the mice were injected intratumorally with dose of exosomes, 20 μg of free 3-3 cAIMPdFSH, 0.1 μg of free 3-3 cAIMPdFSH, or 0.1 μg of 3-3 cAIMPdFSH loaded in PTGFN-overexpressing exosomes (EXOSTING™). Half of the mice were injected again intratumorally at day 11 after the inoculation. Four- or 24-hours post-injection of each injection, the tumors were collected, cytokine levels were measured by in situ hybridization, and CD8 or F4/80 positive cells were counted by immunohistochemistry. Tumor area and stroma area were identified histologically. IFNβ gene expression levels in the tumor (FIG. 77A) and stroma (FIG. 77B) area were increased in the 20 μg free STING agonist and 0.1 μg EXOSTING™ groups at 4 h after single dose. Surprisingly, the level of IFNβ in both tumor and stroma area was significantly decreased in 20 μg free STING agonist group at 4 h after second doses, whereas the level of IFNβ in both tumor and stroma area was maintained in 0.1 μg EXOSTING™ group. In addition, CD8 positive T cells were significantly increased in 0.1 μg EXOSTING™ group at 4 and 24 h after second doses, but were not increased in 20 μg free STING agonist group (FIG. 78A). F4/80 positive cells were decreased in 20 μg free STING agonist group, but cells were recovered in 0.1 μg EXOSTING™ group (FIG. 78B). These data demonstrate that high dose free STING agonist can destroy the immune cells that has ability to induce IFN responses after single dose, which make them unable to induce similar level of IFN responses after second doses and unable to recruit the T cells into the tumor. However, exoSTING do not destroy the immune cells, but induce IFN responses even after multiple treatments, which led increase infiltration of T cells.

Example 29: Comparative In Vivo Efficacy of STING Agonist-Loaded Exosomes and Free STING Agonist in a Murine Model of Melanoma to Show Durable T Cell Responses The results of the previous Example 9 suggest that EXOSTING™ that loaded with ML RR-S2 CDA exhibited the durable T cell responses that block the growth of re-challenged tumor. Here, to determine whether EXOSTING™ that loaded with 3-3 cAIMPdFSH exhibit same responses, C57BL/6 mice were inoculated subcutaneously with $1\times10^6$ B16F10 murine melanoma cells (n=5~10 mice per group). Six, nine, and twelve days post-inoculation, the tumors were injected intratumorally with PBS, exosomes, 100 μg of free ML RR-S2 CDA, or 0.2 μg 3-3 cAIMPdFSH loaded in PTGFRN-overexpressing exosomes. FIG. 79A shows the average tumor growth in the animal groups and FIGS. 79B-E show the tumor growth in individual mice. The ten animals in the 100 μg of free ML RR-S2 CDA and four animals EXOSTING™ group that showed complete response were re-challenged on day 20 by transplantation of $1\times10^6$ B16F10 cells on the opposite flank. Five additional naïve mice were inoculated with the same tumor cell preparation and treated daily with PBS to ensure cell viability and growth kinetics. By day 37 (17 days post-challenge) all mice in the PBS group were sacrificed. Tumors in animals from 100 μg of free ML RR-S2 CDA failed to inhibit the tumor growth in 10 out of 10 animals, while remarkably, tumor growth was undetectable in all four mice in the EXOSTING™ group (FIGS. 80A-D). FIG. 80A shows the average tumor growth in the animal groups and FIGS. 80B-D show the tumor growth in individual mice.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

The present disclosure provides, inter alia, compositions of exosomes encapsulating STING agonists for use as therapeutics. The present disclosure also provides methods of producing exosomes encapsulating STING agonists and methods of administering such exosomes as therapeutics. While various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A composition comprising an extracellular vesicle comprising a stimulator of interferon genes protein (STING) agonist, wherein the extracellular vesicle overexpresses a prostaglandin F2 receptor negative regulator (PTGFRN) protein or a fragment thereof, wherein the STING agonist is a cyclic dinucleotide comprising:

Formula (1)

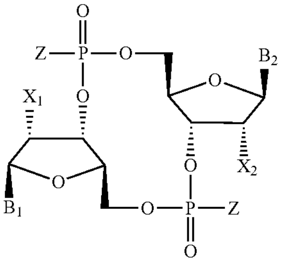

or

Formula (2)

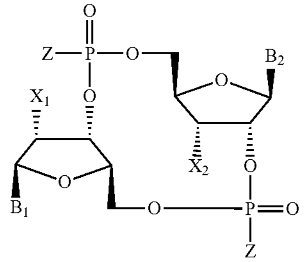

$X_1$ is H, OH, or F;

$X_2$ is H, OH, or F;

Z is OH, $OR_1$, SH or $SR_1$, wherein:

$R_1$ is Na or $NH_4$, or $R_1$ is a pivaloyloxymethyl group;

$B_1$ and $B_2$ are bases chosen from:

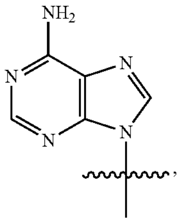

Adenine

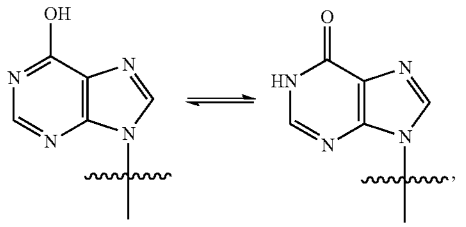

or

Hypoxanthine

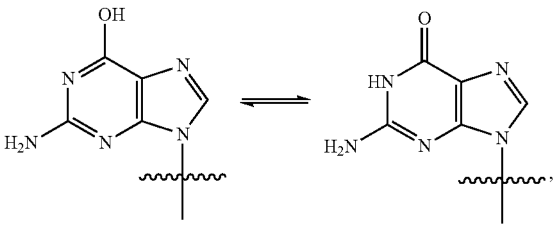

Guanine with the proviso that:

in Formula (I): $X_1$ and $X_2$ are not OH, and in Formula (II): when $X_1$ and $X_2$ are OH, $B_1$ is not Adenine and $B_2$ is not Guanine.

2. The composition of claim 1, wherein the extracellular vesicle is an exosome, a nanovesicle, an apoptotic body, a microvesicle, a lysosome, an endosome, a liposome, a lipid nanoparticle, a micelle, a multilamellar structure, a revesiculated vesicle, or an extruded cell.

3. The composition of claim 2, wherein the STING agonist is associated with the extracellular vesicle.

4. The composition of claim 3, wherein the STING agonist is encapsulated within the extracellular vesicle.

5. The composition of claim 1, wherein the extracellular vesicle further comprises a ligand, a cytokine, or an antibody.

6. The composition of claim 1, wherein the STING agonist is selected from the group consisting of:

CL602

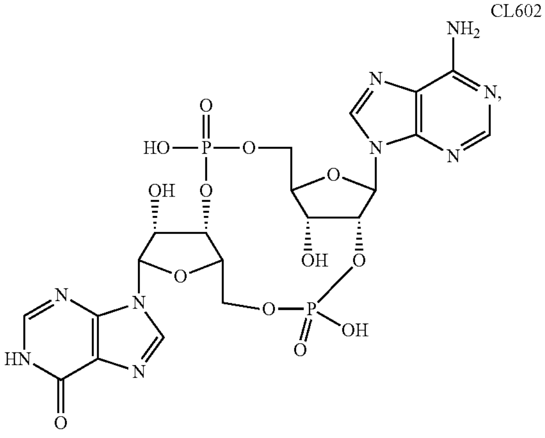

(2′,3′)c-AIMP

CL655

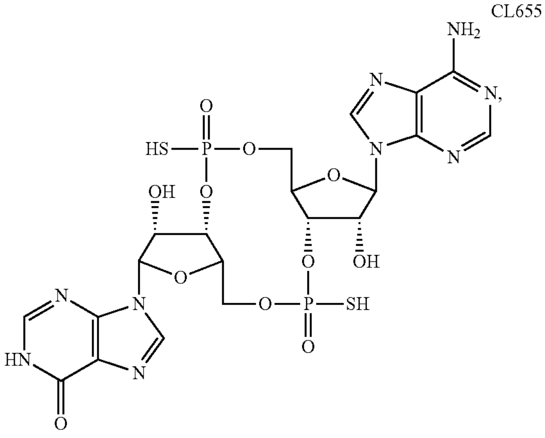

c-AIMP(S)

-continued

CL604

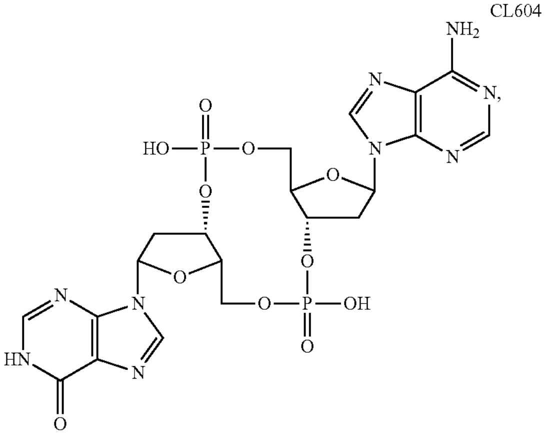

c-(dAMP-dIMP)

CL609

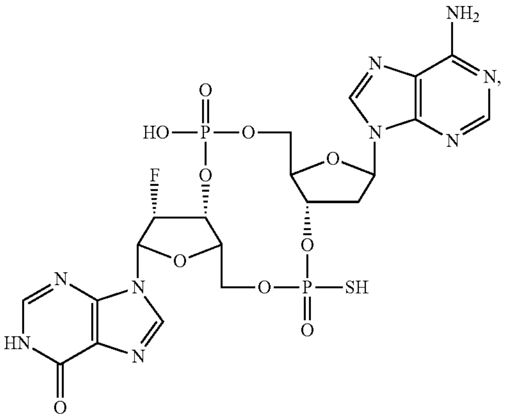

c-(dAMP-2′FdIMP)

CL614

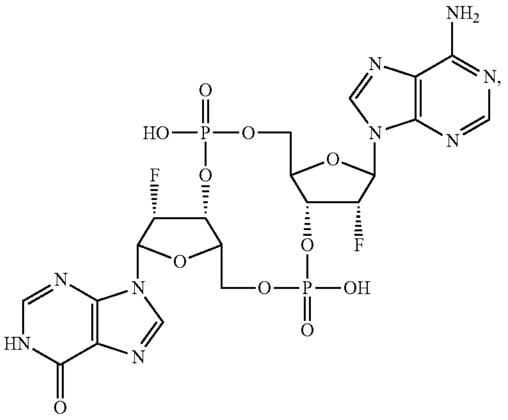

c-(2′FdAMP-2′FdIMP)

-continued
CL656
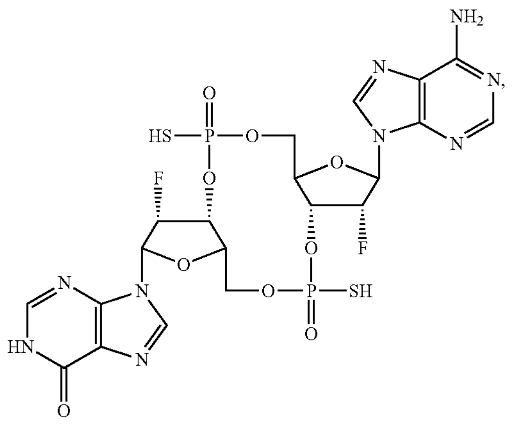
c-[2′FdAMP(S)-2′FdIMP(S)]
CL647
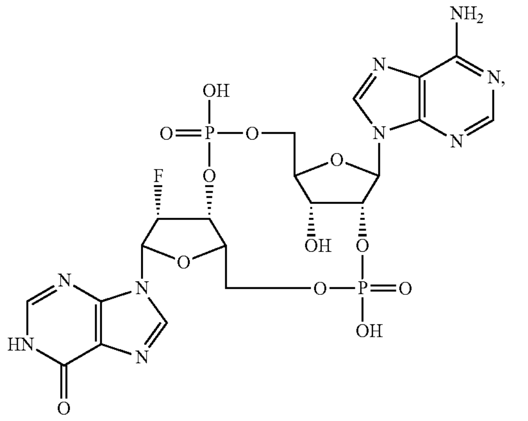
(2′,3′)c-(AMP-2′FdIMP)
CL626
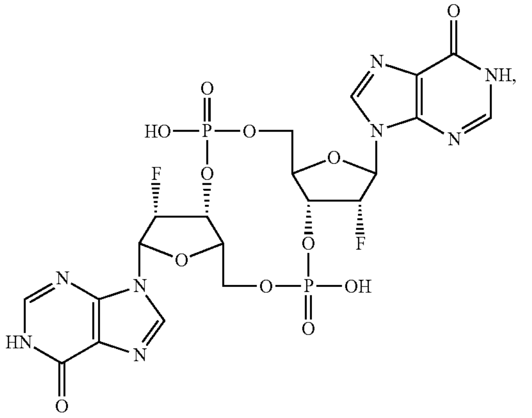
c-di(2′FdIMP)
-continued
CL629
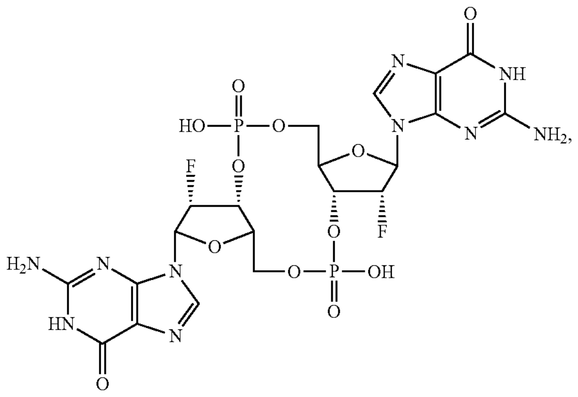
c-di(2′FdGMP)
CL603
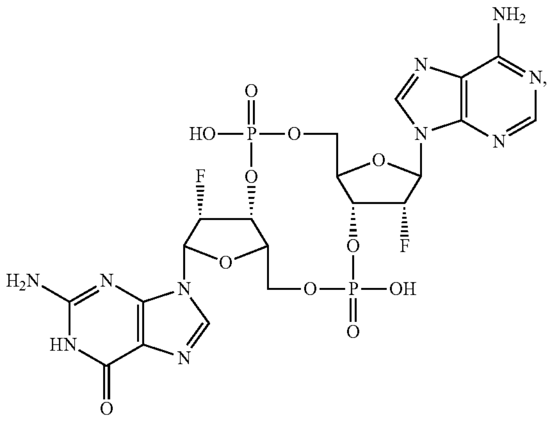
c-[2′FdGMP-2′FdAMP)
CL632
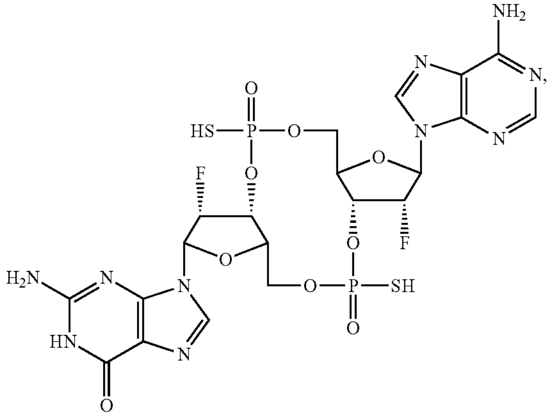
c-[2′FdGMP(S)-2′FdAMP(S)]

-continued

CL633

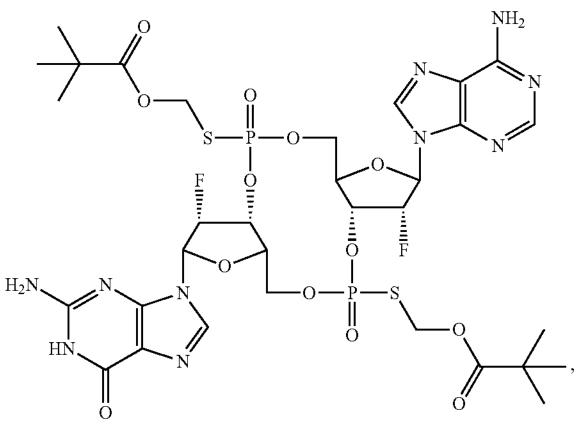

c-[2'FdGMP(S)-2'FdAMP(S)](POM)$_2$

CL659

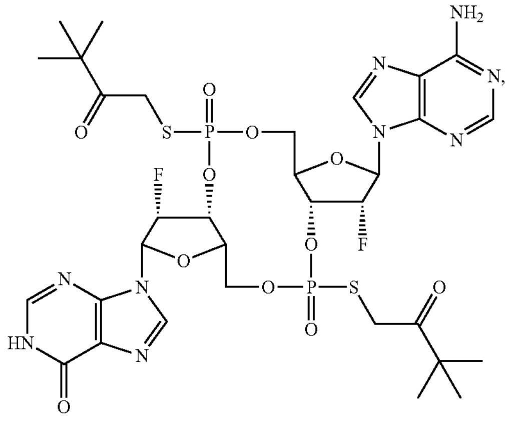

c-[2'FdAMP(S)-2'FdIMP(S)](POM)$_2$ and a pharmaceutically acceptable salt thereof.

7. The composition of claim 3, wherein the extracellular vesicle associated with the STING agonist exhibits one or more of the following characteristics:

(i) activates dendritic cells;

(ii) activates monocyte cells at a lesser degree than the STING agonist alone ("free STING agonist");

(iii) does not activate monocyte cells;

(iv) has a wider therapeutic index compared to the free STING agonist;

(v) has less systemic toxicity than the free STING agonist;

(vi) has less immune cell killing than the free STING agonist;

(vii) has higher cell selectivity than the free STING agonist;

(viii) provides tumor protective immunity at a dose lower than the free STING agonist;

(ix) induces a specific cellular response in vivo in antigen-presenting cells;

(x) is capable of inducing an immune response at a distal region after a local administration; and (xi) is capable of being dosed at a lower level than the free STING agonist.

8. The composition of claim 7, wherein the extracellular vesicle associated with the STING agonist, when administered to a mammal, (a) does not deplete T cells and/or macrophages in the mammal or (b) depletes T cells and/or macrophages in the mammal at a lesser degree than the free STING agonist.

9. A pharmaceutical composition comprising the composition of claim 1 and a pharmaceutically acceptable carrier.

10. A kit comprising the composition of claim 1 and instructions for use.

11. The composition of claim 1, wherein the STING agonist is

CL656

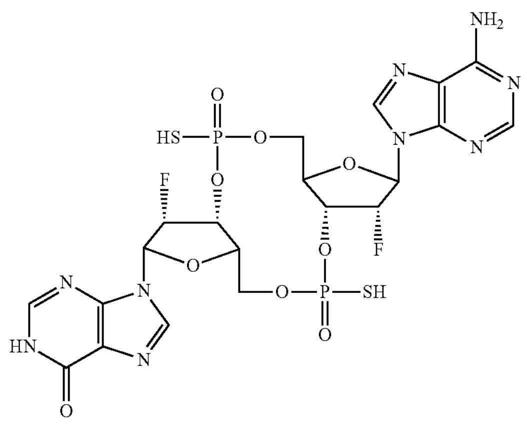

c-[2'FdAMP(S)-2'FdIMP(S)]

or a pharmaceutically acceptable salt thereof.

12. The composition of claim 1, wherein the extracellular vesicle is deglycosylated.

13. The composition of claim 1, wherein the extracellular vesicle is desialylated.

* * * * *